US009458155B2

(12) United States Patent
Hung et al.

(10) Patent No.: US 9,458,155 B2
(45) Date of Patent: Oct. 4, 2016

(54) PYRIDO[4,3-B]INDOLES CONTAINING RIGID MOIETIES

(71) Applicant: Medivation Technologies, Inc., San Francisco, CA (US)

(72) Inventors: David T. Hung, Redwood City, CA (US); Andrew A. Protter, Palo Alto, CA (US); Rajendra Parasmal Jain, Pune (IN); Sarvajit Chakravarty, Mountain View, CA (US)

(73) Assignee: MEDIVATION TECHNOLOGIES, INC, San Francisco, CA (US)

( * ) Notice: Subject to any disclaimer, the term of this patent is extended or adjusted under 35 U.S.C. 154(b) by 0 days.

(21) Appl. No.: 14/531,915

(22) Filed: Nov. 3, 2014

(65) Prior Publication Data
US 2015/0051218 A1 Feb. 19, 2015

Related U.S. Application Data

(62) Division of application No. 12/610,217, filed on Oct. 30, 2009, now Pat. No. 8,907,097.

(60) Provisional application No. 61/110,519, filed on Oct. 31, 2008, provisional application No. 61/173,960, filed on Apr. 29, 2009, provisional application No. 61/245,150, filed on Sep. 23, 2009.

(51) Int. Cl.
*C07D 471/04* (2006.01)
*A01N 43/42* (2006.01)
*C07D 401/14* (2006.01)

(52) U.S. Cl.
CPC ........... *C07D 471/04* (2013.01); *C07D 401/14* (2013.01)

(58) Field of Classification Search
CPC .................................................. C07D 471/04
USPC .............. 514/323, 253.03, 255.05, 256, 292; 546/201, 85
See application file for complete search history.

(56) References Cited

U.S. PATENT DOCUMENTS 3,525,750 A 8/1970 Renner
3,529,062 A 9/1970 Renner
(Continued)

FOREIGN PATENT DOCUMENTS

CH 445 512 A 10/1967
EP 0 466 548 A1 1/1992
(Continued)

OTHER PUBLICATIONS

JiTT "Basic principles of pharmacology" p. 1-11 (2015).*
(Continued)

*Primary Examiner* — Celia Chang
(74) *Attorney, Agent, or Firm* — Morrison & Foerster, LLP

(57) ABSTRACT

This disclosure is directed to pyrido[4,3-b]indoles having rigid moieties. The compounds in one embodiment are pyrido[4,3-b]indoles having an unsaturated hydrocarbon moiety. The compounds in another embodiment are pyrido[4,3-b]indoles having a cycloalkyl, cycloalkenyl or heterocyclyl moiety. Pharmaceutical compositions comprising the compounds are also provided, as are methods of using the compounds in a variety of therapeutic applications, including the treatment of a cognitive disorder, psychotic disorder, neurotransmitter-mediated disorder and/or a neuronal disorder.

19 Claims, 17 Drawing Sheets

(56) References Cited

U.S. PATENT DOCUMENTS

| | | |
|---|---|---|
| 4,754,038 A | 6/1988 | Abou-Gharbia |
| 6,187,785 B1 | 2/2001 | Zefirov et al. |
| 6,828,314 B2 | 12/2004 | Frank et al. |
| 7,071,206 B2 | 7/2006 | Zefirov et al. |
| 8,338,408 B2 | 12/2012 | Hung et al. |
| 8,338,447 B2 | 12/2012 | Hung et al. |
| 8,541,437 B2 | 9/2013 | Ivashchenko et al. |
| 8,546,381 B2 | 10/2013 | Hung et al. |
| 8,569,287 B2 | 10/2013 | Hung et al. |
| 8,741,919 B2 | 6/2014 | Jain et al. |
| 8,791,132 B2 | 7/2014 | Protter et al. |
| 8,815,843 B2 | 8/2014 | Protter et al. |
| 8,859,561 B2 | 10/2014 | Jain et al. |
| 8,906,925 B2 | 12/2014 | Hung et al. |
| 8,907,097 B2 | 12/2014 | Hung et al. |
| 8,927,571 B2 | 1/2015 | Jain et al. |
| 8,999,977 B2 | 4/2015 | Hung et al. |
| 8,999,978 B2 | 4/2015 | Hung et al. |
| 9,006,234 B2 | 4/2015 | Jain et al. |
| 9,006,263 B2 | 4/2015 | Protter et al. |
| 9,034,865 B2 | 5/2015 | Chakravarty et al. |
| 9,034,869 B2 | 5/2015 | Hung et al. |
| 9,034,880 B2 | 5/2015 | Hung et al. |
| 9,035,056 B2 | 5/2015 | Chakravarty et al. |
| 9,040,519 B2 | 5/2015 | Chakravarty et al. |
| 9,045,482 B2 | 6/2015 | Jain et al. |
| 9,051,314 B2 | 6/2015 | Hung et al. |
| 9,079,904 B2 | 7/2015 | Jain et al. |
| 9,085,580 B2 | 7/2015 | Jain et al. |
| 9,096,591 B2 | 8/2015 | Hung et al. |
| 9,115,137 B2 | 8/2015 | Hung et al. |
| 9,181,240 B2 | 11/2015 | Hung et al. |
| 9,187,471 B2 | 11/2015 | Chakravarty et al. |
| 9,193,728 B2 | 11/2015 | Chakravarty et al. |
| 9,199,985 B2 | 12/2015 | Protter et al. |
| 9,199,996 B2 | 12/2015 | Jain et al. |
| 9,211,287 B2 | 12/2015 | Chakravarty et al. |
| 9,255,094 B2 | 2/2016 | Jain et al. |
| 9,260,429 B2 | 2/2016 | Hung et al. |
| 9,271,971 B2 | 3/2016 | Jain et al. |
| 2001/0020028 A1 | 9/2001 | Zefirov et al. |
| 2002/0077318 A1 | 6/2002 | Frank et al. |
| 2002/0115682 A1 | 8/2002 | Zefirov et al. |
| 2003/0225058 A1 | 12/2003 | Frank et al. |
| 2004/0044022 A1 | 3/2004 | Zefirov et al. |
| 2006/0140866 A1 | 6/2006 | Zefirov et al. |
| 2007/0015746 A1 | 1/2007 | Martin et al. |
| 2007/0117834 A1 | 5/2007 | Hung |
| 2007/0117835 A1 | 5/2007 | Hung |
| 2007/0179174 A1 | 8/2007 | Bachurin et al. |
| 2007/0225316 A1 | 9/2007 | Bachurin et al. |
| 2008/0234310 A1 | 9/2008 | Bachurin et al. |
| 2010/0022580 A1 | 1/2010 | Hung et al. |
| 2010/0099700 A1 | 4/2010 | Hung |
| 2010/0152108 A1 | 6/2010 | Hung et al. |
| 2010/0152225 A1 | 6/2010 | Hung |
| 2010/0178277 A1 | 7/2010 | Hung et al. |
| 2010/0286188 A1 | 11/2010 | Bachurin et al. |
| 2011/0112132 A1 | 5/2011 | Bachurin et al. |
| 2011/0237582 A1 | 9/2011 | Jain et al. |
| 2011/0269777 A1 | 11/2011 | Bachurin et al. |
| 2012/0101121 A1 | 4/2012 | Bachurin et al. |
| 2012/0136008 A1 | 5/2012 | Jain et al. |
| 2013/0079352 A1 | 3/2013 | Hung et al. |
| 2013/0123277 A1 | 5/2013 | Jain et al. |
| 2013/0131054 A1 | 5/2013 | Hung et al. |
| 2013/0131077 A1 | 5/2013 | Hung et al. |
| 2013/0137705 A1 | 5/2013 | Jain et al. |
| 2013/0172320 A1 | 7/2013 | Chakravarty et al. |
| 2013/0184303 A1 | 7/2013 | Jain et al. |
| 2013/0184304 A1 | 7/2013 | Jain et al. |
| 2013/0184306 A1 | 7/2013 | Hung et al. |
| 2013/0190293 A1 | 7/2013 | Chakravarty et al. |
| 2013/0190294 A1 | 7/2013 | Protter et al. |
| 2013/0190295 A1 | 7/2013 | Hung et al. |
| 2013/0190304 A1 | 7/2013 | Hung et al. |
| 2013/0190308 A1 | 7/2013 | Jain et al. |
| 2013/0190323 A1 | 7/2013 | Hung et al. |
| 2013/0190328 A1 | 7/2013 | Jain et al. |
| 2013/0190344 A1 | 7/2013 | Jain et al. |
| 2013/0190347 A1 | 7/2013 | Hung et al. |
| 2013/0190348 A1 | 7/2013 | Hung et al. |
| 2013/0190359 A1 | 7/2013 | Jain et al. |
| 2013/0210803 A1 | 8/2013 | Chakravarty et al. |
| 2013/0217703 A1 | 8/2013 | Ivachtchenko et al. |
| 2013/0225558 A1 | 8/2013 | Chakravarty et al. |
| 2014/0024643 A1 | 1/2014 | Hung et al. |
| 2014/0088087 A1 | 3/2014 | Hung et al. |
| 2014/0155384 A1 | 6/2014 | Protter et al. |
| 2014/0213577 A1 | 7/2014 | Hung et al. |
| 2014/0228353 A1 | 8/2014 | Protter et al. |
| 2014/0296209 A1 | 10/2014 | Protter et al. |
| 2014/0303144 A1 | 10/2014 | Protter et al. |
| 2015/0005322 A1 | 1/2015 | Jain et al. |
| 2015/0051218 A1 | 2/2015 | Hung et al. |
| 2015/0182509 A1 | 7/2015 | Hung et al. |
| 2015/0258075 A1 | 9/2015 | Chakravarty et al. |
| 2015/0266884 A1 | 9/2015 | Protter et al. |
| 2015/0315188 A1 | 11/2015 | Protter et al. |
| 2015/0335654 A1 | 11/2015 | Chakravarty et al. |
| 2015/0352087 A1 | 12/2015 | Jain et al. |
| 2016/0030446 A1 | 2/2016 | Chakravarty et al. |

FOREIGN PATENT DOCUMENTS

| | | |
|---|---|---|
| EP | 2 145 887 A2 | 1/2010 |
| EP | 2 236 511 A2 | 10/2010 |
| FR | 1 524 830 A | 5/1968 |
| GB | 1062840 A | 3/1967 |
| JP | 63-163347 A | 7/1988 |
| WO | WO-97/15225 A1 | 5/1997 |
| WO | WO-97/44040 A1 | 11/1997 |
| WO | WO-01/13905 A2 | 3/2001 |
| WO | WO-02/24701 A2 | 3/2002 |
| WO | WO-02/24701 A3 | 3/2002 |
| WO | WO-2005/005951 A2 | 6/2005 |
| WO | WO-2005/005951 A3 | 6/2005 |
| WO | WO-2006/101434 A1 | 9/2006 |
| WO | WO-2007/016353 A2 | 2/2007 |
| WO | WO-2007/016353 A3 | 2/2007 |
| WO | WO-2007/041697 A2 | 4/2007 |
| WO | WO-2007/041697 A3 | 4/2007 |
| WO | WO-2007/087425 A1 | 8/2007 |
| WO | WO-2008/036400 A2 | 3/2008 |
| WO | WO-2008/036400 A3 | 3/2008 |
| WO | WO-2008/036410 A2 | 3/2008 |
| WO | WO-2008/036410 A3 | 3/2008 |
| WO | WO-2008/051599 A2 | 5/2008 |
| WO | WO-2008/051599 A3 | 5/2008 |
| WO | WO-2008/069963 A1 | 6/2008 |
| WO | WO-2008/073231 A1 | 6/2008 |
| WO | WO-2008/123796 A2 | 10/2008 |
| WO | WO-2008/123796 A3 | 10/2008 |
| WO | WO-2008/123800 A2 | 10/2008 |
| WO | WO-2008/123800 A3 | 10/2008 |
| WO | WO-2008/147551 A1 | 12/2008 |
| WO | WO-2009/005771 A1 | 1/2009 |
| WO | WO-2009/017836 A1 | 2/2009 |
| WO | WO-2009/039420 A1 | 3/2009 |
| WO | WO-2009/039420 A9 | 3/2009 |
| WO | WO-2009/055828 A1 | 4/2009 |
| WO | WO-2009/082268 A2 | 7/2009 |
| WO | WO-2009/082268 A3 | 7/2009 |
| WO | WO-2009/094668 A1 | 7/2009 |
| WO | WO-2009/094668 A8 | 7/2009 |
| WO | WO-2009/094668 C1 | 7/2009 |
| WO | WO-2009/111540 A1 | 9/2009 |
| WO | WO-2009/120717 A2 | 10/2009 |
| WO | WO-2009/120717 A3 | 10/2009 |
| WO | WO-2009/120720 A1 | 10/2009 |
| WO | WO-2009/135091 A1 | 11/2009 |
| WO | WO-2010/051501 A1 | 5/2010 |
| WO | WO-2010/051503 A1 | 5/2010 |
| WO | WO-2010/127177 A1 | 11/2010 |

(56) References Cited

FOREIGN PATENT DOCUMENTS

| | | |
|---|---|---|
| WO | WO-2011/014695 A1 | 2/2011 |
| WO | WO-2011/019417 A1 | 2/2011 |
| WO | WO-2011/038161 A1 | 3/2011 |
| WO | WO-2011/038162 A1 | 3/2011 |
| WO | WO-2011/038163 A1 | 3/2011 |
| WO | WO-2011/038164 A1 | 3/2011 |
| WO | WO-2011/103430 A1 | 8/2011 |
| WO | WO-2011/103433 A1 | 8/2011 |
| WO | WO-2011/103448 A1 | 8/2011 |
| WO | WO-2011/103460 A1 | 8/2011 |
| WO | WO-2011/103485 A1 | 8/2011 |
| WO | WO-2011/103487 A1 | 8/2011 |
| WO | WO-2012/112961 A1 | 8/2012 |
| WO | WO-2012/112962 A1 | 8/2012 |
| WO | WO-2012/112963 A1 | 8/2012 |
| WO | WO-2012/112964 A2 | 8/2012 |
| WO | WO-2012/112965 A1 | 8/2012 |
| WO | WO-2012/112966 A1 | 8/2012 |
| WO | WO 2012/154261 A1 | 11/2012 |
| WO | WO-2014/031165 A1 | 2/2014 |
| WO | WO-2014/031167 A1 | 2/2014 |
| WO | WO-2014/031170 A1 | 2/2014 |

OTHER PUBLICATIONS

Morrison "A short course in psychiatry" p. 1-151 (2009).*
Drug action and Pharmacodynamics "Merck Manual" p. 1-8 (2009).*
Neurotransmission "Merck mannual" p. 1-14 (2009).*
Silverman "The ornaic chemistry of . . . " p. 65-73 (1993).*
Neve "functional selectivity . . . " p. 155-157 (2009).*
Abou-Gharbia, M. (Jan. 1, 1989). "Biological Activity of Substituted γ-Carbolines," *Drugs of the Future* 14(5):453-459.
Adham, N. et al. (Jun. 23, 1998). "Functional Characterization of the Recombinant Human 5-Hydroxytryptamine$_{7(a)}$ Receptor Isoform Coupled to Adenylate Cyclase Stimulation," *The Journal of Pharmacology and Experimental Therapeutics.* 287(2):508-514.
Barbero, A. et al. (Jul. 8, 1992). "Ring-Formation from Allyl- and Vinylstannanes Initiated by Treatment with Butyl-Lithium," *Tetrahedron Letters* 33(39):5841-5842.
Bartolini, L. et al. (1996). "Aniracetam Restores Object Recognition Impaired by Age, Scopolamine, and Nucleus Basalis Lesions," *Pharmacology Biochemistry Behavior* 53(2):277-283.
Berge, S.M. et al. (Jan. 1977). "Pharmaceutical Salts," *J. Pharm. Sci.* 66(1):1-19.
Boess, F.G. et al. (1997). "Analysis of the Ligand Binding Site of the 5-HT$_3$ Receptor Using Site Directed Mutagenesis: Importance of Glutamate 106," *Neuropharmacology* 36(4/5):637-647.
Bonhaus, D.W. et al. (1995). "The Pharmacology and Distribution of Human 5-Hydroxytryptamine$_{2B}$ (5-HT$_{2B}$) Receptor Gene Products: Comparison with 5-HT$_{2A}$ and 5-HT$_{2C}$ Receptors," *British Journal of Pharmacology* 115:622-628.
Brown, C.M. et al. (1990). "α$_2$-Adrenoceptor Subtypes and Imidazoline-Like Binding Sites in the Rat Brain," *Br. J. Pharmacol.* 99:803-809.
Bubber, P. et al. (May 2005, e-pub. Apr. 25, 2005). "Mitochondrial Abnormalities in Alzheimer Brain: Mechanistic Implications," *Ann Neurol.* 57(5):695-703.
De Backer, M.D. et al. (Dec. 30, 1993). "Genomic Cloning, Heterologous Expression and Pharmacological Characterization of a Human Histamine H1 Receptor," *Biochemical and Biophysical Research Communications* 197(3):1601-1608.
Dezi, C. (2007). "Modeling of 5-HT$_{2A}$ and 5-HT$_{2C}$ Receptors and of Their Complexes with Actual and Potential Antipsychotic Drugs," PhD Thesis, Pompeu Fabra University, Barcelona, pp. 1-239.
Extended European Search Report mailed on Apr. 23, 2012, for EP Application No. EP 09 82 4200.1, filed on Oct. 30, 2009, 5 pages.
Extended European Search Report mailed on Jul. 10, 2012, for EP Application No. EP 09 82 4199.5, filed on Oct. 30, 2009, 11 pages.

Ennaceur, A. et al. (1988). "A New One-Trial Test for Neurobiological Studies of Memory in Rats. 1: Behavioral Data," *Behav. Brain. Res.* 31:47-59.
Final Office Action mailed on Dec. 2, 2011, for U.S. Appl. No. 12/360,061, filed Jan. 26, 2009, 13 pages.
Galstyan, L.S. et al. (Jan. 1, 1976). "Indole Derivatives," *Armenian Chemical Journal* 3:255-258. (English Translation with Certification.).
Galstyan, L. S. et al. (Jan. 1, 1974). "Indole Derivatives," *Armenian Chemical Journal* 4:331-336. (English Translation with Certification.).
García-Sáinz, J.A. et al. (Jul. 31, 1992). "Species Heterogeneity of Hepatic α$_1$-Adrenoceptors: α$_{1A}$-, and α$_{1B}$- and α$_{1C}$-Subtypes," *Biochemical and Biophysical Research Communications* 186(2):760-767.
Gilliland, S.L. et al. (2000, e-pub. Feb. 29, 2000). "Characterization of Dopaminergic Compounds at hD$_{2short}$, hD$_{4.2}$ and hD$_{4.7}$ Receptors in Agonist-Stimulated [$_{35}$S]GTPγS Binding Assays," *Naunyn-Schmiedeberg's Archives of Pharmacology* 361:498-504.
Grandy, D. K. et al. (Dec. 1989). "Cloning of the cDNA and Gene for a Human D$_2$ Dopamine Receptor," *Proc. Natl. Acad. Sci. USA* 86:9762-9766.
Grossman, C.J. et al. (1993). "Development of a Radioligand Binding Assay for 5-HT$_4$ Receptors in Guinea-Pig and Rat Brain," *Br. J. Pharmacol.* 109:618-624.
Hardy, J. (1996). "New Insights Into the Genetics of Alzheimer's Disease," *Annals of Medicine* 28:255-258.
Hardy, J. (1997). "Amyloid, the Presenilins and Alzheimer's Disease," *Trends Neurosci.* 20(4):154-159.
Hayes, G. et al. (1992). "Structural Subtypes of the Dopamine D2 Receptor are Functionally Distinct: Expression of the Cloned D2$_A$ and D2$_B$ Subtypes in a Heterologous Cell Line," *Mol. Endocrinol.* 6(6):920-926.
Hoyer, D. et al. (1985). "Characterization of the 5-HT$_{1B}$ Recognition Site in Rat Brain: Binding Studies with (-)[$^{125}$I]Iodocyanopindolol," *European Journal of Pharmacology* 118:1-12.
International Search Report mailed on Dec. 31, 2009, for PCT Patent Application No. PCT/US09/62869, filed on Oct. 30, 2009, 5 pages.
Jentsch, J.D. et al. (Aug. 15, 1997). "Enduring Cognitive Deficits and Cortical Dopamine Dysfunction in Monkeys After Long-Term Administration of Phencyclidine," *Science* 277:953-955.
Jerman, J.C. et al. (2001). "Pharmacological Characterisation of Human 5-HT$_2$ Receptor Subtypes," *European Journal of Pharmacology* 414:23-30.
Kenny, B.A. et al. (1995). "Characterization of an α$_{1D}$-Adrenoceptor Mediating the Contractile Response of Rat Aorta to Noradrenaline," *British Journal of Pharmacology* 115:981-986.
Ko-Chetkov, N.K. et al. (1961). "Derivatives of Indole. VII. Synthesis of Some Derivatives of 1,2,3,4,4a,9b-Hexahydro-γ-Carboline," *Zhurnal Obshchei Khimii*, Chemical Abstracts CAPLUS Abstract No. 1961:124840, 6 pages.
Kohen, R. et al. (1996). "Cloning, Characterization, and Chromosomal Localization of a Human 5-HT$_6$ Serotonin Receptor," *J. Neurochem.* 66(1):47-56.
Kroeze, W.K. et al. (2003). "HI-Histamine Receptor Affinity Predicts Short-Term Weight Gain for Typical and Atypical Antipsychotic Drugs," *Neuropsychopharmacology* 28:519-526.
Kucherova, N.F. et al. (1961). "Derivatives of Indole. VIII. 5-Acyl-1,2,3,4,4a,9b-Hexahydro-γ-Carbolines," *Zhurnal Obshchei Khimii*, Chemical Abstracts CAPLUS Abstract No. 1961:124841, 8 pages.
Martin, G.R. (1994). "Receptors for 5-Hydroxytryptamine: Current Perspectives on Classification and Nomenclature," *Neuropharmacology* 33(3/4):261-273.
May, J.A. et al. (2003). "Evaluation of the Ocular Hypotensive Response of Serotonin 5-HT$_{1A}$ and 5-HT$_2$ Receptor Ligands in Conscious Ocular Hypertenisve Cynomolgus Monkeys," *The Journal of Pharmacology and Experimental Therapeutics* 306(1):301-309.
Michel, A.D. et al. (1989). "Identification of a Single α$_1$-Adrenoceptor Corresponding to the α$_{1A}$-Subtype in Rat Submaxillary Gland," *Br. J. Pharmacol.* 98:883-889.

(56) References Cited

OTHER PUBLICATIONS

Miller, K et al. (1992). "Membrane-Bound and Solubilized Brain 5HT$_3$ Receptors: Improved Radioligand Binding Assays Using Bovine Area Postrema or Rat Cortex and the Radioligands $^3$H-GR65630, $^3$H-BRL43694, and $^3$H-LY278584," *Synapse* 11:58-66.

Miller, T.R. et al. (1999). "Analysis of Apparent Noncompetitive Responses to Competitive H$_1$-Histamine Receptor Antagonists in Fluorescent Imaging Plate Reader-Based Calcium Assays," *Journal of Biomolecular Screening* 4(5):249-258.

Monsma, F.J. Jr. et al. (1993). "Cloning and Expression of a Novel Serotonin Receptor with High Affinity for Tricyclic Psychotropic Drugs," *Molecular Pharmacology* 43:320-327.

Non-Final Office Action mailed on Jun. 14, 2011, for U.S. Appl. No. 12/360,061, filed Jan. 26, 2009, 22 pages.

Non-Final Office Action mailed on Feb. 14, 2014, for U.S. Appl. No. 13/498,099, filed Jan. 14, 2013, 20 pages.

Non-Final Office Action mailed on Jul. 31, 2014, for U.S. Appl. No. 13/734,873, filed Jan. 4, 2013, 16 pages.

Pani, L et al. (2007, e-pub. Apr. 6, 2007). "Antipsychotic Efficacy: Relationship to Optimal D$_2$-Receptor Occupancy," *European Psychiatry* 22:276-275.

Pazos, A. et al. (1985). "Mesulergine, A Selective Serotonin-2 Ligand in the Rat Cortex, Does Not Label these Receptors in Porcine and Human Cortex: Evidence for Species Differences in Brain Serotonin-2 Receptors," *European Journal of Pharmacology* 106:531-538.

Pazourkova et al. (2003). "Antioxidant Activity of Pyridoindoles and N-(Alkoxyphenyl)-2-2-(2-oxo-1-aza-1-cycloalkyl) Acetamides in Biological, Enzymic, and Chemical Systems," *Ceska a Slovenska Farmacie,* 52(4): 171-175. (Translation of summary only).

Piercey, M.F. et al. (1988). "Dramatic Limbic and Cortical Effects Mediated by High Affinity PCP Receptors," *Life Sciences* 43(4):379-385.

Prichep, L.S. et al. (1994). "Quantitative EEG Correlates of Cognitive Deterioration in the Elderly," *Neurobiology of Aging* 15(1):85-90.

Reddy, P.H. et al. (2005, e-pub. Apr. 19, 2005). "Are Mitochondria Critical in the Pathogenesis of Alzheimer's Disease?" *Brain Res Rev.* 49(3):618-632.

Rees, S. et al. (Oct. 11, 1994). "Cloning and Characterisation of the Human 5-HT$_{5A}$ Serotonin Receptor," *FEBS Letters* 355:242-246.

Reisberg, B. et al. (Sep. 1982). "The Global Deterioration Scale for Assessment of Primary Degenerative Dementia," *Am. J. Psychiatry* 139(9):1136-1139.

Rodriguez-Spong, B. et al. (2004). "General Principles of Pharmaceutical Solid Polymorphism: a Supramolecular Perspective," *Advanced Drug Delivery Reviews,* 56:241-274.

Roth, B.L. et al. (1994). "Binding of Typical and Atypical Antipsychotic Agents to 5-Hydroxytryptamine-6 and 5-Hydroxytryptamine-7 Receptors," *J. Pharmacol. Exp. Ther.* 268(3):1403-1410.

Ruat, M. et al. (Mar. 1990). "Reversible and Irreversible Labeling and Autoradiographic Localization of the Cerebral Histamine H$_2$ Receptor Using [$^{125}$I]Iodinated Probes," *Proc. Natl. Acad. Sci. USA* 87(5):1658-1662.

Saucier, C. et al. (1997). "Identification of an Endogenous 5-Hydroxytryptamine$_{2A}$ Receptor in NIH-3T3 Cells: Agonist-Induced Down-Regulation Involves Decreases in Receptor RNA and Number," *Journal of Neurochemistry* 68(5):1998-2011.

Scali, C. et al. (1994). "Nerve Growth Factor Increases Extracellular Acetylcholine Levels in the Parietal Cortex and Hippocampus of Aged Rats and Restores Object Recognition," *Neuroscience Letters* 170:117-120.

Senogles, S.E. et al. (Mar. 15, 1990). "Specificity of Receptor-G Protein Interactions. Discrimination of G$_i$ Subtypes by the D$_2$ Dopamine Receptor in a Reconstituted System," *Journal of Biological Chemistry* 265(8):4507-4514.

Shen, Y. et al. (Aug. 25, 1993). "Molecular Cloning and Expression of a 5-Hydroxytryptamine$_7$ Serotonin Receptor Subtype," *The Journal of Biological Chemistry* 268(24):18200-18204.

Swerdlow, R.H. et al. (2002). "Mitochondria in Alzheimer's Disease," *International Review of Neurobiology* 53:341-385.

Tanzi, R.E. et al. (1996). "The Gene Defects Responsible for Familial Alzheimer's Disease," *Neurobiology of Disease* 3:159-168.

Trofimov, F.A. et al. (1967). "Pyridylethylation of γ-Carbolines," *Khimiko-Farmatsevticheskii Zhurnal,* Chemical Abstracts CAPLUS Abstract No. 1961:500029, 4 pages. (have translation).

Uhlén, S. et al. (1994). "The Novel Alpha-2 Adrenergic RadioLigand [$^3$H]-MK912 is Alpha-2C Selective Among Human Alpha-2A, Alpha-2B and Alpha-2C Adrenoceptors," *Journal of Pharmacology and Experimental Therapeutics* 271(3): 1558-1565.

Uhlén, S. et al. (1998). "[$^3$H]RS79948-197 Binding to Human, Rat, Guinea Pig and Pig $\alpha_{2A}$-, $\alpha_{2B}$- and $\alpha_{2C}$-Adrenoceptors. Comparison with MK912, RX821002, Rauwolscine and Yohimbine," *European Journal of Pharmacology* 343:93-101.

U.S. Appl. No. 14/423,027, filed Feb. 20, 2015, by Protter et al.

U.S. Appl. No. 14/701,244, filed Apr. 30, 2015, by Chakravarty et al.

U.S. Appl. No. 14/738,465, filed Jun. 12, 2015, by Jain et al.

Wang, X. et al. (2007, e-pub. Sep. 21, 2007). "Insights Into Amyloid-β-Induced Mitochondrial Dysfunction in Alzheimer Disease," *Free Radical Biology & Medicine* 43:1569-1573.

Wolf, W.A. et al. (1997). "The Serotonin 5-HT$_{2C}$ Receptor Is a Prominent Serotonin Receptor in Basal Ganglia: Evidence from Functional Studies on Serotonin-Mediated Phosphoinositide Hydrolysis," *Journal of Neurochemistry* 69(4):1449-1458.

Written Opinion mailed on Dec. 31, 2009, for PCT Patent Application No. PCT/US09/62869, filed on Oct. 30, 2009, 7 pages.

Yanai, K. et al. (1994). "Binding Characteristics of a Histamine H$_3$-Receptor Antagonist, [$^3$H]S-Methylthioperamide: Comparison with [$^3$H](R)α-Methylhistamine Binding to Rat Tissues," *Jpn. J. Pharmacol.* 65:107-112.

Yu, J-Q. et al. (2002). "Diverse Pathways for the Palladium(II)-Mediated Oxidation of Olefins by *tert*-Butylhydroperoxide," *Organic Letters* 4(16):2727-2730.

Zhu, Y. et al. (2001). "Cloning, Expression, and Pharmacological Characterization of a Novel Human Histamine Receptor," *Molecular Pharmacology* 59(3):434-441.

International Preliminary Report on Patentability mailed on May 12, 2011, for PCT Patent Application No. PCT/US2009/062869, filed on Oct. 30, 2009, 9 pages.

Non-Final Office Action mailed on Mar. 24, 2016, for U.S. Appl. No. 13/498,099, filed Jan. 14, 2013, 10 pages.

Non-Final Office Action mailed on Mar. 28, 2016, for U.S. Appl. No. 13/734,873, filed Jan. 4, 2013, 8 pages.

\* cited by examiner

PYRIDO[4,3-B]INDOLES CONTAINING RIGID MOIETIES

CROSS-REFERENCE TO RELATED APPLICATIONS

This application is a division of U.S. Non-provisional patent application Ser. No. 12/610,217, filed on Oct. 30, 2009, which claims priority to U.S. Provisional Patent Application No. 61/110,519 filed Oct. 31, 2008, U.S. Provisional Patent Application No. 61/173,960 filed Apr. 29, 2009 and U.S. Provisional Patent Application No. 61/245,150 filed Sep. 23, 2009, the disclosures of each of which are hereby incorporated herein by reference in their entireties.

STATEMENT OF RIGHTS TO INVENTIONS MADE UNDER FEDERALLY SPONSORED RESEARCH

Not applicable.

BACKGROUND OF THE INVENTION

Neurotransmitters such as histamine, serotonin, dopamine and norepinephrine mediate a large number of processes in the central nervous system (CNS) as well as outside the CNS. Abnormal neurotransmitter levels are associated with a wide variety of diseases and conditions including, but not limited to, Alzheimer's disease, Parkinson's Disease, autism, Guillain-Barré syndrome, mild cognitive impairment, schizophrenia (such as cognitive impairment associated with schizophrenia (CIAS), positive symptoms, disorganized symptoms, and negative symptoms of schizophrenia), anxiety, multiple sclerosis, stroke, traumatic brain injury, spinal cord injury, diabetic neuropathy, fibromyalgia, bipolar disorders, psychosis, depression, attention-deficit disorder (ADD), attention-deficit hyperactivity disorder (ADHD) and a variety of allergic diseases. Compounds that modulate these neurotransmitters may be useful therapeutics.

Histamine receptors belong to the superfamily of G protein-coupled seven transmembrane proteins. G protein-coupled receptors constitute one of the major signal transduction systems in eukaryotic cells. Coding sequences for these receptors, in those regions believed to contribute to the agonist-antagonist binding site, are strongly conserved across mammalian species. Histamine receptors are found in most peripheral tissue and within the central nervous system. Compounds capable of modulating a histamine receptor may find use in therapy, e.g., histamine antagonists may find use as antihistamines.

Dimebon is a known anti-histamine drug that has also been characterized as a neuroprotective agent useful to treat, inter alia, neurodegenerative diseases. Dimebon has been shown to inhibit the death of brain cells (neurons) in preclinical models of Alzheimer's disease and Huntington's disease, making it a novel potential treatment for these and other neurodegenerative diseases. In addition, dimebon has been shown to improve the mitochondrial function of cells in the setting of cellular stress with very high potency. For example, dimebon treatment improved mitochondrial function and increased the number of surviving cells after treatment with the cell toxin ionomycin in a dose dependent fashion. Dimebon has also been shown to promote neurite outgrowth and neurogenesis, processes important in the formation of new and/or enhanced neuronal cell connections, and evidence of dimebon's potential for use in additional diseases or conditions. See, e.g., U.S. Pat. Nos. 6,187,785 and 7,071,206 and PCT Patent Application Nos. PCT/US2004/041081, PCT/US2007/020483, PCT/US2006/039077, PCT/US2008/077090, PCT/US2007/020516, PCT/US2007/022645, PCT/US2007/002117, PCT/US2008/006667, PCT/US2007/024626, PCT/US2008/009357, PCT/US2007/024623 and PCT/US2008/008121. Hydrogenated pyrido[4,3-b]indoles and uses thereof have been disclosed in PCT Patent Application Nos. PCT/US2008/081390, PCT/US2009/032065 and PCT/US2009/038142. Hydrogenated pyrido[3,4-b]indoles and uses thereof have been described in PCT/US2009/038138. All references disclosed herein and throughout, such as publications, patents, patent applications and published patent applications, are incorporated herein by reference in their entireties.

Although dimebon holds great promise as a drug for the treatment of neurodegenerative diseases and/or diseases in which neurite outgrowth and/or neurogenesis may be implicated in therapy, there remains a need for new and alternative therapies for the treatment of such diseases or conditions. In addition, there remains a need for new and alternative antihistamine drugs, preferably ones in which side-effects such as drowsiness are reduced or eliminated. Compounds that exhibit enhanced and/or more desirable properties than dimebon (e.g., superior safety and efficacy) may find particular use in the treatment of at least those indications for which dimebon is believed to be advantageous. Further, compounds that exhibit a different therapeutic profile than dimebon as determined, e.g. by in vitro and/or in vivo assays, may find use in additional diseases and conditions.

BRIEF SUMMARY OF THE INVENTION

Numerous compounds have been synthesized and tested in biochemical and cell-based assays as well as in in vivo studies.

Tetrahydropyrido[4,3-b]indoles are provided. Compositions and kits comprising the compounds are also provided, as are methods of using and making the compounds. The compounds provided herein may find use as new histamine receptor modulators, as well as modulators of other neurotransmitters. Compounds provided may also find use in treating neurodegenerative diseases. Compounds provided may also find use in treating diseases and/or conditions in which modulation of aminergic G protein-coupled receptors and/or neurite outgrowth may be implicated in therapy. Compounds disclosed herein may find use in the methods disclosed herein, including use in treating, preventing, delaying the onset and/or delaying the development of a cognitive disorder, psychotic disorder, neurotransmitter-mediated disorder and/or a neuronal disorder in an individual in need thereof, such as humans.

In one aspect, the invention embraces compounds of the formula (V):

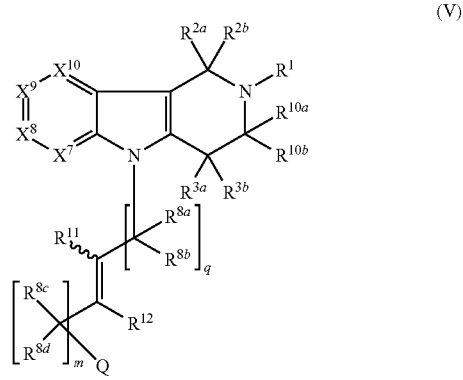

or a salt or solvate thereof;

wherein:

R$^1$ is H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each R$^{2a}$ and R$^{2b}$ is independently H, substituted or unsubstituted C$_1$-C$_8$ alkyl, halo, cyano, hydroxyl, alkoxy, nitro or R$^{2a}$ and R$^{2b}$ are taken together with the carbon to which they are attached to form a carbonyl moiety or a cycloalkyl moiety;

each R$^{3a}$ and R$^{3b}$ is independently H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl or R$^{3a}$ and R$^{3b}$ are taken together with the carbon to which they are attached to form a carbonyl moiety or a cycloalkyl moiety;

each X$^7$, X$^8$, X$^9$ and X$^{10}$ is independently N, CH or CR$^4$;

each m and q is independently 0 or 1;

each R$^4$ is independently hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, C$_1$-C$_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{8a}$, R$^{8b}$, R$^{8c}$ and R$^{8d}$ is independently H, hydroxyl, alkoxy, halo, substituted or unsubstituted aryl, substituted or unsubstituted heteroaryl, substituted or unsubstituted C$_1$-C$_8$ alkyl, substituted or unsubstituted C$_3$-C$_8$ cycloalkyl, substituted or unsubstituted C$_2$-C$_8$ alkenyl, C$_1$-C$_8$ perhaloalkyl, carboxy, carbonylalkoxy, or is taken together with a geminal R$^8$ to form a moiety of the formula —OCH$_2$CH$_2$O—, or is taken together with the carbon to which it is attached and a geminal R$^8$ to form a cycloalkyl moiety or a carbonyl moiety;

each R$^{10a}$ and R$^{10b}$ is independently H, substituted or unsubstituted C$_1$-C$_8$ alkyl, halo, cyano, hydroxyl, alkoxy, nitro or R$^{10a}$ and R$^{10b}$ are taken together with the carbon to which they are attached to form a carbonyl moiety or a cycloalkyl moiety;

each R$^{11}$ and R$^{12}$ is independently is H, halo, alkoxy, substituted or unsubstituted aryl, substituted or unsubstituted heteroaryl, substituted or unsubstituted C$_1$-C$_8$ alkyl, substituted or unsubstituted C$_2$-C$_8$ alkenyl, substituted or unsubstituted C$_3$-C$_8$ cycloalkyl, C$_1$-C$_8$ perhaloalkyl, carboxy, or carbonylalkoxy and the ∼∼∼ bond indicates the presence of either an E or Z double bond configuration; or R$^{11}$ and R$^{12}$ are taken together to form a bond; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, alkoxy, acyloxy, substituted or unsubstituted amino, aminoacyl, aminocarbonylalkoxy, cyano, alkynyl, carboxy, carbonylalkoxy or acylamino.

In one variation, the compound is of the formula (V) where X$^7$, X$^8$, X$^9$, X$^{10}$, R$^1$, R$^{2a}$, R$^{2b}$, R$^{3a}$, R$^{3b}$, R$^{10a}$, R$^{10b}$, Q, q, m, R$^{8a}$, R$^{8b}$, R$^{8c}$, R$^{8d}$, R$^{11}$ and R$^{12}$ are as defined for formula (V), provided that (i) when X$^7$, X$^8$ and X$^{10}$ are each CH and each R$^{2a}$, R$^{2b}$, R$^{3a}$, R$^{3b}$, R$^{10a}$ and R$^{10b}$ is hydrogen, at least one of R$^{11}$ and R$^{12}$ is other than hydrogen and R$^{11}$ and R$^{12}$ are not taken together to form a bond; and (ii) the compound is other than Compound 87. In another variation, the compounds of the invention, and methods of using the compounds and administering the compounds as detailed herein, encompass any of the compounds of the formula (V), including Compound 87. In one aspect, compounds of the formula (V) are provided where q and m are both 0 and at least one of R$^{11}$ and R$^{12}$ is a substituted or unsubstituted alkyl, such as methyl. In another aspect, compounds of the formula (V) are provided where q and m are both 0 and at least one of R$^{11}$ and R$^{12}$ is a substituted or unsubstituted alkyl, such as methyl, and Q is a substituted or unsubstituted aryl, such as phenyl, or a substituted or unsubstituted heteroaryl, such as pyridyl.

In one variation, compounds of the formula (V) are provided, where X$^7$, X$^8$, X$^9$, X$^{10}$, R$^1$, R$^{2a}$, R$^{2b}$, R$^{3a}$, R$^{3b}$, R$^{10a}$, R$^{10b}$, q, m, and Q are as defined for formula (V), each R$^{8a}$, R$^{8b}$, R$^{8c}$ and R$^{8d}$ is independently H, hydroxyl, C$_1$-C$_8$ alkyl, or is taken together with the carbon to which it is attached and a geminal R$^8$ to form a cycloalkyl moiety or a carbonyl moiety; R$^{11}$ is H, substituted or unsubstituted aryl, substituted or unsubstituted heteroaryl, C$_1$-C$_8$ alkyl, C$_3$-C$_8$ cycloalkyl, or C$_1$-C$_8$ perhaloalkyl and the ∼∼∼ bond indicates the presence of either an E or Z double bond configuration; and R$^{12}$ is H, halo, substituted or unsubstituted aryl, substituted or unsubstituted heteroaryl, unsubstituted C$_1$-C$_8$ alkyl, C$_1$-C$_8$ alkyl substituted with a carbonylalkoxy, carboxyl or acylamino moiety, C$_2$-C$_8$ alkenyl, C$_3$-C$_8$ cycloalkyl, or C$_1$-C$_8$ perhaloalkyl.

In another aspect, the invention embraces compounds of the formula (II):

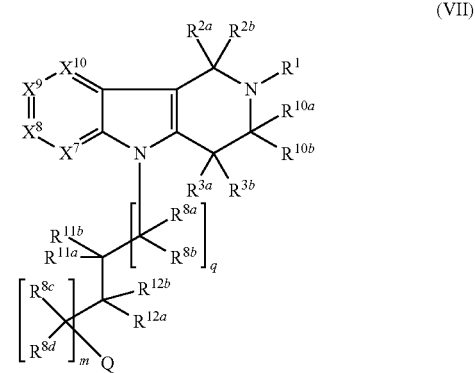

(VII)

or a salt or solvate thereof;

wherein:

R$^1$ is H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety;

each $R^{3a}$ and $R^{3b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl or $R^{3a}$ and $R^{3b}$ are taken together with the carbon to which they are attached to form a carbonyl moiety or a cycloalkyl moiety;

each $X^7$, $X^8$, $X^9$ and $X^{10}$ is independently N, CH or $CR^4$;

each m and q is independently 0 or 1;

each $R^4$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, alkoxy, halo, substituted or unsubstituted aryl, substituted or unsubstituted heteroaryl, substituted or unsubstituted $C_1$-$C_8$ alkyl, substituted or unsubstituted $C_3$-$C_8$ cycloalkyl, $C_2$-$C_8$ alkenyl, $C_1$-$C_8$ perhaloalkyl, carboxy, carbonylalkoxy, or is taken together with a geminal $R^8$ to form a moiety of the formula —$OCH_2CH_2O$—, or is taken together with the carbon to which it is attached and a geminal $R^8$ to form a cycloalkyl moiety or a carbonyl moiety;

each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together with the carbon to which they are attached to form a carbonyl moiety or a cycloalkyl moiety;

each $R^{11a}$ and $R^{12a}$ is independently H, hydroxyl, halo, alkoxy, substituted or unsubstituted aryl, substituted or unsubstituted heteroaryl, substituted or unsubstituted $C_1$-$C_8$ alkyl, substituted or unsubstituted $C_2$-$C_8$ alkenyl, substituted or unsubstituted $C_3$-$C_8$ cycloalkyl, $C_1$-$C_8$ perhaloalkyl, carboxy, or carbonylalkoxy; or $R^{11a}$ and $R^{12a}$ may be taken together to represent a bond;

$R^{11b}$ and $R^{12b}$ are taken together with the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, alkoxy, acyloxy, substituted or unsubstituted amino, aminoacyl, aminocarbonylalkoxy, cyano, alkynyl, carboxy, carbonylalkoxy or acylamino.

In one variation, the compound is of the formula (VII) where $X^7$, $X^8$, $X^9$, $X^{10}$, $R^1$, $R^{2a}$, $R^{2b}$, $R^{3a}$, $R^{3b}$, $R^{10a}$, $R^{10b}$, Q, q, m, $R^{8a}$, $R^{8b}$, $R^{8c}$, $R^{8d}$, $R^{11a}$, $R^{11b}$, $R^{12a}$ and $R^{12b}$ are as defined for formula (VII). In another variation, the compounds of the invention, and methods of using the compounds and administering the compounds as detailed herein, encompass any of the compounds of the formula (VII), including 2-(1,2,3,4-tetrahydro-2,8-dimethyl-5H-pyrido[4,3-b]indol-5-yl)cyclohexanol.

In one variation, compounds of the formula (VII) are provided, where $X^7$, $X^8$, $X^9$, $X^{10}$, $R^1$, $R^{11b}$, $R^{12b}$, q, m, and Q are as defined for formula (VII), each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety; each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together with the carbon to which they are attached to form a carbonyl moiety; each $R^{8a}$, $R^{8b}$, $R^{8c}$ and $R^{8d}$ is independently H, hydroxyl, $C_1$-$C_8$ alkyl, or is taken together with the carbon to which it is attached and a geminal $R^8$ to form a cycloalkyl moiety or a carbonyl moiety; each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together with the carbon to which they are attached to form a carbonyl moiety; and each $R^{11a}$ and $R^{12a}$ is independently H, hydroxyl, or $C_1$-$C_8$ alkyl; or $R^{11a}$ and $R^{12a}$ are taken together to represent a bond.

The invention also includes all salts of compounds referred to herein, such as pharmaceutically acceptable salts. The invention also includes any or all of the stereochemical forms, including any enantiomeric or diastereomeric forms and geometric isomers of the compounds described, or mixtures thereof. Unless stereochemistry is explicitly indicated in a chemical structure or name, the structure or name is intended to embrace all possible stereoisomers, including geometric isomers, of a compound depicted. Unless olefin geometry is explicitly indicated, substituted olefinic bonds may be present as cis or trans or (Z) or (E) isomeric forms, or as mixtures thereof. In addition, where a specific stereochemical form is depicted, it is understood that other stereochemical forms are also embraced by the invention. For example, where only a Z form of a compound is specifically listed, it is understood that the E form of the compound is also embraced. All forms of the compounds are also embraced by the invention, such as crystalline or non-crystalline forms of the compounds. Compositions comprising a compound of the invention are also intended, such as a composition of substantially pure compound, including a specific stereochemical form, including a specific geometric isomer, thereof. Compositions comprising a mixture of compounds of the invention in any ratio are also embraced by the invention, including mixtures of two or more stereochemical forms of a compound of the invention in any ratio, such that racemic, non-racemic, enantio-enriched and scalemic mixtures of a compound are embraced, or mixtures thereof.

The invention is also directed to pharmaceutical compositions comprising a compound of the invention and a pharmaceutically acceptable carrier or excipient. Kits comprising a compound of the invention and instructions for use are also embraced by this invention.

In one aspect, compounds of the invention are used to treat, prevent, delay the onset and/or delay the development of any one or more of the following: cognitive disorders, psychotic disorders, neurotransmitter-mediated disorders and/or neuronal disorders in individuals in need thereof, such as humans. In one variation, compounds of the invention are used to treat, prevent, delay the onset and/or delay the development of diseases or conditions for which the modulation of an aminergic G protein-coupled receptor is believed to be or is beneficial. In one variation, compounds of the invention are used to treat, prevent, delay the onset and/or delay the development of any one or more of diseases or conditions for which neurite outgrowth and/or neurogenesis and/or neurotrophic effects are believed to be or are beneficial. In another variation, compounds of the invention are used to treat, prevent, delay the onset and/or delay the development of diseases or conditions for which the modulation of an aminergic G protein-coupled receptor and neurite outgrowth and/or neurogenesis and/or neurotrophic effects are believed to be or are beneficial. In one variation, the disease or condition is a cognitive disorder, psychotic disorder, neurotransmitter-mediated disorder and/or a neuronal disorder.

In another aspect, compounds of the invention are used to improve cognitive function and/or reduce psychotic effects in an individual, comprising administering to an individual in need thereof an amount of a compound described herein or a pharmaceutically acceptable salt thereof effective to improve cognitive function and/or reduce psychotic effects.

In a further aspect, compounds of the invention are used to stimulate neurite outgrowth and/or promote neurogenesis and/or enhance neurotrophic effects in an individual comprising administering to an individual in need thereof an amount of a compound described herein or a pharmaceutically acceptable salt thereof effective to stimulate neurite outgrowth and/or to promote neurogenesis and/or to enhance neurotrophic effects. Synapse loss is associated with a variety of neurodegenerative diseases and conditions including Alzheimer's disease, schizophrenia, Huntington's disease, Parkinson's disease, amyotrophic lateral sclerosis, stroke, head trauma and spinal cord injury. Compounds of the invention that stimulate neurite outgrowth may have a benefit in these settings.

In another aspect, compounds described herein are used to modulate an aminergic G protein-coupled receptor comprising administering to an individual in need thereof an amount of a compound described herein or a pharmaceutically acceptable salt thereof effective to modulate an aminergic G protein-coupled receptor. In one variation, a compound of the invention modulates at least one of the following receptors: adrenergic receptor (e.g., $\alpha_{1D}$, $\alpha_{2A}$ and/or $\alpha_{2B}$), serotonin receptor (e.g., 5-HT$_{2A}$, 5-HT$_{2C}$, 5-HT$_6$ and/or 5-HT$_7$), dopamine receptor (e.g., D$_{2L}$) and histamine receptor (e.g., H$_1$, H$_2$ and/or H$_3$). In another variation, at least two of the following receptors are modulated: adrenergic receptor (e.g., $\alpha_{1D}$, $\alpha_{2A}$ and/or $\alpha_{2B}$), serotonin receptor (e.g., 5-HT$_{2A}$, 5-HT$_{2C}$, 5-HT$_6$ and/or 5-HT$_7$), dopamine receptor (e.g., D$_{2L}$) and histamine receptor (e.g., H$_1$, H$_2$ and/or H$_3$). In another variation, at least three of the following receptors are modulated: adrenergic receptor (e.g., $\alpha_{1D}$, $\alpha_{2A}$ and/or $\alpha_{2B}$), serotonin receptor (e.g., 5-HT$_{2A}$, 5-HT$_{2C}$, 5-HT$_6$ and/or 5-HT$_7$), dopamine receptor (e.g., D$_{2L}$) and histamine receptor (e.g., H$_1$, H$_2$ and/or H$_3$). In another variation, each of the following receptors is modulated: adrenergic receptor (e.g., $\alpha_{1D}$, $\alpha_{2A}$ and/or $\alpha_{2B}$), serotonin receptor (e.g., 5-HT$_{2A}$, 5-HT$_{2C}$, 5-HT$_6$ and/or 5-HT$_7$), dopamine receptor (e.g., D$_{2L}$) and histamine receptor (e.g., H$_1$, H$_2$ and/or H$_3$). In another variation, at least one of the following receptors is modulated: $\alpha_{1D}$, $\alpha_{2A}$, $\alpha_{2B}$, 5-HT$_{2A}$, 5-HT$_{2C}$, 5-HT$_6$, 5-HT$_7$, D$_{2L}$, H$_1$, H$_2$ and H$_3$. In another variation, at least one of the following receptors is modulated: $\alpha_{1D}$, $\alpha_{2A}$, $\alpha_{2B}$, 5-HT$_{2A}$, 5-HT$_{2C}$, 5-HT$_6$, 5-HT$_7$, D$_2$, H$_1$, H$_2$ and H$_3$. In another variation, at least two or three or four or five or six or seven or eight or nine or ten or eleven of the following receptors are modulated: $\alpha_{1D}$, $\alpha_{2A}$, $\alpha_{2B}$, 5-HT$_{2A}$, 5-HT$_{2C}$, 5-HT$_6$, 5-HT$_7$, D$_{2L}$, H$_1$, H$_2$ and H$_3$. In another variation, at least two or three or four or five or six or seven or eight or nine or ten or eleven of the following receptors are modulated: $\alpha_{1D}$, $\alpha_{2A}$, $\alpha_{2B}$, 5-HT$_{2A}$, 5-HT$_{2C}$, 5-HT$_6$, 5-HT$_7$, D$_2$, H$_1$, H$_2$ and H$_3$. In a particular variation, at least dopamine receptor D$_2$ is modulated. In still another variation, at least dopamine receptor D$_{2L}$ is modulated. In another particular variation, at least dopamine receptor D$_2$ and serotonin receptor 5-HT$_{2A}$ are modulated. In another particular variation, at least dopamine receptor D$_{2L}$ and serotonin receptor 5-HT$_{2A}$ are modulated. In a further particular variation, at least adrenergic receptors $\alpha_{1D}$, $\alpha_{2A}$, $\alpha_{2B}$ and serotonin receptor 5-HT$_6$ are modulated. In another particular variation, at least adrenergic receptors $\alpha_{1D}$, $\alpha_{2A}$, $\alpha_{2B}$, serotonin receptor 5-HT$_6$ and one or more of serotonin receptor 5-HT$_7$, 5-HT$_{2A}$, 5-HT$_{2C}$ and histamine receptor H$_1$ and H$_2$ are modulated. In a further particular variation, histamine receptor H$_1$ is modulated. In another variation, compounds of the invention exhibit any receptor modulation activity detailed herein and further stimulate neurite outgrowth and/or neurogenesis and/or enhance neurotrophic effects. In one variation, compounds detailed herein inhibit binding of a ligand to histamine receptor H$_1$ and/or H$_2$ by less than about 80% as determined by a suitable assay known in the art such as the assays described herein. In another variation, binding of a ligand to histamine receptor H$_1$ and/or H$_2$ is inhibited by less than about any of 75%, 70%, 65%, 60%, 55%, or 50% as determined by a suitable assay known in the art such as the assays described herein. In a further variation, compounds detailed herein: (a) inhibit binding of a ligand to histamine receptor H$_1$ and/or H$_2$ by less than about 80% (which can in different variations be less than about any of 75%, 70%, 65%, 60%, 55%, or 50%) as determined by a suitable assay known in the art such as the assays described herein and (b) inhibit binding of a ligand to dopamine receptor D$_{2L}$ by greater than about any of 80%, 85%, 90%, 95%, 100% or between about 85% and about 95% or between about 90% and about 100%, as determined in a suitable assay known in the art such as the assays described herein. In a further variation, compounds detailed herein: (a) inhibit binding of a ligand to histamine receptor H$_1$ and/or H$_2$ by less than about 80% (which can in different variations be less than about any of 75%, 70%, 65%, 60%, 55%, or 50%) as determined by a suitable assay known in the art such as the assays described herein and (b) inhibit binding of a ligand to a dopamine receptor D$_2$ by greater than about any of 80%, 85%, 90%, 95%, 100% or between about 85% and about 95% or between about 90% and about 100%, as determined in a suitable assay known in the art such as the assays described herein.

A compound of the formula (V) is provided:

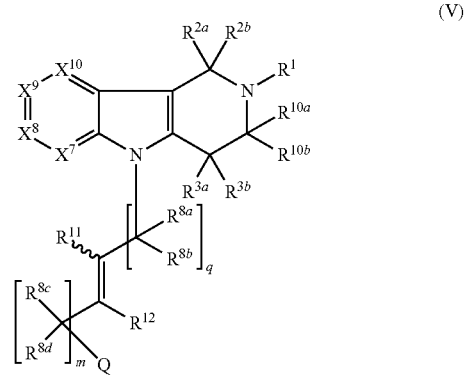

(V)

or a salt or solvate thereof;

wherein:

R$^1$ is H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each R$^{2a}$ and R$^{2b}$ is independently H, substituted or unsubstituted C$_1$-C$_8$ alkyl, halo, cyano, hydroxyl, alkoxy, nitro or R$^{2a}$ and R$^{2b}$ are taken together with the carbon to which they are attached to form a carbonyl moiety or a cycloalkyl moiety;

each R$^{3a}$ and R$^{3b}$ is independently H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl or R$^{3a}$ and R$^{3b}$ are taken together with the carbon to which they are attached to form a carbonyl moiety or a cycloalkyl moiety;

each X$^7$, X$^8$, X$^9$ and X$^{10}$ is independently N, CH or CR$^4$;

each m and q is independently 0 or 1;

each R$^4$ is independently hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, C$_1$-C$_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{8a}$, R$^{8b}$, R$^{8c}$ and R$^{8d}$ is independently H, hydroxyl, alkoxy, halo, substituted or unsubstituted aryl, substituted or unsubstituted heteroaryl, substituted or unsubstituted C$_1$-C$_8$ alkyl, substituted or unsubstituted C$_3$-C$_8$ cycloalkyl, substituted or unsubstituted C$_2$-C$_8$ alkenyl, C$_1$-C$_8$ perhaloalkyl, carboxy, carbonylalkoxy, or is taken together with a geminal R$^8$ to form a moiety of the formula —OCH$_2$CH$_2$O—, or is taken together with the carbon to which it is attached and a geminal R$^8$ to form a cycloalkyl moiety or a carbonyl moiety;

each R$^{10a}$ and R$^{10b}$ is independently H, substituted or unsubstituted C$_1$-C$_8$ alkyl, halo, cyano, hydroxyl, alkoxy, nitro or R$^{10a}$ and R$^{10b}$ are taken together with the carbon to which they are attached to form a carbonyl moiety or a cycloalkyl moiety;

each R$^{11}$ and R$^{12}$ is independently H, halo, alkoxy, substituted or unsubstituted aryl, substituted or unsubstituted heteroaryl, substituted or unsubstituted C$_1$-C$_8$ alkyl, substituted or unsubstituted C$_2$-C$_8$ alkenyl, substituted or unsubstituted C$_3$-C$_8$ cycloalkyl, C$_1$-C$_8$ perhaloalkyl, carboxy, or carbonylalkoxy and the $\sim\sim\sim$ bond indicates the presence of either an E or Z double bond configuration, or R$^{11}$ and R$^{12}$ are taken together to form a bond; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, alkoxy, acyloxy, substituted or unsubstituted amino, aminoacyl, aminocarbonylalkoxy, cyano, alkynyl, carboxy, carbonylalkoxy or acylamino;

provided that when X$^7$, X$^8$ and X$^{10}$ are each CH and each R$^{2a}$, R$^{2b}$, R$^{3a}$, R$^{3b}$, R$^{10a}$ and R$^{10b}$ is hydrogen, at least one of R$^{11}$ and R$^{12}$ is other than hydrogen and R$^{11}$ and R$^{12}$ are not taken together to form a bond. In one aspect, m is 0 and q is 0. In another aspect, X$^7$, X$^8$, X$^9$ and X$^{10}$ are CH or CR$^4$. In a further aspect, at least one of X$^7$, X$^8$, X$^9$ and X$^{10}$ is N. In one variation, two of X$^7$, X$^8$, X$^9$ and X$^{10}$ are N. In another variation, at least one of X$^7$, X$^8$, X$^9$ and X$^{10}$ is CR$^4$, such as when each R$^4$ is independently halo, substituted or unsubstituted C$_1$-C$_8$ alkyl, C$_1$-C$_8$ perhaloalkyl, substituted or unsubstituted heterocyclyl or a substituted or unsubstituted aryl. Q in one aspect is a substituted or unsubstituted pyridyl, phenyl, pyrimidinyl, pyrazinyl, imidazolyl, furanyl, pyrrolyl or thiophenyl group. In another aspect, R$^{11}$ is H or C$_1$-C$_4$ alkyl and R$^{12}$ is independently H, C$_1$-C$_4$ alkyl or C$_1$-C$_4$ perhaloalkyl.

Compound of formulae (1-b1) and (1-b2) are also provided:

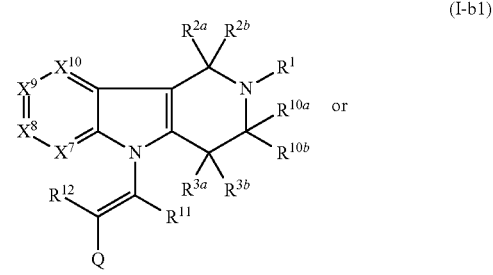

(I-b1)

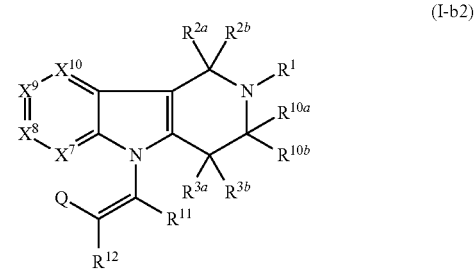

(I-b2)

or a salt or solvate thereof.

Compounds of the formula (VII) are also provided:

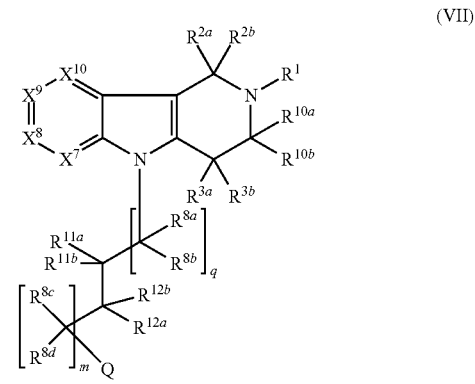

(VII)

or a salt or solvate thereof;

wherein:

R$^1$ is H, hydroxyl, nitro, cyano, halo, substituted or unsubstituted C$_1$-C$_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety;

each $R^{3a}$ and $R^{3b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl or $R^{3a}$ and $R^{3b}$ are taken together with the carbon to which they are attached to form a carbonyl moiety or a cycloalkyl moiety;

each $X^7$, $X^8$, $X^9$ and $X^{10}$ is independently N, CH or $CR^4$;

each m and q is independently 0 or 1;

each $R^4$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, alkoxy, halo, substituted or unsubstituted aryl, substituted or unsubstituted heteroaryl, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxy, carbonylalkoxy, or is taken together with a geminal $R^8$ to form a moiety of the formula —$OCH_2CH_2O$—, or is taken together with the carbon to which it is attached and a geminal $R^8$ to form a cycloalkyl moiety or a carbonyl moiety;

each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together with the carbon to which they are attached to form a carbonyl moiety or a cycloalkyl moiety;

each $R^{10a}$ and $R^{12a}$ is independently H, hydroxyl, alkoxy, halo, substituted or unsubstituted aryl, substituted or unsubstituted heteroaryl, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxy, or carbonylalkoxy; or $R^{10a}$ and $R^{12a}$ are taken together to represent a bond;

$R^{11b}$ and $R^{12a}$ are taken together with the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety; and Q is a substituted or unsubstituted aryl, substituted or unsubstituted heteroaryl, substituted or unsubstituted cycloalkyl, substituted or unsubstituted cycloalkenyl or substituted or unsubstituted heterocyclyl, alkoxy, acyloxy, substituted or unsubstituted amino, aminoacyl, aminocarbonylalkoxy, cyano, alkynyl, carboxy, carbonylalkoxy or acylamino.

Where applicable, in one aspect compounds of the formulae are provided where any one or more of the following apply: (i) m is 0 and q is 0; (ii) $X^7$, $X^8$, $X^9$ and $X^{10}$ are CH or $CR^4$; (iii) at least one of $X^7$, $X^8$, $X^9$ and $X^{10}$ is N; (iv) two of $X^7$, $X^8$, $X^9$ and $X^{10}$ are N; (v) at least one of $X^7$, $X^8$, $X^9$ and $X^{10}$ is $CR^4$; (vi) each $R^4$ is independently halo, substituted or unsubstituted $C_1$-$C_8$ alkyl, $C_1$-$C_8$ perhaloalkyl, substituted or unsubstituted heterocyclyl or a substituted or unsubstituted aryl; (vii) Q is a substituted or unsubstituted pyridyl, phenyl, pyrimidinyl, pyrazinyl, imidazolyl, furanyl, pyrrolyl or thiophenyl group; (viii) each $R^{11a}$ and $R^{12a}$ is independently H, $C_1$-$C_4$ alkyl, or $C_1$-$C_4$ perhaloalkyl; (ix) $R^{11b}$ and $R^{12b}$ are taken together with the carbon atoms to which they are attached to form an optionally substituted cyclopropyl, cyclobutyl, cyclopentyl or cyclohexyl ring; (x) $R^{11b}$ and $R^{12b}$ are taken together with the carbon atoms to which they are attached to form an optionally substituted cyclopropyl ring; (xi) $R^{11b}$ and $R^{12b}$ are taken together with the carbon atoms to which they are attached to form an optionally substituted cyclopropenyl, cyclobutenyl, cyclopentenyl or cyclohexenyl ring; (xi) $R^{11a}$ and $R^{12a}$ are taken together to form a bond.

Compounds of the formula (I-E) are also provided:

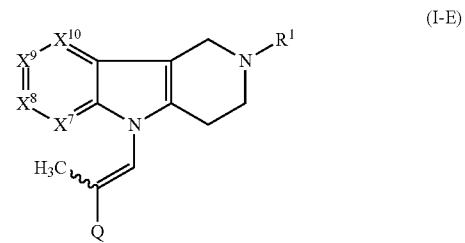

(I-E)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $X^7$, $X^8$, $X^9$ and $X^{10}$ is independently N, CH or $CR^4$;

each $R^4$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy or acylamino or a salt or solvate thereof. In one aspect, $X^7$, $X^8$ and $X^{10}$ are each CH and $X^9$ is $CR^4$. In another aspect, $X^7$, $X^8$ and $X^{10}$ are each CH and $X^9$ is $CR^4$ where $R^4$ is unsubstituted $C_1$-$C_8$ alkyl, halo, $C_1$-$C_8$ perhaloalkyl, or substituted or unsubstituted amino. In a further aspect, $R^4$ is $CF_3$, $CH_3$, F or Cl. In an additional aspect, $R^1$ is substituted or unsubstituted $C_1$-$C_8$ alkyl, or perhaloalkyl. In one variation, $R^1$ is methyl, 2-fluoroethyl, 2,2,2-trifluoroethyl, or 3-hydroxy-3-methyl-but-1-yl. In another variation, Q is substituted aryl or substituted or unsubstituted heteroaryl. In one aspect, Q is substituted phenyl, or substituted or unsubstituted pyridyl, or pyrimidyl. In another aspect, Q is 4-fluorophenyl, 4-methoxyphenyl, 3-fluoro-4-methoxyphenyl, 4-methylcarbamoyl, 4-dimethylcarbamoyl, pyridin-3-yl, pyridin-4-yl, 6-methylpyridin-3-yl, 6-trifluoromethylpyridin-3-yl, or pyrimidin-4-yl. In a further aspect, the ～ bond indicates the presence of an E double bond. In one variation, the ～ bond indicates the presence of an Z double bond.

Compounds of the formula (J-1) are provided:

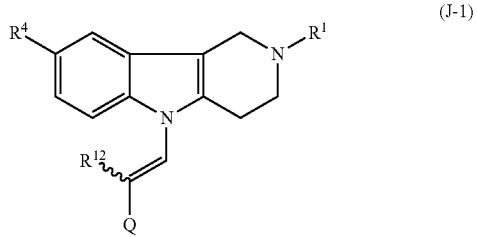

(J-1)

wherein; $R^1$ is methyl, 2-fluoroethyl, 2,2,2-trifluoroethyl, or 3-hydroxy-3-methyl-but-1-yl; $R^4$ is $CF_3$, $CH_3$, F or Cl; $R^{12}$ is halo, substituted or unsubstituted $C_1$-$C_8$ alkyl, substituted or unsubstituted $C_2$-$C_8$ alkenyl, substituted or unsubstituted aryl, substituted or unsubstituted heteroaryl, $C_1$-$C_8$ perhaloalkoxy, $C_1$-$C_8$ alkoxy; and Q is 4-fluorophenyl, 4-methoxyphenyl, 3-fluoro-4-methoxyphenyl, 4-methylcarbamoyl, 4-dimethylcarbamoyl, pyridin-3-yl, pyridin-4-yl, 6-methylpyridin-3-yl, 6-trifluoromethylpyridin-3-yl, or pyrimidin-4-yl; or a salt or solvate thereof. Method of treating a cognitive disorder, psychotic disorder, neurotransmitter-mediated disorder or a neuronal disorder in an individual are provided, comprising administering to an individual in need thereof an effective amount of compound as detailed herein, or a pharmaceutically acceptable salt thereof. Methods of modulating a histamine receptor in an individual are also provided comprising administering to an individual in need thereof a compound as detailed herein, or a pharmaceutically acceptable salt thereof. Use of a compound as detailed herein in the manufacture of a medicament for the treatment of a cognitive disorder, psychotic disorder, neurotransmitter-mediated disorder or a neuronal disorder are also provided. A kit comprising a compound as detailed herein, or a pharmaceutically acceptable salt thereof, and instructions for use in the treatment of a cognitive disorder, psychotic disorder, neurotransmitter-mediated disorder or a neuronal disorder are provided. Methods of treating a cognitive disorder or a disorder characterized by causing at least one symptom associated with impaired cognition are provided, comprising administering to an individual in need thereof a low dose of a compound as detailed herein, or a pharmaceutically acceptable salt thereof. Method of treating (i) a psychotic disorder, (ii) a psychotic disorder in an individual who is also in need of improved cognition or (iii) a disorder characterized by causing at least one psychotic symptom and at least one symptom associated with impaired cognition are also embraced, comprising administering to an individual in need thereof a high dose of a compound as here detailed, or a pharmaceutically acceptable salt thereof. Use of a low dose of a compound as provided herein, or a pharmaceutically acceptable salt thereof, in the manufacture of a medicament for the treatment of a cognitive disorder or a disorder characterized by causing at least one symptom associated with impaired cognition is detailed herein. Also provided is use of a high dose of a compound as detailed herein, or a pharmaceutically acceptable salt thereof in the manufacture of a medicament for the treatment of a (i) psychotic disorder, (ii) a psychotic disorder in an individual who is also in need of improved cognition or (iii) a disorder characterized by causing at least one psychotic symptom and at least one symptom associated with impaired cognition. A kit comprising a low dose of a compound as provided herein, or a pharmaceutically acceptable salt thereof, and instructions for achieving a procognitive effect in the treatment of a cognitive disorder or a disorder characterized by causing at least one symptom associated with impaired cognition are also provided. A kit comprising a high dose of a compound as detailed herein, or a pharmaceutically acceptable salt thereof, and instructions for achieving (i) a procognitive effect in the treatment of a cognitive disorder or a disorder characterized by causing at least one symptom associated with impaired cognition and (ii) an antipsychotic effect in the treatment of a psychotic disorder; a psychotic disorder in an individual who is also in need of improved cognition or a disorder characterized by causing at least one psychotic symptom and at least one symptom associated with impaired cognition is also embraced.

BRIEF DESCRIPTION OF THE FIGURES

FIG. 4A contains data for Compound 90 at doses 0.03, 0.1, 0.3, 1, 3 and 10 mg/kg, p.o. FIG. 4B contains data for Compound 90 at doses 0.03, 0.1, 0.3, 1 and 3 mg/kg, p.o. All treatments were administered 30 minutes before T1.

Time spent by rats exploring the novel and familiar objects during T2 is expressed as mean±SEM. In the figure, n is the number of rats per group; # is p<0.05; ## is p<0.01 and ### is p<0.001 versus novel object and * is p<0.01 and ** is p<0.001 versus vehicle group.

Figure 5:
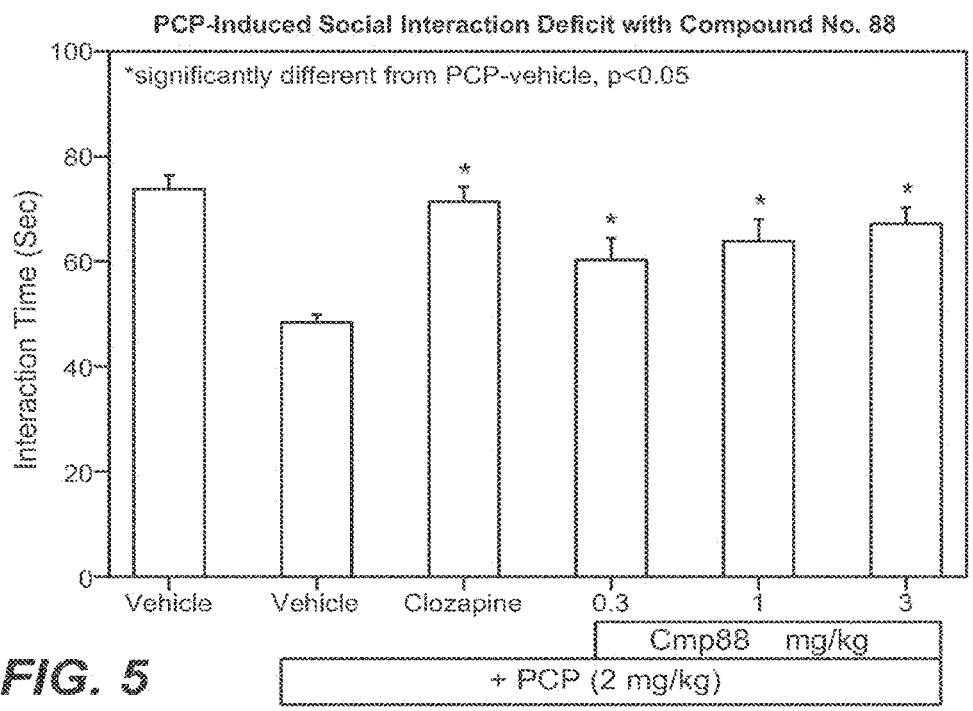

FIG. 5 is a graph of interaction time (seconds) for vehicle, clozapine and Compound 88 in a subchronic PCP-induced Social Interaction Deficit model, showing the effect of Compound 88 on PCP-induced disruption of social interaction. Data represent mean±SEM. In the figure, * is significantly different from PCP-vehicle, p<0.05.

Figure 6:
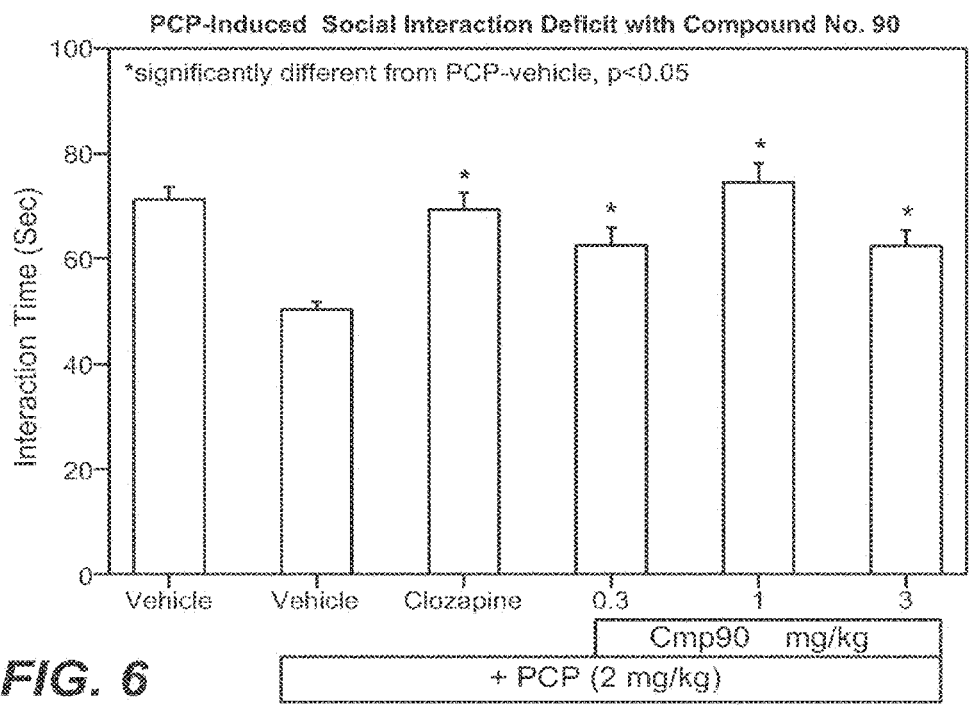

FIG. 6 is a graph of interaction time (seconds) for vehicle, clozapine and Compound 90 in a subchronic PCP-induced Social Interaction Deficit model, showing the effect of Compound 90 on PCP-induced disruption of social interaction. Data represent mean±SEM. In the figure, * is significantly different from PCP-vehicle, p<0.05.

Figure 7:
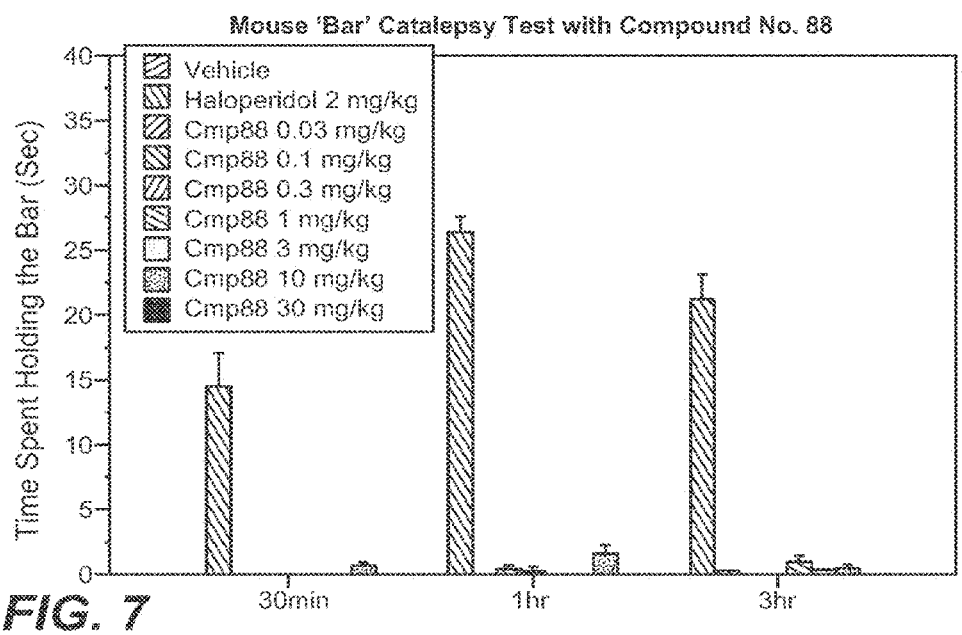

FIG. 7 is a graph of time spent holding the bar (seconds) at three time points (30 minutes, 1 hour and 3 hours) after administration of vehicle, haloperidol or Compound 88 (0.03, 0.1, 0.3, 1, 3, 10 and 30 mg/kg) in an extrapyramidal Syndrome (EPS) model catalepsy Test. The time the mice spent holding bar was averaged over the 3 trials at each time point. Data represent mean±SEM.

Figure 8:
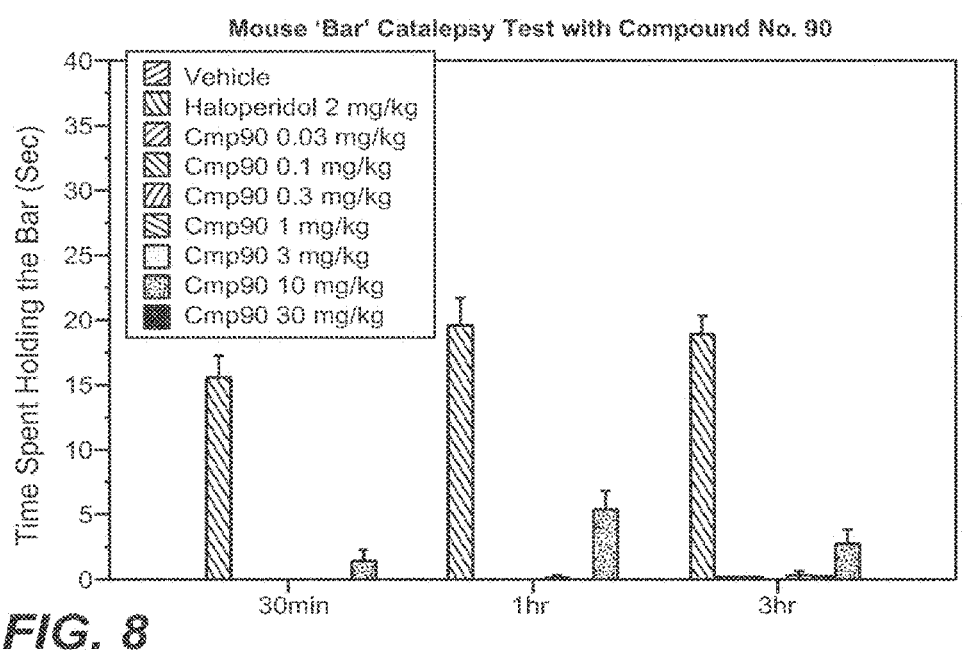

FIG. 8 is a graph of time spent holding the bar (seconds) at three time points (30 minutes, 1 hour and 3 hours) after administration of vehicle, haloperidol or Compound 90 (0.03, 0.1, 0.3, 1, 3, 10 and 30 mg/kg) in an extrapyramidal Syndrome (EPS) model catalepsy Test. The time the mice spent holding bar was averaged over the 3 trials at each time point. Data represent mean±SEM.

Figure 9:
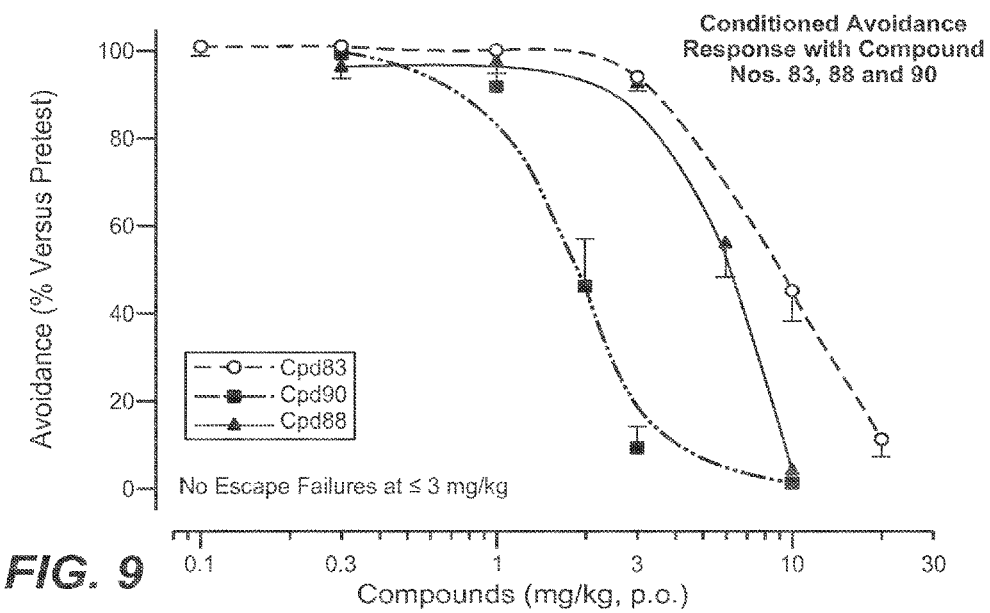

FIG. 9 is a graph depicting avoidance (% versus pretest) versus dose (mg/kg, p.o.) for compounds 83, 90 and 88 in a conditioned avoidance response model.

Figure 10A:
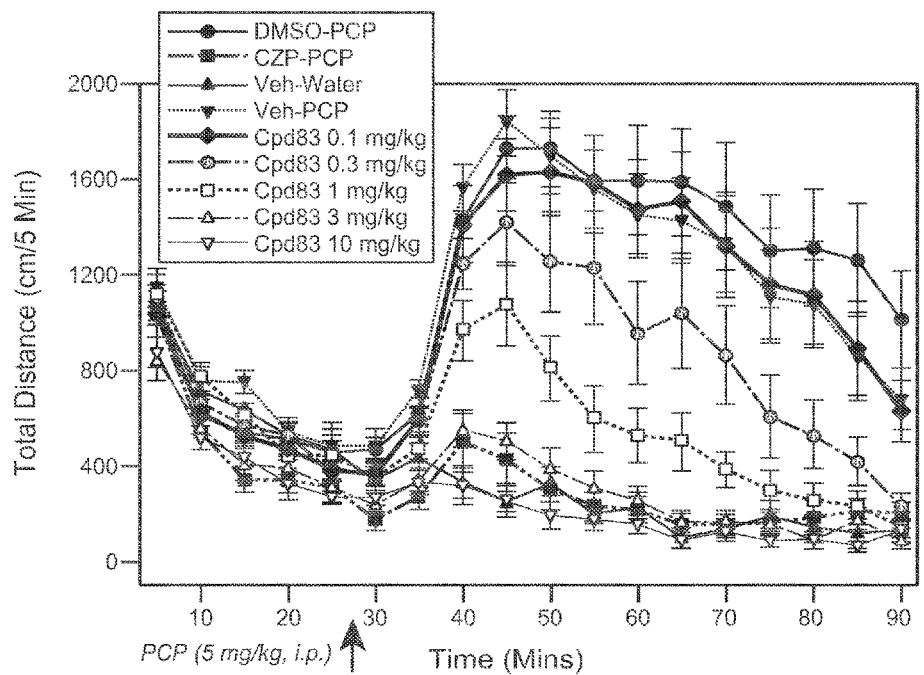
Figure 10B:
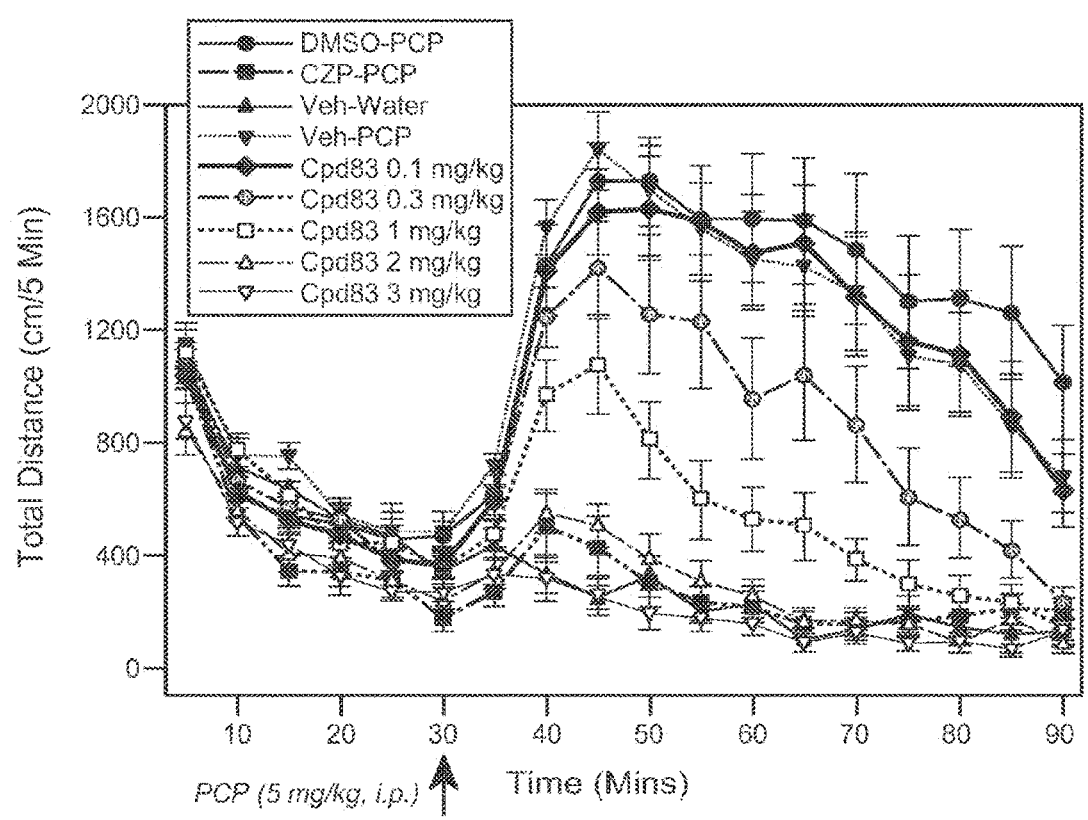
Figure 11A:
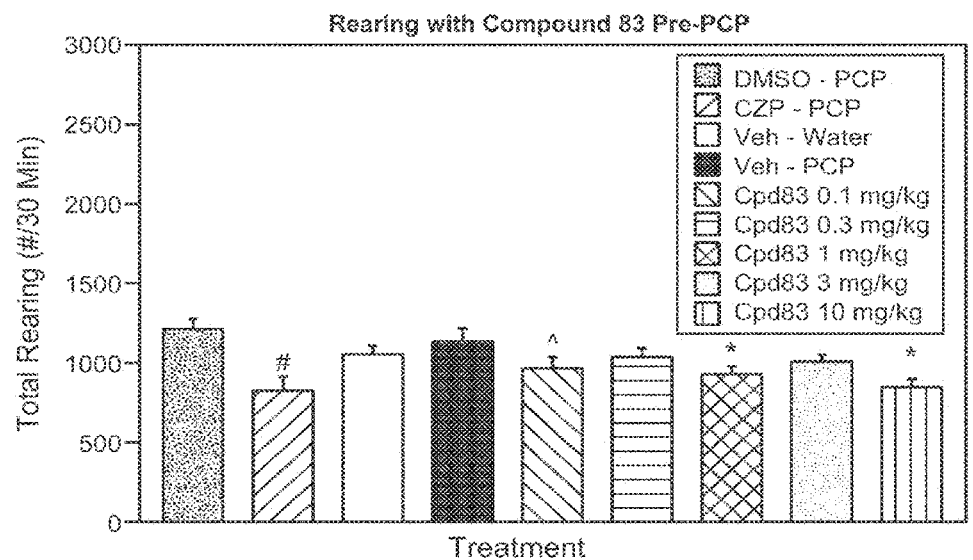
Figure 11B:
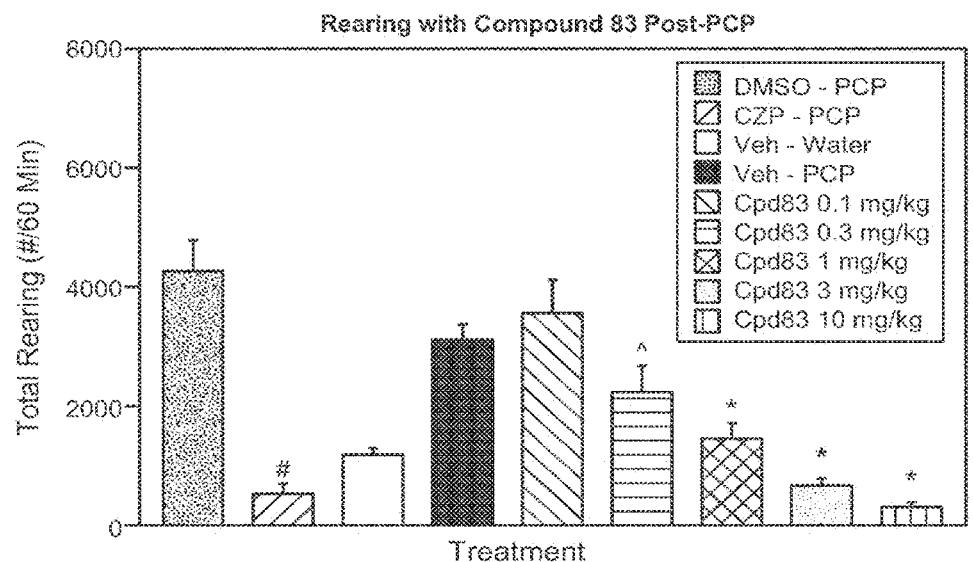
Figure 11C:
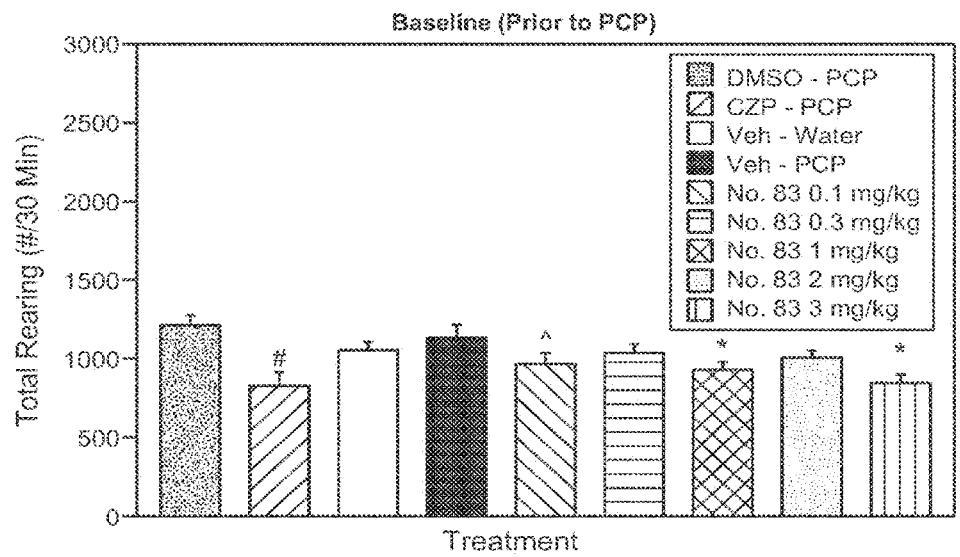
Figure 11D:
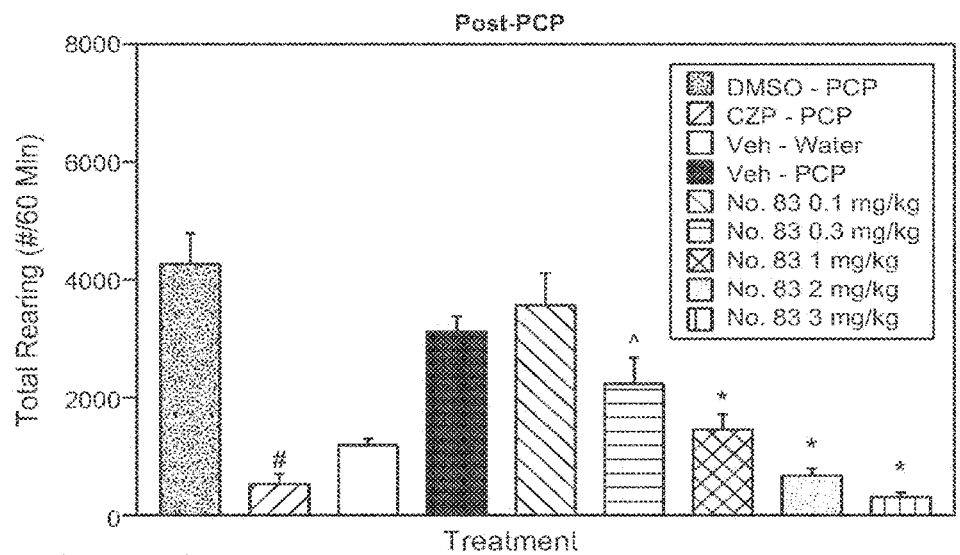

FIGS. 10A and 10B are graphs of Total Distance Traveled (cm/5 min) verses Time (min) pre- and post-injection, showing the results of Compound 83 and clozapine in a PCP Hyperactivity Mouse Model of Schizophrenia. FIG. 10A depicts data for Compound 83 at doses 0.1, 0.3, 1, 3 and 10 mg/kg. FIG. 10B depicts data for Compound 83 at doses 0.1, 0.3, 1, 2 and 3 mg/kg. Total distance traveled in the OF during the 90 minute test period are shown, with data presented as mean±SEM.

FIGS. 11A, 11B, 11C and 11D are graphs of total rearing pre- and post-injection versus treatment, showing the results of Compound 83 in a PCP Hyperactivity Mouse Model of Schizophrenia. Figure A depicts baseline rearing (prior to PCP) and Figure B depicts rearing post-PCP for Compound 83 at doses 0.1, 0.3, 1, 3 and 10 mg/kg. Figure C depicts baseline rearing (prior to PCP) and Figure D depicts rearing post-PCP for Compound 83 at doses 0.1, 0.3, 1, 2 and 3 mg/kg.

Figure 12:
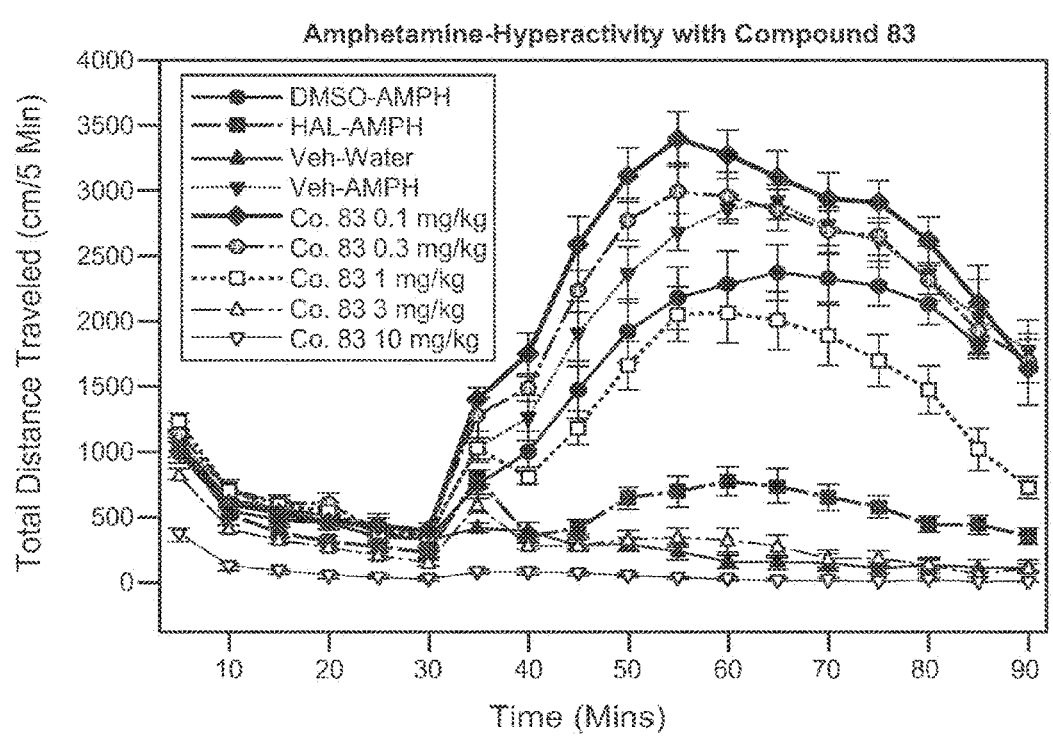

FIG. 12 is a graph of Total Distance Traveled (cm/5 min) verses Time (min), showing the effect of Compound 83 (0.1, 0.3, 1, 3 and 10 mg/kg) in an amphetamine hyperactivity mouse model of schizophrenia.

Figure 13A:
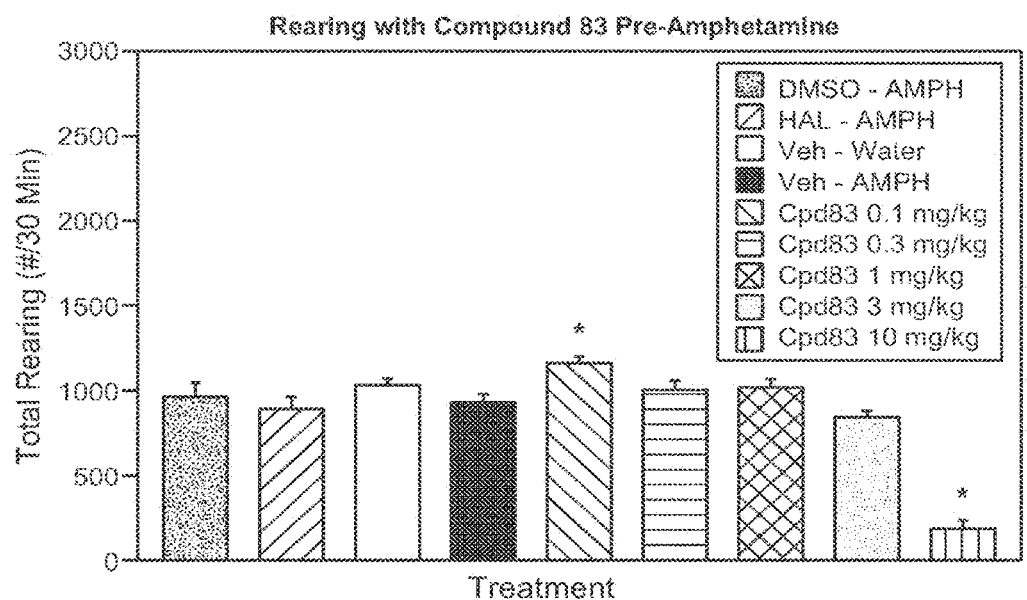
Figure 13B:
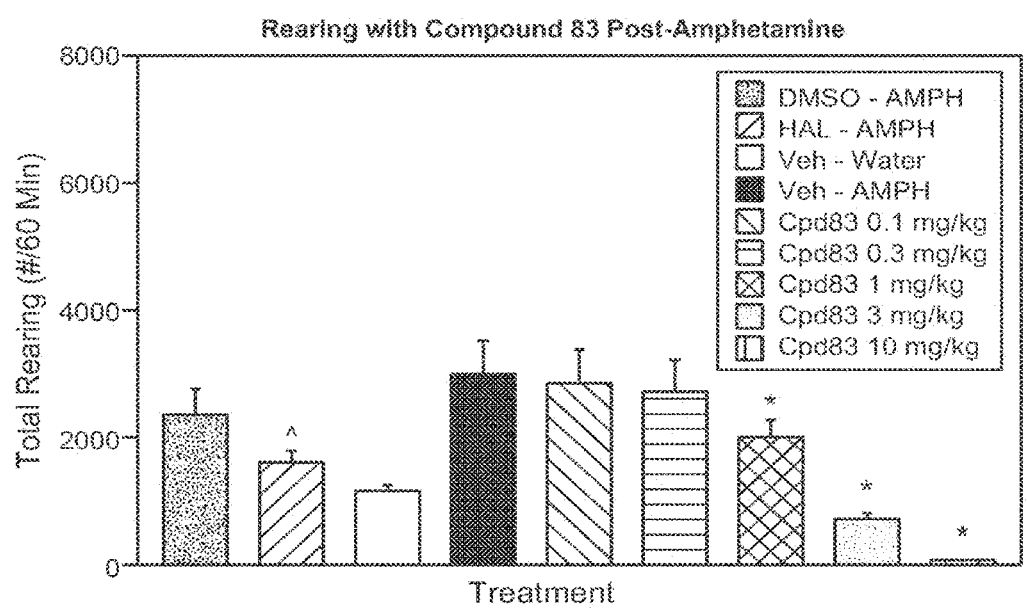

FIGS. 13A and 13B are graphs of total rearing pre- and post-injection versus treatment, showing the results of Compound 83 in an amphetamine hyperactivity mouse model of schizophrenia. Figure A depicts baseline rearing (prior to amphetamine) and Figure B depicts rearing post-amphetamine for Compound 83 at doses 0.1, 0.3, 1, 3 and 10 mg/kg.

Figure 14:
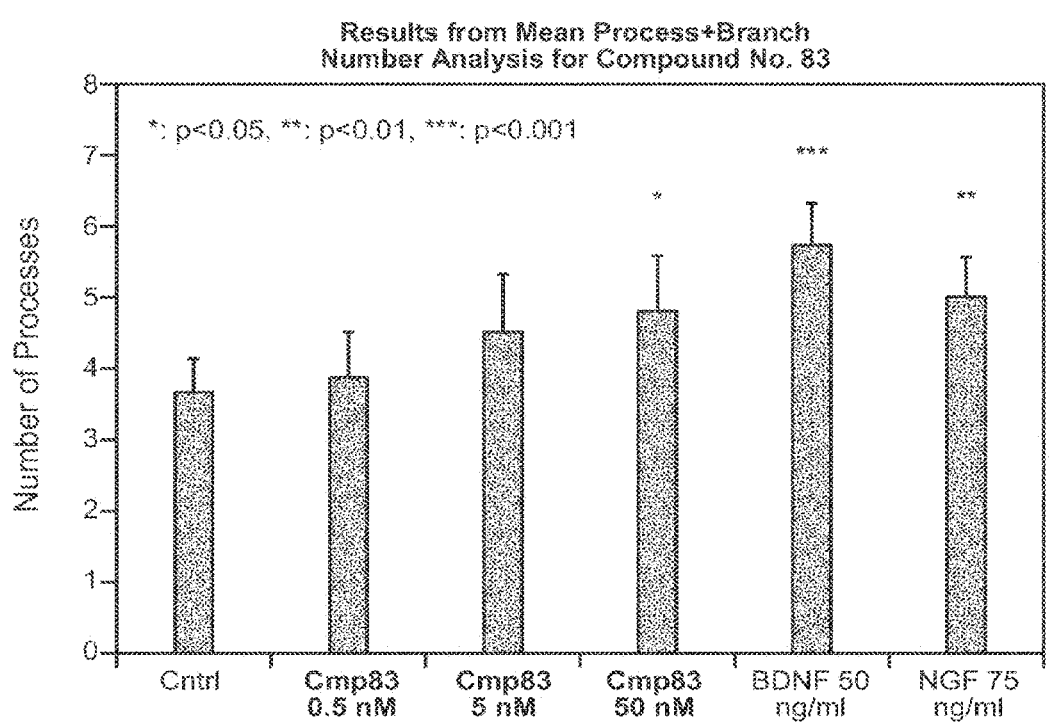

FIG. 14 is a graph of number of processes against treatment, showing the effect of Compound 83 (0.5, 5 and 50 nM), BDNF (50 ng/mL) and NGF (75 ng/mL) on neurite outgrowth in mixed cortical cultures. Results are depicted as mean+SD. In the figure, * is p<0.05,  is p<0.01 and * is p<0.001.

Figure 15:
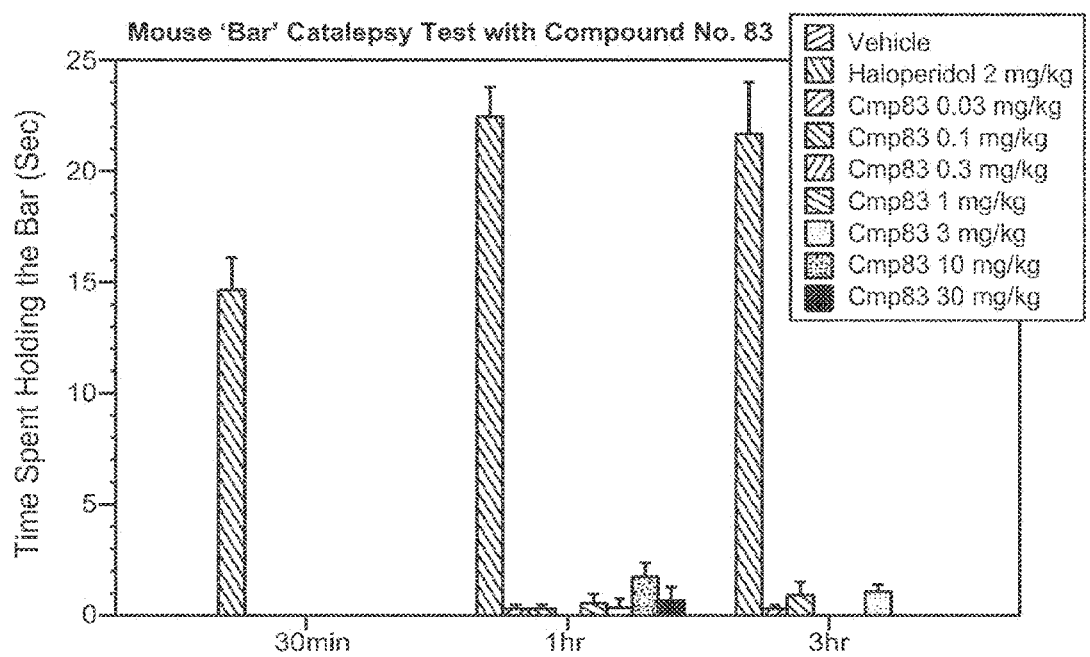

FIG. 15 is a graph of time spent holding the bar (seconds) at three time points (30 minutes, 1 hour and 3 hours) after administration of vehicle, haloperidol or Compound 83 (0.03, 0.1, 0.3, 1, 3, 10 and 30 mg/kg) in an extrapyramidal Syndrome (EPS) model catalepsy Test. The time the mice spent holding bar was averaged over the 3 trials at each time point. Data represent mean±SEM.

Figure 16:
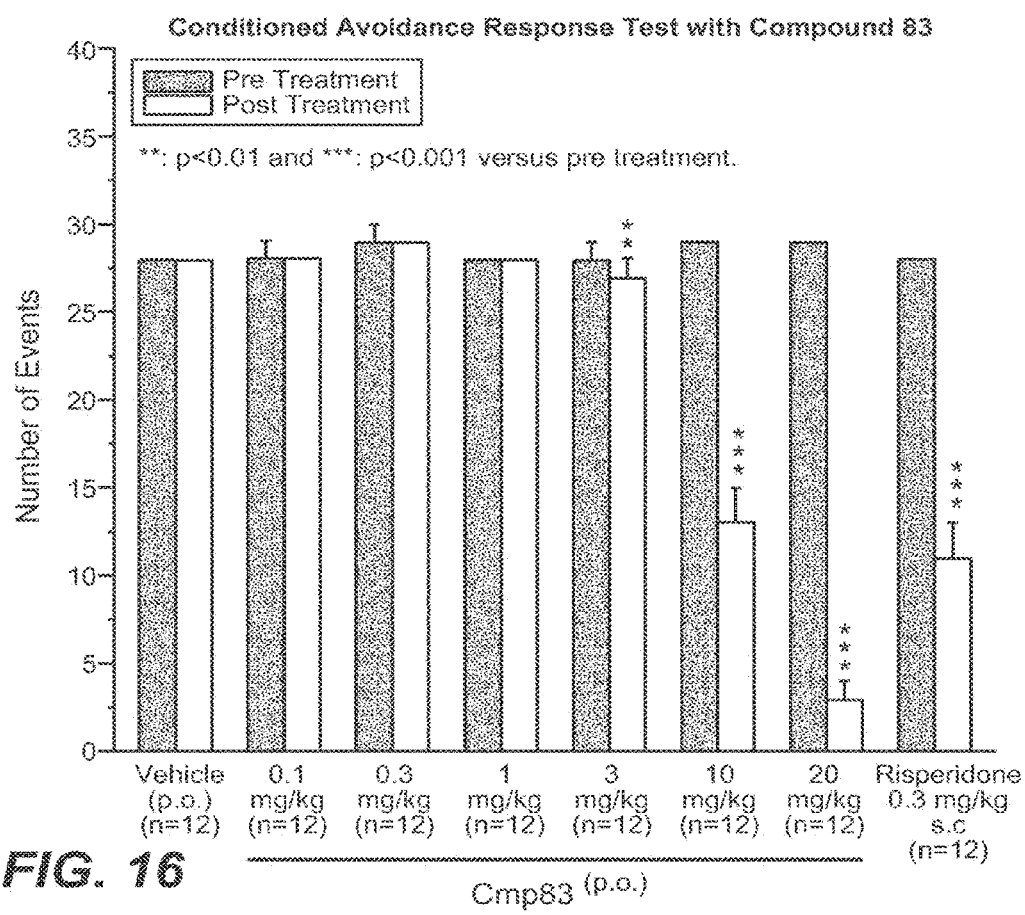

FIG. 16 is a graph of number of avoidance responses pre- and post-treatment, showing the number of avoidance responses observed before and after administration of vehicle (p.o.), Compound 83 (0.1, 0.3, 1, 3, 10 and 20 mg/kg, p.o.) or risperidone (0.3 mg/kg, s.c.) in a conditioned avoidance response test in the rat. Results are presented as mean±SEM with 12 animals per group. In the figure,  is $p<0.01$ and * is $p<0.001$ versus pre-treatment.

Figure 17:
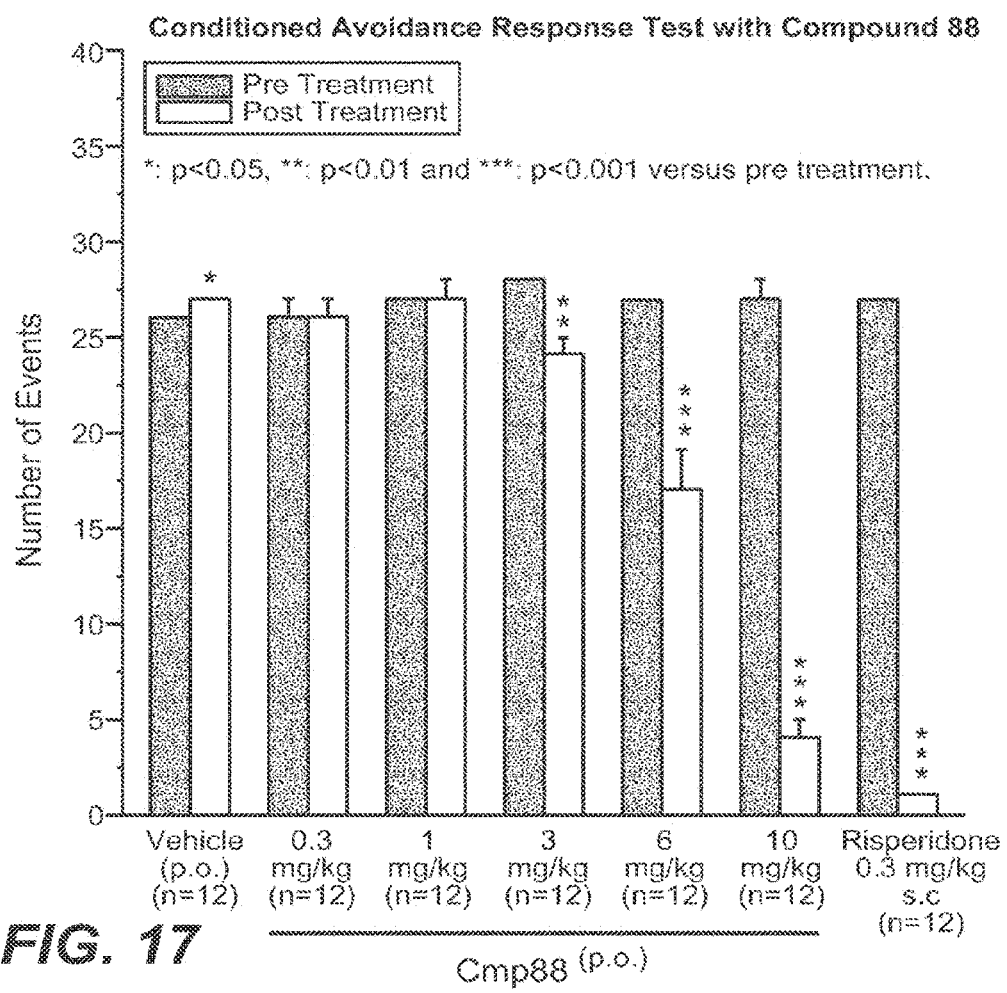

FIG. 17 is a graph of number of avoidance responses pre- and post-treatment, showing the number of avoidance responses observed before and after administration of vehicle (p.o.), Compound 88 (0.3, 1, 3, 6 and 10 mg/kg, p.o.) or risperidone (0.3 mg/kg, s.c.) in a conditioned avoidance response test in the rat. Results are presented as mean±SEM with 12 animals per group. In the figure, * is $p<0.05$,  is $p<0.01$ and * is $p<0.001$ versus pre-treatment.

Figure 18:
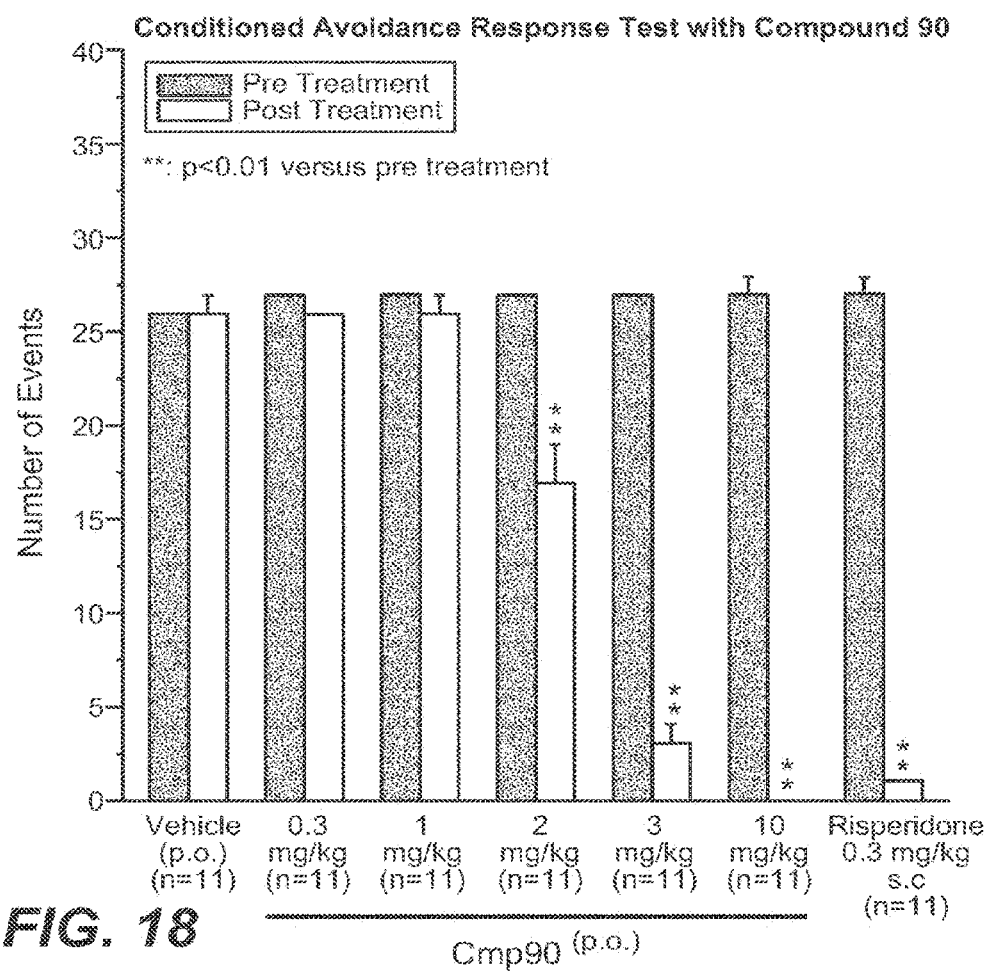

FIG. 18 is a graph of number of avoidance responses pre- and post-treatment, showing the number of avoidance responses observed before and after administration of vehicle (p.o.), Compound 90 (0.3, 1, 2, 3 and 10 mg/kg, p.o.) or risperidone (0.3 mg/kg, s.c.) in a conditioned avoidance response test in the rat. Results are presented as mean±SEM with 11 animals per group. In the figure, ** is $p<0.01$ versus pre-treatment.

DETAILED DESCRIPTION OF THE INVENTION

Definitions

For use herein, unless clearly indicated otherwise, use of the terms "a", "an" and the like refers to one or more.

As used herein, reference to "about" a value or parameter herein includes (and describes) embodiments that are directed to that value or parameter per se. For example, description referring to "about X" includes description of "X".

As used herein, the term "aminergic G protein-coupled receptors" refers to a family of transmembrane proteins involved in cellular communication. Aminergic G protein coupled receptors are activated by biogenic amines and represent a subclass of the superfamily of G protein coupled receptors, which are structurally characterized by seven transmembrane helices. Aminergic G protein-coupled receptors include but are not limited to adrenergic receptors, serotonin receptors, dopamine receptors, histamine receptors and imidazoline receptors.

As used herein, the term "adrenergic receptor modulator" intends and encompasses a compound that binds to or inhibits binding of a ligand to an adrenergic receptor or reduces or eliminates or increases or enhances or mimics an activity of an adrenergic receptor. As such, an "adrenergic receptor modulator" encompasses both an adrenergic receptor antagonist and an adrenergic receptor agonist. In some aspects, the adrenergic receptor modulator binds to or inhibits binding to a ligand to an α1-adrenergic receptor (e.g., $\alpha_{1A}$, $\alpha_{1B}$ and/or $\alpha_{1D}$) and/or a $\alpha_2$-adrenergic receptor (e.g., $\alpha_{2A}$, $\alpha_{2B}$ and/or $\alpha_{2C}$) and/or reduces or eliminates or increases or enhances or mimics an activity of a α1-adrenergic receptor (e.g., $\alpha_{1A}$, $\alpha_{1B}$ and/or $\alpha_{1D}$) and/or a α2-adrenergic receptor (e.g., $\alpha_{2A}$, $\alpha_{2B}$ and/or $\alpha_{2C}$) in a reversible or irreversible manner. In some aspects, the adrenergic receptor modulator inhibits binding of a ligand by at least about or about any one of 10%, 20%, 30%, 40%, 50%, 60%, 70%, 80%, 90%, 95% or 100% as determined in the assays described herein. In some aspects, the adrenergic receptor modulator reduces an activity of an adrenergic receptor by at least or about any of 10%, 20%, 30%, 40%, 50%, 60%, 70%, 80%, 90%, 95% or 100% as compared to the corresponding activity in the same subject prior to treatment with the adrenergic receptor modulator or compared to the corresponding activity in other subjects not receiving the adrenergic receptor modulator. In some aspects, the adrenergic receptor modulator enhances an activity of an adrenergic receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the adrenergic receptor modulator or compared to the corresponding activity in other subjects not receiving the adrenergic receptor modulator. In some aspects, the adrenergic receptor modulator is capable of binding to the active site of an adrenergic receptor (e.g., a binding site for a ligand). In some embodiments, the adrenergic receptor modulator is capable of binding to an allosteric site of an adrenergic receptor.

As used herein, the term "dopamine receptor modulator" intends and encompasses a compound that binds to or inhibits binding of a ligand to a dopamine receptor or reduces or eliminates or increases or enhances or mimics an activity of a dopamine receptor. As such, a "dopamine receptor modulator" encompasses both a dopamine receptor antagonist and a dopamine receptor agonist. In some aspects, the dopamine receptor modulator binds to or inhibits binding of a ligand to a dopamine-1 ($D_1$) and/or a dopamine-2 ($D_2$) receptor or reduces or eliminates or increases or enhances or mimics an activity of a dopamine-1 ($D_1$) and/or a dopamine-2 ($D_2$) receptor in a reversible or irreversible manner. Dopamine $D_2$ receptors are divided into two categories, $D_{2L}$ and $D_{2S}$, which are formed from a single gene by differential splicing. $D_{2L}$ receptors have a longer intracellular domain than $D_{2S}$. In some embodiments, the dopamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the dopamine receptor modulator reduces an activity of a dopamine receptor by at least about or about any of 10%, 20%, 30%, 40%, 50%, 60%, 70%, 80%, 90%, 95% or 100% as compared to the corresponding activity in the same subject prior to treatment with the dopamine receptor modulator or compared to the corresponding activity in other subjects not receiving the dopamine receptor modulator. In some embodiments, the dopamine receptor modulator enhances an activity of a dopamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the dopamine receptor modulator or compared to the corresponding activity in other subjects not receiving the dopamine receptor modulator. In some embodiments, the dopamine receptor modulator is capable of binding to the active site of a dopamine receptor (e.g., a binding site for a ligand). In some embodiments, the dopamine receptor modulator is capable of binding to an allosteric site of a dopamine receptor.

As used herein, the term "serotonin receptor modulator" intends and encompasses a compound that binds to or inhibits binding of a ligand to a serotonin receptor or reduces or eliminates or increases or enhances or mimics an activity of a serotonin receptor. As such, a "serotonin receptor modulator" encompasses both a serotonin receptor antagonist and a serotonin receptor agonist. In some embodiments, the serotonin receptor modulator binds to or inhibits binding of a ligand to a $5\text{-}HT_{1A}$ and/or a $5\text{-}HT_{1B}$ and/or a $5\text{-}HT_{2A}$ and/or a $5\text{-}HT_{2B}$ and/or a $5\text{-}HT_{2C}$ and/or a $5\text{-}HT_3$ and/or a $5\text{-}HT_4$ and/or a $5\text{-}HT_6$ and/or a $5\text{-}HT_7$ receptor or reduces or eliminates or increases or enhances or mimics an activity of a $5\text{-}HT_{1A}$ and/or a $5\text{-}HT_{1B}$ and/or a $5\text{-}HT_{2A}$ and/or a $5\text{-}HT_{2B}$ and/or a $5\text{-}HT_{2C}$ and/or a $5\text{-}HT_3$ and/or a $5\text{-}HT_4$ and/or a $5\text{-}HT_6$ and/or a $5\text{-}HT_7$ receptor in a reversible or irreversible manner. In some embodiments, the serotonin receptor modulator inhibits binding of a ligand by at least about or about any one of 10%, 20%, 30%, 40%, 50%, 60%, 70%, 80%, 90%, 95% or 100% as determined in the assays described herein. In some embodiments, the serotonin receptor modulator reduces an activity of a serotonin receptor by at least about or about any of 10%, 20%, 30%, 40%, 50%, 60%, 70%, 80%, 90%, 95% or 100% as compared to the corresponding activity in the same subject prior to treatment with the serotonin receptor modulator or compared to the corresponding activity in other subjects not receiving the serotonin receptor modulator. In some embodiments, the serotonin receptor modulator enhances an activity of a serotonin receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the serotonin receptor modulator or compared to the corresponding activity in other subjects not receiving the serotonin receptor modulator. In some embodiments, the serotonin receptor modulator is capable of binding to the active site of a serotonin receptor (e.g., a binding site for a ligand). In some embodiments, the serotonin receptor modulator is capable of binding to an allosteric site of a serotonin receptor.

As used herein, the term "histamine receptor modulator" intends and encompasses a compound that binds to or inhibits binding of a ligand to a histamine receptor or reduces or eliminates or increases or enhances or mimics an activity of a histamine receptor. As such, a "histamine receptor modulator" encompasses both a histamine receptor antagonist and a histamine receptor agonist. In some embodiments, the histamine receptor modulator binds to or inhibits binding of a ligand to a histamine $H_1$ and/or $H_2$ and/or $H_3$ receptor or reduces or eliminates or increases or enhances or mimics an activity of a histamine $H_1$ and/or $H_2$ and/or $H_3$ receptor in a reversible or irreversible manner. In some embodiments, the histamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the histamine receptor modulator reduces an activity of a histamine receptor by at least about or about any of 10%, 20%, 30%, 40%, 50%, 60%, 70%, 80%, 90%, 95% or 100% as compared to the corresponding activity in the same subject prior to treatment with the histamine receptor modulator or compared to the corresponding activity in other subjects not receiving the histamine receptor modulator. In some embodiments, the histamine receptor modulator enhances an activity of a histamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the histamine receptor modulator or compared to the corresponding activity in other subjects not receiving the histamine receptor modulator. In some embodiments, the histamine receptor modulator is capable of binding to the active site of a histamine receptor (e.g., a binding site for a ligand). In some embodiments, the histamine receptor modulator is capable of binding to an allosteric site of a histamine receptor.

Unless clearly indicated otherwise, "an individual" as used herein intends a mammal, including but not limited to a human, bovine, primate, equine, canine, feline, porcine, and ovine animals. Thus, the invention finds use in both human medicine and in the veterinary context, including use in agricultural animals and domestic pets. The individual may be a human who has been diagnosed with or is suspected of having a cognitive disorder, a psychotic disorder, a neurotransmitter-mediated disorder and/or a neuronal disorder. The individual may be a human who exhibits one or more symptoms associated with a cognitive disorder, a psychotic disorder, a neurotransmitter-mediated disorder and/or a neuronal disorder. The individual may be a human who has a mutated or abnormal gene associated with a cognitive disorder, a psychotic disorder, a neurotransmitter-mediated disorder and/or a neuronal disorder. The individual may be a human who is genetically or otherwise predisposed to developing a cognitive disorder, a psychotic disorder, a neurotransmitter-mediated disorder and/or a neuronal disorder.

As used herein, "treatment" or "treating" is an approach for obtaining a beneficial or desired result, such as a clinical result. For purposes of this invention, beneficial or desired clinical results include, but are not limited to, alleviation of a symptom and/or diminishment of the extent of a symptom and/or preventing a worsening of a symptom associated with a disease or condition. In one variation, beneficial or desired clinical results include, but are not limited to, alleviation of a symptom and/or diminishment of the extent of a symptom and/or preventing a worsening of a symptom associated with a cognitive disorder, a psychotic disorder, a neurotransmitter-mediated disorder and/or a neuronal disorder. Preferably, treatment of a disease or condition with a compound of the invention or a pharmaceutically acceptable salt thereof is accompanied by no or fewer side effects than are associated with currently available therapies for the disease or condition and/or improves the quality of life of the individual.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of Alzheimer's disease is a method that reduces probability of disease development in a given time frame and/or reduces extent of the disease in a given time frame, when compared to not using the method. Such comparisons are typically based on clinical studies, using a statistically significant number of subjects. For example, Alzheimer's disease development can be detected using standard clinical techniques, such as routine neurological examination, patient interview, neuroimaging, detecting alterations of levels of specific proteins in the serum or cerebrospinal fluid (e.g., amyloid peptides and Tau), computerized tomography (CT) or magnetic resonance imaging (MRI). Similar techniques are known in the art for other diseases and conditions. Development may also refer to disease progression that may be initially undetectable and includes occurrence, recurrence and onset.

As used herein, an "at risk" individual is an individual who is at risk of developing a cognitive disorder, a psychotic disorder, a neurotransmitter-mediated disorder and/or a neuronal disorder that can be treated with a compound of the invention. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). These risk factors include, but are not limited to, age, sex, race, diet, history of previous disease, presence of precursor disease, genetic (i.e., hereditary) considerations, and environmental exposure. For example, individuals at risk for Alzheimer's disease include, e.g., those having relatives who have experienced this disease and those whose risk is determined by analysis of genetic or biochemical markers. Genetic markers of risk for Alzheimer's disease include mutations in the APP gene, particularly mutations at position 717 and positions 670 and 671 referred to as the Hardy and Swedish mutations, respectively (Hardy, *Trends Neurosci.,* 20:154-9, 1997). Other markers of risk are mutations in the presenilin genes (e.g., PS1 or PS2), ApoE4 alleles, a family history of Alzheimer's disease, hypercholesterolemia and/or atherosclerosis. Other such factors are known in the art for other diseases and conditions.

As used herein, the term "pro-cognitive" includes but is not limited to an improvement of one or more mental processes such as memory, attention, perception and/or thinking, which may be assessed by methods known in the art.

As used herein, the term "neurotrophic" effects includes but is not limited to effects that enhance neuron function such as growth, survival and/or neurotransmitter synthesis.

As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g. HIV associated cognitive dysfunction and Lyme disease associated cognitive dysfunction. Examples of cognitive disorders include Alzheimer's Disease, Huntington's Disease, Parkinson's Disease, schizophrenia, amyotrophic lateral sclerosis (ALS), autism, mild cognitive impairment (MCI), stroke, traumatic brain injury (TBI) and age-associated memory impairment (AAMI).

As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression.

As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited, to Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases.

As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

As used herein, the term "neuron" represents a cell of ectodermal embryonic origin derived from any part of the nervous system of an animal. Neurons express well-characterized neuron-specific markers, including neurofilament proteins, NeuN (Neuronal Nuclei marker), MAP2, and class III tubulin. Included as neurons are, for example, hippocampal, cortical, midbrain dopaminergic, spinal motor, sensory, sympathetic, septal cholinergic, and cerebellar neurons.

As used herein, the term "neurite outgrowth" or "neurite activation" refers to the extension of existing neuronal processes (e.g., axons and dendrites) and the growth or sprouting of new neuronal processes (e.g., axons and dendrites). Neurite outgrowth or neurite activation may alter neural connectivity, resulting in the establishment of new synapses or the remodeling of existing synapses.

As used herein, the term "neurogenesis" refers to the generation of new nerve cells from undifferentiated neuronal progenitor cells, also known as multipotential neuronal stem cells. Neurogenesis actively produces new neurons, astrocytes, glia, Schwann cells, oligodendrocytes and/or other neural lineages. Much neurogenesis occurs early in human development, though it continues later in life, particularly in certain localized regions of the adult brain.

As used herein, the term "neural connectivity" refers to the number, type, and quality of connections ("synapses") between neurons in an organism. Synapses form between neurons, between neurons and muscles (a "neuromuscular junction"), and between neurons and other biological structures, including internal organs, endocrine glands, and the like. Synapses are specialized structures by which neurons transmit chemical or electrical signals to each other and to non-neuronal cells, muscles, tissues, and organs. Compounds that affect neural connectivity may do so by establishing new synapses (e.g., by neurite outgrowth or neurite activation) or by altering or remodeling existing synapses. Synaptic remodeling refers to changes in the quality, intensity or type of signal transmitted at particular synapses.

As used herein, the term "neuropathy" refers to a disorder characterized by altered function and/or structure of motor, sensory, and autonomic neurons of the nervous system, initiated or caused by a primary lesion or other dysfunction of the nervous system. Patterns of peripheral neuropathy include polyneuropathy, mononeuropathy, mononeuritis multiplex and autonomic neuropathy. The most common form is (symmetrical) peripheral polyneuropathy, which mainly affects the feet and legs. A radiculopathy involves spinal nerve roots, but if peripheral nerves are also involved the term radiculoneuropathy is used. The form of neuropathy may be further broken down by cause, or the size of predominant fiber involvement, e.g. large fiber or small fiber peripheral neuropathy. Central neuropathic pain can occur in spinal cord injury, multiple sclerosis, and some strokes, as well as fibromyalgia. Neuropathy may be associated with varying combinations of weakness, autonomic changes and sensory changes. Loss of muscle bulk or fasciculations, a particular fine twitching of muscle may also be seen. Sensory symptoms encompass loss of sensation and "positive" phenomena including pain. Neuropathies are associated with a variety of disorders, including diabetes (e.g., diabetic neuropathy), fibromyalgia, multiple sclerosis, and herpes zoster infection, as well as with spinal cord injury and other types of nerve damage.

As used herein, the term "Alzheimer's disease" refers to a degenerative brain disorder characterized clinically by progressive memory deficits, confusion, behavioral problems, inability to care for oneself, gradual physical deterioration and, ultimately, death. Histologically, the disease is characterized by neuritic plaques, found primarily in the association cortex, limbic system and basal ganglia. The major constituent of these plaques is amyloid beta peptide (Aβ), which is the cleavage product of beta amyloid precursor protein (βAPP or APP). APP is a type I transmembrane glycoprotein that contains a large ectopic N-terminal domain, a transmembrane domain and a small cytoplasmic C-terminal tail. Alternative splicing of the transcript of the single APP gene on chromosome 21 results in several isoforms that differ in the number of amino acids. Aβ appears to have a central role in the neuropathology of Alzheimer's disease. Familial forms of the disease have been linked to mutations in APP and the presenilin genes (Tanzi et al., 1996, *Neurobiol. Dis.*, 3:159-168; Hardy, 1996, *Ann. Med.*, 28:255-258). Diseased-linked mutations in these genes result in increased production of the 42-amino acid form of Aβ, the predominant form found in amyloid plaques. Mitochondrial dysfunction has also been reported to be an important component of Alzheimer's disease (Bubber et al., Mitochondrial abnormalities in Alzheimer brain: Mechanistic Implications, *Ann Neurol.*, 2005, 57(5), 695-703; Wang et al., Insights into amyloid-β-induced mitochondrial dysfunction in Alzheimer disease, *Free Radical Biology & Medicine*, 2007, 43, 1569-1573; Swerdlow et al., Mitochondria in Alzheimer's disease, *Int. Rev. Neurobiol.*, 2002, 53, 341-385; and Reddy et al., Are mitochondria critical in the pathogenesis of Alzheimer's disease?, *Brain Res Rev.* 2005, 49(3), 618-32). It has been proposed that mitochondrial dysfunction has a causal relationship with neuronal function (including neurotransmitter synthesis and secretion) and viability. Compounds which stabilize mitochondria may therefore have a beneficial impact on Alzheimer's patients.

As used herein, the term "Huntington's disease" refers to a fatal neurological disorder characterized clinically by symptoms such as involuntary movements, cognition impairment or loss of cognitive function and a wide spectrum of behavioral disorders. Common motor symptoms associated with Huntington's disease include chorea (involuntary writhing and spasming), clumsiness, and progressive loss of the abilities to walk, speak (e.g., exhibiting slurred speech) and swallow. Other symptoms of Huntington's disease can include cognitive symptoms such as loss of intellectual speed, attention and short-term memory and/or behavioral symptoms that can span the range of changes in personality, depression, irritability, emotional outbursts and apathy. Clinical symptoms typically appear in the fourth or fifth decade of life. Huntington's disease is a devastating and often protracted illness, with death usually occurring approximately 10-20 years after the onset of symptoms. Huntington's disease is inherited through a mutated or abnormal gene encoding an abnormal protein called the mutant huntingtin protein; the mutated huntingtin protein produces neuronal degeneration in many different regions of the brain. The degeneration focuses on neurons located in the basal ganglia, structures deep within the brain that control many important functions including coordinating movement, and on neurons on the outer surface of the brain or cortex, which controls thought, perception and memory.

"Amyotrophic lateral sclerosis" or "ALS" is used herein to denote a progressive neurodegenerative disease that affects upper motor neurons (motor neurons in the brain) and/or lower motor neurons (motor neurons in the spinal cord) and results in motor neuron death. As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS).

The term "Parkinson's disease" as used herein refers to any medical condition wherein an individual experiences one or more symptoms associated with Parkinson's disease, such as without limitation one or more of the following symptoms: rest tremor, cogwheel rigidity, bradykinesia, postural reflex impairment, symptoms having good response to 1-dopa treatment, the absence of prominent oculomotor palsy, cerebellar or pyramidal signs, amyotrophy, dyspraxia and/or dysphasia. In a specific embodiment, the present invention is utilized for the treatment of a dopaminergic dysfunction-related disorder. In a specific embodiment, the individual with Parkinson's disease has a mutation or polymorphism in a synuclein, parkin or NURR1 nucleic acid that is associated with Parkinson's disease. In one embodiment, the individual with Parkinson's disease has defective or decreased expression of a nucleic acid or a mutation in a nucleic acid that regulates the development and/or survival of dopaminergic neurons.

As used herein, the term "canine cognitive dysfunction syndrome," or "CCDS" refers to an age-related deterioration of mental function typified by multiple cognitive impairments that affect an afflicted canine's ability to function normally. The decline in cognitive ability that is associated with CCDS cannot be completely attributed to a general medical condition such as neoplasia, infection, sensory impairment, or organ failure. Diagnosis of CCDS in canines, such as dogs, is generally a diagnosis of exclusion, based on thorough behavior and medical histories and the presence of clinical symptoms of CCDS that are unrelated to other disease processes. Owner observation of age-related changes in behavior is a practical means used to detect the possible onset of CCDS in aging domestic dogs. A number of laboratory cognitive tasks may be used to help diagnose CCDS, while blood counts, chemistry panels and urinalysis can be used to rule out other underlying diseases that could mimic the clinical symptoms of CCDS. Symptoms of CCDS include memory loss, which in domestic dogs may be manifested by disorientation and/or confusion, decreased or altered interaction with family members and/or greeting behavior, changes in sleep-wake cycle, decreased activity level, and loss of house training or frequent, inappropriate elimination. A canine suffering from CCDS may exhibit one or more of the following clinical or behavioral symptoms: decreased appetite, decreased awareness of surroundings, decreased ability to recognize familiar places, people or other animals, decreased hearing, decreased ability to climb up and down stairs, decreased tolerance to being alone, development of compulsive behavior or repetitive behaviors or habits, circling, tremors or shaking, disorientation, decreased activity level, abnormal sleep wake cycles, loss of house training, decreased or altered responsiveness to family members, and decreased or altered greeting behavior. CCDS can dramatically affect the health and well-being of an afflicted canine. Moreover, the companionship offered by a pet with CCDS can become less rewarding as the severity of the disease increases and its symptoms become more severe.

As used herein, the term "age-associated memory impairment" or "AAMI" refers to a condition that may be identified as GDS stage 2 on the global deterioration scale (GDS) (Reisberg, et al. (1982) *Am. J. Psychiatry* 139: 1136-1139) which differentiates the aging process and progressive degenerative dementia in seven major stages. The first stage of the GDS is one in which individuals at any age have neither subjective complaints of cognitive impairment nor objective evidence of impairment. These GDS stage 1 individuals are considered normal. The second stage of the GDS applies to those generally elderly persons who complain of memory and cognitive functioning difficulties such as not recalling names as well as they could five or ten years previously or not recalling where they have placed things as well as they could five or ten years previously. These subjective complaints appear to be very common in otherwise normal elderly individuals. AAMI refers to persons in GDS stage 2, who may differ neurophysiologically from elderly persons who are normal and free of subjective complaints, i.e., GDS stage 1. For example, AAMI subjects have been found to have more electrophysiologic slowing on a computer analyzed EEG than GDS stage 1 elderly persons (Prichep, John, Ferris, Reisberg, et al. (1994) *Neurobiol. Aging* 15: 85-90).

As used herein, the term "mild cognitive impairment" or "MCI" refers to a type of cognitive disorder characterized by a more pronounced deterioration in cognitive functions than is typical for normal age-related decline. As a result, elderly or aged patients with MCI have greater than normal difficulty performing complex daily tasks and learning, but without the inability to perform normal social, everyday, and/or professional functions typical of patients with Alzheimer's disease, or other similar neurodegenerative disorders eventually resulting in dementia. MCI is characterized by subtle, clinically manifest deficits in cognition, memory, and functioning, amongst other impairments, which are not of sufficient magnitude to fulfill criteria for diagnosis of Alzheimer's disease or other dementia. MCI also encompasses injury-related MCI, defined herein as cognitive impairment resulting from certain types of injury, such as nerve injury (i.e., battlefield injuries, including post-concussion syndrome, and the like), neurotoxic treatment (i.e., adjuvant chemotherapy resulting in "chemo brain" and the like), and tissue damage resulting from physical injury or other neurodegeneration, which is separate and distinct from mild cognitive impairment resulting from stroke, ischemia, hemorrhagic insult, blunt force trauma, and the like.

As used herein, the term "traumatic brain injury" or "TBI" refers to a brain injury caused by a sudden trauma, such as a blow or jolt or a penetrating head injury, which disrupts the function or damages the brain. Symptoms of TBI can range from mild, moderate to severe and can significantly affect many cognitive (deficits of language and communication, information processing, memory, and perceptual skills), physical (ambulation, balance, coordination, fine motor skills, strength, and endurance), and psychological skills.

"Neuronal death mediated ocular disease" intends an ocular disease in which death of the neuron is implicated in whole or in part. The disease may involve death of photoreceptors. The disease may involve retinal cell death. The disease may involve ocular nerve death by apoptosis. Particular neuronal death mediated ocular diseases include but are not limited to macular degeneration, glaucoma, retinitis pigmentosa, congenital stationary night blindness (Oguchi disease), childhood onset severe retinal dystrophy, Leber congenital amaurosis, Bardet-Biedle syndrome, Usher syndrome, blindness from an optic neuropathy, Leber's hereditary optic neuropathy, color blindness and Hansen-Larson-Berg syndrome.

As used herein, the term "macular degeneration" includes all forms and classifications of macular degeneration known in the art, including, but not limited to diseases that are characterized by a progressive loss of central vision associated with abnormalities of Bruch's membrane, the choroid, the neural retina and/or the retinal pigment epithelium. The term thus encompasses disorders such as age-related macular degeneration (ARMD) as well as rarer, earlier-onset dystrophies that in some cases can be detected in the first decade of life. Other maculopathies include North Carolina macular dystrophy, Sorsby's fundus dystrophy, Stargardt's disease, pattern dystrophy, Best disease, and Malattia Leventinese.

As used herein, the term "autism" refers to a brain development disorder that impairs social interaction and communication and causes restricted and repetitive behavior, typically appearing during infancy or early childhood. The cognitive and behavioral defects are thought to result in part from altered neural connectivity. Autism encompasses related disorders sometimes referred to as "autism spectrum disorder," as well as Asperger syndrome and Rett syndrome.

As used herein, the term "nerve injury" or "nerve damage" refers to physical damage to nerves, such as avulsion injury (i.e., where a nerve or nerves have been torn or ripped) or spinal cord injury (i.e., damage to white matter or myelinated fiber tracts that carry sensation and motor signals to and from the brain). Spinal cord injury can occur from many causes, including physical trauma (i.e., car accidents, sports injuries, and the like), tumors impinging on the spinal column, developmental disorders, such as spina bifida, and the like.

As used herein, the term "myasthenia gravis" or "MG" refers to a non-cognitive neuromuscular disorder caused by immune-mediated loss of acetylcholine receptors at neuromuscular junctions of skeletal muscle. Clinically, MG typically appears first as occasional muscle weakness in approximately two-thirds of patients, most commonly in the extraocular muscles. These initial symptoms eventually worsen, producing drooping eyelids (ptosis) and/or double vision (diplopia), often causing the patient to seek medical attention. Eventually, many patients develop general muscular weakness that may fluctuate weekly, daily, or even more frequently. Generalized MG often affects muscles that control facial expression, chewing, talking, swallowing, and breathing; before recent advances in treatment, respiratory failure was the most common cause of death.

As used herein, the term "Guillain-Barré syndrome" refers to a non-cognitive disorder in which the body's immune system attacks part of the peripheral nervous system. The first symptoms of this disorder include varying degrees of weakness or tingling sensations in the legs. In many instances the weakness and abnormal sensations spread to the arms and upper body. These symptoms can increase in intensity until certain muscles cannot be used at all and, when severe, the patient is almost totally paralyzed. In these cases the disorder is life threatening—potentially interfering with breathing and, at times, with blood pressure or heart rate—and is considered a medical emergency. Most patients, however, recover from even the most severe cases of Guillain-Barré syndrome, although some continue to have a certain degree of weakness.

As used herein, the term "multiple sclerosis" or "MS" refers to an autoimmune condition in which the immune system attacks the central nervous system (CNS), leading to demyelination of neurons. It may cause numerous symptoms, many of which are non-cognitive, and often progresses to physical disability. MS affects the areas of the brain and spinal cord known as the white matter. White matter cells carry signals between the grey matter areas, where the processing is done, and the rest of the body. More specifically, MS destroys oligodendrocytes which are the cells responsible for creating and maintaining a fatty layer, known as the myelin sheath, which helps the neurons carry electrical signals. MS results in a thinning or complete loss of myelin and, less frequently, the cutting (transection) of the neuron's extensions or axons. When the myelin is lost, the neurons can no longer effectively conduct their electrical signals. Almost any neurological symptom can accompany the disease. MS takes several forms, with new symptoms occurring either in discrete attacks (relapsing forms) or slowly accumulating over time (progressive forms). Most people are first diagnosed with relapsing-remitting MS but develop secondary-progressive MS (SPMS) after a number of years. Between attacks, symptoms may go away completely, but permanent neurological problems often persist, especially as the disease advances.

As used herein, the term "schizophrenia" refers to a chronic, mental disorder characterized by one or more positive symptoms (e.g., delusions and hallucinations) and/or negative symptoms (e.g., blunted emotions and lack of interest) and/or disorganized symptoms (e.g., disorganized thinking and speech or disorganized perception and behavior). Schizophrenia as used herein includes all forms and classifications of schizophrenia known in the art, including, but not limited to catatonic type, hebephrenic type, disorganized type, paranoid type, residual type or undifferentiated type schizophrenia and deficit syndrome and/or those described in American Psychiatric Association: *Diagnostic and Statistical Manual of Mental Disorders*, Fourth Edition, Washington D.C., 2000 or in International Statistical Classification of Diseases and Related Health Problems, or otherwise known to those of skill in the art.

"Cognitive impairment associated with schizophrenia" or "CIAS" includes neuropsychological deficits in attention, working memory, verbal learning, and problem solving. These deficits are believed to be linked to impairment in functional status (e.g., social behavior, work performance, and activities of daily living).

As used herein "geroprotective activity" or "geroprotector" means a biological activity that slows down ageing and/or prolongs life and/or increases or improves the quality of life via a decrease in the amount and/or the level of intensity of pathologies or conditions that are not life-threatening but are associated with the aging process and which are typical for elderly people. Pathologies or conditions that are not life-threatening but are associated with the aging process include such pathologies or conditions as loss of sight (cataract), deterioration of the dermatohairy integument (alopecia), and an age-associated decrease in weight due to the death of muscular and/or fatty cells.

As used herein, attention-deficit hyperactivity disorder (ADHD) is the most common child neuropsychiatric condition present in school-aged children, affecting about 5-8% of this population. ADHD refers to a chronic disorder that initially manifests in childhood and is characterized by hyperactivity, impulsivity, and/or inattention. ADHD is characterized by persistent patterns of inattention and/or impulsivity-hyperactivity that are much more extreme than is observed in individuals at the same developmental level or stage. There is considerable evidence, from family and twin studies, that ADHD has a significant genetic component. This disorder is thought to be due to an interaction of environmental and genetic factors. ADHD includes all known types of ADHD. For example, *Diagnostic & Statistical Manual for Mental Disorders* (DSM-IV) identifies three subtypes of ADHD: (1) ADHD, Combined Type which is characterized by both inattention and hyperactivity-impulsivity symptoms; 2. ADHD, Predominantly Inattentive Type which is characterized by inattention but not hyperactivity-impulsivity symptoms; and 3. ADHD, Predominantly Hyperactive-Impulsive Type which is characterized by Hyperactivity-impulsivity but not inattention symptoms.

As used herein, attention-deficit disorder (ADD) refers to a disorder in processing neural stimuli that is characterized by distractibility and impulsivity that can result in inability to control behavior and can impair an individual's social, academic, or occupational function and development. ADD may be diagnosed by known methods, which may include observing behavior and diagnostic interview techniques.

As used herein "allergic disease" refers to a disorder of the immune system which is characterized by excessive activation of mast cells and basophils and production of IgE immunoglobulins, resulting in an extreme inflammatory response. It represents a form of hypersensitivity to an environmental substance known as allergen and is an acquired disease. Common allergic reactions include eczema, hives, hay fever, asthma, food allergies, and reactions to the venom of stinging insects such as wasps and bees. Allergic reactions are accompanied by an excessive release of histamines, and can thus be treated with antihistaminic agents.

As used herein, by "combination therapy" is meant a therapy that includes two or more different compounds. Thus, in one aspect, a combination therapy comprising a compound detailed herein and anther compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound of the invention alone. In some embodiments, a lower amount of each compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound of the invention which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. A pharmaceutically acceptable salt intends ionic interactions and not a covalent bond. As such, an N-oxide is not considered a salt. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1): 1-19. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear, branched, or cyclic univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 8 annular carbon atoms (a "$C_3$-$C_8$ cycloalkyl"). Examples of cycloalkyl groups include adamantyl, decahydronaphthalenyl, cyclopropyl, cyclobutyl, cyclopentyl, cyclohexyl and the like.

"Alkylene" refers to the same residues as alkyl, but having bivalency. Examples of alkylene include methylene (—$CH_2$—), ethylene (—$CH_2CH_2$—), propylene (—$CH_2CH_2CH_2$—), butylene (—$CH_2CH_2CH_2CH_2$—) and the like.

"Alkenyl" refers to an unsaturated hydrocarbon group having at least one site of olefinic unsaturation (i.e., having at least one moiety of the formula C═C) and preferably having from 2 to 10 carbon atoms and more preferably 2 to 8 carbon atoms. Examples of alkenyl include but are not limited to —$CH_2$—CH═CH—$CH_3$ and —$CH_2$—$CH_2$-cyclohexenyl, where the ethyl group of the latter example can be attached to the cyclohexenyl moiety at any available position on the ring. Cycloalkenyl is a subset of alkenyl and can consist of one ring, such as cyclohexyl, or multiple rings, such as norbornenyl. A more preferred cycloalkenyl is an unsaturated cyclic hydrocarbon having from 3 to 8 annular carbon atoms (a "$C_3$-$C_8$ cycloalkenyl"). Examples of cycloalkenyl groups include cyclopropenyl, cyclobutenyl, cyclopentenyl, cyclohexenyl and the like.

"Alkynyl" refers to an unsaturated hydrocarbon group having at least one site of acetylenic unsaturation (i.e., having at least one moiety of the formula C≡C) and preferably having from 2 to 10 carbon atoms and more preferably 2 to 8 carbon atoms and the like.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, cycloalkyl-C(O)O—, substituted cycloalkyl-C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 1 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety. In one variation, an aralkyl is a fused ring system where at least one cycloalkyl moiety is fused with at least one aryl moiety. A "substituted aralkyl" refers to a residue in which an aryl moiety is attached to a substituted alkyl residue and wherein the aralkyl group may be attached to the parent structure at either the aryl or the alkyl residue. When an aralkyl is connected to the parent structure via the alkyl moiety, it may also be referred to as an "alkaryl". More particular alkaryl groups are those having 1 to 3 carbon atoms in the alkyl moiety (a "$C_1$-$C_3$ alkaryl").

"Alkoxy" refers to the group alkyl-O—, which includes, by way of example, methoxy, ethoxy, n-propoxy, isopropoxy, n-butoxy, tert-butoxy, sec-butoxy, n-pentoxy, n-hexoxy, 1,2-dimethylbutoxy, and the like. Similarly, alkenyloxy refers to the group "alkenyl-O—" and alkynyloxy refers to the group "alkynyl-O—". "Substituted alkoxy" refers to the group substituted alkyl-O.

"Unsubstituted amino" refers to the group —$NH_2$.

"Substituted amino" refers to the group —$NR_aR_b$, where either (a) each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, provided that both $R_a$ and $R_b$ groups are not H; or (b) $R_a$ and $R_b$ are joined together with the nitrogen atom to form a heterocyclic or substituted heterocyclic ring.

"Acylamino" refers to the group —C(O)$NR_aR_b$ where $R_a$ and $R_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic or $R_a$ and $R_b$ groups can be joined together with the nitrogen atom to form a heterocyclic or substituted heterocyclic ring.

"Aminoacyl" refers to the group —$NR_aC(O)R_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic or substituted heterocyclic. Preferably, $R_a$ is H or alkyl.

"Aminosulfonyl" refers to the groups —$NRSO_2$-alkyl, —$NRSO_2$ substituted alkyl, —$NRSO_2$-alkenyl, —$NRSO_2$— substituted alkenyl, —$NRSO_2$-alkynyl, —$NRSO_2$-substituted alkynyl, —$NRSO_2$-cycloalkyl, —$NRSO_2$-substituted cycloalkyl, —$NRSO_2$-aryl, —$NRSO_2$-substituted aryl, —$NRSO_2$-heteroaryl, —$NRSO_2$-substituted heteroaryl, —$NRSO_2$-heterocyclic, and —$NRSO_2$-substituted heterocyclic, where R is H or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the groups —$SO_2NH_2$, —$SO_2NR$-alkyl, —$SO_2NR$-substituted alkyl, —$SO_2NR$-alkenyl, —$SO_2NR$-substituted alkenyl, —$SO_2NR$-alkynyl, —$SO_2NR$-substituted alkynyl, —$SO_2NR$-aryl, —$SO_2NR$-substituted aryl, —$SO_2NR$-heteroaryl, —$SO_2NR$-substituted heteroaryl, —$SO_2NR$-heterocyclic, and —$SO_2NR$-substituted heterocyclic, where R is H or alkyl, or —$SO_2NR_2$, where the two R groups are taken together and with the nitrogen atom to which they are attached to form a heterocyclic or substituted heterocyclic ring.

"Sulfonyl" refers to the groups —$SO_2$-alkyl, —$SO_2$-substituted alkyl, —$SO_2$-alkenyl, —$SO_2$-substituted alkenyl, —$SO_2$-alkynyl, —$SO_2$-substituted alkynyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic.

"Aminocarbonylalkoxy" refers to the group —$NR_aC(O)OR_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclyl.

"Carbonylalkylenealkoxy" refers to the group —C(=O)—$(CH_2)_n$—OR where R is a substituted or unsubstituted alkyl and n is an integer from 1 to 100, more preferably n is an integer from 1 to 10 or 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Cyano" refers to the group —CN.

"Oxo" refers to the moiety =O.

"Nitro" refers to the group —$NO_2$.

"Thioalkyl" refers to the groups —S-alkyl.

"Alkylsulfonylamino" refers to the groups —$R^1SO_2NR_aR_b$ where $R_a$ and $R_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, or the $R_a$ and $R_b$ groups can be joined together with the nitrogen atom to form a heterocyclic or substituted heterocyclic ring and $R^1$ is an alkyl group.

"Carbonylalkoxy" refers to as used herein refers to the groups —C(O)O-alkyl, —C(O)O— substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Geminal" refers to the relationship between two moieties that are attached to the same atom. For example, in the residue —$CH_2$—$CHR^1R^2$, $R^1$ and $R^2$ are geminal and $R^1$ may be referred to as a geminal R group to $R^2$.

"Vicinal" refers to the relationship between two moieties that are attached to adjacent atoms. For example, in the residue —$CHR^1$—$CH_2R^2$, $R^1$ and $R^2$ are vicinal and $R^1$ may be referred to as a vicinal R group to $R^2$.

A composition of "substantially pure" compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1% of the (R) form of the compound.

Compounds of the Invention

Compounds according to the invention are detailed herein, including in the Brief Summary of the Invention and the appended claims. The invention includes the use of all of the compounds described herein, including any and all stereoisomers, including geometric isomers (cis/trans) or E/Z isomers, salts and solvates of the compounds described herein, as well as methods of making such compounds.

The invention embraces compounds of the formula (I):

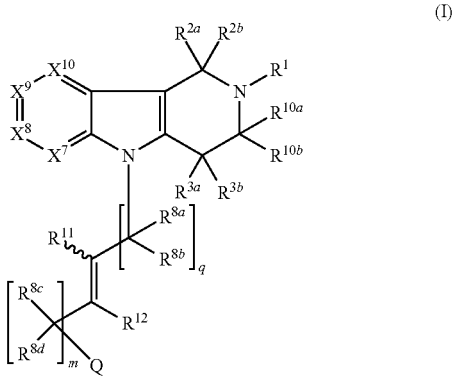

(I)

or a salt or solvate thereof;
wherein:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together to form a carbonyl moiety;

each $X^7$, $X^8$, $X^9$ and $X^{10}$ is independently N, CH or $CR^4$;

each m and q is independently 0 or 1;

each $R^4$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, $C_1$-$C_8$ alkyl, or is taken together with the carbon to which it is attached and a geminal $R^8$ to form a cycloalkyl moiety or a carbonyl moiety;

each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together to form a carbonyl moiety;

$R^{11}$ is H, $C_1$-$C_8$ alkyl, $C_3$-$C_8$ cycloalkyl, or $C_1$-$C_8$ perhaloalkyl and the ∿ bond indicates the presence of either an E or Z double bond configuration;

$R^{12}$ is H, $C_1$-$C_8$ alkyl, $C_3$-$C_8$ cycloalkyl, or $C_1$-$C_8$ perhaloalkyl; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy or acylamino;

provided that when $X^7$, $X^8$ and $X^{10}$ are each CH and each $R^{2a}$, $R^{2b}$, $R^{3a}$, $R^{3b}$, $R^{10a}$ and $R^{10b}$ is hydrogen, then the compound is other than a compound in Table A. The compounds in Table A have the structure of formula (I) where each $R^{2a}$, $R^{2b}$, $R^{3a}$, $R^{3b}$, $R^{10a}$ and $R^{10b}$ is H, each $X^7$, $X^8$ and $X^{10}$ is CH, $R^1$, m, q and Q are as listed in Table A, and $X^9$ is $CR^4$ where $R^4$ is as listed in Table A. When $R^4$ is listed as H, $X^9$ is CH.

TABLE A

| Compound No. | $R^4$ | $R^1$ | q | m | $R^{11}$ | $R^{12}$ | E/Z | Q |
|---|---|---|---|---|---|---|---|---|
| 1x | H | $CH_3$ | 0 | 0 | H | H | Z | Phenyl |
| 2x | H | $CH_3$ | 0 | 0 | H | H | E | Phenyl |
| 3x | H | $CH_3$ | 0 | 0 | H | H | E | 4-Pyridyl |
| 4x | H | $CH_3$ | 0 | 0 | H | H | Z | 3-Pyridyl |
| 5x | H | $CH_3$ | 0 | 0 | H | H | E | 2-Pyridyl |
| 6x | H | t-butyl | 0 | 0 | H | H | Z | 3-Pyridyl |
| 7x | F | $CH_3$ | 0 | 0 | H | H | Z | Phenyl |
| 8x | F | $CH_3$ | 0 | 0 | H | H | E | Phenyl |
| 9x | F | $CH_3$ | 0 | 0 | H | H | E | 4-Pyridyl |
| 10x | F | $CH_3$ | 0 | 0 | H | H | Z | 3-Pyridyl |
| 11x | F | $CH_3$ | 0 | 0 | H | H | E | 2-Pyridyl |

TABLE A-continued

| Compound No. | $R^4$ | $R^1$ | q | m | $R^{11}$ | $R^{12}$ | E/Z | Q |
|---|---|---|---|---|---|---|---|---|
| 12x | CH₃ | CH₃ | 0 | 0 | H | H | Z | Phenyl |
| 13x | CH₃ | CH₃ | 0 | 0 | H | H | E | Phenyl |
| 14x | CH₃ | CH₃ | 0 | 0 | H | H | Z | 3-Pyridyl |
| 15x | CH₃ | CH₃ | 0 | 0 | H | H | E | 4-Pyridyl |
| 16x | CH₃ | Benzyl | 0 | 0 | H | H | Z | 3-Pyridyl |
| 17x | F | CH₃ | 0 | 0 | H | H | E | 4-Fluorophenyl |
| 18x | F | CH₃ | 0 | 0 | H | H | Z | 3-Fluorophenyl |
| 19x | CH₃ | CH₃ | 0 | 0 | H | H | E | 4-CF₃-Phenyl |
| 20x | CH₃ | CH₃ | 0 | 0 | H | H | Z | 3-CF₃-Phenyl |
| 21x | F | CH₃ | 0 | 0 | H | H | E | 4-CF₃-Phenyl |
| 22x | F | CH₃ | 0 | 0 | H | H | Z | 4-OCH₃-Phenyl |
| 23x | F | CH₃ | 0 | 0 | H | H | Z | 4-N(Me)₂-Phenyl |
| 24x | CH₃ | CH₃ | 0 | 0 | H | H | E | 4-Fluorophenyl |

Also provided are methods of using compounds described herein, such as compounds of formula (I), in various therapeutic applications. Method of using compounds of Table A are also encompassed. Thus, provided are methods of using a compound of Formula (I-1):

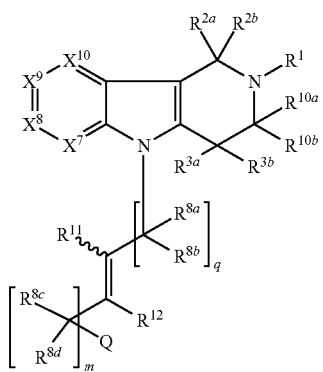

(I-1)

or a salt or solvate thereof;
wherein:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together to form a carbonyl moiety;

each $X^7$, $X^8$, $X^9$ and $X^{10}$ is independently N, CH or $CR^4$;
each m and q is independently 0 or 1;
each $R^4$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, $C_1$-$C_8$ alkyl, or is taken together with the carbon to which it is attached and a geminal $R^8$ to form a cycloalkyl moiety or a carbonyl moiety;

each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together to form a carbonyl moiety;

$R^{11}$ is H, $C_1$-$C_8$ alkyl, $C_3$-$C_8$ cycloalkyl, or $C_1$-$C_8$ perhaloalkyl and the ∼ bond indicates the presence of either an E or Z double bond configuration;

$R^{12}$ is H, $C_1$-$C_8$ alkyl, $C_3$-$C_8$ cycloalkyl, or $C_1$-$C_8$ perhaloalkyl; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy or acylamino.

In one variation, compounds of the formula (V) are provided, where $X^7$, $X^8$, $X^9$, $X^{10}$, $R^1$, $R^{2a}$, $R^{2b}$, $R^{3a}$, $R^{3b}$, $R^{10a}$, $R^{10b}$, Q, q, m, $R^{8a}$, $R^{8b}$, $R^{8c}$, $R^{8d}$ are as defined for formula (I) and $R^{11}$ and $R^{12}$ are independently H, halo, alkoxy, substituted or unsubstituted aryl, substituted or unsubstituted heteroaryl, substituted or unsubstituted $C_1$-$C_8$ alkyl, $C_1$-$C_8$ alkyl substituted with a carbonylalkoxy, carboxyl or acylamino moiety, $C_2$-$C_8$ alkenyl, substituted or unsubstituted $C_3$-$C_8$ cycloalkyl, substituted or unsubstituted $C_3$-$C_8$ cycloalkenyl, substituted or unsubstituted heterocyclyl or $C_1$-$C_8$ perhaloalkyl and the ∼ bond indicates the presence of either an E or Z double bond configuration. In one such variation, $R^{11}$ and $R^{12}$ are other than H. In another variation, $R^{12}$ is other than H, such as when $R^{12}$ is a substituted or unsubstituted $C_1$-$C_8$ alkyl, substituted or unsubstituted aryl, substituted or unsubstituted heteroaryl.

In one variation, the compound is of the formula (I), where at least one of $R^{11}$ and $R^{12}$ is other than H. In one such variation, the compound is of the formula (I) where $R^{11}$ is $C_1$-$C_8$ alkyl. For example, the compound in one aspect is of the formula (I) where $R^{11}$ is methyl. In another such variation, the compound is of the formula (I) where $R^{12}$ is $C_1$-$C_8$ alkyl, $C_3$-$C_8$ cycloalkyl, or $C_1$-$C_8$ perhaloalkyl. For example, the compound in one aspect is of the formula (I) where $R^{12}$ is methyl, ethyl, cyclopropyl or trifluoromethyl. In one aspect, the compound is of the formula (I) where $R^{12}$ is $C_1$-$C_8$ alkyl (e.g., methyl and ethyl). In another aspect, the compound is of the formula (I) where $R^{12}$ is $C_3$-$C_8$ cycloalkyl (e.g., cyclopropyl). In still another aspect, the compound is of the formula (I) where $R^{12}$ is $C_1$-$C_8$ perhaloalkyl (e.g., trifluoromethyl). In another such variation, $R^{11}$ and $R^{12}$ are independently $C_1$-$C_8$ alkyl, $C_3$-$C_8$ cycloalkyl, or $C_1$-$C_8$ perhaloalkyl. In yet another such variation, $R^{11}$ is $C_1$-$C_8$ alkyl and $R^{12}$ is $C_1$-$C_8$ alkyl, $C_3$-$C_8$ cycloalkyl, or $C_1$-$C_8$ perhaloalkyl. For example, a compound in one aspect is of the formula (I) where both $R^{11}$ and $R^{12}$ are methyl and in another aspect where $R^{11}$ is methyl and $R^{12}$ is methyl, ethyl, cyclopropyl or trifluoromethyl. Where applicable, including but not limited to the variations of this paragraph, in a one variation the compound of formula (I) is further defined by Q being a substituted or unsubstituted heteroaryl.

When Q is an unsubstituted or substituted heteroaryl, in one variation it is a heteroaryl containing an annular nitrogen atom. In one aspect, when Q is an unsubstituted or substituted heteroaryl the heteroaryl contains only nitrogen and carbon annular atoms. In a particular variation, Q is an unsubstituted pyridyl that may be bound to the parent structure at any available ring position. For example, in one variation of formula (I), Q is 4-pyridyl, 3-pyridyl or 2-pyridyl. When Q is a substituted heteroaryl in one aspect it is a substituted pyridyl. When Q is a substituted pyridyl, the pyridyl may be substituted with one or more than one substituent and the substituted pyridyl may be bound to the parent structure at any available ring position. For example, in one variation of formula (I), Q is a monosubstituted pyridyl where the substituent is a $C_1$-$C_8$ unsubstituted alkyl (e.g., methyl).

In a particular variation, the compound is of the formula (I) where both q and m are 0 and where at least one of $R^{11}$ and $R^{12}$ is other than H. For example, in one variation, both q and m are 0 and $R^{11}$ and $R^{12}$ are as provided in any of the variations detailed in the preceding paragraph. In a particular such variation, both q and m are 0 and $R^{12}$ is methyl. In still another variation, the compound is of the formula (I) where both q and m are 0, $R^{12}$ is methyl and at least one of (i)-(iii) applies: (i) $X^9$ is $CR^4$ where $R^4$ is halo (e.g., chloro); (ii) Q is a substituted phenyl; and (iii) $X^7$, $X^8$ and $X^{10}$ are each CH. In yet another variation, the compound is of the formula (I) where both q and m are 0, $R^{12}$ is methyl and at least one of (i)-(iii) applies: (i) $X^9$ is $CR^4$ where $R^4$ is halo (e.g., chloro) or unsubstituted $C_1$-$C_8$ alkyl; (ii) Q is a substituted or unsubstituted pyridyl; and (iii) $X^7$, $X^8$ and $X^{10}$ are each CH.

In one variation of formula (I), both q and m are 0, $R^{12}$ is $C_1$-$C_8$ alkyl (e.g., methyl) and at least one of $X^7$-$X^{10}$ is $CR^4$ where $R^4$ is halo. In one such variation, both q and m are 0, $R^{12}$ is $C_1$-$C_8$ alkyl (e.g., methyl), at least one of $X^7$-$X^{10}$ is $CR^4$ where $R^4$ is halo, and the compound further has one or more of the following structural features: (i) Q is a substituted aryl; (ii) $X^7$, $X^8$ and $X^{10}$ are each CH; (iii) $R^{11}$ is H; (iv) $R^{2a}$, $R^{2b}$, $R^{3a}$, $R^{3b}$, $R^{10a}$ and $R^{10b}$ are each H; and (v) $R^1$ is alkyl. In a particular such variation, both q and m are 0, $R^{12}$ is methyl, $X^9$ is $CR^4$ where $R^4$ is chloro. In a more particular such variation, both q and m are 0, $R^{12}$ is methyl, $X^9$ is $CR^4$ where $R^4$ is chloro, and at least one of (i)-(v) applies: (i) Q is a substituted phenyl; (ii) $X^7$, $X^8$ and $X^{10}$ are each CH; (iii) $R^{11}$ is H; (iv) $R^{2a}$, $R^{2b}$, $R^{3a}$, $R^{3b}$, $R^{10a}$ and $R^{10b}$ are each H; and (v) $R^1$ is methyl.

In one variation, the compound is of the formula (I) where q is 0 and m is 1. In one such variation, the compound is of the formula (I) where q is 0, m is 1 and $R^{11}$ and $R^{12}$ are both H. In another aspect, the compound is of the formula (I) where q is 0, m is 1 and Q is an unsubstituted aryl or heteroaryl.

In another variation, the compound is of the formula (I) where Q is a di- or tri-substituted aryl, substituted heteroaryl, substituted or unsubstituted cycloalkyl, substituted or unsubstituted cycloalkenyl or substituted or unsubstituted heterocyclyl. In one aspect, the compound is of the formula (I) where Q is a di- or tri-substituted aryl. When Q is a di- or tri-substituted aryl, the substituents may be the same or different and may be located at any available position on the aryl ring. In one aspect, Q is a di- or tri-substituted phenyl (e.g., 4-methoxy-3-fluorophenyl, 3,4-di-fluorophenyl, 4-chloro-3-fluorophenyl, 3,4-dichlorophenyl, 3-chloro-4-fluorophenyl, 2,4-difluorophenyl, 2,4-dichlorophenyl and 2,4,6-trifluorophenyl). In another aspect, Q is a phenyl substituted with at least one chloro or methyl group (e.g., 4-chlorophenyl and 4-methylphenyl). In yet another aspect, the compound is of the formula (I) where Q is a substituted heteroaryl (e.g., where Q is 6-methyl-3-pyridyl, 6-trifluoromethyl-3-pyridyl, 5-trifluoromethyl-3-pyridyl or pyrimidinyl). In one aspect, Q is a substituted pyridyl such as 6-methyl-3-pyridyl, 6-trifluoromethyl-3-pyridyl and 5-trifluoromethyl-3-pyridyl. In another variation, compounds of formula (I) are provided where Q is an unsubstituted heteroaryl and $R^{12}$ is an unsubstituted $C_1$-$C_8$ alkyl such as methyl. In one such variation, Q is pyridyl (e.g., 4-pyridyl) and $R^{12}$ is methyl.

In one variation, the compound is of the formula (I) where at least one of $X^7$-$X^{10}$ is $CR^4$ where $R^4$ is chloro. In such variation, $X^9$ is $CR^4$ where $R^4$ is chloro. In another variation, $X^9$ is $CR^4$ where $R^4$ is chloro and $X^7$, $X^8$ and $X^{10}$ are CH. In one aspect, the compound is of the formula (I) where at least one of $X^7$-$X^{10}$ is $CR^4$ where $R^4$ is chloro. (e.g., when $X^9$ is $CR^4$ where $R^4$ is chloro) and Q is an unsubstituted aryl (e.g., phenyl), a substituted aryl (e.g., 4-fluorophenyl, 4-chlorophenyl, 4-methoxyphenyl, 3-fluoro-4-methoxyphenyl, 3,4-difluorophenyl, 4-chloro-3-fluorophenyl, 3,4-dichlorophenyl, 3-chloro-4-fluorophenyl, 2,4-difluorophenyl, 2,4,5-trifluorophenyl and 2,4-dichlorophenyl), an unsubstituted heteroaryl (e.g., 3-pyridyl and 4-pyridyl) or a substituted heteroaryl (e.g., 6-methyl-3-pyridyl, 6-trifluoromethyl-3-pyridyl and 5-trifluoromethyl-3-pyridyl). In a particular variation, $X^9$ is $CR^4$ where $R^4$ is chloro, $X^7$, $X^8$ and $X^{10}$ are each CH, $R^1$ is methyl or cyclopropyl and Q is an unsubstituted aryl, a substituted aryl, an unsubstituted heteroaryl or a substituted heteroaryl.

In any variation or aspect of formula (I) detailed herein, in one embodiment, the compound of formula (I) is in the E configuration. Similarly, in any variation or aspect of formula (I) detailed herein, in another embodiment, the compound of formula (I) is in the Z configuration.

In certain embodiments, the compound of formula (I) has the structure:

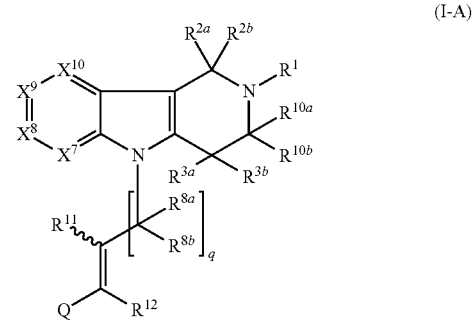

(I-A)

or a salt or solvate thereof;

wherein $R^1$, $R^{2a}$, $R^{2b}$, $R^{3a}$, $R^{3b}$, $R^{8a}$, $R^{8b}$, $R^{10a}$, $R^{10b}$, $R^{11}$, $R^{12}$, q, Q, $X^7$, $X^8$, $X^9$, A and $X^{10}$ are defined as for formula (I) and, where applicable, any variation thereof detailed herein. That is, variations of formula (I) detailed throughout, where applicable, apply to formula (I-A) the same as if each and every variation were specifically and individually listed for formula (I-A). In one variation, compounds of formula (I-A) are detailed herein, provided the compound is other than a compound of Table A. In another variation, compounds of formula (I-A), including those of Table A, and methods of using and administering such compounds are encompassed. In one aspect of formula (I-A), q is 1. In another variation of formula (I-A), q is 0 and $R^{12}$ is other than H (e.g., where $R^{12}$ is $C_1$-$C_8$ alkyl, $C_3$-$C_8$ cycloalkyl, or $C_1$-$C_8$ perhaloalkyl). In another particular variation of formula (I-A), q is 0 and $R^{12}$ is $C_1$-$C_8$ alkyl (e.g., methyl). In one such variation, $R^{12}$ is an unsubstituted $C_1$-$C_8$ alkyl and Q is a substituted or unsubstituted heteroaryl. In one variation of formula (I-A), $R^{12}$ is an unsubstituted $C_1$-$C_8$ alkyl and Q is other than a halo-substituted phenyl. In a more particular variation of formula (I-A), q is 0, $R^{12}$ is $C_1$-$C_8$ alkyl, $X^9$ is $CR^4$ where $R^4$ is halo and each $X^7$, $X^8$ and $X^{10}$ is CH. In an even more particular variation of formula (I-A), q is 0, $R^{12}$ is $C_1$-$C_8$ alkyl, $X^9$ is $CR^4$ where $R^4$ is halo, each $X^7$, $X^8$ and $X^{10}$ is CH, $R^1$ is alkyl (e.g., methyl) and each $R^{2a}$, $R^{2b}$, $R^{3a}$, $R^{3b}$, $R^{10a}$, $R^{10b}$ is H. In any variation or aspect of formula (I-A) detailed herein, in one embodiment, the compound of formula (I-A) is in the E configuration. Similarly, in any variation or aspect of formula (I-A) detailed herein, in another embodiment, the compound of formula (I-A) is in the Z configuration.

In other embodiments, the compound of formula (I) has the structure:

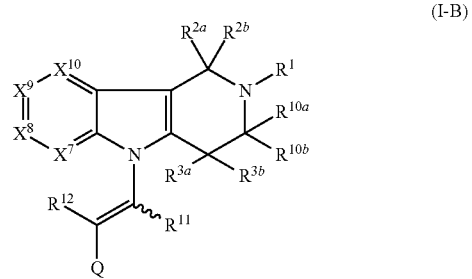

(I-B)

or a salt or solvate thereof;
wherein $R^1$, $R^{2a}$, $R^{2b}$, $R^{3a}$, $R^{3b}$, $R^{10a}$, $R^{10b}$, $R^{11}$, $R^{12}$, Q, $X^7$, $X^8$, $X^9$, and $X^{10}$ are defined as for formula (I) and, where applicable, any variation thereof detailed herein. That is, variations of formula (I) detailed throughout, where applicable, apply to formula (I-B) the same as if each and every variation were specifically and individually listed for formula (I-B). In one variation, compounds of formula (I-B) are detailed herein, provided the compound is other than a compound of Table A. In another variation, compounds of formula (I-B), including those of Table A, and methods of using and administering such compounds are encompassed. In one aspect of formula (I-B), at least one of $R^{11}$ and $R^{12}$ is other than H. In one such variation of formula (I-B), $R^{11}$ is H and $R^{12}$ is $C_1$-$C_8$ alkyl, $C_3$-$C_8$ cycloalkyl, or $C_1$-$C_8$ perhaloalkyl. In one aspect of formula (I-B), $R^{11}$ is H and $R^{12}$ is $C_1$-$C_8$ alkyl. In another variation of formula (I-B) at least one of $R^{11}$ and $R^{12}$ is other than H and $R^1$ is $C_1$-$C_8$ alkyl. In one such variation, $R^{12}$ is an unsubstituted $C_1$-$C_8$ alkyl and Q is a substituted or unsubstituted heteroaryl. In one variation of formula (I-B), $R^{12}$ is an unsubstituted $C_1$-$C_8$ alkyl and Q is other than a halo-substituted phenyl. In a more particular variation of formula (I-B), $R^{11}$ is H, $R^{12}$ is $C_1$-$C_8$ alkyl, $C_3$-$C_8$ cycloalkyl, or $C_1$-$C_8$ perhaloalkyl and $R^1$ is $C_1$-$C_8$ alkyl. In an even more particular variation of formula (I-B), $R^{11}$ is H, $R^{12}$ is $C_1$-$C_8$ alkyl, $X^9$ is $CR^4$ where $R^4$ is halo and each $X^7$, $X^8$ and $X^{10}$ is CH. In another variation of formula (I-B), $R^{11}$ is H, $R^{12}$ is $C_1$-$C_8$ alkyl, $X^9$ is $CR^4$ where $R^4$ is halo, each $X^7$, $X^8$ and $X^{10}$ is CH, $R^1$ is alkyl and each $R^{2a}$, $R^{2b}$, $R^{3a}$, $R^{3b}$, $R^{10a}$, $R^{10b}$ is H. In any variation or aspect of formula (I-B) detailed herein, in one embodiment, the compound of formula (I-B) is in the E configuration. Similarly, in any variation or aspect of formula (I-B) detailed herein, in another embodiment, the compound of formula (I-B) is in the Z configuration. For example, provided are compounds of formula (I-B) where $R^{11}$ is H, $R^{12}$ is $C_1$-$C_8$ alkyl, $X^9$ is $CR^4$ where $R^4$ is halo, each $X^7$, $X^8$ and $X^{10}$ is CH and the compound is in the E configuration. Likewise, also provided are compounds of formula (I-B) where $R^{11}$ is H, $R^{12}$ is $C_1$-$C_8$ alkyl, $X^9$ is $CR^4$ where $R^4$ is halo, each $X^7$, $X^8$ and $X^{10}$ is CH and the compound is in the Z configuration.

In specific embodiments, the compound having formula (I-B) has the structure:

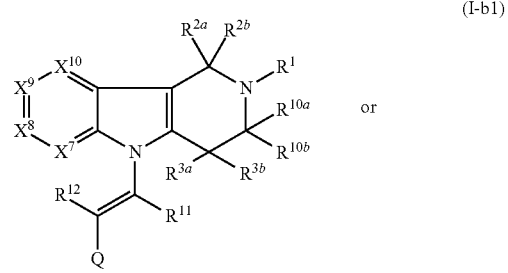

(I-b1)

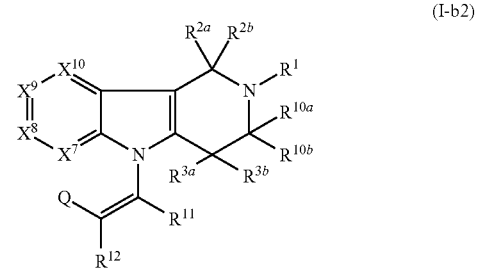

(I-b2)

or a salt or solvate thereof;
wherein $R^1$, $R^{2a}$, $R^{2b}$, $R^{3a}$, $R^{3b}$, $R^{10a}$, $R^{10b}$, $R^{11}$, $R^{12}$, Q, $X^7$, $X^8$, $X^9$, and $X^{10}$ are defined as for formula (I-B) and, where applicable, any variation thereof detailed herein. That is, variations of formula (I-B) and formula (I) detailed throughout, where applicable, apply to formulae (I-b1) and (I-b2) the same as if each and every variation were specifically and individually listed for formulae (I-b1) and (I-b2). In one variation, compounds of formula (I-b1) and (I-b2) are detailed herein, provided the compound is other than a compound of Table A. In another variation, compounds of formula (I-b1) and (I-b2) are provided, including those of Table A, and methods of using and administering such compounds are encompassed. In one variation of formulae (I-b1) and (I-b2), at least one of $R^{11}$ and $R^{12}$ is other than H. In one such variation of formulae (I-b1) and (I-b2), $R^{11}$ is H and $R^{12}$ is $C_1$-$C_8$ alkyl, $C_3$-$C_8$ cycloalkyl, or $C_1$-$C_8$ perhaloalkyl. In one such variation, $R^{12}$ is an unsubstituted $C_1$-$C_8$ alkyl and Q is a substituted or unsubstituted heteroaryl. In another variation, $R^{12}$ is an unsubstituted $C_1$-$C_8$ alkyl and Q is other than a halo-substituted phenyl. In one variation, the compound is of the formula (I-b1) where $R^{12}$ is $C_1$-$C_8$ alkyl (e.g., methyl). In another variation, the compound is of the formula (I-b1) where $R^{11}$ is H and $R^{12}$ is $C_1$-$C_8$ alkyl (e.g., methyl). In a particular variation of formula (I-b1), $R^{11}$ is H, $R^{12}$ is $C_1$-$C_8$ alkyl (e.g., methyl) and $X^9$ is $CR^4$ where $R^4$ is halo (e.g., chloro). In a more particular variation of formula (I-b1), $R^{11}$ is H, $R^{12}$ is $C_1$-$C_8$ alkyl (e.g., methyl), $X^9$ is $CR^4$ where $R^4$ is halo (e.g., chloro) and at least of of (i)-(iv) applies: (i) $X^7$, $X^8$ and $X^{10}$ are each CH; (ii) Q is an unsubstituted aryl (e.g., phenyl), a substituted aryl (e.g., 4-fluorophenyl, 4-chlorophenyl, 4-methyoxyphenyl, 3-fluoro-4-methoxyphenyl, 3,4-difluorophenyl, 4-chloro-3-fluorophenyl, 3,4-dichlorophenyl, 3-chloro-4-fluorophenyl, 2,4-difluorophenyl, 2,4,5-trifluorophenyl and 2,4-dichlorophenyl,), an unsubstituted heteroaryl (e.g., 3-pyridyl and 4-pyridyl) or a substituted heteroaryl (e.g., 6-methyl-3-pyridyl, 6-trifluoromethyl-3-pyridyl and 5-trifluoromethyl-3-pyridyl); (iii) $R^1$ is $C_1$-$C_8$ alkyl (e.g., methyl and cyclopropyl) and (iv) each $R^{2a}$, $R^{2b}$, $R^{3a}$, $R^{3b}$, $R^{10a}$ and $R^{10b}$ is H. In a further variation of formula (I-b1), $R^{11}$ is H, $R^{12}$ is an unsubstituted $C_1$-$C_8$ alkyl, $X^9$ is $CR^4$ where $R^4$ is an unsubstituted $C_1$-$C_8$ alkyl and Q is a substituted or unsubstituted heteroaryl. Such variations are also applicable to formula (I-b2).

In other embodiments, the compound of formula (I) has the structure:

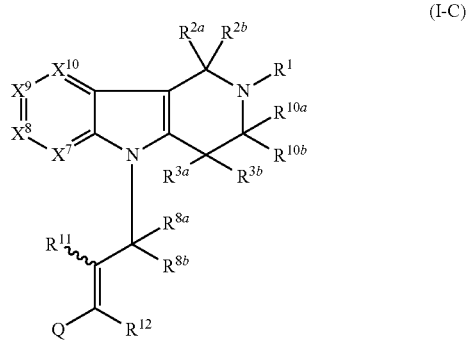

(I-C)

or a salt or solvate thereof;
wherein $R^1$, $R^{2a}$, $R^{2b}$, $R^{3a}$, $R^{3b}$, $R^{8a}$, $R^{8b}$, $R^{10a}$, $R^{10b}$, $R^{11}$, $R^{12}$, Q, $X^7$, $X^8$, $X^9$, A and $X^{10}$ are defined as for formula (I) and, where applicable, any variation thereof detailed herein. That is, variations of formula (I) detailed throughout, where applicable, apply to formula (I-C) the same as if each and every variation were specifically and individually listed for formula (I-C). In one variation of formula (I-C), $R^{8a}$ and $R^{8b}$ are each H. In another variation of formula (I-C), at least one of $R^{11}$ and $R^{12}$ is H. In yet another variation of formula (I-C), both $R^{11}$ and $R^{12}$ are H. In one aspect of formula (I-C), $R^{8a}$ and $R^{8b}$ are each H and at least one of $R^{11}$ and $R^{12}$ is H. In one such aspect of formula (I-C), $R^{8a}$ and $R^{8b}$ are each H, $R^{11}$ is H and $R^{12}$ is $C_1$-$C_8$ alkyl, $C_3$-$C_8$ cycloalkyl, or $C_1$-$C_8$ perhaloalkyl. In another such aspect of formula (I-C), $R^{8a}$, $R^{8b}$, $R^{11}$ and $R^{12}$ are each H. In a particular variation of formula (I-C), $R^{8a}$, $R^{8b}$, $R^{11}$ and $R^{12}$ are each H and at least one of $X^7$-$X^{10}$ is $CR^4$ where $R^4$ is halo (e.g., chloro). In a more particular variation of formula (I-C), $R^{8a}$, $R^{8b}$, $R^{11}$ and $R^{12}$ are each H and $X^9$ is $CR^4$ where $R^4$ is halo (e.g., chloro). In a still more particular variation of formula (I-C), $R^{2a}$, $R^{2b}$, $R^{3a}$, $R^{3b}$, $R^{8a}$, $R^{8b}$, $R^{10a}$, $R^{10b}$, $R^{11}$ and $R^{12}$ are each H, $X^9$ is $CR^4$ where $R^4$ is halo (e.g., chloro) and $R^1$ is $C_1$-$C_8$ alkyl (e.g., methyl). In any variation or aspect of formula (I-C) detailed herein, in one embodiment, the compound of formula (I-C) is in the E configuration. Similarly, in any variation or aspect of formula (I-C) detailed herein, in another embodiment, the compound of formula (I-C) is in the Z configuration.

In specific embodiments, the compound of formula (I-C) has the formula:

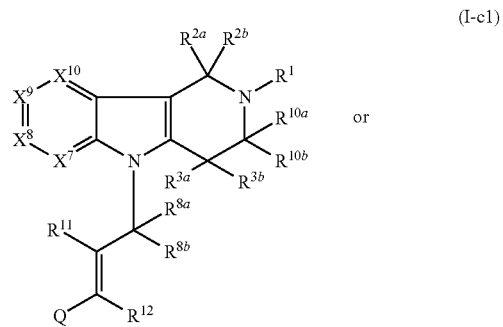

(I-c1)

or

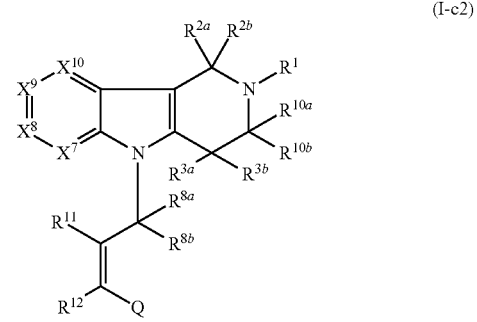

(I-c2)

or a salt or solvate thereof;
wherein $R^1$, $R^{2a}$, $R^{2b}$, $R^{3a}$, $R^{3b}$, $R^{8a}$, $R^{8b}$, $R^{10a}$, $R^{10b}$, $R^{11}$, $R^{12}$, Q, $X^7$, $X^8$, $X^9$, and $X^{10}$ are defined as for formula (I-C) and, where applicable, any variation thereof detailed herein. That is, variations of formula (I-C) and formula (I) detailed throughout, where applicable, apply to formulae (I-c1) and (I-c2) the same as if each and every variation were specifically and individually listed for formulae (I-c1) and (I-c2).

In further embodiments, the compound of formula (I) has the structure:

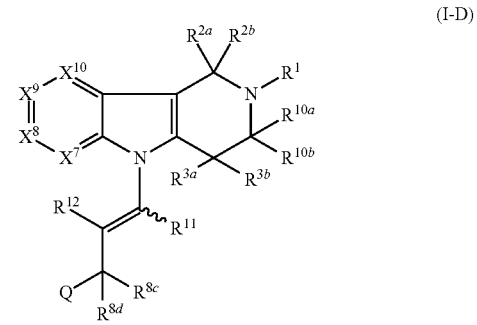

(I-D)

or a salt or solvate thereof;
wherein $R^1$, $R^{2a}$, $R^{2b}$, $R^{3a}$, $R^{3b}$, $R^{3c}$, $R^{3d}$, $R^{10a}$, $R^{10b}$, $R^{11}$, $R^{12}$, Q, $X^7$, $X^8$, $X^9$, and $X^{10}$ are defined as for formula (I)

and, where applicable, any variation thereof detailed herein. That is, variations of formula (I) detailed throughout, where applicable, apply to formula (I-D) the same as if each and every variation were specifically and individually listed for formula (I-D). In one aspect of formula (I-D), at least one of $R^{11}$ and $R^{12}$ is other than H (e.g., when $R^{12}$ is methyl). In another aspect of formula (I-D), at least one of $R^{11}$ and $R^{12}$ is other than H (e.g., when $R^{12}$ is methyl) and $R^{8c}$ and $R^{8d}$ are both H. In still another aspect of formula (I-D), at least one of $R^{11}$ and $R^{12}$ is other than H (e.g., when $R^{12}$ is methyl), $R^{8c}$ and $R^{8d}$ are both H, and at least one of $X^7$-$X^{10}$ is $CR^4$ where $R^4$ is halo. In any variation or aspect of formula (I-D) detailed herein, in one embodiment, the compound of formula (I-D) is in the E configuration. Similarly, in any variation or aspect of formula (I-D) detailed herein, in another embodiment, the compound of formula (I-D) is in the Z configuration.

In specific embodiments, the compound of formula (I-D) has the formula:

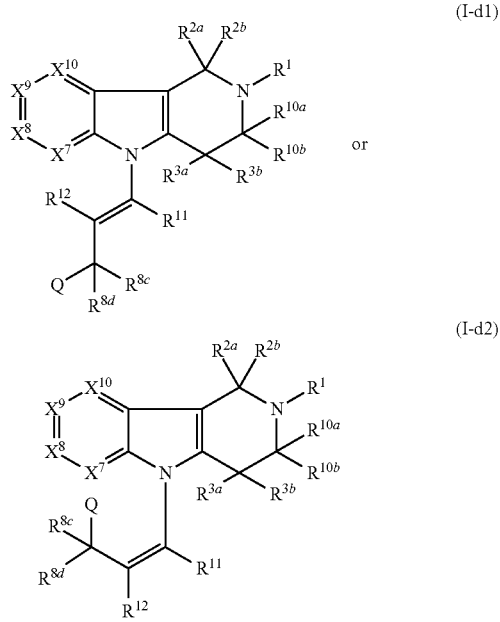

or a salt or solvate thereof;
wherein $R^1$, $R^{2a}$, $R^{2b}$, $R^{3a}$, $R^{3b}$, $R^{3c}$, $R^{8d}$, $R^{10a}$, $R^{10b}$, $R^{11}$, $R^{12}$, Q, $X^7$, $X^8$, $X^9$, and $X^{10}$ are defined as for formula (I-D) and, where applicable, any variation thereof detailed herein. That is, variations of formula (I-D) and formula (I) detailed throughout, where applicable, apply to formulae (I-d1) and (I-d2) the same as if each and every variation were specifically and individually listed for formulae (I-d1) and (I-d2).

In further embodiments, the compound of formula (I) has the structure:

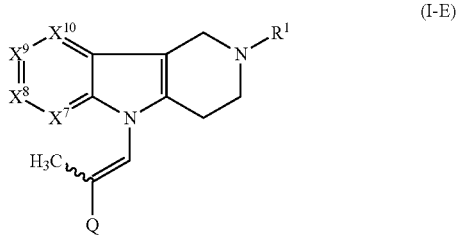

or a salt or solvate thereof;

wherein $R^1$, Q, $X^7$, $X^8$, $X^9$, and $X^{10}$ are defined as for formula (I) and, where applicable, any variation thereof detailed herein. That is, variations of formula (I) detailed throughout, where applicable, apply to formula (I-E) the same as if each and every variation were specifically and individually listed for formula (I-E). In a particular variation of formula (I-E), $X^9$ is $CR^4$ where $R^4$ is halo. In further variations of formula (I-E), $X^9$ is $CR^4$ where $R^4$ is halo and each $X^7$, $X^8$ and $X^{10}$ is CH. In still further variations of formula (I-E), $X^9$ is $CR^4$ where $R^4$ is halo and Q is a substituted aryl. In other variations of formula (I-E), $X^9$ is $CR^4$ where $R^4$ is halo and Q is a substituted or unsubstituted heteroaryl. In one aspect of formula (I-E), $R^1$ is a $C_1$-$C_8$ alkyl (e.g., methyl) and $X^9$ is $CR^4$ where $R^4$ is halo. In another aspect of formula (I-E), $R^1$ is a $C_1$-$C_8$ alkyl (e.g., methyl), $X^9$ is $CR^4$ where $R^4$ is halo (e.g., chloro) and Q is a substituted aryl (e.g., a substituted phenyl). In a further aspect of formula (I-E), $R^1$ is methyl, $R^9$ is $CR^4$ where $R^4$ is chloro, $X^7$, $X^8$ and $X^{10}$ are each CH and Q is a substituted aryl or a substituted or unsubstituted heteroaryl. In another variation of formula (I-E), Q is a substituted or unsubstituted heteroaryl. When Q is an unsubstituted or substituted heteroaryl, in one variation it is a heteroaryl containing an annular nitrogen atom. In one aspect, when Q is an unsubstituted or substituted heteroaryl the heteroaryl contains only nitrogen and carbon annular atoms. In a particular variation, Q is an unsubstituted pyridyl that may be bound to the parent structure at any available ring position. For example, in one variation of formula (I), Q is 4-pyridyl, 3-pyridyl or 2-pyridyl. When Q is a substituted heteroaryl in one aspect it is a substituted pyridyl. When Q is a substituted pyridyl, the pyridyl may be substituted with one or more than one substituent and the substituted pyridyl may be bound to the parent structure at any available ring position. For example, in one variation of formula (I-E), Q is a monosubstituted pyridyl where the substituent is a $C_1$-$C_8$ unsubstituted alkyl (e.g., methyl). In a particular variation of formula (I-E), $X^9$ is $CR^4$ where $R^4$ is an unsubstituted $C_1$-$C_8$ alkyl and Q is a substituted or unsubstituted heteroaryl. In a further variation of formula (I-E), Q is a substituted or unsubstituted pyridyl and at least one of (i)-(iii) applies: (i) $X^9$ is $CR^4$ where $R^4$ is an unsubstituted $C_1$-$C_8$ alkyl; (ii) $R^1$ is an unsubstituted $C_1$-$C_8$ alkyl and (iii) $X^7$, $X^8$ and $X^{10}$ are each CH.

In specific embodiments, the compound of formula (I-E) has the formula:

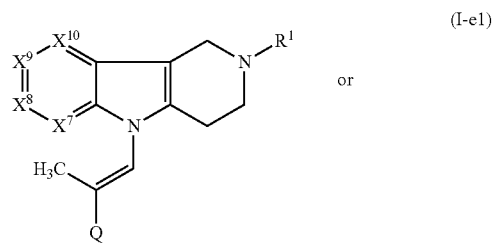

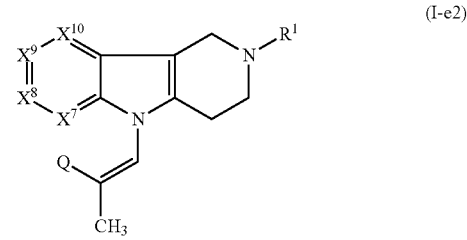

or a salt or solvate thereof;

wherein $R^1$, Q, $X^7$, $X^8$, $X^9$, and $X^{10}$ are defined as for formula (I-E) and, where applicable, any variation thereof detailed herein. That is, variations of formula (I-E) and formula (I) detailed throughout, where applicable, apply to formulae (I-e1) and (I-e2) the same as if each and every variation were specifically and individually listed for formulae (I-e1) and (I-e2). In a particular variation of compounds (1-e1) and (1-e2), Q is a substituted or unsubstituted heteroaryl.

In further embodiments, the compound of formula (I) has the structure:

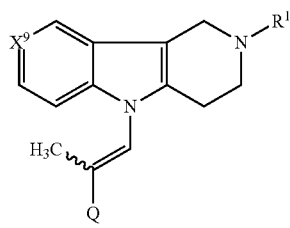

(I-F)

or a salt or solvate thereof;

wherein $X^9$ is CH or $CR^4$ and $R^4$ and Q are defined as for formula (I) and, where applicable, any variation thereof detailed herein. That is, variations of formula (I) detailed throughout, where applicable, apply to formula (I-F) the same as if each and every variation were specifically and individually listed for formula (I-F). In one variation of formula (I-F), $X^9$ is CH or $CR^4$ where $R^4$ is -halo or substituted or unsubstituted $C_1$-$C_8$ alkyl. In a particular variation of formula (I-F), $X^9$ is $CR^4$ where $R^4$ is halo (e.g. chloro). In another particular variation of formula (I-F), $X^9$ is $CR^4$ where $R^4$ is unsubstituted $C_1$-$C_8$ alkyl (e.g. methyl). In a particular variation of formula (I-F), $X^9$ is CH. In further variations of formula (I-F), Q is a substituted or unsubstituted heteroaryl. In one variation, Q is an unsubstituted heteroaryl (e.g. 4-pyridyl or 4-pyrimidyl). In still further variations of formula (I-F), $X^9$ is CH or $CR^4$ where $R^4$ is halo or substituted or unsubstituted $C_1$-$C_8$ alkyl and Q is a substituted or unsubstituted heteroaryl. In one aspect of formula (I-F), $X^9$ is $CR^4$ where $R^4$ is a $C_1$-$C_8$ alkyl (e.g., methyl) and Q is a substituted or unsubstituted heteroaryl. In another aspect of formula (I-F), $X^9$ is $CR^4$ where $R^4$ is halo (e.g., chloro) and Q is a substituted or unsubstituted heteroaryl. In another aspect of formula (I-F), $X^9$ is CH and Q is a substituted or unsubstituted heteroaryl. In a further aspect of formula (I-F), $X^9$ is CH or $CR^4$ where $R^4$ is methyl or chloro and Q is 4-pyridyl.

In specific embodiments, the compound of formula (I-F) has the formula:

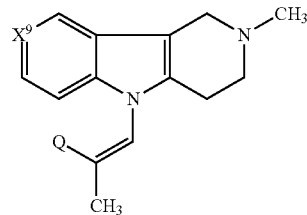

(I-f1)

or

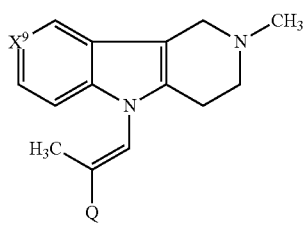

(I-f2)

or a salt or solvate thereof;

wherein $X^9$ is CH or $CR^4$ and $R^4$ and Q are defined as for formula (I-F) and, where applicable, any variation thereof detailed herein. That is, variations of formula (I-F) and formula (I) detailed throughout, where applicable, apply to formulae (I-f1) and (I-f2) the same as if each and every variation were specifically and individually listed for formulae (I-f1) and (I-f2). In one particular aspect of formula (I-f1), $X^9$ is CH or $CR^4$ where $R^4$ is methyl or chloro and Q is 4-pyridyl. In one particular aspect of formula (I-f2), $X^9$ is CH or $CR^4$ where $R^4$ is methyl or chloro and Q is 4-pyridyl.

In one variation, compounds of the formula (J-1) are provided:

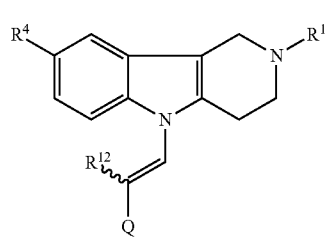

(J-1)

or a salt or solvate thereof, where $R^1$, $R^4$, $R^{12}$ and Q are defined as for formula (I) and, where applicable, any variation thereof detailed herein. That is, variations of formula (I) detailed throughout, where applicable, apply to formula (J-1) the same as if each and every variation were specifically and individually listed for formula (J-1).

In one variation, compounds of the formula (J-1) are provided, or a salt or solvate thereof, where $R^1$ is a substituted or unsubstituted $C_1$-$C_8$ alkyl; $R^4$ is H, halo, trifluoromethyl, a $C_1$-$C_8$ unsubstituted alkyl or a substituted amino; $R^{12}$ is substituted or unsubstituted $C_1$-$C_8$ alkyl, substituted or unsubstituted aryl, halo and alkoxy; Q is substituted aryl or a substituted or unsubstituted heteroaryl and the ~ bond indicates the presence of either an E or Z double bond configuration. In one variation of formula (J-1), $R^1$ is an unsubstituted $C_{1-8}$ alkyl or a $C_1$-$C_8$ alkyl substituted with a halo or hydroxyl group. In one such variation, $R^1$ is methyl, 2-haloethyl (e.g., 2-fluoroethyl), 2,2,2-trifluoroethyl, or a hydroxyl-substituted pentyl group. In a particular variation of formula (J-1), $R^1$ is —$CH_3$, —$CH_2CH_2F$, —$CH_2CF_3$, or —$CH_2CH_2C(CH_3)_2OH$. In another variation of formula (J-1), $R^4$ is H, halo, methyl, trifluoromethyl, or a substituted amino of the formula —N(H)($C_1$-$C_8$ unsubstituted alkyl). When $R^4$ is a halo (e.g., fluoro or chloro), in one aspect $R^4$ is chloro. In one variation of formula (J-1), $R^4$ is H, methyl or chloro. In one variation of formula (J-1), $R^4$ is methyl or chloro. When $R^4$ is a substituted amino of the formula —N(H)($C_1$-$C_8$ unsubstituted alkyl), in one aspect $C_1$-$C_8$ unsubstituted alkyl is a linear $C_1$-$C_8$ unsubstituted alkyl such as methyl or ethyl. In a particular variation of formula (J-1), $R^4$ is —N(H)(CH$_3$). It is understood that any $R^1$ for formula (J-1) may be combined with any $R^4$ of formula (J-1) the same as if each and every combination where specifically and individually listed. For example, compounds of the formula (J-1) are provided where $R^1$ is —CH$_3$, —CH$_2$CH$_2$F, —CH$_2$CF$_3$, or —CH$_2$CH$_2$C(CH$_3$)$_2$OH and $R^4$ is H, chloro, fluoro, methyl, trifluoromethyl, or —N(H)(CH$_3$) Likewise, compounds of the formula (J-1) are provided where $R^1$ is methyl and $R^4$ is H, halo, methyl or a substituted amino of the formula —N(H)(C$_1$-C$_8$ unsubstituted alkyl). In one such aspect, compounds of the formula (J-1) are provided where $R^1$ is methyl and $R^4$ is H, halo or methyl. In one such aspect, compounds of the formula (J-1) are provided where $R^1$ is methyl and $R^4$ is halo (e.g., fluoro or chloro), trifluoromethyl, or methyl. In one variation of formula (J-1), $R^{12}$ is an unsubstituted $C_{1-8}$ alkyl or a $C_1$-$C_8$ alkyl substituted with a halo, hydroxyl, carboxyl or acylamino group. In one such variation, $R^{12}$ is methyl, ethyl, isopropyl, t-butyl, cyclopropyl, cyclobutyl, cyclohexyl, halo (e.g., fluoro), a carboxyl-substituted methyl group or an amido-substituted methyl group. In a particular variation, $R^{12}$ is methyl. When Q of formula (J-1) is a substituted aryl, in one aspect Q is a substituted phenyl. In one aspect, Q is a mono-substituted phenyl. In a particular aspect, Q of formula (J-1) is a halo-substituted phenyl, alkoxy-substituted phenyl or an acylamino-substituted phenyl. Thus, compounds of the formula (J-1) are provided where Q in one variation is a phenyl mono-substituted with a fluoro, $C_1$-$C_8$ alkoxy (e.g., methoxy), an acylamino moiety of the formula —C(O)NH(C$_1$-C$_8$ unsubstituted alkyl) or an acylamino moiety of the formula —C(O)N(C$_1$-C$_8$ unsubstituted alkyl)$_2$, such as 2-fluoro-phenyl, 4-fluoro-phenyl, 4-methoxy-phenyl, 4-(C(O)NH(CH$_3$) and 4-(C(O)N(CH$_3$)$_2$)-phenyl. In one aspect, Q is a di-substituted phenyl. In one aspect, Q of formula (J-1) is a di-halo substituted phenyl group such as 3,4-difluoro-phenyl. In a particular aspect, Q of formula (I-G) is a phenyl group substituted with one halo group and one $C_1$-$C_8$ alkoxy group (e.g., methoxy). Thus, compounds of the formula (J-1) are provided where Q in one variation is a phenyl substituted with a fluoro and a $C_1$-$C_8$ alkoxy group, such as 3-fluoro-4-methoxy-phenyl. When Q of formula (J-1) is a substituted or unsubstituted heteroaryl, in one variation the substituted or unsubstituted heteroaryl is a pyridyl or pyrimidyl moiety. Thus, in one aspect of formula (J-1), Q is an unsubstituted pyridyl or pyrimidyl, such as 3-pyridyl, 4-pyridyl and 4-pyrimidyl. In another aspect of formula (J-1), Q is a substituted pyridyl, such as 6-methyl-3-pyridyl. It is understood that any Q for formula (J-1) may be combined with any $R^1$ and/or $R^4$ of formula (J-1) the same as if each and every combination where specifically and individually listed. For example, compounds of the formula (J-1) are provided where $R^1$ is —CH$_3$, —CH$_2$CH$_2$F, —CH$_2$CF$_3$, or —CH$_2$CH$_2$C(CH$_3$)$_2$OH; $R^4$ is H, chloro, fluoro, methyl, trifluoromethyl, or —N(H)(CH$_3$) and Q is 4-pyridyl, 3-pyridyl, 6-methyl-3-pyridyl, 6-pyrimidyl, 4-fluoro-phenyl, 4-methoxy-phenyl, 3-fluoro-4-methoxy-phenyl or 4-dimethylcarbamoyl-phenyl. Likewise, compounds of the formula (J-1) are provided where $R^1$ is methyl; $R^4$ is H, halo or methyl and Q is an unsubstituted pyridyl. In any variation of formula (J-1), in one aspect, the ⁓ bond indicates the presence of an E double bond configuration. In any variation of formula (J-1), in one aspect, the ⁓ bond indicates the presence of a Z double bond configuration.

In specific variations, compounds of the formula (J-1) have the formula:

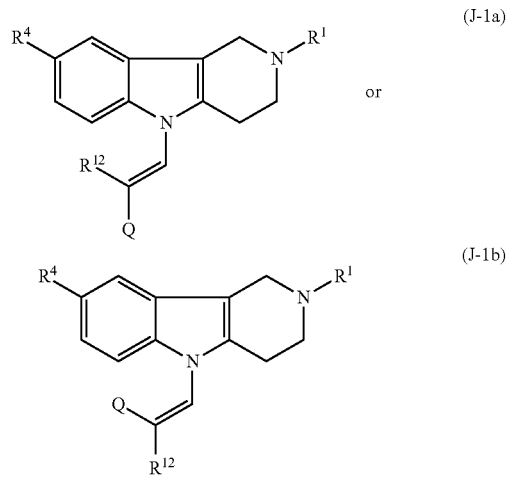

or a salt or solvate thereof; wherein $R^1$, $R^4$, $R^{12}$ and Q are defined as for formula (J-1) and, where applicable, any variation thereof detailed herein. That is, variations of formula (J-1) detailed throughout, where applicable, apply to formulae (J-1a) and (J-1b) the same as if each and every variation were specifically and individually listed for formulae (J-1a) and (J-1b). In one particular aspect of formula (J-1a), $R^1$ is —CH$_3$, —CH$_2$CH$_2$F, —CH$_2$CF$_3$, or —CH$_2$CH$_2$C(CH$_3$)$_2$OH; $R^4$ is H, chloro, fluoro, methyl, trifluoromethyl, or —N(H)(CH$_3$) $R^{12}$ is an unsubstituted $C_{1-8}$ alkyl or a $C_1$-$C_8$ alkyl substituted with a halo, hydroxyl, carboxyl or acylamino group. In one such variation, $R^1$ is methyl, ethyl, isopropyl, t-butyl, cyclopropyl, cyclobutyl, cyclohexyl, halo (e.g., fluoro), a carboxyl-substituted methyl group or a amido-substituted methyl group and Q is 4-pyridyl, 3-pyridyl, 6-methyl-3-pyridyl, 6-pyrimidyl, 4-fluoro-phenyl, 4-methoxy-phenyl, 3-fluoro-4-methoxy-phenyl or 4-dimethylcarbamoyl-phenyl. In another aspect of formula (J-1a), $R^1$ is methyl, $R^4$ is H, chloro or methyl, $R^{12}$ is methyl, and Q is a substituted or unsubstituted pyridyl. In one particular aspect of formula (J-1b), $R^1$ is methyl, $R^4$ is methyl, $R^{12}$ is methyl, and Q is a substituted or unsubstituted pyridyl. Pharmaceutically acceptable salts of compounds of the formula (J-1), (J-1a) and (J-1b) are also provided.

In one variation, compounds of the formula (J-2) are provided:

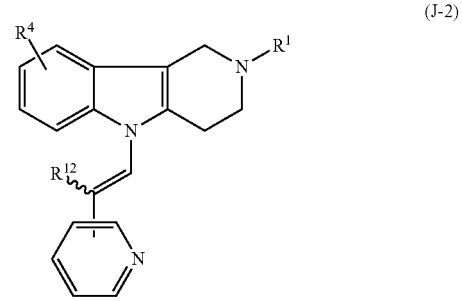

or a salt or solvate thereof, where $R^1$ is a substituted or unsubstituted $C_1$-$C_8$ alkyl; $R^4$ is H, halo or a $C_1$-$C_8$ unsubstituted alkyl, $R^{12}$ is substituted or unsubstituted $C_{1-8}$ alkyl, substituted or unsubstituted aryl, halo and alkoxy and the ⁓ bond indicates the presence of either an E or Z double bond configuration and where R⁴ and the pyridyl moiety may be connected to the parent structure at any available position. In one variation of formula (J-2), $R^1$ is an unsubstituted $C_{1-8}$ alkyl or a $C_1$-$C_8$ alkyl substituted with a halo or hydroxyl group. In one such variation, $R^1$ is methyl, 2-haloethyl (e.g., 2-fluoroethyl), 2,2,2-trifluoroethyl, or a hydroxyl-substituted pentyl group. In a particular variation of formula (J-2), $R^1$ is —CH₃, —CH₂CH₂F, —CH₂CF₃, or —CH₂CH₂C(CH₃)₂OH. In another variation of formula (J-2), $R^4$ is H, halo, trifluoromethyl, or methyl. When $R^4$ is a halo (e.g., fluoro or chloro), in one aspect $R^4$ is chloro. In one variation of formula (J-2), $R^4$ is H, methyl or chloro. In one variation of formula (J-2), $R^4$ is methyl or chloro. In one variation of formula (J-1), $R^{12}$ is an unsubstituted $C_{1-8}$ alkyl or a $C_1$-$C_8$ alkyl substituted with a halo, hydroxyl, carboxyl or acylamino group. In one such variation, $R^1$ is methyl, ethyl, isopropyl, t-butyl, cyclopropyl, cyclobutyl, cyclohexyl, halo (e.g., fluoro), a carboxyl-substituted methyl group or an amido-substituted methyl group. In a particular variation, $R^{12}$ is methyl. It is understood that any $R^1$ for formula (J-2) may be combined with any $R^4$ of formula (J-2) the same as if each and every combination were specifically and individually listed. For example, compounds of the formula (J-2) are provided where $R^1$ is —CH₃, —CH₂CH₂F, —CH₂CF₃, or —CH₂CH₂C(CH₃)₂OH and $R^4$ is H, chloro, fluoro, trifluoromethyl, or methyl. Likewise, compounds of the formula (J-2) are provided where $R^1$ is methyl and $R^4$ is H, halo or methyl. In one such aspect, compounds of the formula (J-2) are provided where $R^1$ is methyl and $R^4$ is halo (e.g., fluoro or chloro), trifluoromethyl, or methyl. In any variation of formula (J-2), in one aspect, the ⌇ bond indicates the presence of an E double bond configuration. In any variation of formula (J-2), in one aspect, the ⌇ bond indicates the presence of a Z double bond configuration.

In specific variations, compounds of the formula (J-2) have the formula:

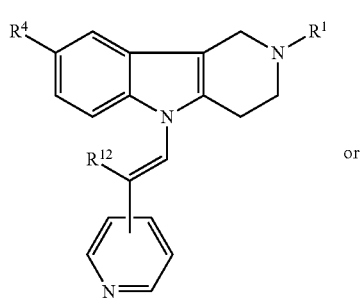

(J-2a)

or

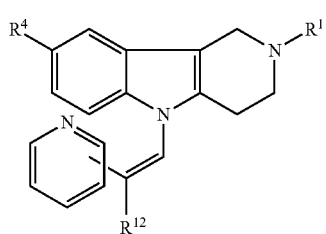

(J-2b)

or a salt or solvate thereof; wherein $R^1$, $R^4$ and $R^{12}$ are defined as for formula (J-2). That is, variations of formula (J-2) detailed throughout, where applicable, apply to formulae (J-2a) and (J-2b) the same as if each and every variation were specifically and individually listed for formulae (J-2a)

and (J-2b). Pharmaceutically acceptable salts of compounds of the formula (J-2), (J-2a) and (J-2b) are also provided.

Compounds of the formula (J-3) and (J-4) are also provided:

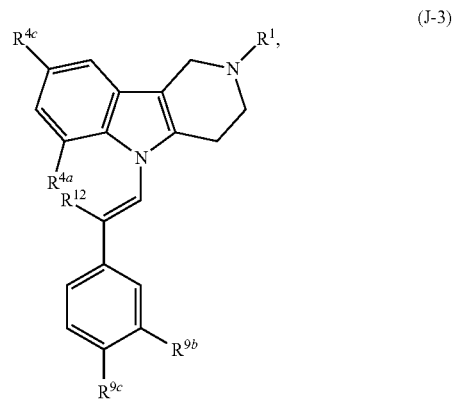

(J-3)

(J-4)

or a salt or solvate thereof, wherein $R^1$ is CH₃, —CH₂CH₂—C(CH₃)₂(OH), —CH₂CF₃, or —CH₂CH₂F; $R^{4a}$ is H or F; $R^{4c}$ is H, CH₃, Cl, F, CF₃, or —NHCH₃; $R^{9b}$ is H or F; $R^{9c}$ is F, OCH₃, —CONH(CH₃) or —CON(CH₃)₂ and $R^{12}$ is an unsubstituted $C_{1-8}$ alkyl or a $C_1$-$C_8$ alkyl substituted with a halo, hydroxyl, carboxyl or acylamino group. In one embodiment of formula (J-3) and (J-4), $R^1$ is CH₃; $R^{4a}$ is H; $R^{4c}$ is CH₃, Cl, F or —NHCH₃; $R^{9b}$ is H or F; $R^{9c}$ is F, OCH₃, —CONH(CH₃) or —CON(CH₃)₂; and $R^{12}$ is methyl, ethyl, isopropyl, t-butyl, cyclopropyl, cyclobutyl, cyclohexyl, halo (e.g., fluoro), a carboxyl-substituted methyl group or a amido-substituted methyl group. In a further embodiment, $R^1$ is CH₃; $R^{4a}$ is H; $R^{4c}$ is CH₃, Cl, F or —NHCH₃; $R^{9b}$ is H; $R^{9c}$ is F, OCH₃; and $R^{12}$ is methyl Compounds of the formula (J-5) and (J-6) are also embraced,

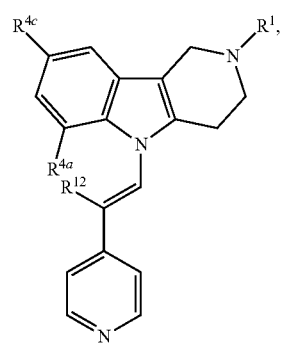

(J-5)

-continued

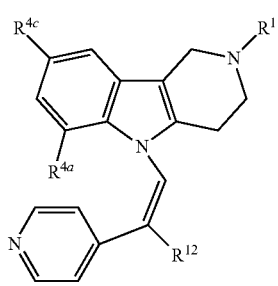
(J-6)

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; $R^{4c}$ is H, $CH_3$, Cl, F, $CF_3$, or —$NHCH_3$; and $R^{12}$ is methyl, ethyl, isopropyl, t-butyl, cyclopropyl, cyclobutyl, cyclohexyl, halo (e.g., fluoro), a carboxyl-substituted methyl group or a amido-substituted methyl group. In one embodiment of formula (J-5) and (J-6) $R^1$ is $CH_3$; $R^{4a}$ is H; $R^{4c}$ is $CH_3$, Cl, F or —$NHCH_3$; and $R^{12}$ is $CH_3$. In yet another variation, $R^1$ is $CH_3$; $R^{4a}$ is H; $R^{4c}$ is $CH_3$, Cl or F; and $R^{12}$ is $CH_3$.

In one variation, compounds of the formula (J-7) or (J-8) are provided

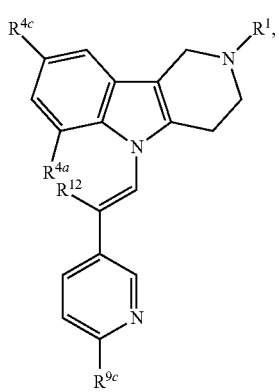
(J-7)

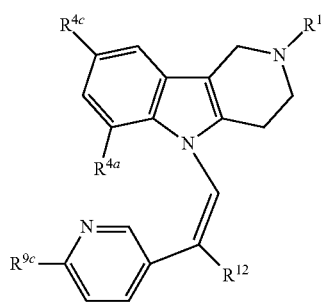
(J-8)

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; $R^{4c}$ is H, $CH_3$, Cl, F, $CF_3$, or —$NHCH_3$; $R^{9c}$ is H, F, $CH_3$, $CF_3$, $OCH_3$, —$CONH(CH_3)$ or —$CON(CH_3)_2$; and $R^{12}$ is methyl, ethyl, isopropyl, t-butyl, cyclopropyl, cyclobutyl, cyclohexyl, halo (e.g., fluoro), a carboxyl-substituted methyl group or a amido-substituted methyl group. In one variation of formula (J-7) and (J-8) $R^1$ is $CH_3$; $R^{4a}$ is H; $R^{4c}$ is $CH_3$, Cl, F, $CF_3$, or —$NHCH_3$; and $R^{9c}$ is H, F, $CF_3$, or $CH_3$; and $R^{12}$ is methyl. In a particular variation, $R^1$ is $CH_3$; $R^{4a}$ is H; $R^{4c}$ is $CH_3$, $CF_3$, Cl or F; and $R^{9c}$ is H, $CF_3$, or $CH_3$.

In another variation, compounds of the formula (J-9) and (J-10) are provided:

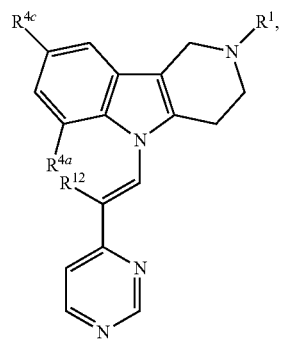
(J-9)

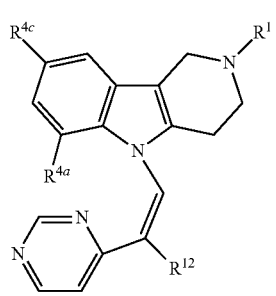
(J-10)

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; and $R^{4c}$ is H, $CH_3$, Cl, F, —$CF_3$, or —$NHCH_3$. $R^{12}$ is methyl, ethyl, isopropyl, t-butyl, cyclopropyl, cyclobutyl, cyclohexyl, halo (e.g., fluoro), a carboxyl-substituted methyl group or a amido-substituted methyl group In one embodiment of formula (J-9) and (J-10), $R^1$ is $CH_3$; $R^{4a}$ is H; and $R^{4c}$ is $CH_3$, Cl, F, $CF_3$, or —$NHCH_3$. In one embodiment $R^1$ is $CH_3$; $R^{4a}$ is H; $R^{4c}$ is $CH_3$, $CF_3$, Cl or F; and $R^{12}$ is methyl.

In one variation, compounds of the formula (I-G) are provided:

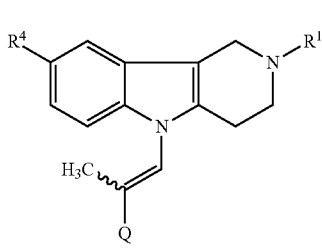
(I-G)

or a salt or solvate thereof, where $R^1$, $R^4$ and Q are defined as for formula (I) and, where applicable, any variation thereof detailed herein. That is, variations of formula (I) detailed throughout, where applicable, apply to formula (I-G) the same as if each and every variation were specifically and individually listed for formula (I-G).

In one variation, compounds of the formula (I-G) are provided, or a salt or solvate thereof, where $R^1$ is a substituted or unsubstituted $C_1$-$C_8$ alkyl; $R^4$ is H, halo, trifluoromethyl, a $C_1$-$C_8$ unsubstituted alkyl or a substituted amino; Q is substituted aryl or a substituted or unsubstituted heteroaryl and the ⌇ bond indicates the presence of either an E or Z double bond configuration. In one variation of formula (I-G), $R^1$ is an unsubstituted $C_{1-8}$ alkyl or a $C_1$-$C_8$ alkyl substituted with a halo or hydroxyl group. In one such variation, $R^1$ is methyl, 2-haloethyl (e.g., 2-fluoroethyl), 2,2,2-trifluoroethyl, or a hydroxyl-substituted pentyl group. In a particular variation of formula (I-G), $R^1$ is —CH$_3$, —CH$_2$CH$_2$F, —CH$_2$CF$_3$, or —CH$_2$CH$_2$C(CH$_3$)$_2$OH. In another variation of formula (I-G), $R^4$ is H, halo, methyl, trifluoromethyl, or a substituted amino of the formula —N(H)(C$_1$-C$_8$ unsubstituted alkyl). When $R^4$ is a halo (e.g., fluoro or chloro), in one aspect $R^4$ is chloro. In one variation of formula (I-G), $R^4$ is H, methyl or chloro. In one variation of formula (I-G), $R^4$ is methyl or chloro. When $R^4$ is a substituted amino of the formula —N(H)(C$_1$-C$_8$ unsubstituted alkyl), in one aspect C$_1$-C$_8$ unsubstituted alkyl is a linear C$_1$-C$_8$ unsubstituted alkyl such as methyl or ethyl. In a particular variation of formula (I-G), $R^4$ is —N(H)(CH$_3$). It is understood that any $R^1$ for formula (I-G) may be combined with any $R^4$ of formula (I-G) the same as if each and every combination where specifically and individually listed. For example, compounds of the formula (I-G) are provided where $R^1$ is —CH$_3$, —CH$_2$CH$_2$F, —CH$_2$CF$_3$, or —CH$_2$CH$_2$C(CH$_3$)$_2$OH and $R^4$ is H, chloro, fluoro, methyl, trifluoromethyl, or —N(H)(CH$_3$). Likewise, compounds of the formula (I-G) are provided where $R^1$ is methyl and $R^4$ is H, halo, methyl or a substituted amino of the formula —N(H)(C$_1$-C$_8$ unsubstituted alkyl). In one such aspect, compounds of the formula (I-G) are provided where $R^1$ is methyl and $R^4$ is H, halo, trifluoromethyl, or methyl. In one such aspect, compounds of the formula (I-G) are provided where $R^1$ is methyl and $R^4$ is halo (e.g., fluoro or chloro) or methyl. When Q of formula (I-G) is a substituted aryl, in one aspect Q is a substituted phenyl. In one aspect, Q is a mono-substituted phenyl. In a particular aspect, Q of formula (I-G) is a halo-substituted phenyl, alkoxy-substituted phenyl or a acylamino-substituted phenyl. Thus, compounds of the formula (I-G) are provided where Q in one variation is a phenyl mono-substituted with a fluoro, C$_1$-C$_8$ alkoxy (e.g., methoxy), an acylamino moiety of the formula —C(O)NH(C$_1$-C$_8$ unsubstituted alkyl) or an acylamino moiety of the formula —C(O)N(C$_1$-C$_8$ unsubstituted alkyl)$_2$, such as 2-fluoro-phenyl, 4-fluoro-phenyl, 4-methoxy-phenyl, 4-(C(O)NH(CH$_3$) and 4-(C(O)N(CH$_3$)$_2$)-phenyl. In one aspect, Q is a di-substituted phenyl. In one aspect, Q of formula (I-G) is a di-halo substituted phenyl group such as 3,4-difluoro-phenyl. In a particular aspect, Q of formula (I-G) is a phenyl group substituted with one halo group and one C$_1$-C$_8$ alkoxy group (e.g., methoxy). Thus, compounds of the formula (I-G) are provided where Q in one variation is a phenyl substituted with a fluoro and a C$_1$-C$_8$ alkoxy group, such as 3-fluoro-4-methoxy-phenyl. When Q of formula (I-G) is a substituted or unsubstituted heteroaryl, in one variation the substituted or unsubstituted heteroaryl is a pyridyl or pyrimidyl moiety. Thus, in one aspect of formula (I-G), Q is an unsubstituted pyridyl or pyrimidyl, such as 3-pyridyl, 4-pyridyl and 4-pyrimidyl. In another aspect of formula (I-G), Q is a substituted pyridyl, such as 6-methyl-3-pyridyl. It is understood that any Q for formula (I-G) may be combined with any $R^1$ and/or $R^4$ of formula (I-G) the same as if each and every combination where specifically and individually listed. For example, compounds of the formula (I-G) are provided where $R^1$ is —CH$_3$, —CH$_2$CH$_2$F, —CH$_2$CF$_3$, or —CH$_2$CH$_2$C(CH$_3$)$_2$OH; $R^4$ is H, chloro, fluoro, trifluoromethyl, methyl or —N(H)(CH$_3$) and Q is 4-pyridyl, 3-pyridyl, 6-methyl-3-pyridyl, 6-trifluoromethyl-3-pyridyl, 6-pyrimidyl, 4-fluoro-phenyl, 4-methoxy-phenyl, 3-fluoro-4-methoxy-phenyl or 4-dimethylcarbamoyl-phenyl. Likewise, compounds of the formula (I-G) are provided where $R^1$ is methyl; $R^4$ is H, halo or methyl and Q is an unsubstituted pyridyl. In any variation of formula (I-G), in one aspect, the ⁀ bond indicates the presence of an E double bond configuration. In any variation of formula (I-G), in one aspect, the ⁀ bond indicates the presence of a Z double bond configuration.

In specific variations, compounds of the formula (I-G) have the formula:

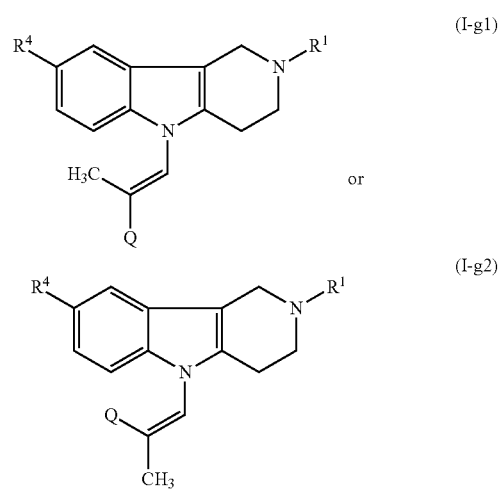

or a salt or solvate thereof; wherein $R^1$, $R^4$ and Q are defined as for formula (I-G) and, where applicable, any variation thereof detailed herein. That is, variations of formula (I-G) detailed throughout, where applicable, apply to formulae (I-g1) and (I-g2) the same as if each and every variation were specifically and individually listed for formulae (I-g1) and (I-g2). In one particular aspect of formula (I-g1), $R^1$ is —CH$_3$, —CH$_2$CH$_2$F, —CH$_2$CF$_3$, or —CH$_2$CH$_2$C(CH$_3$)$_2$OH; $R^4$ is H, chloro, fluoro, methyl trifluoromethyl, or —N(H)(CH$_3$) and Q is 4-pyridyl, 3-pyridyl, 6-methyl-3-pyridyl, 6-trifluoromethyl-3-pyridyl, 6-pyrimidyl, 4-fluoro-phenyl, 4-methoxy-phenyl, 3-fluoro-4-methoxy-phenyl or 4-dimethylcarbamoyl-phenyl. In another aspect of formula (I-g1), $R^1$ is methyl, $R^4$ is H, chloro or methyl and Q is a substituted or unsubstituted pyridyl. In one particular aspect of formula (I-g2), $R^1$ is methyl, $R^4$ is methyl and Q is a substituted or unsubstituted pyridyl. Pharmaceutically acceptable salts of compounds of the formula (I-G), (I-g1) and (I-g2) are also provided.

In one variation, compounds of the formula (I-H) are provided:

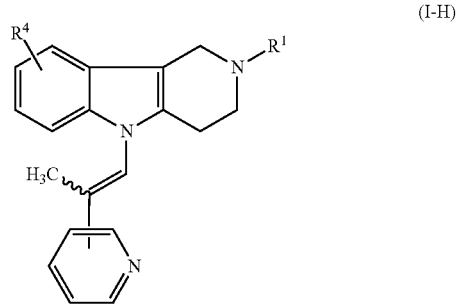

or a salt or solvate thereof, where $R^1$ is a substituted or unsubstituted $C_1$-$C_8$ alkyl; $R^4$ is H, halo or a $C_1$-$C_8$ unsubstituted alkyl and the ～ bond indicates the presence of either an E or Z double bond configuration and where $R^4$ and the pyridyl moiety may be connected to the parent structure at any available position. In one variation of formula (I-H), $R^1$ is an unsubstituted $C_{1-8}$ alkyl or a $C_1$-$C_8$ alkyl substituted with a halo or hydroxyl group. In one such variation, $R^1$ is methyl, 2-haloethyl (e.g., 2-fluoroethyl), 2,2,2-trifluoroethyl, or a hydroxyl-substituted pentyl group. In a particular variation of formula (I-H), $R^1$ is —$CH_3$, —$CH_2CH_2F$, —$CH_2CF_3$, or —$CH_2CH_2C(CH_3)_2OH$. In another variation of formula (I-H), $R^4$ is H, halo, trifluoromethyl, or methyl. When $R^4$ is a halo (e.g., fluoro or chloro), in one aspect $R^4$ is chloro. In one variation of formula (I-H), $R^4$ is H, methyl or chloro. In one variation of formula (I-H), $R^4$ is methyl or chloro. It is understood that any $R^1$ for formula (I-H) may be combined with any $R^4$ of formula (I-H) the same as if each and every combination were specifically and individually listed. For example, compounds of the formula (I-H) are provided where $R^1$ is —$CH_3$, —$CH_2CH_2F$, —$CH_2CF_3$, or —$CH_2CH_2C(CH_3)_2OH$ and $R^4$ is H, chloro, fluoro, trifluoromethyl, or methyl. Likewise, compounds of the formula (I-H) are provided where $R^1$ is methyl and $R^4$ is H, halo or methyl. In one such aspect, compounds of the formula (I-H) are provided where $R^1$ is methyl and $R^4$ is halo (e.g., fluoro or chloro) or methyl. In any variation of formula (I-H), in one aspect, the ～ bond indicates the presence of an E double bond configuration. In any variation of formula (I-H), in one aspect, the ～ bond indicates the presence of a Z double bond configuration.

In specific variations, compounds of the formula (I-H) have the formula:

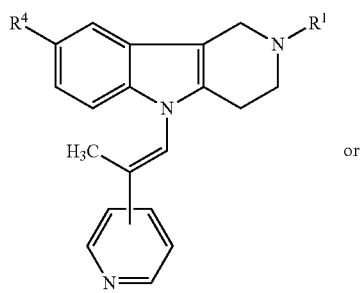

(I-h1)

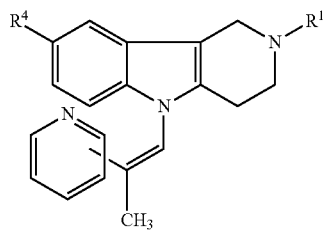

(I-h2)

or a salt or solvate thereof; wherein $R^1$ and $R^4$ are defined as for formula (I-H). That is, variations of formula (I-H) detailed throughout, where applicable, apply to formulae (I-h1) and (I-h2) the same as if each and every variation were specifically and individually listed for formulae (I-h1) and (I-h2). Pharmaceutically acceptable salts of compounds of the formula (I-H), (I-h1) and (I-h2) are also provided.

Compounds of the formula (H-1) and (H-2) are also provided:

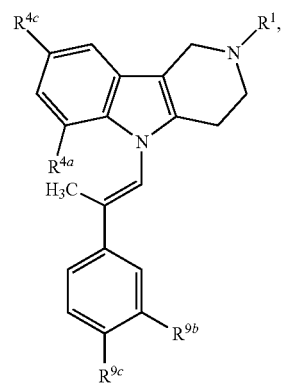

(H-1)

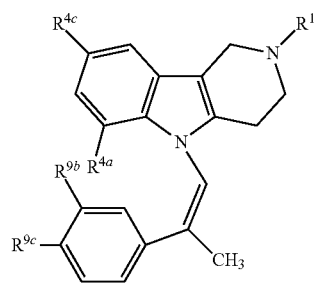

(H-2)

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; $R^{4c}$ is H, $CH_3$, $CF_3$, Cl, F or —$NHCH_3$; $R^{9b}$ is H or F; and $R^{9c}$ is F, $OCH_3$, —$CONH(CH_3)$ or —$CON(CH_3)_2$. In one embodiment of formula (H-1) and (H-2), $R^1$ is $CH_3$; $R^{4a}$ is H; $R^{4c}$ is $CH_3$, Cl, F, $CF_3$, or —$NHCH_3$; $R^{9b}$ is H or F; and $R^{9c}$ is F, $OCH_3$, —$CONH(CH_3)$ or —$CON(CH_3)_2$. In a further embodiment, $R^1$ is $CH_3$; $R^{4a}$ is H; $R^{4c}$ is $CH_3$, Cl, F or —$NHCH_3$; $R^{9b}$ is H; and $R^{9c}$ is F, $OCH_3$.

Compounds of the formula (H-3) and (H-4) are also embraced,

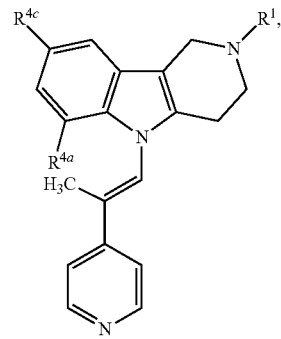

(H-3)

-continued

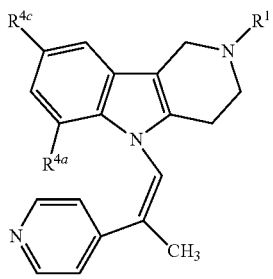
(H-4)

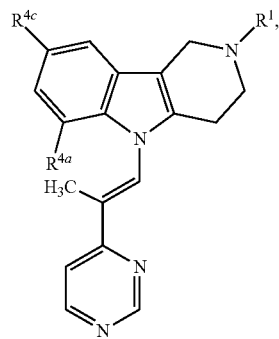
(H-7)

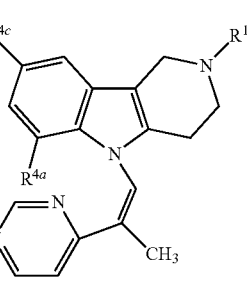
(H-8)

or a salt or solvate thereof, wherein $R^1$ is $CH_3$, —$CH_2CH_2$—$C(CH_3)_2(OH)$ or —$CH_2CH_2F$; $R^{4a}$ is H or F; and $R^{4c}$ is H, $CH_3$, Cl, F or —$NHCH_3$. In one embodiment of formula (H-3) and (H-4), $R^1$ is $CH_3$; $R^{4a}$ is H and $R^{4c}$ is $CH_3$, Cl, F, $CF_3$, or —$NHCH_3$. In yet another variation, $R^1$ is $CH_3$; $R^{4a}$ is H; $R^{4c}$ is $CH_3$, $CF_3$, Cl or F.

In one variation, compounds of the formula (H-5) or (H-6) are provided

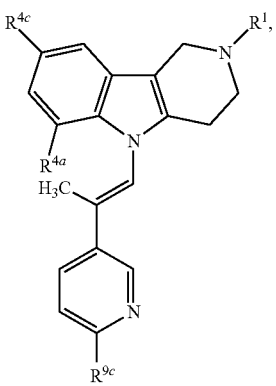
(H-5)

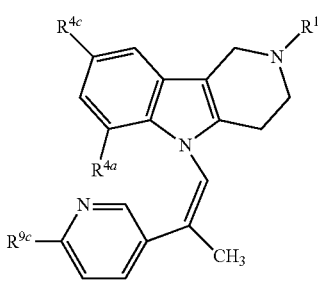
(H-6)

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; $R^{4c}$ is H, $CH_3$, Cl, F, $CF_3$, or —$NHCH_3$; and $R^{9c}$ is H, F, $CH_3$, $CF_3$, $OCH_3$, —$CONH(CH_3)$ or —$CON(CH_3)_2$. In one variation of formula (H-5) and (H-6) $R^1$ is $CH_3$; $R^{4a}$ is H; $R^{4c}$ is $CH_3$, Cl, F, $CF_3$, or —$NHCH_3$; and $R^9$ is H, F, $CF_3$, or $CH_3$. In a particular variation, $R^1$ is $CH_3$; $R^{4a}$ is H; $R^{4c}$ is $CH_3$, Cl or F; and $R^9$ is H, $CF_3$, or $CH_3$.

In another variation, compounds of the formula (H-7) and (H-8) are provided:

or a salt or solvate thereof, wherein $R^1$ is $CH_3$, —$CH_2CH_2$—$C(CH_3)_2(OH)$, —$CH_2CF_3$, or —$CH_2CH_2F$; $R^{4a}$ is H or F; and $R^{4c}$ is H, $CH_3$, $CF_3$, Cl, F or —$NHCH_3$. In one embodiment of formula (H-7) and (H-8), $R^1$ is $CH_3$; $R^{4a}$ is H; and $R^{4c}$ is $CH_3$, Cl, F, $CF_3$, or —$NHCH_3$. In one embodiment $R^1$ is $CH_3$; $R^{4a}$ is H; and $R^{4c}$ is $CH_3$, $CF_3$, Cl or F The substituent groups $R^1$, $R^{2a}$, $R^{2b}$, $R^{3a}$, $R^{3b}$, $R^{8a}$, $R^{8b}$, $R^{8c}$, $R^{8d}$, $R^{10a}$, $R^{10b}$, $R^{11}$, $R^{12}$, m, q, Q, $X^7$, $X^8$, $X^9$, and $X^{10}$ described herein as suitable for compounds of formula (I) are also suitable for compounds of formulae (I-A), (I-B), (I-C), (I-D), (I-E), (I-F), (I-b1), (I-b2), (I-c1), (I-c2), (I-d1), (I-d2), (I-e1), (I-e2), (I-f1) and (I-f2) when applicable. Likewise, substituent groups $R^1$, $R^{2a}$, $R^{2b}$, $R^{3a}$, $R^{3b}$, $R^{8a}$, $R^{8b}$, $R^{8c}$, $R^{8d}$, $R^{10a}$, $R^{10b}$, $R^{11}$, $R^{12}$, m, q, Q, $X^7$, $X^8$, $X^9$, and $X^{10}$ described herein as suitable for compounds of formula (I) are also suitable for compounds of formulae (I-G), (I-g1), (I-g2), (I-H), (I-h1) and (I-h2) when applicable.

The invention also embraces compounds of the formula (III):

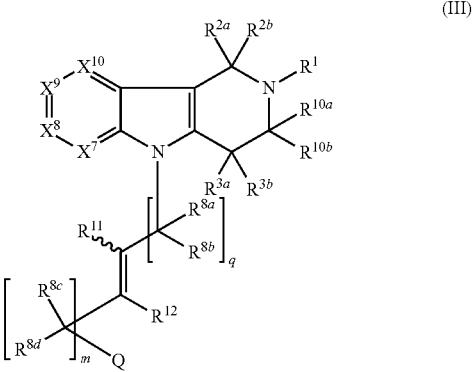
(III)

or a salt or solvate thereof;

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety;

each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together with the carbon to which they are attached to form a carbonyl moiety or a cycloalkyl moiety;

each $X^7$, $X^8$, $X^9$ and $X^{10}$ is independently N, CH or $CR^4$;

each m and q is independently 0 or 1;

each $R^4$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, $C_1$-$C_8$ alkyl, or is taken together with the carbon to which it is attached and a geminal $R^8$ to form a cycloalkyl moiety or a carbonyl moiety;

each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together with the carbon to which they are attached to form a carbonyl moiety or a cycloalkyl moiety;

$R^{11}$ is H, substituted or unsubstituted aryl, substituted or unsubstituted heteroaryl, $C_1$-$C_8$ alkyl, $C_3$-$C_8$ cycloalkyl, or $C_1$-$C_8$ perhaloalkyl and the ∼∼∼ bond indicates the presence of either an E or Z double bond configuration;

$R^{12}$ is H, halo, substituted or unsubstituted aryl, substituted or unsubstituted heteroaryl, $C_1$-$C_8$ alkyl, $C_1$-$C_8$ alkyl substituted with a carbonylalkoxy, carboxyl or acylamino moiety, $C_2$-$C_8$ alkenyl, $C_3$-$C_8$ cycloalkyl, or $C_1$-$C_8$ perhaloalkyl; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy or acylamino;

provided that (i) when $X^7$, $X^8$ and $X^{10}$ are each CH and each $R^{2a}$, $R^{2b}$, $R^{3a}$, $R^{3b}$, $R^{10a}$ and $R^{10b}$ is hydrogen, the compound is other than a compound in Table A, and (ii) the compound is other than Compound 87. In another variation, the compounds of the invention, and methods of using the compounds and administering the compounds as detailed herein, encompass any of the compounds of the formula (III), including Compound 87. In another variation, the compounds of the invention, and methods of using the compounds and administering the compounds as detailed herein, encompass any of the compounds of the formula (III), including those listed in Table A. In another variation, the compounds of the invention, and methods of using the compounds and administering the compounds as detailed herein, encompass any of the compounds of the formula (III), including Compound 87 and those listed in Table A. The substituent groups $R^1$, $R^{2a}$, $R^{2b}$, $R^{3a}$, $R^{3b}$, $R^{8a}$, $R^{8b}$, $R^{8c}$, $R^{8d}$, $R^{10a}$, $R^{10b}$, $R^{11}$, $R^{12}$, m, q, Q, $X^7$, $X^8$, $X^9$, and $X^{10}$ described herein as suitable for compounds of formula (I) are also suitable for compounds of formulae (III). Variations of formula (I) detailed throughout, where applicable, apply to formula (III) the same as if each and every variation were specifically and individually listed for formula (III).

In one variation, the compound is of the formula (III) where $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In another variation, the compound is of the formula (III) where each $R^{2a}$ and $R^{2b}$ is independently H, substituted or unsubstituted $C_1$-$C_8$ alkyl, hydroxyl, alkoxy or $R^{2a}$ and $R^{2b}$ are taken together with the carbon to which they are attached to form a carbonyl moiety or a cycloalkyl moiety and each $R^{10a}$ and $R^{10b}$ is independently H, substituted or unsubstituted $C_1$-$C_8$ alkyl, hydroxyl, alkoxy or $R^{10a}$ and $R^{10b}$ are taken together with the carbon to which they are attached to form a carbonyl moiety or a cycloalkyl moiety. In some variations, the compound is of the formula (III) where $R^1$ is an unsubstituted $C_1$-$C_8$ alkyl (e.g. methyl) and each $R^{2a}$, $R^{2b}$, $R^{3a}$, $R^{3b}$, $R^{10a}$ and $R^{10b}$ is H.

In one variation, the compound is of the formula (III), where at least one of $R^{11}$ and $R^{12}$ is other than H. In one such variation, the compound is of the formula (I) where $R^{11}$ is substituted or unsubstituted aryl, substituted or unsubstituted heteroaryl, $C_1$-$C_8$ alkyl, $C_3$-$C_8$ cycloalkyl, or $C_1$-$C_8$ perhaloalkyl. For example, the compound in one aspect is of the formula (III) where $R^{11}$ is a substituted aryl (e.g. 4-fluorophenyl). In another aspect, the compound is of the formula (III) where $R^{11}$ is an unsubstituted aryl (e.g. phenyl). In another such variation, the compound is of the formula (III) where $R^{12}$ is halo, substituted or unsubstituted aryl, substituted or unsubstituted heteroaryl, unsubstituted $C_1$-$C_8$ alkyl, $C_1$-$C_8$ alkyl substituted with a carbonylalkoxy, carboxyl or acylamino moiety, $C_2$-$C_8$ alkenyl, $C_3$-$C_8$ cycloalkyl, or $C_1$-$C_8$ perhaloalkyl. For example, the compound in one aspect is of the formula (III) where $R^{12}$ is halo, substituted or unsubstituted aryl, substituted or unsubstituted heteroaryl, $C_1$-$C_8$ alkyl substituted with a carbonylalkoxy, carboxyl or acylamino moiety, or $C_2$-$C_8$ alkenyl. In one aspect, the compound is of the formula (III) where $R^{12}$ is halo (e.g., fluoro). In another aspect, the compound is of the formula (III) where $R^{12}$ is a substituted aryl (e.g., 4-fluorophenyl) or unsubstituted aryl (e.g. phenyl). In another aspect, the compound is of the formula (III) where $R^{12}$ is a $C_1$-$C_8$ alkyl substituted with a carbonylalkoxy, carboxyl or acylamino moiety (e.g., ethoxycarbonylmethyl, carboxymethyl or methylaminocarbonylmethyl). In still another aspect, the compound is of the formula (III) where $R^{12}$ is $C_2$-$C_8$ alkenyl (e.g., propen-1-yl). In another such variation, $R^{11}$ is substituted or unsubstituted aryl and $R^{12}$ is H. In yet another such variation, $R^{11}$ is H and $R^{12}$ is halo, substituted or unsubstituted aryl, substituted or unsubstituted heteroaryl, $C_1$-$C_8$ alkyl substituted with a carbonylalkoxy, carboxyl or acylamino moiety, or $C_2$-$C_8$ alkenyl. In one particular variation, the compound is of the formula (III) where $R^{11}$ is substituted or unsubstituted aryl, $R^{12}$ is H, m is 0, q is 1, each $R^{8a}$ and $R^{8b}$ is H, and Q is carboxy or carbonylalkoxy. In another particular variation, the compound is of the formula (III) where $R^{11}$ is H, $R^{12}$ is halo, m and q are 0 and Q is a heteroaryl (e.g. a pyridyl such as 4-pyridyl). In another particular variation, the compound is of the formula (III) where $R^{11}$ is H, $R^{12}$ is substituted or unsubstituted aryl, $C_1$-$C_8$ alkyl substituted with a carbonylalkoxy, carboxyl or acylamino moiety, or $C_2$-$C_8$ alkenyl, m and q are 0 and Q is a substituted aryl (e.g., 4-fluorophenyl) or unsubstituted aryl (e.g. phenyl).

The invention also embraces compounds of the formula (V):

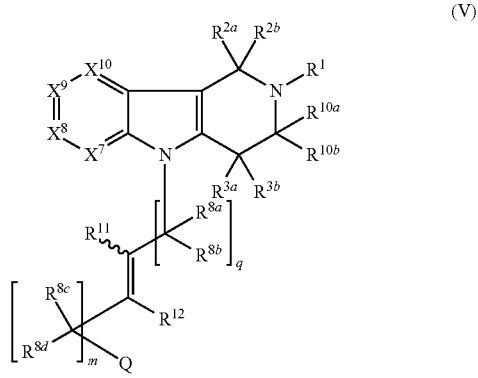

or a salt or solvate thereof;
wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkyl, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety;

each $R^{3a}$ and $R^{3b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl or $R^{3a}$ and $R^{3b}$ are taken together with the carbon to which they are attached to form a carbonyl moiety or a cycloalkyl moiety;

each $X^7$, $X^8$, $X^9$ and $X^{10}$ is independently N, CH or $CR^4$;
each m and q is independently 0 or 1;
each $R^4$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, alkoxy, halo, substituted or unsubstituted aryl, substituted or unsubstituted heteroaryl, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxy, carbonylalkoxy, or is taken together with a geminal $R^8$ to form a moiety of the formula —$OCH_2CH_2O$—, or is taken together with the carbon to which it is attached and a geminal $R^8$ to form a cycloalkyl moiety or a carbonyl moiety;

each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together with the carbon to which they are attached to form a carbonyl moiety or a cycloalkyl moiety;

each $R^{11}$ and $R^{12}$ is independently H, halo, alkoxy, substituted or unsubstituted aryl, substituted or unsubstituted heteroaryl, substituted or unsubstituted $C_1$-$C_8$ alkyl, substituted or unsubstituted $C_2$-$C_8$ alkenyl, substituted or unsubstituted $C_3$-$C_8$ cycloalkyl, $C_1$-$C_8$ perhaloalkyl, carboxy, or carbonylalkoxy and the ~~~ bond indicates the presence of either an E or Z double bond configuration, or $R^{11}$ and $R^{12}$ are taken together to form a bond; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, alkoxy, acyloxy, substituted or unsubstituted amino, aminoacyl, aminocarbonylalkoxy, cyano, alkynyl, carboxy, carbonylalkoxy or acylamino.

In one variation, the compound is of the formula (V) where $X^7$, $X^8$, $X^9$, $X^{10}$, $R^1$, $R^{2a}$, $R^{2b}$, $R^{3a}$, $R^{3b}$, $R^{10a}$, $R^{10b}$, Q, q, m, $R^{8a}$, $R^{8b}$, $R^{8c}$, $R^{8d}$, $R^{11}$ and $R^{12}$ are as defined for formula (V), provided that (i) when $X^7$, $X^8$ and $X^{10}$ are each CH and each $R^{2a}$, $R^{2b}$, $R^{3a}$, $R^{3b}$, $R^{10a}$ and $R^{10b}$ is hydrogen, at least one of $R^{11}$ and $R^{12}$ is other than hydrogen and $R^{11}$ and $R^{12}$ are not taken together to form a bond; and (ii) the compound is other than Compound 87. In one aspect, compounds of the formula (V) are provided where q and m are both 0 and at least one of $R^{11}$ and $R^{12}$ is a substituted or unsubstituted alkyl, such as methyl. In another aspect, compounds of the formula (V) are provided where q and m are both 0 and at least one of $R^{11}$ and $R^{12}$ is a substituted or unsubstituted alkyl, such as methyl, and Q is a substituted or unsubstituted aryl, such as phenyl, or a substituted or unsubstituted heteroaryl, such as pyridyl. In another aspect, compounds of the formula (V) are provided where q and m are both 0, $R^{11}$ is H, $R^{12}$ is methyl and Q is a substituted or unsubstituted heteroaryl, such as pyridyl. In a more particular variation of formula (V), q and m are both 0, $R^{11}$ is H, $R^{12}$ is methyl and Q is a substituted or unsubstituted heteroaryl, such as pyridyl and one or more of the following structural features applies: (i) $X^7$, $X^8$ and $X^{10}$ are each CH; (ii) $X^9$ is CH or $CR^4$ where $R^4$ is halo or an unsubstituted $C_1$-$C_8$ alkyl; (iii) $R^{2a}$ and $R^{2b}$ are both H; (iv) $R^1$ is methyl; (v) $R^{3a}$ and $R^{3b}$ are both H and (vi) $R^{10a}$ and $R^{10b}$ are both H. In one such variation, at least two or three or four or five or all of (i)-(vi) apply. When more than one of (i)-(vi) applies, the provisions may be combined in any manner. In another variation, the compounds provided herein, and methods of using the compounds and administering the compounds as detailed herein, encompass any of the compounds of the formula (V), including Compound 87. The substituent groups $R^1$, $R^{2a}$, $R^{2b}$, $R^{3a}$, $R^{3b}$, $R^{8a}$, $R^{8b}$, $R^{8c}$, $R^{8d}$, $R^{10a}$, $R^{10b}$, $R^{11}$, $R^{12}$, m, q, Q, $X^7$, $X^8$, $X^9$, A and $X^{10}$ described herein as suitable for compounds of formulae (I) and (III) are also suitable for compounds of formula (V). Variations of formulae (I) and (III) detailed throughout, where applicable, apply to formula (V) the same as if each and every variation were specifically and individually listed for formula (V).

In one variation, compounds of the formula (V) are provided, where $X^7$, $X^8$, $X^9$, $X^{10}$, $R^1$, $R^{2a}$, $R^{2b}$, $R^{3a}$, $R^{3b}$, $R^{10a}$, $R^{10b}$, q, m, and Q are as defined for formula (V), each $R^{8a}$, $R^{8b}$, $R^{8c}$ and $R^{8d}$ is independently H, hydroxyl, $C_1$-$C_8$ alkyl, or is taken together with the carbon to which it is attached and a geminal $R^8$ to form a cycloalkyl moiety or a carbonyl moiety; $R^{11}$ is H, substituted or unsubstituted aryl, substituted or unsubstituted heteroaryl, $C_1$-$C_8$ alkyl, $C_3$-$C_8$ cycloalkyl, or $C_1$-$C_8$ perhaloalkyl and the ⁓ bond indicates the presence of either an E or Z double bond configuration; and $R^{12}$ is H, halo, substituted or unsubstituted aryl, substituted or unsubstituted heteroaryl, unsubstituted $C_1$-$C_8$ alkyl, $C_1$-$C_8$ alkyl substituted with a carbonylalkoxy, carboxyl or acylamino moiety, $C_2$-$C_8$ alkenyl, $C_3$-$C_8$ cycloalkyl, or $C_1$-$C_8$ perhaloalkyl. In another variation, the compound is of the formula (V), where $X^7$, $X^8$, $X^9$, $X^{10}$, $R^{2a}$, $R^{2b}$, $R^{3a}$, $R^{3b}$, $R^{10a}$, $R^{10b}$, Q, q, m, $R^{8a}$, $R^{8b}$, $R^{8c}$ and $R^{8d}$ are as defined for formula (V), $R^{11}$ is H, substituted or unsubstituted aryl, substituted or unsubstituted heteroaryl, $C_1$-$C_8$ alkyl, $C_3$-$C_8$ cycloalkyl, or $C_1$-$C_8$ perhaloalkyl and $R^{12}$ is H, halo, substituted or unsubstituted aryl, substituted or unsubstituted heteroaryl, substituted or unsubstituted $C_1$-$C_8$ alkyl, substituted or unsubstituted $C_2$-$C_8$ alkenyl, substituted or unsubstituted $C_3$-$C_8$ cycloalkyl or $C_1$-$C_8$ perhaloalkyl. In another variation, the compound is of the formula (V), where $X^7$, $X^8$, $X^9$, $X^{10}$, $R^1$, $R^{2a}$, $R^{2b}$, $R^{3a}$, $R^{3b}$, $R^{10a}$, $R^{10b}$, Q, q, m, $R^{8a}$, $R^{8b}$, $R^{8c}$, $R^{8d}$ and $R^{11}$ are as defined for formula (V) and $R^{12}$ is $C_1$-$C_8$ alkyl substituted with a carbonylalkoxy, carboxyl or acylamino moiety.

In one embodiment, provided is a compound of formula (V) where at least one $R^{3a}$ and $R^{3b}$ is aryl. In a particular variation of formula (V), at least one of $R^{3a}$ and $R^{3b}$ is phenyl.

In some embodiments, the compound of formula (V) has the formula (V-B):

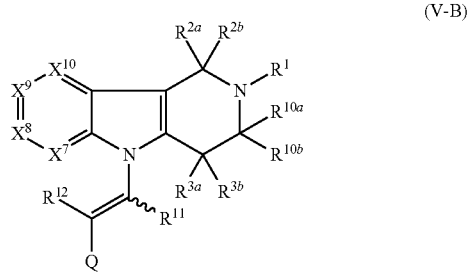

(V-B)

or a salt or solvate thereof;
wherein $R^1$, $R^{2a}$, $R^{2b}$, $R^{3a}$, $R^{3b}$, $R^{10a}$, $R^{10b}$, $R^{11}$, $R^{12}$, Q, $X^7$, $X^8$, $X^9$, and $X^{10}$ are defined as for formula (V) and, where applicable, any variation thereof detailed herein. That is, variations of formula (V) detailed throughout, where applicable, apply to formula (V-B) the same as if each and every variation were specifically and individually listed for formula (V-B). In one variation, compounds of formula (V-B) are detailed herein, provided that (i) when $X^7$, $X^8$ and $X^{10}$ are each CH and each $R^{2a}$, $R^{2b}$, $R^{3a}$, $R^{3b}$, $R^{10a}$ and $R^{10b}$ is hydrogen, at least one of $R^{11}$ and $R^{12}$ is other than hydrogen and $R^{11}$ and $R^{12}$ are not taken together to form a bond; and (ii) the compound is other than Compound 87. In another variation, compounds of formula (V-B), including Compound 87, and methods of using and administering such compounds are encompassed. In one aspect of formula (V-B), at least one of $R^{11}$ and $R^{12}$ is other than H. In one such variation of formula (V-B), $R^{11}$ is H and $R^{12}$ is $C_1$-$C_8$ alkyl, $C_3$-$C_8$ cycloalkyl, or $C_1$-$C_8$ perhaloalkyl. In one aspect of formula (V-B), $R^{11}$ is H and $R^{12}$ is $C_1$-$C_8$ alkyl. In another variation of formula (V-B) at least one of $R^{11}$ and $R^{12}$ is other than H and $R^1$ is $C_1$-$C_8$ alkyl. In one such variation, $R^{12}$ is an unsubstituted $C_1$-$C_8$ alkyl and Q is a substituted or unsubstituted heteroaryl. In one variation of formula (V-B), $R^{12}$ is an unsubstituted $C_1$-$C_8$ alkyl and Q is other than a halo-substituted phenyl. In a more particular variation of formula (V-B), $R^{11}$ is H, $R^{12}$ is $C_1$-$C_8$ alkyl, $C_3$-$C_8$ cycloalkyl, or $C_1$-$C_8$ perhaloalkyl and $R^1$ is $C_1$-$C_8$ alkyl. In an even more particular variation of formula (V-B), $R^{11}$ is H, $R^{12}$ is $C_1$-$C_8$ alkyl, $X^9$ is $CR^4$ where $R^4$ is halo and each $X^7$, $X^8$ and $X^{10}$ is CH. In another variation of formula (V-B), $R^{11}$ is H, $R^{12}$ is $C_1$-$C_8$ alkyl, $X^9$ is $CR^4$ where $R^4$ is halo, each $X^7$, $X^8$ and $X^{10}$ is CH, $R^1$ is alkyl and each $R^{2a}$, $R^{2b}$, $R^{3a}$, $R^{3b}$, $R^{10a}$, $R^{10b}$ is H. In any variation or aspect of formula (V-B) detailed herein, in one embodiment, the compound of formula (V-B) is in the E configuration. Similarly, in any variation or aspect of formula (V-B) detailed herein, in another embodiment, the compound of formula (V-B) is in the Z configuration. For example, provided are compounds of formula (V-B) where $R^{11}$ is H, $R^{12}$ is $C_1$-$C_8$ alkyl, $X^9$ is $CR^4$ where $R^4$ is halo, each $X^7$, $X^8$ and $X^{10}$ is CH and the compound is in the E configuration. Likewise, also provided are compounds of formula (V-B) where $R^{11}$ is H, $R^{12}$ is $C_1$-$C_8$ alkyl, $X^9$ is $CR^4$ where $R^4$ is halo, each $X^7$, $X^8$ and $X^{10}$ is CH and the compound is in the Z configuration.

In one embodiment, the compound is of the formula (V-B), where $R^1$, $R^{2a}$, $R^{2b}$, $R^{3a}$, $R^{3b}$, $R^{10a}$, $R^{10b}$, Q, $X^7$, $X^8$, $X^9$, and $X^{10}$ are defined for formula (V); $R^{11}$ is H, hydroxyl, alkoxy, halo, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxyl, carbonylalkoxy, substituted or unsubstituted aryl, substituted or unsubstituted heteroaryl and $R^{12}$ and Q are independently a substituted or unsubstituted aryl or substituted or unsubstituted heteroaryl. In one variation, $R^{12}$ and Q are the same substituted or unsubstituted aryl or heteroaryl moiety, such as when both $R^{12}$ and Q are phenyl.

In some embodiments, the compound of formula (V) has the formula (V-G):

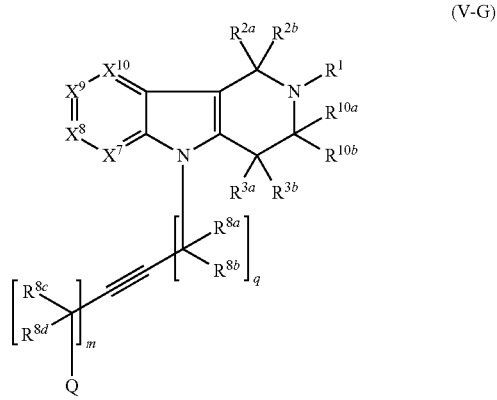

(V-G)

or a salt or solvate thereof; where $X^7$, $X^8$, $X^9$, $X^{10}$, $R^1$, $R^{2a}$, $R^{2b}$, $R^{3a}$, $R^{3b}$, $R^{8a}$, $R^{8b}$, $R^{8c}$, $R^{8d}$, $R^{10a}$, $R^{10b}$, q, m and Q are as defined for formula (V). In one variation, the compound is of the formula (V-G), provided that (i) when q and m are 0, each $R^{2a}$, $R^{2b}$, $R^{3a}$, $R^{3b}$, $R^{10a}$ and $R^{10b}$ is H, each $X^7$, $X^8$, $X^9$ and $X^{10}$ is independently CH or $CR^4$ where $R^4$ is methyl, fluoro or $CF_3$, and Q is phenyl, substituted phenyl, pyridyl or pyrimidyl, the compound is other than a compound specifically described in WO 2008/123796 A2, and (ii) the compound is other than Compound 478, Compound 490 and Compound 495. In another variation, the compounds of the invention, and methods of using the compounds and administering the compounds as detailed herein, encompass any of the compounds of the formula (V-G), including Compound 478, Compound 490 and Compound 495. In another variation, the compounds of the invention, and methods of using the compounds and administering the compounds as detailed herein, encompass any of the compounds of the formula (V-G), including compounds specifically described in WO 2008/123796 A2.

In some embodiments, the compound of formula (V) has the formula (V-H):

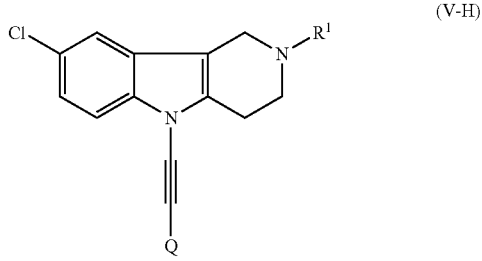

(V-H)

or a salt or solvate thereof; where $R^1$ and Q are as defined for formula (V). In one variation, Q of formula (V-H) is a substituted or unsubstituted aryl, such as phenyl. In one aspect, Q of formula (V-H) is a mono-substituted phenyl, such as a mono-halo substituted phenyl, for example 4-fluoro-phenyl. In another variation Q of formula (V-H) is a mono-substituted phenyl and $R^1$ is an unsubstituted $C_1$-$C_8$ alkyl such as methyl.

The invention further embraces compounds of the formula (IV):

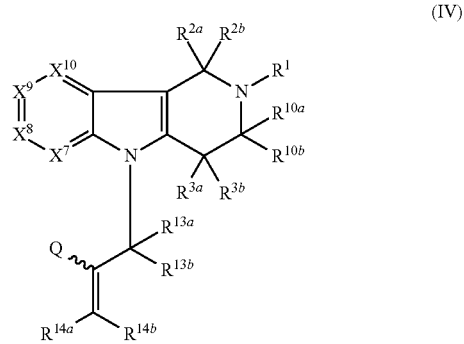

(IV)

or a salt or solvate thereof;
wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety;

each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together with the carbon to which they are attached to form a carbonyl moiety or a cycloalkyl moiety;

each $X^7$, $X^8$, $X^9$ and $X^{10}$ is independently N, CH or $CR^4$;

each $R^4$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together with the carbon to which they are attached to form a carbonyl moiety or a cycloalkyl moiety;

each $R^{13a}$ and $R^{12b}$ is independently H, $C_1$-$C_8$ alkyl, $C_3$-$C_8$ cycloalkyl, or $C_1$-$C_8$ perhaloalkyl; each $R^{14a}$ and $R^{14b}$ is independently H, substituted or unsubstituted $C_1$-$C_8$ alkyl, $C_3$-$C_8$ cycloalkyl, $C_1$-$C_8$ perhaloalkyl, carbonylalkoxy, carboxyl, acylamino or $R^{14a}$ and $R^{14b}$ are taken together with the carbon to which they are attached to form a cycloalkyl moiety, and;

Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy or acylamino and the ∼∼∼ bond indicates the presence of either an E or Z double bond configuration.

In one variation, compounds of the formula (IV) are provided, where $X^7$, $X^8$, $X^9$, $X^{10}$, $R^1$, $R^{2a}$, $R^{2b}$, $R^{3a}$, $R^{3b}$, $R^{10a}$, $R^{10b}$, Q, $R^{13a}$, $R^{13b}$ are as defined for formula (IV) and $R^{14a}$ and $R^{14b}$ are independently H, halo, alkoxy, substituted or unsubstituted aryl, substituted or unsubstituted heteroaryl, substituted or unsubstituted $C_1$-$C_8$ alkyl, $C_1$-$C_8$ alkyl substituted with a carbonylalkoxy, carboxyl or acylamino moiety, $C_2$-$C_8$ alkenyl, substituted or unsubstituted $C_3$-$C_8$ cycloalkyl, substituted or unsubstituted $C_3$-$C_8$ cycloalkenyl, substituted or unsubstituted heterocyclyl or $C_1$-$C_8$ perhaloalkyl.

The substituent groups $R^1$, $R^{2a}$, $R^{2b}$, $R^{3a}$, $R^{3b}$, $R^{10a}$, $R^{10b}$, Q, $X^7$, $X^8$, $X^9$, $X^9$ and $X^{10}$ described herein as suitable for compounds of formula (I) or formula (III) are also suitable for compounds of formulae (IV). Variations of formula (I) and formula (III) with regard to substituent groups $R^1$, $R^{2a}$, $R^{2b}$, $R^{3a}$, $R^{3b}$, $R^{10a}$, $R^{10b}$, Q, $X^7$, $X^8$, $X^9$, and $X^{10}$ detailed throughout, where applicable, apply to formula (IV) the same as if each and every variation were specifically and individually listed for formula (IV).

In some embodiments, the compound is of the formula (IV) where at least one of $R^{13a}$ and $R^{13b}$ is H. In one such variation, each $R^{13a}$ and $R^{13b}$ is H. In another variation, one of $R^{13a}$ and $R^{13b}$ is H and the other one of $R^{13a}$ and $R^{13b}$ is $C_1$-$C_8$ alkyl, $C_3$-$C_8$ cycloalkyl, or $C_1$-$C_8$ perhaloalkyl. In a particular variation, the compound is of the formula (IV) where each $R^{13a}$ and $R^{13b}$ is H and Q is substituted or unsubstituted aryl, substituted or unsubstituted heteroaryl, substituted or unsubstituted cycloalkyl or substituted or unsubstituted heterocyclyl.

In some embodiments, the compound is of the formula (IV) where at least one of $R^{14a}$ and $R^{14b}$ is H. In one such variation, each $R^{14a}$ and $R^{14b}$ is H. In another variation, one of $R^{14a}$ and $R^{14b}$ is H and the other one of $R^{14a}$ and $R^{14b}$ is substituted or unsubstituted $C_1$-$C_8$ alkyl, $C_3$-$C_8$ cycloalkyl, $C_1$-$C_8$ perhaloalkyl, carbonylalkoxy, carboxyl or acylamino. For example, the one of $R^{14a}$ and $R^{14b}$ that is not H is a an unsubstituted $C_1$-$C_8$ alkyl (e.g. methyl, ethyl or propyl), a $C_1$-$C_8$ alkyl substituted with hydroxy (e.g. 2-hydroxyethyl), a carbonylalkoxy, a carboxyl or an acylamino group. In one particular variation, the compound is of the formula (IV) where each $R^{13a}$ and $R^{13b}$ is H and each $R^{14a}$ and $R^{14b}$ is H. In a further variation, the compound is of the formula (IV) where each $R^{13a}$ and $R^{12b}$ is H, each $R^{14a}$ and $R^{14b}$ is H and Q is substituted or unsubstituted aryl, substituted or unsubstituted heteroaryl, substituted or unsubstituted cycloalkyl or substituted or unsubstituted heterocyclyl.

In some embodiments, the compound is of the formula (IV) where each $R^{14a}$ and $R^{14b}$ is independently substituted or unsubstituted $C_1$-$C_8$ alkyl, $C_3$-$C_8$ cycloalkyl, $C_1$-$C_8$ perhaloalkyl, carbonylalkoxy, carboxyl, acylamino or $R^{14a}$ and $R^{14b}$ are taken together with the carbon to which they are attached to form a cycloalkyl moiety. In one such variation, each $R^{14a}$ and $R^{14b}$ is independently substituted or unsubstituted $C_1$-$C_8$ alkyl. For example, each $R^{14a}$ and $R^{14b}$ is methyl or one of $R^{14a}$ and $R^{14b}$ is methyl and the other is a substituted or unsubstituted $C_1$-$C_8$ alkyl other than methyl. In another such variation, $R^{14a}$ and $R^{14b}$ are taken together with the carbon to which they are attached to form a cycloalkyl moiety. For example, $R^{14a}$ and $R^{14b}$ are taken together with the carbon to which they are attached to form a cyclopropyl moiety. In some variations, the compound is of the formula (IV) where each $R^{14a}$ and $R^{14b}$ is independently substituted or unsubstituted $C_1$-$C_8$ alkyl, $C_3$-$C_8$ cycloalkyl, $C_1$-$C_8$ perhaloalkyl, carbonylalkoxy, carboxyl, acylamino or $R^{14a}$ and $R^{14b}$ are taken together with the carbon to which they are attached to form a cycloalkyl moiety, each $R^{13a}$ and $R^{13b}$ is H and Q is substituted or unsubstituted aryl, substituted or unsubstituted heteroaryl, substituted or unsubstituted cycloalkyl or substituted or unsubstituted heterocyclyl.

The invention also embraces compounds of the formula (VI):

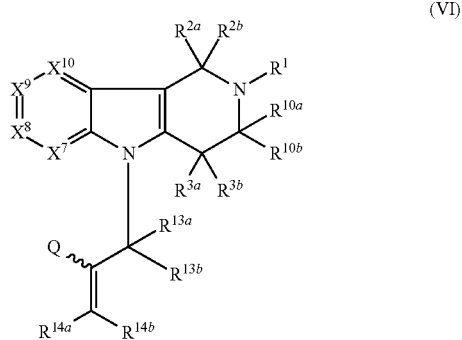

(VI)

or a salt or solvate thereof;

wherein:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety;

each $R^{3a}$ and $R^{3b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl or $R^{3a}$ and $R^{3b}$ are taken together with the carbon to which they are attached to form a carbonyl moiety or a cycloalkyl moiety;

each $X^7$, $X^8$, $X^9$ and $X^{10}$ is independently N, CH or $CR^4$;

each $R^4$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together with the carbon to which they are attached to form a carbonyl moiety or a cycloalkyl moiety;

each $R^{13a}$ and $R^{12b}$ is independently H, halo, alkoxy, substituted or unsubstituted aryl, substituted or unsubstituted heteroaryl, substituted or unsubstituted $C_1$-$C_8$ alkyl, substituted or unsubstituted $C_2$-$C_8$ alkenyl, substituted or unsubstituted $C_3$-$C_8$ cycloalkyl, $C_1$-$C_8$ perhaloalkyl, carboxy, or carbonylalkoxy;

each $R^{14a}$ and $R^{14b}$ is independently H, halo, alkoxy, substituted or unsubstituted aryl, substituted or unsubstituted heteroaryl, substituted or unsubstituted $C_1$-$C_8$ alkyl, substituted or unsubstituted $C_2$-$C_8$ alkenyl, substituted or unsubstituted $C_3$-$C_8$ cycloalkyl, $C_1$-$C_8$ perhaloalkyl, carbonylalkoxy, carboxyl, acylamino or $R^{14a}$ and $R^{14b}$ are taken together with the carbon to which they are attached to form a cycloalkyl moiety; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, alkoxy, acyloxy, substituted or unsubstituted amino, aminoacyl, aminocarbonylalkoxy, cyano, alkynyl, carboxy, carbonylalkoxy or acylamino and the ⁓ bond indicates the presence of either an E or Z double bond configuration.

In one variation, the compound is of the formula (VI) where $X^7$, $X^8$, $X^9$, $X^{10}$, $R^1$, $R^{2a}$, $R^{2b}$, $R^{3a}$, $R^{3b}$, $R^{10a}$, $R^{10b}$, Q, $R^{13a}$, $R^{13b}$, $R^{14a}$ and $R^{14b}$ are as defined for formula (VI), provided that the compound is other than Compound 132. In another variation, the compounds of the invention, and methods of using the compounds and administering the compounds as detailed herein, encompass any of the compounds of the formula (VI), including Compound 132. The substituent groups $R^1$, $R^{2a}$, $R^{2b}$, $R^{3a}$, $R^{3b}$, $R^{10a}$, $R^{10b}$, $R^{13a}$, $R^{13b}$, $R^{14a}$, $R^{14b}$, Q, $X^7$, $X^8$, $X^9$, and $X^{10}$ described herein as suitable for compounds of formula (IV) are also suitable for compounds of formula (VI). Variations of formula (IV) detailed throughout, where applicable, apply to formula (VI) the same as if each and every variation were specifically and individually listed for formula (VI).

In one variation, compounds of the formula (VI) are provided, where $X^7$, $X^8$, $X^9$, $X^{10}$, $R^1$, $R^{2a}$, $R^{2b}$, $R^{3a}$, $R^{3b}$, $R^{10a}$, $R^{10b}$, Q, $R^{13a}$ and $R^{13b}$ are as defined for formula (VI) and each $R^{14a}$ and $R^{14b}$ is independently H, substituted or unsubstituted $C_1$-$C_8$ alkyl, $C_3$-$C_8$ cycloalkyl, $C_1$-$C_8$ perhaloalkyl, carbonylalkoxy, carboxyl, acylamino or $R^{14a}$ and $R^{14b}$ are taken together with the carbon to which they are attached to form a cycloalkyl moiety.

In one embodiment, provided is a compound of formula (VI) where at least one $R^{3a}$ and $R^{3b}$ is aryl. In a particular variation of formula (VI), at least one of $R^{3a}$ and $R^{3b}$ is phenyl.

In one variation, compounds of the formula (VIA) are provided:

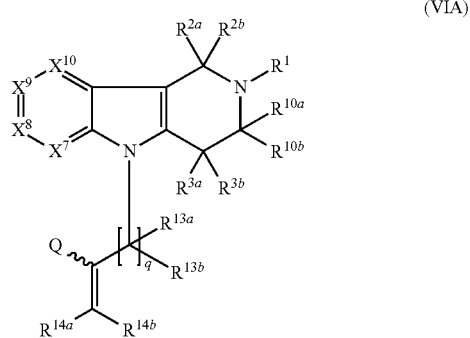

(VIA)

or a salt or solvate thereof; where $X^7$, $X^8$, $X^9$, $X^{10}$, $R^1$, $R^{2a}$, $R^{2b}$, $R^{3a}$, $R^{3b}$, $R^{10a}$, $R^{10b}$, Q, $R^{13a}$, $R^{13b}$, $R^{14a}$, $R^{14b}$ are as defined for formula (VI), or a variation thereof, and q is 0 or 1.

In another aspect, the invention embraces compounds of the formula (II):

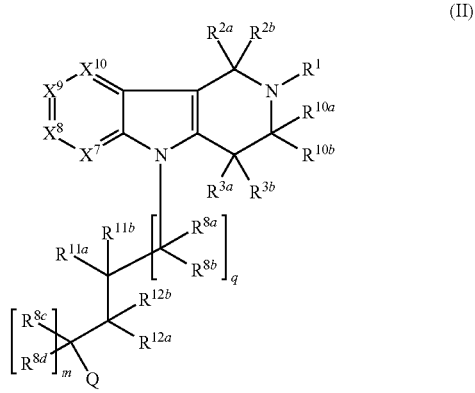

(II)

or a salt or solvate thereof;

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together to form a carbonyl moiety;

each $X^7$, $X^8$, $X^9$ and $X^{10}$ is independently N, CH or $CR^4$;

each m and q is independently 0 or 1;

each $R^4$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, $C_1$-$C_8$ alkyl, or is taken together with the carbon to which it is attached and a geminal $R^8$ to form a cycloalkyl moiety or a carbonyl moiety;

each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together to form a carbonyl moiety;

each $R^{11a}$ and $R^{12a}$ is independently H, hydroxyl, or $C_1$-$C_8$ alkyl; or $R^{11a}$ and $R^{12a}$ may be taken together to represent a bond;

$R^{11b}$ and $R^{12b}$ are taken together with the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety; and Q is a substituted or unsubstituted aryl, substituted or unsubstituted heteroaryl, substituted or unsubstituted cycloalkyl, substituted or unsubstituted cycloalkenyl or substituted or unsubstituted heterocyclyl, substituted or unsubstituted amino, alkoxy, aminoacyl, acyloxy, carbonylalkoxy, aminocarbonylalkoxy or acylamino.

In one variation of formula (II), q is 0 and m are both 0 and $R^{11a}$ and $R^{12a}$ are each H. In another variation of formula (II), q and m are both 0, $R^{11a}$ and $R^{12a}$ are each H and $R^{11b}$ and $R^{12b}$ are taken together with the carbon atoms to which they are attached to form a substituted or unsubstituted cycloalkyl moiety. In yet another variation of formula (II), q and m are both 0, $R^{11a}$ and $R^{12a}$ are each H, $R^{11b}$ and $R^{12b}$ are taken together with the carbon atoms to which they are attached to form a substituted or unsubstituted cycloalkyl moiety and at least one of (i)-(iv) applies: (i) $X^9$ is $CR^4$ where $R^4$ is a $C_1$-$C_8$ alkyl (e.g., methyl) or halo (e.g., chloro); (ii) $R^1$ is a $C_1$-$C_8$ alkyl (e.g., methyl); (iii) each $X^7$, $X^8$ and $X^{10}$ is CH; and (iv) each $R^{2a}$, $R^{2b}$, $R^{3a}$, $R^{3b}$, $R^{10a}$ and $R^{10b}$ is H. Preferably, when Q is a cycloalkyl moiety, it is an unsubstituted $C_3$-$C_8$ cycloalkyl moiety (e.g., cyclopropyl, cyclobutyl, cyclopentyl and cyclohexyl).

In one variation of formula (II), $R^{11a}$ and $R^{12a}$ are taken together to form a bond. In a particular variation of formula (II), $R^{11a}$ and $R^{12a}$ are taken together to form a double bond (such that the bond between the carbon bearing $R^{11a}$ and $R^{11b}$ and the carbon bearing $R^{12a}$ and $R^{12b}$ is a double bond) and together with $R^{11b}$ and $R^{12b}$ are taken to form a cycloalkenyl moiety (e.g., cyclopropenyl, cyclobutenyl, cyclopentenyl and cyclohexenyl). In a further variation of formula (II), $R^{11a}$ and $R^{12a}$ are taken together to form a double bond and together with $R^{11b}$ and $R^{12b}$ are taken to form a cycloalkenyl moiety and at least of of (i)-(v) applies: (i) at least one of $X^7$-$X^{10}$ is $CR^4$ where $R^4$ is halo (e.g., when $X^9$ is $CR^4$ where $R^4$ is chloro); (ii) $R^1$ is $C_1$-$C_8$ alkyl (e.g., methyl); (iii) Q is a substituted or unsubstituted aryl, substituted or unsubstituted heteroaryl, substituted or unsubstituted cycloalkyl, substituted or unsubstituted cycloalkenyl or substituted or unsubstituted heterocyclyl; (iv) q and m are both 0; and (v) each $R^{2a}$, $R^{2b}$, $R^{3a}$, $R^{3b}$, $R^{10a}$ and $R^{10b}$ is H.

In any variation or aspect of formula (II) detailed herein where $R^{11a}$ and $R^{12a}$ are taken together to form a double bond such that $R^{11a}$ and $R^{12a}$ are taken together with $R^{11b}$ and $R^{12b}$ to form a cycloalkenyl moiety. In one embodiment, the compound of formula (II) is in the E configuration. Similarly, in any variation or aspect of formula (II) detailed herein, in another embodiment, the compound of formula (II) is in the Z configuration.

In certain embodiments, the compound of formula (II) has the structure:

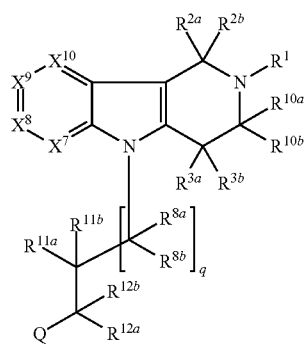

(II-A)

or a salt or solvate thereof;
wherein $R^1$, $R^{2a}$, $R^{2b}$, $R^{3a}$, $R^{3b}$, $R^{8a}$, $R^{8b}$, $R^{10a}$, $R^{10b}$, $R^{11a}$, $R^{11b}$, $R^{12a}$, $R^{12b}$, q, Q, $X^7$, $X^8$, $X^9$, and $X^{10}$ are defined as for formula (II) and, where applicable, any variation thereof detailed herein. That is, variations of formula (II) detailed throughout, where applicable, apply to formula (II-A) the same as if each and every variation were specifically and individually listed for formula (II-A).

In some such embodiments, $R^{11a}$ and $R^{12a}$ are taken together to form a bond and the compound of formula (II-A) has the structure:

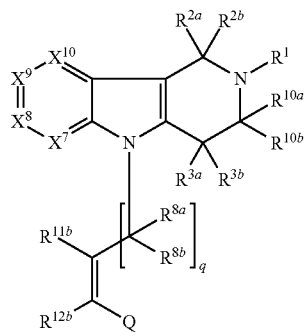

(II-a1)

or a salt or solvate thereof;
wherein $R^1$, $R^{2a}$, $R^{2b}$, $R^{3a}$, $R^{3b}$, $R^{8a}$, $R^{8b}$, $R^{10a}$, $R^{10b}$, $R^{11b}$, $R^{12b}$, q, Q, $X^7$, $X^8$, $X^9$, and $X^{10}$ are defined as for formula (II-A) and, where applicable, any variation thereof detailed herein. That is, variations of formula (II-A) and formula (II) detailed throughout, where applicable, apply to formula (II-a1) the same as if each and every variation were specifically and individually listed for formula (II-a1).

In other embodiments, the compound of formula (II) has the structure:

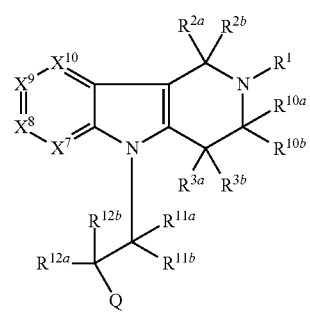

(II-B)

or a salt or solvate thereof;
wherein $R^1$, $R^{2a}$, $R^{2b}$, $R^{3a}$, $R^{3b}$, $R^{10a}$, $R^{10b}$, $R^{11a}$, $R^{11b}$, $R^{12a}$, $R^{12b}$, Q, $X^7$, $X^8$, $X^9$, and $X^{10}$ are defined as for formula (II) and, where applicable, any variation thereof detailed herein. That is, variations of formula (II) detailed throughout, where applicable, apply to formula (II-B) the same as if each and every variation were specifically and individually listed for formula (II-B).

In some such embodiments, $R^{11a}$ and $R^{12a}$ are taken together to form a bond and the compound of formula (II-B) has the structure:

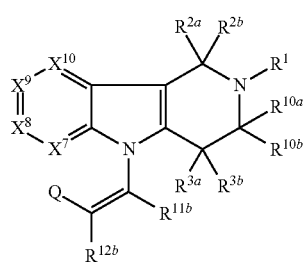

(II-b1)

or a salt or solvate thereof;

wherein $R^1$, $R^{2a}$, $R^{2b}$, $R^{3a}$, $R^{3b}$, $R^{10a}$, $R^{10b}$, $R^{11b}$, $R^{12b}$, Q, $X^7$, $X^8$, $X^9$, and $X^{10}$ are defined as for formula (II-B) and, where applicable, any variation thereof detailed herein. That is, variations of formula (II-B) and formula (II) detailed throughout, where applicable, apply to formula (II-b1) the same as if each and every variation were specifically and individually listed for formula (II-b1).

In other embodiments, the compound of formula (II) has the structure:

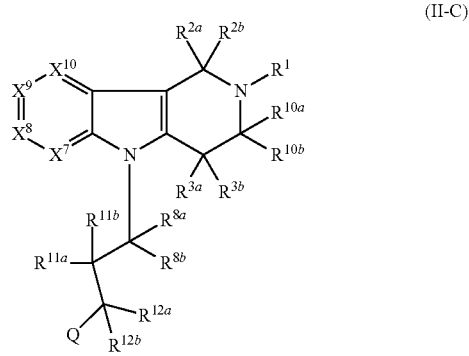

(II-C)

or a salt or solvate thereof;

wherein $R^1$, $R^{2a}$, $R^{2b}$, $R^{3a}$, $R^{3b}$, $R^{8a}$, $R^{8b}$, $R^{10a}$, $R^{10b}$, $R^{11a}$, $R^{11b}$, $R^{12a}$, $R^{12b}$, Q, $X^7$, $X^8$, $X^9$, and $X^{10}$ are defined as for formula (II) and, where applicable, any variation thereof detailed herein. That is, variations of formula (II) detailed throughout, where applicable, apply to formula (II-C) the same as if each and every variation were specifically and individually listed for formula (II-C).

In some such embodiments, $R^{11a}$ and $R^{12a}$ are taken together to form a bond and the compound of formula (II-C) has the structure:

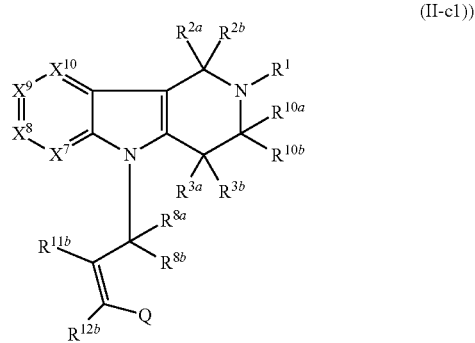

(II-c1)

or a salt or solvate thereof;

wherein $R^1$, $R^{2a}$, $R^{2b}$, $R^{3a}$, $R^{3b}$, $R^{8a}$, $R^{8b}$, $R^{10a}$, $R^{10b}$, $R^{11b}$, $R^{12b}$, Q, $X^7$, $X^8$, $X^9$, and $X^{10}$ are defined as for formula (II-C) and, where applicable, any variation thereof detailed herein. That is, variations of formula (II-C) and formula (II) detailed throughout, where applicable, apply to formula (II-c1) the same as if each and every variation were specifically and individually listed for formula (II-c1).

In further embodiments, the compound of formula (II) has the structure:

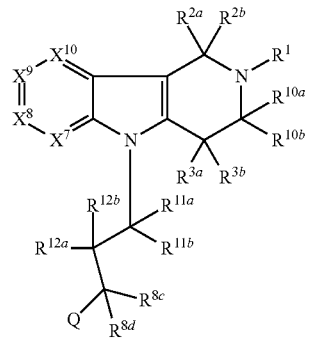

(II-D)

or a salt or solvate thereof;

wherein $R^1$, $R^{2a}$, $R^{2b}$, $R^{3a}$, $R^{3b}$, $R^{3c}$, $R^{8d}$, $R^{10a}$, $R^{10b}$, $R^{11a}$, $R^{11b}$, $R^{12a}$, $R^{12b}$, Q, $X^7$, $X^8$, $X^9$, and $X^{10}$ are defined as for formula (II) and, where applicable, any variation thereof detailed herein. That is, variations of formula (II) detailed throughout, where applicable, apply to formula (II-D) the same as if each and every variation were specifically and individually listed for formula (II-D).

In some such embodiments, $R^{11a}$ and $R^{12a}$ are taken together to form a bond and the compound of formula (II-D) has the structure:

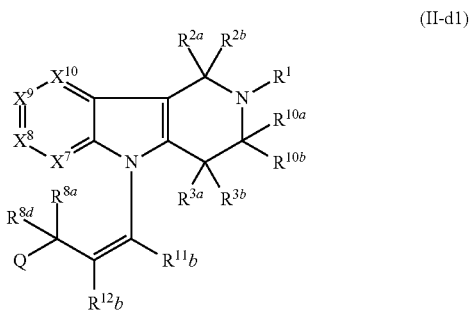

(II-d1)

or a salt or solvate thereof;

wherein $R^1$, $R^{2a}$, $R^{2b}$, $R^{3a}$, $R^{3b}$, $R^{8c}$, $R^{8d}$, $R^{10a}$, $R^{10b}$, $R^{11b}$, $R^{12b}$, Q, $X^7$, $X^8$, $X^9$, and $X^{10}$ are defined as for formula (II-D) and, where applicable, any variation thereof detailed herein. That is, variations of formula (II) detailed throughout, where applicable, apply to formula (II-d1) the same as if each and every variation were specifically and individually listed for formula (II-d1).

The substituent groups $R^1$, $R^{2a}$, $R^{2b}$, $R^{3a}$, $R^{3b}$, $R^{8a}$, $R^{8b}$, $R^{8c}$, $R^{8d}$, $R^{10a}$, $R^{10b}$, $R^{11a}$, $R^{11b}$, $R^{12a}$, $R^{12b}$, m, q, Q, $X^7$, $X^8$, $X^9$, and $X^{10}$ described herein as suitable for compounds of formula (II) are also suitable for compounds of formulae (II-A), (II-B), (II-C), (II-D), (II-a1), (II-b1), (II-c1) and (II-d1).

The invention also embraces compounds of the formula (VII):

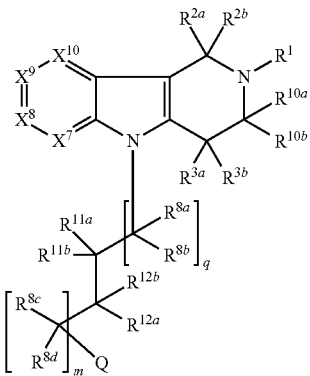

(VII)

or a salt or solvate thereof;
wherein:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety;

each $R^{3a}$ and $R^{3b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl or $R^{3a}$ and $R^{3b}$ are taken together with the carbon to which they are attached to form a carbonyl moiety or a cycloalkyl moiety;

each $X^7$, $X^8$, $X^9$ and $X^{10}$ is independently N, CH or $CR^4$;
each m and q is independently 0 or 1;
each $R^4$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, alkoxy, halo, substituted or unsubstituted aryl, substituted or unsubstituted heterocyclyl, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxy, carbonylalkoxy, or is taken together with a geminal $R^8$ to form a moiety of the formula —$OCH_2CH_2O$—, or is taken together with the carbon to which it is attached and a geminal $R^8$ to form a cycloalkyl moiety or a carbonyl moiety;

each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together with the carbon to which they are attached to form a carbonyl moiety or a cycloalkyl moiety;

each $R^{11a}$ and $R^{12a}$ is independently H, hydroxyl, alkoxy, halo, substituted or unsubstituted aryl, substituted or unsubstituted heteroaryl, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxy, or carbonylalkoxy; or $R^{11a}$ and $R^{12a}$ are taken together to represent a bond;

$R^{11b}$ and $R^{12b}$ are taken together with the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety; and Q is a substituted or unsubstituted aryl, substituted or unsubstituted heteroaryl, substituted or unsubstituted cycloalkyl, substituted or unsubstituted cycloalkenyl or substituted or unsubstituted heterocyclyl, alkoxy, acyloxy, substituted or unsubstituted amino, aminoacyl, aminocarbonylalkoxy, cyano, alkynyl, carboxy, carbonylalkoxy or acylamino.

In one variation, the compound is of the formula (VII) where $X^7$, $X^8$, $X^9$, $X^{10}$, $R^1$, $R^{2a}$, $R^{2b}$, $R^{3a}$, $R^{3b}$, $R^{10a}$, $R^{10b}$, Q, q, m, $R^{8a}$, $R^{8b}$, $R^{8c}$, $R^{8d}$, $R^{11a}$, $R^{11b}$, $R^{12a}$ and $R^{12b}$ are as defined for formula (VII), provided that the compound is other than 2-(1,2,3,4-tetrahydro-2,8-dimethyl-5H-pyrido[4,3-b]indol-5-yl)cyclohexanol. In another variation, the compounds of the invention, and methods of using the compounds and administering the compounds as detailed herein, encompass any of the compounds of the formula (VII), including 2-(1,2,3,4-tetrahydro-2,8-dimethyl-5H-pyrido[4,3-b]indol-5-yl)cyclohexanol. The substituent groups $R^1$, $R^{2a}$, $R^{2b}$, $R^{3a}$, $R^{3b}$, $R^{8a}$, $R^{8b}$, $R^{8c}$, $R^{8d}$, $R^{10a}$, $R^{10b}$, $R^{11a}$, $R^{11b}$, $R^{12a}$, $R^{12b}$, m, q, Q, $X^7$, $X^8$, $X^9$, and $X^{10}$ described herein as suitable for compounds of formula (II) are also suitable for compounds of formula (VII). Variations of formula (II) detailed throughout, where applicable, apply to formula (VII) the same as if each and every variation were specifically and individually listed for formula (VII).

In one variation, compounds of the formula (VII) are provided, where $X^7$, $X^8$, $X^9$, $X^{10}$, $R^1$, $R^{11b}$, $R^{12b}$, q, m, and Q are as defined for formula (VII), each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety; each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together with the carbon to which they are attached to form a carbonyl moiety; each $R^{8a}$, $R^{8b}$, $R^{8c}$ and $R^{8d}$ is independently H, hydroxyl, $C_1$-$C_8$ alkyl, or is taken together with the carbon to which it is attached and a geminal $R^8$ to form a cycloalkyl moiety or a carbonyl moiety; each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together with the carbon to which they are attached to form a carbonyl moiety; and each $R^{11a}$ and $R^{12a}$ is independently H, hydroxyl, or $C_1$-$C_8$ alkyl; or $R^{11a}$ and $R^{12a}$ are taken together to represent a bond.

In one embodiment, provided is a compound of formula (VII) where at least one $R^{3a}$ and $R^{3b}$ is aryl. In a particular variation of formula (VII), at least one of $R^{3a}$ and $R^{3b}$ is phenyl.

The invention also embraces compounds of the formula (VIII):

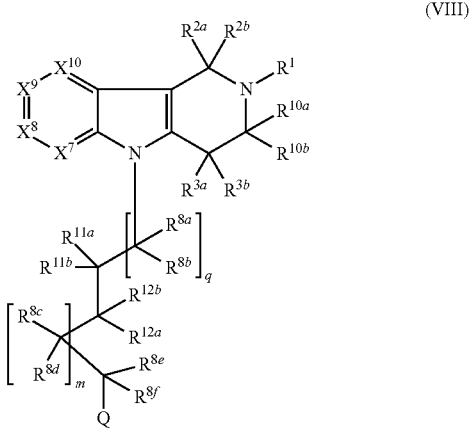

(VIII)

or a salt or solvate thereof;
wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together with the carbon to which they are attached to form a carbonyl moiety or a cycloalkyl moiety;

each $R^{3a}$ and $R^{3b}$ is independently H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl or $R^{3a}$ and $R^{3b}$ are taken together with the carbon to which they are attached to form a carbonyl moiety or a cycloalkyl moiety;

each $X^7$, $X^8$, $X^9$ and $X^{10}$ is independently N, CH or $CR^4$;
each m and q is independently 0 or 1;
each $R^4$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, alkoxy, halo, substituted or unsubstituted aryl, substituted or unsubstituted heteroaryl, substituted or unsubstituted $C_1$-$C_8$ alkyl, substituted or unsubstituted $C_3$-$C_8$ cycloalkyl, substituted or unsubstituted $C_2$-$C_8$ alkenyl, $C_1$-$C_8$ perhaloalkyl, carboxy, carbonylalkoxy, is taken together with the carbon to which it is attached and a geminal $R^{8(a\text{-}f)}$ to form a cycloalkyl moiety or a carbonyl moiety, is taken together with a geminal $R^{8(a\text{-}f)}$ to form a moiety of the formula —$OCH_2CH_2O$—, a methylene or a substituted methylene, is taken together with a vicinal $R^{8(a\text{-}f)}$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^{8(a\text{-}f)}$ to form a bond, provided that (i) at least one of $R^{8c}$ and $R^{8d}$ is taken together with a vicinal $R^{8(a\text{-}f)}$ and the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety or is taken together with a vicinal $R^{8(a\text{-}f)}$ to form a bond, and (ii) when an $R^{8(a\text{-}f)}$ is taken together with a vicinal $R^8$ to form a bond, the geminal $R^{8(a\text{-}f)}$ is other than hydroxyl;

each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together with the carbon to which they are attached to form a carbonyl moiety or a cycloalkyl moiety; and Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, alkoxy, acyloxy, substituted or unsubstituted amino, aminoacyl, aminocarbonylalkoxy, cyano, alkynyl, carboxy, carbonylalkoxy or acylamino.

In another variation, compounds of the Formulae or pharmaceutically acceptable salts thereof are embraced, provided that the compounds are other than compounds in Table B or a pharmaceutically acceptable salt thereof. In a particular variation, compounds of the formula (I) are embraced, provided the compounds are other than any of compounds 1x-99x. In one variation, compounds of the formula (III) are embraced, provided the compounds are other than any of compounds 1x-99x. In another variation, compounds of the formula (V) are embraced, provided the compounds are other than any of compounds 1x-129x. In still another variation, compounds of the formula (VIII) are embraced, provided the compounds are other than any of compounds 1x-129x. In yet another variation, compounds of the formula (IV) are embraced, provided the compounds are other than compound 130x. In another variation, compounds of the formula (VI) are embraced, provided the compounds are other than compound 130x. In still a further variation, compounds of the formulae detailed herein are provided, wherein the compounds include a compound of Table B or a pharmaceutically acceptable salt thereof. In addition, methods provided herein, including methods of treatment as detailed herein, in one variation employ compounds according to the formulae detailed herein, including compounds of Table B.

TABLE B

| No. | Compound Name |
|---|---|
| 1x | 2,3,4,5-tetrahydro-2-methyl-5-[(1Z)-2-phenylethenyl]-1H-Pyrido[4,3-b]indole |
| 2x | 2,3,4,5-tetrahydro-2-methyl-5-[(1E)-2-phenylethenyl]-1H-Pyrido[4,3-b]indole |
| 3x | 2,3,4,5-tetrahydro-2-methyl-5-[(1E)-2-(4-pyridinyl)ethenyl]-1H-Pyrido[4,3-b]indole |
| 4x | 2,3,4,5-tetrahydro-2-methyl-5-[(1Z)-2-(3-pyridinyl)ethenyl]-1H-Pyrido[4,3-b]indole |

TABLE B-continued

| No. | Compound Name |
|---|---|
| 5x | 2,3,4,5-tetrahydro-2-methyl-5-[(1E)-2-(2-pyridinyl)ethenyl]-1H-Pyrido[4,3-b]indole |
| 6x | 2-(1,1-dimethylethyl)-2,3,4,5-tetrahydro-5-[(1Z)-2-(3-pyridinyl)ethenyl]-1H-Pyrido[4,3-b]indole |
| 7x | 8-fluoro-2,3,4,5-tetrahydro-2-methyl-5-[(1Z)-2-phenylethenyl]-1H-Pyrido[4,3-b]indole |
| 8x | 8-fluoro-2,3,4,5-tetrahydro-2-methyl-5-[(1E)-2-phenylethenyl]-1H-Pyrido[4,3-b]indole |
| 9x | 8-fluoro-2,3,4,5-tetrahydro-2-methyl-5-[(1E)-2-(4-pyridinyl)ethenyl]-1H-Pyrido[4,3-b]indole |
| 10x | 8-fluoro-2,3,4,5-tetrahydro-2-methyl-5-[(1Z)-2-(3-pyridinyl)ethenyl]-1H-Pyrido[4,3-b]indole |
| 11x | 8-fluoro-2,3,4,5-tetrahydro-2-methyl-5-[(1E)-2-(2-pyridinyl)ethenyl]-1H-Pyrido[4,3-b]indole |
| 12x | 2,3,4,5-tetrahydro-2,8-dimethyl-5-[(1Z)-2-phenylethenyl]-1H-Pyrido[4,3-b]indole |
| 13x | 2,3,4,5-tetrahydro-2,8-dimethyl-5-[(1E)-2-phenylethenyl]-1H-Pyrido[4,3-b]indole |
| 14x | 2,3,4,5-tetrahydro-2,8-dimethyl-5-[(1Z)-2-(3-pyridinyl)ethenyl]-1H-Pyrido[4,3-b]indole |
| 15x | 2,3,4,5-tetrahydro-2,8-dimethyl-5-[(1E)-2-(4-pyridinyl)ethenyl]-1H-Pyrido[4,3-b]indole |
| 16x | 2,3,4,5-tetrahydro-8-methyl-2-(phenylmethyl)-5-[(1Z)-2-(3-pyridinyl)ethenyl]-1H-Pyrido[4,3-b]indole |
| 17x | 8-fluoro-5-[(1E)-2-(4-fluorophenyl)ethenyl]-2,3,4,5-tetrahydro-2-methyl-1H-Pyrido[4,3-b]indole |
| 18x | 8-fluoro-5-[(1Z)-2-(3-fluorophenyl)ethenyl]-2,3,4,5-tetrahydro-2-methyl-1H-Pyrido[4,3-b]indole |
| 19x | 2,3,4,5-tetrahydro-2,8-dimethyl-5-[(1E)-2-[4-(trifluoromethyl)phenyl]ethenyl]-1H-Pyrido[4,3-b]indole |
| 20x | 2,3,4,5-tetrahydro-2,8-dimethyl-5-[(1Z)-2-[3-(trifluoromethyl)phenyl]ethenyl]-1H-Pyrido[4,3-b]indole |
| 21x | 8-fluoro-2,3,4,5-tetrahydro-2-methyl-5-[(1E)-2-[4-(trifluoromethyl)phenyl]ethenyl]-1H-Pyrido[4,3-b]indole |
| 22x | 8-fluoro-2,3,4,5-tetrahydro-5-[(1Z)-2-(4-methoxyphenyl)ethenyl]-2-methyl-1H-Pyrido[4,3-b]indole |
| 23x | 4-[(1Z)-2-(8-fluoro-1,2,3,4-tetrahydro-2-methyl-5H-pyrido[4,3-b]indol-5-yl)ethenyl]-N,N-dimethyl-Benzenamine |
| 24x | 5-[(1E)-2-(4-fluorophenyl)ethenyl]-2,3,4,5-tetrahydro-2,8-dimethyl-1H-Pyrido[4,3-b]indole |
| 25x | 2,3,4,5-tetrahydro-2,8-dimethyl-5-[2-(2-pyridinyl)ethenyl]-1H-Pyrido[4,3-b]indole |
| 26x | 2,3,4,5-tetrahydro-8-methyl-5-[2-(4-pyridinyl)ethenyl]-1H-Pyrido[4,3-b]indole |
| 27x | 8-fluoro-2,3,4,5-tetrahydro-5-[2-(4-methoxyphenyl)ethenyl]-2-methyl-1H-Pyrido[4,3-b]indole |
| 28x | 2,3,4,5-tetrahydro-8-methyl-5-(2-phenylethenyl)-2-(3-pyridinylmethyl)-1H-Pyrido[4,3-b]indole |
| 29x | 2,3,4,5-tetrahydro-2,8-dimethyl-5-[2-(4-pyridinyl)ethenyl]-1H-Pyrido[4,3-b]indole |
| 30x | 2,3,4,5-tetrahydro-2-methyl-5-(2-phenylethenyl)-8-(trifluoromethyl)-1H-Pyrido[4,3-b]indole |
| 31x | 2,3,4,5-tetrahydro-2-methyl-5-[2-(3-pyridinyl)ethenyl]-1H-Pyrido[4,3-b]indole |
| 32x | 2,3,4,5-tetrahydro-8-methyl-2-[1-[(4-methylphenyl)sulfonyl]-4-piperidinyl]-5-[2-(2-pyridinyl)ethenyl]-1H-Pyrido[4,3-b]indole |
| 33x | 2,3,4,5-tetrahydro-8-methoxy-2-methyl-5-[2-(2-pyridinyl)ethenyl]-1H-Pyrido[4,3-b]indole |
| 34x | 2,3,4,5-tetrahydro-8-methyl-2-(4-piperidinyl)-5-[2-(2-pyridinyl)ethenyl]-1H-Pyrido[4,3-b]indole |
| 35x | 8-fluoro-5-[2-(4-fluorophenyl)ethenyl]-2,3,4,5-tetrahydro-2-methyl-1H-Pyrido[4,3-b]indole |
| 36x | 9-hydroxy-2-methyl-3-[2-[1,3,4,5-tetrahydro-8-methyl-5-(2-phenylethenyl)-2H-pyrido[4,3-b]indol-2-yl]ethyl]-4H-Pyrido[1,2-a]pyrimidin-4-one |
| 37x | 2,3,4,5-tetrahydro-8-methoxy-2-methyl-5-[2-(4-pyridinyl)ethenyl]-1H-Pyrido[4,3-b]indole |
| 38x | N,N-dimethyl-4-[2-(1,2,3,4-tetrahydro-2,8-dimethyl-5H-pyrido[4,3-b]indol-5-yl)ethenyl]-Benzenamine |
| 39x | 2,3,4,5-tetrahydro-8-methyl-5-(2-phenylethenyl)-1H-Pyrido[4,3-b]indole |
| 40x | 2,3,4,5-tetrahydro-2,8-dimethyl-5-[2-(3-pyridinyl)ethenyl]-1H-Pyrido[4,3-b]indole |
| 41x | 2,3,4,5-tetrahydro-8-methyl-2-[1-[(4-methylphenyl)sulfonyl]-4-piperidinyl]-5-[2-(4-pyridinyl)ethenyl]-1H-Pyrido[4,3-b]indole |
| 42x | 8-bromo-2,3,4,5-tetrahydro-2-methyl-5-[2-(2-pyridinyl)ethenyl]-1H-Pyrido[4,3-b]indole |
| 43x | 2,3,4,5-tetrahydro-8-methyl-2-(4-piperidinyl)-5-[2-(3-pyridinyl)ethenyl]-1H-Pyrido[4,3-b]indole |
| 44x | 8-fluoro-2,3,4,5-tetrahydro-2-methyl-5-[2-[4-(trifluoromethyl)phenyl]ethenyl]-1H-Pyrido[4,3-b]indole |
| 45x | 2,9-dimethyl-3-[2-[1,3,4,5-tetrahydro-8-methyl-5-(2-phenylethenyl)-2H-pyrido[4,3-b]indol-2-yl]ethyl]-4H-Pyrido[1,2-a]pyrimidin-4-one |
| 46x | 8-fluoro-2,3,4,5-tetrahydro-2-methyl-5-[2-(4-pyridinyl)ethenyl]-1H-Pyrido[4,3-b]indole |
| 47x | 2,3,4,5-tetrahydro-5-[2-(4-methoxyphenyl)ethenyl]-2,8-dimethyl-1H-Pyrido[4,3-b]indole |
| 48x | 1,3,4,5-tetrahydro-8-methyl-5-(2-phenylethenyl)-2H-Pyrido[4,3-b]indole-2-carboxylic acid ethyl ester |
| 49x | 2,3,4,5-tetrahydro-8-methoxy-2-methyl-5-[2-(3-pyridinyl)ethenyl]-1H-Pyrido[4,3-b]indole |
| 50x | 2,3,4,5-tetrahydro-2-methyl-5-[2-(4-methylphenyl)ethenyl]-1H-Pyrido[4,3-b]indole |
| 51x | 8-fluoro-2,3,4,5-tetrahydro-2-methyl-5-[2-(2-pyridinyl)ethenyl]-1H-Pyrido[4,3-b]indole |
| 52x | 2,3,4,5-tetrahydro-8-methyl-2-(4-piperidinyl)-5-[2-(4-pyridinyl)ethenyl]-1H-Pyrido[4,3-b]indole |
| 53x | 5-[2-(4-ethylphenyl)ethenyl]-2,3,4,5-tetrahydro-2,8-dimethyl-1H-Pyrido[4,3-b]indole |
| 54x | 6,7,8,9-tetrahydro-2-methyl-3-[2-[1,3,4,5-tetrahydro-8-methyl-5-(2-phenylethenyl)-2H-pyrido[4,3-b]indol-2-yl]ethyl]-4H-Pyrido[1,2-a]pyrimidin-4-one |
| 55x | 2,3,4,5-tetrahydro-2-methyl-5-[2-(4-pyridinyl)ethenyl]-8-(trifluoromethyl)-1H-Pyrido[4,3-b]indole |
| 56x | 5-[2-(4-fluorophenyl)ethenyl]-2,3,4,5-tetrahydro-2,8-dimethyl-1H-Pyrido[4,3-b]indole |
| 57x | 2,3,4,5-tetrahydro-8-methyl-2-[(4-methylphenyl)sulfonyl]-5-(2-phenylethenyl)-1H-Pyrido[4,3-b]indole |
| 58x | 8-fluoro-2,3,4,5-tetrahydro-2-methyl-5-[2-(3-pyridinyl)ethenyl]-1H-Pyrido[4,3-b]indole |
| 59x | 2,3,4,5-tetrahydro-2,8-dimethyl-5-(2-phenylethenyl)-1H-Pyrido[4,3-b]indole |

TABLE B-continued

| No. | Compound Name |
|---|---|
| 60x | 2,3,4,5-tetrahydro-2-methyl-5-[2-(2-pyridinyl)ethenyl]-8-(trifluoromethyl)-1H-Pyrido[4,3-b]indole |
| 61x | 2,3,4,5-tetrahydro-8-methyl-2-(1-methyl-4-piperidinyl)-5-[2-(2-pyridinyl)ethenyl]-1H-Pyrido[4,3-b]indole |
| 62x | 2,3,4,5-tetrahydro-2,8-dimethyl-5-[2-[4-(1-methylethyl)phenyl]ethenyl]-1H-Pyrido[4,3-b]indole |
| 63x | 1-[2-[1,3,4,5-tetrahydro-8-methyl-5-(2-phenylethenyl)-2H-pyrido[4,3-b]indol-2-yl]ethyl]-2-Imidazolidinone |
| 64x | 2,3,4,5-tetrahydro-2-methyl-5-[2-(4-pyridinyl)ethenyl]-1H-Pyrido[4,3-b]indole-8-carboxylic acid |
| 65x | 2,3,4,5-tetrahydro-2,8-dimethyl-5-[2-[4-(trifluoromethyl)phenyl]ethenyl]-1H-Pyrido[4,3-b]indole |
| 66x | 2,3,4,5-tetrahydro-8-methyl-5-(2-phenylethenyl)-2-[2-(2-pyridinyl)ethyl]-1H-Pyrido[4,3-b]indole |
| 67x | 2,3,4,5-tetrahydro-2-methyl-5-[2-(3-pyridinyl)ethenyl]-8-(trifluoromethyl)-1H-Pyrido[4,3-b]indole |
| 68x | 2,3,4,5-tetrahydro-2,8-dimethyl-5-[2-(4-methylphenyl)ethenyl]-1H-Pyrido[4,3-b]indole |
| 69x | 2,3,4,5-tetrahydro-2-methyl-5-[2-(2-pyridinyl)ethenyl]-1H-Pyrido[4,3-b]indole-8-carbonitrile |
| 70x | 2,3,4,5-tetrahydro-8-methyl-2-(1-methyl-4-piperidinyl)-5-[2-(3-pyridinyl)ethenyl]-1H-Pyrido[4,3-b]indole |
| 71x | 5-[2-[4-(1,1-dimethylethyl)phenyl]ethenyl]-2,3,4,5-tetrahydro-2,8-dimethyl-1H-Pyrido[4,3-b]indole |
| 72x | 2,3,4,5-tetrahydro-8-methyl-5-[2-(2-pyridinyl)ethenyl]-1H-Pyrido[4,3-b]indole |
| 73x | 2,3,4,5-tetrahydro-2-methyl-5-[2-(4-pyridinyl)ethenyl]-1H-Pyrido[4,3-b]indole |
| 74x | 2,3,4,5-tetrahydro-2-methyl-5-[2-(4-methylphenyl)ethenyl]-8-(trifluoromethyl)-1H-Pyrido[4,3-b]indole |
| 75x | 2,3,4,5-tetrahydro-8-methyl-5-(2-phenylethenyl)-2-[2-(4-pyridinyl)ethyl]-1H-Pyrido[4,3-b]indole |
| 76x | 2,3,4,5-tetrahydro-2,8-dimethyl-5-[2-(6-methyl-3-pyridinyl)ethenyl]-1H-Pyrido[4,3-b]indole |
| 77x | 2,3,4,5-tetrahydro-8-methoxy-2-methyl-5-(2-phenylethenyl)-1H-Pyrido[4,3-b]indole |
| 78x | 2,3,4,5-tetrahydro-2-methyl-8-(3-pyridinyl)-5-[2-(2-pyridinyl)ethenyl]-1H-Pyrido[4,3-b]indole |
| 79x | 2,3,4,5-tetrahydro-8-methyl-2-(1-methyl-4-piperidinyl)-5-[2-(4-pyridinyl)ethenyl]-1H-Pyrido[4,3-b]indole |
| 80x | 2,3,4,5-tetrahydro-2-methyl-5-[2-(2-pyridinyl)ethenyl]-1H-Pyrido[4,3-b]indole |
| 81x | 2,3,4,5-tetrahydro-8-methyl-5-[2-(3-pyridinyl)ethenyl]-1H-Pyrido[4,3-b]indole |
| 82x | 2,3,4,5-tetrahydro-2,8-dimethyl-5-[2-(2-pyrazinyl)ethenyl]-1H-Pyrido[4,3-b]indole |
| 83x | 8-fluoro-2,3,4,5-tetrahydro-2-methyl-5-[2-(4-methylphenyl)ethenyl]-1H-Pyrido[4,3-b]indole |
| 84x | 5-hydroxy-6-methyl-4-[[1,3,4,5-tetrahydro-8-methyl-5-(2-phenylethenyl)-2H-pyrido[4,3-b]indol-2-yl]methyl]-3-Pyridinemethanol |
| 85x | 8-fluoro-2,3,4,5-tetrahydro-2-methyl-5-[2-(6-methyl-3-pyridinyl)ethenyl]-1H-Pyrido[4,3-b]indole |
| 86x | 8-fluoro-2,3,4,5-tetrahydro-2-methyl-5-(2-phenylethenyl)-1H-Pyrido[4,3-b]indole |
| 87x | 2,3,4,5-tetrahydro-2-methyl-8-(phenylsulfonyl)-5-[2-(2-pyridinyl)ethenyl]-1H-Pyrido[4,3-b]indole |
| 88x | 2,3,4,5-tetrahydro-8-methyl-2-[(4-methylphenyl)sulfonyl]-5-[2-(2-pyridinyl)ethenyl]-1H-Pyrido[4,3-b]indole |
| 89x | 2,3,4,5-tetrahydro-2,8-dimethyl-5-[3-(4-methylphenyl)-2-propen-1-yl]-1H-Pyrido[4,3-b]indole |
| 90x | 8-fluoro-2,3,4,5-tetrahydro-2-methyl-5-[(2E)-3-phenyl-2-propen-1-yl]-1H-Pyrido[4,3-b]indole |
| 91x | 2,3,4,5-tetrahydro-5-[3-(4-methoxyphenyl)-2-propen-1-yl]-2,8-dimethyl-1H-Pyrido[4,3-b]indole |
| 92x | 2,3,4,5-tetrahydro-2,8-dimethyl-5-[(2Z)-3-phenyl-2-propen-1-yl]-1H-Pyrido[4,3-b]indole |
| 93x | 5-[3-(4-fluorophenyl)-2-propen-1-yl]-2,3,4,5-tetrahydro-2,8-dimethyl-1H-Pyrido[4,3-b]indole |
| 94x | 8-fluoro-2,3,4,5-tetrahydro-2-methyl-5-[(2Z)-3-phenyl-2-propen-1-yl]-1H-Pyrido[4,3-b]indole |
| 95x | 8-fluoro-2,3,4,5-tetrahydro-2-methyl-5-(3-phenyl-2-propen-1-yl)-1H-Pyrido[4,3-b]indole |
| 96x | 8-fluoro-2,3,4,5-tetrahydro-2-methyl-5-[3-(4-methylphenyl)-2-propen-1-yl]-1H-Pyrido[4,3-b]indole |
| 97x | 2,3,4,5-tetrahydro-8-methoxy-2-methyl-5-[3-(4-methylphenyl)-2-propen-1-yl]-1H-Pyrido[4,3-b]indole |
| 98x | 2,3,4,5-tetrahydro-2,8-dimethyl-5-[(2E)-3-phenyl-2-propen-1-yl]-1H-Pyrido[4,3-b]indole |
| 99x | 5-[(1Z)-2-(4-fluorophenyl)-1-propen-1-yl]-2,3,4,5-tetrahydro-2,8-dimethyl-1H-Pyrido[4,3-b]indole |
| 100x | 2,3,4,5-tetrahydro-2,8-dimethyl-5-[3-(2-pyridinyl)-2-propyn-1-yl]-1H-Pyrido[4,3-b]indole |
| 101x | 2,3,4,5-tetrahydro-2,8-dimethyl-5-(2-phenylethynyl)-1H-Pyrido[4,3-b]indole |
| 102x | 5-[2-(4-fluorophenyl)ethynyl]-2,3,4,5-tetrahydro-2,8-dimethyl-1H-Pyrido[4,3-b]indole |
| 103x | 8-fluoro-2,3,4,5-tetrahydro-2-methyl-5-[2-(4-pyridinyl)ethynyl]-1H-Pyrido[4,3-b]indole |
| 104x | 2,3,4,5-tetrahydro-2-methyl-5-[2-(2-pyridinyl)ethynyl]-1H-Pyrido[4,3-b]indole |
| 105x | 2,3,4,5-tetrahydro-2,8-dimethyl-5-[2-(3-pyridinyl)ethynyl]-1H-Pyrido[4,3-b]indole |
| 106x | 2,3,4,5-tetrahydro-2,8-dimethyl-5-[2-[2-(trifluoromethyl)phenyl]ethynyl]-1H-Pyrido[4,3-b]indole |
| 107x | 8-fluoro-2,3,4,5-tetrahydro-2-methyl-5-(2-phenylethynyl)-1H-Pyrido[4,3-b]indole |
| 108x | 8-fluoro-5-[2-(4-fluorophenyl)ethynyl]-2,3,4,5-tetrahydro-2-methyl-1H-Pyrido[4,3-b]indole |
| 109x | 2,3,4,5-tetrahydro-5-[2-(3-methoxyphenyl)ethynyl]-2,8-dimethyl-1H-Pyrido[4,3-b]indole |
| 110x | 6-fluoro-2,3,4,5-tetrahydro-2-methyl-5-[2-(3-pyridinyl)ethynyl]-1H-Pyrido[4,3-b]indole |
| 111x | 5-[2-(3-fluorophenyl)ethynyl]-2,3,4,5-tetrahydro-2,8-dimethyl-1H-Pyrido[4,3-b]indole |
| 112x | 2,3,4,5-tetrahydro-2-methyl-5-[2-(3-pyridinyl)ethynyl]-1H-Pyrido[4,3-b]indole |
| 113x | 2,3,4,5-tetrahydro-2,8-dimethyl-5-[2-(4-pyridinyl)ethynyl]-1H-Pyrido[4,3-b]indole |
| 114x | 5-[2-(2-fluorophenyl)ethynyl]-2,3,4,5-tetrahydro-2,8-dimethyl-1H-Pyrido[4,3-b]indole |
| 115x | 8-fluoro-2,3,4,5-tetrahydro-2-methyl-5-[2-(2-pyridinyl)ethynyl]-1H-Pyrido[4,3-b]indole |
| 116x | 8-fluoro-5-[2-(3-fluorophenyl)ethynyl]-2,3,4,5-tetrahydro-2-methyl-1H-Pyrido[4,3-b]indole |

TABLE B-continued

| No. | Compound Name |
|---|---|
| 117x | 2,3,4,5-tetrahydro-5-[2-(2-methoxyphenyl)ethynyl]-2,8-dimethyl-1H-Pyrido[4,3-b]indole |
| 118x | 2,3,4,5-tetrahydro-2,8-dimethyl-5-[2-[4-(trifluoromethyl)phenyl]ethynyl]-1H-Pyrido[4,3-b]indole |
| 119x | 2,3,4,5-tetrahydro-2-methyl-5-[2-(4-pyridinyl)ethynyl]-1H-Pyrido[4,3-b]indole |
| 120x | 2,3,4,5-tetrahydro-2-methyl-5-[2-(3-pyridinyl)ethynyl]-8-(trifluoromethyl)-1H-Pyrido[4,3-b]indole |
| 121x | 2,3,4,5-tetrahydro-5-[2-(4-methoxyphenyl)ethynyl]-2,8-dimethyl-1H-Pyrido[4,3-b]indole |
| 122x | 8-fluoro-2,3,4,5-tetrahydro-2-methyl-5-[2-(3-pyridinyl)ethynyl]-1H-Pyrido[4,3-b]indole |
| 123x | 8-fluoro-2,3,4,5-tetrahydro-2-methyl-5-[2-[4-(trifluoromethyl)phenyl]ethynyl]-1H-Pyrido[4,3-b]indole |
| 124x | 2,3,4,5-tetrahydro-2-methyl-5-(2-phenylethynyl)-1H-Pyrido[4,3-b]indole |
| 125x | 2,3,4,5-tetrahydro-2,8-dimethyl-5-[2-(2-pyridinyl)ethynyl]-1H-Pyrido[4,3-b]indole |
| 126x | 2,3,4,5-tetrahydro-2,8-dimethyl-5-[2-[3-(trifluoromethyl)phenyl]ethynyl]-1H-Pyrido[4,3-b]indole |
| 127x | 2,3,4,5-tetrahydro-2-methyl-5-[2-(5-pyrimidinyl)ethynyl]-1H-Pyrido[4,3-b]indole |
| 128x | 8-fluoro-2,3,4,5-tetrahydro-5-[2-(4-methoxyphenyl)ethynyl]-2-methyl-1H-Pyrido[4,3-b]indole |
| 129x | N,N-dimethyl-4-[2-(1,2,3,4-tetrahydro-2,8-dimethyl-5H-pyrido[4,3-b]indol-5-yl)ethynyl]-Benzenamine |
| 130x | 5-[2-(4-fluorophenyl)-2-propen-1-yl]-2,3,4,5-tetrahydro-2,8-dimethyl-1H-Pyrido[4,3-b]indole |

In compounds of formulae (I), (II), (III), (IV), (V), (VI), (VII) and (VIII), $R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In specific embodiments, $R^1$ is a substituted or unsubstituted $C_1$-$C_8$ alkyl, acyl, acyloxy, carbonylalkoxy, substituted or unsubstituted heterocyclyl or substituted or unsubstituted aryl. In more specific embodiments, $R^1$ is an unsubstituted $C_1$-$C_8$ alkyl such as methyl and cyclopropyl.

In certain embodiments, compounds of formulae (I), (II), (III), (IV), (V), (VI), (VII) and (VIII) are provided where $R^1$ is selected from the following moieties:

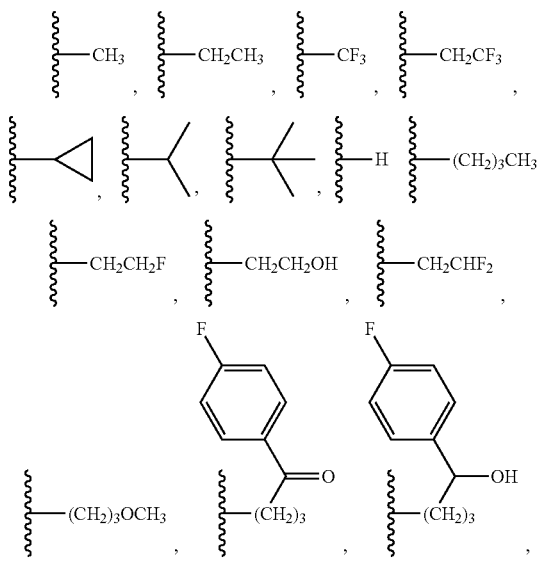

-continued

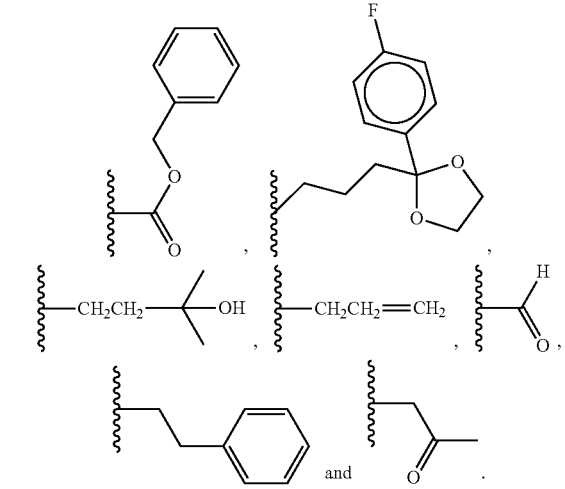

In compounds of formulae (I), (II), (III), (IV), (V), (VI), (VII) and (VIII), the ring comprising N, $R^{2a}$, $R^{2b}$, $R^{10a}$, $R^{10b}$, $R^{3a}$ and $R^{3b}$ is sometimes referred to herein as the C-ring.

In compounds of formulae (I), (II), (III), (IV), (V), (VI), (VII) and (VIII), each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together to form a carbonyl moiety. In specific embodiments, each $R^{2a}$ and $R^{2b}$ is independently H, methyl, fluoro or $R^{2a}$ and $R^{2b}$ are taken together to form a carbonyl moiety. In a specific embodiment, $R^{2a}$ and $R^{2b}$ are both H.

In compounds of formulae (I), (II), (III), (IV), (V), (VI), (VII) and (VIII), each $R^{3a}$ and $R^{3b}$ is independently H, substituted or unsubstituted $C_1$-$C_8$ alkyl, halo, cyano, hydroxyl, alkoxy, nitro or $R^{2a}$ and $R^{2b}$ are taken together to form a carbonyl moiety. In specific embodiments, each $R^{3a}$ and $R^{3b}$ is independently H or fluoro. In another specific embodiment, $R^{3a}$ and $R^{3b}$ are both H. In a further specific embodiment, $R^{3a}$ and $R^{3b}$ are both H and $R^{2a}$ and $R^{2b}$ are both H.

In compounds of formulae (I), (II), (III), (IV), (V), (VI), (VII) and (VIII), each $R^{10a}$ and $R^{10b}$ is independently H, substituted or unsubstituted $C_1$-$C_8$ alkyl, halo, cyano, hydroxyl, alkoxy, nitro or $R^{10a}$ and $R^{10b}$ are taken together to form a carbonyl moiety. In specific embodiments, each $R^{10a}$ and $R^{10b}$ is independently H, halo, hydroxyl or methyl or $R^{10a}$ and $R^{10b}$ are taken together to form a carbonyl moiety. In another specific embodiment, $R^{10a}$ and $R^{10b}$ are both H. In a further specific embodiment, $R^{10a}$ and $R^{10b}$ are both H and $R^{2a}$, $R^{2b}$, $R^{3a}$ and $R^{3b}$ are each H.

In compounds of formulae (I), (II), (III), (IV), (V), (VI), (VII) and (VIII), the ring comprising $X^7$, $X^8$, $X^9$ and $X^{10}$ is sometimes referred to herein as the A-ring. In compounds of formulae (I), (II), (III), (IV), (V), (VI), (VII) and (VIII), each $X^7$, $X^8$, $X^9$ and $X^{10}$ is independently N, CH or $CR^4$. In certain embodiments, each $X^7$, $X^8$, $X^9$ and $X^{10}$ is CH or $CR^4$, such that the A-ring is an optionally substituted phenyl ring. In specific embodiments, $X^9$ is $CR^4$ where $R^4$ is halo or alkyl and $X^7$, $X^8$ and $X^{10}$ are each CH. In other embodiments, one of $X^7$, $X^8$, $X^9$ and $X^{10}$ is N, and the others are CH or $CR^4$, such that the A-ring is an optionally substituted pyridine ring. In further embodiments, two of $X^7$, $X^8$, $X^9$ and $X^{10}$ are N, and the others are CH or $CR^4$, such that the A-ring is an optionally substituted pyrimidine or pyrazine ring. In one variation of formula (I), $X^9$ is $CR^4$ where $R^4$ is halo or alkyl, $X^7$, $X^8$ and $X^{10}$ are each CH and $R^{12}$ is other than H. In one variation of formula (II), $X^9$ is $CR^4$ where $R^4$ is halo or alkyl, $X^7$, $X^8$ and $X^{10}$ are each CH and either (a) $R^{11a}$ and $R^{12a}$ are both H and $R^{11b}$ and $R^{12b}$ are taken together to form a substituted or unsubstituted cycloalkyl; or (b) $R^{11a}$ and $R^{12a}$ are taken together to form a double bond and together with $R^{11b}$ and $R^{12b}$ form a cycloalkenyl moiety.

In compounds of formulae (I), (II), (III), (IV), (V), (VI), (VII) and (VIII), each $R^4$, where present, is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl. In one variation, at least one of $X^7$-$X^{10}$ is $CR^4$ where $R^4$ is halo. In a particular variation, one of $X^7$-$X^{10}$ is $CR^4$ where $R^4$ is chloro and the others are CH. In a specific variation, $X^7$, $X^8$ and $X^{10}$ are each CH and $X^9$ is $CR^4$ where $R^4$ is chloro.

In certain embodiments of formulae (I), (II), (III), (IV), (V), (VI), (VII) and (VIII), each $R^4$, where present, is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl. In further embodiments, each $R^4$ is independently hydroxyl, halo, $C_1$-$C_4$ perhaloalkyl, substituted or unsubstituted $C_1$-$C_4$ alkyl, substituted or unsubstituted aryl, substituted or unsubstituted heteroaryl, or $C_1$-$C_4$ alkoxy; or in still a further variation, each $R^4$ is independently halo, unsubstituted $C_1$-$C_4$ alkyl or $C_1$-$C_4$ perhaloalkyl.

In specific embodiments, the A-ring is a phenyl, pyridyl, pyrimidinyl or pyrazinyl ring, optionally substituted with 0-2 $R^4$ groups (i.e., $(R^4)_n$) where n is 0, 1 or 2. In some such embodiments, n is 1 or 2 and each $R^4$ is independently halo, methyl or $CF_3$.

In compounds of formulae (I), (II), (III), (IV), (V), (VI), (VII) and (VIII), each $R^{8a}$, $R^{8b}$, $R^{8c}$ and $R^{8d}$, where present, is independently H, hydroxyl, $C_1$-$C_8$ alkyl or is taken together with the carbon to which it is attached and a geminal $R^8$ to form a cycloalkyl moiety or a carbonyl moiety. In specific embodiments, each $R^{8a}$, $R^{8b}$, $R^{8c}$ and $R^{8d}$, where present, is independently H, hydroxyl, methyl or is taken together with the carbon to which it is attached and a geminal $R^8$ to form a carbonyl moiety. In another specific embodiment, each $R^{8a}$, $R^{8b}$, $R^{8c}$ and $R^{8d}$, where present, is H.

In specific embodiments of formulae (I), (II) and (III), q is 0 and m is 0. In other embodiments, q is 1 and m is 0. In compounds of formula (I), when m is 0, the group Q is directly bonded to the carbon atom bearing $R^{12}$, and $R^{8c}$ and $R^{8d}$ and the carbon to which they are attached are absent. In compounds of formula (II), when m is 0, the group Q is directly bonded to the carbon atom bearing $R^{12a}$ and $R^{12b}$, and $R^{8c}$ and $R^{8d}$ and the carbon to which they are attached are absent.

In further embodiments of formulae (I), (II) and (III), q is 0 and m is 1. When q is 0, $R^{8a}$ and $R^{8b}$ and the carbon to which they are attached are absent.

In certain preferred embodiments of formulae (I), (II) and (III), q is 0, and m is 0. In other embodiments, q is 1, and m is 0. In other embodiments, q is 0, and m is 1.

In compounds of formula (I), $R^{11}$ is H, $C_1$-$C_8$ alkyl, $C_3$-$C_8$ cycloalkyl, or $C_1$-$C_8$ perhaloalkyl, and $R^{12}$ is H, $C_1$-$C_8$ alkyl, $C_3$-$C_8$ cycloalkyl, or $C_1$-$C_8$ perhaloalkyl. In one variation, compounds are of the formula (I) where $R^{11}$ is H or $C_1$-$C_8$ alkyl, and $R^{12}$ is H, $C_1$-$C_8$ alkyl, $C_3$-$C_8$ cycloalkyl, or $C_1$-$C_8$ perhaloalkyl. In some embodiments, each $R^{11}$ and $R^{12}$ is independently H or optionally substituted $C_1$-$C_8$ alkyl. In certain embodiments, each $R^{11}$ and $R^{12}$ is independently H or $C_1$-$C_4$ alkyl. In specific embodiments, each $R^{11}$ and $R^{12}$ is independently H or methyl. In other embodiments, $R^{11}$ is H or $C_1$-$C_4$ alkyl and $R^{12}$ is $C_1$-$C_4$ perhaloalkyl, preferably trifluoromethyl. In further embodiments, $R^{11}$ is H or Me, and $R^{12}$ is Me, Et, cyclopropyl or $CF_3$. In some embodiments, the olefin bearing substituents $R^{11}$ and $R^{12}$ has the trans-orientation; in other embodiments, the olefin has the cis-orientation.

In some embodiments of formula (II), each $R^{11a}$ and $R^{12a}$ is independently H, hydroxyl, or $C_1$-$C_8$ alkyl. In certain embodiments, each $R^{11a}$ and $R^{12a}$ is independently H or $C_1$-$C_4$ alkyl. In specific embodiments, each $R^{11a}$ and $R^{12a}$ is independently H or methyl. In other embodiments, $R^{11a}$ and $R^{12a}$ may be taken together to represent a bond, such that the bond between the carbon atoms to which $R^{11a}$ and $R^{12a}$ are attached is a double bond, and the ring formed between $R^{11b}$ and $R^{12b}$ is an unsaturated carbocyclic or heterocyclic ring.

In compounds of formula (II), $R^{11b}$ and $R^{12b}$ are taken together with the carbon atoms to which they are attached to form a substituted or unsubstituted $C_3$-$C_8$ cycloalkyl, substituted or unsubstituted $C_3$-$C_8$ cycloalkenyl or substituted or unsubstituted heterocyclyl moiety. In some embodiments, when $R^{11b}$ and $R^{12b}$ are taken together to form a cycloalkenyl ring, $R^{11a}$ and $R^{12a}$ are taken together to represent a bond.

In certain embodiment of formula (II), $R^{11b}$ and $R^{12b}$ are taken together with the carbon atoms to which they are attached to form an optionally substituted cyclopropyl, cyclobutyl, cyclopentyl or cyclohexyl ring. In some such embodiments, the cycloalkyl ring is substituted with hydroxyl, $C_1$-$C_4$ alkyl, or oxo (=O). In other embodiments, the cycloalkyl ring is unsubstituted.

In other embodiment of formula (II), $R^{11b}$ and $R^{12b}$ are taken together with the carbon atoms to which they are attached to form an optionally substituted cyclopropenyl, cyclobutenyl, cyclopentenyl or cyclohexenyl ring. In some such embodiments, $R^{11a}$ and $R^{12a}$ are taken together to represent a bond between the carbon atoms to which they are attached. In some embodiments, the cycloalkenyl ring is optionally substituted with hydroxyl, $C_1$-$C_4$ alkyl, or oxo (=O). In other embodiments, the cycloalkenyl ring is unsubstituted.

In further embodiments, $R^{11b}$ and $R^{12b}$ are taken together with the carbon atoms to which they are attached to form an optionally substituted heterocyclic ring containing one or more heteroatoms selected from the group consisting of N, O and S, which heterocyclic ring may be saturated or unsaturated.

In certain variations of formula (II), $R^{11b}$ and $R^{12b}$ are taken together with the carbon atoms to which they are attached to form a cycloalkyl or cycloalkenyl ring selected from the following structures, each of which may be optionally substituted:

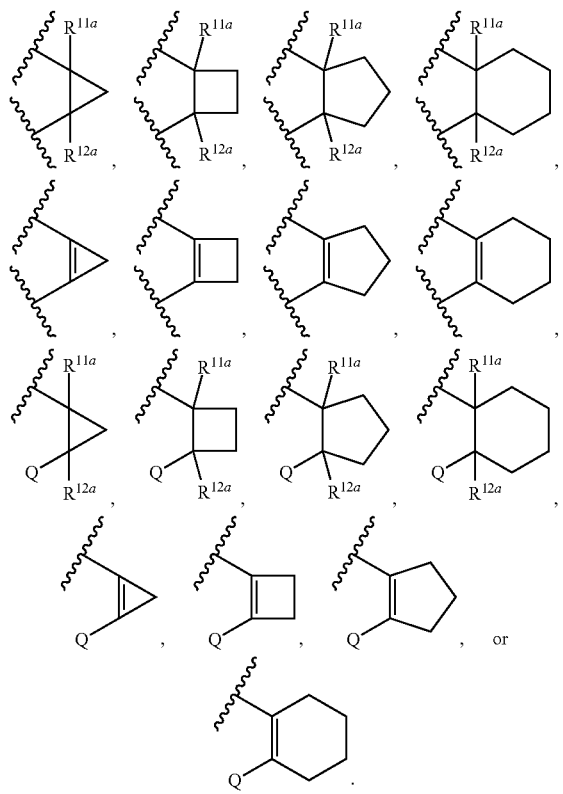

In compounds of formulae (I), (II), (III), (IV), (V), (VI), (VII) and (VIII), Q is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy or acylamino. In one variation, compounds are of the formula (I), (II), (III), (IV), (V), (VI), (VII) or (VIII) where Q is a substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl or substituted or a unsubstituted heterocyclyl. In certain embodiments, Q is a substituted or unsubstituted 5- or 6-membered aryl or heteroaryl. In some such embodiments, Q is a substituted or unsubstituted phenyl, pyridyl or pyrimidinyl ring. When Q is substituted, it is frequently substituted with from 1-3 substituents selected from group consisting of halo, $C_1$-$C_4$ alkyl, $C_1$-$C_4$ perhaloalkyl, and $C_1$-$C_4$ alkoxy.

In a particular variation of formulae (I), (II), (III), (IV), (V), (VI), (VII) and (VIII), Q is a substituted heteroaryl, a monosubstituted aryl group substituted with a chloro or alkyl group or a di- or tri-substituted aryl moiety. For instance, Q in one variation is selected from the group consisting of 4-methoxy-3-fluorophenyl, 3,4-di-fluorophenyl, 4-chloro-3-fluorophenyl, 3,4-dichlorophenyl, 3-chloro-4-fluorophenyl, 2,4-difluorophenyl, 2,4-dichlorophenyl, 2,4,6-trifluorophenyl, 4-chlorophenyl, 4-methylphenyl, 6-methyl-3-pyridyl, 6-trifluoromethyl-3-pyridyl, 5-trifluoromethyl-3-pyridyl and pyrimidinyl. In one aspect, Q is a substituted pyridyl such as 6-methyl-3-pyridyl, 6-trifluoromethyl-3-pyridyl and 5-trifluoromethyl-3-pyridyl.

In some embodiments of formulae (I), (II), (III), (IV), (V), (VI), (VII) and (VIII), $R^1$ is a substituted or unsubstituted $C_1$-$C_8$ alkyl, acyl, acyloxy, carbonylalkoxy, substituted or unsubstituted heterocyclyl or substituted or unsubstituted aryl; each $R^{2a}$ and $R^{2b}$ is independently H, methyl, fluoro or $R^{2a}$ and $R^{2b}$ are taken together to form a carbonyl moiety; each $R^{3a}$ and $R^{3b}$ is independently H or fluoro; and each $R^{10a}$ and $R^{10b}$ is independently H, halo, hydroxyl or methyl or $R^{10a}$ and $R^{10b}$ are taken together to form a carbonyl moiety. In particular variations of formulae (I), (II), (III), (IV), (V), (VI), (VII) and (VIII), $R^1$ is an unsubstituted $C_1$-$C_8$ alkyl and $R^{2a}$, $R^{2b}$, $R^{3a}$, $R^{3b}$, $R^{10a}$ and $R^{10b}$ are each H. In still a further variation of formulae (I), (II), (III), (IV), (V), (VI), (VII) and (VIII), $R^1$ is an unsubstituted $C_1$-$C_8$ alkyl, $R^{2a}$, $R^{2b}$, $R^{3a}$, $R^{3b}$, $R^{10a}$ and $R^{10b}$, are each H and Q is selected from the group consisting of 4-methoxy-3-fluorophenyl, 3,4-di-fluorophenyl, 4-chloro-3-fluorophenyl, 3,4-dichlorophenyl, 3-chloro-4-fluorophenyl, 2,4-difluorophenyl, 2,4-dichlorophenyl, 2,4,6-trifluorophenyl, 4-chlorophenyl, 4-methylphenyl, 6-methyl-3-pyridyl, 6-trifluoromethyl-3-pyridyl, 5-trifluoromethyl-3-pyridyl and pyrimidinyl. In still a further variation of formulae (I), (II), (III), (IV), (V), (VI), (VII) and (VIII), $R^1$ is an unsubstituted $C_1$-$C_8$ alkyl, $R^{2a}$, $R^{2b}$, $R^{3a}$, $R^{3b}$, $R^{10a}$ and $R^{10b}$ are each H and $X^9$ is $CR^4$ where $R^4$ is chloro. In yet a further variation of formulae (I), (II), (III), (IV), (V), (VI), (VII) and (VIII), $R^1$ is an unsubstituted $C_1$-$C_8$ alkyl, $R^{2a}$, $R^{2b}$, $R^{3a}$, $R^{3b}$, $R^{10a}$ and $R^{10b}$ are each H, $X^9$ is $CR^4$ where $R^4$ is chloro and Q is a substituted or unsubstituted aryl or a substituted or substituted heteroaryl. In one such variation, Q is a substituted phenyl.

In particular embodiments of the formula (I), (II), (III), (IV), (V), (VI), (VII) or (VIII), each $X^7$, $X^8$, $X^9$ and $X^{10}$ is CH or $CR^4$. In other embodiments, the compound is of the formula (I), (II), (III), (IV), (V), (VI), (VII) or (VIII) where at least one of $X^7$, $X^8$, $X^9$ and $X^{10}$ is N. Another variation provides a compound of the formula (I), (II), (III), (IV), (V), (VI), (VII) or (VIII) where at least two of $X^7$, $X^8$, $X^9$ and $X^{10}$ are N. A further variation provides a compound of the formula (I), (II), (III), (IV), (V), (VI), (VII) or (VIII) where two of $X^7$, $X^8$, $X^9$ and $X^{10}$ are N and two of $X^7$, $X^8$, $X^9$ and $X^{10}$ are CH or $CR^4$. Compounds of the formula (I), (II), (III), (IV), (V), (VI), (VII) or (VIII), where one of $X^7$, $X^8$, $X^9$ and $X^{10}$ is N and three of $X^7$, $X^8$, $X^9$ and $X^{10}$ are CH or $CR^4$ are also embraced by this invention.

In another variation, a compound of the invention is of the formula (I), (II), (III), (IV), (V), (VI), (VII) or (VIII) wherein the A-ring is an aromatic moiety selected from the following structures:

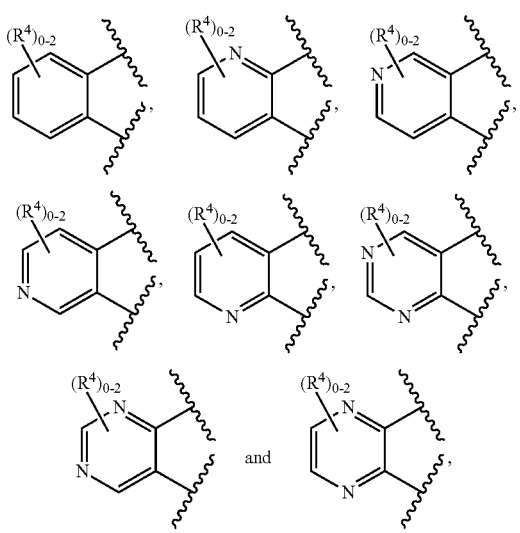

where each $R^4$ is as defined for formula (I). In a particular variation, each $R^4$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or amino, alkylsulfonylamino or acyl. In a further variation, each $R^4$ is independently halo, unsubstituted $C_1$-$C_4$ alkyl, $C_1$-$C_4$ perhaloalkyl, or $C_1$-$C_4$ alkoxy.

In still a further variation, a compound of the invention is of the formula (I), (II), (III), (IV), (V), (VI), (VII) or (VIII), wherein the A-ring is an aromatic moiety selected from the following structures:

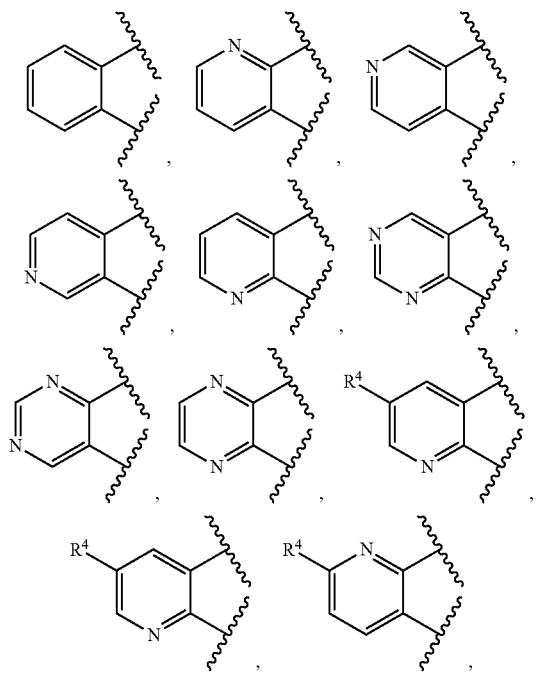

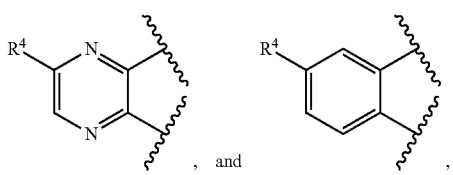

wherein $R^4$ is as defined in formula (I); or in a particular variation, where $R^4$ is hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or amino, alkylsulfonylamino or acyl; or in still a further variation, where each $R^4$ is independently halo, unsubstituted $C_1$-$C_4$ alkyl, $C_1$-$C_4$ perhaloalkyl, or $C_1$-$C_4$ alkoxy.

In a further variation, a compound of the invention is of the formula (I), (II), (III), (IV), (V), (VI), (VII) or (VIII), wherein the A-ring is an aromatic moiety selected from the following structures:

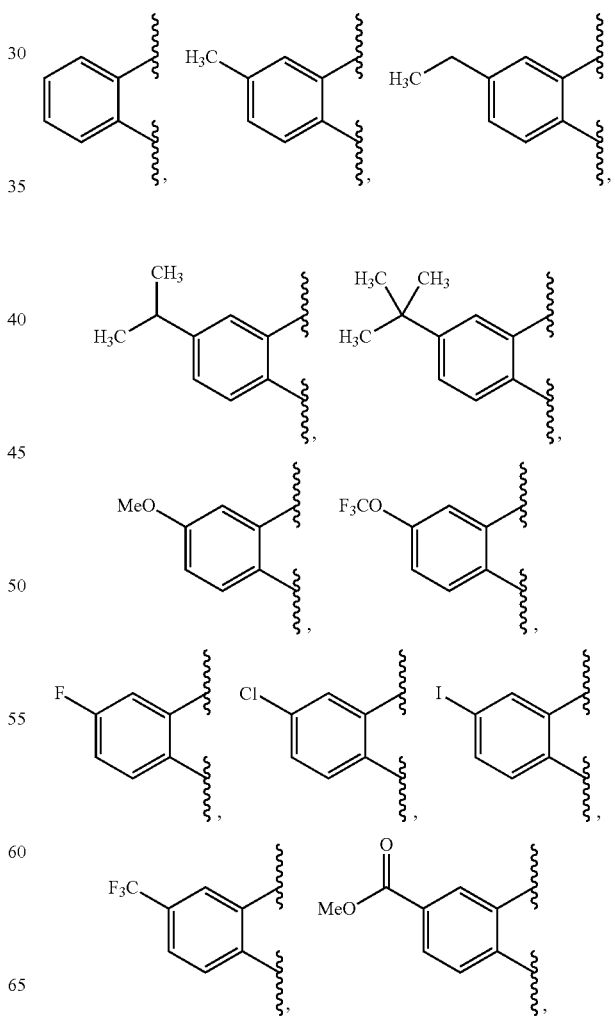

-continued

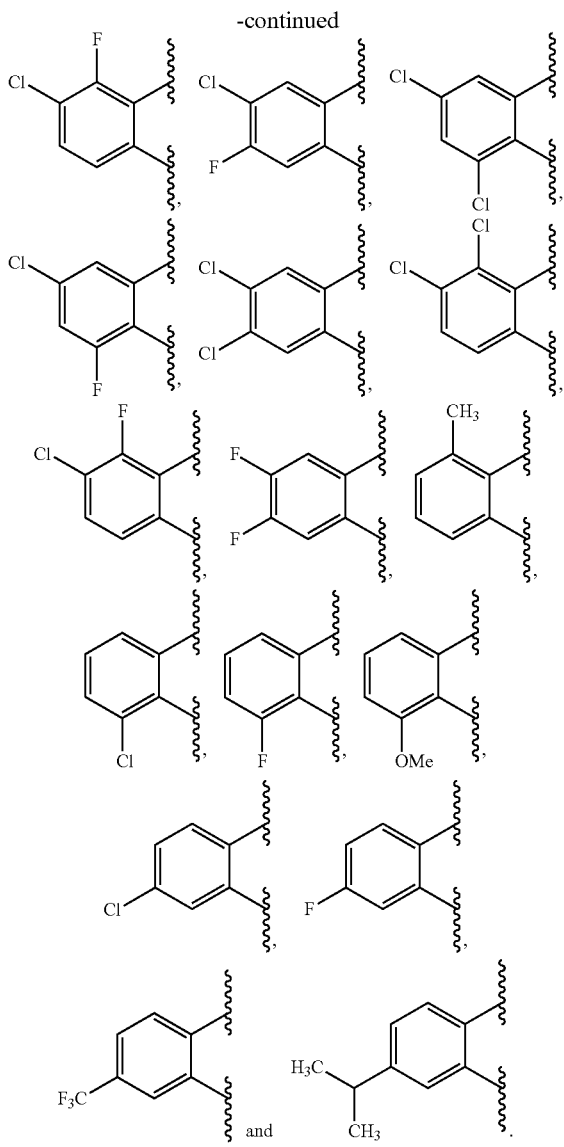

Any formula detailed herein, where applicable, may in one variation have $X^7$, $X^8$, $X^9$ and $X^{10}$ taken together to provide an aromatic moiety detailed herein above. It is understood that by "where applicable" it is intended that in one variation such $X^7$, $X^8$, $X^9$ and $X^{10}$ groups are taken together to provide a moiety hereinabove if the formula encompasses such a structure. For example, if a given formula does not encompass structures wherein $X^7$, $X^8$, $X^9$ and $X^{10}$ groups are taken together provide a pyridyl moiety, then a pyridyl moiety as detailed hereinabove is not applicable to that particular formula, but remains applicable to formulae that do encompass structures where $X^7$, $X^8$, $X^9$ and $X^{10}$ groups are taken together provide a pyridyl moiety.

In another embodiment, a compound of the invention is of the formula (I), (II), (III), (IV), (V), (VI), (VII) or (VIII), wherein $X^7$-$X^{10}$ are as defined in formula (I) or as detailed in any variation herein, where $R^1$ is H, substituted or unsubstituted $C_1$-$C_8$ alkyl, acyl, acyloxy, carbonylalkoxy, substituted or unsubstituted heterocyclyl, substituted or unsubstituted aryl, substituted or unsubstituted heteroaryl, substituted or unsubstituted aralkyl. In a further embodiment, a compound of the invention is of the formula (I), (II), (III), (IV), (V), (VI), (VII) or (VIII), wherein $X^7$-$X^{10}$ are as defined in formula (I) or as detailed in any variation herein, where $R^1$ is a substituted or unsubstituted $C_1$-$C_8$ alkyl, acyl, acyloxy, carbonylalkoxy, substituted or unsubstituted heterocyclyl or substituted or unsubstituted aryl. In a particular variation, a compound of the invention is of the formula (I), wherein $X^7$-$X^{10}$ are as defined in formula (I), (II), (III), (IV), (V), (VI), (VII) or (VIII) or as detailed in any variation herein, where $R^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methyl-cycloprop-2-yl, or 1-hydroxy-1,2,2-trimethyl-cycloprop-3-yl.

In another variation, the compound of the invention is of the formula (I), (II), (III), (IV), (V), (VI), (VII) or (VIII), where $X^7$-$X^{10}$ and $R^1$ are as defined in formula (I) or as detailed in any variation herein, where $R^{2a}$ and $R^{2b}$ are independently H, substituted or unsubstituted $C_1$-$C_8$ alkyl, halo, cyano, nitro or $R^{2a}$ and $R^{2b}$ are taken together to form a carbonyl moiety and each $R^{3a}$ and $R^{3b}$ is independently H, substituted or unsubstituted $C_1$-$C_8$ alkyl, halo, cyano or nitro. In another variation, the compound of the invention is of the formula (I), (II), (III), (IV), (V), (VI), (VII) or (VIII), where $X^7$-$X^{10}$ and $R^1$ are as defined in formula (I), (II), (III), (IV), (V), (VI), (VII) or (VIII) or as detailed in any variation herein, where each $R^{2a}$ and $R^{2b}$ is independently H, unsubstituted $C_1$-$C_8$ alkyl, halo or $R^{2a}$ and $R^{2b}$ are taken together to form a carbonyl moiety and each $R^{3a}$ and $R^{3b}$ is independently H, unsubstituted $C_1$-$C_8$ alkyl, halo or $R^{3a}$ and $R^{3b}$ are taken together to form a carbonyl moiety. In still a further variation, the compound of the invention is of the formula (I), (II), (III), (IV), (V), (VI), (VII) or (VIII), where $X^7$-$X^{10}$ and $R^1$ are as defined in formula (I) or as detailed in any variation herein, where each $R^{2a}$ and $R^{2b}$ is independently H, unsubstituted $C_1$-$C_8$ alkyl, halo or $R^{2a}$ and $R^{2b}$ are taken together to form a carbonyl moiety; and each $R^{3a}$ and $R^{3b}$ is independently H, unsubstituted $C_1$-$C_8$ alkyl, halo or $R^{3a}$ and $R^{3b}$ are taken together to form a carbonyl moiety. The invention also embraces compounds of the invention according to formula (I), (II), (III), (IV), (V), (VI), (VII) or (VIII), where $X^7$-$X^{10}$ and $R^1$ are as defined in formula (I), (II), (III), (IV), (V), (VI), (VII) or (VIII) or as detailed in any variation herein, where each $R^{2a}$ and $R^{2b}$ is independently H, methyl, halo or $R^{2a}$ and $R^{2b}$ are taken together to form a carbonyl moiety and each $R^{3a}$ and $R^{3b}$ is independently H, methyl, halo or $R^{3a}$ and $R^{3b}$ are taken together to form a carbonyl moiety.

The invention further embraces compounds of the invention according to formula (I), (II), (III), (IV), (V), (VI), (VII) or (VIII), where $X^7$-$X^{10}$ and $R^1$ are as defined in formula (I), (II), (III), (IV), (V), (VI), (VII) or (VIII) or as detailed in any variation herein, where each $R^{2a}$, $R^{2b}$, $R^{3a}$ and $R^{3b}$ is H. In one variation, a compound of the invention is of the formula (I), (II), (III), (IV), (V), (VI), (VII) or (VIII) where $X^7$-$X^{10}$ and $R^1$ are as defined in formula (I) or as detailed in any variation herein, where at least one of $R^{2a}$, $R^{2b}$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety.

In another variation, a compound of the invention is of the formula (I), (II), (III), (IV), (V), (VI), (VII) or (VIII) where $X^7$-$X^{10}$ and $R^1$ are as defined in formula (I), (II), (III), (IV), (V), (VI), (VII) or (VIII) or as detailed in any variation herein, where at least two of $R^{2a}$, $R^{2b}$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety. In yet another variation, a compound of the invention is of the formula (I), (II), (III), (IV), (V), (VI), (VII) or (VIII) where $X^7$-$X^{10}$ and $R^1$ are as defined in formula (I), (II), (III), (IV), (V), (VI), (VII) or (VIII) or as detailed in any variation herein, where at least one of $R^{2a}$, $R^{2b}$, $R^{3a}$ and $R^{3b}$ is fluoro or methyl or is taken together with a geminal $R^2$ or $R^3$ to form a carbonyl moiety.

In still another variation, a compound of the invention is of the formula (I), (II), (III), (IV), (V), (VI), (VII) or (VIII) where $X^7$-$X^{10}$ and $R^1$ are as defined in formula (I), (II), (III), (IV), (V), (VI), (VII) or (VIII) or as detailed in any variation herein, where either $R^{2a}$ and $R^{2b}$ or $R^{3a}$ and $R^{3b}$ are each methyl or fluoro (e.g., both $R^{2a}$ and $R^{2b}$ are methyl or one is fluoro and one is methyl) or are taken together to form a carbonyl moiety. In one variation, $R^{2a}$ and $R^{2b}$ are taken together to form a carbonyl moiety. In another variation, at least one of $R^{2a}$ and $R^{2b}$ is hydroxyl or alkoxy. In a particular variation, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl moiety. In another variation, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl moiety.

The invention also embraces compounds according to formula (I), (II), (III), (IV), (V), (VI), (VII) or (VIII), where $X^7$-$X^{10}$, $R^1$, $R^{2a}$, $R^{2b}$, $R^{3a}$ and $R^{3b}$ are as defined in formula (I), (II), (III), (IV), (V), (VI), (VII) or (VIII) or as detailed in any variation herein, where each $R^{10a}$ and $R^{10b}$ is independently H, halo, an unsubstituted $C_1$-$C_8$ alkyl, hydroxyl or $R^{10a}$ and $R^{10b}$ are taken together to form a carbonyl moiety. Also embraced are compounds according to formula (I), (II), (III), (IV), (V), (VI), (VII) or (VIII), where $X^7$-$X^{10}$, $R^1$, $R^{2a}$, $R^{2b}$, $R^{3a}$ and $R^{3b}$ are as defined in formula (I), (II), (III), (IV), (V), (VI), (VII) or (VIII) or as detailed in any variation herein, where each $R^{10a}$ and $R^{10b}$ is independently H, halo, an unsubstituted $C_1$-$C_4$ alkyl, hydroxyl or $R^{10a}$ and $R^{10b}$ are taken together to form a carbonyl moiety. In another variation, a compound of the invention is of the formula (I), (II), (III), (IV), (V), (VI), (VII) or (VIII), where $X^7$-$X^{10}$, $R^1$, $R^{2a}$, $R^{2b}$, $R^{3a}$ and $R^{3b}$ are as defined in formula (I), (II), (III), (IV), (V), (VI), (VII) or (VIII) or as detailed in any variation herein, where each $R^{10a}$ and $R^{10b}$ is independently H, bromo, methyl, hydroxyl or $R^{10a}$ and $R^{10b}$ are taken together to form a carbonyl moiety.

In yet another variation, a compound of the invention is of the formula (I), (II), (III), (IV), (V), (VI), (VII) or (VIII), where $X^7$-$X^{10}$, $R^1$, $R^{2a}$, $R^{2b}$, $R^{3a}$ and $R^{3b}$ are as defined in formula (I), (II), (III), (IV), (V), (VI), (VII) or (VIII) or as detailed in any variation herein, where at least one of $R^{10a}$ and $R^{10b}$ is an unsubstituted $C_1$-$C_8$ alkyl, hydroxyl, halo or $R^{10a}$ and $R^{10b}$ are taken together to form a carbonyl moiety. In still a further variation, a compound of the invention is of the formula (I), (II), (III), (IV), (V), (VI), (VII) or (VIII), where $X^7$-$X^{10}$, $R^1$, $R^{2a}$, $R^{2b}$, $R^{3a}$ and $R^{3b}$ are as defined in formula (I), (II), (III), (IV), (V), (VI), (VII) or (VIII) or as detailed in any variation herein, where at least one of $R^{10a}$ and $R^{10b}$ is methyl, bromo, hydroxyl or $R^{10a}$ and $R^{10b}$ are taken together to form a carbonyl moiety.

In another variation, a compound of the invention is of the formula (I), (II), (III), (IV), (V), (VI), (VII) or (VIII), where $X^7$-$X^{10}$, $R^1$, $R^{2a}$, $R^{2b}$, $R^{3a}$ and $R^{3b}$ are as defined in formula (I), (II), (III), (IV), (V), (VI), (VII) or (VIII) or as detailed in any variation herein, where both $R^{10a}$ and $R^{10b}$ are methyl. In another variation, a compound of the invention is of the formula (I), (II), (III), (IV), (V), (VI), (VII) or (VIII), where $X^7$-$X^{10}$, $R^1$, $R^{2a}$, $R^{2b}$, $R^{3a}$ and $R^{3b}$ are as defined in formula (I), (II), (III), (IV), (V), (VI), (VII) or (VIII) or as detailed in any variation herein, where $R^{10a}$ and $R^{10b}$ are taken together to form a carbonyl moiety. In another variation, a compound of the invention is of the formula (I), (II), (III), (IV), (V), (VI), (VII) or (VIII), where $X^7$-$X^{10}$, $R^1$, $R^{2a}$, $R^{2b}$, $R^{3a}$ and $R^{3b}$ are as defined in formula (I), (II), (III), (IV), (V), (VI), (VII) or (VIII) or as detailed in any variation herein, where $R^{10a}$ is H and $R^{10b}$ is methyl. In another variation, a compound of the invention is of the formula (I), (II), (III), (IV), (V), (VI), (VII) or (VIII), where $X^7$-$X^{10}$, $R^1$, $R^{2a}$, $R^{2b}$, $R^{3a}$ and $R^{3b}$ are as defined in formula (I) or as detailed in any variation herein, where $R^{10a}$ is H and $R^{10b}$ is bromo. When the carbon of formula (I) bearing $R^{10a}$ and $R^{10b}$ is optically active, it may be in the (S)- or (R)-configuration and compositions comprising substantially pure (R) or (S) compound or mixtures thereof in any amount are embraced by this invention.

In compounds of formula (I), (II), (III) or (IV), the ring comprising N, $R^{2a}$, $R^{2b}$, $R^{10a}$, $R^{10b}$, $R^{3a}$, and $R^{3b}$ is sometimes referred to herein as the C-ring. In some embodiments, the C-ring is a ring selected from the structures:

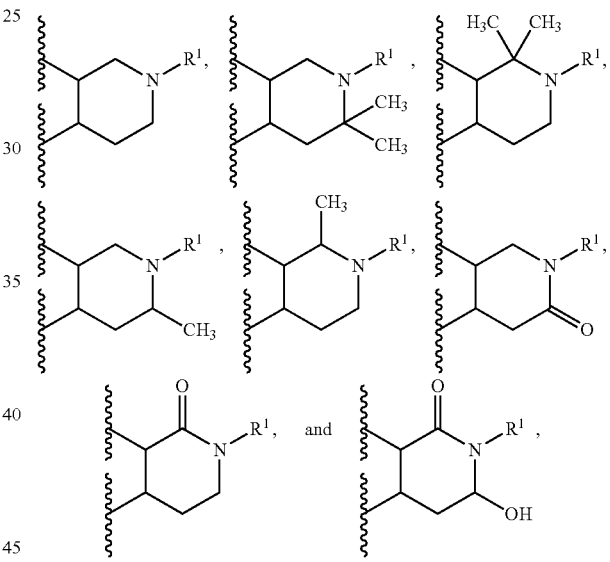

where $R^1$ in the structures above is as defined for formula (I) or any particular variation detailed herein. In some embodiments, the C-ring is a ring of the structure:

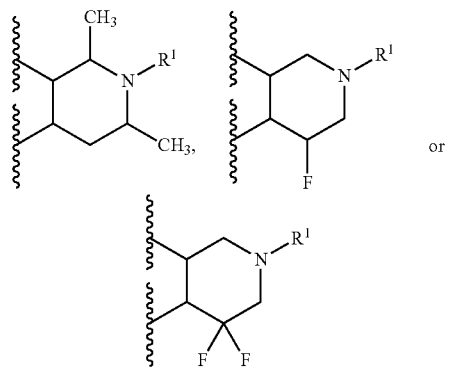

where $R^1$ is as defined for formula (I) or any particular variation detailed herein. Any formula detailed herein, where applicable, may in one variation have a C-ring according to the structures above.

In compounds of formula (I), (II), (III), (IV), (V), (VI), (VII) or (VIII), Q is a substituted or unsubstituted aryl, substituted or unsubstituted heteroaryl, which may be but is not limited to a substituted or unsubstituted pyridyl, phenyl, pyrimidinyl, pyrazinyl, imidazolyl, furanyl, pyrrolyl or thiophenyl group. In one variation, a compound of the invention is of the formula (I), (II), (III), (IV), (V), (VI), (VII) or (VIII) or any variation of the foregoing detailed herein, where Q is a substituted or unsubstituted phenyl or pyridyl group. In a particular variation, Q is a phenyl or pyridyl group substituted with at least one methyl, trifluoromethyl, methoxy or halo substituent. In another variation, a compound of the invention is of the formula (I), (II), (III), (IV), (V), (VI), (VII) or (VIII) or any variation of the foregoing detailed herein, where Q is a pyridyl, phenyl, pyrimidinyl, pyrazinyl, imidazolyl, furanyl, pyrrolyl or thiophenyl group substituted with at least one substituted or unsubstituted $C_1$-$C_4$ alkyl, $C_1$-$C_4$ alkoxy, halo or $C_1$-$C_4$ perhaloalkyl moiety.

In still another variation, a compound of the invention is of the formula (I), (II), (III), (IV), (V), (VI), (VII) or (VIII) or any variation of the foregoing detailed herein, where Q is a substituted or unsubstituted $C_3$-$C_8$ cycloalkyl or a substituted or unsubstituted heterocyclyl. In another variation, Q is a substituted or unsubstituted $C_3$-$C_8$ cycloalkyl or a substituted or unsubstituted heterocyclyl. In yet another variation, a compound of the invention is of the formula (I), (II), (III), (IV), (V), (VI), (VII) or (VIII) or any variation of the foregoing detailed herein, where Q is a substituted or unsubstituted pyridyl, phenyl, pyrazinyl, piperazinyl, pyrrolidinyl or thiomorpholinyl group. In a particular variation, Q is a pyridyl, phenyl, pyrazinyl, piperazinyl, pyrrolidinyl or thiomorpholinyl group substituted with at least one methyl, $CF_3$, methoxy or halo group.

In one variation, a compound of the invention is of the formula (I), (II), (III), (IV), (V), (VI), (VII) or (VIII) or any variation of the foregoing detailed herein, where Q is an unsubstituted cycloalkyl or an unsubstituted heterocyclyl. In another variation, Q is an unsubstituted $C_3$-$C_8$ cycloalkyl or an unsubstituted heterocyclyl. In another variation, a compound of the invention is of the formula (I) or any variation of the foregoing detailed herein, where Q is a substituted or unsubstituted cyclohexyl, morpholinyl, piperazinyl, thiomorpholinyl, cyclopentyl or pyrrolidinyl moiety. In yet another variation, a compound of the invention is of the formula (I), (II), (III), (IV), (V), (VI), (VII) or (VIII) or any variation of the foregoing detailed herein, where Q is a substituted cyclohexyl, morpholinyl, piperazinyl, thiomorpholinyl, cyclopentyl or pyrrolidinyl moiety substituted with at least one carbonyl, hydroxymethyl, methyl or hydroxyl group. Q groups may be attached to the parent structure at any available position on the Q moiety. Thus, although specific attachment points for certain Q moieties are depicted herein, it is understood that such Q moieties, may also be connected to the parent structure at any available position. For example, if a 2-fluoro-phenyl is depicted herein, it is understood that other mono-fluoro-phenyls are intended, e.g., 3-fluoro-phenyl and 4-fluoro-phenyl. It is also understood that any formula detailed herein, where applicable, may in one variation have a Q moiety as detailed herein and below.

In another variation, a compound of the invention is of formula (I), (II), (III), (IV), (V), (VI), (VII) or (VIII), or any variation of the foregoing detailed herein, where Q is a moiety selected from the structures:

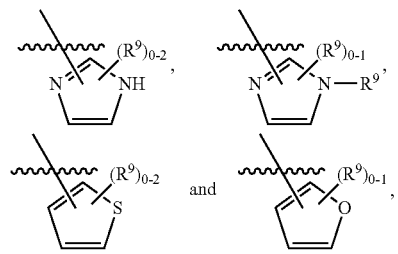

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In one variation, Q is substituted with two $R^9$ groups. In a further variation, Q is selected from the aromatic structures detailed where the residue has the moiety $(R^9)_0$ such that Q either contains no $R^9$ functionality or a moiety of the formula N—$R^9$.

In still another variation, a compound of the invention is of the formula (I), (II), (III), (IV), (V), (VI), (VII) or (VIII) or any variation of the foregoing detailed herein, where Q is a moiety selected from the structures:

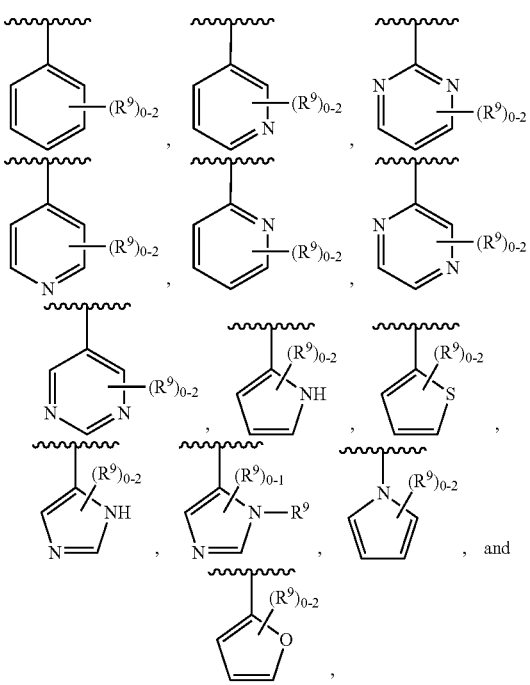

wherein each $R^9$ is independently a halo, cyano, nitro, perhaloalkyl ($C_1$-$C_8$), perhaloalkoxy ($C_1$-$C_8$), substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In one variation, Q is substituted with two $R^9$ groups. In a further variation, Q is selected from the aromatic structures detailed where the residue has the moiety $(R^9)_0$ such that Q either contains no $R^9$ functionality or a moiety of the formula N—$R^9$.

In one variation, Q is substituted with no more than one $R^9$ group. In another variation, Q is substituted with only one $R^9$ group. In one variation, Q is substituted with two $R^9$ groups. In a further variation, Q is selected from the aromatic structures detailed where the residue has the moiety $(R^9)_0$ such that Q either contains no $R^9$ functionality or a moiety of the formula N—$R^9$.

In another variation, a compound of the invention is of the formula (I), (II), (III), (IV), (V), (VI), (VII) or (VIII) or any variation of the foregoing detailed herein, where Q is a moiety selected from the structures:

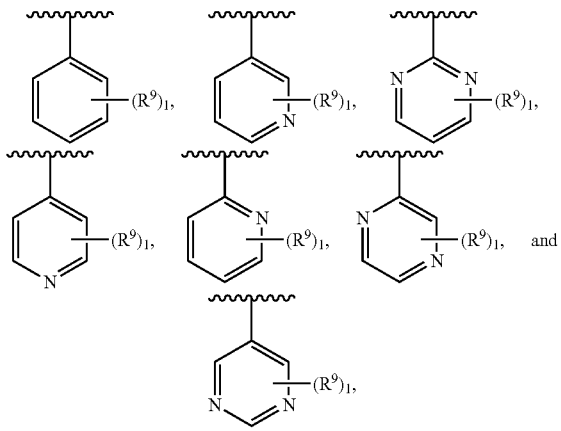

and wherein $R^9$ is connected to Q ortho or para to the position at which Q is connected to the carbon bearing $R^{8c}$ and $R^{8d}$ when m is 1, or the carbon bearing $R^{12}$ when m is 0. In a particular variation, Q is a structure of the formula:

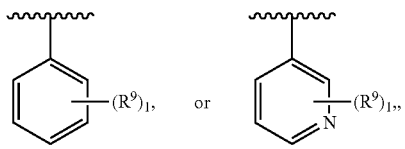

and $R^9$ is connected to Q para to the position at which Q is connected to the carbon bearing $R^{8c}$ and $R^{8d}$ when m is 1, or the carbon bearing $R^{12}$ when m is 0.

In another variation, a compound of the invention is of the formula (II) or any variation of the foregoing detailed herein, where Q is a moiety selected from the structures:

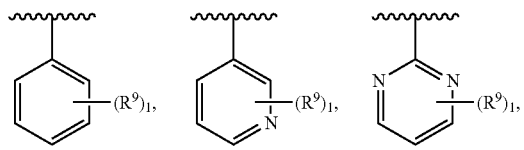

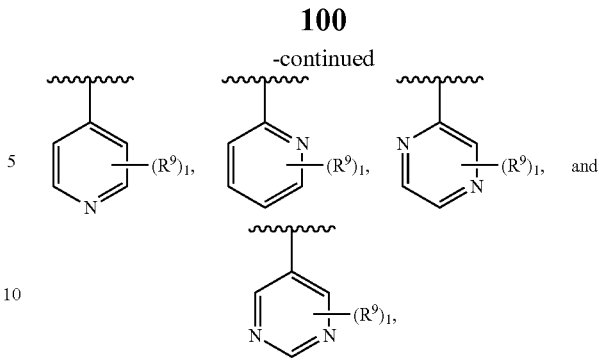

and wherein $R^9$ is connected to Q ortho or para to the position at which Q is connected to the carbon bearing $R^{8c}$ and $R^{8d}$ when m is 1, or the carbon bearing $R^{12a}$ and $R^{12b}$ when m is 0. In a particular variation, Q is a structure of the formula:

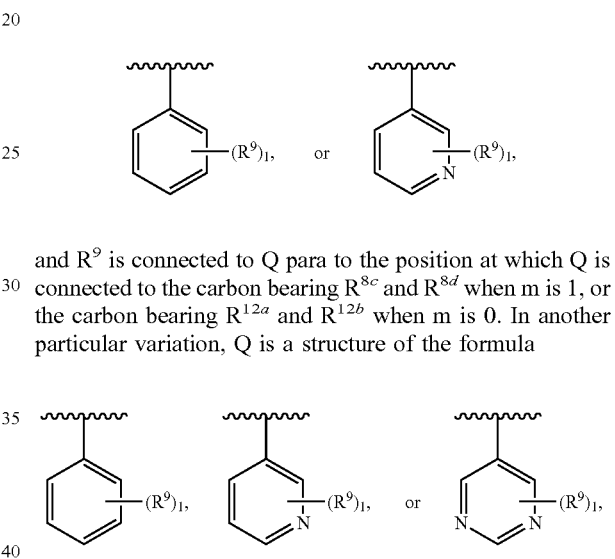

and $R^9$ is connected to Q para to the position at which Q is connected to the carbon bearing $R^{8c}$ and $R^{8d}$ when m is 1, or the carbon bearing $R^{12a}$ and $R^{12b}$ when m is 0. In another particular variation, Q is a structure of the formula where each $R^9$ is independently alkyl, perhaloalkyl or halo.

In another variation, a compound of the invention is of the formula (I), (II), (III), (IV), (V), (VI), (VII) or (VIII) or any variation of the foregoing detailed herein, where Q is a moiety selected from the structures:

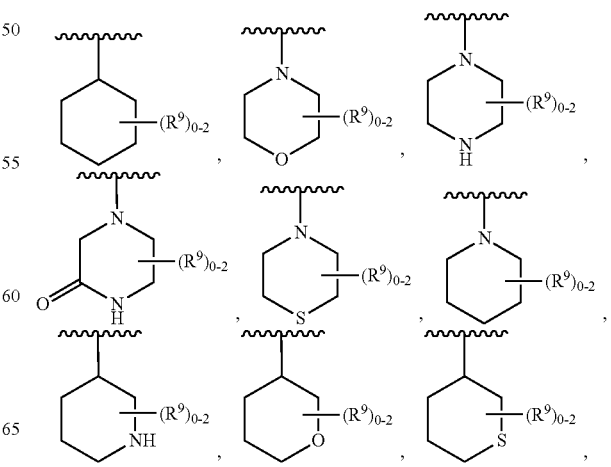

-continued

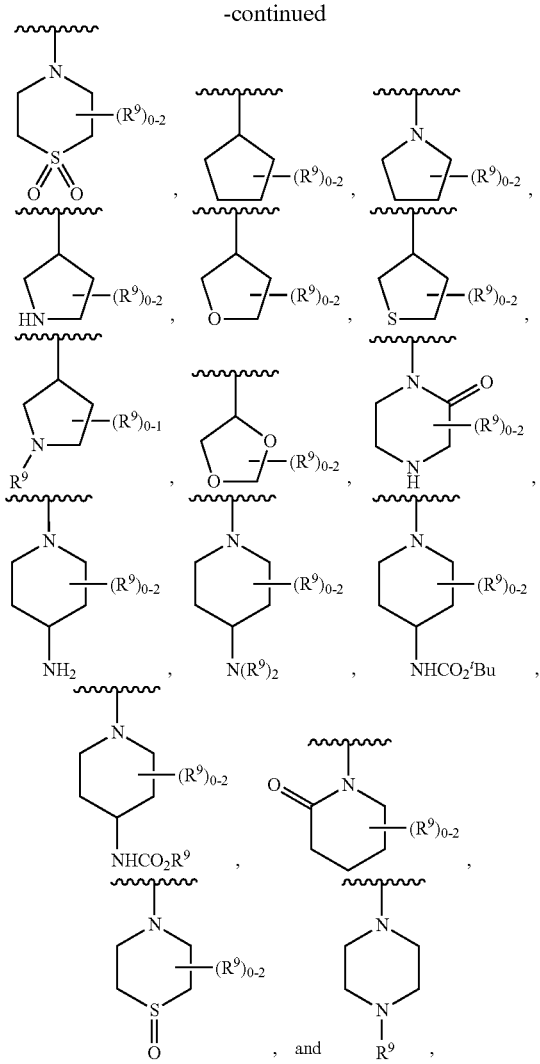

wherein each R⁹ is independently a halo, cyano, nitro, perhaloalkyl, perhaloalkoxy, substituted or unsubstituted C₁-C₈ alkyl, substituted or unsubstituted C₂-C₈ alkenyl, substituted or unsubstituted C₂-C₈ alkynyl, acyl, acyloxy, carbonylalkoxy, thioalkyl, alkoxy, substituted or unsubstituted amino, acylamino, sulfonylamino, sulfonyl, carbonyl, aminoacyl or aminocarbonylamino. In one variation, Q is substituted with no more than one R⁹ group. In another variation, Q is substituted with only one R⁹ group. In yet another variation, Q is substituted with two R⁹ groups. In a particular variation, Q is selected from the carbocyclic and heterocyclic structures detailed where the residue has the moiety (R⁹)₀ such that Q either contains no R⁹ functionality or a moiety of the formula N—R⁹.

In any structure or variation detailed herein containing an R⁹ group, in one variation, each R⁹ is independently a substituted or unsubstituted C₁-C₄ alkyl, halo, trifluoromethyl or hydroxyl. In another variation, each R⁹ is independently methyl, —CH₂OH, isopropyl, halo, trifluoromethyl or hydroxyl.

In another variation, a compound of the invention is of the formula (I), (II), (III), (IV), (V), (VI), (VII) or (VIII) or any variation of the foregoing detailed herein, where Q is a moiety selected from the structures:

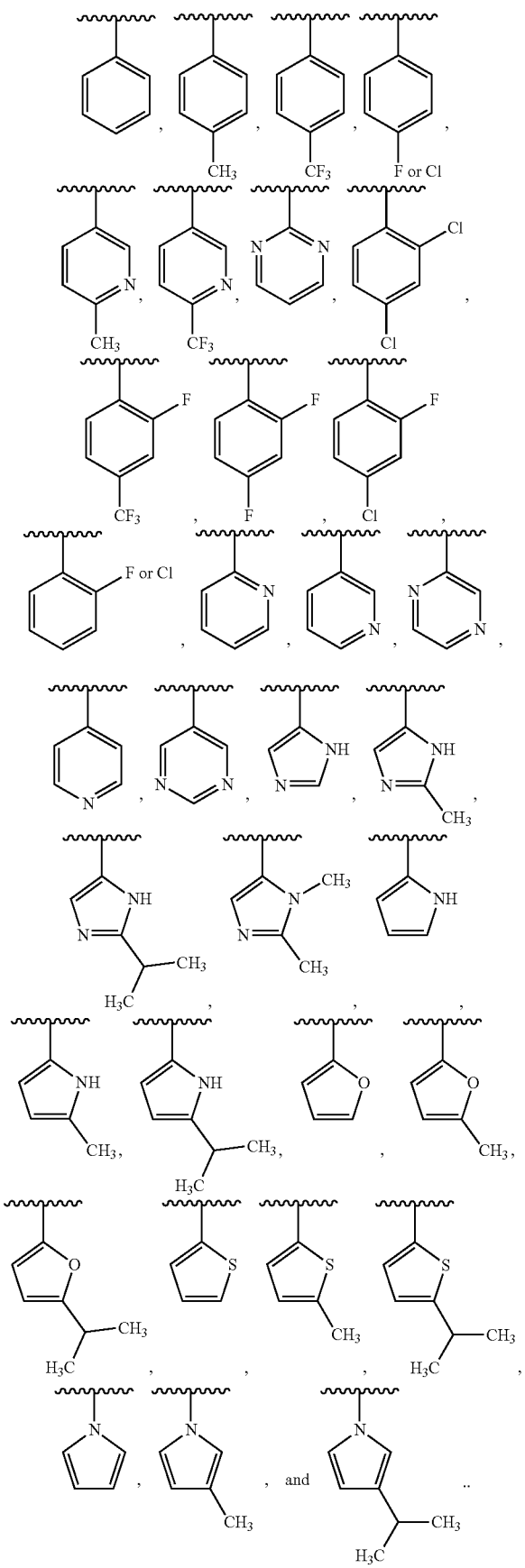

In another variation, a compound of the invention is of the formula (I), (II), (III), (IV), (V), (VI), (VII) or (VIII) or any variation of the foregoing detailed herein, where Q is a moiety selected from the structures:

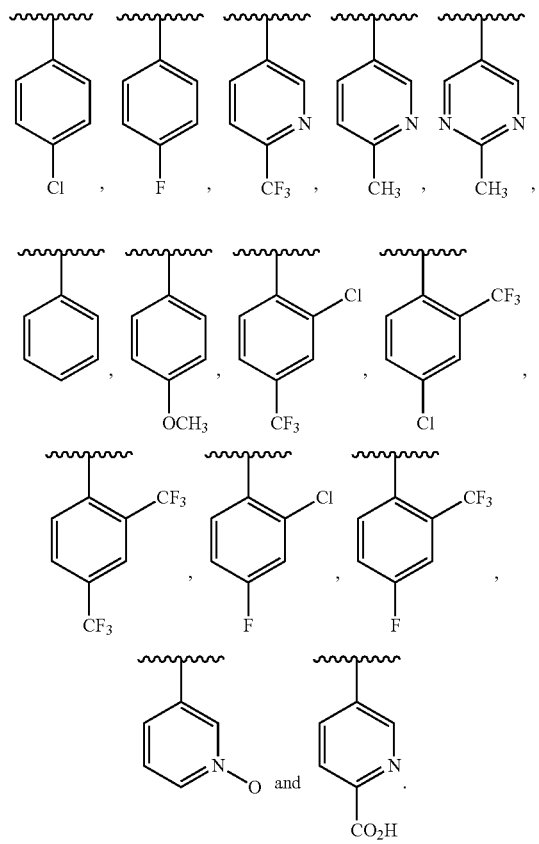

In yet another variation, a compound of the invention is of the formula (I), (II), (III), (IV), (V), (VI), (VII) or (VIII) or any variation of the foregoing detailed herein, where Q is a moiety selected from the structures:

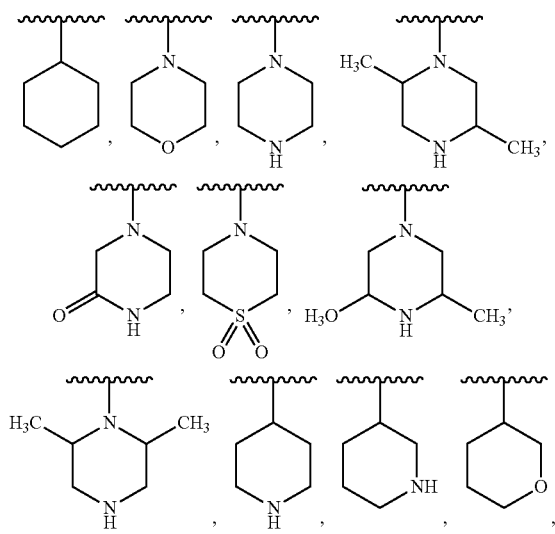

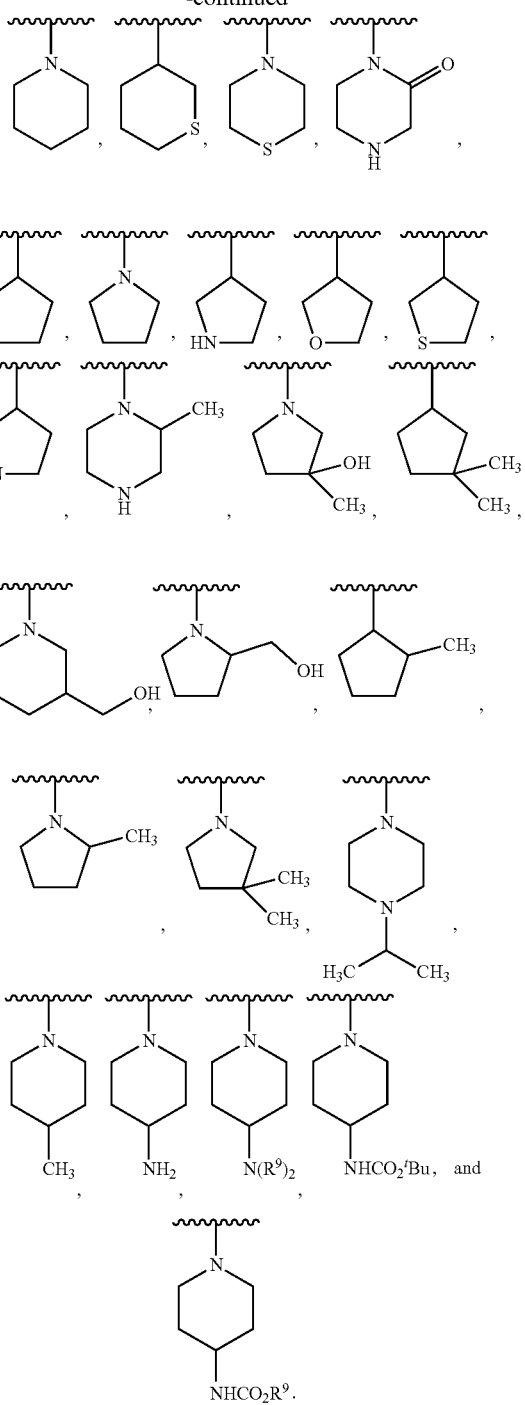

In another variation, a compound of the invention is of the formula (I), (II), (III), (IV), (V), (VI), (VII) or (VIII) or any variation of the foregoing detailed herein, where Q is an substituted or unsubstituted amino, alkoxy, aminoacyl, acyloxy, carbonylalkoxy, aminocarbonylalkoxy or acylamino moiety. In a particular variation, Q is an unsubstituted amino. In another variation, Q is substituted amino of the formula —N($C_1$-$C_8$alkyl)$_2$ such as the moiety —N(Me)$_2$ or —N(CH$_3$)(CH$_2$CH$_3$). In another variation, Q is a substituted amino of the formula —N(H)(cycloalkyl or substituted cycloalkyl), such as a moiety of the formula:

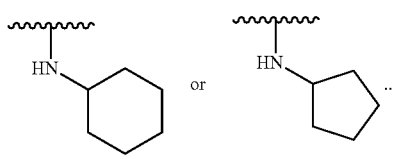 [SMILES: *NC1CCCCC1 ; *NC1CCCC1]

In another variation, Q is a substituted amino of the formula —N(H)(aryl or substituted aryl), such as a moiety of the formula:

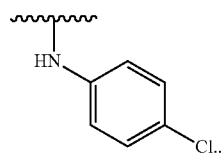 [SMILES: *Nc1ccc(Cl)cc1]

In a particular variation, Q is an amino or substituted amino, m is 1 and $R^{8c}$ and $R^{8d}$ are taken together to form a carbonyl moiety. In yet another variation, Q is an acylamino moiety. In still another variation, Q is an acylamino moiety, and either (1) m is 1 and $R^{8c}$ and $R^{8d}$ are both hydrogen or (2) m is 0.

In another variation, Q is an alkoxy group of the formula —O—$C_1$-$C_8$ alkyl, such as the moiety —O—$CH_2CH_3$. In yet another variation, Q is an alkoxy group, m is 1 and $R^{8c}$ and $R^{8d}$ are taken together to form a carbonyl moiety. In still a further variation, Q is a carbonylalkoxy moiety. In yet another variation, Q is a carbonylalkoxy moiety and either (1) m is 1 and $R^{8c}$ and $R^{8d}$ are both hydrogen or (2) m is 0.

In still another variation, Q is an acyloxy, aminocarbonylalkoxy or acylamino moiety. In one variation, Q is an acyloxy, aminocarbonylalkoxy or acylamino moiety and either (1) m is 1 and $R^{8c}$ and $R^{8d}$ are both hydrogen or (2) m is 0.

The invention also embraces compounds of the formula (I), (II), (III), (IV), (V), (VI), (VII) or (VIII) or any variation of the foregoing detailed herein, where Q is an aminoacyl moiety. In one variation, Q is an aminoacyl group where at least one of $R_a$ and $R_b$ is H, such as when Q is of the formula —NHC(O)$R_b$. In one variation, Q is an aminoacyl moiety selected from the group consisting of: —NHC(O)-heterocyclyl, —NHC(O)-substituted heterocyclyl, —NHC(O)-alkyl, —NHC(O)-cycloalkyl, —NHC(O)-aralkyl and —NHC(O)-substituted aryl. In another variation, Q is an aminoacyl moiety selected from the group consisting of: —NHC(O)—$C_5$-$C_7$ heterocyclyl, —NHC(O)—$C_1$-$C_6$ alkyl, —NHC(O)—$C_3$-$C_7$ cycloalkyl, —NHC(O)—$C_1$-$C_3$ aralkyl and —NHC(O)-substituted phenyl. In a particular variation, Q is a moiety of the formula:

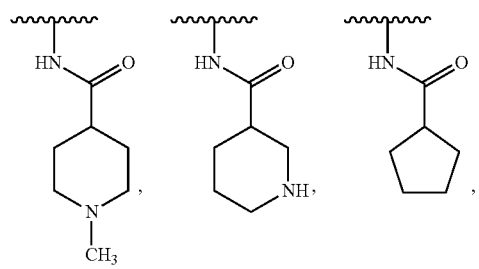

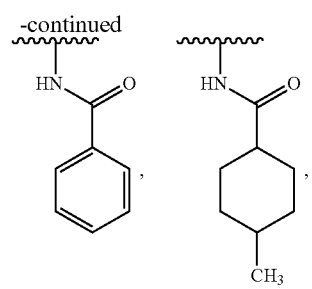

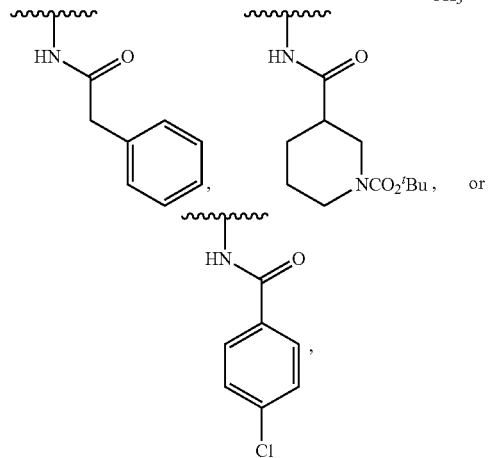

In one variation, a compound of the invention is of the formula (I), (II), (III), (IV), (V), (VI), (VII) or (VIII) or any variation of the foregoing detailed herein, where Q is acyloxy.

In one variation, a compound of the invention is of the formula (I), (II), (III), (IV), (V), (VI), (VII) or (VIII) or any variation of the foregoing detailed herein, where Q is a carbonylalkoxy moiety. In one variation, Q is a carbonylalkoxy moiety of the formula —C(O)—O—R where R is H, alkyl, substituted alkyl or alkaryl. In one variation, Q is carbonylalkoxy moiety of the formula —C(O)—O—$C_1$-$C_6$ alkyl. In a particular variation, Q is a carbonylalkoxy moiety of the formula —C(O)—O—$C_2H_5$. In one variation, Q is a carbonylalkoxy moiety selected from the group consisting of: —C(O)—O—$C_1$-$C_{10}$ alkyl, —C(O)—O—$C_1$-$C_3$ alkaryl, —C(O)—O—$C_1$-$C_3$ substituted alkyl and —C(O)—OH. In another variation, Q is —C(O)—O—$C_1$-$C_6$ alkyl. In a particular variation, Q is a moiety of the formula:

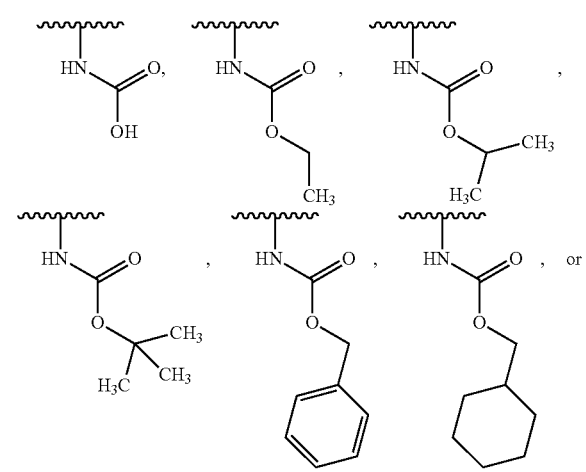

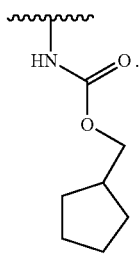

In another variation, a compound of the invention is of the formula (I), (II), (III), (IV), (V), (VI), (VII) or (VIII) or any variation of the foregoing detailed herein, where Q is an aminocarbonylalkoxy moiety. In one variation, Q is an aminocarbonylalkoxy moiety of the formula —NHC(O)—O—$R_b$. In another variation, Q is an aminocarbonylalkoxy moiety of the formula —NHC(O)—O—$R_b$ where $R_b$ is a substituted alkyl group. In a particular variation, Q is a moiety of the formula —NH—C(O)—O—$CH_2$—$CCl_3$.

The invention also embraces compounds of the formula (I), (II), (III), (IV), (V), (VI), (VII) or (VIII) or any variation of the foregoing detailed herein, where Q is an acylamino moiety. In one variation, Q is an acylamino group where at least one of $R_a$ and $R_b$ is H, such as when Q is of the formula —C(O)N(H)($R_b$). In another variation, Q is an acylamino group where both $R_a$ and $R_b$ are alkyl. In one variation, Q is an acylamino moiety selected from the group consisting of: —C(O)—N(H)(alkyl), —C(O)—N(alkyl)$_2$, —C(O)—N(H)(aralkyl) and —C(O)—N(H)(aryl). In another variation, Q is an acylamino moiety selected from the group consisting of: —C(O)—N(H)$_2$, —C(O)—N(H)($C_1$-$C_8$ alkyl), —C(O)—N($C_1$-$C_6$ alkyl)$_2$ and —C(O)—N(H)($C_1$-$C_3$aralkyl). In a particular variation, Q is a moiety of the formula:

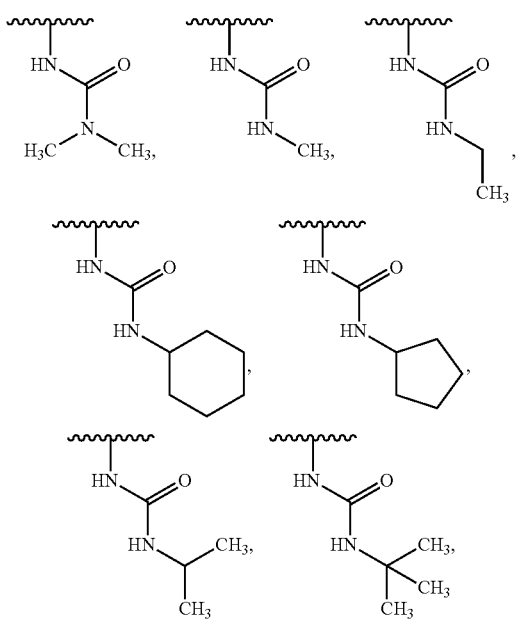

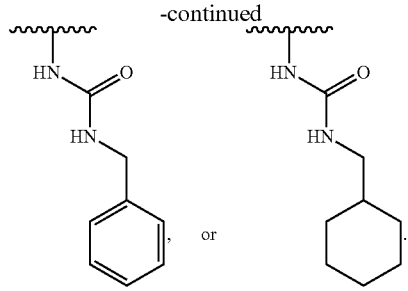

In a further variation, a compound of the invention is of the formula (I), (II), (III), (IV), (V), (VI), (VII) or (VIII) where $R^1$ is an unsubstituted alkyl, $R^{2a}$, $R^{2b}$, $R^{3a}$, $R^{3b}$, $R^{10a}$ and $R^{10b}$ are each H, each $X^7$, $X^8$, $X^9$ and $X^{10}$ is independently N or CH, each $R^{8a}$, $R^{8b}$, $R^{8c}$, and $R^{8d}$ is independently H or hydroxyl, and Q is a substituted or unsubstituted aryl, substituted or unsubstituted heteroaryl, including but not limited to a substituted or unsubstituted phenyl or pyridyl group. Where Q is a substituted phenyl or pyridyl group, in one variation it is substituted with at least one methyl or halo group.

In yet a further variation, a compound of the invention is of the formula (I), (II), (III), (IV), (V), (VI), (VII) or (VIII) where $R^1$ is a substituted or unsubstituted $C_1$-$C_8$ alkyl, acyl, acyloxy, carbonylalkoxy, substituted or unsubstituted heterocyclyl, substituted or unsubstituted aryl; each $R^{2a}$ and $R^{2b}$ is independently H, unsubstituted $C_1$-$C_8$ alkyl or halo; each $R^{3a}$ and $R^{3b}$ is independently H or halo; each $X^7$, $X^8$, $X^9$ and $X^{10}$ is CH or $CR^4$, where $R^4$ is as defined in formula (I), (II), (III), (IV), (V), (VI), (VII) or (VIII) or in a particular variation, $R^4$ is halo, pyridyl, methyl or trifluoromethyl; $R^{10a}$ and $R^{10b}$ are both H, and Q is a substituted or unsubstituted aryl, substituted or unsubstituted heteroaryl, including but not limited to a substituted or unsubstituted pyridyl, phenyl, pyrimidinyl, pyrazinyl, imidazolyl, furanyl, pyrrolyl or thiophenyl group. In a particular variation, Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In one variation, a compound of the variation detailed herein is provided wherein $R^1$ is propylate, methyl, ethyl, cyclopropyl, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In still a further variation, a compound of the invention is of the formula (I), (II), (III), (IV), (V), (VI), (VII) or (VIII) where $R^1$ is a substituted or unsubstituted $C_1$-$C_8$ alkyl; each $R^{2a}$, $R^{2b}$, $R^{3a}$ and $R^{3b}$ is independently H or halo; each $R^4$ is independently halo, $C_1$-$C_8$ perhaloalkyl, substituted or a unsubstituted $C_1$-$C_8$ alkyl; each $R^{8a}$, $R^{8b}$, $R^{8c}$ and $R^{8d}$ is H; and Q is a substituted or unsubstituted cyclohexyl, morpholinyl, piperazinyl, thiomorpholinyl, cyclopentyl or pyrrolidinyl moiety. The invention also embraces a compound of the formula (I) where $R^1$ is a methyl; at least one of $X^7$, $X^8$, $X^9$ and $X^{10}$ is $CR^4$, and each $R^4$ is independently halo, methyl or trifluoromethyl. The invention embraces compounds where Q in any variation detailed is substituted with at least one carbonyl, hydroxymethyl, methyl or hydroxyl group, to the extent such substituent makes chemical sense.

In a particular variation, the compound is of the formula (I), (II), (III), (IV), (V), (VI), (VII) or (VIII) where $R^1$ is a substituted or unsubstituted $C_1$-$C_8$ alkyl; each $R^{2a}$ and $R^{2b}$ is independently H, a substituted or unsubstituted $C_1$-$C_8$ alkyl or $R^{2a}$ and $R^{2b}$ are taken together to form a carbonyl moiety; $R^{3a}$ and $R^{3b}$ are both H; each $R^4$ is independently halo or a substituted or unsubstituted $C_1$-$C_8$ alkyl; each $R^{8a}$, $R^{8b}$, $R^{8c}$, and $R^{8d}$ is H; each $R^{10a}$ and $R^{10b}$ is independently H, halo, a substituted or unsubstituted $C_1$-$C_8$ alkyl, hydroxyl, alkoxy or $R^{10a}$ and $R^{10b}$ are taken together to form a carbonyl moiety, provided that at least one of $R^{10a}$ and $R^{10b}$ is other than H. In one aspect of this variation, Q may be a substituted or unsubstituted pyridyl, phenyl, pyrazinyl, piperazinyl, pyrrolidinyl or thiomorpholinyl group. In another aspect of this variation, Q is a pyridyl, phenyl, pyrazinyl, piperazinyl, pyrrolidinyl or thiomorpholinyl group substituted with at least one methyl or halo group. In yet another aspect of this variation, $X^7$, $X^8$, $X^9$ and $X^{10}$ are CH or $CR^4$ and each $R^4$ is independently halo or methyl.

In another variation, a compound of the invention is of a formula detailed herein, e.g., formula (I), (II) or (III) or any variation of the foregoing detailed herein, or a compound according to any one of the formulae (I-A), (I-B), (I-C), (I-D), (I-E), (I-F), (I-G) (I-b1), (I-b2), (I-c1), (I-c2), (I-d1), (I-d2), (I-e1), (I-e2), (I-f1), (I-f2), (I-g1) and (I-g2) where Q is a substituted or unsubstituted cycloalkyl or heterocyclyl selected from the structures:

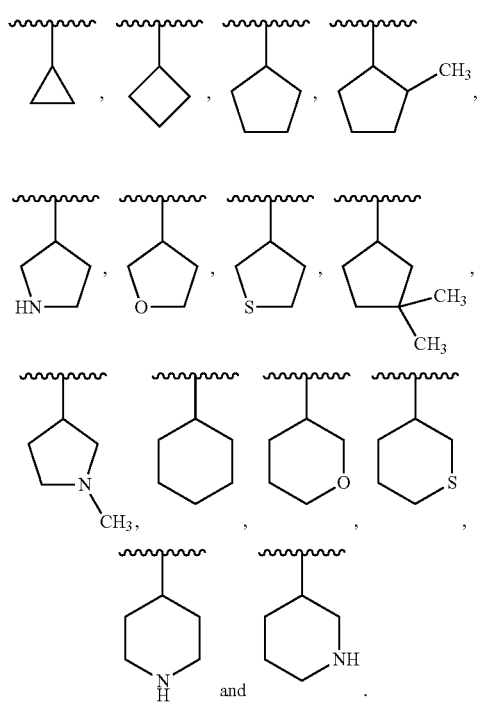

In another variation, a compound of the invention is of a formula detailed herein, e.g., formula (I), (II) or (III) or any variation of the foregoing detailed herein, or a compound according to any one of the formulae (I-A), (I-B), (I-C), (I-D), (I-E), (I-F), (I-G), (I-b1), (I-b2), (I-c1), (I-c2), (I-d1), (I-d2), (I-e1), (I-e2), (I-f1), (I-f2), (I-g1) and (I-g2) where Q is a substituted or unsubstituted heteroaryl selected from the structures:

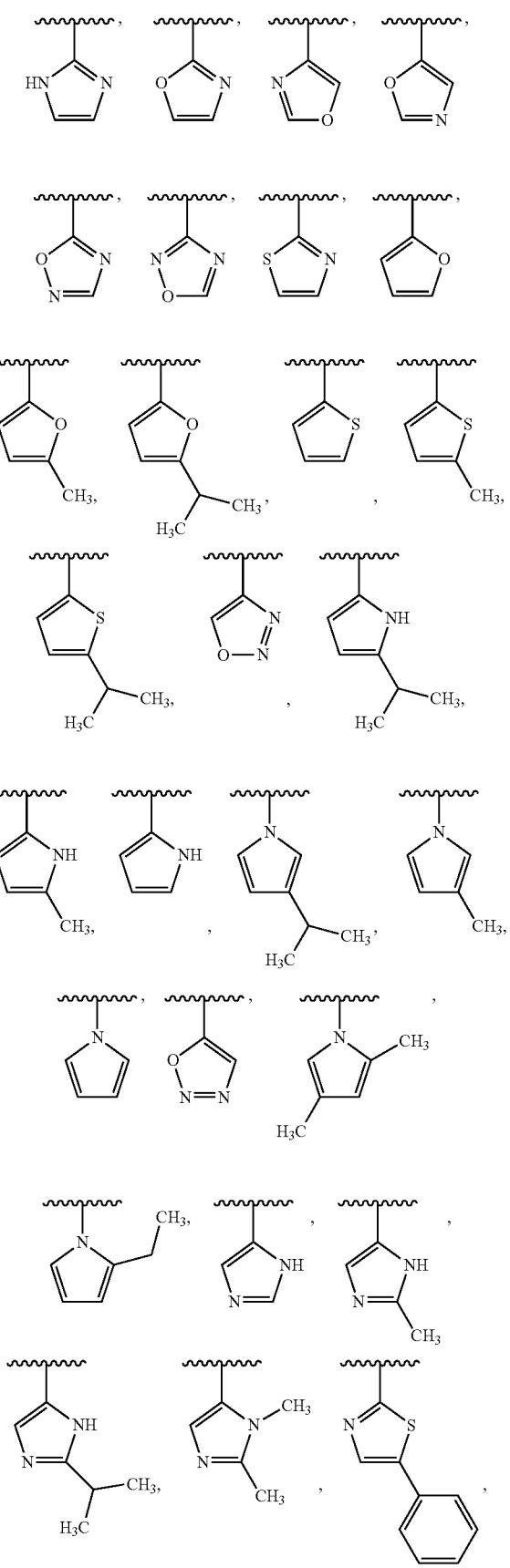

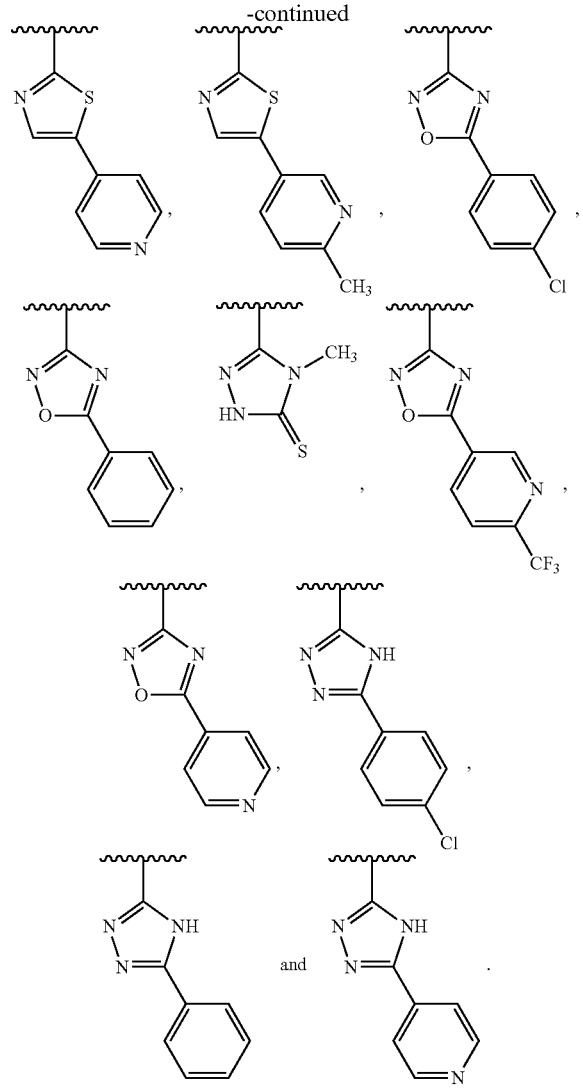
In another variation, a compound of the invention is of a formula detailed herein, e.g., formula (I), (II) or (III) or any variation of the foregoing detailed herein, or a compound according to any one of the formulae (I-A), (I-B), (I-C), (I-D), (I-E), (I-F), (I-G), (I-b1), (I-b2), (I-c1), (I-c2), (I-d1), (I-d2), (I-e1), (I-e2), (I-f1), (I-f2), (I-g1) and (I-g2) where Q is a substituted or unsubstituted phenyl selected from the structures:
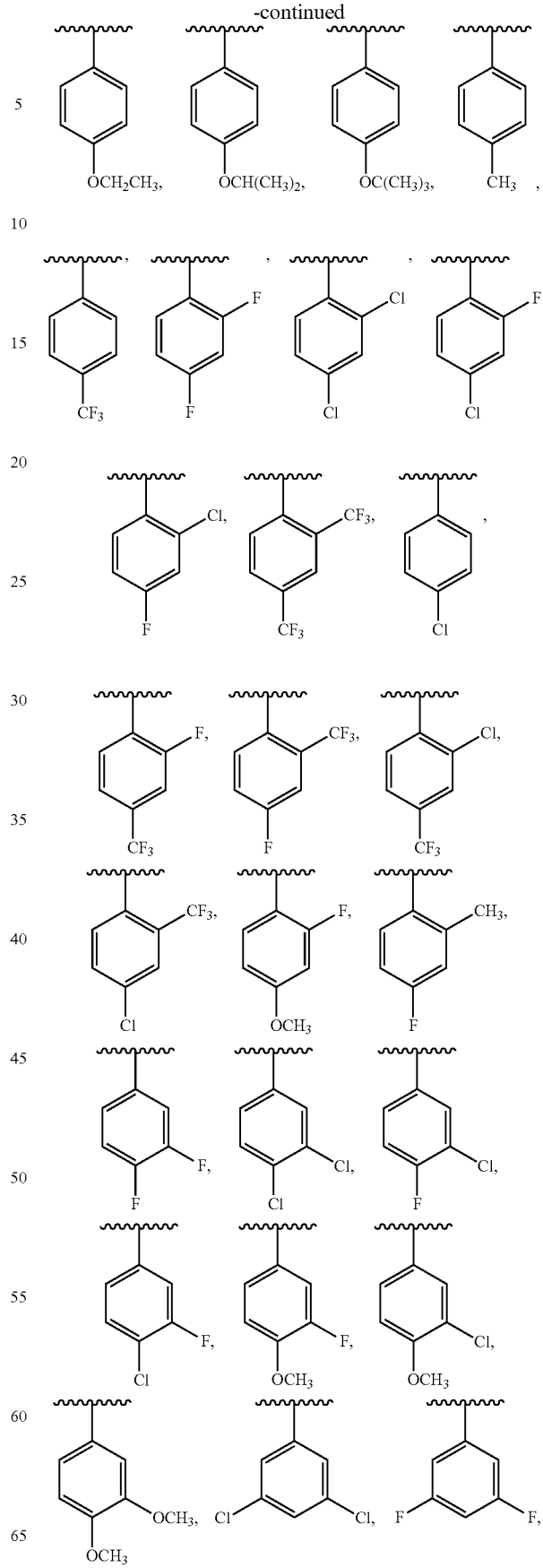

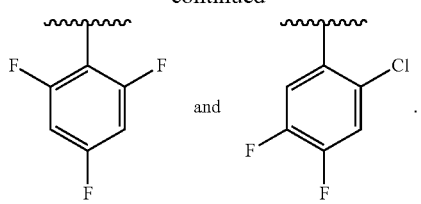

In another variation, a compound of the invention is of a formula detailed herein, e.g., formula (I), (II) or (III) or any variation of the foregoing detailed herein, or a compound according to any one of the formulae (I-A), (I-B), (I-C), (I-D), (I-E), (I-F), (I-G), (I-b1), (I-b2), (I-c1), (I-c2), (I-d1), (I-d2), (I-e1), (I-e2), (I-f1), (I-f2), (I-g1) and (I-g2) where Q is a substituted or unsubstituted heteroaryl selected from the structures:

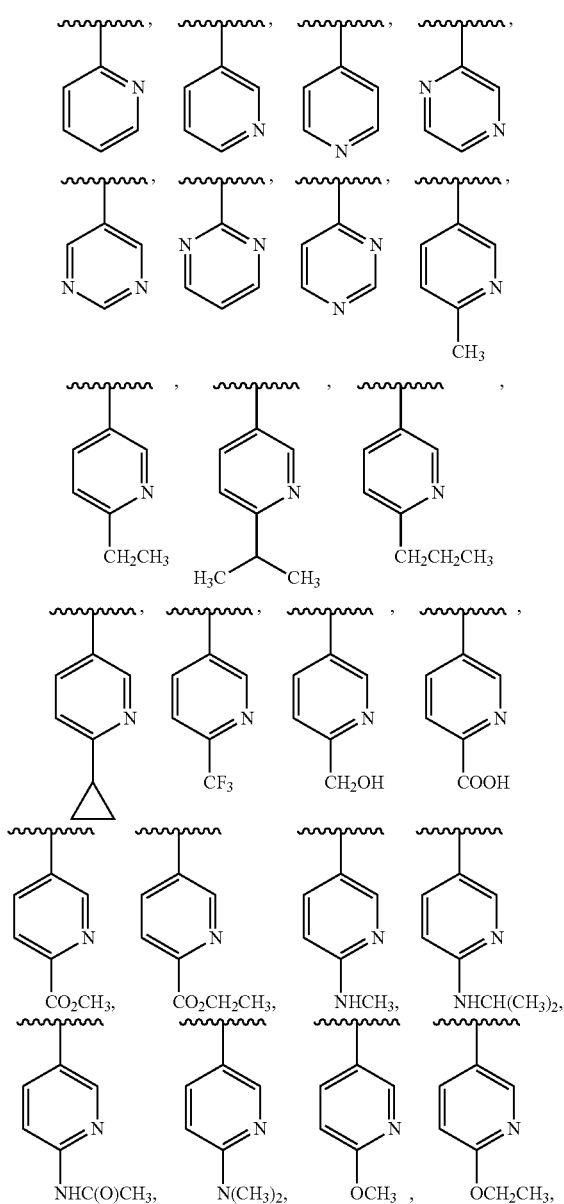

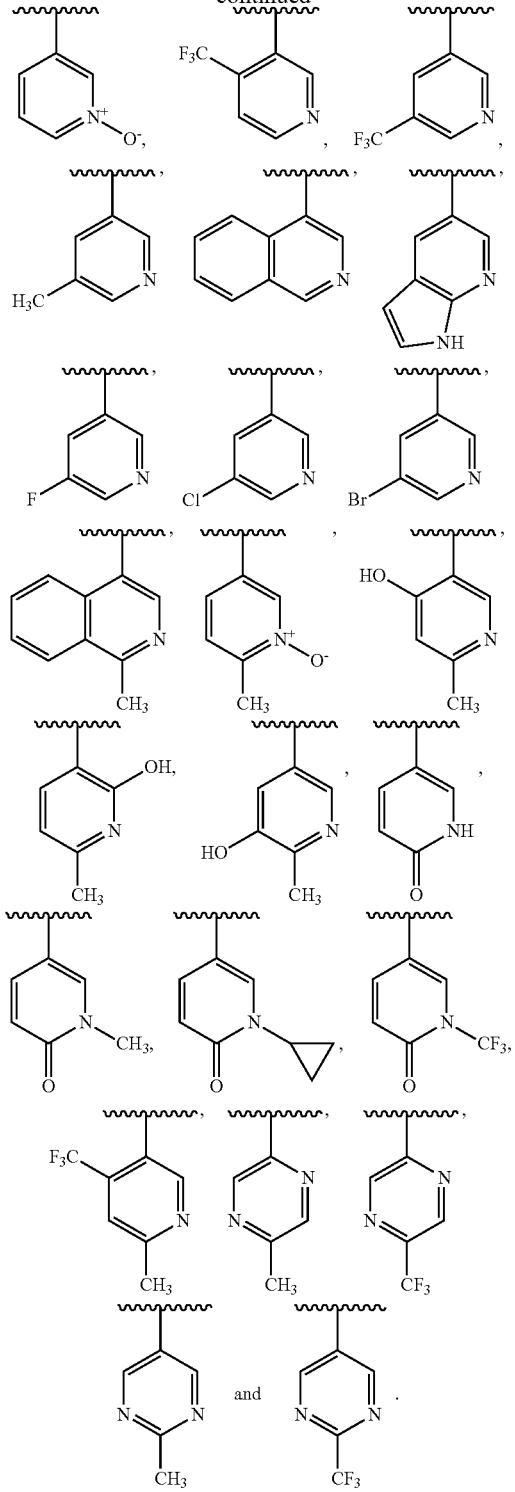

The embodiments and variations described herein for Formula (I) are also suitable for compounds of formulae (I-A), (I-B), (I-C), (I-D), (I-E), (I-F), (I-G), (I-b1), (I-b2), (I-c1), (I-c2), (I-d1), (I-d2), (I-e1), (I-e2), (I-f1), (I-f2), (I-g1) and (I-g2). The embodiments and variations described herein for Formula (II) are also suitable for compounds of formulae (II-A), (II-B), (II-C), (II-D), (II-a1), (II-b1), (II-c1) and (II-d1). Where appropriate, substituents described herein for formula (I) and variations thereof are also suitable for compounds of formulae (II), (III), (IV), (V), (VI) and (VII), and variations thereof.

Strikingly, it has been discovered that compounds included in the invention that contain a substituted vinyl moiety, such as methylvinyl, exhibit a lower binding affinity to $H_1$ as compared to their unsubstituted vinyl counterparts. To illustrate, compound 106 (which contains a methylvinyl moiety) exhibits a lower binding affinity to $H_1$ as compared to its unsubstituted vinyl counterpart, compound 415. Likewise, compound 85 (which contains a methylvinyl moiety) exhibits a lower binding affinity to $H_1$ as compared to its unsubstituted vinyl counterpart, compound 95. The structures of compounds 106, 415, 85 and 95 are shown below, with the methylvinyl moieties of compounds 106 and 85 encircled by dotted lines.

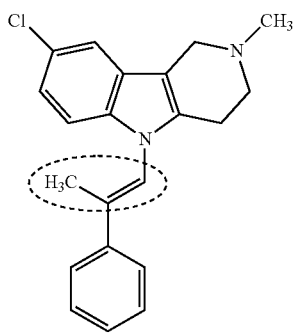

106

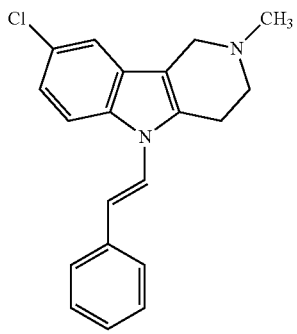

415

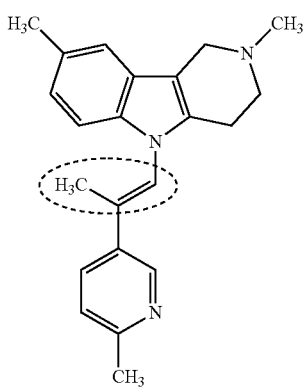

85

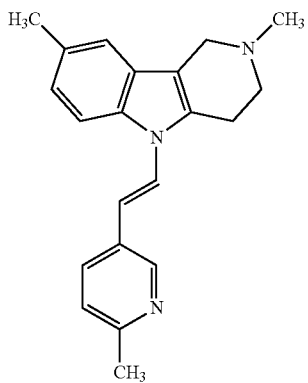

95

Thus, it is believed that substituted vinyl moieties, such as methylvinyl, may be responsible for reduced $H_1$ affinity.

Compounds that exhibit affinity for the histamine receptor $H_1$ may induce undesirable side effects, such as metabolic syndrome, diabetes type 2, weight gain, hyperlipidemia, hyperglycemia, hypertension and drowsiness (Kroeze et al., *Neuropsychopharmacology* (2003) 28, 519-526). The number and extent of undesirable side effects increases with increasing affinity for the $H_1$ receptor Thus, in one aspect, compounds of the formulae herein display reduced, low or no affinity to histamine receptor $H_1$. Compounds with low affinity to $H_1$ are those compounds which display less than about 80% inhibition of binding of a ligand to $H_1$. Inhibition of binding of a ligand to $H_1$ for all variations detailed herein is determined by a suitable assay known in the art such as the assay described herein. In some variations, compounds of the formulae herein inhibit binding of a ligand to $H_1$ by less than about any of 80%, 75%, 70%, 65%, 60% 55% and 50%. In one variation, compounds of the formulae herein inhibit binding of a ligand to $H_1$ by between about 50% to about 80%. In aspect, compounds of the formulae herein inhibit binding of a ligand to $H_1$ by less than about any of 80%, 75%, 70%, 65%, 60% 55% and 50% at any concentration, such as those detailed herein, e.g., 0.1 µM and 1 µM. In one variation, compounds of the formulae herein inhibit binding of Pyrilamine to $H_1$ as determined in the assay described herein. In a further variation, percent inhibition of binding to $H_1$ is measured by assays detailed herein.

Compounds containing a substituted vinyl moiety, such as methylvinyl moiety, are detailed herein wherein the compounds exhibit reduced $H_1$ affinity as compared to their unsubstituted vinyl counterparts. In one aspect, compounds that contain a substituted vinyl moiety, such as a methylvinyl moiety, exhibit low or no $H_1$ affinity and thus provide compounds with fewer or lesser undesirable side effects than compounds containing an unsubstituted vinyl moiety. In one variation, compounds as detailed herein containing a substituted vinyl moiety, such as methylvinyl, inhibit binding of a ligand to $H_1$ by less than about any of 80%, 75%, 70%, 65%, 60% 55% and 50%. In another variation, compounds as detailed herein containing a substituted vinyl moiety, such as methylvinyl, inhibit binding of a ligand to $H_1$ by less than about any of 50%, 40%, 30%, 20%, 10% and 5%.

Representative examples of compounds detailed herein, including intermediates and final compounds according to the invention are depicted in the tables below. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the invention embraces all salts and solvates of the compounds depicted here, as well as the non-salt and non-solvate form of the compound, as is well understood by the skilled artisan. In some embodiments, the salts of the compounds of the invention are pharmaceutically acceptable salts.

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. Taking compound 1 as an example, a composition of substantially pure compound 1 intends a composition that contains no more than 35% impurity, wherein the impurity denotes a compound other than compound 1 or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity.

In one variation, the compounds herein are synthetic compounds prepared for administration to an individual. In another variation, compositions are provided containing a compound in substantially pure form. In another variation, the invention embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

General Description of Biological Assays

The binding properties of compounds disclosed herein to a panel of aminergic G protein-coupled receptors including adrenergic receptors, dopamine receptors, serotonin receptors, histamine receptors and an imidazoline receptor may be determined. Binding properties may be assessed by methods known in the art, such as competitive binding assays. In one variation, compounds are assessed by the binding assays detailed herein. Compounds disclosed herein may also be tested in cell-based assays or in in vivo models for further characterization. In one aspect, compounds disclosed herein are of any formula detailed herein and further display one or more of the following characteristics: inhibition of binding of a ligand to an adrenergic receptor (e.g., $\alpha_{1D}$, $\alpha_{2A}$ and $\alpha_{2B}$), inhibition of binding of a ligand to a serotonin receptor (e.g., $5\text{-HT}_{2A}$, $5\text{-HT}_{2C}$, $5\text{-HT}_6$ and $5\text{-HT}_7$), inhibition of binding of a ligand to a dopamine receptor (e.g., $D_{2L}$), and inhibition of binding of a ligand to a histamine receptor (e.g., $H_1$, $H_2$ and $H_3$); agonist/antagonist activity to a serotonin receptor (e.g., $5\text{-HT}_{2A}$, $5\text{-HT}_6$); agonist/antagonist activity to a dopamine receptor (e.g., $D_{2L}$, $D_{2S}$); agonist/antagonist activity to a histamine receptor (e.g., $H_1$); activity in a neurite outgrowth assay; efficacy in a preclinical model of memory dysfunction associated with cholinergic dysfunction/hypofunction; efficacy in a preclinical model of attention impulsivity and executive function, and efficacy in a preclinical model of schizophrenia.

In one variation, inhibition of binding of a ligand to a receptor is measured in the assays described herein. In another variation, inhibition of binding of a ligand is measured in an assay known in the art. In one variation, binding of a ligand to a receptor is inhibited by at least about 80% as determined in a suitable assay known in the art such as the assays described herein. In one variation, binding of a ligand to a receptor is inhibited by greater than about any one of 80%, 85%, 90%, 95%, 100%, or between about 85% and about 95% or between about 90 and about 100% as determined in a suitable assay known in the art such as the assays described herein. In one variation, binding of a ligand to a receptor is inhibited by at least about 80%±20% as determined in an assay known in the art.

In one variation, a compound of the invention inhibits binding of a ligand to at least one receptor and as many as eleven as detailed herein (e.g. $\alpha_{1D}$, $\alpha_{2A}$, $\alpha_{2B}$, $5\text{-HT}_{2A}$, $5\text{-HT}_{2C}$, $5\text{-HT}_6$, $5\text{-HT}_7$, $D_{2L}$, $H_1$, $H_2$, $H_3$). In one variation, a compound of the invention inhibits binding of a ligand to at least one receptor and as many as eleven as detailed herein (e.g. $\alpha_{1D}$, $\alpha_{2A}$, $\alpha_{2B}$, $5\text{-HT}_{2A}$, $5\text{-HT}_{2C}$, $5\text{-HT}_6$, $5\text{-HT}_7$, $D_2$, $H_1$, $H_2$, $H_3$). In one variation, a compound of the invention inhibits binding of a ligand to at least one and as many as eleven receptors detailed herein and further displays agonist or antagonist activity to one or more receptors detailed herein (e.g., serotonin receptor $5\text{-HT}_{2A}$, serotonin receptor $5\text{-HT}_6$, dopamine receptor $D_{2L}$, dopamine receptor $D_{2S}$ and histamine receptor $H_1$) as measured in the assays described herein. In one variation, agonist response of serotonin receptor $5\text{-HT}_{2A}$ is inhibited by compounds of the invention by at least about any one of 50%, 50%, 70%, 80%, 90%, 100%, 110%, 120%, 130%, 140%, 150% as determined in a suitable assay such as the assay described herein.

In one variation, a compound of the invention displays the above described neurotransmitter receptor binding profile i.e. inhibits binding of a ligand to at least one receptor and as many as eleven as detailed herein and further stimulates neurite outgrowth, e.g. as measured by the assays described herein. Certain compounds of the invention showed activity in neurite outgrowth assays using primary neurons in culture. Data is presented indicating that a compound of the invention has activity comparable in magnitude to that of naturally occurring prototypical neurotrophic proteins such as brain derived neurotrophic factor (BDNF) and nerve growth factor (NGF). Notably, neurite outgrowth plays a critical part of new synaptogenesis, which is beneficial for the treatment of neuronal disorders. In one variation, neuronal disorders include ADHD. In one variation, neurite outgrowth is observed with a potency of about 1 µM as measured in a suitable assay known in the art such as the assays described herein. In another variation, neurite outgrowth is observed with a potency of about 500 nM. In a further variation, neurite outgrowth is observed with a potency of about 50 nM. In another variation, neurite outgrowth is observed with a potency of about 5 nM.

In another variation, a compound of the invention inhibits binding of a ligand to at least one receptor and as many as eleven as detailed herein, further displays agonist or antagonist activity to one or more receptors detailed herein and further stimulates neurite outgrowth.

In a further variation, a compound of the invention inhibits binding of a ligand to at least one and as many as eleven receptors as detailed herein and/or display the above described neurotransmitter receptor binding profile and further shows efficacy in a preclinical model of memory dysfunction associated with cholinergic dysfunction/hypofunction, and in preclinical models of attention/impulsivity and executive function, i.e. shows pro-cognitive effects in a preclinical model of memory dysfunction. Compounds of the invention have been shown to be effective in a preclinical model of memory dysfunction associated with cholinergic hypofunction (see relevant Examples). As $H_1$ antagonism may contribute to sedation, weight gain and reduced cognition, low affinity (less than about 80% inhibition of binding of Pyrilamine at 1 µM in the assay described herein) for this receptor may be associated with pro-cognitive effects and a more desirable side effect profile. Furthermore, compounds of the invention with increased potency as a $5\text{-}HT_6$ antagonist may have cognition-enhancing effects as serotonin acting through this receptor may impair memory.

In another variation, a compound of the invention inhibits binding of a ligant to at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction, in preclinical models of attention/impulsivity and executive function, and further displays agonist or antagonist activity to one or more receptors detailed herein.

In a further variation, a compound of the invention inhibits binding of a ligand to at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction, and in preclinical models of attention/impulsivity and executive function, and further stimulates neurite outgrowth.

In another variation, a compound of the invention inhibits at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction, in preclinical models of attention/impulsivity and executive function, further displays agonist or antagonist activity to one or more receptor detailed herein and further stimulates neurite outgrowth.

In a further variation, a compound of the invention inhibits binding of a ligand to at least one and as many as eleven receptors and further possesses anti-psychotic effects as measured in a preclinical model of schizophrenia, i.e., shows efficacy in a preclinical model of schizophrenia.

In another variation, a compound of the invention inhibits binding of a ligand to at least one and as many as eleven receptors, further shows efficacy in a preclinical model of schizophrenia and further displays agonist or antagonist activity to one or more receptors detailed herein.

In a further variation, a compound of the invention inhibits binding of a ligand to at least one and as many as eleven receptors, further shows efficacy in a preclinical model of schizophrenia and further stimulates neurite outgrowth.

In a further variation, a compound of the invention inhibits binding of a ligand to at least one and as many as eleven receptors, further shows efficacy in a preclinical model of memory dysfunction associated with cholinergic dysfunction/hypofunction such as enhancement of memory retention and reduction of memory impairment, and in preclinical models of attention/impulsivity and executive function, and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein and further shows efficacy in a preclinical model of memory dysfunction associated with cholinergic dysfunction/hypofunction such as enhancement of memory retention and reduction of memory impairment, and in preclinical models of attention/impulsivity and executive function.

In another variation, a compound of the invention inhibits binding of a ligand to at least one and as many as eleven receptors, further shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function.

In a further variation, a compound of the invention inhibits binding of a lignad to at least one and as many as eleven receptors detailed herein, further displays agonist or antagonist activity to one or more receptors detailed herein, further stimulates neurite outgrowth and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein, further stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function.

In another variation, a compound of the invention stimulates neurite outgrowth. In another variation, a compound of the invention shows efficacy in a preclinical model of schizophrenia and further stimulates neurite outgrowth. In another variation, a compound of the invention stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function. In another variation, a compound of the invention shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function.

In one aspect, compounds of the invention inhibit binding of a ligand to adrenergic receptors $\alpha_{1D}$, $\alpha_{2A}$, $\alpha_{2B}$ and inhibit binding of a ligand to serotonin receptor 5-HT$_6$. In another variation, compounds of the invention inhibit binding of a ligand to adrenergic receptors $\alpha_{1D}$, $\alpha_{2A}$, $\alpha_{2B}$, to serotonin receptor 5-HT$_6$ and to any one or more of the following receptors: serotonin receptor 5-HT$_7$, 5-HT$_{2A}$ and 5-HT$_{2C}$. In another variation, compounds of the invention inhibit binding of a ligand to adrenergic receptors $\alpha_{1D}$, $\alpha_{2A}$, $\alpha_{2B}$, to serotonin receptor 5-HT$_6$ and to any one or more of the following receptors: serotonin receptor 5-HT$_7$, 5-HT$_{2A}$ and 5-HT$_{2C}$ and further show weak inhibition of binding of a ligand to histamine receptor H$_1$ and/or H$_2$. In one variation, compounds of the invention that also display strong inhibition of binding of a ligand to the serotonin receptor 5-HT$_7$ are particularly desired. In another variation, compounds of the invention inhibit binding of a ligand to adrenergic receptors $\alpha_{1D}$, $\alpha_{2A}$, $\alpha_{2B}$, to serotonin receptor 5-HT$_6$ and further show weak inhibition of binding of a ligand to histamine receptor H$_1$ and/or H$_2$. Weak inhibition of binding of a ligand to the histamine H$_1$ receptor is permitted as agonists of this receptor have been implicated in stimulating memory as well as weight gain. In one variation, binding to histamine receptor H$_1$ is inhibited by less than about 80%. In another variation, binding of a ligand to histamine receptor H$_1$ is inhibited by less than about any of 75%, 70%, 65%, 60%, 55%, or 50% as determined by a suitable assay known in the art such as the assays described herein.

In another variation, compounds of the invention inhibit binding of a ligand to a dopamine receptor D$_2$. In another variation, compounds of the invention inhibit binding of a ligand to dopamine receptor D$_{2L}$. In another variation, compounds of the invention inhibit binding of a ligand to dopamine receptor D$_2$ and to serotonin receptor 5-HT$_{2A}$. In another variation, compounds of the invention inhibit binding of a ligand to dopamine receptor D$_{2L}$ and to serotonin receptor 5-HT$_{2A}$. In another variation, compounds of the invention inhibit binding of a ligand to histamine receptor H$_1$. In certain aspects, compounds of the invention further show one or more of the following properties: strong inhibition of binding of a ligand to the serotonin 5-HT$_7$ receptor, strong inhibition of binding of a ligand to the serotonin 5-HT$_{2A}$ receptor, strong inhibition of binding of a ligand to the serotonin 5-HT$_{2C}$ receptor, weak inhibition of binding of a ligand to the histamine H$_1$ receptor, weak inhibition of binding of ligands to the histamine H$_2$ receptor, and antagonist activity to serotonin receptor 5-HT$_{2A}$.

In one variation, compounds of the invention show any of the receptor binding aspects detailed herein and further display agonist/antagonist activity to one or more of the following receptors: serotonin receptor 5-HT$_{2A}$, serotonin receptor 5-HT$_6$, dopamine receptor D$_{2L}$, dopamine receptor D$_{2S}$ and histamine receptor H$_1$. In one variation, compounds of the invention show any of the receptor binding aspects detailed herein and further stimulate neurite outgrowth. In one variation, compounds of the invention show any of the receptor binding aspects detailed herein and further show efficacy in a preclinical model of memory dysfunction associated with cholinergic dysfunction/hypofunction, such as enhancement of memory retention and reduction of memory impairment and in preclinical models of attention/impulsivity and executive function. In one variation, compounds of the invention show any of the receptor binding aspects detailed herein and further show efficacy in a preclinical model of schizophrenia. In one variation, compounds of the invention show any of the receptor binding aspects detailed herein and further show efficacy in any one or more of agonist/antagonist assays (e.g., to serotonin receptor 5-HT$_{2A}$, 5-HT$_6$, dopamine receptor D$_{2L}$, dopamine receptor D$_{2S}$ and histamine receptor H$_1$), neurite outgrowth, a preclinical model of memory dysfunction associated with cholinergic dysfunction/hypofunction and a preclinical model of schizophrenia.

In some aspects, compounds of the invention inhibit binding of a ligand to adrenergic receptors $\alpha_{1D}$, $\alpha_{2A}$, $\alpha_{2B}$, serotonin receptor 5-HT$_6$ and a dopamine receptor D$_2$ by at least about 80% as determined in a suitable assay known in the art such as the assays described herein. In one variation binding is inhibited by at least about 80% as measured in a suitable assay such as the assays described herein. In some aspects, compounds of the invention inhibit binding of a ligand to adrenergic receptors $\alpha_{1D}$, $\alpha_{2A}$, $\alpha_{2B}$, serotonin receptor 5-HT$_6$ and dopamine receptor D$_{2L}$ by at least about 80% as determined in a suitable assay known in the art such as the assays described herein. In one variation binding is inhibited by at least about 80% as measured in a suitable assay such as the assays described herein. In one variation, binding of a ligand to a receptor is inhibited by greater than about any one of 80%, 85%, 90%, 95%, 100%, or between about 85 and about 95% or between about 90 and about 100% as determined in a suitable assay known in the art such as the assays described herein.

In some aspects, compounds of the invention display the above described neurotransmitter receptor binding profile and further show antipsychotic effects. It is recognized that compounds of the invention have binding profiles similar to compounds with antipsychotic activity and several compounds of the invention have been shown to be effective in a preclinical model of schizophrenia (see relevant Examples). In addition, compounds of the invention might possess the cognitive enhancing properties of dimebon and thus add to the beneficial pharmacology profile of these antipsychotic molecules. In one variation, compounds of the invention display the above described neurotransmitter receptor binding profile and further show pro-cognitive effects in a preclinical model of memory dysfunction such as enhancement of memory retention and reduction of memory impairment. In another variation, compounds of the invention display the above described neurotransmitter receptor binding profile and do not show pro-cognitive effects in a preclinical model of memory dysfunction, learning and memory.

In one variation, compounds of the invention demonstrate pro-cognitive effects in a preclinical model of memory dysfunction, learning and memory. In a further variation, compounds of the invention possess anti-psychotic effects in a preclinical model of schizophrenia. In a further variation, compounds of the invention demonstrate pro-cognitive effects in a preclinical model of memory dysfunction, learning and memory and further possess anti-psychotic effects in a preclinical model of schizophrenia.

Overview of the Methods

The compounds described herein may be used to treat, prevent, delay the onset and/or delay the development of cognitive disorders, psychotic disorders, neurotransmitter-mediated disorders and/or neuronal disorders in individuals, such as humans. In one aspect, the compounds described herein may be used to treat, prevent, delay the onset and/or delay the development of a cognitive disorder. In one variation, cognitive disorder as used herein includes and intends disorders that contain a cognitive component, such as psychotic disorders (e.g., schizophrenia) containing a cognitive component (e.g., CIAS). In one variation, cognitive disorder includes ADHD. In another aspect, the compounds described herein may be used to treat, prevent, delay the onset and/or delay the development of a psychotic disorder. In one variation, psychotic disorder as used herein includes and intends disorders that contain a psychotic component, for example cognitive disorders (e.g., Alzheimer's disease) that contain a psychotic component (e.g., psychosis of Alzheimer's Disease or dementia). In one variation, methods of improving at least one cognitive and/or psychotic symptom associated with schizophrenia are provided. In one aspect, methods of improving cognition in an individual who has or is suspected of having CIAS are provided. In a particular aspect, methods of treating schizophrenia are provided wherein the treatment provides for an improvement in one or more negative symptom and/or one or more positive symptom and/or one or more disorganized symptom of schizophrenia. In yet another aspect, the compounds described herein may be used to treat, prevent, delay the onset and/or delay the development of a neurotransmitter-mediated disorders disorder. In one aspect, a neurotransmitter-mediated disorder includes ADHD. In one embodiment, the neurotransmitter-mediated disorder includes spinal cord injury, diabetic neuropathy, allergic diseases (including food allergies) and diseases involving geroprotective activity such as age-associated hair loss (alopecia), age-associated weight loss and age-associated vision disturbances (cataracts). In another variation, the neurotransmitter-mediated disorder includes spinal cord injury, diabetic neuropathy, fibromyalgia and allergic diseases (including food allergies). In still another embodiment, the neurotransmitter-mediated disorder includes Alzheimer's disease, Parkinson's Disease, autism, Guillain-Barré syndrome, mild cognitive impairment, multiple sclerosis, stroke and traumatic brain injury. In yet another embodiment, the neurotransmitter-mediated disorder includes schizophrenia, anxiety, bipolar disorders, psychosis, depression and ADHD. In one variation, depression as used herein includes and intends treatment-resistant depression, depression related to a psychotic disorder, or depression related to a bipolar disorder. In another aspect, the compounds described herein may be used to treat, prevent, delay the onset and/or delay the development of a neuronal disorder. In one aspect, the compounds described herein may also be used to treat, prevent, delay the onset and/or delay the development of cognitive disorders, psychotic disorders, neurotransmitter-mediated disorders and/or neuronal disorders for which the modulation of an aminergic G protein-coupled receptor is believed to be or is beneficial.

The invention also provides methods of improving cognitive functions and/or reducing psychotic effects comprising administering to an individual in need thereof an amount of a compound of the invention or a pharmaceutically acceptable salt thereof effective to improve cognitive functions and/or reduce psychotic effects. In a particular variation, a method of treating schizophrenia is provided, wherein the treatment provides an improvement in at least one cognitive function, such as an improvement in a cognitive function in an individual who has or is suspected of having CIAS. In a further variation, a method of treating schizophrenia is provided wherein the method reduces psychotic effects associated with schizophrenia. In one embodiment, a method of treating schizophrenia is provided wherein the method improves the negative symptoms of schizophrenia in an individual in need thereof. In one embodiment, a method of treating schizophrenia is provided wherein the method improves the positive symptoms of schizophrenia in an individual in need thereof. In a further variation, a method of treating schizophrenia is provided wherein the method both improves cognitive function and reduces psychotic effects in an individual in need thereof. A method of improving one or more negative, positive and disorganized symptoms of schizophrenia is also provided, where the method entails administering a compound as detailed herein, or a pharmaceutically acceptable salt thereof, to an individual in need of such improvement. In one variation, a method of improving at least one negative symptom of schizophrenia is provided, where the method entails administering a compound as detailed herein, or a pharmaceutically acceptable salt thereof, to an individual in need of such improvement. In another variation, a method of improving at leat one negative and at least one positive symptom of schizophrenia is provided, where the method entails administering a compound as detailed herein, or a pharmaceutically acceptable salt thereof, to an individual in need of such improvement. In yet another variation, a method of improving at least one negative and at least one disorganized symptom of schizophrenia is also provided, where the method entails administering a compound as detailed herein, or a pharmaceutically acceptable salt thereof, to an individual in need of such improvement. In still another variation, a method of improving at least one positive and at least one disorganized symptom of schizophrenia is also provided, where the method entails administering a compound as detailed herein, or a pharmaceutically acceptable salt thereof, to an individual in need of such improvement. In still a further variation, a method of improving at least one negative, at least one positive and at least one disorganized symptom of schizophrenia is provided, where the method entails administering a compound as detailed herein, or a pharmaceutically acceptable salt thereof, to an individual in need of such improvement.

The invention also provides methods of stimulating neurite outgrowth and/or promoting neurogenesis and/or enhancing neurotrophic effects in an individual comprising administering to an individual in need thereof an amount of a compound of the invention or a pharmaceutically acceptable salt thereof effective to stimulate neurite outgrowth and/or to promote neurogenesis and/or to enhance neurotrophic effects.

The invention further encompasses methods of modulating an aminergic G protein-coupled receptor comprising administering to an individual in need thereof an amount of a compound of the invention or a pharmaceutically acceptable salt thereof effective to modulate an aminergic G protein-coupled receptor.

It is to be understood that methods described herein also encompass methods of administering compositions comprising the compounds of the invention.

Methods for Treating, Preventing, Delaying the Onset, and/or Delaying the Development Cognitive Disorders, Psychotic Disorders, Neurotransmitter-Mediated Disorders and/or Neuronal Disorders In one aspect, the invention provides methods for treating, preventing, delaying the onset, and/or delaying the development of cognitive disorders, psychotic disorders, neurotransmitter-mediated disorders and/or neuronal disorders for which the modulation of an aminergic G protein-coupled receptor is believed to be or is beneficial, the method comprising administering to an individual in need thereof a compound of the invention. In some variations, modulation of adrenergic receptor $\alpha_{1D}$, $\alpha_{2A}$, $\alpha_{2B}$, serotonin receptor 5-$HT_{2A}$, 5-$HT_6$, 5-$HT_7$, histamine receptor $H_1$ and/or $H_2$ is expected to be or is beneficial for the cognitive disorders, psychotic disorders, neurotransmitter-mediated disorders and/or neuronal disorders. In some variations, modulation of adrenergic receptor $\alpha_{1D}$, $\alpha_{2A}$, $\alpha_{2B}$ and a serotonin receptor 5-$HT_6$ receptor is expected to be or is beneficial for the cognitive disorders, psychotic disorders, neurotransmitter-mediated disorders and/or neuronal disorders. In some variations, modulation of adrenergic receptor $\alpha_{1D}$, $\alpha_{2A}$, $\alpha_{2B}$, and a serotonin receptor 5-$HT_6$ receptor and modulation of one or more of the following receptors serotonin 5-$HT_7$, 5-$HT_{2A}$, 5-$HT_{2C}$ and histamine $H_1$ and $H_2$ is expected to be or is beneficial for the cognitive disorders, psychotic disorders, neurotransmitter-mediated disorders and/or neuronal disorders. In some variations, modulation of a dopamine receptor $D_2$ is expected to be or is beneficial for the cognitive disorders, psychotic disorders, neurotransmitter-mediated disorders and/or neuronal disorders. In some variations, modulation of dopamine receptor $D_{2L}$ is expected to be or is beneficial for the cognitive disorders, psychotic disorders, neurotransmitter-mediated disorders and/or neuronal disorders. In some variations, modulation of a dopamine receptor $D_2$ is expected to be or is beneficial for the cognitive disorders, psychotic disorders, neurotransmitter-mediated disorders and/or neuronal disorders. In certain variations, modulation of a dopamine $D_{2L}$ receptor and serotonin receptor 5-$HT_{2A}$ is expected to be or is beneficial for the cognitive disorders, psychotic disorders, neurotransmitter-mediated disorders and/or neuronal disorders. In some variations, the cognitive disorders, psychotic disorders, neurotransmitter-mediated disorders and/or neuronal disorders are treated, prevented and/or their onset or development is delayed by administering a compound of the invention.

Methods to Improve Cognitive Functions and/or Reduce Psychotic Effects

The invention provides methods for improving cognitive functions by administering a compound of the invention to an individual in need thereof. In some variations, modulation of one or more of adrenergic receptor $\alpha_{1D}$, $\alpha_{2A}$, $\alpha_{1D}$, serotonin receptor 5-$HT_{2A}$, 5-$HT_6$, 5-$HT_7$, histamine receptor $H_1$ and/or $H_2$ is desirable or expected to be desirable to improve cognitive functions. In some variations modulation of $\alpha_{1D}$, $\alpha_{2A}$, $\alpha_{2B}$ adrenergic receptors and a serotonin 5-$HT_6$ receptor is desirable or expected to be desirable to improve cognitive functions. In some variations, modulation of $\alpha_{1D}$, $\alpha_{2A}$, $\alpha_{2B}$ adrenergic receptors and serotonin receptor 5-$HT_6$ and modulation of one or more of the following receptors: serotonin receptor 5-$HT_7$, 5-$HT_{2A}$, 5-$HT_{2C}$ and histamine receptor $H_1$ and $H_2$, is desirable or expected to be desirable to improve cognitive functions. In another aspect, the invention encompasses methods to reduce psychotic effects by administering a compound of the invention to an individual in need thereof. In some embodiments, modulation of a dopamine $D_2$ receptor is expected to be or is desirable to reduce psychotic effects. In some embodiments, modulation of a dopamine $D_{2L}$ receptor is expected to be or is desirable to reduce psychotic effects. In some embodiments, modulation of a dopamine $D_2$ receptor and a serotonin 5-$HT_{2A}$ receptor is expected to be or is desirable to reduce psychotic effects. In some embodiments, modulation of a dopamine $D_{2L}$ receptor and a serotonin 5-$HT_{2A}$ receptor is expected to be or is desirable to reduce psychotic effects. In some variations, a compound of the invention is administered to an individual in need thereof.

Methods to Stimulate Neurite Outgrowth, Promote Neurogenesis and/or Enhance Neurotrophic Effects In a further aspect, the invention provides methods of stimulating neurite outgrowth and/or enhancing neurogenesis and/or enhancing neurotrophic effects comprising administering a compound of the invention or pharmaceutically acceptable salt thereof under conditions sufficient to stimulate neurite outgrowth and/or to enhance neurogenesis and/or enhance neurotrophic effects to an individual in need thereof. In some variations, a compound of the invention stimulates neurite outgrowth at a potency of about 1 µM as measured in a suitable assay such as the assays described herein. In some variations, a compound of the invention stimulates neurite outgrowth at a potency of about 500 nM as measured in a suitable assay such as the assays described herein. In some variations, a compound of the invention stimulates neurite outgrowth at a potency of about 50 nM as measured in a suitable assay such as the assays described herein. In some variations, a compound of the invention stimulates neurite outgrowth at a potency of about 5 nM as measured in a suitable assay such as the assays described herein.

Methods to Modulate an Aminergic G Protein-Coupled Receptor

The invention further contemplates methods for modulating the activity of an aminergic G-protein-coupled receptor comprising administering a compound of the invention or pharmaceutically acceptable salt thereof under conditions sufficient to modulate the activity of an aminergic G protein-coupled receptor. In some variations, the aminergic G protein-coupled receptor is a $\alpha_{1D}$, $\alpha_{2A}$, $\alpha_{2B}$ adrenergic receptor and a serotonin 5-$HT_6$ receptor. In some variations, the aminergic G protein-coupled receptor is a $\alpha_{1D}$, $\alpha_{2A}$, $\alpha_{2B}$ adrenergic receptor and a serotonin 5-$HT_6$ and 5-$HT_7$ receptor. In some variations, the aminergic G protein-coupled receptor is a $\alpha_{1D}$, $\alpha_{2A}$, $\alpha_{2B}$ adrenergic receptor, a serotonin 5-$HT_6$ and one or more of the following receptors: serotonin 5-$HT_7$, 5-$HT_{2A}$ and 5-$HT_{2C}$ and histamine $H_1$ and $H_2$ receptor. In some variations, the aminergic G protein-coupled receptor is a dopamine $D_2$ receptor. In some variations, the aminergic G protein-coupled receptor is a dopamine $D_{2L}$ receptor. In some variations, the aminergic G protein-coupled receptor is a dopamine $D_2$ receptor and a serotonin 5-$HT_{2A}$ receptor. In some variations, the aminergic G protein-coupled receptor is a dopamine $D_{2L}$ receptor and a serotonin 5-$HT_{2A}$ receptor. In some variations, the aminergic G protein-coupled receptor is a histamine $H_1$ receptor.

Dose-Dependent Therapy (DDT)

Dose dependent therapy refers to the concept that a single molecule may be used for different indications depending on the dose at which it is administered. It has been shown that compounds included in the invention exert pro-cognitive effects (where in one aspect pro-cognitive effects are achieved by reducing one or more symptoms associated with impaired cognition) when administered at low dose, whereas at high dose, these compounds induce both pro-cognitive and anti-psychotic effects (where in one aspect anti-psychotic effects are achieved by reducing one or more symptoms associated with a psychotic disorder). These compounds are further referred to as Dose-Dependent Therapy compounds (DDT compounds). When administered at high dose, DDT compounds in one aspect show fewer and/or lesser side-effects such as, e.g., extrapyramidal syndrome (EPS), as compared to other anti-psychotics, such as anti-psychotics which are not 5-$HT_{2A}$ receptor modulators. It is believed that EPS is caused, at least in part, by high $D_2$ receptor occupancy, the effect of which can be counteracted by compounds displaying a high affinity to the serotonin receptor 5-$HT_{2A}$. EPS can be determined using various scales known in the art such as the Abnormal Involuntary Movement Scale (AIMS), Barnes Akathisia Rating Scale (BARS), Simpson-Angus Rating Scale (SARS), Extrapyramidal Symptoms Rating Scale (ESRS) and the Extrapyramidal Symptoms Rating Scale-Abbreviated (ESRS-A). DDT compounds in one aspect are 5-$HT_{2A}$ modulators, and preferably are antagonists of 5-$HT_{2A}$. In one variation, DDT compounds have low or no affinity for the histamine receptor $H_1$, which is also implicated in undesirable side effects such as metabolic syndrome, diabetes type 2, weight gain, hyperlipidemia, hyperglycemia, hypertension and drowsiness (Kroeze et al., *Neuropsychopharmacology* (2003) 28, 519-526).

DDT Compounds

DDT compounds modulate at least serotonin receptor 5-$HT_{2A}$ and/or serotonin receptor 5-$HT_6$ and modulate dopamine receptor $D_2$, such as $D_{2L}$. In one aspect, DDT compounds inhibit binding of a ligand to at least 5-$HT_{2A}$ and/or 5-$HT_6$ and binding of a ligand to $D_2$. Inhibition of binding for all variations detailed herein is determined in a suitable assay known in the art, such as the assays described herein. In one aspect, DDT compounds act as antagonists of 5-$HT_{2A}$ and/or 5-$HT_6$ and act as antagonists of $D_2$. In another aspect, DDT compounds act as antagonists of 5-$HT_{2A}$ and $D_2$. In another aspect, DDT compounds act as antagonists of 5-$HT_{2A}$, 5-$HT_6$ and $D_2$. In one variation, DDT compounds inhibit binding of a ligand to 5-$HT_{2A}$ and/or 5-$HT_6$ by at least about 50% at a DDT concentration of about 0.1 µM and inhibit binding of a ligand to $D_2$ by at least about 90% at a DDT concentration of about 1 µM. In another variation, DDT compounds inhibit binding of a ligand to 5-$HT_{2A}$ and/or 5-$HT_6$ by greater than about any of 50%, 60%, 70% and 80% at a DDT concentration of at least about 0.1 µM. In a further variation, DDT compounds inhibit binding of a ligand to 5-$HT_{2A}$ and/or 5-$HT_6$ by greater than about any of 50%, 60%, 70% and 80% at a DDT concentration of less than about 0.1 µM (e.g., greater than about 0.01 µM and less than about 0.1 µM). In a further variation, DDT compounds inhibit binding of a ligand to 5-$HT_{2A}$ and/or 5-$HT_6$ by at least about 80% at a DDT concentration of about 0.1 µM. In one variation, DDT compounds inhibit binding to of a ligand to $D_2$ by at least about 90% at a DDT concentration of greater than about 1 µM. In another variation, DDT compounds inhibit binding of a ligand to $D_2$ by at least about 90% at a DDT concentration of between about 1 µM to about 3 µM. In one variation, DDT compounds inhibit binding of Ketanserin, LSD and Spiperone to 5-$HT_{2A}$, 5-$HT_6$ and $D_2$, respectively, as determined in the assays described herein. In another variation, binding of a ligand to 5-$HT_{2A}$ and/or 5-$HT_6$ is inhibited by greater than about any of 80%, 85%, 90% and 95%, or by about 100% at a DDT concentration of about 0.1 µM. In a further variation, binding of a ligand to 5-$HT_{2A}$ and/or 5-$HT_6$ is inhibited between about 85% to about 95% or between about 90% to about 100% at a DDT concentration of about 0.1 µM. In another variation, binding of a ligand to $D_2$ is inhibited by greater than about any of 90% and 95%, or by about 100% at a DDT concentration of about 1 µM. In a further variation, binding of a ligand to $D_2$ is inhibited by between about 90% to about 100% at a concentration of about 1 µM. In another variation, inhibition of binding of a ligand to 5-$HT_{2A}$ and/or 5-$HT_6$ is at least 80%±20% at a DDT concentration of about 0.1 µM and binding of a ligand to $D_2$ is inhibited by at least about 90% at a concentration of about 1 µM as determined in assays known in the art. In one aspect, DDT compounds inhibit binding of a ligand to 5-$HT_{2A}$ and $D_2$. In another aspect, DDT compounds inhibit binding of a ligand to 5-$HT_6$ and $D_2$. In yet another aspect, DDT compounds inhibit binding of a ligand to 5-$HT_{2A}$, 5-$HT_6$ and $D_2$. In one variation, percent inhibition of binding to 5-$HT_{2A}$, 5-$HT_6$ and $D_2$ is measured by assays detailed herein.

In one aspect, DDT compounds display low affinity to histamine receptor $H_1$. Compounds with low affinity to $H_1$ are those compounds which display less than about 80% inhibition of binding of a ligand to $H_1$. Inhibition of binding of a ligand to $H_1$ for all variations detailed herein is determined by a suitable assay known in the art such as the assay described herein. In some variations, DDT compounds inhibit binding of a ligand to $H_1$ by less than about any of 80%, 75%, 70%, 65%, 60% 55% and 50%. In one variation, DDT compounds inhibit binding of a ligand to $H_1$ by between about 50% to about 80%. In some variations, DDT compounds inhibit binding by less than about 80% at any DDT concentration, e.g., at about 0.1 µM to about 1 µM. In one variation, DDT compounds inhibit binding of Pyrilamine to H1 as determined in the assay described herein. In a further variation, percent inhibition of binding to $H_1$ is measured by assays detailed herein.

In some aspects, DDT compounds act as 5-$HT_{2A}$ and $D_2$ antagonists. Antagonist activity for all variations is measured in suitable assays known in the art such as the assays described herein. In one variation, 5-$HT_{2A}$ activity is inhibited by at least about 70% at a DDT concentration of about 0.1 µM. In another variation, 5-$HT_{2A}$ activity is inhibited by greater than about any of 70%, 75%, 80%, 85%, 90%, 95%, or by about 100% at a DDT concentration of about 0.1 µM. In one variation, $D_2$ activity is inhibited by at least about 70% at a DDT concentration of about 1 µM. In another variation, $D_2$ activity is inhibited by greater than about any of 70%, 75%, 80%, 85%, 90%, 95%, or by about 100% at a DDT concentration of about 1 µM. In one variation, percent inhibition of activity is determined in the assays described herein. In one aspect, DDT compounds inhibit 5-$HT_{2A}$ and $D_2$ activity. In another aspect, DDT compounds inhibit 5-$HT_{2A}$, 5-$HT_6$ and $D_2$ activity.

In one aspect, DDT compounds display any of the activities detailed herein for DDT compounds and further have a structure of the formulae provided herein. In one aspect, DDT compounds contain a substituted vinyl moiety, such as a methylvinyl moiety. Accordingly, in a particular aspect, DDT compounds are of the formula (I-C), or any variation thereof, including compounds of the formulae (I-c1) and (I-c2), where at least one of $R^{11}$ and $R^{12}$ is other than H, such as when at least one of $R^{11}$ and $R^{12}$ is a $C_1$-$C_8$ alkyl, $C_3$-$C_8$ cycloalkyl, or $C_1$-$C_8$ perhaloalkyl. DDT compounds may also be of the formula (I-D), or any variation thereof, including compounds of the formulae (I-d1) and (I-d2), where at least one of $R^{11}$ and $R^{12}$ is other than H. In one variation, DDT compounds are of the formula (I-E), or any variation thereof, including compounds of the formulae (I-e1) and (I-e2). In another variation, DDT compounds are of the formula (I-F), or any variation thereof, including compounds of the formulae (I-f1) and (I-f2). In still another variation, DDT compounds are of the formula (J-1), or any variation thereof, including compounds of the formulae (J-1a) and (J-1b). In still another variation, DDT compounds are of the formula (J-2), or any variation thereof, including compounds of the formulae (J-1a) and (J-1b). DDT compounds may also be of the formula (J-1), (J-2), (J-3), (J-4), (J-5), (J-6), (J-7) or (J-8). In still another variation, DDT compounds are of the formula (I-G), or any variation thereof, including compounds of the formulae (I-g1) and (I-g2). In yet another variation, DDT compounds are of the formula (I-H), or any variation thereof, including compounds of the formulae (I-h1) and (I-h2). DDT compounds may also be of the formula (H-1), (H-2), (H-3), (H-4), (H-5), (H-6), (H-7) or (H-8). In another aspect, DDT compounds are of the formula (II-a1) or (II-b1) or (II-c1) or (II-d1) where at least one of $R^{11}$ and $R^{12}$ is other than H (e.g., methyl). In another aspect, DDT compounds are of the formula (III) or any variation thereof where at least one of $R^{11}$ and $R^{12}$ is other than H (e.g., methyl). In another aspect, DDT compounds are of the formula (V) or any variation thereof, such as formula (V-B), where at least one of $R^{11}$ and $R^{12}$ is other than H (e.g., methyl).

DDT compounds may be present as pharmaceutically acceptable salts, or solvates thereof. Pharmaceutical compositions comprising a DDT compound and a pharmaceutically acceptable carrier are also embraced. These pharmaceutical compositions may take a form suitable for oral, buccal, parenteral, nasal, topical or rectal administration or a form suitable for administration by inhalation.

High Dose

In one aspect, high dose of a DDT compound corresponds to an amount that results in at least 65% of receptor occupancy of dopamine receptor $D_2$, which may be assessed by known methods, such as Positron Emission Tomography (PET) (Pani et al., *European Psychiatry* (2007) 22, 276-275). In some variations, a high dose provides $D_2$ occupancy that is greater than any one of 65%, 70%, 75%, 80%, 85% and 90%. In one variation, a high dose provides $D_2$ occupancy that is at least 65%. In another variation, a high dose provides a $D_2$ occupancy that is from at least 65% to 90%, or from at least 65% to 85%, or from at least 65% to 80%, or from at least 65% to 75%, or from at least 65% to 70%, or from at least 70% to 90%, or from at least 70% to 85%, or from at least 70% to 80%, or from at least 70% to 75%, or from at least 75% to 90%, or from at least 75% to 85%, or from at least 75% to 80%, or from at least 80% to 90%. In one variation, a high dose provides $D_2$ occupancy that is less than 80% and greater than 65%.

In another aspect, high dose of a DDT compound corresponds to a daily dose of at least about 1 mg/kg. In another variation, high dose corresponds to a daily dose of about 1 mg/kg. In another variation, high dose corresponds to a daily dose of at least about 1 mg/kg to at least about 3 mg/kg. In yet another variation, high dose corresponds to a daily dose of at least about 1 mg/kg to about 5 mg/kg. In a further variation, high dose corresponds to a daily dose of greater than 1 mg/kg.

In a further aspect, high dose of a DDT compound corresponds to an amount that induces anti-psychotic effects as determined by the Positive and Negative Syndrome Scale (PANSS). In another variation, anti-psychotic effects are measured by one or more of the following: PANSS, Brief Psychiatric Rating Scale (BPRS), Positive symptom sub-scale of PANSS, Young Mania Rating Scale (Y-MRS), Mania Rating Scale (MRS). In a further variation, anti-psychotic effects are measured by another scale and/or test known in the art.

In another aspect of the invention, high dose of a DDT compound corresponds to at least about 100 times the amount that induces pro-cognitive effects but does not induce anti-psychotic effects. In one variation, pro-cognitive effects are determined by cognition scales known in the art such as the Measurement and Treatment Research to Improve Cognition in Schizophrenia MATRICS. In another variation, pro-cognitive effects are determined by measuring the cognitive components of one or more of the following scales and/or tests: MATRICS, Negative Symptoms Assessment scale (NSA), Scale for the Assessment of Negative Symptoms (SANS), Schedule for the Deficit Syndrome (GDS), Negative symptom sub-scale of PANSS, MATRICS Consensus Cognition Battery (MCCB), CNSVitalSigns, CogState battery, Cognitive Drug Research battery (CDR), Brief Assessment of Cognition in Schizophrenia (BACS), Schizophrenia Cognition Rating Scale (SCoRS), Clinical Global Impression of Cognition in Schizophrenia (CGI-CogS), Repeatable Battery for the Assessment of Neuropsychological Status (RBANS), Test of Adaptive Behavior in Schizophrenia (TABS), Independent Living Skills Inventory (ILS), UCSD Performance-Based Skills Assessment (UPSA), Cognitive Assessment Interview (CAI), Global Assessment of Function from CAI (GAF), Quality of Life Scale (QLS), Maryland Assessment of Social Competence (MASC), Calgary Depression Scale (CDS), and Montgomery-Asberg Depression Rating Scale (MADRS). In a further variation, pro-cognitive effects are determined by another scale and/or test known in the art.

Low Dose

In one aspect, low dose of a DDT compound corresponds to an amount that results in less than 65% receptor occupancy of dopamine receptor $D_2$. In some variations, a low dose provides $D_2$ occupancy that is less than any one of 65%, 60%, 55% and 50%.

In another aspect, low dose of a DDT compound corresponds to a daily dose of about 0.03 mg/kg. In another variation, low dose corresponds to a daily dose of about 0.03 to about 0.3 mg/kg. In another variation, low dose corresponds to a daily dose of about 0.3 mg/kg. In yet another variation, low dose corresponds to a daily dose of about 0.03 to about 1 mg/kg. In a further variation, low dose corresponds to a daily dose of about 0.01 mg/kg. In yet another variation, low dose corresponds to a daily dose of 0.01 to about 1 mg/kg. In a further variation, low dose corresponds to a daily dose of about 0.5 mg/kg. In yet another variation, low dose corresponds to a daily dose of less than about 0.5 mg/kg. In another variation, low dose corresponds to a daily dose of less than 1 mg/kg.

In a further aspect, low dose of a DDT compound corresponds to an amount that induces pro-cognitive effects as determined by cognition scales such as MATRICS but does not induce anti-psychotic effects. In another variation, pro-cognitive effects are determined by measuring the cognitive components of one or more of the following scales and/or tests: MATRICS, Negative Symptoms Assessment scale (NSA), Scale for the Assessment of Negative Symptoms (SANS), Schedule for the Deficit Syndrome (GDS), Negative symptom sub-scale of PANSS, MATRICS Consensus Cognition Battery (MCCB), CNSVitalSigns, CogState battery, Cognitive Drug Research battery (CDR), Brief Assessment of Cognition in Schizophrenia (BACS), Schizophrenia Cognition Rating Scale (SCoRS), Clinical Global Impression of Cognition in Schizophrenia (CGI-CogS), Repeatable Battery for the Assessment of Neuropsychological Status (RBANS), Test of Adaptive Behavior in Schizophrenia (TABS), Independent Living Skills Inventory (ILS), UCSD Performance-Based Skills Assessment (UPSA), Cognitive Assessment Interview (CAI), Global Assessment of Function from CAI (GAF), Quality of Life Scale (QLS), Maryland Assessment of Social Competence (MASC), Calgary Depression Scale (CDS), and Montgomery-Asberg Depression Rating Scale (MADRS). In a further variation, pro-cognitive effects are determined by another scale and/or test known in the art.

In another aspect of the invention, low dose of a DDT compound corresponds to at least about $\frac{1}{100}$ the amount that induces anti-psychotic effects. In one variation, anti-psychotic effects are determined by assays such as PANSS. In another variation, anti-psychotic effects are measured by one or more of the following: PANSS, Brief Psychiatric Rating Scale (BPRS), Positive symptom sub-scale of PANSS, Young Mania Rating Scale (Y-MRS), Mania Rating Scale (MRS). In a further variation, anti-psychotic effects are measured by another scale and/or test known in the art.

Unit Dosage Forms

DDT compounds may be provided in various unit dosage forms. In one aspect, single therapy dosages are provided. In one variation, a unit dosage form comprises a low dose as described herein of a DDT compound. In another variation, a unit dosage form comprises a high dose as described herein of a DDT compound.

In another aspect, combination therapy dosage forms are provided. In one variation, combination dosage forms comprise a low dose as described herein of a DDT compound and a second drug suitable for anti-psychotic therapy. In another variation, combination dosage forms comprise a high dose as described herein of a DDT compound and a second drug suitable for anti-psychotic therapy.

Kits

The present invention further provides for kits comprising DDT compounds with instructions for achieving pro-cognitive effects at low dose as detailed herein or pro-cognitive effects and anti-psychotic effects at high dose as detailed herein. In one aspect, kits comprise a low dose of a DDT compound and instructions for achieving only pro-cognitive effects. In some variations, pro-cognitive effects include (i) improvement of CIAS such as improvement of any one or more of memory (e.g., short term memory, working memory, social memory), attention, impulsivity, verbal fluency and executive function and/or (ii) improvement of negative symptoms of schizophrenia such as improvement of any one or more of blunted affect, avolition, anhedonia, alogia, dysphoria, suicidality, hopelessness, depression and low mood. Thus, kits for use to achieve pro-cognitive effects in one aspect comprise a low dose of a DDT compound as described herein. In another variation, kits for use to achieve pro-cognitive effects comprise a unit dosage form containing a low dose of a DDT compound as described herein.

In a further aspect, kits of the present invention comprise a high dose of a DDT compound and instructions for achieving both pro-cognitive and anti-psychotic effects. In some variations, anti-psychotic effects comprise improvement of any one or more of psychotic symptoms such as positive symptoms of schizophrenia (e.g., delusions, hallucinations, disorganized thought and agitation). Kits comprising a high dose of a DDT compound may be used to achieve one or more pro-cognitive effects and one or more anti-psychotic effects. Thus, kits for use to achieve pro-cognitive and anti-psychotic effects in one aspect comprise a high dose of a DDT compound as described herein. In another variation, kits for use to achieve pro-cognitive and anti-psychotic effects comprise a unit dosage form containing a high dose of a DDT compound as detailed herein. In a further variation, kits for use to achieve pro-cognitive and anti-psychotic effects comprise a low dose of a DDT compound and a second drug suitable for anti-psychotic therapy. In yet another variation, kits for use to achieve pro-cognitive and anti-psychotic effects comprise a high dose of a DDT compound and a second drug suitable for anti-psychotic therapy. In one aspect, kits for use to achieve pro-cognitive and anti-psychotic effects comprise DDT compounds in unit dosage forms as detailed herein.

Methods of Treatment

The invention provides methods of treating diseases or conditions in which cognition and/or psychosis are implicated. The present invention provides methods of treating cognitive disorders and/or psychotic disorders by administering a DDT compound at a pharmaceutically effective dose to a subject in need thereof. In one variation, cognitive disorder as used herein includes and intends disorders that contain a cognitive component, such as psychotic disorders (e.g., schizophrenia) containing a cognitive component (e.g., CIAS). In one variation, psychotic disorder as used herein includes and intends disorders that contain a psychotic component, for example cognitive disorders (e.g., Alzheimer's disease) that contain a psychotic component (e.g., psychosis of Alzheimer's Disease or dementia).

In one aspect, the present invention encompasses methods of improving cognition by administering a DDT compound at a pharmaceutically effective dose to a subject in need thereof. In one variation, improving cognition comprises reducing one or more symptoms associated with impaired cognition. In a further aspect, the present invention provides methods of (i) improving cognition and (ii) reducing symptoms associated with psychotic disorders in a subject in need thereof. In yet another aspect, the present invention encompasses methods of improving cognition and not reducing symptoms associated with psychotic disorders in a subject in need thereof. In yet a further aspect, the present invention provides methods of improving cognition and not significantly reducing symptoms associated with psychotic disorders in a subject in need thereof. In some variations, a subject in need thereof is an individual who is refractory to other pro-cognitive and/or anti-psychotic therapy.

In one aspect, the invention is directed to methods of improving cognition and/or reducing symptoms associated with impaired cognition by administering a DDT compound at either low or high dose. In one variation improving cognition comprises (i) improvement of CIAS such as improvement of any one or more of memory (e.g., short term memory, working memory, social memory), attention, impulsivity, verbal fluency and executive function and/or (ii) improvement of negative symptoms of schizophrenia such as improvement of any one or more of blunted affect, avolition, anhedonia, alogia, dysphoria, suicidality, hopelessness, depression and low mood.

In a further aspect, the invention provides methods of both (i) improving cognition (e.g., as set forth herein) and/or reducing symptoms associated with impaired cognition and (ii) reducing symptoms associated with psychotic disorders by administering a DDT compound at high dose. In one variation, reducing symptoms associated with psychotic disorders comprises improvement of any one or more of psychotic symptoms such as positive symptoms of schizophrenia (e.g., delusions, hallucinations, disorganized thought and agitation). In one variation, the invention is directed to methods of treating schizophrenia by administering a high dose of a DDT compound. In another variation, the invention provides methods of reducing one or more symptom of positive symptoms of schizophrenia by administering a high dose of a DDT compound. In a further variation, the invention encompasses methods of reducing one or more symptom of positive and/or one or more symptom of negative symptoms of schizophrenia by administering a high dose of a DDT compound. In yet another variation, the invention provides methods of reducing one or more symptom of positive symptoms and/or one or more symptom of CIAS by administering a high dose of a DDT compound. In yet another variation, the invention provides methods of reducing one or more symptom of positive symptoms and/or one or more symptom of negative symptoms and/or one or more of disorganized symptoms of schizophrenia by administering a high dose of a DDT compound.

In another aspect, the invention is directed to methods of improving cognition and/or reducing symptoms associated with impaired cognition and not reducing symptoms associated with psychotic disorders by administering a DDT compound at low dose. In one variation improving cognition comprises (i) improvement of CIAS such as improvement of any one or more of memory (e.g., short term memory, working memory, social memory), attention, impulsivity, verbal fluency and executive function and/or (ii) improvement of negative symptoms of schizophrenia such as improvement of any one or more of blunted affect, avolition, anhedonia, alogia, dysphoria, suicidality, hopelessness, depression and low mood.

In yet another aspect, the invention encompasses methods of improving cognition and/or reducing symptoms associated with impaired cognition without significantly improving symptoms associated with psychotic disorders by administering a DDT compound at low dose.

Methods of Manufacturing a Medicament

In a further aspect of the invention use of DDT compounds and compositions thereof in the manufacture of a medicament is provided. Particularly, the manufacture of a medicament for use in the treatment of diseases or conditions in which cognition and/or psychosis are implicated are described herein. Further, pharmaceutical compositions of DDT compounds are also intended for use in the manufacture of a medicament for use in treatment of diseases or conditions in which cognition and/or psychosis are implicated.

Method of Determining a Dose/Treatment

The present invention further encompasses methods of determining a suitable or optimal dose of a DDT compound to either (i) achieve pro-cognitive effects alone or (ii) achieve both pro-cognitive effects and anti-psychotic effects in an individual in need thereof. In one aspect, a suitable dose is determined by measuring the percentage of $D_2$ occupancy and adjusting an individual's dosage in response thereto. In one variation, dosage is increased to achieve anti-psychotic effects if $D_2$ occupancy is less than 65% as determined by methods known in the art such as PET. In another variation, dosage is increased to achieve anti-psychotic effects if $D_2$ occupancy is less than any one of 65%, 60%, 55%, and 50%. In a further variation, dosage is reduced to achieve pro-cognitive and not anti-psychotic effects if $D_2$ occupancy is at least 65%. In yet another variation, dosage is reduced to achieve pro-cognitive and not anti-psychotic effects if $D_2$ occupancy is at greater than any one of 65%, 70%, 75%, 80% and 90%. In a further variation, dosage is reduced to achieve pro-cognitive and no significant anti-psychotic effects if $D_2$ occupancy is greater than 65%. One indication of at least 65% D2 occupancy or greater than any one of 65%, 70%, 75%, 80% and 90% D2 occupancy is the reduction in the number or severity of one or more symptoms associated with a psychotic disorder.

In another aspect, a suitable dose is determined by assessing pro-cognitive and/or anti-psychotic effects in an individual and adjusting an individual's dosage in response thereto. For example, in one variation, an individual's dosage is increased from a first dosage to a higher, second dosage, in order to achieve anti-psychotic effects at the second dosage level, if it is determined that the first dosage does not induce anti-psychotic effects in the individual, as may be assessed by suitable test and/or scales known in the art. In another variation, dosage is reduced from a first dosage to a lower, second dosage wherein the second dosage still achieves anti-psychotic effects but reduces side effects as compared to the first dosage. Side effects may be determined by suitable tests and/or scales known in the art. In another variation, dosage is decreased from a first dosage to a lower, second dosage, in order to achieve pro-cognitive and not anti-psychotic effects. In another variation, dosage is decreased from a first dosage to a lower, second dosage, in order to achieve pro-cognitive and not anti-psychotic effects and wherein the dosage induces fewer or lesser side effects than the first dosage. Thus, in yet another variation, dosage is reduced to a minimum dosage which still achieves pro-cognitive effects but reduces side-effects as determined by suitable tests and/or scales.

In one aspect, an individual's therapy is monitored as set forth above for a period of time, such as one week, two weeks, three weeks, one month, two months, three months, four months, five months, 6 months or more (such as throughout the course of an individual's therapy), to adjust an individual's dosage level as needed. As such, individualized therapy as detailed herein provides for methods of measuring therapeutic parameters and adjusting dosage in response thereto in order to achieve an optimal dosage amount according to an individual's initial and continued response to therapy.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to formula (I), (II), (III), (IV), (V), (VI), (VII) or (VIII) or a variation thereof unless otherwise indicated.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

The following abbreviations are used herein: thin layer chromatography (TLC); hour (h); minute (min.); second (sec.); ethanol (EtOH); dimethylsulfoxide (DMSO); N,N-dimethylformamide (DMF); trifluoroacetic acid (TFA); tetrahydrofuran (THF); EtOAc (EtOAc); Normal (N); aqueous (aq.); methanol (MeOH); dichloromethane (DCM); RT (RT); Retention factor (Rf).

A method of synthesizing carboline intermediates used in the synthesis of compounds of the invention is shown as General Method 1. Although identifiers such as $R^4$ and $R^1$ are shown in the method below, it is understood that these moieties apply to the compounds detailed herein even if different identifiers or variations thereof are used elsewhere (e.g., it is understood that compounds may include more than one $R^4$).

General Method 1.

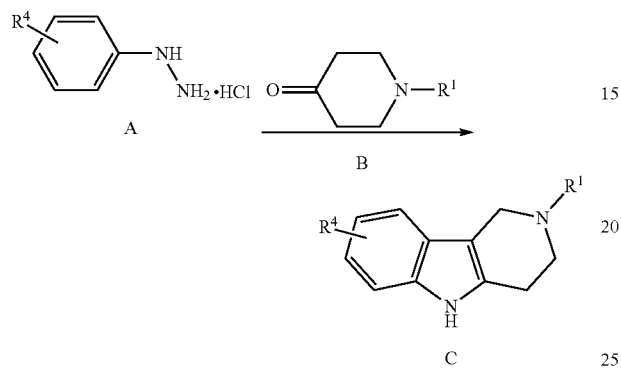

Compound A (1 equiv.) and compound B (0.76-1.4 equiv.) are mixed in a suitable solvent such as EtOH and heated at 80° C. for 16 h (overnight) after which the solvent is removed in vacuo. The remaining residue is basified, e.g., with saturated aq. NaHCO$_3$. The aqueous layer is extracted with DCM and the combined organic layers are dried over sodium sulfate, concentrated in vacuo, and purified, e.g., by silica gel chromatography (230-400 mesh) using a suitable solvent gradient such as either a MeOH-DCM gradient or an EtOAc-hexane gradient.

Representative carboline compounds prepared according to General Method 1 are shown in Table 1.

TABLE 1

Representative Carboline Compounds

| Compound No. | Structure |
|---|---|
| 1 | 6-Cl, 2-CH$_3$ tetrahydro-β-carboline |
| 2 | 7-isopropyl, 2-CH$_3$ tetrahydro-β-carboline |
| 3 | 7-CH$_3$, 2-CH$_3$ tetrahydro-β-carboline |
| 4 | 7-Cl, 8-F, 2-CH$_3$ tetrahydro-β-carboline |
| 5 | 2-CH$_3$ tetrahydro-β-carboline |
| 6 | 6-Cl, 7-F, 2-CH$_3$ tetrahydro-β-carboline |
| 7 | 2-ethyl tetrahydro-β-carboline |
| 8 | 7-CO$_2$CH$_3$, 2-CH$_3$ tetrahydro-β-carboline |
| 9 | 7-CH$_3$, 2-ethyl tetrahydro-β-carboline |
| 10 | 7-OCF$_3$, 2-CH$_3$ tetrahydro-β-carboline |
| 11 | 6-Cl, 8-Cl, 2-CH$_3$ tetrahydro-β-carboline |

TABLE 1-continued

Representative Carboline Compounds

| Compound No. | Structure |
|---|---|
| 12 | 1,8-dimethyl-2,3,4,5-tetrahydro-1H-pyrido[4,3-b]indole |
| 13 | 6-chloro-9-fluoro-2-methyl-2,3,4,5-tetrahydro-1H-pyrido[4,3-b]indole |
| 14 | 7-tert-butyl-2-methyl-2,3,4,5-tetrahydro-1H-pyrido[4,3-b]indole |
| 15 | 7-ethyl-2-methyl-2,3,4,5-tetrahydro-1H-pyrido[4,3-b]indole |
| 16 | 7-iodo-2-methyl-2,3,4,5-tetrahydro-1H-pyrido[4,3-b]indole |
| 17 | 7-chloro-2-cyclopropyl-2,3,4,5-tetrahydro-1H-pyrido[4,3-b]indole |
| 18 | 8-fluoro-2-methyl-2,3,4,5-tetrahydro-1H-pyrido[4,3-b]indole |

A method of synthesizing epoxide intermediates used in the synthesis of compounds of the invention is shown as General Method 2. Although identifiers such as R⁹ and R are shown in the method below, it is understood that these moieties apply to the compounds detailed herein even if different identifiers or variations thereof are used elsewhere. It is also understood that modifications to the specific materials shown are intended, e.g., where Compound L can be a heteroaryl group such as pyridyl.

General Method 2.

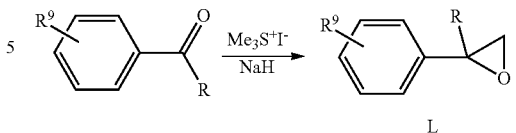

DMSO is added to NaH 60% dispersion in oil (1-1.8 equiv.) and heated to 65° C. for 1 h. THF (10 mL) is added to the solution at 65° C. and heating is continued for another 10 min. The reaction mixture is then cooled to 0° C. and Trimethylsulfonium iodide (1-1.2 equiv.) is added. The reaction mixture is stirred for another 10 min. after which appropriate aldehyde/ketone (1 equiv.) is added as a solution in THF. The reaction mixture is further stirred at RT until the reaction is complete (monitored by TLC and LCMS). The reaction mixture is then poured in ice water and the product is extracted in organic solvent (ether or EtOAc), dried over sodium sulfate and concentrated at 25° C. to obtain the product.

Representative oxirane compounds prepared according to General Method 2 are shown in Table 2.

TABLE 2

Representative Oxirane Compounds

| Compound No. | Structure |
|---|---|
| 19 | 2-methyl-5-(oxiran-2-yl)pyridine |
| 20 | 2-(4-chloro-3-fluorophenyl)-2-methyloxirane |
| 21 | 2-(4-fluorophenyl)-2-methyloxirane |
| 22 | 2-(4-chlorophenyl)-2-methyloxirane |
| 23 | 2-(p-tolyl)oxirane |
| 24 | 2-(4-fluorophenyl)-2,3-dimethyloxirane |
| 25 | 3-(oxiran-2-yl)pyridine |
| 26 | 2-(4-methoxyphenyl)-2-methyloxirane |

TABLE 2-continued

Representative Oxirane Compounds

| Compound No. | Structure |
|---|---|
| 27 | 2,6-difluoro-4-fluoro-phenyl with methyl-oxirane |
| 28 | 4-fluoro-phenyl with CF3 and methyl-oxirane |
| 29 | 2,4-dichloro-phenyl with methyl-oxirane |
| 30 | 6-(trifluoromethyl)pyridin-3-yl with methyl-oxirane |
| 31 | 2,4-difluoro-phenyl with methyl-oxirane |
| 32 | 6-fluoropyridin-3-yl with oxirane |
| 33 | 3,4-dichloro-phenyl with methyl-oxirane |
| 34 | 4-fluoro-phenyl with cyclopropyl-oxirane |
| 35 | 3,4-difluoro-phenyl with methyl-oxirane |
| 36 | 4-fluoro-phenyl with ethyl-oxirane |
| 37 | 3-chloro-4-fluoro-phenyl with methyl-oxirane |
| 38 | phenyl with methyl-oxirane |
| 39 | 3-fluoro-4-methoxy-phenyl with methyl-oxirane |
| 40 | 6-methylpyridin-3-yl with methyl-oxirane |
| 41 | 3-fluoro-4-methoxy-phenyl with oxirane |
| 42 | 2-methylpyrimidin-5-yl with methyl-oxirane |
| 167 | pyridin-4-yl with isopropyl-oxirane |
| 168 | pyridin-4-yl with ethyl-oxirane |
| 169 | pyridin-4-yl with methyl-oxirane |
| 170 | pyrimidin-4-yl with methyl-oxirane |

A general method of synthesizing alcohol intermediates by epoxide ring opening using a carboline is shown as General Method 3. Although identifiers such as $R^2$, $R^3$, etc. are shown in the method below, it is understood that these moieties apply to the compounds detailed herein even if different identifiers or variations thereof are used elsewhere. For example, although compound C in the method below lists substituent identifier $R^2$, it is understood that compound C is the same as that obtained from General Method 1 which utilizes identifier $R^4$. It is also understood that modifications to the specific materials shown are intended, e.g., where Compound L can be a heteroaryl group such as pyridyl.

General Method 3.

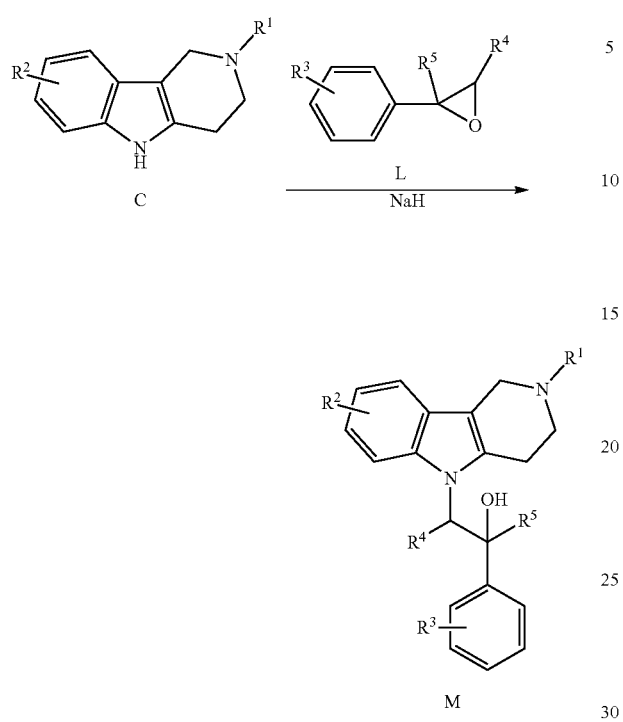

Compound C (1 equiv.), compound L (2-7.5 equiv.) and NaH (1-3 equiv.) are heated in DMF at 120° C. for 16 h. The contents are quenched by MeOH and evaporated to dryness. The resulting crude product is purified by silica gel chromatography (230-400 mesh) using MeOH-DCM gradient followed by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL).

Representative pyrido[4,3b]indo-5-yl alcohol compounds prepared according to General Method 3 are shown in Table 3.

TABLE 3

Representative Pyrido[4,3b]indo-5-yl Alcohol Compounds

| Compound No. | Structure |
|---|---|
| 43 | (structure) |
| 44 | (structure) |
| 45 | (structure) |
| 46 | (structure) |
| 47 | (structure) |

TABLE 3-continued

Representative Pyrido[4,3b]indo-5-yl Alcohol Compounds

| Compound No. | Structure |
|---|---|
| 48 | (structure) |
| 49 | (structure) |
| 50 | (structure) |
| 51 | (structure) |
| 52 | (structure) |
| 53 | (structure) |
| 54 | (structure) |
| 55 | (structure) |

TABLE 3-continued

Representative Pyrido[4,3b]indo-5-yl Alcohol Compounds

| Compound No. | Structure |
|---|---|
| 56 | 7-Cl, 2-CH₃ pyrido[4,3-b]indole, N-CH₂-CH(OH)-(pyridin-3-yl) |
| 57 | 7-Cl, 2-CH₃ pyrido[4,3-b]indole, N-CH₂-C(CH₃)(OH)-(4-methoxyphenyl) |
| 58 | 7-Cl, 2-CH₃ pyrido[4,3-b]indole, N-CH₂-C(CH₃)(OH)-(4-trifluoromethylphenyl) |
| 59 | 7-Cl, 2-CH₃ pyrido[4,3-b]indole, N-CH₂-C(CH₃)(OH)-(3-fluoro-4-methoxyphenyl) |
| 60 | 8-CH₃, 2-CH₃ pyrido[4,3-b]indole, N-CH₂-C(CH₃)(OH)-(pyridin-3-yl) |
| 61 | 8-Cl, 2-CH₃ pyrido[4,3-b]indole, N-CH₂-C(CH₃)(OH)-(pyridin-3-yl) |
| 62 | 8-CH₃, 2-CH₃ pyrido[4,3-b]indole, N-CH₂-C(CH₃)(OH)-(pyridin-4-yl) |
| 63 | 8-Cl, 2-CH₃ pyrido[4,3-b]indole, N-CH₂-C(CH₃)(OH)-(pyridin-4-yl) |

TABLE 3-continued

Representative Pyrido[4,3b]indo-5-yl Alcohol Compounds

| Compound No. | Structure |
|---|---|
| 64 | 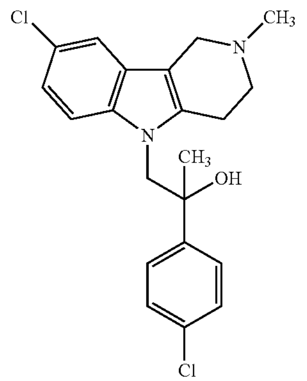 [SMILES: CN1CCc2c(c3cc(Cl)ccc3n2CC(C)(O)c2ccc(F)cc2)C1] |
| 65 | 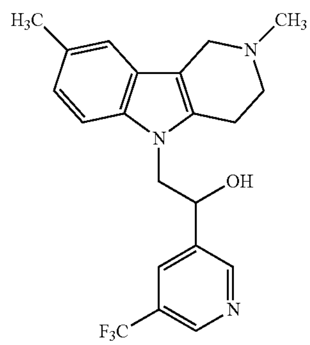 |
| 66 | 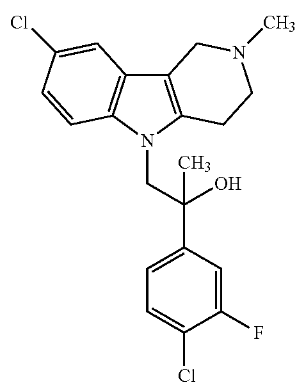 |
| 67 | 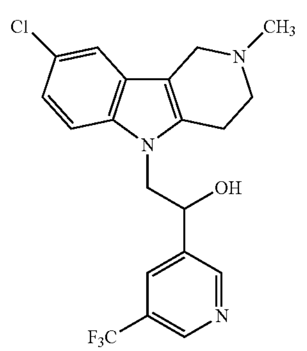 [SMILES: CN1CCc2c(c3cc(Cl)ccc3n2CC(O)c2cncc(C(F)(F)F)c2)C1] |
| 68 | |
| 69 | |
| 70 | |

TABLE 3-continued
Representative Pyrido[4,3b]indo-5-yl Alcohol Compounds
| Compound No. | Structure |
|---|---|
| 71 | 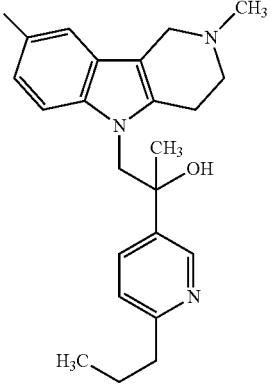 |
| 72 | 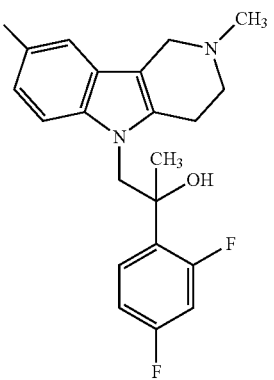 |
| 73 | 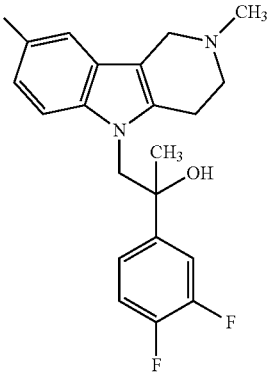 |
| 74 | 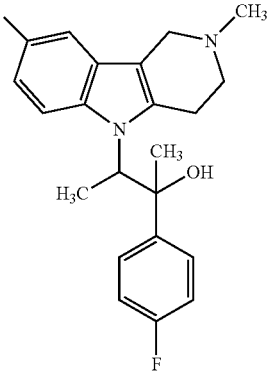 |
| 75 | 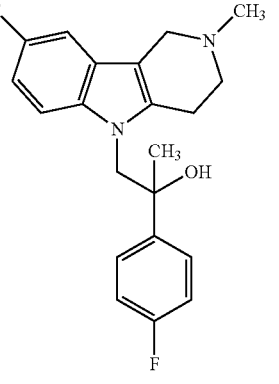 |
| 76 | 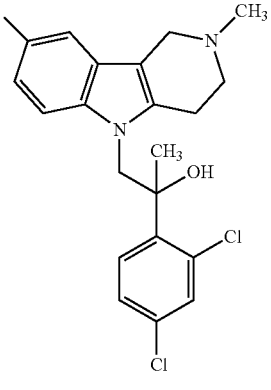 |
| 77 | 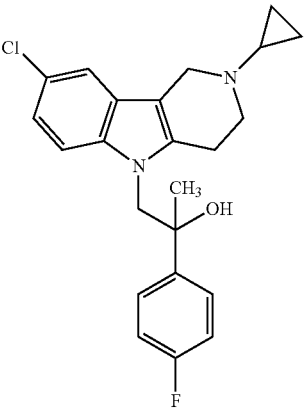 [SMILES: CC(O)(Cn1c2c(c3cc(Cl)ccc31)CN(C1CC1)CC2)c1ccc(F)cc1] |
| 78 | 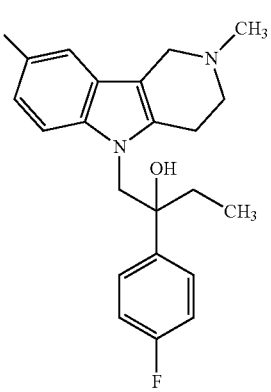 |

TABLE 3-continued

Representative Pyrido[4,3b]indo-5-yl Alcohol Compounds

| Compound No. | Structure |
|---|---|
| 79 | (structure) |
| 80 | (structure) |
| 81 | (structure) |
| 82 | (structure) |
| 171 | (structure) |
| 172 | (structure) |
| 173 | (structure) |
| 174 | (structure) |

TABLE 3-continued

Representative Pyrido[4,3b]indo-5-yl Alcohol Compounds

| Compound No. | Structure |
|---|---|
| 175 | [structure] |
| 176 | [structure] |
| 177 | [structure] |
| 178 | [structure] |
| 180 | [structure] |
| 181 | [structure] |
| 182 | [structure] |
| 183 | [structure] |

TABLE 3-continued

Representative Pyrido[4,3b]indo-5-yl Alcohol Compounds

| Compound No. | Structure |
|---|---|
| 184 | 7-chloro-2-methyl-5-(2-hydroxy-2-(pyridin-4-yl)propyl)-2,3,4,5-tetrahydro-1H-pyrido[4,3-b]indole |
| 185 | 6-fluoro-2-methyl-5-(2-hydroxy-2-(pyridin-4-yl)propyl)-2,3,4,5-tetrahydro-1H-pyrido[4,3-b]indole |
| 186 | 2-methyl-5-(2-hydroxy-2-(pyridin-4-yl)propyl)-2,3,4,5-tetrahydro-1H-pyrido[4,3-b]indole |
| 187 | 8-methyl-2-methyl-5-(2-hydroxy-2-(4-hydroxyphenyl)propyl)-2,3,4,5-tetrahydro-1H-pyrido[4,3-b]indole |
| 188 | 8-methoxy-2-methyl-5-(2-hydroxy-2-(pyridin-4-yl)propyl)-2,3,4,5-tetrahydro-1H-pyrido[4,3-b]indole |
| 189 | 7,8-dichloro-2-methyl-5-(2-hydroxy-2-(pyridin-4-yl)propyl)-2,3,4,5-tetrahydro-1H-pyrido[4,3-b]indole |
| 190 | 8,9-dichloro-2-methyl-5-(2-hydroxy-2-(pyridin-4-yl)propyl)-2,3,4,5-tetrahydro-1H-pyrido[4,3-b]indole |
| 191 | 8-methyl-2-methyl-5-(2-hydroxy-2-(4-methoxyphenyl)propyl)-2,3,4,5-tetrahydro-1H-pyrido[4,3-b]indole |

TABLE 3-continued

Representative Pyrido[4,3b]indo-5-yl Alcohol Compounds

| Compound No. | Structure |
|---|---|
| 192 | (structure) |
| 193 | (structure) |
| 194 | (structure) |
| 195 | (structure) |
| 196 | (structure) |
| 197 | (structure) |
| 198 | (structure) |
| 199 | (structure) |

TABLE 3-continued

Representative Pyrido[4,3b]indo-5-yl Alcohol Compounds

| Compound No. | Structure |
|---|---|
| 200 | 8-methyl, 2-methyl pyrido[4,3-b]indole with N-CH2-C(OH)(CH3)-pyrazin-2-yl substituent |
| 341 | 8-methyl, 2-(2,2,2-trifluoroethyl) pyrido[4,3-b]indole with N-CH2-C(OH)(CH3)-pyridin-4-yl substituent |
| 342 | 8-methyl, 2-cyclopropyl pyrido[4,3-b]indole with N-CH2-C(OH)(CH3)-pyridin-4-yl substituent |
| 343 | 6-methoxy, 2-methyl pyrido[4,3-b]indole with N-CH2-C(OH)(CH3)-pyridin-4-yl substituent |
| 344 | 8-isopropyl, 2-methyl pyrido[4,3-b]indole with N-CH2-C(OH)(CH3)-pyridin-4-yl substituent |
| 345 | 8-methyl, 2,3-dimethyl pyrido[4,3-b]indole with N-CH2-C(OH)(CH3)-pyridin-4-yl substituent |
| 464 | 8-chloro pyrido[4,3-b]indole with 2-N-(CH2)3-C(O)-(4-fluorophenyl) and 5-N-CH2-C(OH)(CH3)-pyridin-4-yl substituents |
| 465 | 8-methyl, 2-methyl pyrido[4,3-b]indole with N-CH2-C(OH)(phenyl)2 substituent |

TABLE 3-continued

Representative Pyrido[4,3b]indo-5-yl Alcohol Compounds

| Compound No. | Structure |
|---|---|
| 466 | 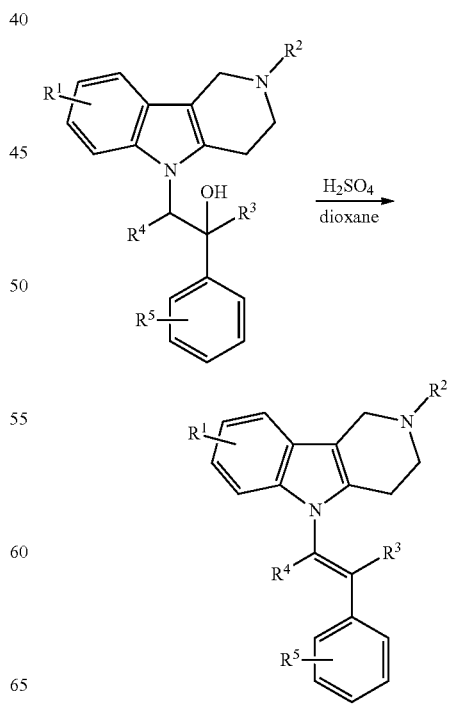 |
| 467 | 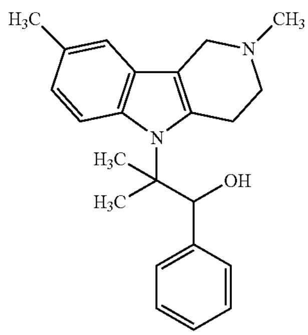 |
| 468 | 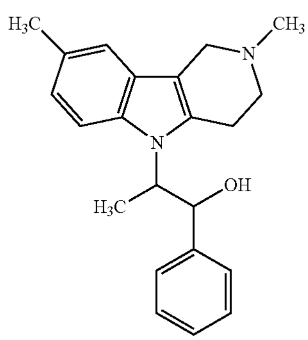 |
| 469 | 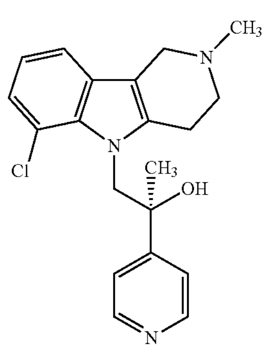 [SMILES: CN1CCc2c(c3cccc(Cl)c3n2C[C@@](C)(O)c2ccncc2)C1] |
| 470 | |

A method of synthesizing certain compounds by dehydration of alcohol intermediates is shown as General Method 4. Although identifiers such as $R^2$, $R^3$, etc. are shown in the method below, it is understood that these moieties apply to the compounds detailed herein even if different identifiers or variations thereof are used elsewhere. It is also understood that modifications to the specific materials shown are intended.

General Method 4.

-continued

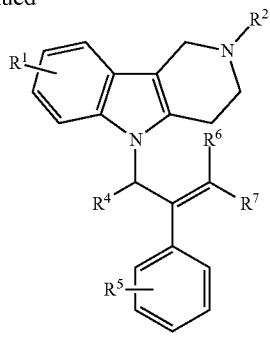

Indol-5-yl alcohol derivative (1 equiv.) is refluxed with 25% sulfuric acid until the reaction is complete. The reaction mixture is then cooled to 5° C. and basified with KOH to pH 9-10. The product is extracted in EtOAc, extracts are washed with 10 mL of water followed by brine, dried over sodium sulfate and evaporated under vacuum to obtain the crude product that is purified by silica gel chromatography and/or HPLC.

Certain compounds detailed herein are synthesized according to General Method 5.

General Method 5.

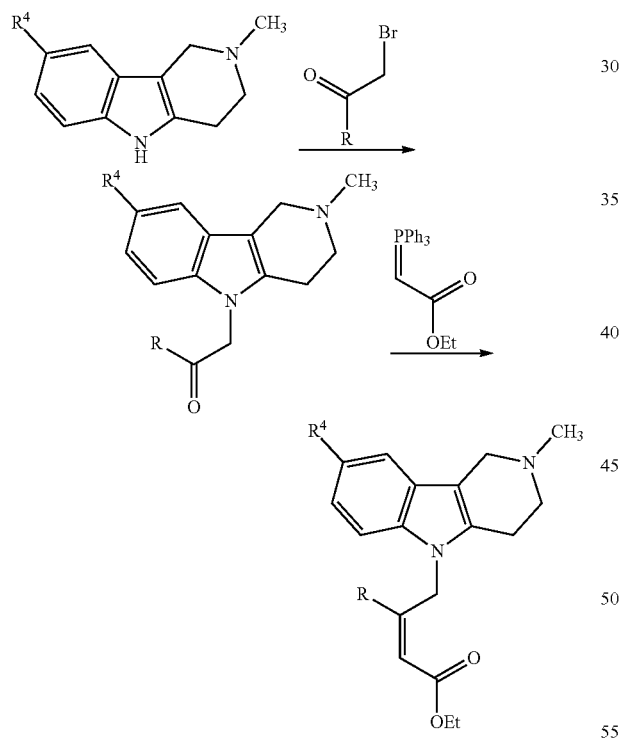

To a solution of appropriate 2,3,4,5-tetrahydro-1H-pyrido[4,3-b]indole (1 equiv.) in N-methyl-2-pyrrolidone is added KOH (7 equiv.). The reaction mixture is stirred at RT for 20 min. A solution of appropriate 2-bromoethanone (1 equiv.) in N-methyl-2-pyrrolidone is added dropwise and stirring is continued for additional 2-4 h. The reaction is monitored by LCMS and TLC. The reaction mixture is diluted by adding water and extracted with EtOAc. The organic layer is washed with water, dried over anhydrous sodium sulfate and concentrated under reduced pressure. The residue is purified by silica gel chromatography.

Appropriate 2-(3,4-dihydro-1H-pyrido[4,3-b]indol-5(2H)-yl)ethanone (100 mg, 3 mmol) is dissolved in toluene and (carbethoxymethylene)triphenylphosphorane (200 mg, 0.56 mmol) is added. The reaction mixture is heated overnight at 100° C. Solvent is removed under reduced pressure and the residue is purified by silica gel chromatography.

Representative compounds prepared according to the General Methods described herein are shown in Table 4. Isomeric compounds obtained by the Methods are shown in Table 5.

TABLE 4

Representative Compounds Containing Rigid Linkers

| Compound No. | Structure |
|---|---|
| 83 | ![structure with Cl, CH3, H3C, F substituents on pyrido-indole core] |
| 84 | ![structure with Cl, CH3, H3C, CF3, pyridine] |
| 85 | ![structure with H3C, CH3, H3C, pyridine, CH3] |

TABLE 4-continued
Representative Compounds Containing Rigid Linkers
| Compound No. | Structure |
|---|---|
| 86 | 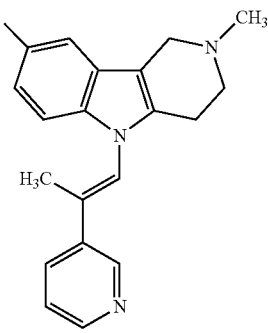 |
| 87 | 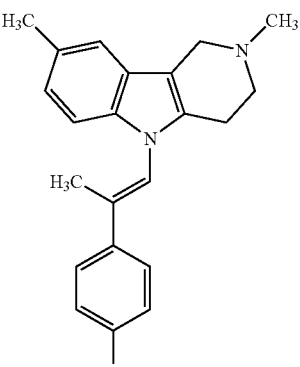 |
| 88 | 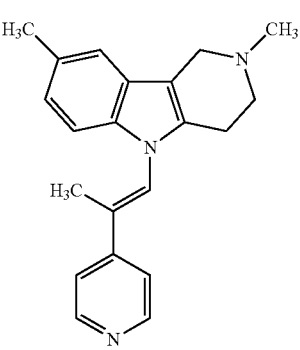 |
| 89 | 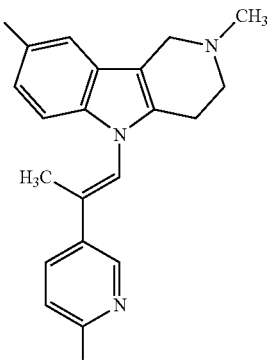 |
| 90 | 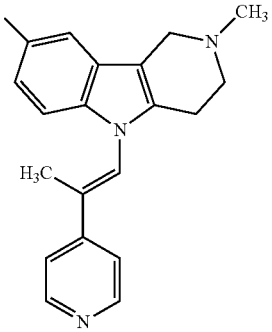 |
| 91 | 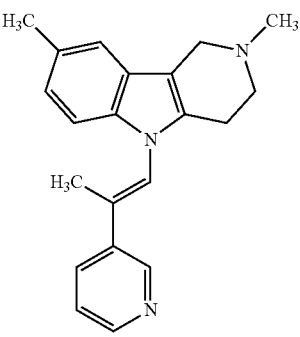 |
| 92 | 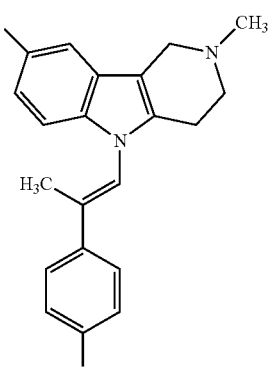 |
| 93 | 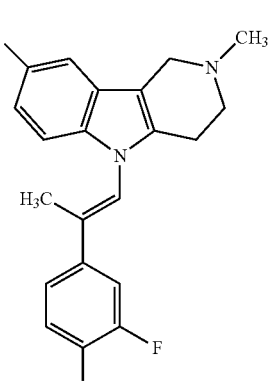 |

TABLE 4-continued

Representative Compounds Containing Rigid Linkers

| Compound No. | Structure |
|---|---|
| 94 | [structure] |
| 95 | [structure] |
| 96 | [structure] |
| 97 | [structure] |
| 98 | [structure] |
| 99 | [structure] |
| 100 | [structure] |
| 101 | [structure] |

TABLE 4-continued
Representative Compounds Containing Rigid Linkers
| Compound No. | Structure |
|---|---|
| 102 | 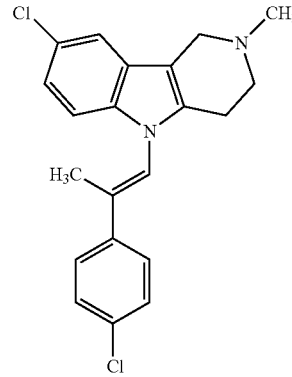 |
| 103 | 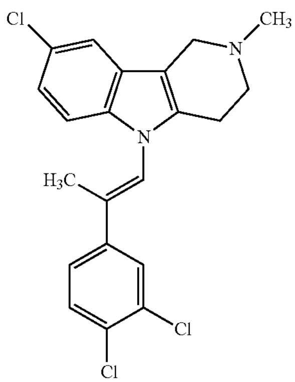 [SMILES: C/C(=C\n1c2c(c3cc(Cl)ccc31)CN(C)CC2)c1ccc(Cl)c(Cl)c1] |
| 104 | 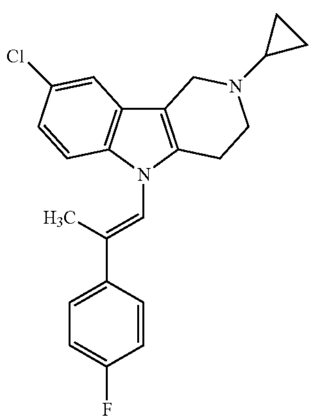 [SMILES: C/C(=C\n1c2c(c3cc(Cl)ccc31)CN(C1CC1)CC2)c1ccc(F)cc1] |
| 105 | 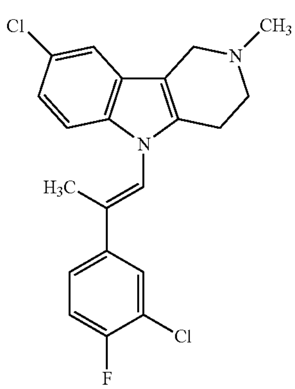 [SMILES: C/C(=C\n1c2c(c3cc(Cl)ccc31)CN(C)CC2)c1ccc(F)c(Cl)c1] |
| 106 | 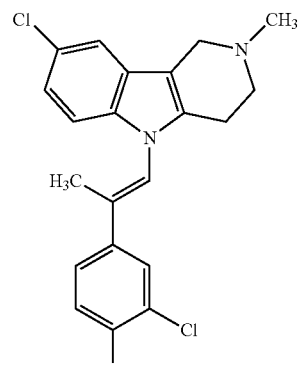 |
| 107 | |
| 108 | |
| 109 | |

TABLE 4-continued
Representative Compounds Containing Rigid Linkers
| Compound No. | Structure |
|---|---|
| 110 | 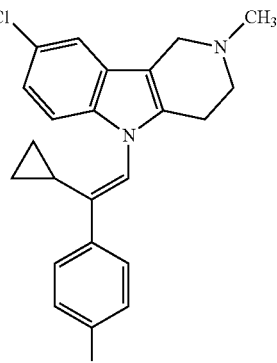 |
| 111 | 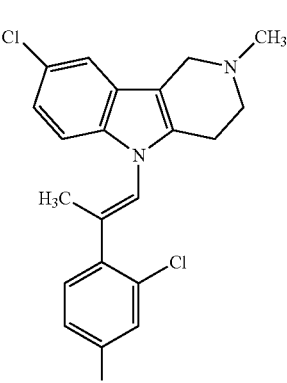 |
| 112 | 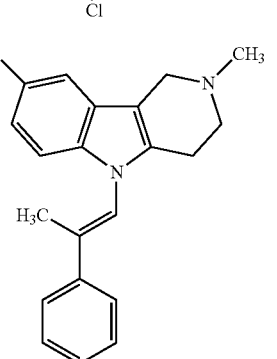 |
| 113 | 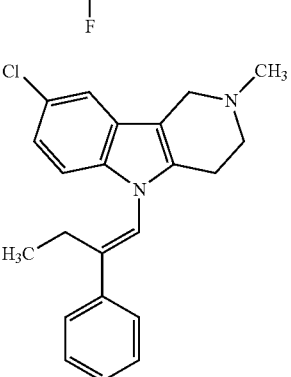 |
| 114 | 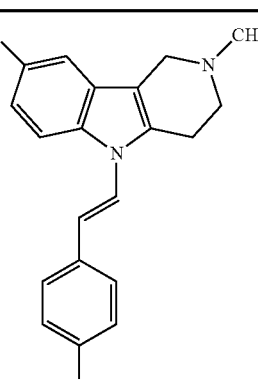 |
| 115 | 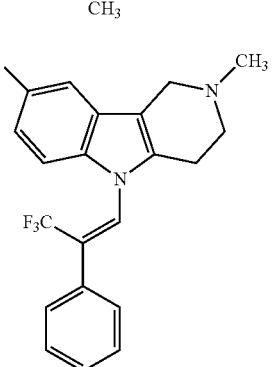 |
| 116 | 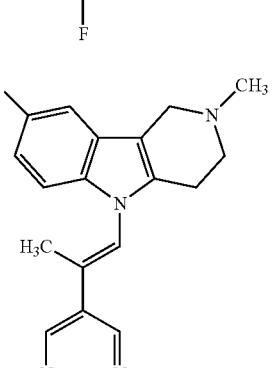 |
| 117 | 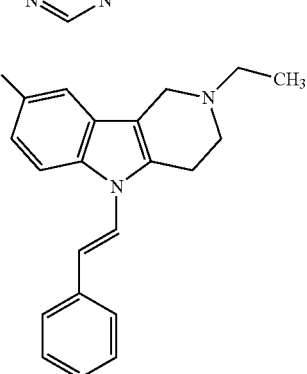 |

TABLE 4-continued

Representative Compounds Containing Rigid Linkers

| Compound No. | Structure |
|---|---|
| 118 | (structure) |
| 119 | (structure) |
| 120 | (structure) |
| 121 | (structure) |
| 122 | (structure) |
| 123 | (structure) |
| 125 | (structure) |
| 126 | (structure) |
| 127 | (structure) |

TABLE 4-continued
Representative Compounds Containing Rigid Linkers
| Compound No. | Structure |
|---|---|
| 202 | 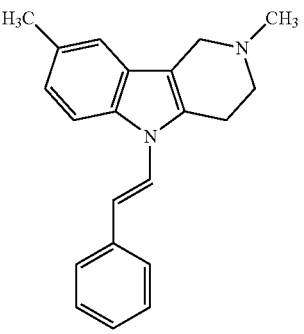 |
| 203 | 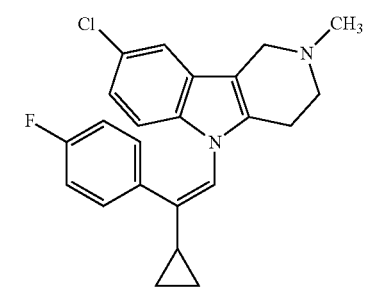 [SMILES: CN1CCc2c(c3cc(Cl)ccc3n2/C=C(\c2ccc(F)cc2)C2CC2)C1] |
| 204 | 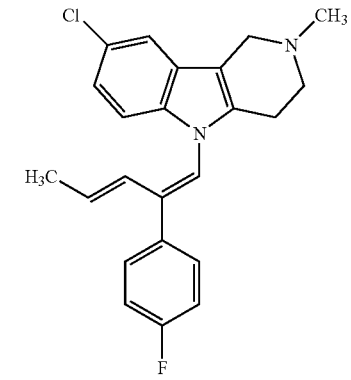 [SMILES: C/C=C/C(=C\n1c2c(c3cc(Cl)ccc31)CN(C)CC2)c1ccc(F)cc1] |
| 205 | 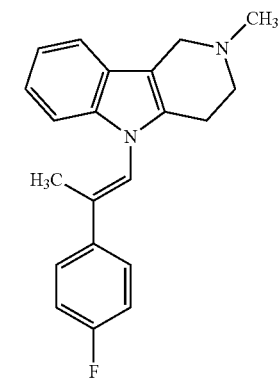 [SMILES: C/C(=C\n1c2c(c3ccccc31)CN(C)CC2)c1ccc(F)cc1] |
| 206 | 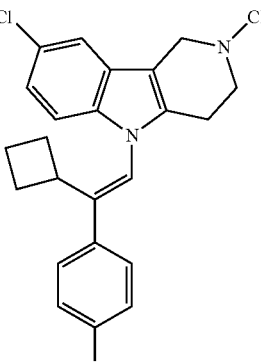 |
| 207 | 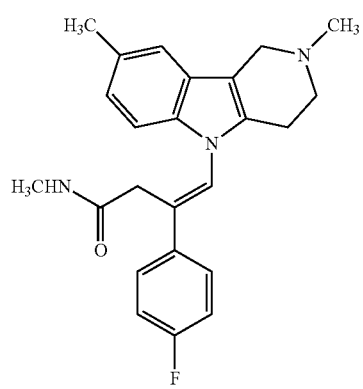 |
| 208 | 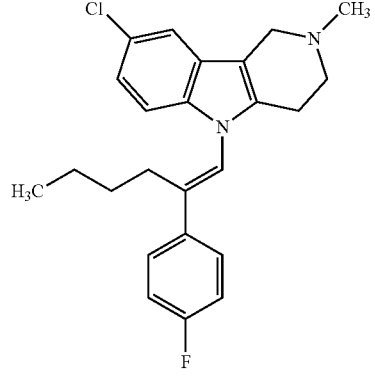 [SMILES: CCCC/C(=C\n1c2c(c3cc(Cl)ccc31)CN(C)CC2)c1ccc(F)cc1] |
| 209 | 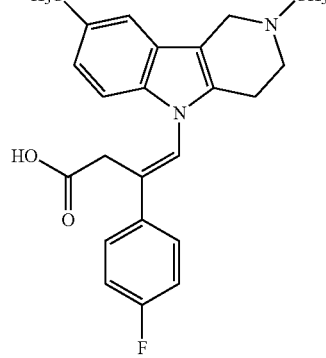 |

TABLE 4-continued

Representative Compounds Containing Rigid Linkers

| Compound No. | Structure |
|---|---|
| 210 | (structure) |
| 211 | (structure) |
| 212 | (structure) |
| 213 | (structure) |
| 214 | (structure) |
| 215 | (structure) |
| 216 | (structure) |
| 217 | (structure) |

TABLE 4-continued

Representative Compounds Containing Rigid Linkers

| Compound No. | Structure |
|---|---|
| 218 | 8-methyl-5-[2-(3,5-dichlorophenyl)prop-1-enyl]-2-methyl-2,3,4,5-tetrahydro-1H-pyrido[4,3-b]indole |
| 219 | 7-chloro-5-[2-(pyridin-4-yl)prop-1-enyl]-2-methyl-2,3,4,5-tetrahydro-1H-pyrido[4,3-b]indole |
| 220 | 8-methyl-5-[2-(2-chloro-4,5-difluorophenyl)prop-1-enyl]-2-methyl-2,3,4,5-tetrahydro-1H-pyrido[4,3-b]indole |
| 221 | 8-methyl-5-[2-(2-chloro-4,5-difluorophenyl)prop-1-enyl]-2-methyl-2,3,4,5-tetrahydro-1H-pyrido[4,3-b]indole |
| 222 | 6-chloro-5-[2-(pyridin-4-yl)prop-1-enyl]-2-methyl-2,3,4,5-tetrahydro-1H-pyrido[4,3-b]indole |
| 223 | 6-fluoro-5-[2-(pyridin-4-yl)prop-1-enyl]-2-methyl-2,3,4,5-tetrahydro-1H-pyrido[4,3-b]indole |
| 224 | 8-methyl-5-[2-(pyridin-4-yl)prop-1-enyl]-2-methyl-2,3,4,5-tetrahydro-1H-pyrido[4,3-b]indole |
| 225 | 8-methyl-5-[2-(3-fluorophenyl)prop-1-enyl]-2-methyl-2,3,4,5-tetrahydro-1H-pyrido[4,3-b]indole |
| 226 | 8-methyl-5-[2-(3-fluorophenyl)prop-1-enyl]-2-methyl-2,3,4,5-tetrahydro-1H-pyrido[4,3-b]indole |

TABLE 4-continued

Representative Compounds Containing Rigid Linkers

| Compound No. | Structure |
|---|---|
| 227 | [structure: 7-fluoro-2-methyl-tetrahydro-β-carboline N-substituted with (E)-2-(4-fluorophenyl)prop-1-enyl] |
| 228 | [structure: 7-chloro-2-methyl-tetrahydro-β-carboline N-substituted with (E)-2-(4-fluorophenyl)prop-1-enyl] |
| 229 | [structure: 7-trifluoromethyl-2-methyl-tetrahydro-β-carboline N-substituted with (E)-2-(4-fluorophenyl)prop-1-enyl] |
| 230 | [structure: 7-methyl-2-methyl-tetrahydro-β-carboline N-substituted with (E)-2-(3,4-difluorophenyl)prop-1-enyl] |
| 231 | [structure: 8-methyl-2-methyl-tetrahydro-pyrido-indole N-substituted with (E)-2-(3,4-dichlorophenyl)prop-1-enyl] |
| 232 | [structure: 8,9-dichloro-2-methyl-tetrahydro-pyrido-indole N-substituted with (E)-2-(4-fluorophenyl)prop-1-enyl] |
| 233 | [structure: 8-chloro-2-methyl-tetrahydro-pyrido-indole N-substituted with (Z)-2-(3-fluorophenyl)prop-1-enyl] |
| 234 | [structure: 8-chloro-2-methyl-tetrahydro-pyrido-indole N-substituted with (E)-2-(3-fluorophenyl)prop-1-enyl] |

TABLE 4-continued

Representative Compounds Containing Rigid Linkers

| Compound No. | Structure |
|---|---|
| 235 | (structure) |
| 236 | (structure) |
| 237 | (structure) |
| 238 | (structure) |
| 239 | (structure) |
| 240 | (structure) |
| 241 | (structure) |
| 242 | (structure) |
| 243 | (structure) |

TABLE 4-continued

Representative Compounds Containing Rigid Linkers

| Compound No. | Structure |
|---|---|
| 244 | (structure) |
| 245 | (structure) |
| 246 | (structure) |
| 247 | (structure) |
| 248 | (structure) |
| 249 | (structure) |
| 250 | (structure) |
| 251 | (structure) |

TABLE 4-continued

Representative Compounds Containing Rigid Linkers

| Compound No. | Structure |
|---|---|
| 252 | 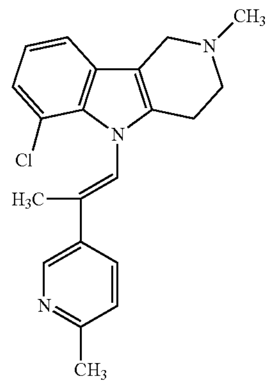 [SMILES: C/C(=C\n1c2c(c3cccc(Cl)c31)CN(C)CC2)c1ccc(C)nc1] |
| 253 | 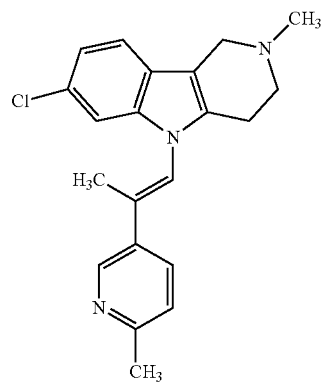 [SMILES: C/C(=C\n1c2c(c3ccc(Cl)cc31)CN(C)CC2)c1ccc(C)nc1] |
| 254 | 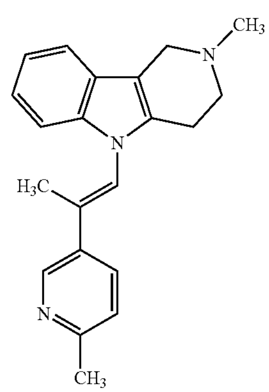 [SMILES: C/C(=C\n1c2c(c3ccccc31)CN(C)CC2)c1ccc(C)nc1] |
| 255 | 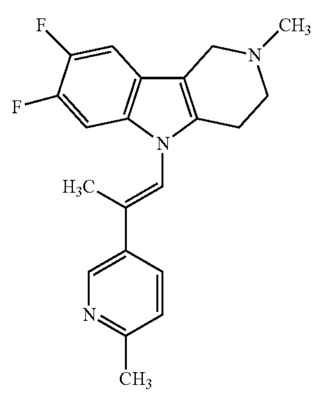 [SMILES: C/C(=C\n1c2c(c3cc(F)c(F)cc31)CN(C)CC2)c1ccc(C)nc1] |
| 256 | |
| 257 | |
| 258 | |
| 259 | |

TABLE 4-continued
Representative Compounds Containing Rigid Linkers
| Compound No. | Structure |
|---|---|
| 260 | 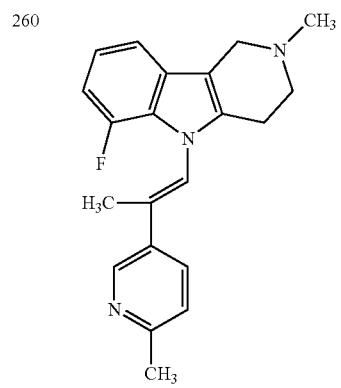 |
| 261 | 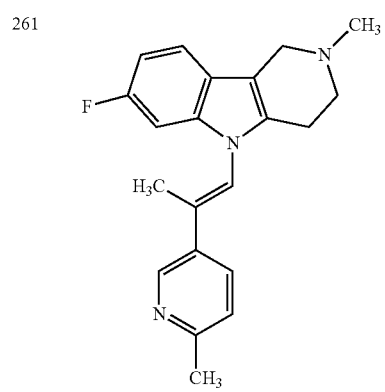 |
| 262 | 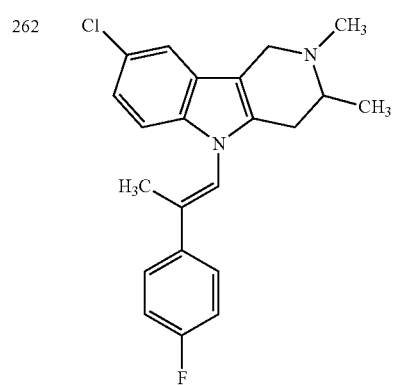 |
| 263 | 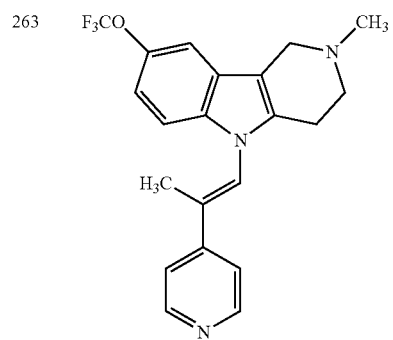 |
| 264 | 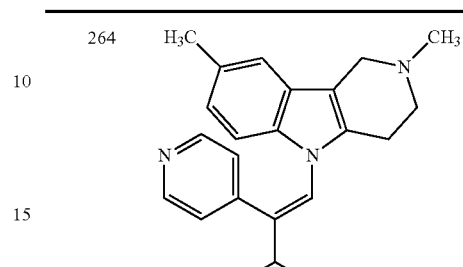 |
| 265 | 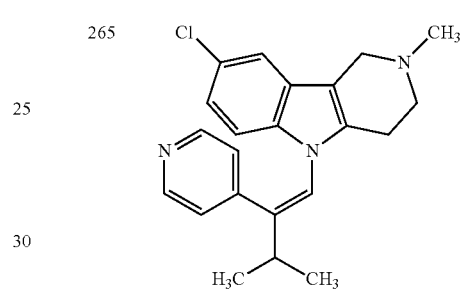 |
| 266 | 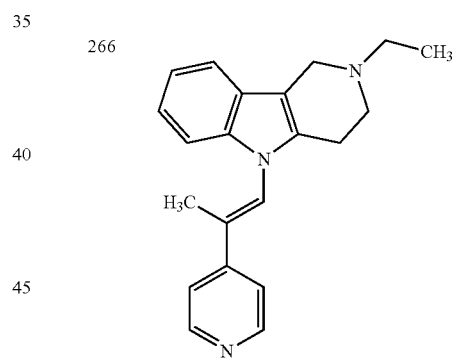 |
| 267 | 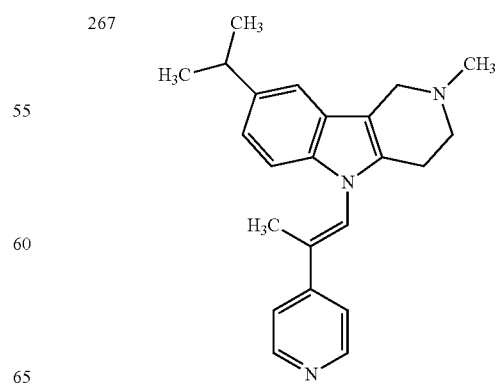 |

TABLE 4-continued

Representative Compounds Containing Rigid Linkers

| Compound No. | Structure |
|---|---|
| 268 | (structure) |
| 269 | (structure) |
| 270 | (structure) |
| 271 | (structure) |
| 272 | (structure) |
| 273 | (structure) |
| 274 | (structure) |
| 275 | (structure) |

TABLE 4-continued

Representative Compounds Containing Rigid Linkers

| Compound No. | Structure |
|---|---|
| 276 | (structure) |
| 277 | (structure) |
| 278 | (structure) |
| 279 | (structure) |
| 280 | (structure) |
| 281 | (structure) |
| 282 | (structure) |
| 283 | (structure) |

TABLE 4-continued

Representative Compounds Containing Rigid Linkers

| Compound No. | Structure |
|---|---|
| 284 | (structure) |
| 285 | (structure) |
| 286 | (structure) |
| 287 | (structure) |
| 288 | (structure) |
| 289 | (structure) |
| 290 | (structure) |
| 291 | (structure) |

TABLE 4-continued

Representative Compounds Containing Rigid Linkers

| Compound No. | Structure |
|---|---|
| 292 | (structure) |
| 293 | (structure) |
| 294 | (structure) |
| 295 | (structure) |
| 296 | (structure) |
| 297 | (structure) |
| 298 | (structure) |
| 299 | (structure) |

TABLE 4-continued
Representative Compounds Containing Rigid Linkers
| Compound No. | Structure |
|---|---|
| 300 | 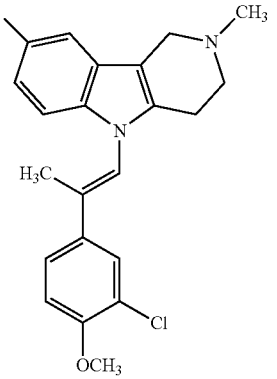 |
| 301 | 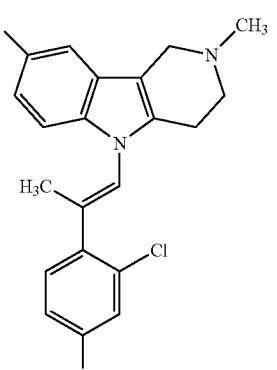 |
| 302 | 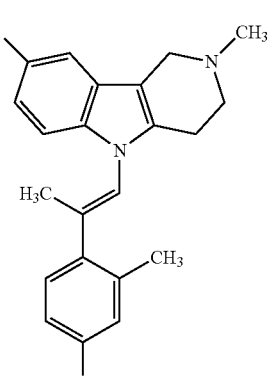 |
| 303 | 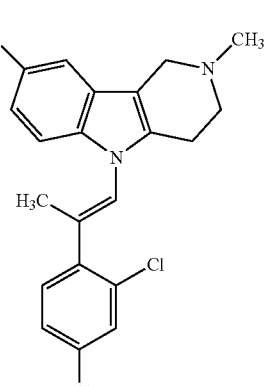 |
| 304 | 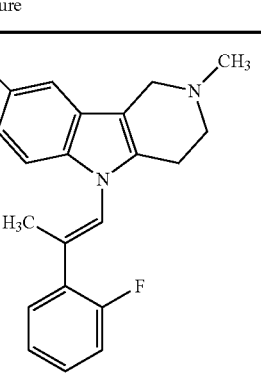 |
| 305 | 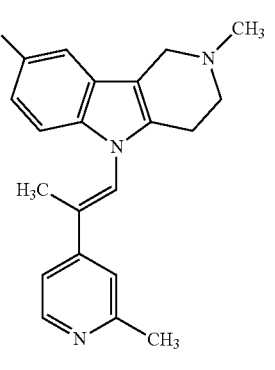 |
| 306 | 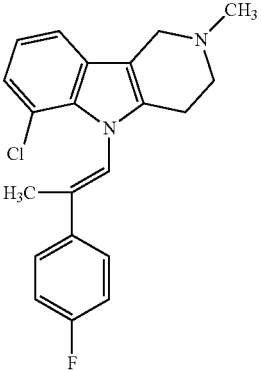 [SMILES: C/C(=C\n1c2c(c3cccc(Cl)c31)CN(C)CC2)c1ccc(F)cc1] |
| 307 | 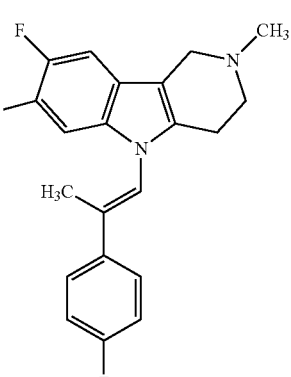 |

TABLE 4-continued

Representative Compounds Containing Rigid Linkers

| Compound No. | Structure |
|---|---|
| 308 | 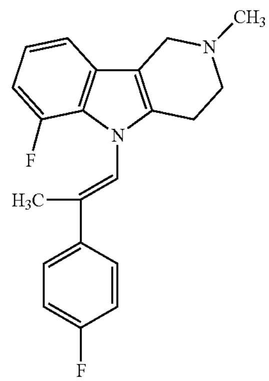 [SMILES: C/C(=C\n1c2c(c3cccc(F)c31)CN(C)CC2)c1ccc(F)cc1] |
| 309 | 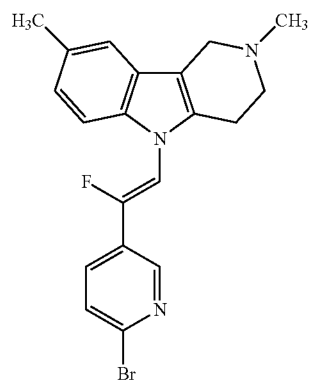 |
| 310 | 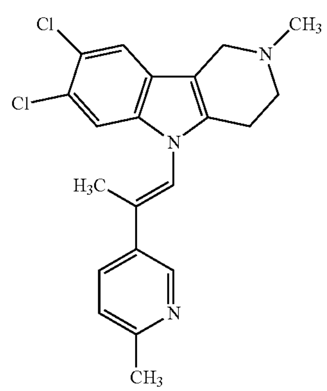 [SMILES: C/C(=C\n1c2c(c3cc(Cl)c(Cl)cc31)CN(C)CC2)c1ccc(C)nc1] |
| 311 | 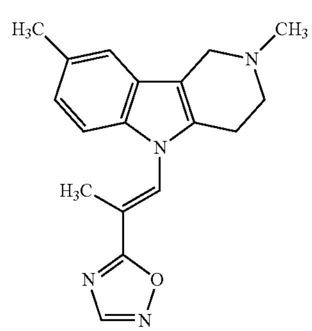 |
| 312 | |
| 313 | |
| 314 | |
| 315 | |

TABLE 4-continued

Representative Compounds Containing Rigid Linkers

| Compound No. | Structure |
|---|---|
| 316 | 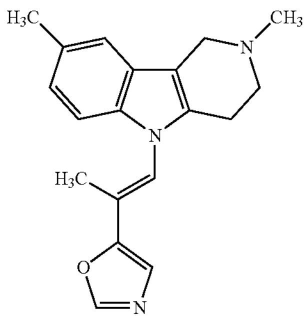 |
| 317 | 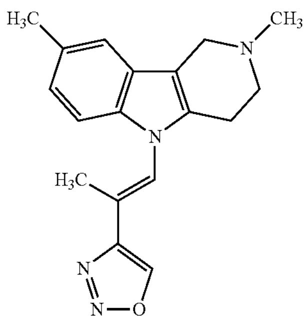 |
| 318 | 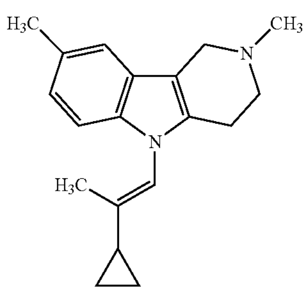 |
| 319 | 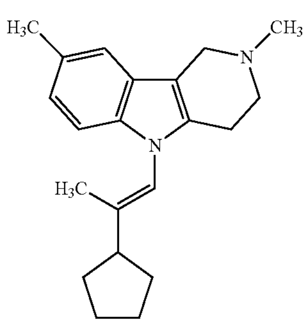 |
| 320 | |
| 321 | |
| 322 | |
| 323 | |

TABLE 4-continued

Representative Compounds Containing Rigid Linkers

| Compound No. | Structure |
|---|---|
| 324 | (structure) |
| 325 | (structure) |
| 326 | (structure) |
| 327 | (structure) |
| 328 | (structure) |
| 329 | (structure) |
| 330 | (structure) |
| 331 | (structure) |

TABLE 4-continued

Representative Compounds Containing Rigid Linkers

| Compound No. | Structure |
|---|---|
| 332 | (structure) |
| 333 | (structure) |
| 334 | (structure) |
| 335 | (structure) |
| 336 | (structure) |
| 337 | (structure) |
| 338 | (structure) |
| 339 | (structure) |

TABLE 4-continued

Representative Compounds Containing Rigid Linkers

| Compound No. | Structure |
|---|---|
| 340 | (structure) |
| 346 | (structure) |
| 367 | (structure) |
| 368 | (structure) |
| 369 | (structure) |
| 370 | (structure) |
| 371 | (structure) |
| 372 | (structure) |
| 373 | (structure) |

TABLE 4-continued
Representative Compounds Containing Rigid Linkers
| Compound No. | Structure |
|---|---|
| 374 | 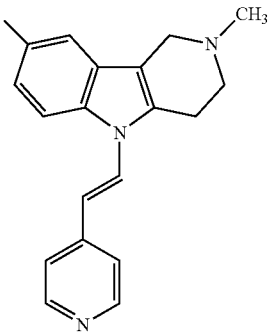 |
| 375 | 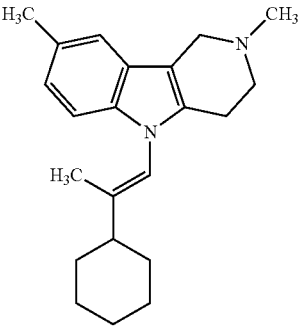 |
| 376 | 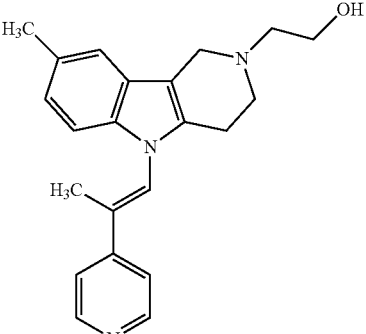 |
| 377 | 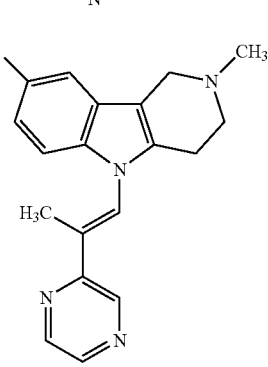 |
| 378 | 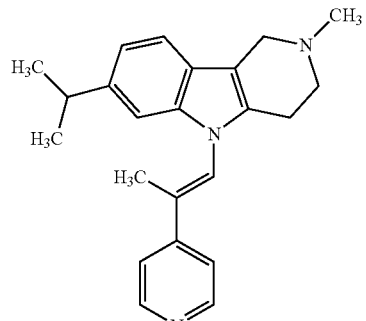 |
| 379 | 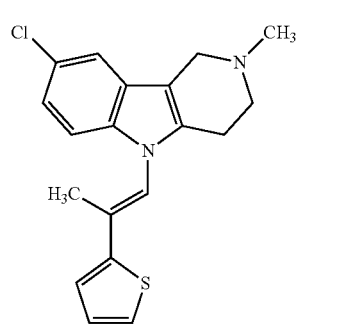 [SMILES: C/C(=C\n1c2c(c3cc(Cl)ccc31)CN(C)CC2)c1cccs1] |
| 380 | 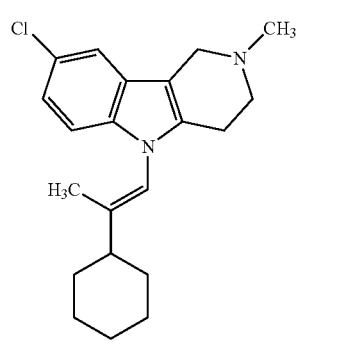 [SMILES: C/C(=C\n1c2c(c3cc(Cl)ccc31)CN(C)CC2)C1CCCCC1] |
| 381 | 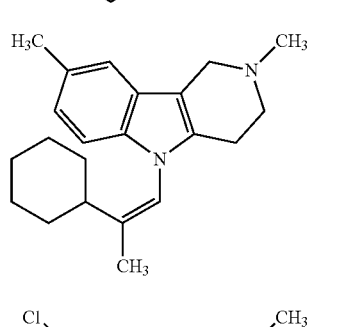 |
| 382 | 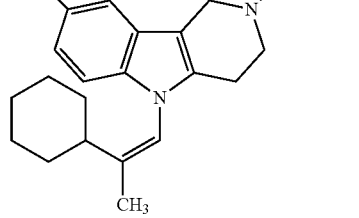 |

TABLE 4-continued

Representative Compounds Containing Rigid Linkers

| Compound No. | Structure |
|---|---|
| 383 | 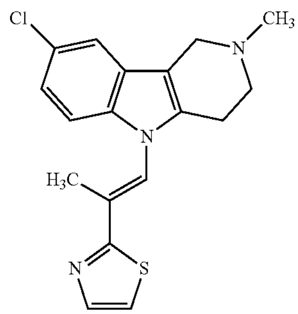 [SMILES: C/C(=C\n1c2c(c3cc(Cl)ccc31)CN(C)CC2)c1nccs1] |
| 384 | 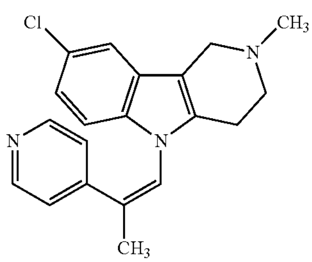 [SMILES: C/C(=C/n1c2c(c3cc(Cl)ccc31)CN(C)CC2)c1ccncc1] |
| 385 | 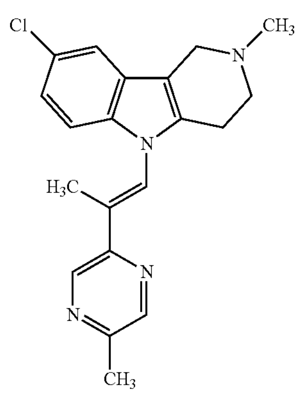 [SMILES: C/C(=C\n1c2c(c3cc(Cl)ccc31)CN(C)CC2)c1cnc(C)cn1] |
| 386 | 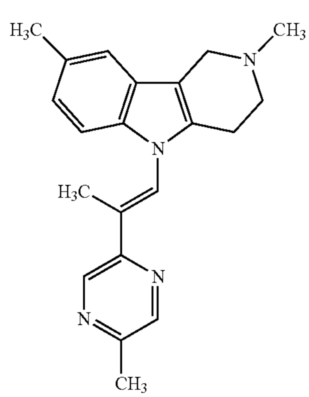 |
| 387 | |
| 388 | |
| 389 | |
| 390 | |

TABLE 4-continued

Representative Compounds Containing Rigid Linkers

| Compound No. | Structure |
|---|---|
| 391 | [chemical structure] |
| 392 | [chemical structure] |
| 393 | [chemical structure] |
| 394 | [chemical structure] |
| 395 | [chemical structure] |
| 396 | [chemical structure] |
| 397 | [chemical structure] |
| 398 | [chemical structure] |

TABLE 4-continued

Representative Compounds Containing Rigid Linkers

| Compound No. | Structure |
|---|---|
| 399 | (structure) |
| 400 | (structure) |
| 401 | (structure) |
| 402 | (structure) |
| 403 | (structure) |
| 404 | (structure) |
| 405 | (structure) |
| 406 | (structure) |

TABLE 4-continued
Representative Compounds Containing Rigid Linkers
| Compound No. | Structure |
|---|---|
| 407 | 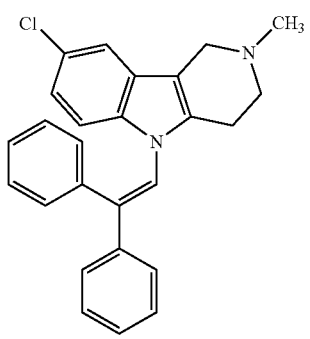 [SMILES: CN1CCc2c(c3cc(Cl)ccc3n2C=C(c2ccccc2)c2ccccc2)C1] |
| 409 | 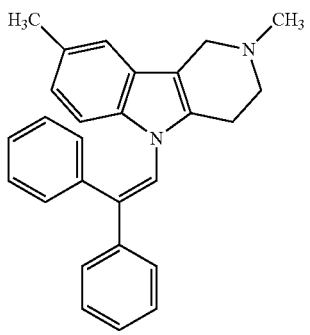 [SMILES: Cc1ccc2c(c1)c1c(n2C=C(c2ccccc2)c2ccccc2)CCN(C)C1] |
| 410 | 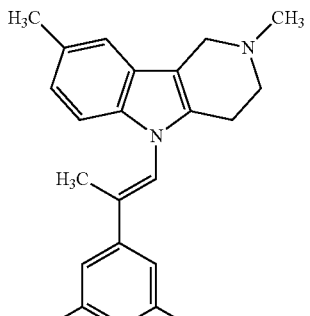 |
| 411 | 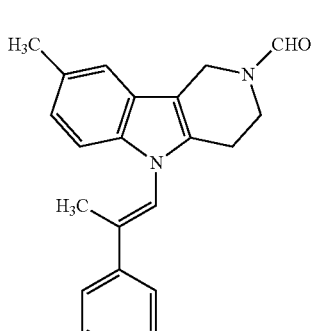 |
| 412 | 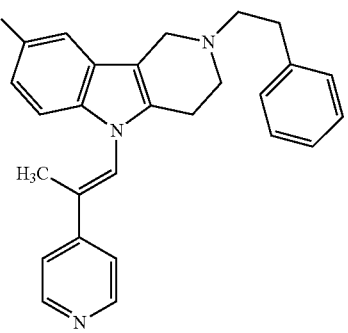 |
| 413 | 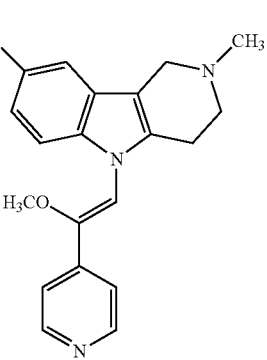 |
| 414 | 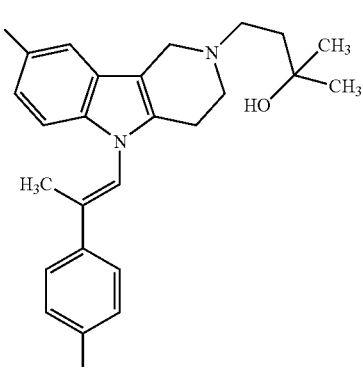 |
| 415 | 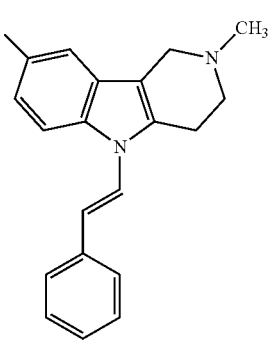 |

TABLE 4-continued

Representative Compounds Containing Rigid Linkers

| Compound No. | Structure |
|---|---|
| 416 | 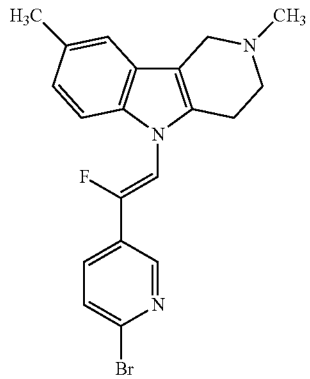 |
| 417 | 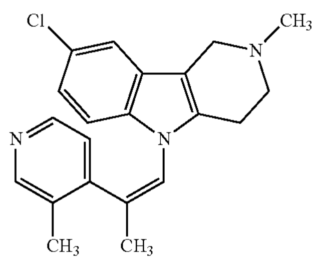 [SMILES: C/C(=C/n1c2c(c3cc(Cl)ccc31)CN(C)CC2)c1ccncc1C] |
| 418 | 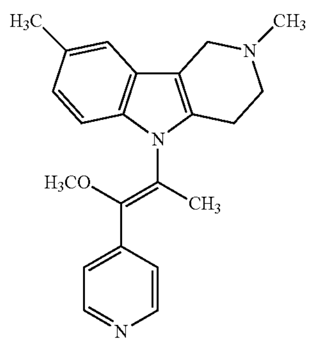 |
| 419 | 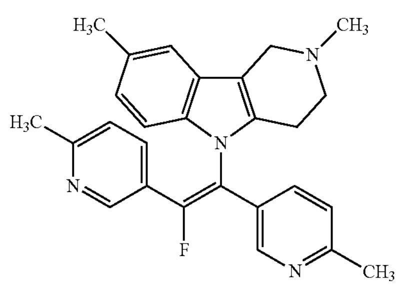 |
| 420 | 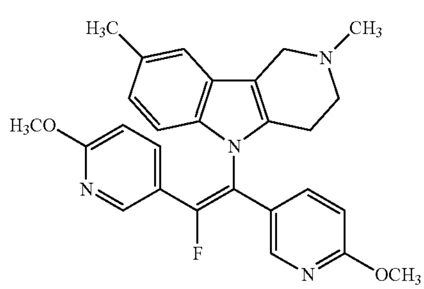 [SMILES: COc1ccc(/C(F)=C(/c2ccc(OC)nc2)n2c3c(c4cc(C)ccc42)CN(C)CC3)cn1] |
| 421 | |
| 422 | |
| 423 | |
| 424 | |

TABLE 4-continued
Representative Compounds Containing Rigid Linkers
| Compound No. | Structure |
|---|---|
| 425 | 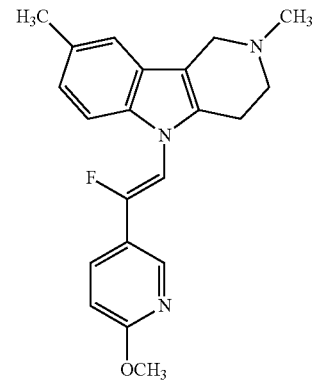 |
| 426 | 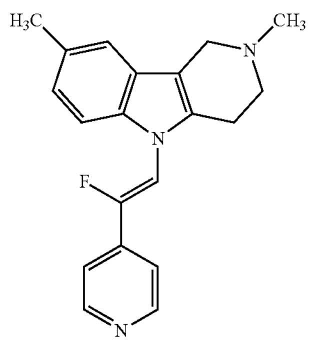 |
| 427 | 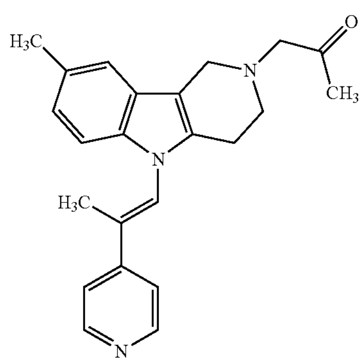 [SMILES: CC(=O)CN1CCc2c(c3cc(C)ccc3n2/C=C(\C)c2ccncc2)C1] |
| 428 | 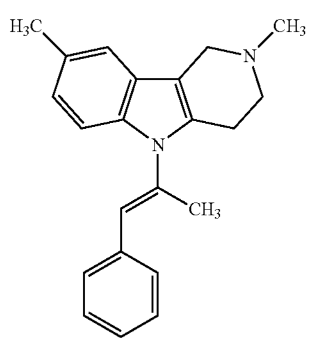 |
| 429 | 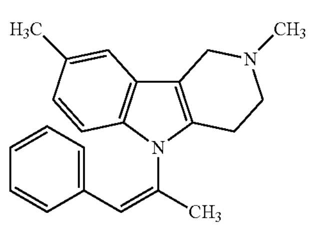 [SMILES: C/C(=C/c1ccccc1)n1c2c(c3cc(C)ccc31)CN(C)CC2] |
| 430 | 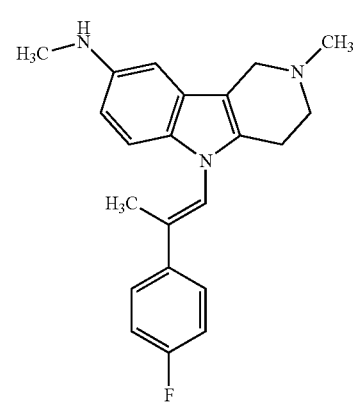 |
| 431 | 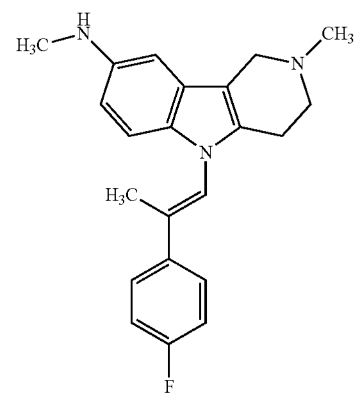 |
| 432 | 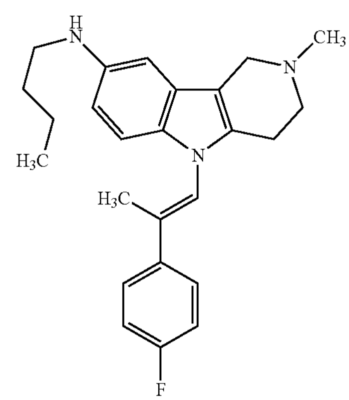 [SMILES: CCCCNc1ccc2c(c1)c1c(n2/C=C(\C)c2ccc(F)cc2)CCN(C)C1] |
| 433 | 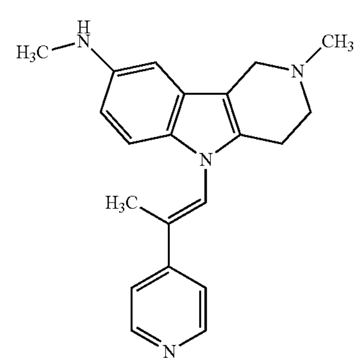 |

TABLE 4-continued

Representative Compounds Containing Rigid Linkers

| Compound No. | Structure |
|---|---|
| 435 | (structure) |
| 436 | (structure) |
| 437 | (structure) |
| 438 | (structure) |
| 439 | (structure) |
| 440 | (structure) |
| 441 | (structure) |

TABLE 4-continued

Representative Compounds Containing Rigid Linkers

| Compound No. | Structure |
|---|---|
| 442 | |
| 443 | |
| 444 | |
| 445 | 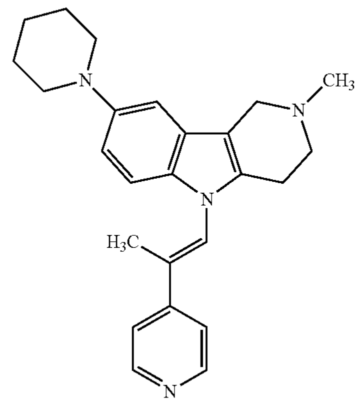 [SMILES: C/C(=C\n1c2c(c3cc(N4CCCCC4)ccc31)CN(C)CC2)c1ccncc1] |
| 446 | 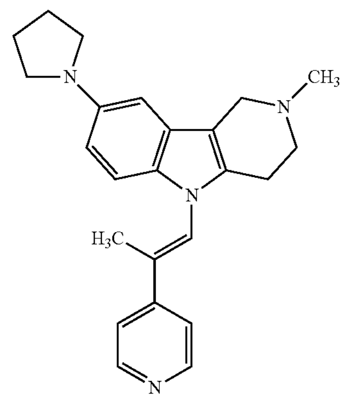 [SMILES: C/C(=C\n1c2c(c3cc(N4CCCC4)ccc31)CN(C)CC2)c1ccncc1] |
| 447 | 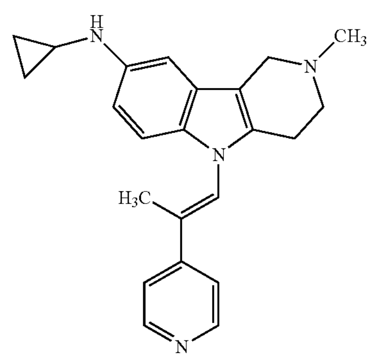 [SMILES: C/C(=C\n1c2c(c3cc(NC4CC4)ccc31)CN(C)CC2)c1ccncc1] |
| 448 | 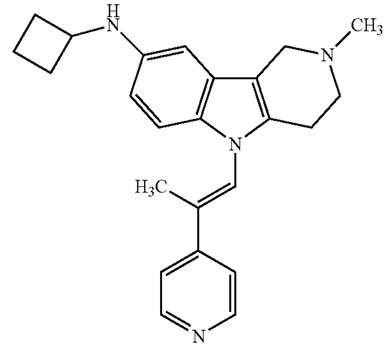 [SMILES: C/C(=C\n1c2c(c3cc(NC4CCC4)ccc31)CN(C)CC2)c1ccncc1] |

TABLE 4-continued

Representative Compounds Containing Rigid Linkers

| Compound No. | Structure |
|---|---|
| 449 | 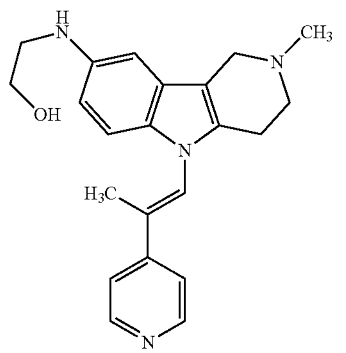 [SMILES: C/C(=C\n1c2c(c3cc(NCCO)ccc31)CN(C)CC2)c1ccncc1] |
| 450 | 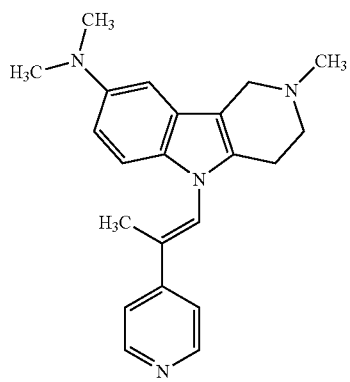 |
| 451 | 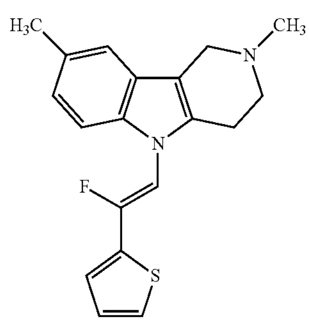 |
| 452 | 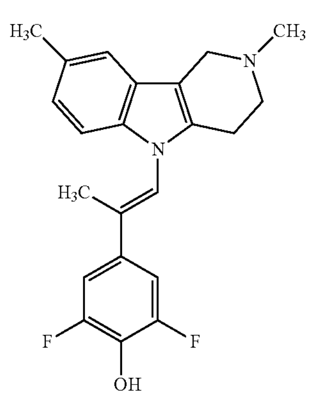 |
| 453 | 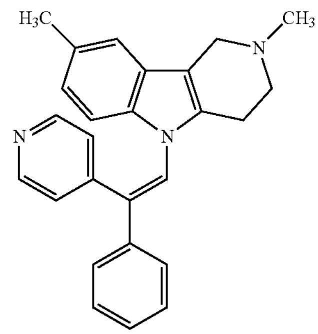 [SMILES: Cc1ccc2c(c1)c1c(n2/C=C(/c2ccccc2)c2ccncc2)CCN(C)C1] |
| 454 | 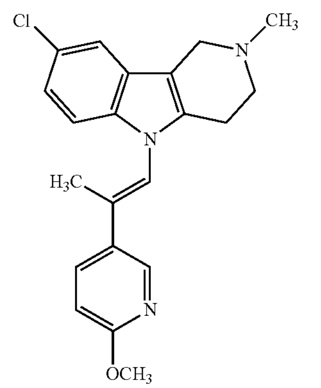 [SMILES: COc1ccc(/C(C)=C/n2c3c(c4cc(Cl)ccc42)CN(C)CC3)cn1] |
| 455 | 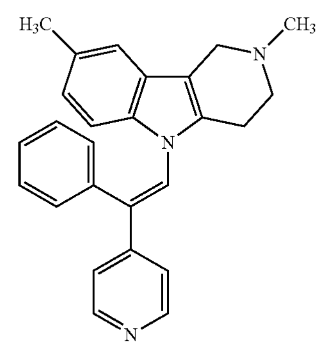 [SMILES: Cc1ccc2c(c1)c1c(n2/C=C(\c2ccccc2)c2ccncc2)CCN(C)C1] |
| 456 | 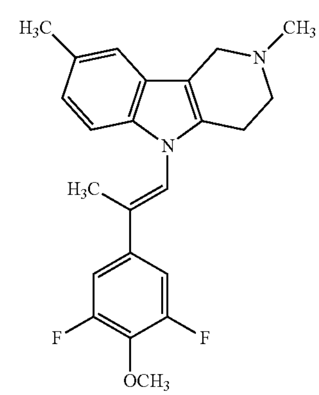 |

TABLE 4-continued

Representative Compounds Containing Rigid Linkers

| Compound No. | Structure |
|---|---|
| 457 | (structure) |
| 458 | (structure) |
| 459 | (structure) |
| 460 | (structure) |
| 461 | (structure) |
| 462 | (structure) |
| 471 | (structure) |
| 472 | (structure) |

TABLE 4-continued

Representative Compounds Containing Rigid Linkers

| Compound No. | Structure |
|---|---|
| 473 | (structure) |
| 474 | (structure) |
| 475 | (structure) |
| 476 | (structure) |
| 477 | (structure) |
| 478 | (structure) |
| 479 | (structure) |

TABLE 4-continued
Representative Compounds Containing Rigid Linkers
| Compound No. | Structure |
|---|---|
| 480 | 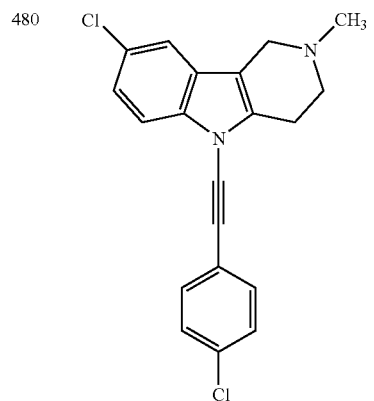 |
| 481 | 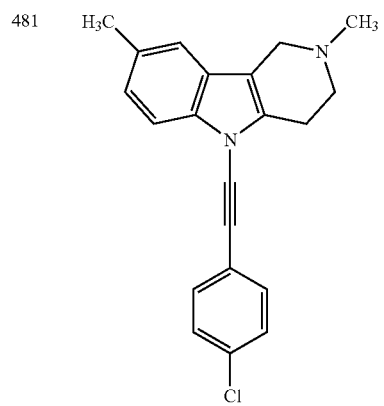 |
| 482 | 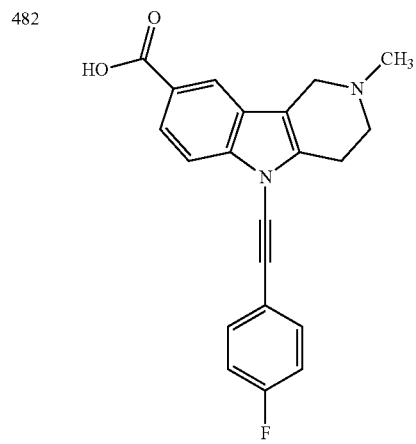 |
| 483 | 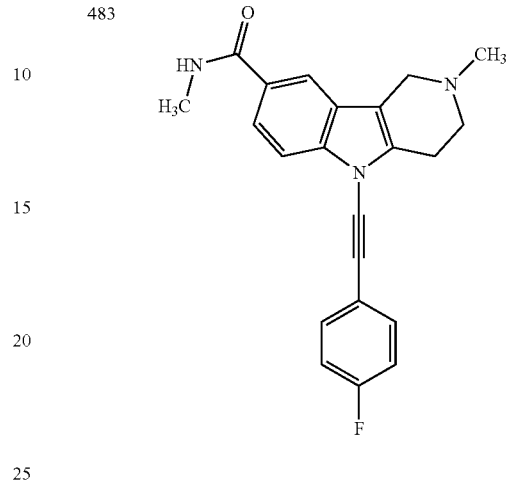 |
| 484 | 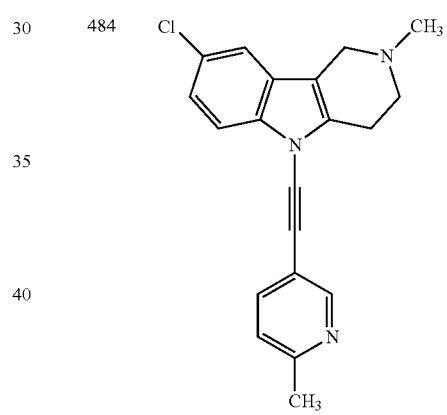 |
| 485 | 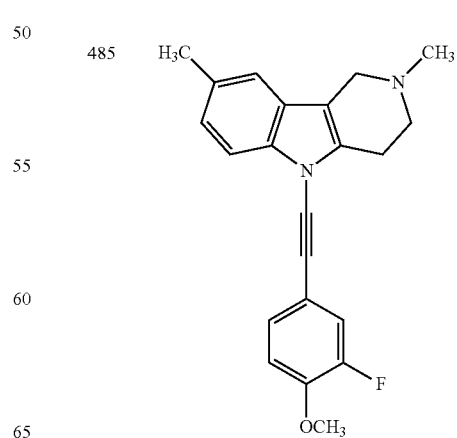 |

TABLE 4-continued
Representative Compounds Containing Rigid Linkers
| Compound No. | Structure |
|---|---|
| 486 | 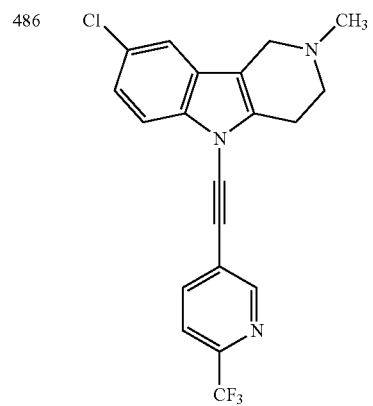 |
| 487 | 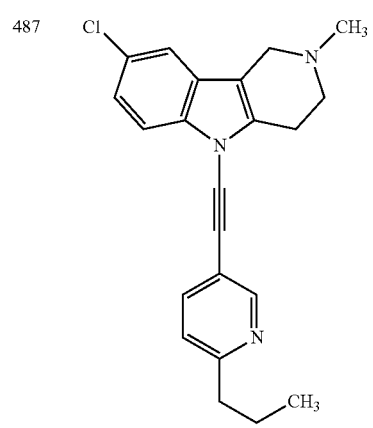 |
| 488 | 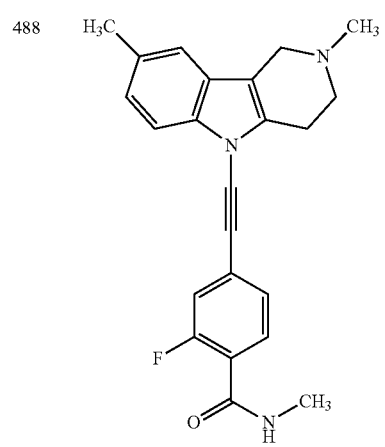 |
TABLE 4-continued
Representative Compounds Containing Rigid Linkers
| Compound No. | Structure |
|---|---|
| 489 | 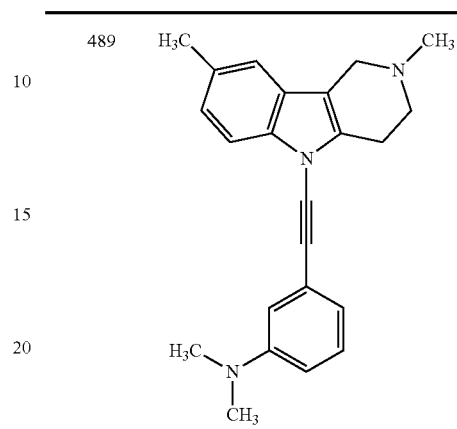 |
| 490 | 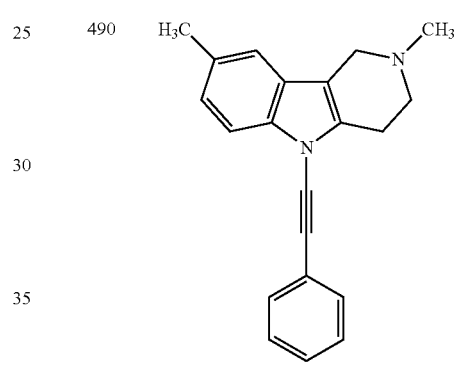 |
| 491 | 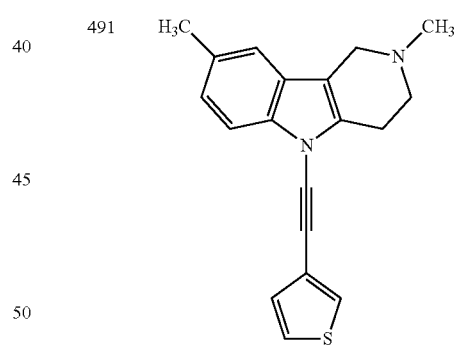 |
| 492 | 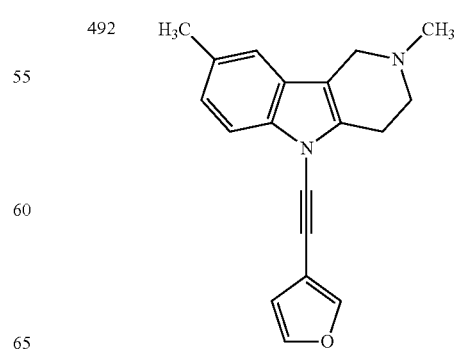 |

TABLE 4-continued

Representative Compounds Containing Rigid Linkers

| Compound No. | Structure |
|---|---|
| 493 | (structure) |
| 494 | (structure) |
| 495 | (structure) |
| 496 | (structure) |
| 497 | (structure) |
| 498 | (structure) |
| 499 | (structure) |
| 500 | (structure) |

Although certain compounds of Table 4 are explicitly listed as both the (Z) and the (E) form (e.g., Compound 83 is the (E) form and Compound 397 is the (Z) form), it is understood that all forms of compounds of Table 4 are intended. Thus, for compounds of Table 4 that are listed only as a single form, it is understood that all other forms are also embraced by the invention and are provided herein the same as if each and every stereochemical form were specifically

241 and individually listed. In particular, where only the (Z) form of a compound is listed in Table 4, the (E) form of such compound is also provided herein the same as if the (E) form were specifically and individually listed in Table 4. Likewise, where only the (E) form of a compound is listed in Table 4, the (Z) form of such compound is also provided herein the same as if the (Z) form were specifically and individually listed in Table 4.

TABLE 5

Additional compounds

| Compound No. | Structure |
|---|---|
| 128 | 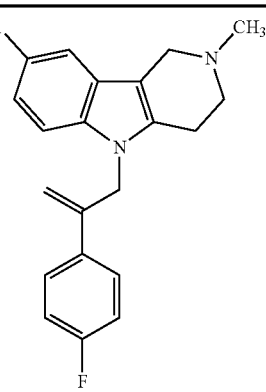 |
| 129 | 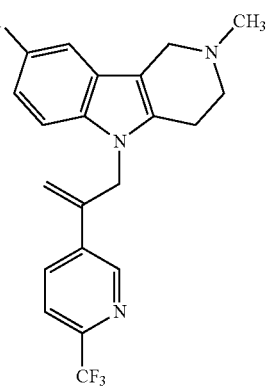 |
| 130 | 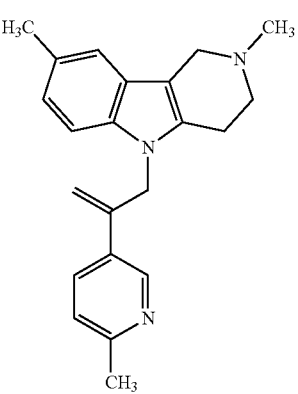 |

242

TABLE 5-continued

Additional compounds

| Compound No. | Structure |
|---|---|
| 131 | 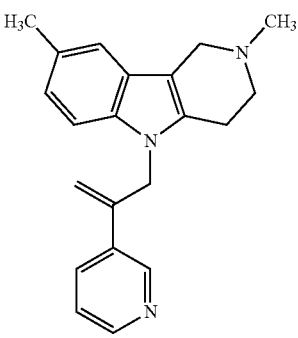 |
| 132 | 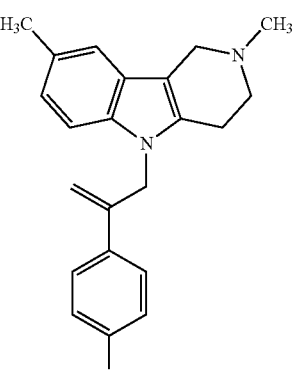 |
| 133 | 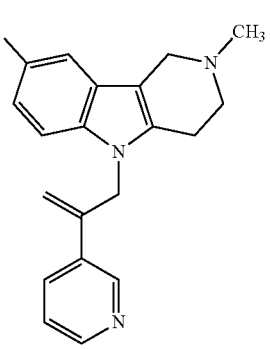 |
| 134 | 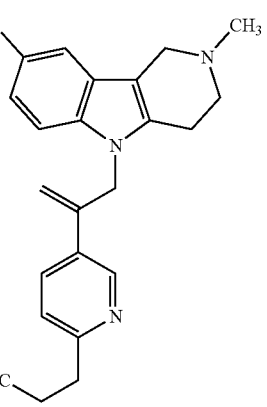 |

TABLE 5-continued
Additional compounds
| Compound No. | Structure |
|---|---|
| 135 | 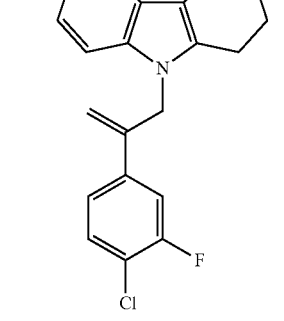 |
| 136 | 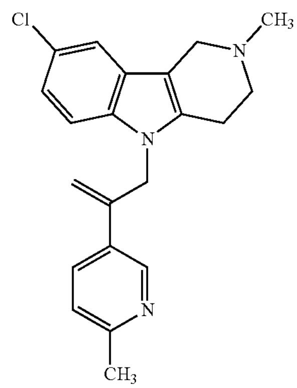 [SMILES: C=C(Cn1c2c(c3cc(Cl)ccc31)CN(C)CC2)c1ccc(C)nc1] |
| 137 | 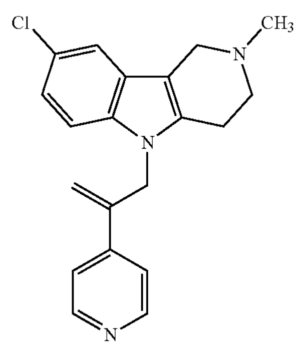 [SMILES: C=C(Cn1c2c(c3cc(Cl)ccc31)CN(C)CC2)c1ccncc1] |
| 138 | 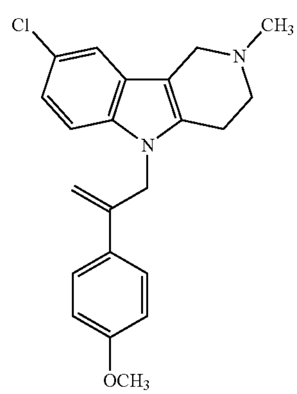 [SMILES: C=C(Cn1c2c(c3cc(Cl)ccc31)CN(C)CC2)c1ccc(OC)cc1] |
| 139 | 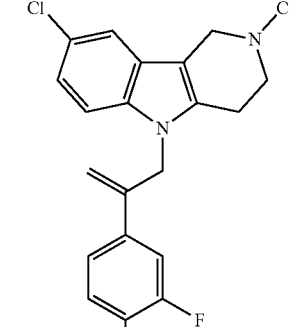 |
| 140 | |
| 141 | |
| 142 | |

TABLE 5-continued

Additional compounds

| Compound No. | Structure |
|---|---|
| 143 | 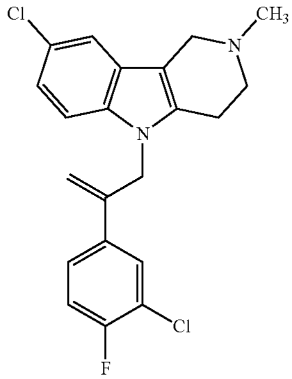 [SMILES: C=C(Cn1c2c(c3cc(Cl)ccc31)CN(C)CC2)c1ccc(F)c(Cl)c1] |
| 144 | 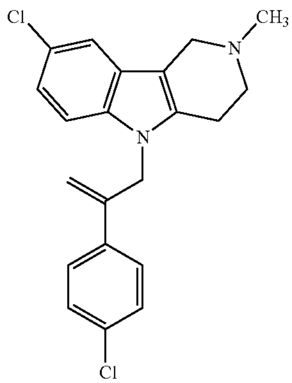 [SMILES: C=C(Cn1c2c(c3cc(Cl)ccc31)CN(C)CC2)c1ccc(Cl)cc1] |
| 145 | 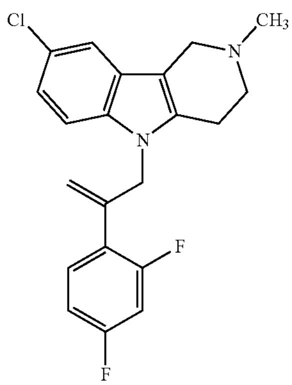 [SMILES: C=C(Cn1c2c(c3cc(Cl)ccc31)CN(C)CC2)c1ccc(F)cc1F] |
| 146 | 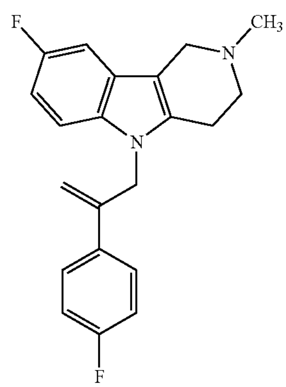 [SMILES: C=C(Cn1c2c(c3cc(F)ccc31)CN(C)CC2)c1ccc(F)cc1] |
| 147 | 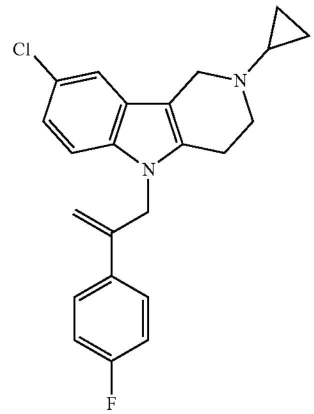 [SMILES: C=C(Cn1c2c(c3cc(Cl)ccc31)CN(C1CC1)CC2)c1ccc(F)cc1] |
| 148 | 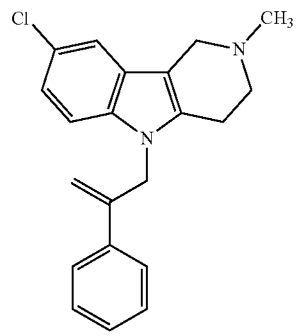 [SMILES: C=C(Cn1c2c(c3cc(Cl)ccc31)CN(C)CC2)c1ccccc1] |
| 149 | 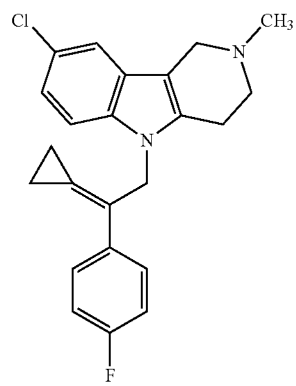 [SMILES: CN1CCc2c(c3cc(Cl)ccc3n2CC(=C2CC2)c2ccc(F)cc2)C1] |
| 150 | 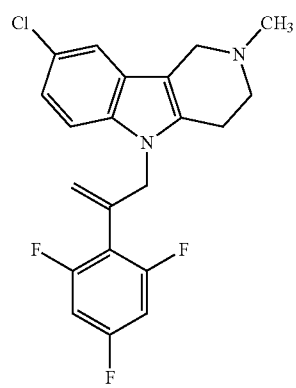 [SMILES: C=C(Cn1c2c(c3cc(Cl)ccc31)CN(C)CC2)c1c(F)cc(F)cc1F] |

TABLE 5-continued

Additional compounds

| Compound No. | Structure |
|---|---|
| 151 | (8-Cl-2-methyl-tetrahydro-β-carboline, N-CH2-C(=CH2)-pyrimidin-5-yl) |
| 152 | (8-Cl-2-methyl-tetrahydro-β-carboline, N-CH(CH3)-C(=CH2)-(4-F-phenyl)) |
| 153 | (8-methyl-2-methyl-tetrahydro-β-carboline, N-CH2-C(=CH2)-phenyl) |
| 154 | (8-Cl-2-methyl-tetrahydro-β-carboline, N-CH2-C(=CH2)-(2,4-diCl-phenyl)) |
| 155 | (8-I-2-methyl-tetrahydro-β-carboline, N-CH2-C(=CH2)-(4-F-phenyl)) |
| 156 | (8-Cl-2-methyl-tetrahydro-β-carboline, N-CH2-C(=CH-CH3)-(4-F-phenyl)) |
| 347 | (8-methyl-2-methyl-tetrahydro-β-carboline, N-CH2-C(phenyl)=CH-C(=O)-O-CH2CH3) |
| 348 | (8-Cl-2-methyl-tetrahydro-β-carboline, N-CH2-C(4-F-phenyl)=CH-CH2-CH2-OH) |

TABLE 5-continued

Additional compounds

| Compound No. | Structure |
|---|---|
| 349 | (structure) |
| 350 | (structure) |
| 351 | (structure) |
| 352 | (structure) |
| 353 | (structure) |
| 354 | (structure) |
| 355 | (structure) |
| 356 | (structure) |

TABLE 5-continued

Additional compounds

| Compound No. | Structure |
|---|---|
| 357 | (structure) |
| 358 | (structure) |
| 359 | (structure) |
| 360 | (structure) |
| 361 | (structure) |
| 362 | (structure) |
| 363 | (structure) |
| 364 | (structure) |

TABLE 5-continued

Additional compounds

| Compound No. | Structure |
|---|---|
| 365 | (structure) |
| 408 | (structure) |

Compounds of formula (II) may be prepared by the reaction schemes shown below. Representative examples shown below may be prepared by the methods suggested in Table 6.

TABLE 6

Representative compounds of formula (II)

| Compound No. | Structure | General method of preparation |
|---|---|---|
| 157 | (structure) | Scheme A |
| 158 | (structure) | Scheme A |
| 159 | (structure) | Scheme A |
| 160 | (structure) | Scheme A |
| 161 | (structure) | Scheme B |
| 164 | (structure) | Scheme B |
| 165 | (structure) | Scheme B |

TABLE 6-continued

Representative compounds of formula (II)

| Compound No. | Structure | General method of preparation |
|---|---|---|
| 166 | (6-chloro-2-methyl-tetrahydro-β-carboline with cyclohexenyl-pyridyl substituent) | Scheme B |
| 201 | (7-methyl-2-methyl-tetrahydro-β-carboline with cyclohexenyl-(6-methylpyridyl) substituent) | Scheme B |

Scheme A

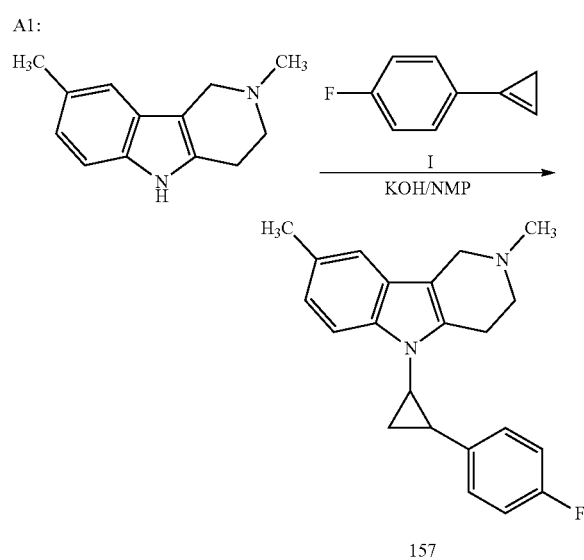

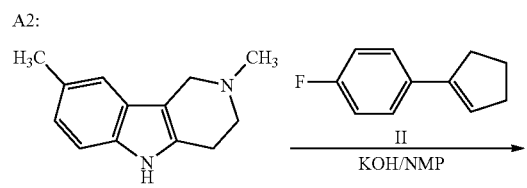

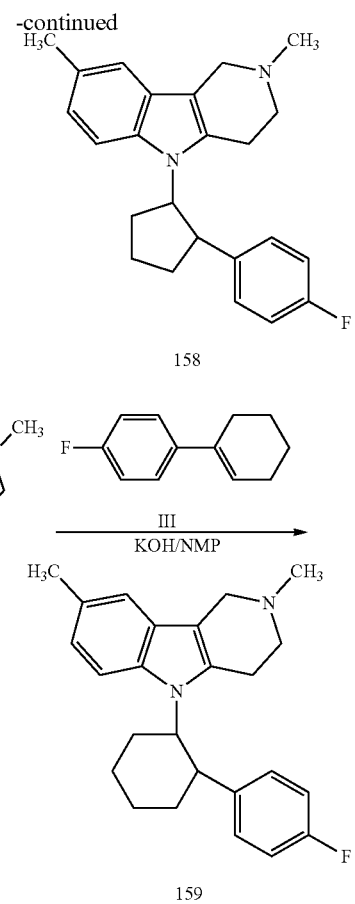

General Method 6. General Method of Synthesis Using Scheme A

Step 1: Synthesis of the Carbolines:

The carbolines in Scheme A can be obtained by the reaction of a suitably substituted phenyl hydrazine with 1-methyl-4-piperidone, under standard conditions. Typically, 1-methyl-4-piperidone (1 equiv.) and appropriately substituted arylhydrazine hydrochloride (1 equiv.) are refluxed in a mixture of 7% sulfuric acid in 1,4-dioxane overnight under nitrogen. The mixture is poured on to ice and basified with 50% aq NaOH. The resulting precipitate is filtered, washed well with water, and dried in air to provide the substituted 2,3,4,5-tetrahydro-1H-pyrido[4,3-b]indole derivative.

Step 2: Synthesis of 1-cycloalkenyl-4-halobenzenes:

Compounds I through IV in Scheme A can be obtained, e.g., by the methods described in Barbero et al., *Tet. Letters* (1992), 33(39):5841-42.

Step 3: The reaction of 1-cycloalkenyl-4-halobenzene with Carbolines:

Typically, a mixture appropriately substituted 2,3,4,5-tetrahydro-1H-pyrido[4,3-b]indole (1 equiv.), 1-cycloalkenyl-4-halobenzene (3 equiv.) and KOH (7 equiv.) in NMP (0.5 mL/mmol) is stirred and heated at 100° C. for 3 h. The reaction mixture is cooled to RT and diluted by adding ice and satd. aqueous NaCl. The aqueous layer is extracted with EtOAc and organic layer is washed with brine, dried over anhydrous sodium sulfate and concentrated under vacuum to obtain the product.

In each of the cases shown in Scheme A the final compounds are mixtures of isomers illustrated below. While the route suggested in scheme A provides access to the chemically pure compounds, the separation of isomers is a secondary step that has to be carried out in order to complete the synthesis of the unique isomers, if required.

A1:

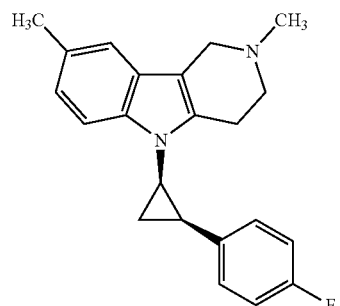

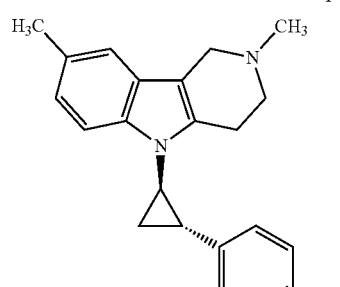

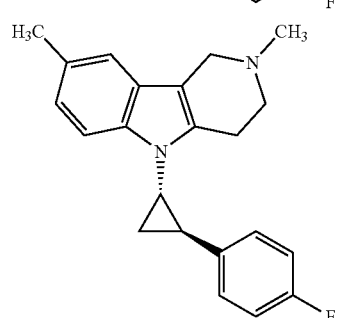

A2:

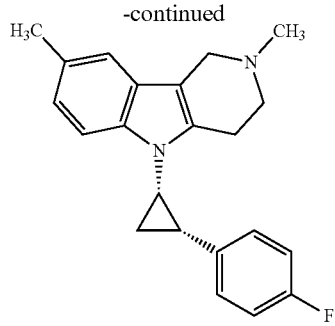

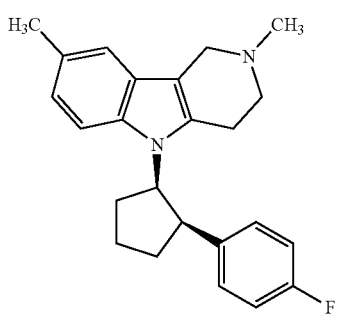

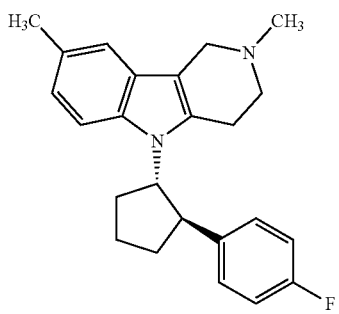

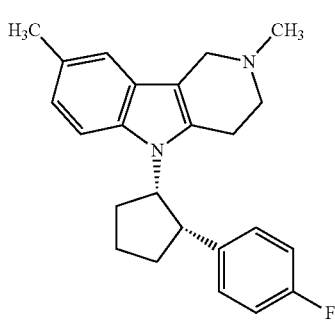

A3:
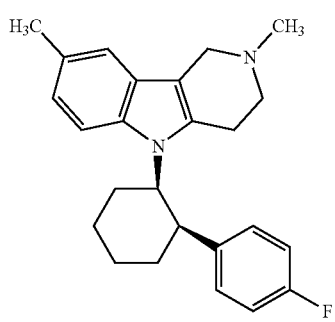
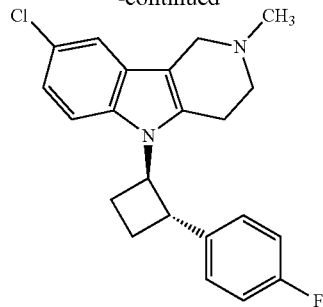
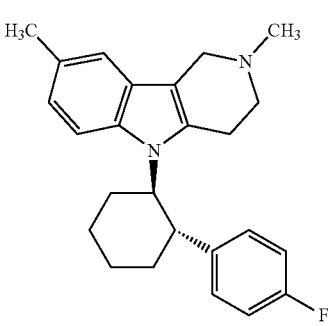
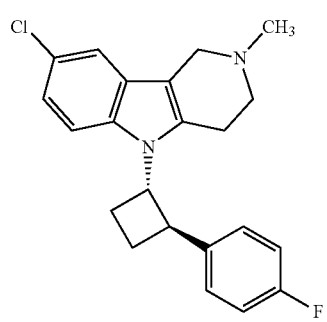
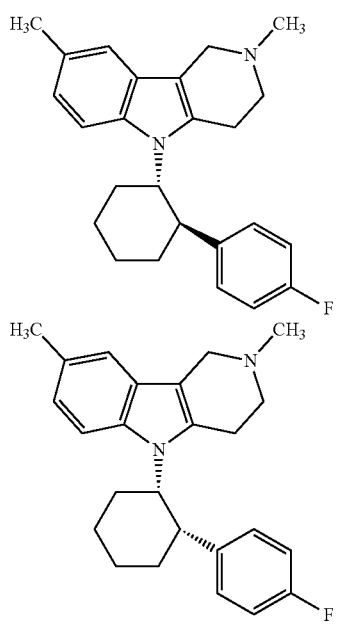
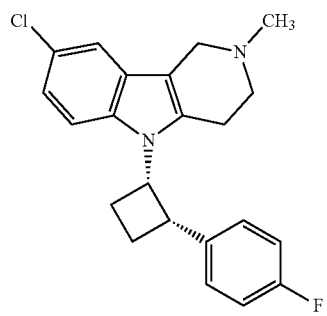 [SMILES: CN1CCc2c(c3cc(Cl)ccc3n2[C@H]2CC[C@H]2c2ccc(F)cc2)C1]
A4:
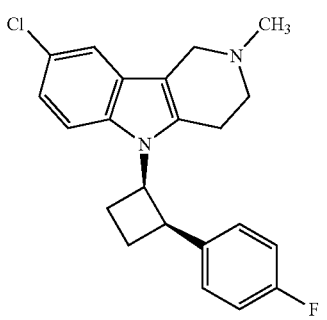
Synthesis of Intermediates I through IV in Scheme A
It is envisaged that intermediate I through IV would be synthesized using methodologies akin to, but not limited to those described in Barbero et al., *Tet. Letters* (1992), 33(39): 5841-42, which describes the synthesis of a molecule such as intermediate IV, without the p-fluoro group on the phenyl ring.
Scheme B
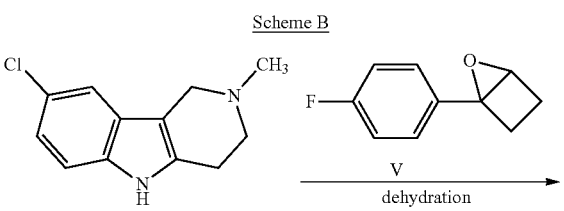

-continued

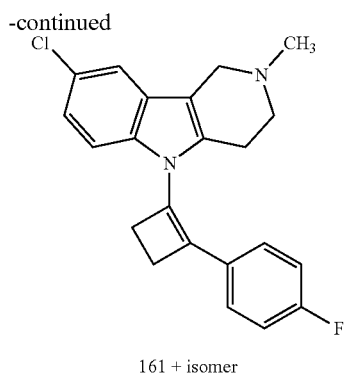

161 + isomer

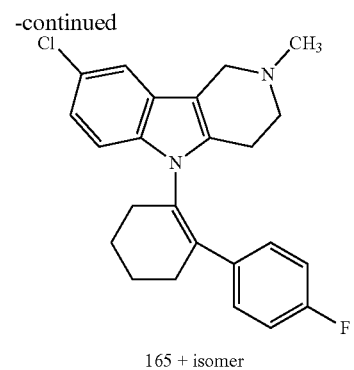

165 + isomer

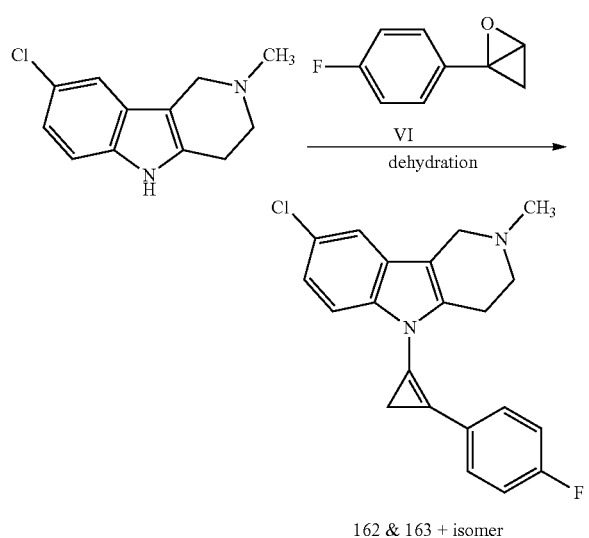

162 & 163 + isomer

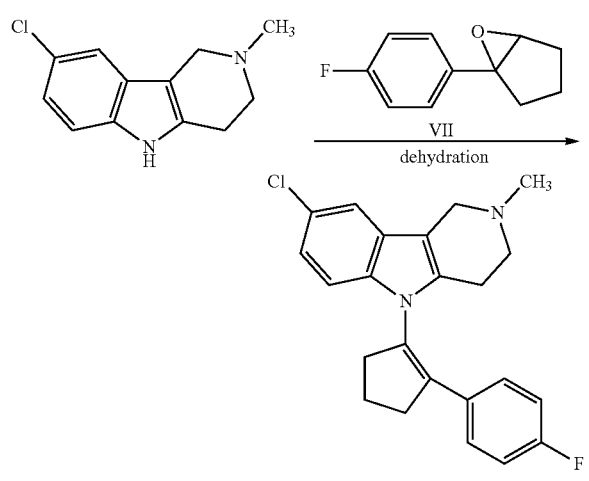

164 + isomer

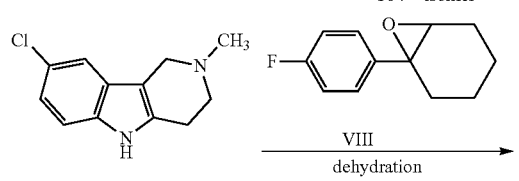

General Method 7. General Method of Synthesis Using Scheme B

Step 1: Synthesis of the Carbolines:

The carbolines in scheme B can be obtained by the reaction of a suitably substituted phenyl hydrazine with 1-methyl-4-piperidone, under standard conditions. Typically 1-methyl-4-piperidone (1 equiv.) and appropriately substituted arylhydrazine hydrochloride (1 equiv.) are refluxed in a mixture of 7% sulfuric acid in 1,4-dioxane overnight under nitrogen. The mixture is poured on to ice and basified with 50% aq NaOH. The resulting precipitate is filtered, washed well with water, and dried in air to provide substituted 2,3,4,5-tetrahydro-1H-pyrido[4,3-b]indole derivative.

Step 2: Synthesis of 1-(4-halophenyl)-5-oxabicyclo[m.n.0] alkanes:

Compounds V through VIII in Scheme B can be obtained by, e.g., the methods outlined in Yu & Corey, *Org. Letters* (2002), 4(16):2727-30.

Step 3: Synthesis of 1-(4-halophenyl)-5-oxabicyclo[m.n.0] alkanes with Carbolines:

Typically, appropriately substituted 2,3,4,5-tetrahydro-1H-pyrido[4,3-b]indole (1 equiv.) is dissolved in DMF (2 mL/mmol). To this solution sodium hydride (2.2 equiv.) is added in portions at RT and stirred for 10 min. Appropriate 1-(4-halophenyl)-5-oxabicyclo[m.n.0]alkanes (2 equiv.) in DMF (0.5 mL/mmol) is added dropwise for 10 min. and stirred overnight at RT. The reaction mixture is quenched with MeOH and concentrated to dryness. Water is added to the residue and product is extracted in EtOAc. The organic layer is dried over anhydrous sodium sulfate and evaporated under reduced pressure to obtain the product.

Step 4: Dehydration Step:

Typically, appropriately substituted 2-(3,4-dihydro-1H-pyrido[4,3-b]indol-5(2H)-yl)ethanol (1 equiv.) is taken in 25% aqueous sulfuric acid, and stirred at 90° C. for 3 h. The reaction mixture is cooled and basified with aq. KOH solution and extracted with EtOAc. The organic layer is dried over anhydrous sodium sulfate and evaporated under reduced pressure to obtain the product.

Synthesis of Intermediates V Through VIII in Scheme B

It is envisaged that intermediate V through VIII would be synthesized using methodologies akin to, but not limited to those described in Yu & Corey, *Org. Letters* (2002), 4(16): 2727-30, which describes the synthesis of a molecule such as intermediate VII, without the p-fluoro group on the phenyl ring.

The compounds depicted may be prepared as salts even if salts are not depicted and it is understood that the invention embraces all salts and solvates of the compounds depicted here, as well as the non-salt and non-solvate form of the compound, as is well understood by the skilled artisan.

A representative compound was prepared as shown in Scheme C.

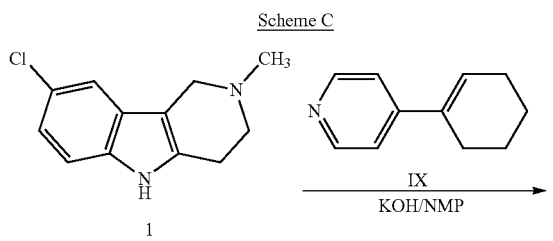

Scheme C

1

General Method 8. General Method of Synthesis Using Scheme C

Step 1: Synthesis of the Carboline 1:

Sulfuric acid (3.5 mL) is added to a solution of 4-chlorophenylhydrazine hydrochloride (1 equiv.) in dioxane (50 mL), and stirred for 5 min. at RT. N-methyl-4-piperidone (1 equiv.) is added and the mixture is heated at 80° C. for 2 h. After completion of reaction (as analyzed by TLC), reaction mixture is concentrated to approximately 20 mL under reduced pressure and basified to pH 10 using 10% aqueous KOH solution, extracted with EtOAc, dried over anhydrous sodium sulfate and concentrated under reduced pressure to obtain the desired compound.

Step 2: Synthesis of 4-cyclohexenylpyridine:

Compounds IX can be obtained by methods outlined in, Barbero et al., *Tet. Letters* (1992), 33(39):5841-42.

Step 3: The Reaction of Carboline C1 with 3-cyclohexenylpyridine:

To a solution of 8-chloro-2-methyl-2,3,4,5-tetrahydro-1H-pyrido[4,3-b]indole (0.1 g, 0.45 mmol) in N-methyl-2-pyrrolidone (1.0 mL) is added powdered KOH (0.140 g, 2.5 mmol) and stirred for 10 min. at RT. 3-Cyclohexenylpyridine (1.25 mmol) is added and the reaction mixture is stirred for additional 4 h at 100° C. After completion of reaction (as analyzed by TLC), reaction mixture is diluted with water (15 mL) and extracted with EtOAc (3×20 mL). The organic layer is dried over anhydrous sodium sulfate and concentrated under reduced pressure to obtain the product.

Certain compounds detailed herein are synthesized according to General Method 9.

General Method 9.

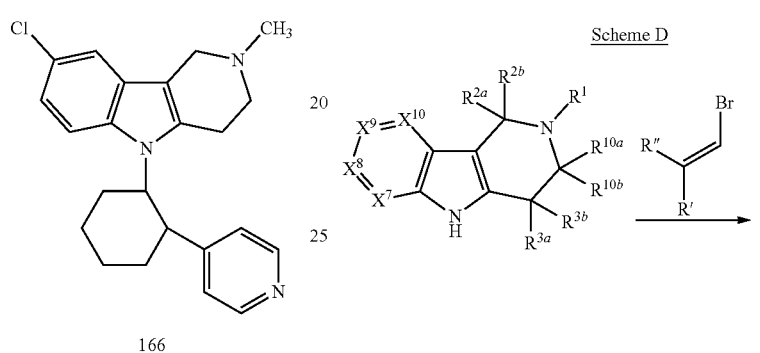

Scheme D

A pyrido[4,3-b]indole compound such as ones listed in Table 1 is coupled with an appropriately substituted vinyl bromide under similar conditions as described in Examples 293 and 294 to give 5-vinyl-pyrido[4,3-b]indole compounds as shown in Scheme D.

General Method 10

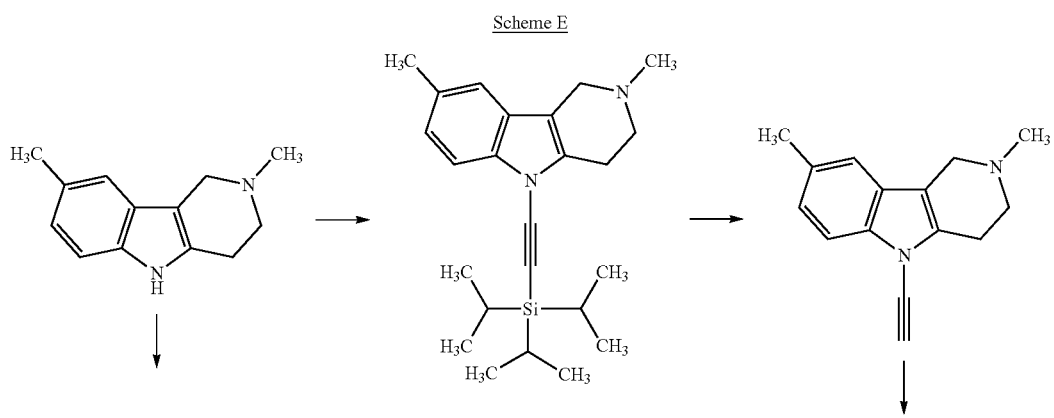

Scheme E

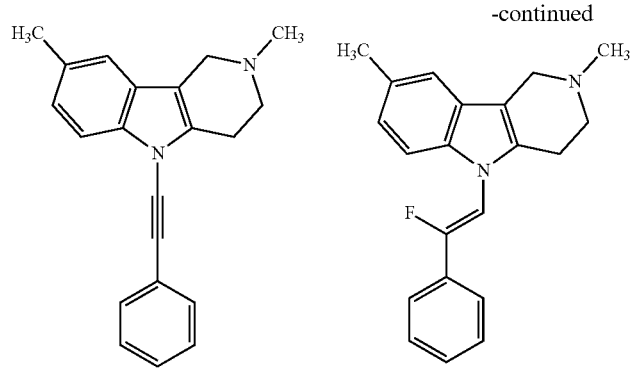
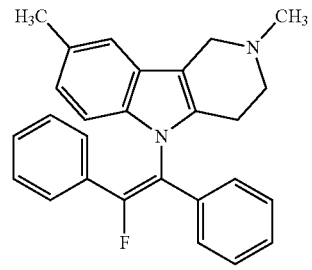

+

Alkynes of the type shown in Scheme E can be prepared by coupling a carboline of the type in Table 1 with an appropriately substituted phenyl-acetylene, or similar acetylene-linked aromatic compound, using copper/phenanthroline coupling agents as described in Examples 475-498, or by treatment of the carboline with base followed by addition of a haloethynyl-benzene. Alternatively, the fluorinated alkene products can be synthesized from the intermediate alkyne compound by palladium-mediated coupling with a haloaromatic in the presence of fluoride ion, as described in Examples 353 or 379.

The methods detailed above may be adapted as known by those of skill in the art to make compounds detailed herein. Particular examples of each of the General Methods are provided in the Examples below.

The following Examples are provided to illustrate but not to limit the invention.

All references disclosed herein are incorporated by reference in their entireties.

EXAMPLES

Example 1

Preparation of 8-Chloro-2-methyl-2,3,4,5-tetrahydro-1H-pyrido[4,3-b]indole (Compound 1)

Sulfuric acid (3.5 mL) was added to a solution of 4-chlorophenylhydrazine hydrochloride (2.0 g, 11.2 mmol) in dioxane (50 mL), and stirred for 5 min. at RT. N-methyl piperidone (0.76-1.4 equiv.) was added and the mixture was heated at 80° C. for 2 h. After reaction completion as determined by thin layer chromatography (TLC), the reaction mixture was concentrated to approximately 20 mL under reduced pressure and basified to pH 10 using a 10% aqueous KOH solution. The reaction product was extracted with EtOAc (3×50 mL), dried over anhydrous sodium sulfate and concentrated under reduced pressure using a rotary evaporator to obtain the product (1.3 g) as a brown solid. $^1$H NMR (CDCl$_3$, freebase) δ (ppm): 7.40 (s, 1H), 7.20-7.10 (d, 1H), 7.10-7.00 (d, 1H), 3.60 (s, 2H), 2.90 (s, 4H), 2.60 (s, 3H).

Example 1A

4-Chlorophenyl hydrazine hydrochloride (30 g, 167.59 mmol) was dissolved in dioxane (300 mL) and 1-methyl-4-piperidone (28 mL, 234.63 mmol) was added. Sulfuric acid (14.4 mL) was added dropwise and the mixture was heated at 80° C. for 3 h. After completion of reaction (monitored by TLC), the dioxane layer was decanted and the residue was basified with 10% aqueous KOH solution. The resulting solid was filtered and washed with water (2 L) and finally with hexane (500 mL). The product was dried under vacuum at RT. Yield: 30 g as a light brown solid.

Example 2

Preparation of 2,8-Dimethyl-2,3,4,5-tetrahydro-1H-pyrido[4,3-b]indole (Compound 3)

Sulfuric acid (2 mL) was added to a solution of p-tolyl hydrazine hydrochloride (6.0 g, 37 mmol) in dioxane (60 mL), and stirred for 5 min. at RT. N-Methyl piperidone (5.03 g, 41 mmol) was added and the mixture was heated at 80° C. for 2 h. After reaction completion as determined by TLC), the reaction mixture was concentrated to approximately 20 mL under reduced pressure and basified to pH 10 using 10% aqueous KOH solution. The reaction mixture was extracted with EtOAc (3×300 mL), dried over anhydrous sodium sulfate and concentrated under reduced pressure using a rotary evaporator to provide the desired compound as a brown colored solid (4.0 g, 52% yield). $^1$H NMR (DMSO-d$_6$, di-HCl salt) δ (ppm): 7.30 (s, 1H), 7.20-7.10 (d, 1H), 7.10-7.00 (d, 1H), 3.80 (s, 2H), 2.90 (s, 4H), 2.60 (s, 3H), 2.40 (s, 3H).

Example 2A

Water (26.25 kg) was charged to a 50-L glass cylindrical jacketed reactor followed by p-tolylhydrazine HCl 7 (1.75 kg). Dissolution occurred after 15 min of stirring at RT and N-methyl-4-piperidone (1.56 kg) was added over a period of 4 min. The batch was heated to a range of 45-55° C. and concentrated HCl was added (37%, 3.97 kg) over 50 min. The solution was held for 17 h before a sample was taken, at which point the HPLC IPC indicated 0.07A % p-tolylhydrazine remaining. The reaction was cooled to 30-45° C. and addition of approximately 4.5 L of 6.25 N NaOH brought the solution to pH 3.2. Slight precipitation that occurred at this pH did not re-dissolve after the addition was discontinued. MTBE (1.94 kg) was added and precipitation continued upon further addition of approximately 4 L of 6.25 N NaOH to bring the final pH to 12.4. The suspension was allowed to stir for 30 min at 30-45° C. and was cooled over 1.5 h to a range of 5-15° C. The batch was held for 30 min followed by a fast filtration. The cake was washed with water (8.75 kg) and cold MTBE (3.89 kg) and conditioned on the filter for 1 h before being transferred to drying trays. The batch was dried under reduced pressure at 70° C. for 68 h to reduce the water level to <1.0%. The carboline free base (1.99 kg) was isolated in 90% yield (>99.9A % by HPLC). $^1$H NMR (DMSO-d$_6$, free base) δ (ppm) 7.2 (d, 1H), 7.15 (s, 1H), 6.95 (d, 1H), 4.5 (m, 1H), 4.2 (m, 1H), 3.6 (m, 1H), 3.2 (m, 1H), 3.0 (m, 2H), 2.9 (s, 3H), 2.4 (s, 3H).

Example 3

Preparation of 2,3,4,5-tetrahydro-2-methyl-1H-pyrido[4,3-b]indole (Compound 5)

Phenyl hydrazine hydrochloride (1 equiv.) and 1-methylpiperidin-4-one hydrochloride (0.76-1.4 equiv.) is dissolved in EtOH and stirred at 80-90° C. overnight. The reaction is monitored by TLC. Upon completion, the reaction mixture is cooled to RT and the solvent is evaporated to dryness. The residue is dissolved in EtOAc and washed with a saturated sodium bicarbonate solution. The organic layer is dried over anhydrous sodium sulfate and evaporated to dryness to afford 2-methyl-2,3,4,5-tetrahydro-1H-pyrido[4,3-b]indole.

Example 3A

Phenyl hydrazine hydrochloride (5 g, 34.57 mmol) and 1-methylpiperidin-4-one hydrochloride (4.5 g, 30.1 mmol, 1 eq.) was dissolved in of ethanol (150 mL) and stirred at 80-90° C. for overnight. The reaction was monitored by TLC. The mixture was cooled to RT, solvent was concentrated under reduced pressure. The residue was dissolved in EtOAc, washed with saturated sodium bicarbonate solution. Organic layer was dried over anhydrous sodium sulfate and concentrated under reduced pressure to afford 3.0 g of 2-methyl-2,3,4,5-tetrahydro-1H-pyrido[4,3-b]indole. $^1$H NMR (CDCl$_3$, free base) δ (ppm) 8.0 (bs, 1H), 7.4 (d, 1H), 7.35 (d, 1H), 7.2-7.0 (m, 2H), 3.7 (s, 2H), 2.9 (s, 4H), 2.6 (s, 3H).

Example 4

Preparation of 2-ethyl-2,3,4,5-tetrahydro-1H-pyrido[4,3-b]indole (Compound 7)

To a solution of phenylhydrazine hydrochloride (1 equiv.) in EtOH is added 1-ethylpiperidin-4-one hydrochloride (0.76-1.4 equiv.) and the reaction mixture is heated at 80° C. for 16 h. After completion of the reaction, e.g., as monitored by liquid chromatography-mass spectrometry (LCMS), the reaction mixture is concentrated to dryness and basified with aq. saturated NaHCO$_3$ and extracted in EtOAc. The organic layer is separated, dried over sodium sulfate and concentrated to obtain 2-ethyl-2,3,4,5-tetrahydro-1H-pyrido[4,3-b]indole.

Example 4A

To a solution of phenylhydrazine hydrochloride (1 equiv) in ethanol was added 1-ethylpiperidin-4-one hydrochloride (1 equiv) and heated at 80° C. for 16 h. After completion of the reaction (monitored by LCMS). The reaction mixture was concentrated under vacuum and basified with aq. saturated NaHCO$_3$, extracted with EtOAc, the organic layer was separated dried over sodium sulfate and concentrated under reduced pressure to obtain 2-ethyl-2,3,4,5-tetrahydro-1H-pyrido[4,3-b]indole. $^1$H NMR (CDCl$_3$, free base) δ (ppm) 7.8 (bs, 1H), 7.4 (d, 1H), 7.2-7.0 (m, 3H), 3.7 (s, 2H), 2.9 (s, 4H), 2.7-2.6 (q, 2H), 1.2 (t, 3H).

Example 5

Preparation of 2-ethyl-2,3,4,5-tetrahydro-8-methyl-1H-pyrido[4,3-b]indole (Compound 9)

To a solution of p-tolylhydrazine hydrochloride (1 equiv.) in EtOH is added 1-ethylpiperidin-4-one hydrochloride (0.76-1.4 equiv.) and the contents are heated at 80° C. for 16 h. After completion of the reaction, as monitored by LCMS, the reaction mixture is concentrated to dryness and basified with aq. saturated NaHCO$_3$. The reaction product is extracted with EtOAc and the organic layer is separated, dried over sodium sulfate and concentrated to obtain 2-ethyl-8-methyl-2,3,4,5-tetrahydro-1H-pyrido[4,3-b]indole.

Example 5A

To a solution of p-tolylhydrazine hydrochloride (5.0 g, 31.5 mmol) in Ethanol (150 mL) was added 1-ethylpiperidin-4-one hydrochloride (4.0 g, 24.5 mmol) and heated at 80° C. for 16 h. After completion of the reaction (monitored by LCMS). The reaction mixture was concentrated to dryness and basified with aq. saturated NaHCO$_3$, extracted with EtOAc, the organic layer was separated dried over sodium sulfate and concentrated under vacuum to obtain 4.8 g (Yield 71.0%) of 2-ethyl-8-methyl-2,3,4,5-tetrahydro-1H-pyrido[4,3-b]indole. $^1$H NMR (CDCl$_3$, free base) δ (ppm) 7.7 (bs, 1H), 7.2-7.1 (m, 2H), 6.9 (d, 1H), 3.8 (s, 2H), 2.9 (s, 4H), 2.7 (q, 2H), 2.4 (s, 3H), 1.2 (t, 3H).

Example 6

Preparation of 6,8-dichloro-2,3,4,5-tetrahydro-2-methyl-1H-pyrido[4,3-b]indole (Compound 11)

2,4-Dichlorophenyl hydrazine hydrochloride (1 equiv.) is taken in 7% sulfuric acid in 1,4-dioxan. N-Methylpiperidine-4-one (0.76-1.4 equiv.) is added and the contents are stirred at RT for 15 min., followed by heating at 80° C. for 14 h. After completion of the reaction, as monitored by LCMS, the solvent is removed in vacuo, basified with saturated aq. NaHCO$_3$ and extracted with EtOAc. The organic layer is separated, dried over anhydrous sodium sulfate and concentrated. The resulting crude product is purified by column chromatography to afford 6,8-dichloro-2-methyl-2,3,4,5-tetrahydro-1H-pyrido[4,3-b]indole.

Example 6A 2,4-Dichlorophenylhydrazine hydrochloride (1.0 g, 4.68 mmol) was dissolved in 7% H$_2$SO$_4$ in 1,4-dioxan (50 mL) and N-methylpiperidine-4-one (0.76 g, 5.0 mmol) was added and stirred at RT for 15 min, heated at 80° C. for 14 h. After completion of the reaction (monitored by LCMS), solvent was removed in vacuum, basified with saturated aq. NaHCO$_3$ and extracted with EtOAc. Organic layer was separated, dried over anhydrous sodium sulfate and concentrated under vacuum. The resulting product was purified by column chromatography to afford 0.58 g of 6,8-dichloro-2-methyl-2,3,4,5-tetrahydro-1H-pyrido[4,3-b]indole.

Example 7

Preparation of 8-chloro-6-fluoro-2,3,4,5-tetrahydro-2-methyl-1H-pyrido[4,3-b]indole (Compound 13)

4-Chloro-2-fluorophenyl hydrazine hydrochloride (1 equiv.) is taken in 7% sulfuric acid in 1,4-dioxan. N-Methylpiperidine-4-one (0.76-1.4 equiv.) is added and the contents are stirred at RT for 10 min. The reaction mixture is then stirred at 100° C. for 6 h. The reaction is monitored by TLC and LCMS. After completion of the reaction, the reaction mixture is concentrated and then slowly quenched with aq. NaHCO$_3$ solution, followed by extraction with EtOAc. The organic layer is dried over anhydrous sodium sulfate and evaporated to dryness. The crude product is purified by column chromatography to afford 8-chloro-6-fluoro-2-methyl-2,3,4,5-tetrahydro-1H-pyrido[4,3-b]indole.

Example 7A

4-Chloro-2-fluoro hydrazine hydrochloride (3 g, 15.3 mmol) was dissolved in 7% H$_2$SO$_4$ in 1,4-dioxane (150 mL), N-methylpiperidine-4-one (2.28 g, 15.3 mmol) was added and stirred at RT for 10 min. Reaction mixture was stirred at 100° C. for 6 h. Reaction was monitored by TLC & LCMS. After completion of the reaction, reaction mixture was concentrated under vacuum and slowly quenched with aq. NaHCO$_3$ solution, extracted with EtOAc. Organic layer was dried over anhydrous sodium sulfate and concentrated under vacuum and purified by column chromatography to afford 1.2 g of 8-chloro-6-fluoro-2-methyl-2,3,4,5-tetrahydro-1H-pyrido[4,3-b]indole. $^1$H NMR (CDCl$_3$, freebase) δ (ppm) 8.1 (bs, 1H), 7.15 (s, 1H), 6.9-6.8 (d, 1H), 3.65 (s, 2H), 2.95-2.8 (dd, 4H), 2.6 (s, 3H).

Example 8

Preparation of 8-Ethyl-2-methyl-2,3,4,5-tetrahydro-1H-pyrido[4,3-b]indole (Compound 15)

Sulfuric acid is added to a solution of 4-ethyl phenyl hydrazine hydrochloride (1 equiv.) in dioxane, and stirred for 5 min. at RT. N-Methyl piperidone (0.76-1.4 equiv.) is added and the mixture is heated at 80° C. for 3 h. After completion, as monitored by TLC, the reaction mixture is concentrated under reduced pressure and basified to pH 10 using 10% aqueous KOH solution, extracted with EtOAc, dried over anhydrous sodium sulfate and concentrated under reduced pressure using rotary evaporator to provide the desired compound.

Example 8A

Sulfuric acid (2 mL) was added to a solution of 4-Ethyl phenyl hydrazine hydrochloride (2.0 g, 11 mmol) in dioxane (30 mL), and allowed to stir for 5 min at RT. N-methylpiperidone (1.7 g, 13 mmol) was added and the mixture was heated at 80° C. for 3 h. After completion of reaction (monitored by TLC), reaction mixture was concentrated to ~20 mL under reduced pressure and basified to pH 10 using 10% aqueous KOH solution. The mixture was extracted with EtOAc (3×100 mL), dried over anhydrous sodium sulfate and concentrated under reduced pressure using rotary evaporator to provide the desired compound as a brown colored solid (0.35 g, 82% yield).

Example 9

Preparation of 8-Isopropyl-2-methyl-2,3,4,5-tetrahydro-1H-pyrido[4,3-b]indole (Compound 2)

Sulfuric acid is added to a solution of 4-isopropyl phenyl hydrazine hydrochloride (1 equiv.) in dioxane, and stirred for 5 min. at RT. N-Methyl piperidone (0.76-1.4 equiv.) is added and the mixture is heated at 80° C. for 2 h. After completion, as monitored by TLC, the reaction mixture is concentrated under reduced pressure and basified to pH 10 using 10% aqueous KOH solution, extracted with EtOAc, dried over anhydrous sodium sulfate and concentrated under reduced pressure using rotary evaporator to provide the desired compound.

Example 9A

Sulfuric acid (14 mL) was added to a solution of 4-Isopropyl phenyl hydrazine hydrochloride (7.0 g, 37 mmol) in dioxane (186 mL) and allowed to stir for 5 min at RT. N-methyl piperidone (4.6 mL, 37 mmol) was added and the mixture was heated at 80° C. for 2 h. After completion of reaction (monitored by TLC), reaction mixture was concentrated to ~20 mL under reduced pressure and basified to pH 10 using 10% aqueous KOH solution. The mixture was extracted with EtOAc (3×200 mL), dried over anhydrous sodium sulfate and concentrated under reduced pressure using rotary evaporator to provide the desired compound as yellow colored solid (7.0 g, 82% yield). $^1$H NMR (DMSO-d$_6$, free base) δ (ppm) 10.6 (s, 1H), 7.16 (s, 1H), 7.13 (d, 1H), 6.88 (d, 1H), 3.48 (s, 2H), 2.9 (m, 1H), 2.74 (m, 2H), 2.68 (m, 2H), 2.40 (s, 3H), 1.21 (d, 6H).

Example 10

Preparation of 8-chloro-9-fluoro-2,3,4,5-tetrahydro-2-methyl-1H-pyrido[4,3-b]indole (Compound 4)

Sulfuric acid is added to a solution of 4-chloro-3-fluorophenyl hydrazine hydrochloride (1 equiv.) in dioxane, and stirred for 5 min. at RT. N-Methyl piperidone (0.76-1.4 equiv.) is added and the mixture is heated at 80° C. for 3 h. After completion, as monitored by TLC, the reaction mixture is concentrated under reduced pressure and basified to pH 10 using 10% aqueous KOH solution, extracted with EtOAc, dried over anhydrous sodium sulfate and concentrated under reduced pressure using rotary evaporator to give a mixture or regioisomeric products. For this Example, silica gel chromatography separates the title compound from the other regioisomer (Compound 6) obtained in Example 11.

Example 10A

Sulfuric acid (1.0 mL) was added to a solution of 4-chloro-3-fluorophenylhydrazine hydrochloride (0.5 g, 2.1 mmol) in dioxane (15 mL), and allowed to stir for 5 min at RT. N-methylpiperidone (0.3 mL, 2.3 mmol) was added and the mixture was heated at 80° C. for 3 h. After completion of reaction (monitored by TLC), reaction mixture was concentrated under reduced pressure and basified to pH 10 using 10% aqueous KOH solution. The mixture was extracted with EtOAc (3×100 mL), dried over anhydrous sodium sulfate and concentrated under reduced pressure using rotary evaporator to give the mixture of 6 (major) and 7 (minor) as a brown colored solid (0.17 g, 33% yield).

Example 11

Preparation of 8-Chloro-7-fluoro-2-methyl-2,3,4,5-tetrahydro-1H-pyrido[4,3-b]indole (Compound 6)

Sulfuric acid is added to a solution of 4-chloro-3-fluorophenyl hydrazine hydrochloride (1 equiv.) in dioxane, and stirred for 5 min. at RT. N-Methyl piperidone (0.76-1.4 equiv.) is added and the mixture is heated at 80° C. for 3 h. After completion, as monitored by TLC, the reaction mixture is concentrated under reduced pressure and basified to pH 10 using 10% aqueous KOH solution, extracted with EtOAc, dried over anhydrous sodium sulfate and concentrated under reduced pressure using rotary evaporator to give a mixture or regioisomeric products. For this Example, silica gel chromatography separates the title compound from the other regioisomer (Compound 4) obtained in Example 10.

Example 11A

Sulfuric acid (1.0 mL) was added to a solution of 4-chloro-3-fluoro phenyl hydrazine hydrochloride (0.5 g, 2.1 mmol) in dioxane (15 mL), and allowed to stir for 5 min at RT. N-methylpiperidone (0.3 mL, 2.3 mmol) was added and the mixture was heated at 80° C. for 3 h. After completion of reaction (monitored by TLC), reaction mixture was concentrated under reduced pressure and basified to pH 10 using 10% aqueous KOH solution. The mixture was extracted with EtOAc (3×100 mL), dried over anhydrous sodium sulfate and concentrated under reduced pressure using rotary evaporator to give the mixture of 6 (major) and 7 (minor) as a brown colored solid (0.17 g, 33% yield). $^1$H NMR (DMSO-$d_6$, free base) δ (ppm) 11.1 (s, 1H), 7.48 (d, 1H), 7.27 (d, 1H), 3.5 (s, 2H), 2.76 (m, 2H), 2.70 (m, 2H), 2.41 (s, 3H).

Example 12

Preparation of Methyl 2,3,4,5-tetrahydro-2-methyl-1H-pyrido(4,3-b)indole-8-carboxylate (Compound 8)

Methyl-4-hydrazinylbenzoate hydrochloride (1 equiv.) and 1-methylpiperidin-4-one HCl (0.76-1.4 equiv.) are taken in aqueous HCl and heated at 100° C. overnight (the product was detected by LCMS). The reaction mixture is concentrated and refluxed (90° C.) in methanolic HCl overnight (product was detected by LCMS and TLC). The reaction mixture is concentrated and basified with aqueous NaHCO$_3$ solution and extracted with EtOAc. The crude product is crystallized in DCM and ether and hexane.

Example 12A

Methyl-4-hydrazinylbenzoate hydrochloride (10 g, 50 mmol) and 1-methylpiperidin-4-one hydrochloride (7.3 g, 50 mmol) were dissolved in aqueous HCl and heated at 100° C. overnight (product was detected by LCMS). The reaction mixture was concentrated under vacuum and refluxed (90° C.) in methanolic HCl overnight (product was detected by LCMS & TLC). The reaction mixture was concentrated under vacuum and basified with aqueous NaHCO$_3$ solution and extracted with EtOAc, dried over anhydrous sodium sulfate and concentrated under reduced pressure to obtain product. The product was crystallized in DCM and ether and hexane. Yield 5.1 g. $^1$H NMR (DMSO-$d_6$, free base) δ (ppm): 8.55 (s, 1H), 8.27 (s, 1H) 7.82-7.79 (d, 1H), 7.24-7.20 (d, 1H), 3.94 (s, 3H), 3.72 (s, 2H), 3.85 (s, 4H) 2.60 (s, 3H).

Example 13

Preparation of 2,3,4,5-tetrahydro-2-methyl-8-(trifluoromethoxy)-1H-pyrido[4,3-b]indole (Compound 10)

(4-(Trifluoromethoxy)phenyl)hydrazine hydrochloride (1 equiv.) is taken in 7% sulfuric acid in 1,4-dioxane. 1-Methylpiperidin-4-one hydrochloride (0.76-1.4 equiv.) is added and the mixture is stirred at 80° C. for 6 h. The reaction is monitored by TLC and LCMS. After completion of the reaction, the reaction mixture is concentrated, then slowly quenched with aq. NaHCO$_3$ solution and extracted with EtOAc. The organic layer is dried over anhydrous sodium sulfate, evaporated to dryness and purified by column chromatography to afford 2-methyl-8-(trifluoromethoxy)-2,3,4,5-tetrahydro-1H-pyrido[4,3-b]indole.

Example 13A (4-(Trifluoromethoxy)phenyl)hydrazine hydrochloride (1 g, 4.37 mmol) was dissolved in 7% H$_2$SO$_4$ in 1,4-dioxane (50 mL), 1-methylpiperidin-4-one hydrochloride (0.65 g, 4.37 mmol) was added and stirred at 80° C. for 6 h. Reaction was monitored by TLC & LCMS. After completion of the reaction, reaction mixture was concentrated under vacuum and slowly quenched with aq. NaHCO$_3$ solution, extracted with EtOAc. Organic layer was dried over anhydrous sodium sulfate and concentrated under reduced pressure and purified by column chromatography to afford 0.9 g of 2-methyl-8-(trifluoromethoxy)-2,3,4,5-tetrahydro-1H-pyrido[4,3-b]indole. $^1$H NMR (CDCl$_3$, free base) δ (ppm) 7.9 (bs, 1H), 7.3-7.2 (m, 2H), 7.1-6.9 (d, 1H), 3.7 (s, 2H), 2.9-2.8 (m, 4H), 2.6 (s, 3H).

Example 14

Preparation of 2,3,4,5-tetrahydro-2,6-dimethyl-1H-pyrido[4,3-b]indole (Compound 12)

O-Tolyl hydrazine hydrochloride (1 equiv.) is taken in EtOH. 1-Methylpiperidin-4-one hydrochloride (0.76-1.4 equiv.) and ethanolic HCl is added (pH acidic) and the contents are stirred at 80° C. for 5 h. The reaction is monitored by TLC. After completion of the reaction, the reaction mixture is concentrated. The residue is dissolved in aq NaHCO$_3$ solution and extracted with EtOAc. The organic layer is dried over anhydrous sodium sulfate and evaporated under reduced pressure to afford 2,6-dimethyl-2,3,4,5-tetrahydro-1H-pyrido[4,3-b]indole.

Example 14A

O-Tolyl hydrazine hydrochloride (3.0 g, 18.9 mmol) was dissolved in of ethanol (10 mL), 1-methylpiperidin-4-one hydrochloride (2.8 g, 18.9 mmol) and ethanolic HCl (10 mL) was added (pH acidic) and stirred at 80° C. for 5 h. Reaction was monitored by TLC. After completion of the reaction, reaction mixture was concentrated under vacuum. Residue was dissolved in aq NaHCO$_3$ solution, extracted with EtOAc. Organic layer was dried over anhydrous sodium sulfate and evaporated under reduced pressure to afford 2.5 g of 2,6-dimethyl-2,3,4,5-tetrahydro-1H-pyrido[4,3-b]indole. $^1$H NMR (CDCl$_3$, free base) δ (ppm) 7.65 (s, 1H), 7.01 (t, 1H), 6.9 (d, 1H), 3.61 (s, 2H), 2.89-2.80 (m, 4H), 2.58 (s, 3H), 2.41 (s, 3H).

Example 15

Preparation of 8-tert-butyl-2,3,4,5-tetrahydro-2-methyl-1H-pyrido[4,3-b]indole (Compound 14)

(4-tert-Butylphenyl)hydrazine hydrochloride (1 equiv.) is taken in 7% sulfuric acid in 1,4-dioxane. 1-Methylpiperidin-4-one hydrochloride (0.76-1.4 equiv.) is added and the contents are stirred at 80° C. for 3 h. The reaction is monitored by TLC and LCMS. After completion of the reaction, the reaction mixture is concentrated and then quenched with aq. NaHCO$_3$ solution, followed by extracted with EtOAc. The organic layer is dried over anhydrous sodium sulfate, evaporated to dryness and purified by column chromatography (5% MeOH-DCM) to afford 8-tert-butyl-2-methyl-2,3,4,5-tetrahydro-1H-pyrido[4,3-b]indole.

Example 15A (4-tert-Butylphenyl)hydrazine hydrochloride (1 g, 4.98 mmol) was dissolved in 7% H$_2$SO$_4$ in 1,4-dioxane (50 mL), 1-methylpiperidin-4-1 hydrochloride (0.742 g, 4.98 mmol) was added and stirred at 80° C. for 3 h. Reaction was monitored by TLC & LCMS. After completion of the reaction, reaction mixture was concentrated under vacuum and quenched with aq. NaHCO$_3$ solution, extracted with EtOAc. Organic layer was dried over anhydrous sodium sulfate and concentrated under vacuum and purified by column chromatography (5% Methanol-DCM) to afford 0.51 g of 8-tert-butoxy-2-methyl-2,3,4,5-tetrahydro-1H-pyrido[4,3-b]indole. $^1$H NMR (DMSO-d$_6$, free base) δ (ppm) 11.1 (bs, 1H), 10.6 (bs, 1H), 7.4 (s, 1H), 7.3-7.2 (d, 1H), 7.2-7.1 (d, 1H), 4.6-4.5 (m, 1H), 4.3 (bs, 1H), 3.7 (bs, 1H), 3.5 (bs, 1H), 3.2-3.3 (m, 2H), 2.9 (s, 3H), 1.3 (s, 9H).

Example 16

Preparation of 2,3,4,5-tetrahydro-8-iodo-2-methyl-1H-pyrido[4,3-b]indole (Compound 16)

To a solution of compound 4-iodophenylhydrazine (1 equiv.) in 1,4-dioxane (50 mL) is added conc. sulfuric acid, followed by dropwise addition of 1-methyl-4-piperidone (1 equiv.) at RT. The reaction mixture is heated at 70° C. for 90 min., evaporated, diluted with water and the pH is adjusted to 12 with 40 mL of 15% aq. KOH solution. The reaction mixture is extracted with EtOAc, followed by brine wash, dried over sodium sulfate and evaporated under vacuum. The crude product is column purified over 230-400 silica gel using a gradient of 0-5% of MeOH in EtOAc. Note 1: The reaction temperature should be 70° C. Higher temperature results in the de-iodo carboline.

Example 16A

To a suspension of 4-iodophenylhydrazine hydrochloride (2.0 g, 0.0074 mol) in dioxane (30 mL) at RT was added conc. H$_2$SO$_4$ (0.7 mL, 0.0171 mol) dropwise and the reaction mixture was stirred for 5 min. To this was added N-methyl-4-piperidone (0.838 g, 0.0074 mol) and the reaction mixture was stirred at RT for 10 min and heated at 70° C. for 90 min. Reaction monitored by TLC. The solvent was evaporated and pH adjusted to 9-10 by 10% KOH Solution. The product was extracted with (3×50 mL) EtOAc. Combined organic layer washed with water and brine and dried over sodium sulfate, concentrated under vacuum and product purified by column chromatography (100-200 mesh silica) in solvent system (0-10%, DCM/MeOH). Obtained 1.8 g of brown solid. $^1$H NMR (CDCl$_3$, free base) δ (ppm) 7.70 (s, 1H), 7.38 (d, 1H), 7.05 (d, 1H), 3.60 (s, 2H), 2.90 (m, 4H), 2.58 (s, 3H).

Example 17

Preparation of 8-chloro-2-cyclopropyl-2,3,4,5-tetrahydro-1H-pyrido[4,3-b]indole (Compound 17)

Sulfuric acid is added to a solution of 4-Chloro phenyl hydrazine hydrochloride (1 equiv.) in dioxane and stirred for 5 min. at RT. N-cyclopropyl piperidone (1 equiv.) is added and the mixture is heated at 80° C. for 2 h. After completion, as monitored by TLC, the reaction mixture is concentrated under reduced pressure and basified to pH 10 using 10% aqueous KOH solution. The reaction product is extracted with EtOAc, dried over anhydrous sodium sulfate and concentrated under reduced pressure using rotary evaporator to provide the desired compound.

Example 17A

Sulfuric acid (3.5 mL) was added to a solution of 4-chlorophenylhydrazine hydrochloride (1 eq.) in dioxane (50 mL), and allowed to stir for 5 min at RT. N-cyclopropylpiperidone (1 eq.) was added and the mixture was heated at 80° C. for 2 h. After completion of reaction (monitored by TLC), reaction mixture was concentrated to ~20 mL under reduced pressure and basified to pH 10 using 10% aqueous KOH solution. The mixture was extracted with EtOAc (3×200 mL), dried over anhydrous sodium sulfate and concentrated under reduced pressure using rotary evaporator to provide the desired compound as a brown colored solid (1.3 g, 53% yield).

Example 18

Preparation of 8-fluoro-2,3,4,5-tetrahydro-2-methyl-1H-pyrido[4,3-b]indole (Compound 18)

Sulfuric acid is added to a solution of 4-fluorophenyl hydrazine hydrochloride (1 equiv.) in dioxane and stirred for 5 min. at RT. N-Methyl piperidone (0.76-1.4 equiv.) is added and the mixture is heated at 80° C. for 2 h. After completion, as monitored by TLC, the reaction mixture is concentrated under reduced pressure and basified to pH 10 using 10% aqueous KOH solution. The reaction mixture is extracted with EtOAc, dried over anhydrous sodium sulfate and concentrated under reduced pressure using rotary evaporator to provide the desired compound.

Example 18A

Sulfuric acid (3.5 mL) was added to a solution of 4-fluorophenylhydrazine hydrochloride (2.0 g, 12.3 mmol) in dioxane (50 mL), and allowed to stir for 5 min at RT. N-methylpiperidone (1.38 g, 12 mmol) was added and the mixture was heated at 80° C. for 2 h. After completion (TLC), reaction mixture was concentrated to ~20 mL under reduced pressure and basified to pH 10 using 10% aqueous KOH solution. The reaction mixture was extracted with EtOAc (3×200 mL), dried over anhydrous sodium sulfate and concentrated under reduced pressure using rotary evaporator to provide the desired compound as a brown colored solid (1.3 g, 53% yield). $^1$H NMR (CDCl$_3$, free base) δ (ppm) 7.90 (bs, 1H), 7.18 (m, 1H), 7.05 (d, 1H), 6.82 (t, 1H), 3.60 (s, 2H), 2.90 (m, 2H), 2.82 (m, 2H), 2.38 (s, 3H).

Example 19

Preparation of 2-methyl-5-(oxiran-2-yl)pyridine (Compound 19)

DMSO is added to NaH 60% dispersion in oil (1-1.8 equiv.) and heated to 65° C. for 1 h. THF is added to the mixture at the same temperature and heated for another 10 min. After 10 min., the reaction mixture is cooled to 0° C. Trimethylsulfonium iodide (1-1.2 equiv.) is added and the contents are stirred for 10 min. A solution of 6-methylnicotinaldehyde (1 equiv.) in THF is added dropwise. After complete addition, the reaction mixture is stirred at RT for 2 h, and monitored by LCMS. The reaction mixture is poured in ice water, extracted in diethyl ether, dried over sodium sulfate and concentrated at 25° C. to get crude product 2-methyl-5-(oxiran-2-yl)pyridine.

Example 19A

DMSO (4 mL) was added to NaH 60% dispersion in oil (0.314 g, 7.8 mmol, 1.3 eq.) and heated it to 65° C. for 1 h. THF (10 mL) was added at the same temperature and heated for another 10 min. After 10 min, reaction mixture was cooled to 0° C. Trimethylsulfonium iodide (1.2 g, 5.9 mmol, 1 eq.) was added and stirred for 10 min and solution of 6-methylnicotinaldehyde (0.720 g, 5.9 mmol, 1 eqv) in THF was added dropwise. After complete of addition, reaction mixture was stirred at RT for 2 h. Product was detected by LCMS. Reaction mixture was poured in ice water. Product was extracted in diethyl ether (4×50 mL), dried over sodium sulfate and concentrated under vacuum at 25° C. to get product 2-methyl-5-(oxiran-2-yl)pyridine (1.1 g).

Example 20

Preparation of 2-(4-fluorophenyl)-2-methyloxirane (Compound 21)

To a solution of trimethylsulfonium iodide (1-1.2 equiv.) in DMSO is added sodium hydride 50%-55% dispersion in oil (1-1.8 equiv.) portionwise over 5 min. and stirred for 1 h at RT. A solution of 1-(4-fluorophenyl)ethanone (1 equiv.) in DMSO is added to the reaction mixture dropwise over 20 min. and stirred at RT for 4 h. The reaction is monitored by TLC and at completion the reaction mixture is poured in water (100 mL) and extracted with EtOAc. The combined organic extract is washed with water, followed by brine, dried over sodium sulfate and evaporated to dryness.

Example 20A

To a solution of trimethylsulfonium iodide (3.5 g, 17.15 mmol, 1.2 eq.) in DMSO (30 mL) was added sodium hydride 50%-55% dispersion in oil (0.97 g, 22.2 mmol, 1.5 eq.) portionwise over 5 min. and stirred for an hour at RT. A solution of 1-(4-fluorophenyl)ethanone (2 g, 14.47 mmol, 1 eq.) in DMSO (10 mL) was added to the reaction mixture dropwise over 20 min. It was stirred at RT for 4 h. TLC was checked and the reaction mixture was poured in 100 mL water and extracted with EtOAc (3×100 mL). The combined organic extract was washed with water (2×150 mL), followed by brine. It was dried over sodium sulfate and concentrated under vacuum. Yield: 2.2 g brown oil. $^1$H NMR (Acetone-d$_6$, free base) δ (ppm) 7.43-7.39 (dd, 2H), 7.11 (t, 2H), 2.95 and 2.72 (dd, 2H), 1.65 (s, 3H).

Example 21

Preparation of 2-p-tolyloxirane (Compound 23)

To a solution of Trimethylsulfonium iodide (1-1.2 equiv.) in DMSO is added sodium hydride 60% dispersion in oil (1-1.8 equiv.) portionwise over 5 min. and stirred for 1 h at RT. A solution of 4-methylbenzaldehyde (1 equiv.) in DMSO is added to the reaction mixture dropwise over 20 min. and stirred at RT for 4 h. The reaction is monitored by TLC and the reaction mixture poured in water and extracted with EtOAc. The combined organic extract is washed with water, followed by brine, and dried over anhydrous sodium sulfate and evaporated to dryness to afford 2-p-tolyloxirane as crude product.

Example 21A

To a solution of trimethylsulfonium iodide (10.28 g, 50.37 mmol, 1.2 eq.) in DMSO (70 mL) was added sodium hydride 60% dispersion in oil (2.82 g, 70.5 mmol, 1.7 eq.) portionwise over 5 min. and stirred for an hour at RT. A solution of 4-methylbenzaldehyde (5.0 g, 42.0 mmol, 1 eq.) in DMSO (25 mL) was added to the reaction mixture dropwise over 20 min. It was stirred at RT for 4 h. TLC was checked and the reaction mixture was poured in 150 mL water and extracted with EtOAc. The combined organic extract was washed with water and brine. It was dried over anhydrous sodium sulfate and concentrated under vacuum to afford 5.2 g of 2-p-tolyloxirane as product. $^1$H NMR (CDCl$_3$, free base) δ (ppm) 7.2-7.1 (m, 4H), 3.81-3.8 (t, 1H), 3.2-3.1 (m, 1H), 2.6-2.5 (m, 1H), 2.4 (s, 3H).

Example 22

Preparation of 3-(oxiran-2-yl)pyridine (Compound 25)

Sodium hydride 50% dispersion in oil (1-1.8 equiv.) is taken in DMSO and heated at 65° C. for 1 h. THF is added to at the mixture at the same temperature and heated for 10 min. The reaction mixture is cooled to 0° C. and Trimethylsulfonium iodide (1-1.2 equiv.) is added, followed by nicotinaldehyde (1 equiv.) and the contents are stirred at RT for 1 h. The reaction is monitored by TLC and LCMS. After completion of the reaction, the reaction mixture is poured in ice and extracted with diethyl ether, dried over anhydrous sodium sulfate and evaporated under reduced pressure to afford crude product (3-(oxiran-2-yl)pyridine).

Example 22A

Sodium hydride 50% dispersion in oil (1.64 g, 34.2 mmol, 1.8 eq.) was dissolved in DMSO (12 mL) and heated at 65° C. for 1 h. THF (36 mL) was added at the same temperature and heated for 10 min. Reaction mixture was cooled to 0° C. and trimethylsulfonium iodide (3.81 g, 18.6 mmol, 1 eq.) was added, followed by nicotinaldehyde (2 g, 18.6 mmol, 1 eq.) and stirred for 1 h. Reaction was monitored by TLC and LCMS. After completion of the reaction, reaction mixture was poured in ice and extracted with diethyl ether, dried over anhydrous sodium sulfate and evaporated under reduced pressure to afford 1 g of product (3-(oxiran-2-yl)pyridine). $^1$H NMR (CDCl$_3$, free base) δ (ppm) 8.6-8.5 (m, 2H), 7.5 (d, 1H), 7.3 (m, 1H), 3.9 (t, 1H), 3.2 (t, 1H), 2.9 (t, 1H).

Example 23

Preparation of 2-(2,4,6-trifluorophenyl)-2-methyloxirane (Compound 27)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents were stirred for 10 min. after which the solution of 1-(2,4,6-trifluorophenyl)ethanone (1 equiv.) in THF is added dropwise. After complete addition, the reaction mixture is stirred at RT for 2 h; the reaction is monitored for completion. After completion, the reaction mixture is poured in ice water, extracted in diethyl ether dried over sodium sulfate and concentrated at 25° C. to get the crude product.

Example 23A

DMSO was added to NaH (1 equiv) and heated to 65° C. for 1 h. THF was added at same temp. and heated for another 10 min. After 10 min, reaction mixture was cooled to 0° C. Trimethylsulfonium iodide (1 equiv) was added and stirred for 10 min after which the solution of 1-(2,4,6-trifluorophenyl)ethanone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product.

Example 24

Preparation of 2-(2,4-dichlorophenyl)-2-methyloxirane (Compound 29)

DMSO is added to NaH (1-1.8 equiv.) and heated to 65° C. for one h. THF is added at same temperature and heated for another 10 min. After 10 min., the reaction mixture is cooled to 0° C. Trimethylsulfonium iodide (1-1.2 equiv.) is added and the contents are stirred for 10 min. after which the solution of 1-(2,4-dichlorophenyl)ethanone (1 equiv.) in THF is added dropwise. After complete addition, the reaction mixture is stirred at RT for 2 h; the reaction is monitored by LCMS. After completion, the reaction mixture is poured in ice water, extracted in diethyl ether, dried over sodium sulfate and concentrated at 25° C. to get the crude product.

Example 24A

DMSO was added to NaH (1 equiv) and heated to 65° C. for 1 h. THF was added at same temperature and heated for another 10 min. After 10 min, reaction mixture was cooled to 0° C. Trimethylsulfonium iodide (1 equiv) was added and stirred for 10 min after which the solution of 1-(2,4-dichlorophenyl)ethanone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product. $^1$H NMR (CDCl$_3$, freebase) δ (ppm): 7.40 (d, 1H), 7.23 (m, 2H), 3.01 (d, 1H), 2.79 (d, 1H), 1.62 (s, 3H).

Example 25

Preparation of 2-(2,4-difluorophenyl)-2-methyloxirane (Compound 31)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents are stirred for 10 min. after which the solution of 1-(2,4-difluorophenyl)ethanone (1 equiv.) in THF is added dropwise. After complete addition, the reaction mixture is stirred at RT for 2 h; the reaction is monitored by LCMS. After completion, the reaction mixture is poured in ice water, extracted in diethyl ether, dried over sodium sulfate and concentrated at 25° C. to get the crude product.

Example 25A

DMSO was added to NaH (1 equiv) and heated to 65° C. for 1 h. THF was added at same temperature and heated for another 10 min. After 10 min, reaction mixture was cooled to 0° C. Trimethylsulfonium iodide (1 equiv) was added and stirred for 10 min after which the solution of 1-(2,4-difluorophenyl)ethanone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product. $^1$H NMR (CDCl$_3$, freebase) δ (ppm): 7.41 (m, 1H), 6.81 (m, 2H), 2.98 (d, 1H), 2.79 (d, 1H), 1.59 (s, 3H).

Example 26

Preparation of 2-(3,4-dichlorophenyl)-2-methyloxirane (Compound 33)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents are stirred for 10 min. after which the solution of 1-(3,4-dichlorophenyl)ethanone (1 equiv.) in THF is added dropwise. After complete addition, the reaction mixture is stirred at RT for 2 h; the reaction is monitored by LCMS. After completion, the reaction mixture is poured in ice water, extracted in diethyl ether, dried over sodium sulfate and concentrated at 25° C. to get the crude product.

Example 26A

DMSO was added to NaH (1 equiv) and heated to 65° C. for 1 h. THF was added at same temp. and heated for another 10 min. After 10 min, reaction mixture was cooled to 0° C. Trimethylsulfonium iodide (1 equiv) was added and stirred for 10 min after which the solution of 1-(3,4-dichlorophenyl)ethanone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product. $^1$H NMR (CDCl$_3$, freebase) δ (ppm): 7.42 (d, 1H), 7.39 (m, 1H), 7.18 (m, 1H), 2.98 (d, 1H), 2.76 (d, 1H), 1.65 (s, 3H).

Example 27

Preparation of 2-(3,4-difluorophenyl)-2-methyloxirane (Compound 35)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents are stirred for 10 min. after which the solution of 1-(3,4-difluorophenyl)ethanone (1 equiv.) in THF is added dropwise. After complete addition, the reaction mixture is stirred at RT for 2 h; the reaction is monitored by LCMS. The reaction mixture is poured in ice water, extracted in diethyl ether dried over sodium sulfate and concentrated at 25° C. to get the crude product.

Example 27A

DMSO was added to NaH (1 equiv) and heated to 65° C. for 1 h. THF was added at same temperature and heated for another 10 min. After 10 min, reaction mixture was cooled to 0° C. Trimethylsulfonium iodide (1 equiv) was added and stirred for 10 min after which the solution of 1-(3,4-difluorophenyl)ethanone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product. $^1$H NMR (CDCl$_3$, freebase) δ (ppm): 7.17 (m, 3H), 2.99 (d, 1H), 2.79 (d, 1H), 1.71 (s, 3H).

Example 28

Preparation of 2-(3-chloro-4-fluorophenyl)-2-methyloxirane (Compound 37)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents were stirred for 10 min. after which the solution of 1-(3-chloro-4-fluorophenyl)ethanone (1 equiv.) in THF is added dropwise. After complete addition, the reaction mixture is stirred at RT for 2 h; the reaction is monitored by LCMS. After completion, the reaction mixture is poured in ice water, extracted in diethyl ether, dried over sodium sulfate and concentrated at 25° C. to get the crude product.

Example 28A

DMSO was added to NaH (1 equiv) and heated to 65° C. for 1 h. THF was added at same temperature and heated for another 10 min. After 10 min, reaction mixture was cooled to 0° C. Trimethylsulfonium iodide (1 equiv) was added and stirred for 10 min after which the solution of 1-(3-chloro-4-fluorophenyl)ethanone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product.

Example 29

Preparation of 2-(3-fluoro-4-methoxyphenyl)-2-methyloxirane (Compound 39)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents are stirred for 10 min. after which the solution of 1-(3-fluoro-4-methoxyphenyl)ethanone (1 equiv.) in THF is added dropwise. After complete addition, the reaction mixture is stirred at RT for 2 h; the reaction is monitored by LCMS. After completion, the reaction mixture is poured in ice water, extracted in diethyl ether, dried over sodium sulfate and concentrated at 25° C. to get the crude product.

Example 29A

DMSO was added to NaH (1 equiv) and heated to 65° C. for 1 h. THF was added at same temp. and heated for another 10 min. After 10 min, reaction mixture was cooled to 0° C. Trimethylsulfonium iodide (1 equiv) was added and stirred for 10 min. after which the solution of 1-(3-fluoro-4-methoxyphenyl)ethanone (1 equiv) in THF was added dropwise. After complete addition, the reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product. $^1$H NMR (CDCl$_3$, freebase) δ (ppm): 7.12 (m, 2H), 6.87 (m, 1H), 3.84 (s, 3H), 2.91 (d, 1H), 2.78 (d, 1H), 1.68 (s, 3H).

Example 30

Preparation of 2-(3-fluoro-4-methoxyphenyl)oxirane (Compound 41)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents stirred for 10 min. after which the solution of 3-fluoro-4-methoxybenzaldehyde (1 equiv.) in THF is added dropwise. After complete addition, the reaction mixture is stirred at RT for 2 h; the reaction is monitored by LCMS. The reaction mixture is poured in ice water, extracted in diethyl ether (4×50 mL), dried over sodium sulfate and concentrated at 25° C. to get the crude product.

Example 30A

DMSO was added to NaH (1 equiv) and heated to 65° C. for 1 h. THF was added at same temp. and heated for another 10 min. After 10 min, reaction mixture was cooled to 0° C. Trimethylsulfonium iodide (1 equiv) was added and stirred for 10 min after which the solution of 3-fluoro-4-methoxybenzaldehyde (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product.

Example 31

Preparation of 2-(4-chloro-3-fluorophenyl)-2-methyloxirane Compound 20)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents stirred for 10 min. after which the solution of 1-(4-chloro-3-fluorophenyl)ethanone (1 equiv.) in THF is added dropwise. After complete addition, the reaction mixture is stirred at RT for 2 h; the reaction is monitored by LCMS. The reaction mixture is poured in ice water, extracted in diethyl ether, dried over sodium sulfate and concentrated at 25° C. to get the crude product.

Example 31A

DMSO was added to NaH (1 equiv) and heated to 65° C. for 1 h. THF was added at same temperature and heated for another 10 min. After 10 min, reaction mixture was cooled to 0° C. Trimethylsulfonium iodide (1 equiv) was added and stirred for 10 min after which the solution of 1-(4-chloro-3-fluorophenyl)ethanone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product.

Example 32

Preparation of 2-(4-chlorophenyl)-2-methyloxirane (Compound 22)

DMSO was added to NaH (1 equiv.) and heated to 65° C. for 1 h. THF was added at the same temperature and heated for another 10 min. After 10 min., the reaction mixture was cooled to 0° C. Trimethylsulfonium iodide (1 equiv.) was added and the contents were stirred for 10 min. after which the solution of 1-(4-chlorophenyl)ethanone (1 equiv.) in THF was added dropwise. After complete addition, the reaction mixture was stirred at RT for 2 h; the reaction was monitored by LCMS. After completion, the reaction mixture was poured in ice water, extracted in diethyl ether (4×50 mL), dried over sodium sulfate and concentrated at 25° C. to get the crude product. $^1$H NMR (CDCl$_3$, freebase) δ (ppm): 7.38 (m, 4H), 2.97 (d, 1H), 2.78 (d, 1H), 1.69 (s, 3H).

Example 33

Preparation of 2-(4-fluorophenyl)-2,3-dimethyloxirane (Compound 24)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents stirred for 10 min. after which the solution of 1-(4-fluorophenyl)ethanone (1 equiv.) in THF is added dropwise. After complete addition, the reaction mixture is stirred at RT for 2 h; the reaction is monitored by LCMS. After completion, the reaction mixture was poured in ice water, extracted in diethyl ether, dried over sodium sulfate and concentrated at 25° C. to get the crude product.

Example 33A

DMSO was added to NaH (1 equiv) and heated to 65° C. for 1 h. THF was added at same temperature and heated for another 10 min. After 10 min, reaction mixture was cooled to 0° C. Triethylsulfonium iodide (1 equiv) was added and stirred for 10 min after which the solution of 1-(4-fluorophenyl)ethanone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated at 25° C. to get the product.

Example 34

Preparation of 2-(4-methoxyphenyl)-2-methyloxirane (Compound 26)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents are stirred for 10 min. after which the solution of 1-(4-methoxyphenyl)ethanone (1 equiv.) in THF is added dropwise. After complete addition, the reaction mixture is stirred at RT for 2 h; the reaction is monitored by LCMS. After completion, the reaction mixture is poured in ice water, extracted in diethyl ether, dried over sodium sulfate and concentrated at 25° C. to get the crude product.

Example 33A

DMSO was added to NaH (1 equiv) and heated to 65° C. for 1 h. THF was added at same temperature and heated for another 10 min. After 10 min, reaction mixture was cooled to 0° C. Trimethylsulfonium iodide (1 equiv) was added and stirred for 10 min after which the solution of 1-(4-methoxyphenyl)ethanone (1 equiv) in THF was added drop wise. After complete addition, reaction mixture was stirred at room temperature for 2 h. Product was detected by LCMS. Reaction mixture was poured in ice water. Product was extracted in diethyl ether (4×50 mL), dried over sodium sulfate and concentrated at 25° C. to get the product. $^1$H NMR (CDCl$_3$, freebase) δ (ppm): 7.24 (d, 2H), 6.83 (d, 2H), 3.8 (s, 3H), 2.98 (d, 1H), 2.78 (d, 1H), 1.71 (s, 3H).

Example 35

Preparation of 2-(trifluoromethyl)-2-(4-fluorophenyl)oxirane (Compound 28)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents stirred for 10 min. after which the solution of 2,2,2-trifluoro-1-(4-fluorophenyl)ethanone (1 equiv.) in THF is added dropwise. After complete addition, the reaction mixture is stirred at RT for 2 h; the reaction is monitored by LCMS. The reaction mixture is poured in ice water, extracted in diethyl ether, dried over sodium sulfate and concentrated at 25° C. to get the crude product.

Example 35A

DMSO was added to NaH (1 equiv) and heated to 65° C. for 1 h. THF was added at same temp. and heated for another 10 min. After 10 min, reaction mixture was cooled to 0° C. Trimethylsulfonium iodide (1 equiv) was added and stirred for 10 min after which the solution of 2,2,2-trifluoro-1-(4-fluorophenyl)ethanone (1 equiv) in THF was added dropwise. After complete addition, reaction mixture was stirred at RT for 2 h. Product was detected by LCMS. Reaction mixture was poured in ice water. Product was extracted in diethyl ether (4×50 mL), dried over sodium sulfate and concentrated under vacuum at 25° C. to get the product.

Example 36

Preparation of 2-(trifluoromethyl)-5-(2-methyloxiran-2-yl)pyridine (Compound 30)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents stirred for 10 min. after which the solution of 5-acetyl-2-(trifluoromethyl) pyridine (1 equiv.) in THF is added dropwise. After complete addition, the reaction mixture is stirred at RT for 2 h; the reaction is monitored by LCMS. After completion, the reaction mixture is poured in ice water, extracted in diethyl ether, dried over sodium sulfate and concentrated at 25° C. to get the crude product.

Example 36A

DMSO was added to NaH (1 equiv) and heated to 65° C. for 1 h. THF was added at same temperature and heated for another 10 min. After 10 min, reaction mixture was cooled to 0° C. Trimethylsulfonium iodide (1 equiv) was added and stirred for 10 min after which the solution of 1-(6-(trifluoromethyl)pyridin-3-yl)ethanone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product.

Example 37

Preparation of 2-(trifluoromethyl)-5-(oxiran-2-yl)pyridine (Compound 32)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents stirred for 10 min. after which the solution of 6-(trifluoromethyl)pyridine-3-carbaldehyde (1 equiv.) in THF is added dropwise. After complete addition, the reaction mixture is stirred at RT for 2 h; the reaction is monitored by LCMS. After completion, the reaction mixture is poured in ice water, extracted in diethyl ether, dried over sodium sulfate and concentrated at 25° C. to get the crude product.

Example 37A

DMSO was added to NaH (1 equiv) and heated to 65° C. for 1 h. THF was added at same temp. and heated for another 10 min. After 10 min, reaction mixture was cooled to 0° C. Trimethylsulfonium iodide (1 equiv) was added and stirred for 10 min after which the solution of 6-(trifluoromethyl)pyridine-3-carbaldehyde (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product.

Example 38

Preparation of 2-cyclopropyl-2-(4-fluorophenyl)oxirane (Compound 34)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents are stirred for 10 min. after which the solution of cyclopropyl(4-fluorophenyl)methanone (1 equiv.) in THF is added dropwise. After complete addition, the reaction mixture is stirred at RT for 2 h; the reaction is monitored by LCMS. After completion, the reaction mixture is poured in ice water, extracted in diethyl ether, dried over sodium sulfate and concentrated at 25° C. to get the crude product.

Example 38A

DMSO was added to NaH (1 equiv) and heated to 65° C. for 1 h. THF was added at same temp. and heated for another 10 min. After 10 min, reaction mixture was cooled to 0° C. Trimethylsulfonium iodide (1 equiv) was added and stirred for 10 min after which the solution of cyclopropyl(4-fluorophenyl)methanone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product. $^1$H NMR (CDCl$_3$, freebase) δ (ppm): 7.05 (m, 4H), 2.9 (d, 1H), 2.7 (d, 1H), 0.87 (m, 1H), 0.61 (m, 2H), 0.45 (m, 2H).

Example 39

Preparation of 2-ethyl-2-(4-fluorophenyl)oxirane (Compound 36)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents stirred for 10 min. after which the solution of 1-(4-fluorophenyl)propan-1-one (1 equiv.) in THF is added dropwise. After complete addition, the reaction mixture is stirred at RT for 2 h; the reaction is monitored by LCMS. After completion, the reaction mixture is poured in ice water, extracted in diethyl ether, dried over sodium sulfate and concentrated at 25° C. to get the crude product.

Example 39A

DMSO was added to NaH (1 equiv) and heated to 65° C. for 1 h. THF was added at same temperature and heated for another 10 min. After 10 min, reaction mixture was cooled to 0° C. Trimethylsulfonium iodide (1 equiv) was added and stirred for 10 min after which the solution of 1-(4-fluorophenyl)propan-1-one (1 equiv) in THF was added dropwise. After complete addition, reaction mixture was stirred at RT for 2 h. Product was detected by LCMS. Reaction mixture was poured in ice water. Product was extracted in diethyl ether (4×50 mL), dried over sodium sulfate and concentrated at 25° C. to get the product.

Example 40

Preparation of 2-methyl-2-phenyloxirane (Compound 38)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents are stirred for 10 min. after which the solution of acetophenone (1 equiv.) in THF is added dropwise. After complete addition, the reaction mixture is stirred at RT for 2 h; the reaction is monitored by LCMS. The reaction mixture is poured in ice water, extracted in diethyl ether, dried over sodium sulfate and concentrated at 25° C. to get the crude product.

Example 40A

DMSO was added to NaH (1 equiv) and heated to 65° C. for 1 h. THF was added at same temperature and heated for another 10 min. After 10 min, reaction mixture was cooled to 0° C. Trimethylsulfonium iodide (1 equiv) was added and stirred for 10 min after which the solution of acetophenone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product. $^1$H NMR (CDCl$_3$, freebase) δ (ppm): 7.35 (m, 5H), 2.95 (d, 1H), 2.8 (d, 1H), 1.75 (s, 3H).

Example 41

Preparation of 2-methyl-5-(2-methyloxiran-2-yl)pyridine (Compound 40)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents stirred for 10 min. after which the solution of 1-(6-methylpyridin-3-yl)ethanone (1 equiv.) in THF is added dropwise. After complete addition, the reaction mixture is stirred at RT for 2 h; the reaction is monitored by LCMS. After completion, the reaction mixture is poured in ice water, extracted in diethyl ether, dried over sodium sulfate and concentrated at 25° C. to get the crude product.

Example 41A

DMSO was added to NaH (1 equiv) and heated to 65° C. for 1 h. THF was added at same temp. and heated for another 10 min. After 10 min, reaction mixture was cooled to 0° C. Trimethylsulfonium iodide (1 equiv) was added and stirred for 10 min after which the solution of 1-(6-methylpyridin-3-yl)ethanone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product.

Example 42

Preparation of 2-methyl-5-(2-methyloxiran-2-yl)pyrimidine (Compound 42)

DMSO is added to NaH (1-1.8 equiv.) and heated to 65° C. for 1 h. THF is added at the same temperature and heated for another 10 min. After 10 min., the reaction mixture is cooled to 0° C. Trimethylsulfonium iodide (1-1.2 equiv.) is added and the contents stirred for 10 min. after which the solution of 1-(2-methylpyrimidin-5-yl)ethanone (1 equiv.) in THF is added dropwise. After complete addition, the reaction mixture is stirred at RT for 2 h; the reaction is monitored by LCMS. The reaction mixture is poured in ice water, extracted in diethyl ether, dried over sodium sulfate and concentrated at 25° C. to get the crude product.

Example 42A

DMSO was added to NaH (1 equiv) and heated to 65° C. for 1 h. THF was added at same temp. and heated for another 10 min. After 10 min, reaction mixture was cooled to 0° C. Trimethylsulfonium iodide (1 equiv) was added and stirred for 10 min after which the solution of 1-(2-methylpyrimidin-5-yl)ethanone (1 equiv) in THF was added dropwise. After complete addition, reaction mixture was stirred at RT for 2 h. Product was detected by LCMS. Reaction mixture was poured in ice water. Product was extracted with diethyl ether (4×50 mL), dried over sodium sulfate and concentrated under vacuum at 25° C. to get the product.

Example 43

Preparation of racemic-2-(1,2,3,4-tetrahydro-2,8-dimethylpyrido[4,3-b]indol-5-yl)-1-p-tolylethanol (Compound 43)

3,4,5-Tetrahydro-2,8-dimethyl-1H-pyrido[4,3-b]indole (2.2 g, 11 mmol, 1 equiv.), 4-methylstyrene oxide (5.8 g, 44 mmol, 4 equiv.) and NaH (1.3 g, 32.5 mmol, 2.95 eq) were heated in DMF (70 mL) at 120° C. for 16 h (overnight). The contents were quenched by MeOH and evaporated to dryness. The resulting crude product was purified by silica gel chromatography (230-400 mesh) using EtOAc-hexane gradient to obtain 1.3 g of racemic-2-(1,2,3,4-tetrahydro-2,8-dimethylpyrido[4,3-b]indol-5-yl)-1-p-tolylethanol. The free base was converted into its hydrochloride salt by treatment of ethanolic HCl. $^1$H NMR (DMSO-d6, HCl salt) δ (ppm): 10.30 (s, 1H), 7.42-7.0 (m, 7H), 5.6 (m, 1H), 4.90-4.80 (m, 1H), 4.60-4.55 (d, 1H), 4.30-4.00 (m, 3H), 3.70 (s, 1H), 3.4 (m, 1H), 3.22-3.10 (d, 1H), 3.00-2.90 (m, 3H), 2.80-2.60 (d, 1H), 2.40 (s, 3H), 2.30 (s, 3H).

Example 44

Preparation of 1-(8-chloro-1,2,3,4-tetrahydro-2-methylpyrido[4,3-b]indol-5-yl)-2-(4-fluorophenyl)propan-2-ol (Compound 45)

To a solution of carboline (290 mg, 1.314 mmol, 1.0 equiv.) in DMF (6 mL) was added 38 mg of sodium hydride 55-60% dispersion in oil, in one portion, and heated to 120° C. for 1 h under stirring. The reaction mixture was cooled to 0° C. and epoxide (400 mg, 2.628 mmol, 2 equiv.) was added dropwise over 5 min. The temperature was raised to 120° C. again and stirred at the same temperature for 2 h. The reaction mixture was brought to RT and partitioned between 60 mL of EtOAc and 15 mL of water. The organic layer was separated and the aqueous layer extracted with EtOAc (1×50 mL). The combined organic layer was washed with water and then with brine, dried over sodium sulfate and concentrated under vacuum to yield crude product (600 mg). The crude product was purified by column chromatography (flash) over 230-400 silica gel (deactivated with 1% triethylamine/hexane) using a gradient of 5 to 15% MeOH/EtOAc. $^1$H NMR and LCMS were found to be consistent. Yield: 150 mg free base. The pure compound was converted to its oxalate salt with 1 equiv. of oxalic acid in THF. $^1$H NMR (CD$_3$OD, oxalate salt) δ (ppm): 7.4 (m, 3H), 7.18 (d, 1H), 6.98 (m, 3H), 4.45 (bs, 2H), 4.3 (d, 1H), 4.19 (d, 1H), 3.6- (bs, 2H), 3.0 (s, 3H), 3.1-2.9 (m, 2H), 1.60 (s, 3H).

Example 45

Preparation of 1-(8-chloro-1,2,3,4-tetrahydro-2-methylpyrido[4,3-b]indol-5-yl)-2-(6-methylpyridin-3-yl)propan-2-ol (Compound 47)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 mL), and heated to 120° C. for 1 h with stirring. The reaction mixture was cooled to 0° C. and 2-methyl-5-(2-methyloxiran-2-yl)pyridine (400 mg, 2.68 mmol, 2.0 equiv.) was added dropwise over 5 min. The temperature was raised to 120° C. and stirred for 2 h. The reaction mixture was cooled to RT and partitioned between EtOAc (60 mL) and water (15 mL). The organic layer was separated and the aqueous layer was extracted with EtOAc (1×20 mL). The combined organic layer was washed with water followed by brine, dried over sodium sulfate and concentrated under vacuum to provide the crude product. The product was purified by flash column chromatography over silica gel (230-400 mesh, deactivated with 1% triethylamine/hexane) using a gradient of 5 to 15% MeOH/EtOAc to yield the free base. The pure compound was converted to its oxalate salt. The analytical sample was prepared by dissolving free base in 10 mL THF and treatment with 1 equiv. of oxalic acid dihydrate. $^1$H NMR (DMSO-d6, oxalate salt) δ (ppm): 8.50 (s, 1H), 7.70 (d, 1H), 7.47 (s, 1H), 7.42 (d, 1H), 7.15 (d, 1H), 7.03 (d, 1H), 4.40 (m, 2H), 4.30 (m, 1H), 4.10 (m, 1H), 3.50 (m, 1H), 3.10 (m, 3H), 2.90 (s, 3H), 2.45 (s, 3H), 1.60 (m, 3H).

Example 46

Preparation of 1-(8-chloro-1,2,3,4-tetrahydro-2-methylpyrido[4,3-b]indol-5-yl)-2-(pyrimidin-5-yl)propan-2-ol (Compound 49)

Sodium hydride (1-3 equiv.) is added to a solution of 8-chloro-2,3,4,5-tetrahydro-2-methyl-1H-pyrido[4,3-b]indole (1.0 equiv.) in DMF (6 mL), and heated to 120° C. for 1 h with stirring. The reaction mixture is cooled to 0° C. and 5-(2-methyloxiran-2-yl)pyrimidine (2-7.5 equiv.) is added dropwise over 5 min. The temperature is raised to 120° C. and stirred for 2 h. The reaction mixture is cooled to RT and partitioned between EtOAc (60 mL) and water (15 mL). The organic layer is separated and the aqueous layer is extracted with EtOAc. The combined organic layers are washed with water followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 46A

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 ml), and heated to 120 deg C. for 1 hour with stirring. The reaction mixture was cooled to 0 deg C. and 5-(2-methyloxiran-2-yl)pyrimidine (400 mg, 2.9 mmol, 2.2 equiv) was added dropwise over 5 minutes. The temperature was raised to 120 deg C. and stirred for 2 hours. The reaction mixture was cooled to RT and partitioned between EtOAc (60 ml) and water (15 ml). The organic layer was separated and the aqueous layer was extracted with EtOAc (1×20 ml). The combined organic layer was washed with water and followed by brine, dried over sodium sulfate and concentrated under vacuum to provide the crude product. The product was purified by flash column chromatography over silica gel (230-400 mesh, pretreated with 1% triethylamine/hexane) using a gradient of 5 to 15% MeOH/EtOAc to yield the product.

Example 47

Preparation of racemic-2-(2-ethyl-1,2,3,4-tetrahydro-8-methylpyrido[4,3-b]indol-5-yl)-1-p-tolyle-thanol (Compound 51)

2-Ethyl-2,3,4,5-tetrahydro-8-methyl-1H-pyrido[4,3-b]indole (214 mg, 1 mmol), 4-methylstyrene oxide (1 mL, 7.5 mmol) and NaH (120 mg, 3 mmol) were heated in DMF (4 mL) at 120° C. for 16 h (overnight) to obtain 50 mg of racemic-2-(2-ethyl-1,2,3,4-tetrahydro-8-methylpyrido[4,3-b]indol-5-yl)-1-p-tolylethanol as a TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL). $^1$H NMR (CDCl$_3$, TFA salt) δ (ppm): 13.20 (bs, 1H), 7.4-7.0 (m, 7H), 5.05-4.97 (m, 1H), 4.70 (t, 1H), 4.25-4.10 (m, 3H), 3.70-3.60 (m, 1H), 3.40-3.10 (m, 5H), 2.5 (s, 3H), 2.38 (s, 3H), 1.41 (t, 3H).

Example 48

Preparation of racemic-2-(1,2,3,4-tetrahydro-2-methylpyrido[4,3-b]indol-5-yl)-1-p-tolylethanol (Compound 53)

2,3,4,5-Tetrahydro-2-methyl-1H-pyrido[4,3-b]indole (400 mg, 2.1 mmol), 4-methylstyrene oxide (2.1 g, 15.7 mmol) and NaH (252 mg, 6.3 mmol) were heated in DMF (5 mL) at 120° C. for 16 h to obtain 75 mg of racemic-2-(1,2,3,4-tetrahydro-2-methylpyrido[4,3-b]indol-5-yl)-1-p-tolylethanol as a TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., inject ion vol. 5 mL). $^1$H NMR (CDCl$_3$, TFA salt) δ (ppm): 13.45-13.20 (bs, 1H), 7.40-7.05 (m, 8H), 5.0-4.9 (t, 1H), 4.8-4.6 (t, 1H), 4.25-4.05 (m, 3H), 3.70-3.60 (m, 1H), 3.40-3.30 (m, 2H), 3.05 (m, 1H), 3.00-2.91 (m, 3H), 2.3 (s, 3H).

Example 49

Preparation of racemic-2-(2-ethyl-1,2,3,4-tetrahydropyrido[4,3-b]indol-5-yl)-1-p-tolylethanol (Compound 44)

2-Ethyl-2,3,4,5-tetrahydro-1H-pyrido[4,3-b]indole (400 mg, 2.0 mmol), 4-methylstyrene oxide (2.01 g, 15 mmol) and NaH (240 mg, 6 mmol) were heated in DMF (6 mL) at 120° C. for 16 h to obtain 120 mg of racemic-2-(2-ethyl-1,2,3,4-tetrahydropyrido[4,3-b]indol-5-yl)-1-p-tolylethanol as a TFA salt after purification by reverse-phase chromatography (C-18, 500 mm×50 mm, Mobile Phase A=0.05% TFA in water, B=0.05% TFA in acetonitrile, Gradient: 10% B to 80% B in 30 min., injection vol. 5 mL). $^1$H NMR (CDCl$_3$, TFA salt) δ (ppm): 13.40-13.10 (bs, 1H), 7.40-7.30 (t, 2H), 7.29-7.10 (m, 6H), 5.07-4.95 (m, 1H), 4.75-4.60 (t, 1H), 4.25-4.02 (m, 3H), 3.75-3.65 (m, 1H), 3.40-3.0 (m, 5H), 2.35 (S, 3H), 1.47-1.40 (t, 3H).

Example 50

Preparation of 1-(1,2,3,4-tetrahydro-2,8-dimethyl-pyrido[4,3-b]indol-5-yl)-2-phenylpropan-2-ol (Compound 46)

Sodium hydride (1-3 equiv.) is added to a solution of 2,3,4,5-tetrahydro-2,8-dimethyl-1H-pyrido[4,3-b]indole (1.0 equiv.) in DMF, and heated to 120° C. for 1 h with stirring. The reaction mixture is cooled to 0° C. and 2-methyl-2-phenyloxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 51

Preparation of 2-(2,8-dimethyl-3,4-dihydro-1H-pyrido[4,3-b]indol-5(2H)-yl)-1-(6-methylpyridin-3-yl)ethanol (Compound 48)

2,8-Dimethyl-2,3,4,5-tetrahydro-1H-pyrido[4,3-b]indole (1.35 g, 6.65 mmol) was taken in DMF (10 mL). NaH (0.9 g, 19.5 mmol) was added portionwise at RT and the contents were stirred for 15 min. 2-Methyl-5-(oxiran-2-yl)pyridine (0.9 g, 6.65 mmol) was added to the reaction mixture dropwise at RT. After complete addition, the reaction mixture was stirred at RT for 2 h, the reaction was monitored by LCMS. The reaction mixture was quenched with MeOH and concentrated to dryness. Water (20 mL) was added and the reaction mixture was extracted in EtOAc (2×100 mL), dried over sodium sulfate and concentrated to provide a dark brown crude oil. This product was purified by HPLC to obtain pure 2-(2,8-dimethyl-3,4-dihydro-1H-pyrido[4,3-b]indol-5(2H)-yl)-1-(6-methylpyridin-3-yl)ethanol as the TFA salt (310 mg). $^1$H NMR (CD$_3$OD, TFA salt) δ (ppm): 8.5 (s, 1H), 8.4 (s, 1H), 7.8 (d, 1H), 7.2 (s, 1H), 7.0 (s, 1H), 6.9 (d, 1H), 5.2 (bs, 1H), 4.7 (d, 1H), 4.4 (m, 3H), 3.9 (bs, 1H), 3.5 (m, 1H), 3.3 (s, 2H), 3.1 (s, 3H), 2.7 (s, 3H), 2.3 (s, 3H).

Example 52

Preparation of 2-(8-chloro-2-methyl-3,4-dihydro-1H-pyrido[4,3-b]indol-5(2H)-yl)-1-(6-(trifluoromethyl)pyridin-3-yl)ethanol (Compound 50)

Sodium hydride (1-3 equiv.) is added to a solution of 8-chloro-2,3,4,5-tetrahydro-2-methyl-1H-pyrido[4,3-b]indole (1.0 equiv.) in DMF, and heated to 120° C. for 1 h with stirring. The reaction mixture is cooled to 0° C. and 5-acetyl-2-(trifluoromethyl)pyridine (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer extracted with EtOAc. The combined organic layers are washed with water followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 53

Preparation of 1-(1,2,3,4-tetrahydro-2,8-dimethyl-pyrido[4,3-b]indol-5-yl)-2-(6-methylpyridin-3-yl)propan-2-ol (Compound 52)

A mixture of compound 2,3,4,5-tetrahydro-2,8-dimethyl-1H-pyrido[4,3-b]indole (1.5 g, 7.5 mmol, 1 equiv.) and NaH (252 mg, 10.5 mmol, 1.4 equiv.) in DMF (30 mL) were heated to 120° C. for 1 h. The reaction mixture was cooled to RT and 2-methyl-5-(2-methyloxiran-2-yl)pyridine (2.46 g, 16.5 mmol, 2.2 equiv.) in DMF (17 mL) was added dropwise over 12 min. The temperature was again raised to 120° C. and stirred for 3 h. The reaction mixture was cooled to RT and water (5 mL) was added, diluted with EtOAc (700 mL) and the organic layer was washed with water (3×100 mL) and then with brine, dried over sodium sulfate and concentrated under vacuum. The compound was purified by column chromatography over 230-400 silica gel using a gradient of 10-20% MeOH in EtOAc. Yield: 2.3 g (87%). ¹H NMR (DMSO-d6, oxalate salt) δ (ppm): 8.52 (bs, 1H), 7.73-7.71 (d, 1H), 7.31-7.29 (d, 1H), 7.17-7.15 (m, 2H), 6.88-6.86 (d, 1H), 4.34 (bs, 2H), 4.24-4.40 (dd, 2H), 3.47 (bs, 2H), 2.98 (bs, 2H), 2.91 (s, 3H), 2.42 (s, 3H), 2.35 (s, 3H), 1.48 (s, 3H).

Example 54

Preparation of 2-(1,2,3,4-tetrahydro-2,8-dimethyl-pyrido[4,3-b]indol-5-yl)-1-(pyridin-3-yl)ethanol (Compound 54)

Carboline (500 mg, 2.5 mmol) was dissolved in DMF (5 mL). To this solution was added NaH (60%, 180 mg, 4.5 mmol) at RT and the reaction mixture was stirred for 10-15 min. after which 3-(oxiran-2-yl)pyridine (450 mg, 3.7 mmol) was added. The reaction mixture was stirred at RT for 4 h and the reaction was monitored by LCMS. After completion, the reaction mixture was poured on ice water and extracted with EtOAc. The organic layer was dried on sodium sulfate and concentrated under reduced pressure. The residue was purified by HPLC to obtain 420 mg of product as a white solid (TFA salt). TLC (silica gel) 5:95 MeOH:DCM, Rf 0.1 was observed. ¹H NMR (CD₃OD, TFA salt) δ (ppm): 8.60 (d, 2H), 8.20 (bs, 1H), 7.85 (bs, 1H), 7.20 (s, 1H), 7.0 (d, 1H), 6.9 (d, 1H), 5.2 (bs, 1H), 4.8 (d, 2H), 4.4 (m, 4H), 3.9 (bs, 1H), 3.60- (bs, 2H), 3.10- (s, 3H), 2.40 (s, 3H).

Example 55

Preparation of 2-(8-chloro-1,2,3,4-tetrahydro-2-methylpyrido[4,3-b]indol-5-yl)-1-(pyridin-3-yl)ethanol (Compound 56)

Chloro carboline (500 mg, 2.27 mmol) was taken in DMF. NaH (180 mg, 4.5 mmol) was added at RT and stirred for 10-15 min. Neat epoxide (450 mg, 3.7 mmol) was added dropwise at RT. The reaction was stirred at RT for 4 h and the reaction was monitored by LCMS. After completion, the reaction mixture was poured on ice water and extracted with EtOAc, dried and concentrated. The residue was purified by HPLC. 465 mg of product as a white solid (TFA salt). TLC: 5% MeOH-DCM, Rf 0.1 was observed. ¹H NMR (CD₃OD, TFA salt) δ (ppm): 8.80 (s, 2H), 8.40 (s, 1H), 7.9 (t, 1H), 7.40 (s, 1H), 7.20 (d, 1H), 7.0 (d, 1H), 5.25 (bs, 1H), 4.7 (d, 1H), 4.4 (m, 2H), 4.3 (d, 1H), 3.9 (bs, 1H), 3.5 (bs, 1H), 3.3 (m, 2H), 3.10 (s, 3H).

Example 56

Preparation of 2-(4-fluorophenyl)-1-(1,2,3,4-tetra-hydro-2,8-dimethylpyrido[4,3-b]indol-5-yl)propan-2-ol (Compound 55)

A mixture of 2,3,4,5-tetrahydro-2,8-dimethyl-1H-pyrido [4,3-b]indole (2.6 g, 13.1 mmol, 1 equiv.) and NaH (55%, 750 mg, 17.2 mmol, 1.3 equiv.) in 60 mL of THF was heated to 120° C. for 1 h. The reaction mixture was cooled to RT and compound 2-(4-fluorophenyl)-2-methyloxirane (4 g, 26 mmol, 2 equiv.) in DMF (25 mL) was added dropwise for 5 min. at RT followed by heating at 120° C. for 2 h. The reaction mixture was cooled to RT and water (10 mL) was added followed by dilution with EtOAc (800 mL), which was washed with water (3×150 mL) and then brine, dried over sodium sulfate and concentrated under vacuum. The product was purified using column chromatography over 230-400 Silica gel (flash) using 15% MeOH in EtOAc as eluent. Yield: 3 g (66%). ¹H NMR (DMSO-d6, oxalate salt) δ (ppm): 7.5 (m, 2H), 7.3 (d, 1H), 7.12 (m, 3H), 6.8 (d, 1H), 4.3 (bs, 1H), 4.2 (m, 2H), 4.0 (m, 3H), 3.4 (bs, 1H), 3.0 (m, 1H), 2.9 (s, 3H), 2.3 (s, 3H), 1.5 (m, 3H).

Example 57

Preparation of 1-(8-chloro-1,2,3,4-tetrahydro-2-methylpyrido[4,3-b]indol-5-yl)-2-(4-methoxyphe-nyl)propan-2-ol (Compound 57)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 mL), and heated to 120° C. for 1 h with stirring. The reaction mixture was cooled to 0° C. and 2-(4-methoxyphe-nyl)-2-methyloxirane (400 mg, 2.43 mmol, 1.85 equiv.) was added dropwise over 5 min. The temperature was raised to 120° C. and stirred for 2 h. The reaction mixture was cooled to RT and partitioned between EtOAc (60 mL) and water (15 mL). The organic layer was separated and the aqueous layer was extracted with EtOAc (20 mL). The combined organic layer was washed with water and followed by brine, dried over sodium sulfate and concentrated under vacuum to provide the crude product. The product was purified by flash column chromatography over silica gel (230-400 mesh, deactivated with 1% triethylamine/hexane) using a gradient of 5 to 15% MeOH/EtOAc to yield the free base. The pure compound was converted to its oxalate salt. The analytical sample was prepared by dissolving free base in THF (10 mL) and treatment with 1 equiv. of oxalic acid dihydrate. ¹H NMR (DMSO-d6, oxalate salt) δ (ppm): 7.45 (m, 2H), 7.38 (d, 2H), 7.04 (d, 1H), 6.86 (d, 2H), 4.20 (m, 2H), 4.08 (m, 2H), 3.72 (s, 3H), 3.60 (m, 2H), 3.0 (m, 2H), 2.84 (m, 3H), 1.50 (s, 3H).

Example 58

Preparation of 1-(8-chloro-1,2,3,4-tetrahydro-2-methylpyrido[4,3-b]indol-5-yl)-2-(3-fluoro-4-methoxyphenyl)propan-2-ol (Compound 59)

Sodium hydride (38 mg, 1.6 mmol, 1.2 equiv.) was added to a solution of 8-chloro-2,3,4,5-tetrahydro-2-methyl-1H-pyrido[4,3-b]indole (290 mg, 1.31 mmol, 1.0 equiv.) in DMF (6 mL), and heated to 120° C. for 1 h with stirring. The reaction mixture was cooled to 0° C. and 2-(3-fluoro-4methoxyphenyl)-2-methyloxirane (400 mg, 2.2 mmol, 1.7 equiv.) was added dropwise over 5 min. The temperature was raised to 120° C. and stirred for 2 h. The reaction mixture was cooled to RT and partitioned between EtOAc (60 mL) and water (15 mL). The organic layer was separated and the aqueous layer was extracted with EtOAc (20 mL). The combined organic layers were washed with water and followed by brine, dried over sodium sulfate and concentrated under vacuum to provide the crude product. The product was purified by flash column chromatography over silica gel (230-400 mesh, deactivated with 1% triethylam-ine/hexane) using a gradient of 5 to 15% MeOH/EtOAc to yield the free base. The pure compound was converted to its oxalate salt. The analytical sample was prepared by dissolv-ing free base in 10 mL THF and treatment with 1 equiv. of oxalic acid dihydrate. ¹H NMR (DMSO-d6, oxalate salt) δ

(ppm): 7.45 (m, 2H), 7.24 (m, 2H), 7.07 (m, 2H), 4.24 (m, 2H), 4.11 (m, 2H), 3.88 (s, 3H), 2.97 (m, 4H), 2.84 (s, 3H), 1.45 (s, 3H).

Example 59

Preparation of 1-(8-chloro-1,2,3,4-tetrahydro-2-methylpyrido[4,3-b]indol-5-yl)-2-(6-(trifluoromethyl)pyridin-3-yl)propan-2-ol (Compound 58)

Sodium hydride (1-3 equiv.) is added to a solution of 8-chloro-2,3,4,5-tetrahydro-2-methyl-1H-pyrido[4,3-b]indole (1.0 equiv.) in DMF, and heated to 120° C. for 1 h with stirring. The reaction mixture is cooled to 0° C. and 2-(trifluoromethyl)-5-(2-methyloxiran-2-yl)pyridine (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer was extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 60

Preparation of 1-(1,2,3,4-tetrahydro-2,8-dimethyl-pyrido[4,3-b]indol-5-yl)-2-(pyridin-3-yl)propan-2-ol (Compound 60)

Sodium hydride (1-3 equiv.) was added to a solution of 2,3,4,5-tetrahydro-2,8-dimethyl-1H-pyrido[4,3-b]indole (1.0 equiv.) in DMF, and heated to 120° C. for 1 h with stirring. The reaction mixture was cooled to 0° C. and 3-(2-methyloxiran-2-yl)pyridine (2-7.5 equiv.) was added dropwise over 5 min. The temperature was raised to 120° C. and stirred for 2 h. The reaction mixture was cooled to RT and partitioned between EtOAc and water. The organic layer was separated and the aqueous layer was extracted with EtOAc. The combined organic layers were washed with water and followed by brine, dried over sodium sulfate and concentrated under vacuum to provide the crude product. The product was purified by flash column chromatography over silica gel (230-400 mesh, deactivated with 1% triethylamine/hexane) using a gradient of 5 to 15% MeOH/EtOAc to yield the free base. The pure compound was converted to its oxalate salt. The analytical sample was prepared by dissolving free base in THF and treatment with 1 equiv. of oxalic acid dihydrate. $^1$H NMR (CD$_3$OD, TFA salt) δ (ppm): 8.51 (m, 2H), 8.36 (m, 1H), 7.69 (m, 1H), 7.15 (s, 1H), 6.76 (m, 2H), 4.67 (m, 1H), 4.34 (m, 3H), 3.84 (m, 1H), 3.47 (m, 2H), 3.24 (m, 1H), 3.11 (s, 3H), 2.40 (s, 3H), 1.80 (s, 3H).

Example 61

Preparation of 1-(8-chloro-1,2,3,4-tetrahydro-2-methylpyrido[4,3-b]indol-5-yl)-2-(pyridin-3-yl)propan-2-ol (Compound 61)

Sodium hydride (1-3 equiv.) was added to a solution of 8-chloro-2,3,4,5-tetrahydro-2-methyl-1H-pyrido[4,3-b]indole (1.0 equiv.) in DMF, and heated to 120° C. for 1 h with stirring. The reaction mixture was cooled to 0° C. and 3-(2-methyloxiran-2-yl)pyridine (2-7.5 equiv.) was added dropwise over 5 min. The temperature was raised to 120° C. and stirred for 2 h. The reaction mixture was cooled to RT and partitioned between EtOAc and water. The organic layer was separated and the aqueous layer was extracted with EtOAc. The combined organic layers were washed with water and followed by brine, dried over sodium sulfate and concentrated under vacuum to provide the crude product. The product was purified by flash column chromatography over silica gel (230-400 mesh, deactivated with 1% triethylamine/hexane) using a gradient of 5 to 15% MeOH/EtOAc to yield the free base. The pure compound was converted to its oxalate salt. The analytical sample was prepared by dissolving free base in THF and treatment with 1 equiv. of oxalic acid dihydrate. $^1$H NMR (CD$_3$OD, oxalate salt) δ (ppm): 8.43 (s, 1H), 8.34 (d, 1H), 7.87 (d, 1H), 7.37 (s, 1H), 7.30 (m, 1H), 6.97 (m, 1H), 6.93 (d, 1H), 4.48 (m, 2H), 4.32 (m, 2H), 3.71 (m, 2H), 3.12 (s, 3H), 2.81 (m, 2H), 1.70 (s, 3H).

Example 62

Preparation of 1-(1,2,3,4-tetrahydro-2,8-dimethyl-pyrido[4,3-b]indol-5-yl)-2-(pyridin-4-yl)propan-2-ol (Compound 62)

Sodium hydride (1-3 equiv.) was added to a solution of 2,3,4,5-tetrahydro-2,8-dimethyl-1H-pyrido[4,3-b]indole (1.0 equiv.) in DMF, and heated to 120° C. for 1 h with stirring. The reaction mixture was cooled to 0° C. and 4-(2-methyloxiran-2-yl)pyridine (2-7.5 equiv.) was added dropwise over 5 min. The temperature was raised to 120° C. and stirred for 2 h. The reaction mixture was cooled to RT and partitioned between EtOAc and water. The organic layer was separated and the aqueous layer was extracted with EtOAc. The combined organic layers were washed with water and followed by brine, dried over sodium sulfate and concentrated under vacuum to provide the crude product. The product was purified by flash column chromatography over silica gel (230-400 mesh, deactivated with 1% triethylamine/hexane) using a gradient of 5 to 15% MeOH/EtOAc to yield the free base. The pure compound was converted to its oxalate salt. The analytical sample was prepared by dissolving free base in THF and treatment with 1 equiv. of oxalic acid dihydrate. $^1$H NMR (CD$_3$OD, oxalate salt) δ (ppm): 8.38 (d, 2H), 7.50 (d, 2H), 7.15 (s, 1H), 7.06 (d, 1H), 6.86 (d, 1H), 4.45 (m, 2H), 4.31 (m, 1H), 4.22 (m, 1H), 3.61 (m, 2H), 3.19 (m, 1H), 3.06 (s, 3H), 2.78 (m, 2H), 2.35 (s, 3H), 1.60 (s, 3H).

Example 63

Preparation of 1-(8-chloro-1,2,3,4-tetrahydro-2-methylpyrido[4,3-b]indol-5-yl)-2-(pyridin-4-yl)propan-2-ol (Compound 63)

Sodium hydride (1-3 equiv.) was added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture was cooled to 0° C. and 4-(2-methyloxiran-2-yl)pyridine (2-7.5 equiv.) was added dropwise over 5 min. The temperature was raised to 120° C. and stirred for 2 h. The reaction mixture was cooled to RT and partitioned between EtOAc and water. The organic layer was separated and the aqueous layer was extracted with EtOAc. The combined organic layers were washed with water and followed by brine, dried over sodium sulfate and concentrated under vacuum to provide the crude product. The product was purified by flash column chromatography over silica gel (230-400 mesh, deactivated with 1% triethylamine/hexane) using a gradient of 5 to 15% MeOH/EtOAc to yield the free base. The pure compound was converted to its oxalate salt. The analytical sample was prepared by dissolving free base in THF and treatment with 1 equiv. of oxalic acid dihydrate. $^1$H NMR (CDCl$_3$, oxalate salt) δ (ppm): d 8.42 (d, 2H), 7.35-7.20 (m, 3H), 7.00-6.90 (m, 2H), 4.10 (q, 2H), 3.50 (q, 2H), 2.95-2.68 (m, 4H), 2.42 (s, 3H), 1.55 (s, 3H).

Example 64

Preparation of 1-(5-(trifluoromethyl)pyridin-3-yl)-2-(1,2,3,4-tetrahydro-2,8-dimethylpyrido[4,3-b]indol-5-yl)ethanol (Compound 65)

Sodium hydride (1-3 equiv.) is added to a solution of 2,3,4,5-tetrahydro-2,8-dimethyl-1H-pyrido[4,3-b]indole (1.0 equiv.) in DMF and heated to 120° C. for 1 h with stirring. The reaction mixture is cooled to 0° C. and 3-(trifluoromethyl)-5-(oxiran-2-yl)pyridine (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 65

Preparation of 2-(8-chloro-1,2,3,4-tetrahydro-2-methylpyrido[4,3-b]indol-5-yl)-1-(5-(trifluoromethyl)pyridin-3-yl)ethanol (Compound 67)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 3-(trifluoromethyl)-5-(oxiran-2-yl)pyridine (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 66

Preparation of 2-(8-chloro-1,2,3,4-tetrahydro-2-methylpyrido[4,3-b]indol-5-yl)-1-(3-fluoro-4-methoxyphenyl)ethanol (Compound 69)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 2-(3-fluoro-4-methoxyphenyl)oxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 67

Preparation of 1-(8-chloro-1,2,3,4-tetrahydro-2-methylpyrido[4,3-b]indol-5-yl)-2-(6-propylpyridin-3-yl)propan-2-ol (Compound 71)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 5-(2-methyloxiran-2-yl)-2-propylpyridine (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 68

Preparation of 1-(8-chloro-1,2,3,4-tetrahydro-2-methylpyrido[4,3-b]indol-5-yl)-2-(3,4-difluorophenyl)propan-2-ol (Compound 73)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 2-(3,4-difluorophenyl)-2-methyloxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc.

The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 69

Preparation of 1-(8-chloro-1,2,3,4-tetrahydro-2-methylpyrido[4,3-b]indol-5-yl)-2-(4-chlorophenyl)propan-2-ol (Compound 64)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 2-(4-chlorophenyl)-2-methyloxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 70

Preparation of 1-(8-chloro-1,2,3,4-tetrahydro-2-methylpyrido[4,3-b]indol-5-yl)-2-(4-chloro-3-fluorophenyl)propan-2-ol (Compound 66)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 2-(4-chloro-3-fluorophenyl)-2-methyloxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 71

Preparation of 1-(8-chloro-1,2,3,4-tetrahydro-2-methylpyrido[4,3-b]indol-5-yl)-2-(3,4-dichlorophenyl)propan-2-ol (Compound 68)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 2-(3,4-dichlorophenyl)-2-methyloxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 72

Preparation of 1-(8-chloro-1,2,3,4-tetrahydro-2-methylpyrido[4,3-b]indol-5-yl)-2-(3-chloro-4-fluorophenyl)propan-2-ol (Compound 70)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 2-(3-chloro-4-fluorophenyl)-2-methyloxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer was extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 73

Preparation of 1-(8-chloro-1,2,3,4-tetrahydro-2-methylpyrido[4,3-b]indol-5-yl)-2-(2,4-difluorophenyl)propan-2-ol (Compound 72)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 2-(2,4-difluorophenyl)-2-methyloxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 74

Preparation of 1-(8-fluoro-1,2,3,4-tetrahydro-2-methylpyrido[4,3-b]indol-5-yl)-2-(4-fluorophenyl)propan-2-ol (Compound 75)

Sodium hydride (1-3 equiv.) is added to a solution of 8-fluoro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 2-(4-fluorophenyl)-2-methyloxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer was extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 75

Preparation of 1-(8-chloro-2-cyclopropyl-1,2,3,4-tetrahydropyrido[4,3-b]indol-5-yl)-2-(4-fluorophenyl)propan-2-ol (Compound 77)

Sodium hydride (1-3 equiv.) is added to a solution of 8-chloro-2-cyclopropyl-2,3,4,5-tetrahydro-1H-pyrido[4,3-b]indole (1.0 equiv.) in DMF and heated to 120° C. for 1 h with stirring. The reaction mixture is cooled to 0° C. and 2-(4-fluorophenyl)-2-methyloxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 76

Preparation of 1-(8-chloro-1,2,3,4-tetrahydro-2-methylpyrido[4,3-b]indol-5-yl)-2-phenylpropan-2-ol (Compound 79)

Sodium hydride (1-3 equiv.) was added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture was cooled to 0° C. and 2-methyl-2-phenyloxirane (2-7.5 equiv.) was added dropwise over 5 min. The temperature was raised to 120° C. and stirred for 2 h. The reaction mixture was cooled to RT and partitioned between EtOAc and water. The organic layer was separated and the aqueous layer was extracted with EtOAc. The combined organic layers were washed with water and followed by brine, dried over sodium sulfate and concentrated under vacuum to provide the crude product. The product was purified by flash column chromatography over silica gel (230-400 mesh, deactivated with 1% triethylamine/hexane) using a gradient of 5 to 15% MeOH/EtOAc to yield the free base. The pure compound was converted to its oxalate salt. The analytical sample was prepared by dissolving free base in THF and treatment with 1 equiv. of oxalic acid dihydrate. $^1$H NMR (CDCl$_3$, freebase) δ (ppm): 7.38 (d, 1H), 7.21 (m, 5H), 6.93 (m, 2H), 4.15 (m, 2H), 3.4 (m, 2H), 2.78 (m, 2H), 2.61 (m, 2H), 2.4 (s, 3H), 1.59 (s, 3H).

Example 77

Preparation of 1-(8-chloro-1,2,3,4-tetrahydro-2-methylpyrido[4,3-b]indol-5-yl)-2-(2,4,6-trifluorophenyl)propan-2-ol (Compound 81)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 2-(2,4,6-trifluorophenyl)-2-methyloxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 78

Preparation of 3-(8-chloro-1,2,3,4-tetrahydro-2-methylpyrido[4,3-b]indol-5-yl)-2-(4-fluorophenyl)butan-2-ol (Compound 74)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 2-(4-fluorophenyl)-2,3-dimethyloxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 79

Preparation of 1-(8-chloro-1,2,3,4-tetrahydro-2-methylpyrido[4,3-b]indol-5-yl)-2-(2,4-dichlorophenyl)propan-2-ol (Compound 76)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 2-(2,4-dichlorophenyl)-2-methyloxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 80

Preparation of 1-(8-chloro-1,2,3,4-tetrahydro-2-methylpyrido[4,3-b]indol-5-yl)-2-(4-fluorophenyl)butan-2-ol (Compound 78)

Sodium hydride (1-3 equiv.) was added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture was cooled to 0° C. and 2-ethyl-2-(4-fluorophenyl)oxirane (2-7.5 equiv.) was added dropwise over 5 min. The temperature was raised to 120° C. and stirred for 2 h. The reaction mixture was cooled to RT and partitioned between EtOAc and water. The organic layer was separated and the aqueous layer was extracted with EtOAc. The combined organic layers were washed with water and followed by brine, dried over sodium sulfate and concentrated under vacuum to provide the crude product. The product was purified by flash column chromatography over silica gel (230-400 mesh, deactivated with 1% triethylamine/hexane) using a gradient of 5 to 15% MeOH/EtOAc to yield the free base. The pure compound was converted to its oxalate salt. The analytical sample was prepared by dissolving free base in THF and treatment with 1 equiv. of oxalic acid dihydrate. $^1$H NMR (CDCl$_3$, oxalate salt) δ (ppm): 7.38 (m, 3H), 7.10 (d, 1H), 7.0 (m, 3H), 4.20 (m, 1H), 4.10 (m, 1H), 3.80 (m, 2H), 2.80 (m, 3H), 2.61 (m, 1H), 2.50 (s, 3H), 2.15 (m, 2H), 1.80 (m, 1H), 0.7 (t, 3H).

Example 81

Preparation of 3-(8-chloro-1,2,3,4-tetrahydro-2-methylpyrido[4,3-b]indol-5-yl)-1,1,1-trifluoro-2-(4-fluorophenyl)propan-2-ol (Compound 80)

Sodium hydride (1-3 equiv.) is added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture is cooled to 0° C. and 2-(trifluoromethyl)-2-(4-fluorophenyl)oxirane (2-7.5 equiv.) is added dropwise over 5 min. The temperature is raised to 120° C. and stirred for 2 h. The reaction mixture is cooled to RT and partitioned between EtOAc and water. The organic layer is separated and the aqueous layer is extracted with EtOAc. The combined organic layers are washed with water and followed by brine, dried over sodium sulfate and concentrated under vacuum to provide the crude product. The product is purified by flash column chromatography over silica gel (230-400 mesh, deactivated with 1% triethylamine/hexane) using a gradient of 5 to 15% MeOH/EtOAc to yield the free base. The pure compound is converted to its oxalate salt. The analytical sample is prepared by dissolving free base in THF and treatment with 1 equiv. of oxalic acid dihydrate.

Example 82

Preparation of 2-(8-chloro-1,2,3,4-tetrahydro-2-methylpyrido[4,3-b]indol-5-yl)-1-cyclopropyl-1-(4-fluorophenyl)ethanol (Compound 82)

Sodium hydride (1-3 equiv.) was added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture was cooled to 0° C. and 2-cyclopropyl-2-(4-fluorophenyl)oxirane (2-7.5 equiv.) was added dropwise over 5 min. The temperature was raised to 120° C. and stirred for 2 h. The reaction mixture was cooled to RT and partitioned between EtOAc and water. The organic layer was separated and the aqueous layer was extracted with EtOAc. The combined organic layers were washed with water and followed by brine, dried over sodium sulfate and concentrated under vacuum to provide the crude product. The product was purified by flash column chromatography over silica gel (230-400 mesh, deactivated with 1% triethylamine/hexane) using a gradient of 5 to 15% MeOH/EtOAc to yield the free base. The pure compound was converted to its oxalate salt. The analytical sample was prepared by dissolving free base in THF and treatment with 1 equiv. of oxalic acid dihydrate. $^1$H NMR (CD$_3$OD, oxalate salt) δ (ppm): 7.40 (m, 3H), 7.20 (m, 1H), 7.0 (m, 3H), 4.42 (m, 1H), 4.38 (m, 1H), 4.15 (m, 1H), 3.60 (m, 2H), 3.45 (m, 1H), 3.0 (m, 4H), 1.50 (m, 1H), 1.1 (m, 1H), 0.5 (m, 4H).

Example 83

Preparation of 8-chloro-5-((E)-2-(4-fluorophenyl)prop-1-enyl)-2,3,4,5-tetrahydro-2-methyl-1H-pyrido[4,3-b]indole and 8-chloro-5-(2-(4-fluorophenyl)allyl)-2,3,4,5-tetrahydro-2-methyl-1H-pyrido[4,3-b]indole (Compounds 83 and 128)

1-(8-Chloro-1,2,3,4-tetrahydro-2-methylpyrido[4,3-b]indol-5-yl)-2-(4-fluorophenyl)propan-2-ol (1 g, 2.68 mmol, 1 equiv.) was refluxed with 7 mL of 25% sulfuric acid for 2 h. It was brought to RT and then cooled to 5° C. with an ice-water bath. 15% aq. solution of KOH was dropwise added to the reaction mixture to attain pH 9-10. It was then extracted with EtOAc (3×10 mL). The combined organic extracts were washed with 10 mL of water followed by brine, dried over sodium sulfate and evaporated under vacuum. It was then column purified using 100-200 silica gel, using a gradient of MeOH-EtOAc (0-10%) to obtain a mixture of isomers (150 mg), which was separated by HPLC. Yield: 15 mg of 8-chloro-5-((E)-2-(4-fluorophenyl)prop-1-enyl)-2,3,4,5-tetrahydro-2-methyl-1H-pyrido[4,3-b]indole and 25 mg of 8-chloro-5-(2-(4-fluorophenyl)allyl)-2,3,4,5-tetrahydro-2-methyl-1H-pyrido[4,3-b]indole (as a TFA salt). The isomers can alternatively be separated by silica gel chromatography using an EtOAc: hexane (80:20) eluent. TLC: three runs in EtOAc: hexane (80:20).

8-Chloro-5-(2-(4-fluorophenyl)allyl)-2,3,4,5-tetrahydro-2-methyl-1H-pyrido[4,3-b]indole: $^1$H NMR (DMSO-d6, TFA salt) δ (ppm): 10.1 (bs, 1H), 7.64 (m, 2H), 7.59 (d, 2H), 7.24 (m, 2H), 7.19 (d, 1H), 5.35 (s, 1H), 5.21 (m, 2H), 4.65 (d, 1H), 4.3 (s, 2H), 3.76 (s, 1H), 3.5 (bs, 1H), 3.0 (s, 2H), 2.97 (s, 3H).

Example 84

Preparation of 2,3,4,5-tetrahydro-2,8-dimethyl-5-((E)-2-(6-methylpyridin-3-yl)prop-1-enyl)-1H-pyrido[4,3-b]indole and 2,3,4,5-tetrahydro-2,8-dimethyl-5-(2-(6-methylpyridin-3-yl)allyl)-1H-pyrido[4,3-b]indole (Compounds 85 and 130)

1-(1,2,3,4-Tetrahydro-2,8-dimethylpyrido[4,3-b]indol-5-yl)-2-(6-methylpyridin-3-yl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 was achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 2,3,4,5-tetrahydro-2,8-dimethyl-5-((E)-2-(6-methylpyridin-3-yl)prop-1-enyl)-1H-pyrido[4,3-b]indole and 2,3,4,5-tetrahydro-2,8-dimethyl-5-(2-(6-methylpyridin-3-yl)allyl)-1H-pyrido[4,3-b]indole, which are separated by HPLC.

Example 85

Preparation of 5-((E)-2-(4-fluorophenyl)prop-1-enyl)-2,3,4,5-tetrahydro-2,8-dimethyl-1H-pyrido[4,3-b]indole and 5-(2-(4-fluorophenyl)allyl)-2,3,4,5-tetrahydro-2,8-dimethyl-1H-pyrido[4,3-b]indole (Compounds 87 and 132)

2-(4-Fluorophenyl)-1-(1,2,3,4-tetrahydro-2,8-dimethylpyrido[4,3-b]indol-5-yl)propan-2-ol (4.6 g, 13.05 mmol, 1 equiv.) was heated to reflux with 14 mL of 25% aq. sulfuric acid for 2 h. The reaction mixture was cooled to 0-5° C. and made alkaline with 15% aq. KOH solution and extracted with THF:EtOAc (1:1 mixture, 2×30 mL). The combined organic layer was washed with water (15 mL) and then brine, dried over sodium sulfate and evaporated under vacuum. 4.1 g of crude product was obtained which contained 5-((Z)-2-(4-fluorophenyl)prop-1-enyl)-2,3,4,5-tetrahydro-2,8-dimethyl-1H-pyrido[4,3-b]indole as the minor isomer. This isomer was isolated by repeated flash chromatography using 230-400 mesh silica gel using EtOAc as eluent. Yield: 500 mg of 5-((E)-2-(4-fluorophenyl)prop-1-enyl)-2,3,4,5-tetrahydro-2,8-dimethyl-1H-pyrido[4,3-b]indole and 1 g of 5-(2-(4-fluorophenyl)allyl)-2,3,4,5-tetrahydro-2,8-dimethyl-1H-pyrido[4,3-b]indole were isolated as pure products.

5-(2-(4-Fluorophenyl)allyl)-2,3,4,5-tetrahydro-2,8-dimethyl-1H-pyrido[4,3-b]indole: $^1$H NMR (DMSO-d6, oxalate salt) δ (ppm): 7.70-7.50 (m, 2H), 7.40-7.30 (d, 1H), 7.30-7.18 (m, 3H), 7.00-6.85 (d, 1H), 5.30 (s, 1H), 5.17 (s, 2H), 4.40 (bs, 2H), 4.28 (s, 2H), 3.50 (bs, 1H), 3.10-3.00 (t, 2H), 2.90 (s, 3H), 2.30 (s, 3H).

Example 86

Preparation of 8-chloro-2,3,4,5-tetrahydro-2-methyl-5-4E)-2-(6-methylpyridin-3-yl)prop-1-enyl)-1H-pyrido[4,3-b]indole and 8-chloro-2,3,4,5-tetrahydro-2-methyl-5-(2-(6-methylpyridin-3-yl)allyl)-1H-pyrido[4,3-b]indole (Compounds 89 and 136)

1-(8-Chloro-1,2,3,4-tetrahydro-2-methylpyrido[4,3-b]indol-5-yl)-2-(6-methylpyridin-3-yl)propan-2-ol (1 equiv.) was refluxed with 25% sulfuric acid for 2 h. The reaction mixture was cooled to 5° C. with an ice-water bath. KOH (15% aq. solution) was added dropwise to the reaction mixture until pH 9-10 was achieved. The reaction mixture was extracted with EtOAc. The combined organic layers were washed with water followed by brine, dried over sodium sulfate and evaporated under vacuum. The crude product was purified by column chromatography over silica gel (100-200 mesh) using a gradient of MeOH-EtOAc (0-10%) to obtain a mixture of 8-chloro-2,3,4,5-tetrahydro-2-methyl-5-((E)-2-(6-methylpyridin-3-yl)prop-1-enyl)-1H-pyrido[4,3-b]indole and 8-chloro-2,3,4,5-tetrahydro-2-methyl-5-(2-(6-methylpyridin-3-yl)allyl)-1H-pyrido[4,3-b]indole, which were separated by HPLC.

8-Chloro-2,3,4,5-tetrahydro-2-methyl-5-(2-(6-methylpyridin-3-yl)allyl)-1H-pyrido[4,3-b]indole: $^1$H NMR (DMSO-d6, TFA salt) δ (ppm): 8.74 (m, 1H), 8.16 (m, 1H), 7.59 (m, 2H), 7.52 (d, 1H), 7.19 (d, 1H), 5.54 (d, 1H), 5.28 (m, 2H), 4.65 (m, 1H), 4.45 (m, 1H), 4.29 (m, 1H), 3.76 (m, 1H), 3.49 (m, 1H), 3.08 (m, 2H), 2.98 (s, 3H), 2.55 (s, 3H).

Example 87

Preparation of 8-chloro-5-((E)-2-(6-(trifluoromethyl)pyridin-3-yl)prop-1-enyl)-2,3,4,5-tetrahydro-2-methyl-1H-pyrido[4,3-b]indole and 8-chloro-5-(2-(6-(trifluoromethyl)pyridin-3-yl)allyl)-2,3,4,5-tetrahydro-2-methyl-1H-pyrido[4,3-b]indole (Compounds 84 and 129)

1-(8-Chloro-1,2,3,4-tetrahydro-2-methylpyrido[4,3-b]indol-5-yl)-2-(6-(trifluoromethyl)pyridin-3-yl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-5-((E)-2-(6-(trifluoromethyl)pyridin-3-yl)prop-1-enyl)-2,3,4,5-tetrahydro-2-methyl-1H-pyrido[4,3-b]indole and 8-chloro-5-(2-(6-(trifluoromethyl)pyridin-3-yl)allyl)-2,3,4,5-tetrahydro-2-methyl-1H-pyrido[4,3-b]indole, which are separated by HPLC.

Example 88

Preparation of 2,3,4,5-tetrahydro-2,8-dimethyl-5-((E)-2-(pyridin-3-yl)prop-1-enyl)-1H-pyrido[4,3-b]indole and 2,3,4,5-tetrahydro-2,8-dimethyl-5-(2-(pyridin-3-yl)allyl)-1H-pyrido[4,3-b]indole (Compounds 91 and 131)

1-(1,2,3,4-Tetrahydro-2,8-dimethylpyrido[4,3-b]indol-5-yl)-2-(pyridin-3-yl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 2,3,4,5-tetrahydro-2,8-dimethyl-5-((E)-2-(pyridin-3-yl)prop-1-enyl)-1H-pyrido[4,3-b]indole and 2,3,4,5-tetrahydro-2,8-dimethyl-5-(2-(pyridin-3-yl)allyl)-1H-pyrido[4,3-b]indole, which are separated by HPLC.

Example 89

Preparation of 8-chloro-2,3,4,5-tetrahydro-2-methyl-5-((E)-2-(pyridin-3-yl)prop-1-enyl)-1H-pyrido[4,3-b]indole and 8-chloro-2,3,4,5-tetrahydro-2-methyl-5-(2-(pyridin-3-yl)allyl)-1H-pyrido[4,3-b]indole (Compounds 86 and 133)

1-(8-Chloro-1,2,3,4-tetrahydro-2-methylpyrido[4,3-b]indol-5-yl)-2-(pyridin-3-yl)propan-2-ol (1 equiv.) was refluxed with 25% sulfuric acid for 2 h. The reaction mixture was cooled to 5° C. with an ice-water bath. KOH (15% aq. solution) was added dropwise to the reaction mixture until pH 9-10 was achieved. The reaction mixture was extracted with EtOAc. The combined organic layers were washed with water followed by brine, dried over sodium sulfate and evaporated under vacuum. The crude product was purified by column chromatography over silica gel (100-200 mesh) using a gradient of MeOH-EtOAc (0-10%) to obtain a mixture of 8-chloro-2,3,4,5-tetrahydro-2-methyl-5-((E)-2-(pyridin-3-yl)prop-1-enyl)-1H-pyrido[4,3-b]indole and 8-chloro-2,3,4,5-tetrahydro-2-methyl-5-(2-(pyridin-3-yl)allyl)-1H-pyrido[4,3-b]indole, which were separated by HPLC.

8-Chloro-2,3,4,5-tetrahydro-2-methyl-5-(2-(pyridin-3-yl)allyl)-1H-pyrido[4,3-b]indole: $^1$H NMR (CD$_3$OD, TFA salt) δ (ppm): 8.80 (m, 1H), 8.63 (m, 1H), 8.34 (m, 1H), 7.75 (m, 1H), 7.51 (s, 1H), 7.44 (d, 1H), 7.19 (d, 1H), 5.61 (m, 1H), 5.27 (m, 2H), 4.73 (m, 2H), 4.36 (m, 1H), 3.86 (m, 1H), 3.59 (m, 1H), 3.2 (m, 2H), 3.11 (s, 3H).

Example 90

Preparation of 2,3,4,5-tetrahydro-2,8-dimethyl-5-((E)-2-(pyridin-4-yl)prop-1-enyl)-1H-pyrido[4,3-b]indole and 2,3,4,5-tetrahydro-2,8-dimethyl-5-(2-(pyridin-4-yl)allyl)-1H-pyrido[4,3-b]indole (Compounds 88 and 135)

1-(1,2,3,4-Tetrahydro-2,8-dimethylpyrido[4,3-b]indol-5-yl)-2-(pyridin-4-yl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 was achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 2,3,4,5-tetrahydro-2,8-dimethyl-5-((E)-2-(pyridin-4-yl)prop-1-enyl)-1H-pyrido[4,3-b]indole and 2,3,4,5-tetrahydro-2,8-dimethyl-5-(2-(pyridin-4-yl)allyl)-1H-pyrido[4,3-b]indole, which are separated by HPLC.

Example 91

Preparation of 8-chloro-2,3,4,5-tetrahydro-2-methyl-5-((E)-2-(pyridin-4-yl)prop-1-enyl)-1H-pyrido[4,3-b]indole and 8-chloro-2,3,4,5-tetrahydro-2-methyl-5-(2-(pyridin-4-yl)allyl)-1H-pyrido[4,3-b]indole (Compounds 90 and 137)

1-(8-Chloro-1,2,3,4-tetrahydro-2-methylpyrido[4,3-b]indol-5-yl)-2-(pyridin-4-yl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 was achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-2,3,4,5-tetrahydro-2-methyl-5-((E)-2-(pyridin-4-yl)prop-1-enyl)-1H-pyrido[4,3-b]indole and 8-chloro-2,3,4,5-tetrahydro-2-methyl-5-(2-(pyridin-4-yl)allyl)-1H-pyrido[4,3-b]indole, which are separated by HPLC.

Example 92

Preparation of 8-chloro-2,3,4,5-tetrahydro-5-((E)-2-(4-methoxyphenyl)prop-1-enyl)-2-methyl-1H-pyrido[4,3-b]indole and 8-chloro-2,3,4,5-tetrahydro-5-(2-(4-methoxyphenyl)allyl)-2-methyl-1H-pyrido[4,3-b]indole (Compounds 92 and 138)

1-(8-Chloro-1,2,3,4-tetrahydro-2-methylpyrido[4,3-b]indol-5-yl)-2-(4-methoxyphenyl) propan-2-ol (1 equiv.) is heated to 55° C. with sulfuric acid in water for 2.5 h. The reaction mixture is cooled to 5-10° C. and neutralized by dropwise addition of satd. aq. sodium hydrogen carbonate solution followed by extraction with EtOAc. The combined organic extract is washed with water, then brine, dried over sodium sulfate and evaporated under vacuum to obtain 8-chloro-2,3,4,5-tetrahydro-5-((E)-2-(4-methoxyphenyl)prop-1-enyl)-2-methyl-1H-pyrido[4,3-b]indole and 8-chloro-2,3,4,5-tetrahydro-5-(2-(4-methoxyphenyl)allyl)-2-methyl-1H-pyrido[4,3-b]indole, which are separated by HPLC.

Example 93

Preparation of 8-chloro-5-((E)-2-(3-fluoro-4-methoxyphenyl)prop-1-enyl)-2,3,4,5-tetrahydro-2-methyl-1H-pyrido[4,3-b]indole and 8-chloro-5-(2-(3-fluoro-4-methoxyphenyl)allyl)-2,3,4,5-tetrahydro-2-methyl-1H-pyrido[4,3-b]indole (Compounds 93 and 140)

1-(8-Chloro-1,2,3,4-tetrahydro-2-methylpyrido[4,3-b]indol-5-yl)-2-(3-fluoro-4-methoxyphenyl)propan-2-ol (1 equiv.) was refluxed with 25% sulfuric acid for 2 h. The reaction mixture was cooled to 5° C. with an ice-water bath. KOH (15% aq. solution) was added dropwise to the reaction mixture until pH 9-10 was achieved. The reaction mixture was extracted with EtOAc. The combined organic layers were washed with water followed by brine, dried over sodium sulfate and evaporated under vacuum. The crude product was purified by column chromatography over silica gel (100-200 mesh) using a gradient of MeOH-EtOAc (0-10%) to obtain 8-chloro-5-((E)-2-(3-fluoro-4-methoxyphenyl)prop-1-enyl)-2,3,4,5-tetrahydro-2-methyl-1H-pyrido[4,3-b]indole and 8-chloro-5-(2-(3-fluoro-4-methoxyphenyl)allyl)-2,3,4,5-tetrahydro-2-methyl-1H-pyrido[4,3-b]indole, which were separated by HPLC.

8-Chloro-5-(2-(3-fluoro-4-methoxyphenyl)allyl)-2,3,4,5-tetrahydro-2-methyl-1H-pyrido[4,3-b]indole: $^1$H NMR (DMSO-d6, TFA salt) δ (ppm): 7.57 (m, 2H), 7.51 (d, 1H), 7.36 (d, 1H), 7.16 (m, 2H), 5.36 (s, 1H), 5.25 (m, 2H), 4.65 (m, 1H), 4.29 (m, 2H), 3.38 (s, 3H), 3.76 (m, 1H), 3.50 (m, 1H), 3.07 (m, 2H), 2.98 (s, 3H).

Example 94

Preparation of 2,3,4,5-tetrahydro-2,8-dimethyl-5-((E)-2-(6-methylpyridin-3-yl)vinyl)-1H-pyrido[4,3-b]indole (Compound 95)

2-(1,2,3,4-Tetrahydro-2,8-dimethylpyrido[4,3-b]indol-5-yl)-1-(6-methylpyridin-3-yl)ethanol (1 equiv.) was refluxed with 25% sulfuric acid for 2 h. The reaction mixture was cooled to 5° C. with an ice-water bath. KOH (15% aq. solution) was added dropwise to the reaction mixture until pH 9-10 was achieved. The reaction mixture was extracted with EtOAc. The combined organic layers were washed with water followed by brine, dried over sodium sulfate and evaporated under vacuum. The crude product was purified by column chromatography over silica gel (100-200 mesh) using a gradient of MeOH-EtOAc (0-10%).

Example 95

Preparation of 5-4E)-2-(5-(trifluoromethyl)pyridin-3-yl)vinyl)-2,3,4,5-tetrahydro-2,8-dimethyl-1H-pyrido[4,3-b]indole (Compound 97)

1-(5-(Trifluoromethyl)pyridin-3-yl)-2-(1,2,3,4-tetrahydro-2,8-dimethylpyrido[4,3-b]indol-5-yl)ethanol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%).

Example 96

Preparation of 8-chloro-5-((E)-2-(5-(trifluoromethyl)pyridin-3-yl)vinyl)-2,3,4,5-tetrahydro-2-methyl-1H-pyrido[4,3-b]indole (Compound 99)

2-(8-Chloro-1,2,3,4-tetrahydro-2-methylpyrido[4,3-b]indol-5-yl)-1-(5-(trifluoromethyl) pyridin-3-yl)ethanol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%).

Example 97

Preparation of 5-(3-fluoro-4-methoxystyryl)-8-chloro-2,3,4,5-tetrahydro-2-methyl-1H-pyrido[4,3-b]indole (Compound 94)

2-(8-Chloro-1,2,3,4-tetrahydro-2-methylpyrido[4,3-b]indol-5-yl)-1-(3-fluoro-4-methoxyphenyl)ethanol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%).

Example 98

Preparation of 8-chloro-2,3,4,5-tetrahydro-2-methyl-5-4E)-2-(6-propylpyridin-3-yl)prop-1-enyl)-1H-pyrido[4,3-b]indole and 8-chloro-2,3,4,5-tetrahydro-2-methyl-5-(2-(6-propylpyridin-3-yl)allyl)-1H-pyrido[4,3-b]indole (Compounds 96 and 134)

1-(8-Chloro-1,2,3,4-tetrahydro-2-methylpyrido[4,3-b]indol-5-yl)-2-(6-propylpyridin-3-yl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-2,3,4,5-tetrahydro-2-methyl-5-((E)-2-(6-propylpyridin-3-yl)prop-1-enyl)-1H-pyrido[4,3-b]indole and 8-chloro-2,3,4,5-tetrahydro-2-methyl-5-(2-(6-propylpyridin-3-yl)allyl)-1H-pyrido[4,3-b]indole, which are separated by HPLC.

Example 99

Preparation of 8-chloro-5-((E)-2-(3,4-difluorophenyl)prop-1-enyl)-2,3,4,5-tetrahydro-2-methyl-1H-pyrido[4,3-b]indole and 8-chloro-5-(2-(3,4-difluorophenyl)allyl)-2,3,4,5-tetrahydro-2-methyl-1H-pyrido[4,3-b]indole (Compounds 98 and 142)

1-(8-Chloro-1,2,3,4-tetrahydro-2-methylpyrido[4,3-b]indol-5-yl)-2-(3,4-difluorophenyl) propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-5-((E)-2-(3,4-difluorophenyl)prop-1-enyl)-2,3,4,5-tetrahydro-2-methyl-1H-pyrido[4,3-b]indole and 8-chloro- 5-(2-(3,4-difluorophenyl)allyl)-2,3,4,5-tetrahydro-2-methyl-1H-pyrido[4,3-b]indole, which are separated by HPLC.

Example 100

Preparation of 8-chloro-5-((E)-2-(4-chlorophenyl)prop-1-enyl)-2,3,4,5-tetrahydro-2-methyl-1H-pyrido[4,3-b]indole and 8-chloro-5-(2-(4-chlorophenyl)allyl)-2,3,4,5-tetrahydro-2-methyl-1H-pyrido[4,3-b]indole (Compounds 100 and 144)

1-(8-Chloro-1,2,3,4-tetrahydro-2-methylpyrido[4,3-b]indol-5-yl)-2-(4-chlorophenyl) propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-5-((E)-2-(4-chlorophenyl)prop-1-enyl)-2,3,4,5-tetrahydro-2-methyl-1H-pyrido[4,3-b]indole and 8-chloro-5-(2-(4-chlorophenyl)allyl)-2,3,4,5-tetrahydro-2-methyl-1H-pyrido[4,3-b]indole, which are separated by HPLC.

Example 101

Preparation of 8-chloro-5-((E)-2-(4-chloro-3-fluorophenyl)prop-1-enyl)-2,3,4,5-tetrahydro-2-methyl-1H-pyrido[4,3-b]indole and 8-chloro-5-(2-(4-chloro-3-fluorophenyl)allyl)-2,3,4,5-tetrahydro-2-methyl-1H-pyrido[4,3-b]indole (Compounds 101 and 139)

1-(8-Chloro-1,2,3,4-tetrahydro-2-methylpyrido[4,3-b]indol-5-yl)-2-(4-chloro-3-fluorophenyl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product was purified by column chromatography over silica gel (100-200 mesh) using a gradient of MeOH-EtOAc (0-10%) to obtain a mixture of 8-chloro-5-((E)-2-(4-chloro-3-fluorophenyl)prop-1-enyl)-2,3,4,5-tetrahydro-2-methyl-1H-pyrido[4,3-b]indole and 8-chloro-5-(2-(4-chloro-3-fluorophenyl)allyl)-2,3,4,5-tetrahydro-2-methyl-1H-pyrido[4,3-b]indole, which are separated by HPLC.

Example 102

Preparation of 8-chloro-5-((E)-2-(3,4-dichlorophenyl)prop-1-enyl)-2,3,4,5-tetrahydro-2-methyl-1H-pyrido[4,3-b]indole and 8-chloro-5-(2-(3,4-dichlorophenyl)allyl)-2,3,4,5-tetrahydro-2-methyl-1H-pyrido[4,3-b]indole (Compounds 103 and 141)

1-(8-Chloro-1,2,3,4-tetrahydro-2-methylpyrido[4,3-b]indol-5-yl)-2-(3,4-dichlorophenyl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-5-((E)-2-(3,4-dichlorophenyl)prop-1-enyl)-2,3,4,5-tetrahydro-2-methyl-1H-pyrido[4,3-b]indole and 8-chloro-5-(2-(3,4-dichlorophenyl)allyl)-2,3,4,5-tetrahydro-2-methyl-1H-pyrido[4,3-b]indole, which are separated by HPLC.

Example 103

Preparation of 8-chloro-5-((E)-2-(3-chloro-4-fluorophenyl)prop-1-enyl)-2,3,4,5-tetrahydro-2-methyl-1H-pyrido[4,3-b]indole and 8-chloro-5-(2-(3-chloro-4-fluorophenyl)allyl)-2,3,4,5-tetrahydro-2-methyl-1H-pyrido[4,3-b]indole (Compounds 105 and 143)

1-(8-Chloro-1,2,3,4-tetrahydro-2-methylpyrido[4,3-b]indol-5-yl)-2-(3-chloro-4-fluorophenyl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-5-((E)-2-(3-chloro-4-fluorophenyl)prop-1-enyl)-2,3,4,5-tetrahydro-2-methyl-1H-pyrido[4,3-b]indole and 8-chloro-5-(2-(3-chloro-4-fluorophenyl)allyl)-2,3,4,5-tetrahydro-2-methyl-1H-pyrido[4,3-b]indole, which are separated by HPLC.

Example 104

Preparation of 8-chloro-5-((E)-2-(2,4-difluorophenyl)prop-1-enyl)-2,3,4,5-tetrahydro-2-methyl-1H-pyrido[4,3-b]indole and 8-chloro-5-(2-(2,4-difluorophenyl)allyl)-2,3,4,5-tetrahydro-2-methyl-1H-pyrido[4,3-b]indole (Compounds 107 and 145)

1-(8-Chloro-1,2,3,4-tetrahydro-2-methylpyrido[4,3-b]indol-5-yl)-2-(2,4-difluorophenyl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-5-((E)-2-(2,4-difluorophenyl)prop-1-enyl)-2,3,4,5-tetrahydro-2-methyl-1H-pyrido[4,3-b]indole and 8-chloro-5-(2-(2,4-difluorophenyl)allyl)-2,3,4,5-tetrahydro-2-methyl-1H-pyrido[4,3-b]indole, which are separated by HPLC.

Example 105

Preparation of 8-fluoro-5-((E)-2-(4-fluorophenyl)prop-1-enyl)-2,3,4,5-tetrahydro-2-methyl-1H-pyrido[4,3-b]indole and 8-fluoro-5-(2-(4-fluorophenyl)allyl)-2,3,4,5-tetrahydro-2-methyl-1H-pyrido[4,3-b]indole (Compounds 102 and 146)

1-(8-Fluoro-1,2,3,4-tetrahydro-2-methylpyrido[4,3-b]indol-5-yl)-2-(4-fluorophenyl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-fluoro-5-((E)-2-(4-fluorophenyl)prop-1-enyl)-2,3,4,5-tetrahydro-2-methyl-1H-pyrido[4,3-b]indole and 8-fluoro-5-(2-(4-fluorophenyl)allyl)-2,3,4,5-tetrahydro-2-methyl-1H-pyrido[4,3-b]indole, which are separated by HPLC.

Example 106

Preparation of 8-chloro-2-cyclopropyl-5-((E)-2-(4-fluorophenyl)prop-1-enyl)-2,3,4,5-tetrahydro-1H-pyrido[4,3-b]indole and 8-chloro-2-cyclopropyl-5-(2-(4-fluorophenyl)allyl)-2,3,4,5-tetrahydro-1H-pyrido[4,3-b]indole (Compounds 104 and 147)

1-(8-Chloro-2-cyclopropyl-1,2,3,4-tetrahydropyrido[4,3-b]indol-5-yl)-2-(4-fluorophenyl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-2-cyclopropyl-5-((E)-2-(4-fluorophenyl)prop-1-enyl)-2,3,4,5-tetrahydro-1H-pyrido[4,3-b]indole and 8-chloro-2-cyclopropyl-5-(2-(4-fluorophenyl)allyl)-2,3,4,5-tetrahydro-1H-pyrido[4,3-b]indole, which are separated by HPLC.

Example 107

Preparation of 8-chloro-2,3,4,5-tetrahydro-2-methyl-5-((E)-2-phenylprop-1-enyl)-1H-pyrido[4,3-b]indole and 8-chloro-2,3,4,5-tetrahydro-2-methyl-5-(2-phenylallyl)-1H-pyrido[4,3-b]indole (Compounds 106 and 148)

1-(8-Chloro-1,2,3,4-tetrahydro-2-methylpyrido[4,3-b]indol-5-yl)-2-phenylpropan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-2,3,4,5-tetrahydro-2-methyl-5-((E)-2-phenylprop-1-enyl)-1H-pyrido[4,3-b]indole and 8-chloro-2,3,4,5-tetrahydro-2-methyl-5-(2-phenylallyl)-1H-pyrido[4,3-b]indole, which are separated by HPLC.

Example 108

Preparation of 8-chloro-5-((E)-2-(2,4,6-trifluorophenyl)prop-1-enyl)-2,3,4,5-tetrahydro-2-methyl-1H-pyrido[4,3-b]indole and 8-chloro-5-(2-(2,4,6-trifluorophenyl)allyl)-2,3,4,5-tetrahydro-2-methyl-1H-pyrido[4,3-b]indole (Compounds 108 and 150)

1-(8-Chloro-1,2,3,4-tetrahydro-2-methylpyrido[4,3-b]indol-5-yl)-2-(2,4,6-trifluorophenyl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-5-((E)-2-(2,4,6-trifluorophenyl)prop-1-enyl)-2,3,4,5-tetrahydro-2-methyl-1H-pyrido[4,3-b]indole and 8-chloro-5-(2-(2,4,6-trifluorophenyl)allyl)-2,3,4,5-tetrahydro-2-methyl-1H-pyrido[4,3-b]indole, which are separated by HPLC.

Example 109

Preparation of 8-chloro-5-4E)-3-(4-fluorophenyl)but-2-en-2-yl)-2,3,4,5-tetrahydro-2-methyl-1H-pyrido[4,3-b]indole and 8-chloro-5-(3-(4-fluorophenyl)but-3-en-2-yl)-2,3,4,5-tetrahydro-2-methyl-1H-pyrido[4,3-b]indole (Compounds 109 and 152)

3-(8-Chloro-1,2,3,4-tetrahydro-2-methylpyrido[4,3-b]indol-5-yl)-2-(4-fluorophenyl)butan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-5-((E)-3-(4-fluorophenyl)but-2-en-2-yl)-2,3,4,5-tetrahydro-2-methyl-1H-pyrido[4,3-b]indole and 8-chloro-5-(3-(4-fluorophenyl)but-3-en-2-yl)-2,3,4,5-tetrahydro-2-methyl-1H-pyrido[4,3-b]indole, which are separated by HPLC.

Example 110

Preparation of 8-chloro-5-((E)-2-(2,4-dichlorophenyl)prop-1-enyl)-2,3,4,5-tetrahydro-2-methyl-1H-pyrido[4,3-b]indole and 8-chloro-5-(2-(2,4-dichlorophenyl)allyl)-2,3,4,5-tetrahydro-2-methyl-1H-pyrido[4,3-b]indole (Compounds 111 and 154)

1-(8-Chloro-1,2,3,4-tetrahydro-2-methylpyrido[4,3-b]indol-5-yl)-2-(2,4-dichlorophenyl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column

Example 111

Preparation of 8-chloro-5-((E)-2-(4-fluorophenyl)but-1-enyl)-2,3,4,5-tetrahydro-2-methyl-1H-pyrido[4,3-b]indole and 8-chloro-5-(-2-(4-fluorophenyl)but-2-enyl)-2,3,4,5-tetrahydro-2-methyl-1H-pyrido[4,3-b]indole (Compounds 113 and 156)

1-(8-Chloro-1,2,3,4-tetrahydro-2-methylpyrido[4,3-b]indol-5-yl)-2-(4-fluorophenyl)butan-2-ol (1 equiv.) is refluxed with 25% sulfuric acid (7 mL) for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-5-((E)-2-(4-fluorophenyl)but-1-enyl)-2,3,4,5-tetrahydro-2-methyl-1H-pyrido[4,3-b]indole and 8-chloro-5-(-2-(4-fluorophenyl)but-2-enyl)-2,3,4,5-tetrahydro-2-methyl-1H-pyrido[4,3-b]indole, which are separated by HPLC.

Example 112

Preparation of 8-chloro-5-((Z)-3,3,3-trifluoro-2-(4-fluorophenyl)prop-1-enyl)-2,3,4,5-tetrahydro-2-methyl-1H-pyrido[4,3-b]indole (Compound 115)

3-(8-Chloro-1,2,3,4-tetrahydro-2-methylpyrido[4,3-b]indol-5-yl)-1,1,1-trifluoro-2-(4-fluorophenyl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%).

Example 113

Preparation of 8-chloro-5-((E)-2-cyclopropyl-2-(4-fluorophenyl)vinyl)-2,3,4,5-tetrahydro-2-methyl-1H-pyrido[4,3-b]indole and 8-chloro-5-(2-cyclopropylidene-2-(4-fluorophenyl)ethyl)-2,3,4,5-tetrahydro-2-methyl-1H-pyrido[4,3-b]indole (Compounds 110 and 149)

2-(8-Chloro-1,2,3,4-tetrahydro-2-methylpyrido[4,3-b]indol-5-yl)-1-cyclopropyl-1-(4-fluorophenyl)ethanol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-5-((E)-2-cyclopropyl-2-(4-fluorophenyl)vinyl)-2,3,4,5-tetrahydro-2-methyl-1H-pyrido[4,3-b]indole and 8-chloro-5-(2-cyclopropylidene-2-(4-fluorophenyl)ethyl)-2,3,4,5-tetrahydro-2-methyl-1H-pyrido[4,3-b]indole, which are separated by HPLC.

Example 114

Preparation of 5-((E)-2-(4-fluorophenyl)prop-1-enyl)-2,3,4,5-tetrahydro-8-iodo-2-methyl-1H-pyrido[4,3-b]indole and 5-(2-(4-fluorophenyl)allyl)-2,3,4,5-tetrahydro-8-iodo-2-methyl-1H-pyrido[4,3-b]indole (Compounds 112 and 155)

2-(4-Fluorophenyl)-1-(1,2,3,4-tetrahydro-8-iodo-2-methylpyrido[4,3-b]indol-5-yl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 5-((E)-2-(4-fluorophenyl)prop-1-enyl)-2,3,4,5-tetrahydro-8-iodo-2-methyl-1H-pyrido[4,3-b]indole and 5-(2-(4-fluorophenyl)allyl)-2,3,4,5-tetrahydro-8-iodo-2-methyl-1H-pyrido[4,3-b]indole, which are separated by HPLC.

Example 115

Preparation of 2-(2-methyl-1,2,3,4-tetrahydro-8-methylpyrido[4,3-b]indol-5-yl)-1-p-tolylethene (Compound 114)

2-(1,2,3,4-Tetrahydro-2,8-dimethylpyrido[4,3-b]indol-5-yl)-1-p-tolylethanol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%).

Example 116

Preparation of 8-chloro-2,3,4,5-tetrahydro-2-methyl-5-4E)-2-(pyrimidin-5-yl)prop-1-enyl)-1H-pyrido[4,3-b]indole and 8-chloro-2,3,4,5-tetrahydro-2-methyl-5-(2-(pyrimidin-5-yl)allyl)-1H-pyrido[4,3-b]indole (Compounds 116 and 151)

1-(8-Chloro-1,2,3,4-tetrahydro-2-methylpyrido[4,3-b]indol-5-yl)-2-(pyrimidin-5-yl)propan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 8-chloro-2,3,4,5-tetrahydro-2-methyl-5-((E)-2-(pyrimidin-5-yl)prop-1-enyl)-1H-pyrido[4,3-b]indole and 8-chloro-2,3,4,5-tetrahydro-2-methyl-5-(2-(pyrimidin-5-yl)allyl)-1H-pyrido[4,3-b]indole, which are separated by HPLC.

Example 117

Preparation of 2-(2-ethyl-1,2,3,4-tetrahydro-8-methylpyrido[4,3-b]indol-5-yl)-1-p-tolylethene (Compound 117)

2-(2-Ethyl-1,2,3,4-tetrahydro-8-methylpyrido[4,3-b]indol-5-yl)-1-p-tolylethanol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%).

Example 118

Preparation of 2-(1,2,3,4-tetrahydro-2-methylpyrido[4,3-b]indol-5-yl)-1-p-tolylethene (Compound 118)

2-(1,2,3,4-Tetrahydro-2-methylpyrido[4,3-b]indol-5-yl)-1-p-tolylethanol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%).

Example 119

Preparation of 2-(2-ethyl-1,2,3,4-tetrahydropyrido[4,3-b]indol-5-yl)-1-p-tolylethene (Compound 119)

2-(2-Ethyl-1,2,3,4-tetrahydropyrido[4,3-b]indol-5-yl)-1-p-tolylethanol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%).

Example 120

Preparation of 2,3,4,5-tetrahydro-2,8-dimethyl-5-((E)-2-phenylprop-1-enyl)-1H-pyrido[4,3-b]indole and 2,3,4,5-tetrahydro-2,8-dimethyl-5-(2-phenylallyl)-1H-pyrido[4,3-b]indole (Compounds 121 and 153)

1-(1,2,3,4-Tetrahydro-2,8-dimethylpyrido[4,3-b]indol-5-yl)-2-phenylpropan-2-ol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%) to obtain a mixture of 2,3,4,5-tetrahydro-2,8-dimethyl-5-((E)-2-phenylprop-1-enyl)-1H-pyrido[4,3-b]indole and 2,3,4,5-tetrahydro-2,8-dimethyl-5-(2-phenylallyl)-1H-pyrido[4,3-b]indole, which are separated by HPLC.

Example 121

Preparation of 2,3,4,5-tetrahydro-2,8-dimethyl-5-((E)-2-(pyridin-3-yl)vinyl)-1H-pyrido[4,3-b]indole (Compound 123)

2-(1,2,3,4-Tetrahydro-2,8-dimethylpyrido[4,3-b]indol-5-yl)-1-(pyridin-3-yl)ethanol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%).

Example 122

Preparation of 8-chloro-2,3,4,5-tetrahydro-2-methyl-5-((E)-2-(pyridin-3-yl)vinyl)-1H-pyrido[4,3-b]indole (Compound 120)

2-(8-Chloro-1,2,3,4-tetrahydro-2-methylpyrido[4,3-b]indol-5-yl)-1-(pyridin-3-yl)ethanol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%).

Example 123

Preparation of 8-chloro-5-4E)-2-(6-(trifluoromethyl)pyridin-3-yl)vinyl)-2,3,4,5-tetrahydro-2-methyl-1H-pyrido[4,3-b]indole (Compound 122)

2-(8-Chloro-1,2,3,4-tetrahydro-2-methylpyrido[4,3-b]indol-5-yl)-1-(6-(trifluoromethyl)pyridin-3-yl)ethanol (1 equiv.) is refluxed with 25% sulfuric acid for 2 h. The reaction mixture is cooled to 5° C. with an ice-water bath. KOH (15% aq. solution) is added dropwise to the reaction mixture until pH 9-10 is achieved. The reaction mixture is extracted with EtOAc. The combined organic layers are washed with water followed by brine, dried over sodium sulfate and evaporated under vacuum. The crude product is purified by column chromatography over silica gel (100-200 mesh) using a gradient of MeOH-EtOAc (0-10%).

Example 124

Preparation of 5-allyl-8-chloro-2,3,4,5-tetrahydro-2-methyl-1H-pyrido[4,3-b]indole To a suspension of NaH (60% dispersion in oil, 240 mg, 6 mmol) in DMF (15 mL) at 0° C. was added 8-chloro-2-methyl-2,3,4,5-tetrahydro-1H-pyrido[4,3-b]indole (1.1 g, 5 mmol) and the reaction mixture was stirred at 0° C. for 30 min, followed by addition of allyl bromide (0.51 mL, 6 mmol). The reaction mixture was allowed to warm to and was stirred at 25° C. for 3 h. MeOH was added and the reaction mixture was evaporated to dryness. The residue was purified by flash chromatography on silica gel using MeOH-DCM gradient. $^1$H NMR (DMSO-d6) δ (ppm): 7.53 (s, 1H), 7.47 (d, 1H), 7.15 (d, 1H), 5.94 (m, 1H), 5.1 (m, 1H), 4.83 (m, 1H), 4.78 (s, 2H), 4.25 (s, 2H), 3.44 (s, 2H), 3.02 (s, 2H), 2.86 (s, 3H).

Example 125

Preparation of 8-chloro-2,3,4,5-tetrahydro-2-methyl-5-((E)-3-(6-methylpyridin-3-yl)allyl)-1H-pyrido[4,3-b]indole (Compound 125)

5-Allyl-8-chloro-2,3,4,5-tetrahydro-2-methyl-1H-pyrido[4,3-b]indole (300 mg, 1.15 mmol, 1 equiv.) and 5-bromo-2-methylpyridine (198 mg, 1.15 mmol, 1 equiv.) were heated to 100° C. with palladium acetate (7.8 mg, 0.034 mmol), triphenyl phosphine (18 mg, 0.069 mmol) and triethyl amine (0.35 mL, 2 equiv.) in THF (6 mL) for 14 h. The reaction mixture was cooled to RT and diluted with THF (10 mL), filtered over a Celite bed and concentrated. The concentrate was dissolved in EtOAc (20 mL) and washed with water (5 mL) followed by brine. The organic layer was dried over anhydrous sodium sulfate, and evaporated under reduced pressure to obtain crude product that was purified by HPLC. $^1$H NMR (CD$_3$OD) δ (ppm): 8.57 (s, 1H), 8.39-8.37 (d, 1H), 7.74-7.72 (d, 1H), 7.51 (s, 1H), 7.41 (d, 1H), 7.17 (d, 1H), 6.78-6.72 (m, 1H), 6.28-6.24 (d, 1H), 5.02 (m, 2H), 4.7 (bs, 1H), 4.36 (bs, 1H), 3.87 (bs, 1H), 3.6 (bs, 1H), 3.29-3.24 (m, 2H), 3.12-3.10 (s, 3H), 2.7 (s, 3H).

Example 126

Preparation of 5-(4-fluorocinnamyl)-8-chloro-2,3,4,5-tetrahydro-2-methyl-1H-pyrido[4,3-b]indole (Compound 126)

5-Allyl-8-chloro-2,3,4,5-tetrahydro-2-methyl-1H-pyrido[4,3-b]indole (200 mg, 0.76 mmol, 1 equiv.) and 4-fluoro-bromobenzene (134 mg, 0.76 mmol, 1 equiv.) were heated to 100° C. with palladium acetate (5 mg, 0.023 mmol), triphenyl phosphine (12 mg, 0.046 mmol) and triethyl amine (0.22 mL, 2 equiv.) in THF (5 mL) for 14 h. The reaction mixture was cooled to RT and diluted with THF (10 mL), filtered over a Celite bed and concentrated. The concentrate was dissolved in EtOAc (20 mL) and washed with water (5 mL) followed by brine. The organic layer was dried over anhydrous sodium sulfate, and evaporated under reduced pressure to obtain crude product that was purified by HPLC. $^1$H NMR (DMSO-d6) δ (ppm): 10.0 (bs, 1H), 7.61-7.58 (d, 2H), 7.44-7.40 (dd, 2H), 7.20-7.11 (m, 3H), 6.4 (d, 1H), 6.3 (m, 1H), 5.0 (m, 2H), 4.62 (d, 1H), 4.29-4.25 (m, 1H), 3.78 (m, 1H), 3.5 (m, 1H), 3.18 (m, 2H), 2.98 (s, 3H).

Example 127

Preparation of 8-chloro-2,3,4,5-tetrahydro-2-methyl-5-4E)-3-(pyridin-4-yl)allyl)-1H-pyrido[4,3-b]indole (Compound No. 127)

5-Allyl-8-chloro-2,3,4,5-tetrahydro-2-methyl-1H-pyrido[4,3-b]indole (400 mg, 1.52 mmol, 1 equiv.) and 4-bromopyridine (240 mg, 1.52 mmol, 1 equiv.) were heated to 100° C. with palladium acetate (10 mg, 0.046 mmol), triphenyl phosphine (24 mg, 0.092 mmol) and triethyl amine (0.44 mL, 2 equiv.) in 10 mL of THF for 14 h. The reaction mixture was cooled to RT and diluted with THF (10 mL), filtered over a Celite bed and concentrated. The concentrate was dissolved in EtOAc (40 mL) and washed with water (10 mL) followed by brine. The organic layer was dried over anhydrous sodium sulfate, and evaporated under reduced pressure to obtain crude product that was purified by HPLC. $^1$H NMR (DMSO-d6) δ (ppm): 0.64 (bs, 1H), 8.68-8.66 (d, 2H), 7.79-7.77 (d, 2H), 7.6-7.56 (m, 2H), 7.2-7.1 (d, 1H), 7.0-6.9 (m, 1H), 6.5-6.4 (d, 1H), 5.15-5.03 (m, 2H), 4.64-4.60 (d, 1H), 4.3-4.25 (m, 1H), 3.79-3.76 (m, 1H), 3.52-3.50 (m, 1H), 3.17 (bs, 2H), 2.98 (s, 3H).

Example 128

Preparation of 8-chloro-5-(2-(3-pyridyl)cyclohex-1-yl)-2,3,4,5-tetrahydro-2-methyl-1H-pyrido[4,3-b]indole Step 1: Synthesis of 8-Chloro-2-methyl-2,3,4,5-tetrahydro-1H-pyrido[4,3-b]indole 8-Chloro-2-methyl-2,3,4,5-tetrahydro-1H-pyrido[4,3-b]indole was prepared according to Example 1.

Step 2: Synthesis of 3-cyclohexenylpyridine

3-Cyclohexenylpyridine was obtained as outlined in Barbero et al., *Tet. Letters* (1992), 33(39):5841-42.

Step 3: Preparation of title compound

To a solution of 8-Chloro-2-methyl-2,3,4,5-tetrahydro-1H-pyrido[4,3-b]indole (0.1 g, 0.45 mmol) in N-methyl-2-pyrrolidone (1.0 mL) was added powdered KOH (0.140 g, 2.5 mmol) and stirred for 10 min. at RT. 4-cyclohexenylpyridine (1.25 mol) was added and the reaction mixture was stirred for additional 4 h at 100° C. After completion of reaction (as analyzed by TLC), the reaction mixture was diluted with water (15 mL) and extracted with EtOAc (3×20 mL). The organic layer was dried over anhydrous sodium sulfate and concentrated under reduced pressure to obtain the product.

Example 144

Preparation of (E)-8-chloro-5-(2-(4-fluorophenyl) prop-1-enyl)-2,3,4,5-tetrahydro-2-methyl-1H-pyrido [4,3-b]indole (Compound 83)

1-(8-Chloro-1,2,3,4-tetrahydro-2-methylpyrido[4,3-b]indol-5-yl)-2-(4-fluorophenyl)propan-1-ol (1 g, 2.68 mmol, 1 equiv.) was refluxed with 25% sulfuric acid (7 mL) for 2 h, cooled to RT and then cooled to 5° C. in ice-water bath. 15% aqueous solution of KOH was added dropwise to the reaction mixture (pH 9-10), followed by extraction with EtOAc (3×10 mL). The combined organic extracts were washed with water (10 mL) followed by brine, dried over sodium sulfate and evaporated under vacuum and purified by column chromatography using 100-200 silica gel, using a gradient of MeOH-EtOAc (0-10%) to obtain a mixture of isomers (150 mg), which was separated by HPLC. Yield: 15 mg. $^1$H NMR (CD$_3$OD, TFA salt) δ (ppm): 7.68 (t, 2H), 7.54 (s, 1H), 7.21 (s, 2H), 7.16 (t, 2H), 6.97 (s, 1H), 4.8 (bs, 1H), 4.39 (bs, 1H), 3.85 (bs, 1H), 3.60 (bs, 1H), 3.13 (bs, 5H), 1.92 (s, 3H).

Example 145

Preparation of (E)-5-(2-(4-fluorophenyl)prop-1-enyl)-2,3,4,5-tetrahydro-2,8-dimethyl-1H-pyrido[4,3-b]indole (Compound 87)

2-(4-fluorophenyl)-1-(1,2,3,4-tetrahydro-2,8-dimethyl-pyrido[4,3-b]indol-5-yl)propan-2-ol (4.6 g, 13.05 mmol, 1 equiv.) was heated to reflux with 25% aqueous sulfuric acid (14 mL) for 2 h. The reaction mixture was cooled to 0-5° C. and made alkaline with 15% aqueous KOH solution and extracted with THF:EtOAc (1:1 mixture, 2×30 mL). The combined organic layer was washed with water (15 mL) and brine, dried over sodium sulfate and evaporated under vacuum to obtain the crude product that was purified by flash chromatography on silica gel using EtOAc as eluent. $^1$H NMR (DMSO-d6, oxalate salt) δ (ppm): 10.0 (bs, 1H), 7.7 (m, 2H), 7.2 (m, 3H), 7.10 (d, 2H), 7.0 (d, 1H), 4.6 (d, 1H), 4.3 (d, 1H), 3.7 (bs, 1H), 3.49 (bs, 1H), 3.0 (bs, 2H), 3.0 (s, 3H), 2.4 (s, 3H), 1.8 (s, 3H).

Example 146

Preparation of (E)-8-chloro-2,3,4,5-tetrahydro-5-(2-(4-methoxyphenyl)prop-1-enyl)-2-methyl-1H-pyrido[4,3-b]indole (Compound 92)

1-(8-Chloro-1,2,3,4-tetrahydro-2-methylpyrido[4,3-b]indol-5-yl)-2-(4-methoxyphenyl)propan-2-ol (500 mg, 1.3 mmol, 1 equiv.) was heated to 55° C. with sulfuric acid (0.375 mL) in water (5 mL) for 2.5 h, cooled to 5-10° C. and neutralized by dropwise addition of saturated aqueous sodium hydrogen carbonate solution followed by extraction with EtOAc (2×15 mL). The combined organic extract was washed with water (10 mL), brine, dried over sodium sulfate and evaporated under reduced pressure to obtain 330 mg of product. $^1$H NMR (DMSO-d6, oxalate salt) δ (ppm): 7.60 (m, 3H), 7.24 (d, 1H), 7.19 (d, 1H), 7.10 (d, 1H), 7.0 (m, 2H), 4.40 (m, 2H), 3.80 (s, 3H), 3.10 (m, 4H), 2.80 (s, 3H), 1.80 (s, 3H).

Example 147

Preparation of (E)-8-chloro-5-(2-(3-fluoro-4-methoxyphenyl)prop-1-enyl)-2,3,4,5-tetrahydro-2-methyl-1H-pyrido[4,3-b]indole (Compound 93)

1-(8-Chloro-1,2,3,4-tetrahydro-2-methylpyrido[4,3-b]indol-5-yl)-2-(3-fluoro-4-methoxyphenyl)propan-2-ol (1 g, 2.48 mmol, 1 equiv.) was refluxed with 25% sulfuric acid (7 mL) for 2 h. The reaction mixture was cooled to 5° C. in ice-water bath. KOH (15% aqueous solution) was added dropwise to the reaction mixture until pH 9-10 was achieved. The reaction mixture was extracted with EtOAc (3×10 mL). The combined organic layer was washed with water (10 mL) followed by brine, dried over sodium sulfate and evaporated under vacuum. The crude product was purified by silica gel chromatography (100-200 mesh) using a gradient of MeOH-EtOAc (0-10%) to obtain a mixture of isomers, which were separated by HPLC. $^1$H NMR (DMSO-d6, oxalate salt) δ (ppm): 7.60 (m, 2H), 7.43 (m, 1H), 7.22-7.15 (m, 4H), 4.40 (m, 2H), 3.80 (s, 3H), 3.10 (m, 4H), 2.80 (s, 3H), 1.80 (s, 3H).

Example 148

Preparation of 2,3,4,5-tetrahydro-2,8-dimethyl-5-((E)-2-(6-methylpyridin-3-yl)vinyl)-1H-pyrido[4,3-b]indole (Compound 95)

2-(1,2,3,4-Tetrahydro-2,8-dimethylpyrido[4,3-b]indol-5-yl)-1-(6-methylpyridin-3-yl)ethanol (1 g, 2.98 mmol, 1 eq) was refluxed with 25% sulfuric acid (7 mL) for 2 h. The reaction mixture was cooled to 5° C. with an ice-water bath. KOH (15% aq. solution) was added dropwise to the reaction mixture until pH 9-10 was achieved. The reaction mixture was extracted with EtOAc (3×10 mL). The combined organic layers were washed with water (10 mL) followed by brine, dried over sodium sulfate and evaporated under vacuum. The crude product was purified by column chromatography over silica gel (100-200 mesh) using a gradient of MeOH-EtOAc (0-10%). $^1$H NMR (CD$_3$OD, TFA salt) δ (ppm): 8.8 (s, 1H), 8.55 (d, 1H), 7.95 (d, 1H), 7.75 (m, 2H), 7.35 (s, 1H), 7.28 (d, 1H), 7.0 (d, 1H), 4.8 (bs, 1H), 4.4 (bs, 1H), 3.9 (bs, 1H), 3.6 (bs, 1H), 3.4 (t, 2H), 3.15 (s, 3H), 2.75 (s, 3H), 2.45 (s, 3H).

Example 149

Preparation of (E)-8-chloro-2,3,4,5-tetrahydro-2-methyl-5-(2-(pyridin-4-yl)prop-1-enyl)-1H-pyrido[4,3-b]indole (Compound 90)

1-(8-Chloro-1,2,3,4-tetrahydro-2-methylpyrido[4,3-b]indol-5-yl)-2-(pyridin-4-yl)propan-2-ol (1 g, 2.81 mmol, 1 equiv.) was refluxed with 25% sulfuric acid (7 mL) for 2 h. The reaction mixture was cooled to 5° C. in ice-water bath. KOH (15% aqueous solution) was added dropwise to the reaction mixture until pH 9-10 was achieved. The reaction mixture was extracted with EtOAc (3×10 mL). The combined organic layer was washed with water (10 mL) followed by brine, dried over sodium sulfate and evaporated under vacuum. The crude product was purified by silica gel chromatography (100-200 mesh) using a gradient of MeOH-EtOAc (0-10%) followed by HPLC to provide pure product. $^1$HNMR (DMSO, Oxalate Salt) δ (ppm): 8.60 (d, 2H), 7.62 (m, 3H), 7.40 (s, 1H), 7.30 (d, 1H), 7.20 (d, 1H), 4.40 (m, 2H), 3.10 (m, 4H), 2.99 (s, 3H), 1.90 (s, 3H).

Example 150

Preparation of (E)-8-chloro-2,3,4,5-tetrahydro-2-methyl-5-(2-(6-methylpyridin-3-yl)prop-1-enyl)-1H-pyrido[4,3-b]indole (Compound 89)

1-(8-Chloro-1,2,3,4-tetrahydro-2-methylpyrido[4,3-b]indol-5-yl)-2-(6-methylpyridin-3-yl)propan-2-ol (1 g, 2.70 mmol, 1 equiv.) was refluxed with 25% sulfuric acid (7 mL) for 2 h. The reaction mixture was cooled to 5° C. in ice-water bath. KOH (15% aqueous solution) was added dropwise to the reaction mixture until pH 9-10 was achieved. The reaction mixture was extracted with EtOAc (3×10 mL). The combined organic layer was washed with water (10 mL) followed by brine, dried over sodium sulfate and evaporated under vacuum. The crude product was purified by silica gel chromatography (100-200 mesh) using a gradient of MeOH-EtOAc (0-10%) to obtain a mixture of isomers, which were separated by HPLC. $^1$H NMR (CD$_3$OD, oxalate salt) δ (ppm): 8.70 (s, 1H), 8.05 (d, 1H), 7.55 (s, 1H), 7.40 (d, 1H), 7.35 (m, 2H), 7.20 (m, 1H), 5.0 (m, 2H), 4.50 (m, 2H), 4.25 (m, 1H), 3.70 (m, 2H), 3.10 (s, 3H), 2.80 (m, 2H), 2.60 (s, 3H).

Example 151

Preparation of (E)-2,3,4,5-tetrahydro-2,8-dimethyl-5-(2-(pyridin-4-yl)prop-1-enyl)-1H-pyrido[4,3-b]indole (Compound 88)

1-(1,2,3,4-Tetrahydro-2,8-dimethylpyrido[4,3-b]indol-5-yl)-2-(pyridin-4-yl)propan-2-ol (6 g, 17.91 mmol) was dissolved in DCM (75 mL). DMF (1 mL) was added and the reaction mixture was cooled to 0° C. Thionyl chloride (3.89 mL, 53.73 mmol) was diluted with DCM (75 mL) and added to the above reaction mixture dropwise. The reaction mixture was stirred at RT for 3 h. Progress of the reaction was monitored by TLC (10% MeOH-DCM). Upon completion of the reaction, the reaction mixture was evaporated to dryness and the residue was basified with saturated aqueous NaHCO$_3$ with cooling. The product was extracted with EtOAc, the organic layer was washed with water; dried over anhydrous sodium sulfate and concentrated. The residue was purified by silica gel chromatography (100-200 mesh) eluting with 2% MeOH-DCM to obtain 1.7 g of product as the free base. $^1$HNMR (DMSO, Oxalate salt) δ (ppm): 8.70 (s, 1H), 7.69 (d, 2H), 7.46 (m, 1H), 7.31 (s, 1H), 7.13 (d, 1H), 7.06 (m, 1H), 6.85 (s, 1H), 3.70 (m, 2H), 3.10 (m, 2H), 3.0 (s, 3H), 2.66 (m, 1H), 2.40 (s, 3H), 2.20 (m, 2H), 1.90 (m, 2H).

Example 152

Preparation of (E)-2,8-dimethyl-5-styryl-2,3,4,5-tetrahydro-1H-pyrido[4,3-b]indole (Compound 202)

2,8-Dimethyl-2,3,4,5-tetrahydro-1H-pyrido[4,3-b]indole (100 mg, 0.5 mmol), B-bromo styrene (91 mg, 0.55 mmol), CuI (9 mg, 0.05 mmol), L-proline (11 mg, 0.1 mmol) and potassium phosphate (212 mg, 1 mmol) taken in DMF (3 mL) under inert atmosphere, heated overnight at 80° C. The reaction mixture was cooled to RT, quenched with water, extracted with EtOAc, dried over anhydrous sodium sulfate and evaporated under reduced pressure. The crude product was purified by column chromatography to afford 35 mg of title compound as the free base. $^1$H NMR (CDCl$_3$, HCl salt) δ (ppm): 7.60-7.55 (d, 1H), 7.50-7.45 (m, 3H), 7.42-7.38 (m, 2H), 7.25-7.20 (m, 2H), 7.15-7.10 (d, 1H), 6.80-6.75 (d, 1H), 3.75 (s, 2H), 3.12-3.05 (m, 2H), 2.98-2.90 (m, 2H), 2.67 (s, 3H), 2.50 (s, 3H).

Example 153

Preparation of (E)-8-chloro-2,3,4,5-tetrahydro-2-methyl-5-(2-phenylprop-1-enyl)-1H-pyrido[4,3-b]indole (Compound 106)

1-(8-Chloro-1,2,3,4-tetrahydro-2-methylpyrido[4,3-b]indol-5-yl)-2-phenylpropan-2-ol (1 g, 2.82 mmol, 1 equiv.) was refluxed with 25% sulfuric acid (7 mL) for 2 h. The reaction mixture was cooled to 5° C. in ice-water bath. KOH (15% aqueous solution) was added dropwise to the reaction mixture until pH 9-10 was achieved. The reaction mixture was extracted with EtOAc (3×10 mL). The combined organic layer was washed with water (10 mL) followed by brine, dried over sodium sulfate and evaporated under vacuum. The crude product was purified by silica gel chromatography (100-200 mesh) using a gradient of MeOH-EtOAc (0-10%) to obtain a mixture of isomers, which were separated by HPLC. $^1$H NMR (DMSO-d6, oxalate salt) δ (ppm): 7.66 (m, 2H), 7.60 (m, 1H), 7.40 (m, 3H), 7.25 (d, 1H), 7.18 (d, 1H), 7.08 (s, 1H), 3.60 (m, 2H), 3.40 (m, 2H), 3.0 (m, 2H), 2.85 (m, 3H), 1.90 (s, 3H).

Example 154

Preparation of (E)-8-chloro-5-(2-cyclopropyl-2-(4-fluorophenyl)vinyl)-2,3,4,5-tetrahydro-2-methyl-1H-pyrido[4,3-b]indole (Compound 110)

2-(8-Chloro-1,2,3,4-tetrahydro-2-methylpyrido[4,3-b]indol-5-yl)-1-cyclopropyl-1-(4-fluorophenyl)ethanol (1 g, 2.51 mmol, 1 equiv) was refluxed with 25% sulfuric acid (7 mL) for 2 h. The reaction mixture was cooled to 5° C. in ice-water bath. KOH (15% aqueous solution) was added dropwise to the reaction mixture until pH 9-10 was achieved. The reaction mixture was extracted with EtOAc (3×10 mL). The combined organic layer was washed with water (10 mL) followed by brine, dried over sodium sulfate and evaporated under vacuum. The crude product was purified by silica gel chromatography (100-200 mesh) using a gradient of MeOH-EtOAc (0-10%) to obtain a mixture of isomers, which were separated by HPLC. $^1$H NMR (CD$_3$OD, TFA salt) δ (ppm): 7.50 (m, 2H), 7.40 (d, 1H), 7.20 (m, 3H), 7.05 (m, 1H), 6.80 (d, 1H), 4.75 (m, 1H), 4.40 (m, 1H), 3.90 (m, 1H), 3.60 (m, 1H), 3.30 (m, 3H), 3.12 (s, 3H), 2.80 (m, 1H), 2.0 (m, 1H), 1.80 (m, 1H), 1.15 (m, 1H).

Example 155

Preparation of (Z)-8-chloro-5-(2-cyclopropyl-2-(4-fluorophenyl)vinyl)-2-methyl-2,3,4,5-tetrahydro-1H-pyrido[4,3-b]indole (Compound 203)

2-(8-Chloro-1,2,3,4-tetrahydro-2-methylpyrido[4,3-b]indol-5-yl)-1-cyclopropyl-1-(4-fluorophenyl)ethanol (1 g, 2.51 mmol, 1 equiv) was refluxed with 25% sulfuric acid (7 mL) for 2 h. The reaction mixture was cooled to 5° C. KOH (15% aqueous solution) was added dropwise to the reaction mixture until pH 9-10. The reaction mixture was extracted with EtOAc (3×10 mL). The combined organic layer was washed with water (10 mL) followed by brine, dried over sodium sulfate and evaporated under vacuum. The crude product was purified by silica gel chromatography (100-200 mesh) using a gradient of MeOH-EtOAc (0-10%) to obtain a mixture of isomers, which were separated by HPLC. $^1$H NMR (CD$_3$OD, TFA salt) δ (ppm): 7.40 (s, 1H), 7.20 (d, 1H), 7.10 (m, 3H), 6.90 (m, 2H), 6.70 (s, 1H), 4.60 (m, 1H), 4.22 (m, 1H), 3.70 (m, 1H), 3.40 (m, 1H), 3.0 (s, 3H), 2.80 (m, 2H), 1.80 (m, 1H), 1.0 (m, 2H), 0.8 (m, 2H).

Example 156

Preparation of 8-chloro-5-((1E,3E)-2-(4-fluorophenyl)penta-1,3-dienyl)-2-methyl-2,3,4,5-tetrahydro-1H-pyrido[4,3-b]indole (Compound 204)

2-(8-Chloro-1,2,3,4-tetrahydro-2-methylpyrido[4,3-b]indol-5-yl)-1-cyclopropyl-1-(4-fluorophenyl)ethanol (398 g, 1 mmol) was dissolved thionyl chloride (3 mL) and stirred for 5 min. at RT. The solution was heated at 50° C. for 2 h. Excess thionyl chloride was removed under reduced pressure and the residue was dissolved in N-methyl-2-pyrrolidone (3 mL). KOH (472 mg, 8.4 mmol) was added and the reaction mixture was heated at 100° C. for 2 h. The reaction mixture was cooled to RT and diluted with ice-cold water. The aqueous layer was extracted with EtOAc, the organic layer was washed with water, dried over sodium sulfate, and concentrated, under reduced pressure. The residue was purified by silica gel chromatography (100-200 mesh) eluting with 2% MeOH-DCM followed by HPLC. $^1$H NMR (CD$_3$OD, TFA salt) δ (ppm): 7.58 (s, 1H), 7.48 (m, 2H), 7.20 (m, 4H), 6.60 (s, 1H), 6.0 (d, 1H), 5.80 (m, 1H), 4.75 (m, 2H), 4.40 (m, 1H), 3.82 (m, 1H), 3.58 (m, 1H), 3.20 (m, 1H), 3.10 (s, 3H), 2.0 (d, 3H).

Example 157

Preparation of (E)-5-(2-(4-fluorophenyl)prop-1-enyl)-2-methyl-2,3,4,5-tetrahydro-1H-pyrido[4,3-b]indole (Compound 205)

(E)-8-Chloro-5-(2-(4-fluorophenyl)prop-1-enyl)-2-methyl-2,3,4,5-tetrahydro-1H-pyrido[4,3-b]indole (0.200 g) was dissolved in MeOH which was hydrogenated over 10% Pd—C at 40° C. and 30 bars H$_2$. The progress of reaction was monitored by TLC. The solvent was evaporated and the residue was purified by HPLC. $^1$H NMR (CDCl$_3$, TFA salt) δ (ppm): 7.58 (m, 2H), 7.42 (m, 1H), 7.25 (m, 3H), 7.15 (m, 2H), 6.80 (s, 1H), 4.80 (m, 1H), 4.20 (m, 1H), 3.90 (m, 1H), 3.35 (m, 2H), 3.05 (s, 3H), 2.90 (m, 1H), 1.95 (s, 3H).

Example 158

Preparation of (E)-8-chloro-5-(2-cyclobutyl-2-(4-fluorophenyl)vinyl)-2-methyl-2,3,4,5-tetrahydro-1H-pyrido[4,3-b]indole (Compound 206)

2-(8-Chloro-1,2,3,4-tetrahydro-2-methylpyrido[4,3-b]indol-5-yl)-1-cyclobutyl-1-(4-fluorophenyl)ethanol (500 mg, 1.2 mmol) was dissolved in thionyl chloride (5 mL) and the solution was stirred at RT for 3 h. Excess thionyl chloride was removed under reduced pressure and the residue was dissolved in N-methyl-2-pyrrolidone (3 mL) and the solution was stirred for 5 min. at RT. Powdered KOH (637 mg, 11 mmol) was added and the reaction mixture was heated at 100° C. for 3 h. The reaction mixture was cooled to RT and diluted with water. The precipitate obtained was filtered and washed with hexane, followed by purification by HPLC. $^1$H NMR (DMSO-d6, oxalate salt) δ (ppm): 7.58 (m, 1H), 7.45 (d, 1H), 7.25 (m, 1H), 7.10 (d, 1H), 7.0 (m, 3H), 6.70 (m, 1H), 4.30-4.20 (m, 3H), 3.65 (m, 2H), 3.50 (m, 2H), 2.90 (m, 2H), 2.80 (s, 3H), 2.20 (m, 2H), 1.80 (m, 1H), 1.60-1.30 (m, 1H).

Example 159

Preparation of (E)-4-(2,8-dimethyl-3,4-dihydro-1H-pyrido[4,3-b]indol-5(2H)-yl)-3-(4-fluorophenyl)-N-methylbut-3-enamide (Compound 207)

Ethyl 4-(2,8-dimethyl-3,4-dihydro-1H-pyrido[4,3-b]indol-5(2H)-yl)-3-(4-fluorophenyl)but-2-enoate (50 mg, 0.123 mmol; prepared according to General Method 5) in 40% aqueous methyl amine (1 mL) was heated overnight at 100° C. The reaction mixture was cooled to RT and diluted with water (5 mL). A white solid precipitated out which was filtered and dried under vacuum. $^1$H NMR (CD$_3$OD, HCl salt) δ (ppm): 7.60 (m, 2H), 7.30 (d, 1H), 7.20 (m, 3H), 7.10 (m, 1H), 7.0 (d, 1H), 4.70 (m, 1H), 4.35 (m, 1H), 3.80 (m, 2H), 3.60 (m, 2H), 3.30 (m, 3H), 3.15 (s, 3H), 2.55 (s, 3H), 2.40 (s, 2H).

Example 160

Preparation of (E)-8-chloro-5-(2-(4-fluorophenyl)hex-1-enyl)-2-methyl-2,3,4,5-tetrahydro-1H-pyrido[4,3-b]indole (Compound 208)

1-(8-Chloro-2-methyl-3,4-dihydro-1H-pyrido[4,3-b]indol-5(2H)-yl)-2-(4-fluorophenyl)hexan-2-ol (800 mg, 1.8 mmol) was dissolved in thionyl chloride (5 mL) and the solution was stirred at RT for 2 h. The reaction mixture was concentrated under reduced pressure. The residue was dissolved in N-methyl-2-pyrrolidone, stirred for 5 min. at RT, powdered KOH (725 mg, 1.2 mmol) added, and then heated at 100° C. for 3 h. The reaction mixture was cooled to RT and diluted with ice-water to obtain solid product which was filtered and washed with hexane. The product was purified by HPLC. $^1$H NMR (DMSO-d6, oxalate salt) δ (ppm): 7.70 (m, 2H), 7.50 (m, 1H), 7.36 (m, 2H), 7.0 (m, 2H), 6.85 (m, 1H), 4.40 (m, 2H), 4.20 (m, 2H), 3.60 (m, 1H), 3.50 (m, 1H), 3.38 (m, 1H), 3.05 (m, 1H), 2.90 (s, 3H), 2.70 (m, 1H), 2.30 (m, 1H), 1.35 (m, 2H), 0.9 (t, 3H).

Example 161

Preparation of (E)-4-(2,8-dimethyl-3,4-dihydro-1H-pyrido[4,3-b]indol-5(2H)-yl)-3-(4-fluorophenyl)but-3-enoic acid (Compound 209)

A mixture of ethyl 4-(2,8-dimethyl-3,4-dihydro-1H-pyrido[4,3-b]indol-5(2H)-yl)-3-(4-fluorophenyl)but-2-enoate (50 mg, 0.123 mmol; prepared according to General Method 5) and 40% aqueous N,N-dimethylamine (1 mL) was heated overnight at 100° C. The reaction mixture was cooled to RT, diluted with water (5 mL) and extracted with EtOAc. The organic layer was dried over anhydrous sodium sulfate and concentrated to obtain the crude product, which was triturated with ether to obtain a pale yellow solid. $^1$H NMR (CD$_3$OD, freebase) δ (ppm): 7.65 (m, 2H), 7.30 (d, 1H), 7.20 (m, 3H), 7.05 (d, 1H), 6.90 (d, 1H), 4.35 (m, 2H), 3.50 (m, 2H), 3.20 (m, 4H), 3.0 (s, 3H), 2.40 (s, 3H).

Example 162

Preparation of (Z)-8-chloro-5-(2-(2,4-dichlorophenyl)prop-1-enyl)-2,3,4,5-tetrahydro-2-methyl-1H-pyrido[4,3-b]indole (Compound 111)

1-(8-Chloro-1,2,3,4-tetrahydro-2-methylpyrido[4,3-b]indol-5-yl)-2-(2,4-dichlorophenyl)propan-2-ol (1 g, 2.36 mmol, 1 equiv.) was refluxed with 25% sulfuric acid (7 mL) for 2 h. The reaction mixture was cooled to 5° C. in ice-water bath. KOH (15% aqueous solution) was added dropwise to the reaction mixture until pH 9-10 was achieved. The reaction mixture was extracted with EtOAc (3×10 mL). The combined organic layer was washed with water (10 mL) followed by brine, dried over sodium sulfate and evaporated under vacuum. The crude product was purified by silica gel chromatography (100-200 mesh) using a gradient of MeOH-EtOAc (0-10%) to obtain a mixture of isomers, which were separated by HPLC. $^1$H NMR (CDCl$_3$, TFA salt) δ (ppm):

7.30 (m, 2H), 7.18 (d, 1H), 7.15 (d, 1H), 7.0 (d, 1H), 6.80 (d, 1H), 6.70 (s, 1H), 4.70 (m, 1H), 4.05 (m, 1H), 3.80 (m, 1H), 3.30 (m, 1H), 3.05 (m, 1H), 2.98 (s, 3H), 2.90 (m, 1H), 2.30 (s, 3H).

Example 163

Preparation of (E)-8-chloro-5-(2-(2,4-dichlorophenyl)prop-1-enyl)-2-methyl-2,3,4,5-tetrahydro-1H-pyrido[4,3-b]indole (Compound 210)

1-(8-Chloro-1,2,3,4-tetrahydro-2-methylpyrido[4,3-b]indol-5-yl)-2-(2,4-dichlorophenyl)propan-2-ol (1 g, 2.36 mmol, 1 equiv) was refluxed with 25% sulfuric acid (7 mL) for 2 h. The reaction mixture was cooled to 5° C. in ice-water bath. KOH (15% aqueous solution) was added dropwise to the reaction mixture until pH 9-10. The reaction mixture was extracted with EtOAc (3×10 mL). The combined organic layer was washed with water (10 mL) followed by brine, dried over sodium sulfate and evaporated under reduced pressure. The crude product was purified by silica gel chromatography (100-200 mesh) using a gradient of MeOH-EtOAc (0-10%) to obtain a mixture of isomers, which were separated by HPLC. $^1$H NMR (CDCl$_3$, TFA salt) δ (ppm): 7.50 (d, 1H), 7.40 (d, 1H), 7.36-7.20 (m, 4H), 6.55 (d, 1H), 4.78 (m, 1H), 4.10 (m, 1H), 3.90 (m, 1H), 3.40 (m, 3H), 3.0 (s, 3H), 1.80 (s, 3H).

Example 164

Preparation of (E)-8-chloro-5-(2-(4-chlorophenyl)prop-1-enyl)-2,3,4,5-tetrahydro-2-methyl-1H-pyrido[4,3-b]indole (Compound 100)

1-(8-Chloro-1,2,3,4-tetrahydro-2-methylpyrido[4,3-b]indol-5-yl)-2-(4-chlorophenyl)propan-2-ol (1 g, 2.57 mmol, 1 equiv.) was refluxed with 25% sulfuric acid (7 mL) for 2 h. The reaction mixture was cooled to 5° C. in ice-water bath. KOH (15% aqueous solution) was added dropwise to the reaction mixture until pH 9-10 was achieved. The reaction mixture was extracted with EtOAc (3×10 mL). The combined organic layer was washed with water (10 mL) followed by brine, dried over sodium sulfate and evaporated under vacuum. The crude product was purified by silica gel chromatography (100-200 mesh) using a gradient of MeOH-EtOAc (0-10%) to obtain a mixture of isomers, which were separated by HPLC. $^1$H NMR (CD$_3$OD, HCl salt) δ (ppm): 7.65 (d, 2H), 7.55 (s, 1H), 7.45 (d, 2H), 7.22 (s, 2H), 7.05 (s, 1H), 4.75 (m, 1H), 4.40 (m, 1H), 3.86 (m, 1H), 3.60 (m, 1H), 3.16 (m, 2H), 3.12 (s, 3H), 1.95 (s, 3H).

Example 165

Preparation of (E)-5-(2-(4-chlorophenyl)prop-1-enyl)-2,8-dimethyl-2,3,4,5-tetrahydro-1H-pyrido[4,3-b]indole (Compound 211)

2,8-Dimethyl-2,3,4,5-tetrahydro-1H-pyrido[4,3-b]indole (36 mg, 0.181 mmol) was dissolved in DMF (4 mL). Copper (I) iodide (4 mg, 0.0181 mmol), L-proline (4 mg, 0.0362 mmol) and potassium phosphate (77 mg, 0.362 mmol) were added and the reaction mixture was stirred for 10 min. at RT. 1-(1-Bromoprop-1-en-2-yl)-4-chlorobenzene (50 mg, 0.2183 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh). Yield: 90 mg Example 166

Preparation of (Z)-8-chloro-5-(2-(2-fluorophenyl)prop-1-enyl)-2-methyl-2,3,4,5-tetrahydro-1H-pyrido[4,3-b]indole (Compound 212)

8-Chloro-2-methyl-2,3,4,5-tetrahydro-1H-pyrido[4,3-b]indole (200 mg, 1 mmol) was dissolved in DMF (5 mL), Copper (I) iodide (19 mg, 0.1 mmol) L-proline (23 mg, 0.2 mmol) and potassium phosphate (424 mg, 2 mmol) were added and the reaction mixture was stirred for 10 min. at RT. 1-(1-Bromoprop-1-en-2-yl)-2-fluorobenzene (260 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-1% MeOH-DCM. The product was further purified by HPLC. Yield: 10 mg. $^1$H NMR (CDCl$_3$, TFA salt) δ (ppm): 7.25 (s, 1H), 7.10 (m, 3H), 6.90 (m, 2H), 6.82 (m, 1H), 6.70 (s, 1H), 4.62 (d, 1H), 4.0 (d, 1H), 3.70 (m, 1H), 3.20 (m, 1H), 2.92 (m, 1H), 2.82 (s, 3H), 2.70 (m, 1H), 2.0 (s, 3H).

Example 167

Preparation of (E)-8-chloro-5-(2-(2-fluorophenyl)prop-1-enyl)-2-methyl-2,3,4,5-tetrahydro-1H-pyrido[4,3-b]indole (Compound 213)

8-Chloro-2-methyl-2,3,4,5-tetrahydro-1H-pyrido[4,3-b]indole (200 mg, 1 mmol) was dissolved in DMF (5 mL). Copper (I) iodide (19 mg, 0.1 mmol), L-proline (23 mg, 0.2 mmol) and potassium phosphate (424 mg, 2 mmol) were added and the reaction mixture was stirred for 10 min. at RT. 1-(1-Bromoprop-1-en-2-yl)-2-fluorobenzene (260 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-1% MeOH-DCM. The product was further purified by HPLC. Yield: 5 mg. $^1$H NMR (CDCl$_3$, TFA salt) δ (ppm): 7.40 (m, 3H), 7.20 (m, 4H), 6.70 (d, 1H), 4.80 (m, 1H), 4.20 (m, 1H), 3.80 (m, 1H), 3.40-3.20 (m, 3H), 3.05 (s, 3H), 1.85 (s, 3H).

Example 168

Preparation of (E)-5-(2-(3-fluoro-4-methoxyphenyl)prop-1-enyl)-2,8-dimethyl-2,3,4,5-tetrahydro-1H-pyrido[4,3-b]indole (Compound 214)

2,8-Dimethyl-2,3,4,5-tetrahydro-1H-pyrido[4,3-b]indole (68 mg, 0.34 mmol) was dissolved in DMF (3 mL). Copper (I) iodide (6.5 mg, 0.034 mmol) L-proline (7.8 mg, 0.068 mmol) and potassium phosphate (144 mg, 0.68 mmol) were added and the reaction mixture was stirred for 10 min. at RT. 4-(1-Bromoprop-1-en-2-yl)-2-fluoro-1-methoxybenzene (100 mg, 0.408 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh). $^1$H NMR (CD$_3$OD, HCl salt) δ (ppm): 7.42 (m, 2H), 7.30 (s, 1H), 7.18 (d, 1H), 7.10 (m, 2H), 7.0 (s, 1H), 4.75 (m, 1H), 4.40 (m, 1H), 3.95 (s, 3H), 3.85 (m, 1H), 3.60 (m, 1H), 3.20 (m, 2H), 3.10 (s, 3H), 2.42 (s, 3H), 1.90 (s, 3H).

Example 169

Preparation of (E)-8-chloro-5-(2-(3,5-dichlorophenyl)prop-1-enyl)-2-methyl-2,3,4,5-tetrahydro-1H-pyrido[4,3-b]indole (Compound 215)

8-Chloro-2-methyl-2,3,4,5-tetrahydro-1H-pyrido[4,3-b]indole (220 mg, 1 mmol) was dissolved in DMF. Copper (I) iodide (19 mg, 0.1 mmol), L-proline (23 mg, 0.2 mmol) and potassium phosphate (424 mg, 2 mmol) were added and the reaction mixture was stirred for 10 min. at RT. 1-(1-Bromoprop-1-en-2-yl)-3,5-dichlorobenzene (318 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. Yield: 135 mg. $^1$H NMR (CD$_3$OD, oxalate salt) δ (ppm): 7.50 (s, 1H), 6.25 (s, 1H), 7.18 (d, 1H), 7.10 (d, 1H), 7.0 (s, 2H), 6.90 (s, 1H), 4.40 (m, 2H), 3.60 (m, 2H), 3.0 (s, 3H), 2.90 (m, 2H), 2.30 (s, 3H).

Example 170

Preparation of (E)-8-fluoro-2-methyl-5-(2-(pyridin-4-yl)prop-1-enyl)-2,3,4,5-tetrahydro-1H-pyrido[4,3-b]indole (Compound 216)

1-(8-Fluoro-1,2,3,4-tetrahydro-2-methylpyrido[4,3-b]indol-5-yl)-2-(pyridin-4-yl)propan-2-ol (1 g, 2.9 mmol) was dissolved in thionyl chloride (10 mL) and the solution was stirred for 2 h. Excess thionyl chloride was removed under reduced pressure and the residue was dissolved in N-methyl-2-pyrrolidone (6 mL) and the solution was stirred for 5 min. at RT. Powdered KOH (1.7 g, 31 mmol) was added and the reaction mixture was heated at 100° C. for 2 h. The reaction mixture was cooled to RT, diluted with ice water and extracted with EtOAc. The organic layer washed with water, dried over sodium sulfate, and concentrated under reduced pressure. The residue was purified by silica gel chromatography eluting with 5% MeOH-DCM. $^1$HNMR (CD$_3$OD, HCl salt) δ (ppm): 8.85 (d, 2H), 8.40 (d, 2H), 7.80 (s, 1H), 7.30 (m, 2H), 7.05 (m, 1H), 4.75 (d, 1H), 4.40 (d, 1H), 3.90 (m, 1H), 3.60 (m, 1H), 3.30 (m, 2H), 3.18 (s, 3H), 2.20 (s, 3H).

Example 171

Preparation of (E)-2-methyl-5-(2-(pyridin-4-yl)prop-1-enyl)-2,3,4,5-tetrahydro-1H-pyrido[4,3-b]indole (Compound 217)

1-(1,2,3,4-Tetrahydro-2-methylpyrido[4,3-b]indol-5-yl)-2-(pyridin-4-yl)propan-2-ol (600 mg, 1.86 mmol) was dissolved in thionyl chloride (8 mL) and the solution was stirred for 1 h. Excess thionyl chloride was removed under reduced pressure and the residue was dissolved in N-methyl-2-pyrrolidone (3 mL) and the solution was stirred for 5 min. at RT. Powdered KOH (690 mg, 12.32 mmol) was added and the reaction mixture was heated at 100° C. for 1-2 h. The reaction mixture was cooled to RT, diluted with ice water and extracted with EtOAc. The organic layer washed with water, dried over sodium sulfate, and concentrated under reduced pressure. The residue was purified by silica gel chromatography eluting with 2% MeOH-DCM. $^1$H NMR (CD$_3$OD, HCl salt) δ (ppm): 8.85 (d, 2H), 8.40 (d, 2H), 7.82 (d, 1H), 7.60 (d, 1H), 7.30 (m, 2H), 7.20 (m, 1H), 4.80 (d, 1H), 4.40 (d, 1H), 3.90 (m, 1H), 3.60 (m, 2H), 3.20 (m, 1H), 3.10 (s, 3H), 2.20 (s, 3H).

Example 172

Preparation of (E)-5-(2-(3,5-dichlorophenyl)prop-1-enyl)-2,8-dimethyl-2,3,4,5-tetrahydro-1H-pyrido[4,3-b]indole (Compound 218)

2,8-Dimethyl-2,3,4,5-tetrahydro-1H-pyrido[4,3-b]indole (200 mg, 1 mmol) was dissolved in DMF. Copper (I) iodide (19 mg, 0.1 mmol) L-proline (23 mg, 0.2 mmol) and potassium phosphate (424 mg, 2 mmol) were added and the reaction mixture was stirred for 10 min. at RT. 1-(1-Bromoprop-1-en-2-yl)-3,5-dichlorobenzene (318 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. The product was further purified by HPLC. The free base was converted into oxalate salt by treatment of oxalic acid (1 equiv) in THF. Yield: 18 mg as the oxalate salt. $^1$H NMR (CD$_3$OD, oxalate salt) δ (ppm): 7.25 (s, 2H), 7.10 (d, 1H), 7.0 (m, 3H), 6.90 (s, 1H), 4.50 (m, 2H), 3.58 (m, 2H), 3.0 (s, 3H), 2.80 (m, 2H), 2.38 (s, 3H), 2.30 (s, 3H).

Example 173

Preparation of (E)-7-chloro-2-methyl-5-(2-(pyridin-4-yl)prop-1-enyl)-2,3,4,5-tetrahydro-1H-pyrido[4,3-b]indole (Compound 219)

1-(7-Chloro-2-methyl-3,4-dihydro-1H-pyrido[4,3-b]indol-5(2H)-yl)-2-(p yridin-4-yl)propan-2-ol (1 g, 2.8 mmol) in SOCl$_2$ (10 mL) was stirred RT for 2 h. The reaction mixture was concentrated under reduced pressure. The residue was dissolved in N-methyl-2-pyrrolidone (6 mL), KOH (1.5 g, 28 mmol) was added and heated at 100° C. for 2 h. The reaction mixture was cooled to RT, diluted with water and extracted with EtOAc. The organic layer was washed with water and concentrated and purified by silica gel chromatography, 100-200 mesh (eluent in 5% MeOH-DCM). $^1$H NMR (CD$_3$OD, HCl salt) δ (ppm): 8.90 (d, 2H), 8.40 (d, 2H), 7.80 (s, 1H), 7.55 (d, 1H), 7.38 (s, 1H), 7.22 (d, 1H), 4.80 (d, 1H), 4.40 (d, 1H), 3.90 (m, 1H), 3.60 (m, 2H), 3.25 (m, 1H), 3.18 (s, 3H), 2.20 (s, 3H).

Example 174

Preparation of (Z)-5-(2-(2-chloro-4,5-difluorophenyl)prop-1-enyl)-2,8-dimethyl-2,3,4,5-tetrahydro-1H-pyrido[4,3-b]indole (Compound 220)

2,8-Dimethyl-2,3,4,5-tetrahydro-1H-pyrido[4,3-b]indole (200 mg, 1 mmol) was dissolved in DMF. Copper (I) iodide (19 mg, 0.1 mmol) L-proline (23 mg, 0.2 mmol) and potassium phosphate (424 mg, 2 mmol) were added and the reaction mixture was stirred for 10 min. at RT. 1-(1-Bromoprop-1-en-2-yl)-2-chloro-4,5-difluorobenzene (321 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. The product was further purified by HPLC. Yield: 10 mg as the TFA salt. $^1$H NMR (CD$_3$OD, TFA salt) δ (ppm): 7.30 (m, 1H), 7.18 (s, 1H), 7.10 (m, 2H), 6.95 (d, 1H), 6.90 (s, 1H), 4.40 (d, 1H), 4.22 (d, 1H), 3.80 (m, 1H), 3.45 (m, 1H), 3.10 (m, 2H), 3.0 (s, 3H), 2.38 (s, 3H), 2.30 (s, 3H).

Example 175

Preparation of (E)-5-(2-(2-chloro-4,5-difluorophenyl)prop-1-enyl)-2,8-dimethyl-2,3,4,5-tetrahydro-1H-pyrido[4,3-b]indole (Compound 221)

2,8-Dimethyl-2,3,4,5-tetrahydro-1H-pyrido[4,3-b]indole (200 mg, 1 mmol) was dissolved in DMF. Copper (I) iodide (19 mg, 0.1 mmol), L-proline (23 mg, 0.2 mmol) and potassium phosphate (424 mg, 2 mmol) were added and the reaction mixture was stirred for 10 min. at RT. 1-(1-Bromoprop-1-en-2-yl)-2-chloro-4,5-difluorobenzene (321 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. The product was further purified by HPLC. Yield: 12 mg as the TFA salt. $^1$H NMR (CD$_3$OD, TFA salt) δ (ppm): 7.50 (m, 2H), 7.32 (s, 1H), 7.25 (d, 1H), 7.15 (d, 1H), 6.70 (s, 1H), 4.75 (m, 1H), 4.38 (m, 1H), 3.90 (m, 1H), 3.60 (m, 1H), 3.25 (m, 2H), 3.15 (s, 3H), 2.42 (s, 3H), 1.90 (s, 3H).

Example 176

Preparation of (E)-6-chloro-2-methyl-5-(2-(pyridin-4-yl)prop-1-enyl)-2,3,4,5-tetrahydro-1H-pyrido[4,3-b]indole (Compound 222)

1-(6-Chloro-2-methyl-3,4-dihydro-1H-pyrido[4,3-b]indol-5(2H)-yl)-2-(pyridin-4-yl)propan-2-ol (650 mg, 1.8 mmol) in SOCl$_2$ (6.5 mL) was stirred at RT for 2 h. The progress of reaction was monitored by TLC and $^1$H NMR. The reaction mixture was concentrated under reduced pressure. The residue was dissolved in N-methyl-2-pyrrolidone (3 mL), KOH (737 mg, 13.1 mmol) was added and the reaction mixture was heated at 100° C. for 2 h. After it was cooled to RT, the reaction mixture was diluted with water and extracted with EtOAc. Organic was separated, dried over sodium sulfate and concentrated under reduced pressure. The residue was purified by silica gel chromatography (eluent 5% MeOH-DCM). $^1$H NMR (CD$_3$OD, HCl salt) δ (ppm): 8.70 (d, 2H), 7.80 (d, 2H), 7.56 (s, 1H), 7.45 (d, 1H), 7.25 (d, 1H), 7.10 (t, 1H), 4.80 (m, 2H), 4.40 (m, 2H), 3.90 (m, 1H), 3.20 (m, 1H), 3.15 (s, 3H), 1.95 (s, 3H).

Example 177

Preparation of 5-cyclohexenyl-2,8-dimethyl-2,3,4,5-tetrahydro-1H-pyrido[4,3-b]indole (Compound 211)

To a solution of 2-(2,8-dimethyl-3,4-dihydro-1H-pyrido[4,3-b]indol-5(2H)yl)cyclohexyl methanesulfonate (0.33 g, 0.87 mmol) in NMP (3 mL), KOH (0.49 g, 8.7 mmol) was added at RT. The reaction mixture was heated overnight at 120° C. The reaction was monitored by LCMS. Upon completion, the reaction mixture was diluted with water and extracted with EtOAc. The combined organic layer was separated, dried over sodium sulfate and concentrated under reduced pressure and purified by column chromatography (silica gel 3% MeOH in DCM) to afford 200 mg of the desired product. $^1$H NMR (CDCl$_3$, HCl salt) δ (ppm): 7.50 (d, 2H), 7.40 (d, 2H), 7.23 (d, 1H), 7.1-7.0 (m, 2H), 6.9 (s, 1H), 3.8 (s, 2H), 3.0-2.8 (m, 4H), 2.6 (s, 3H), 2.45 (s, 3H), 2.0 (s, 3H).

Example 178

Preparation of (E)-8-chloro-2,3,4,5-tetrahydro-2-methyl-5-(2-(pyridin-3-yl)prop-1-enyl)-1H-pyrido[4,3-b]indole (Compound 86)

1-(8-Chloro-1,2,3,4-tetrahydro-2-methylpyrido[4,3-b]indol-5-yl)-2-(pyridin-3-yl)propan-2-ol (1 g, 2.81 mmol, 1 equiv.) was refluxed with 25% sulfuric acid (7 mL) for 2 h. The reaction mixture was cooled to 5° C. in an ice-water bath. KOH (15% aqueous solution) was added dropwise to the reaction mixture until pH 9-10 was achieved. The reaction mixture was extracted with EtOAc (3×10 mL). The combined organic layer was washed with water (10 mL) followed by brine, dried over sodium sulfate and evaporated under reduced pressure. The crude product was purified by silica gel chromatography (100-200 mesh) using a gradient of MeOH-EtOAc (0-10%) to obtain a mixture of isomers, which were separated by HPLC. $^1$HNMR (DMSO, TFA salt) δ (ppm): 8.90 (s, 1H), 8.60 (d, 1H), 8.10 (d, 1H), 7.50 (m, 2H), 7.22 (d, 2H), 7.10 (d, 1H), 3.6 (m, 2H), 2.70 (m, 4H), 2.45 (s, 3H), 1.90 (s, 3H).

Example 179

Preparation of (E)-6-fluoro-2-methyl-5-(2-(pyridin-4-yl)prop-1-enyl)-2,3,4,5-tetrahydro-1H-pyrido[4,3-b]indole (Compound 223)

1-(6-Fluoro-2-methyl-3,4-dihydro-1H-pyrido[4,3-b]indol-5(2H)-yl)-2-(pyridin-4-yl)propan-2-ol (510 mg, 1.5 mmol) was dissolved in thionylchloride (5 mL) and stirred at RT for 2 h. The reaction mixture was concentrated under reduced pressure. The residue was dissolved in N-methyl-2-pyrrolidone (3 mL) and stirred for 5 min. at RT. Powdered KOH (616 mg, 10 mmol) was added, and the stirring was continued for additional 10 min. The reaction mixture was heated at 100° C. for 2 h. The progress of reaction was monitored by TLC and NMR. The reaction mixture was diluted with water and extracted with EtOAc, washed with water, concentrated to obtain the crude product which was purified by HPLC. $^1$H NMR (DMSO-d6, TFA salt) δ (ppm): 8.80 (d, 2H), 8.0 (d, 2H), 7.70 (s, 1H), 7.40 (d, 1H), 7.30 (m, 1H), 7.10 (m, 1H), 4.80 (m, 1H), 4.30 (m, 1H), 3.80 (m, 2H), 3.10 (m, 2H), 3.0 (s, 3H), 2.0 (s, 3H).

Example 180

Preparation of (Z)-2,8-dimethyl-5-(2-(pyridin-4-yl)prop-1-enyl)-2,3,4,5-tetrahydro-1H-pyrido[4,3-b]indole (Compound 224)

2,8-Dimethyl-2,3,4,5-tetrahydro-1H-pyrido[4,3-b]indole (200 mg, 1 mmol), copper sulfate (50 mg, 0.2 mmol), 1,10-phenanthroline (72 mg, 0.4 mmol), potassium phosphate (425 mg, 2 mmol) and 4-(1-bromoprop-1-en-2-yl)pyridine (237 mg, 1.2 mmol) were mixed in DMF (10 mL) and the reaction mixture was purged with nitrogen. The reaction mixture was heated overnight at 80° C. The reaction mixture was diluted with EtOAc and filtered through Celite. The filtrate was concentrated under reduced pressure and the residue was purified by silica gel chromatography (10% MeOH in DCM) to obtain (E)-2,8-dimethyl-5-(2-(pyridin-4-yl)prop-1-enyl)-2,3,4,5-tetrahydro-1H-pyrido[4,3-b]indole (167 mg) as a brown semi solid that was further purified by HPLC to obtain the product as the TFA salt. $^1$HNMR (DMSO, TFA salt) δ (ppm): 8.40 (m, 2H), 7.20 (s, 1H), 7.10 (m, 3H), 6.95 (d, 1H), 6.86 (d, 1H), 4.40 (m, 2H), 4.22 (m, 2H), 2.90 (s, 3H), 2.80 (m, 2H), 2.38 (s, 3H), 2.30 (s, 3H).

Example 181

Preparation of (Z)-5-(2-(3-fluorophenyl)prop-1-enyl)-2,8-dimethyl-2,3,4,5-tetrahydro-1H-pyrido[4,3-b]indole (Compound 225)

2,8-Dimethyl-2,3,4,5-tetrahydro-1H-pyrido[4,3-b]indole (200 mg, 1 mmol) was dissolved in DMF. Copper (I) iodide (19 mg, 0.1 mmol) L-proline (23 mg, 0.2 mmol) and potassium phosphate (424 mg, 2 mmol) were added and the reaction mixture was stirred for 10 min. at RT. 1-(1-Bromoprop-1-en-2-yl)-3-fluorobenzene (258 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. The product was further purified by HPLC. Yield: 40 mg as the TFA salt. $^1$H NMR (CDCl$_3$, TFA salt) δ (ppm): 7.22 (d, 1H), 7.18 (s, 1H), 7.10 (m, 2H), 6.85 (t, 1H), 6.70 (s, 1H), 6.62 (d, 2H), 4.65 (d, 1H), 4.05 (d, 1H), 3.50 (m, 1H), 3.15 (m, 1H), 2.80 (s, 3H), 2.60 (m, 1H), 2.42 (s, 3H), 2.38 (m, 1H), 2.30 (s, 3H).

Example 182

Preparation of (E)-5-(2-(3-fluorophenyl)prop-1-enyl)-2,8-dimethyl-2,3,4,5-tetrahydro-1H-pyrido[4,3-b]indole (Compound 226)

2,8-Dimethyl-2,3,4,5-tetrahydro-1H-pyrido[4,3-b]indole (200 mg, 1 mmol) was dissolved in DMF. Copper (I) iodide (19 mg, 0.1 mmol) L-proline (23 mg, 0.2 mmol) and potassium phosphate (424 mg, 2 mmol) were added and the reaction mixture was stirred for 10 min. at RT. 1-(1-Bromoprop-1-en-2-yl)-3-fluorobenzene (258 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. The product was further purified by HPLC. Yield: 6 mg as the TFA salt. $^1$H NMR (CDCl$_3$, TFA salt) δ (ppm): 7.40 (m, 1H), 7.30 (d, 1H), 7.22 (m, 2H), 7.10 (m, 3H), 6.90 (s, 1H), 4.80 (d, 1H), 4.20 (d, 1H), 3.90 (m, 1H), 3.40 (m, 1H), 3.30 (m, 1H), 3.10 (s, 3H), 2.95 (m, 1H), 2.45 (s, 3H), 1.95 (s, 3H).

Example 183

Preparation of (E)-8-chloro-5-(2-(3,4-dichlorophenyl)prop-1-enyl)-2,3,4,5-tetrahydro-2-methyl-1H-pyrido[4,3-b]indole (Compound 103)

8-Chloro-2-methyl-2,3,4,5-tetrahydro-1H-pyrido[4,3-b]indole (69 mg, 0.31 mmol) was dissolved in DMF (5 mL). Copper (I) iodide (6 mg, 0.032 mmol) L-proline (7 mg, 0.063 mmol) and potassium phosphate (134 mg, 0.63 mmol) were added and the reaction mixture was stirred for 10 min. at RT. 4-(1-Bromoprop-1-en-2-yl)-1,2-dichlorobenzene (100 mg, 0.378 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh) followed by HPLC. Yield: 13 mg as the TFA salt. $^1$H NMR (CD$_3$OD, TFA salt) δ (ppm): 7.82 (d, 1H), 7.62 (d, 2H), 7.58 (d, 1H), 7.22 (m, 2H), 7.10 (s, 1H), 4.80 (m, 1H), 4.40 (m, 1H), 3.90 (m, 1H), 3.62 (m, 1H), 3.20 (m, 2H), 3.15 (s, 3H), 1.95 (s, 3H).

Example 184

Preparation of (E)-8-fluoro-5-(2-(4-fluorophenyl)prop-1-enyl)-2,3,4,5-tetrahydro-2-methyl-1H-pyrido[4,3-b]indole (Compound 102)

1-(8-Fluoro-1,2,3,4-tetrahydro-2-methylpyrido[4,3-b]indol-5-yl)-2-(4-fluorophenyl)propan-2-ol (1 g, 2.80 mmol, 1 equiv.) was refluxed with 25% sulfuric acid (7 mL) for 2 h. The reaction mixture was cooled to 5° C. in ice-water bath. KOH (15% aqueous solution) was added dropwise to the reaction mixture until pH 9-10 was achieved. The reaction mixture was extracted with EtOAc (3×10 mL). The combined organic layer was washed with water (10 mL) followed by brine, dried over sodium sulfate and evaporated under vacuum. The crude product was purified by silica gel chromatography (100-200 mesh) using a gradient of MeOH-EtOAc (0-10%) to obtain a mixture of isomers, which were separated by HPLC. $^1$H NMR (DMSO-d6, oxalate salt) δ (ppm): 7.75 (m, 2H), 7.38-7.20 (m, 4H), 7.10 (s, 1H), 7.0 (t, 1H), 4.30 (m, 2H), 3.05 (s, 3H), 2.90 (m, 4H), 1.90 (s, 3H).

Example 185

Preparation of (E)-7-fluoro-5-(2-(4-fluorophenyl)prop-1-enyl)-2-methyl-2,3,4,5-tetrahydro-1H-pyrido[4,3-b]indole (Compound 227)

7-Fluoro-2-methyl-2,3,4,5-tetrahydro-1H-pyrido[4,3-b]indole (200 mg, 0.98 mmol) was dissolved in DMF (5 mL). Copper (I) iodide (18 mg, 0.09 mmol) L-proline (22 mg, 0.19 mmol) and potassium phosphate (410 mg, 1.96 mmol) were added and the reaction mixture was stirred for 10 min.

at RT. 1-(1-Bromoprop-1-en-2-yl)-4-fluorobenzene (250 mg, 1.17 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh). $^1$H NMR (DMSO-d6, oxalate salt) δ (ppm): 7.76 (m, 2H), 7.50 (m, 1H), 7.30 (t, 2H), 7.10 (d, 2H), 7.0 (t, 1H), 4.30 (m, 2H), 3.0 (s, 3H), 2.80 (m, 4H), 1.90 (s, 3H).

Example 186

Preparation of (E)-7-chloro-5-(2-(4-fluorophenyl) prop-1-enyl)-2-methyl-2,3,4,5-tetrahydro-1H-pyrido [4,3-b]indole (Compound 228)

7-Chloro-2-methyl-2,3,4,5-tetrahydro-1H-pyrido[4,3-b] indole (220 mg, 0.90 mmol) was dissolved in DMF (5 mL). Copper (I) iodide (17 mg, 0.09 mmol), L-proline (20 mg, 0.18 mmol) and potassium phosphate (380 mg, 1.8 mmol) were added and the reaction mixture was stirred for 10 min. at RT. 1-(1-Bromoprop-1-en-2-yl)-4-fluorobenzene (230 mg, 1.09 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh). $^1$H NMR (DMSO-d6, oxalate salt) δ (ppm): 7.78 (m, 2H), 7.52 (d, 1H), 7.30 (m, 3H), 7.16 (d, 1H), 7.10 (s, 1H), 4.30 (m, 2H), 3.0 (s, 3H), 2.82 (m, 4H), 1.85 (s, 3H).

Example 187

Preparation of (E)-5-(2-(4-fluorophenyl)prop-1-enyl)-2-methyl-7-(trifluoromethyl)-2,3,4,5-tetrahydro-1H-pyrido[4,3-b]indole (Compound 229)

2-Methyl-7-trifluoromethyl-2,3,4,5-tetrahydro-1H-pyrido[4,3-b]indole (200 mg, 0.78 mmol) was dissolved in DMF (5 mL). Copper (I) iodide (14 mg, 0.078 mmol), L-proline (17 mg, 0.156 mmol) and potassium phosphate (330 mg, 1.56 mmol) were added and the reaction mixture was stirred for 10 min. at RT. 1-(1-Bromoprop-1-en-2-yl)-4-fluorobenzene (200 mg, 0.94 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh). Yield: 25 mg. $^1$H NMR (DMSO-d6, oxalate salt) δ (ppm): 7.80 (m, 2H), 7.76 (d, 1H), 7.60 (s, 1H), 7.42 (d, 1H), 7.30 (t, 2H), 7.20 (s, 1H), 4.35 (m, 2H), 3.05 (s, 3H), 2.90 (m, 4H), 1.82 (s, 3H).

Example 188

Preparation of (E)-8-chloro-5-(2-(3,4-difluorophenyl)prop-1-enyl)-2,3,4,5-tetrahydro-2-methyl-1H-pyrido[4,3-b]indole (Compound 98)

8-Chloro-2-methyl-2,3,4,5-tetrahydro-1H-pyrido[4,3-b] indole (79 mg, 0.36 mmol) was dissolved in DMF (6 mL). Copper (I) iodide (8 mg, 0.036 mmol), L-proline (9 mg, 0.086 mmol) and potassium phosphate (183 mg, 0.86 mmol) were added and the reaction mixture was stirred for 10 min. at RT. 4-(1-Bromoprop-1-en-2-yl)-1,2-difluorobenzene (100 mg, 0.43 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh). Yield: 39 mg. $^1$H NMR (CD$_3$OD, oxalate salt) δ (ppm): 7.60 (m, 1H), 7.56 (s, 1H), 7.45 (m, 1H), 7.36 (m, 1H), 7.20 (s, 2H), 7.02 (s, 1H), 4.50 (m, 2H), 3.70 (m, 2H), 3.18 (m, 2H), 3.10 (s, 3H), 1.95 (s, 3H).

Example 189

Preparation of (E)-5-(2-(3,4-difluorophenyl)prop-1-enyl)-2,8-dimethyl-2,3,4,5-tetrahydro-1H-pyrido[4,3-b]indole (Compound 230)

2,8-Dimethyl-2,3,4,5-tetrahydro-1H-pyrido[4,3-b]indole (72 mg, 0.36 mmol) was dissolved in DMF (5 mL). Copper (I) iodide (7 mg, 0.036 mmol), L-proline (8 mg, 0.072 mmol) and potassium phosphate (153 mg, 0.72 mmol) were added and the reaction mixture was stirred for 10 min. at RT. 4-(1-Bromoprop-1-en-2-yl)-1,2-difluorobenzene (100 mg, 0.43 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh). Yield: 110 mg. $^1$H NMR (DMSO-d6, oxalate salt) δ (ppm): 7.80 (m, 1H), 7.50 (d, 2H), 7.30 (s, 1H), 7.20 (s, 1H), 7.10 (d, 1H), 7.0 (d, 1H), 4.36 (m, 2H), 3.60 (m, 2H), 3.0 (m, 2H), 2.90 (s, 3H), 2.40 (s, 3H), 1.90 (s, 3H).

Example 190

Preparation of (E)-5-(2-(3,4-dichlorophenyl)prop-1-enyl)-2,8-dimethyl-2,3,4,5-tetrahydro-1H-pyrido[4,3-b]indole (Compound 231)

2,8-Dimethyl-2,3,4,5-tetrahydro-1H-pyrido[4,3-b]indole (63 mg, 0.32 mmol) was dissolved in DMF (5 mL). Copper (I) iodide (6 mg, 0.032 mmol), L-proline (7 mg, 0.064 mmol) and potassium phosphate (136 mg, 0.64 mmol) were added and the reaction mixture was stirred for 10 min. at RT. 4-(1-Bromoprop-1-en-2-yl)-1,2-dichlorobenzene (100 mg, 0.38 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh) followed by HPLC. Yield: 11 mg as the TFA salt. $^1$H NMR (DMSO-d6, oxalate salt) δ (ppm): 7.95 (d, 1H), 7.70 (m, 2H), 7.30 (s, 2H), 7.10 (d, 1H), 7.0 (d, 1H), 4.30 (m, 2H), 3.40 (m, 2H), 3.0 (m, 2H), 2.90 (s, 3H), 2.40 (s, 3H), 1.90 (s, 3H).

Example 191

Preparation of (E)-8,9-dichloro-5-(2-(4-fluorophenyl)prop-1-enyl)-2-methyl-2,3,4,5-tetrahydro-1H-pyrido[4,3-b]indole (Compound 232)

8,9-Dichloro-2-methyl-2,3,4,5-tetrahydro-1H-pyrido[4,3-b]indole (200 mg, 0.78 mmol) was dissolved in DMF.

Copper (I) iodide (14 mg, 0.078 mmol), L-proline (17 mg, 0.156 mmol) and potassium phosphate (330 mg, 1.56 mmol) were added and the reaction mixture was stirred for 10 min. at RT. 1-(1-Bromoprop-1-en-2-yl)-4-fluorobenzene (200 mg, 0.94 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. The product was further purified by HPLC. $^1$H NMR (CDCl$_3$, TFA salt) δ (ppm): 7.50 (m, 2H), 7.25 (m, 1H), 7.10 (t, 2H), 7.05 (d, 1H), 6.75 (s, 1H), 5.10 (d, 1H), 4.40 (d, 1H), 3.90 (m, 1H), 3.38 (m, 1H), 3.22 (m, 1H), 3.05 (s, 3H), 2.90 (m, 1H), 1.90 (s, 3H).

Example 192

Preparation of (Z)-8-chloro-5-(2-(3-fluorophenyl) prop-1-enyl)-2-methyl-2,3,4,5-tetrahydro-1H-pyrido [4,3-b]indole (Compound 233)

8-Chloro-2-methyl-2,3,4,5-tetrahydro-1H-pyrido[4,3-b] indole (220 mg, 1 mmol) was dissolved in DMF. Copper (I) iodide (19 mg, 0.1 mmol), L-proline (23 mg, 0.2 mmol) and potassium phosphate (424 mg, 2 mmol) were added and the reaction mixture was stirred for 10 min. at RT. 1-(1-Bromoprop-1-en-2-yl)-3-fluorobenzene (258 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. The product was further purified by HPLC. Yield: 85 mg. $^1$H NMR (CD$_3$OD, TFA salt) δ (ppm): 7.42 (s, 1H), 7.20 (d, 1H), 7.12 (m, 2H), 6.90 (t, 1H), 7.82 (d, 2H), 6.78 (dd, 1H), 4.60 (d, 1H), 4.30 (d, 1H), 3.70 (m, 1H), 3.40 (m, 1H), 3.0 (s, 3H), 2.80 (m, 2H), 2.30 (s, 3H).

Example 193

Preparation of (E)-8-chloro-5-(2-(3-fluorophenyl) prop-1-enyl)-2-methyl-2,3,4,5-tetrahydro-1H-pyrido [4,3-b]indole (Compound 234)

8-Chloro-2-methyl-2,3,4,5-tetrahydro-1H-pyrido[4,3-b] indole (220 mg, 1 mmol) was dissolved in DMF. Copper (I) iodide (19 mg, 0.1 mmol), L-proline (23 mg, 0.2 mmol) and potassium phosphate (424 mg, 2 mmol) were added and the reaction mixture was stirred for 10 min. at RT. 1-(1-Bromoprop-1-en-2-yl)-3-fluorobenzene (258 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. The product was further purified by HPLC. Yield: 30 mg. $^1$H NMR (CD$_3$OD, TFA salt) δ (ppm): 7.56 (s, 1H), 7.50 (m, 2H), 7.40 (d, 1H), 7.22 (s, 2H), 7.15 (m, 1H), 7.05 (s, 1H), 4.70 (m, 1H), 4.40 (m, 1H), 3.82 (m, 1H), 3.60 (m, 1H), 3.20 (m, 2H), 3.10 (s, 3H), 1.95 (s, 3H).

Example 194

Preparation of (E)-4-(1-(2,8-dimethyl-3,4-dihydro-1H-pyrido[4,3-b]indol-5(2H)-yl)prop-1-en-2-yl) phenol (Compound 235)

To a stirred solution of 1-(1,2,3,4-tetrahydro-2,8-dimethylpyrido[4,3-b]indol-5-yl)-2-(4-methoxyphenyl)propan-2-ol (0.145 g, 0.39 mmol) in DCM (10 mL) at −78° C. was added borontribromide (0.293 g in 5 mL DCM). The reaction mixture was stirred at −78° C. for 30 min. and then at 25° C. for 1 h. The solution was poured into ice water, basified with saturated aqueous NaHCO$_3$ and extracted with EtOAc. The organic layer was dried over anhydrous sodium sulfate and evaporated under reduced pressure. The residue was purified by HPLC to obtain 12 mg of product as the TFA salt. $^1$H NMR (CD$_3$OD, TFA salt) δ (ppm): 7.50 (d, 2H), 7.30 (s, 1H), 7.16 (d, 1H), 7.08 (d, 1H), 6.90 (s, 1H), 6.82 (d, 2H), 4.70 (m, 1H), 4.40 (m, 1H), 3.80 (m, 1H), 3.60 (m, 1H), 3.10 (m, 5H), 2.40 (s, 3H), 1.85 (s, 3H).

Example 195

Preparation of (E)-5-(2-(4-methoxyphenyl)prop-1-enyl)-2,8-dimethyl-2,3,4,5-tetrahydro-1H-pyrido[4, 3-b]indole (Compound 236)

2,8-Dimethyl-2,3,4,5-tetrahydro-1H-pyrido[4,3-b]indole (36.7 mg, 0.184 mmol) was dissolved in DMF (6 mL). Copper (I) iodide (4 mg, 0.0184 mmol), L-proline (4.2 mg, 0.037 mmol) and potassium phosphate (78 mg, 0.37 mmol) were added and the reaction mixture was stirred for 10 min. at RT. 1-(1-Bromoprop-1-en-2-yl)-4-methoxybenzene (50 mg, 0.22 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh). Yield: 45 mg. $^1$H NMR (DMSO-d6, oxalate salt) δ (ppm): 7.60 (d, 2H), 7.25 (s, 1H), 7.10 (d, 1H), 7.0 (m, 4H), 4.30 (m, 2H), 3.80 (s, 3H), 3.50 (m, 2H), 2.98 (m, 2H), 2.85 (s, 3H), 2.38 (s, 3H), 1.80 (s, 3H).

Example 196

Preparation of (Z)-8-chloro-5-(2-(2-chlorophenyl) prop-1-enyl)-2-methyl-2,3,4,5-tetrahydro-1H-pyrido [4,3-b]indole (Compound 237)

8-Chloro-2-methyl-2,3,4,5-tetrahydro-1H-pyrido[4,3-b] indole (220 mg, 1 mmol) was dissolved in DMF. Copper (I) iodide (19 mg, 0.1 mmol), L-proline (23 mg, 0.2 mmol) and potassium phosphate (424 mg, 2 mmol) were added and the reaction mixture was stirred for 10 min. at RT. 1-(1-Bromoprop-1-en-2-yl)-2-chlorobenzene (277 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. Yield: 50 mg. $^1$H NMR (CD$_3$OD, TFA salt) δ (ppm): 7.38 (d, 1H), 7.25 (m, 2H), 7.16-7.0 (m, 4H), 6.85 (s, 1H), 4.40 (m, 1H), 4.30 (m, 1H), 3.70 (m, 1H), 3.50 (m, 1H), 3.10 (m, 2H), 3.0 (s, 3H), 2.30 (s, 3H).

Example 197

Preparation of (E)-8-chloro-5-(2-(2-chlorophenyl) prop-1-enyl)-2-methyl-2,3,4,5-tetrahydro-1H-pyrido [4,3-b]indole (Compound 238)

8-Chloro-2-methyl-2,3,4,5-tetrahydro-1H-pyrido[4,3-b] indole (220 mg, 1 mmol) was dissolved in DMF. Copper (I) iodide (19 mg, 0.1 mmol), L-proline (23 mg, 0.2 mmol) and potassium phosphate (424 mg, 2 mmol) were added and the reaction mixture was stirred for 10 min. at RT. 1-(1-Bromoprop-1-en-2-yl)-2-chlorobenzene (277 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. The product was further purified by HPLC. Yield: 20 mg. $^1$H NMR (CD$_3$OD, TFA salt) δ (ppm): 7.58 (s, 1H), 7.50 (m, 2H), 7.40 (m, 3H), 7.22 (d, 1H), 6.60 (s, 1H), 4.40 (m, 2H), 3.70 (m, 2H), 3.22 (m, 2H), 3.15 (s, 3H), 1.90 (s, 3H).

Example 198

Preparation of (E)-2,3,4,5-tetrahydro-2,8-dimethyl-5-(2-(pyridin-3-yl)prop-1-enyl)-1H-pyrido[4,3-b] indole (Compound 91)

2,8-Dimethyl-2,3,4,5-tetrahydro-1H-pyrido[4,3-b]indole (600 mg, 3 mmol) was dissolved in DMF (12 mL). Copper (I) iodide (114 mg, 0.6 mmol), L-proline (100 mg, 0.87 mmol) and potassium phosphate (1.2 g, 6 mmol) were added and the reaction mixture was stirred for 10 min. at RT. 3-(1-Bromoprop-1-en-2-yl)pyridine (0.772 g, 3.9 mmol) was added dropwise and the reaction mixture was purged with nitrogen. The reaction mixture was heated at 85° C. for 2 h and 140° C. for 5 h (prolonged heating in some cases was required). DMF was evaporated under reduced pressure, the residue was diluted with water and the solid was filtered. The solid material was purified by silica gel chromatography (100-200 mesh). Yield: 85 mg. $^1$HNMR (CD$_3$OD, TFA salt) δ (ppm): 9.05 (d, 1H), 8.78 (d, 1H), 8.60 (d, 1H), 7.90 (m, 1H), 7.30 (d, 2H), 7.18 (d, 1H), 7.10 (d, 1H), 4.75 (m, 1H), 4.40 (m, 1H), 3.82 (m, 1H), 3.60 (m, 1H), 3.20 (m, 2H), 3.10 (s, 3H), 2.42 (s, 3H), 2.10 (s, 3H).

Example 199

Preparation of (Z)-8-methoxy-2-methyl-5-(2-(pyridin-4-yl)prop-1-enyl)-2,3,4,5-tetrahydro-1H-pyrido [4,3-b]indole (Compound 239)

1-(8-Methoxy-2-methyl-2,3,4,4a-tetrahydro-1H-pyrido [4,3-b]indol-5(9bH)-yl)-2-(pyridin-4-yl)propan-2-ol (500 mg, 1.4 mmol) was dissolved in thionylchloride (5 mL) was stirred at RT for 2 h. The reaction mixture was concentrated under reduced pressure. The residue was dissolved in N-methyl-2-pyrrolidone (4 mL) and stirred for 5 min. Powdered KOH (798 mg, 14.2 mmol) was added and stirring was continued at RT for additional 5 min. The reaction mixture was heated at 100° C. for 1 h. The progress of reaction was monitored by TLC and NMR. The reaction mixture was cooled at RT, diluted with water and extracted with EtOAc. The organic layer was washed with water, dried over anhydrous sodium sulfate and concentrated and purified the compound by HPLC. $^1$H NMR (CD$_3$OD, TFA salt) δ (ppm): 8.25 (d, 2H), 7.0 (m, 4H), 6.90 (d, 1H), 6.70 (d, 1H), 3.90 (m, 2H), 3.80 (s, 3H), 3.0 (t, 2H), 2.70 (s, 3H), 2.62 (m, 2H), 1.95 (s, 3H).

Example 200

Preparation of (Z)-8-chloro-5-(2-(2-chloro-4,5-difluorophenyl)prop-1-enyl)-2-methyl-2,3,4,5-tetrahydro-1H-pyrido[4,3-b]indole (Compound 240)

8-Chloro-2-methyl-2,3,4,4a,5,9b-hexahydro-1H-pyrido [4,3-b]indole (220 mg, 1 mmol) was dissolved in DMF. Copper (I) iodide (19 mg, 0.1 mmol), L-proline (23, 0.2 mmol) and potassium phosphate (424 mg, 2 mmol) were added and the reaction mixture was stirred for 10 min. at RT. 1-(1-Bromoprop-1-en-2-yl)-2-chloro-4,5-difluorobenzene (321 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. The product was further purified by HPLC. Yield: 30 mg as the TFA salt. $^1$H NMR (CD$_3$OD, TFA salt) δ (ppm): 7.40 (d, 1H), 7.30 (m, 1H), 7.22 (d, 1H), 7.15 (t, 1H), 7.08 (d, 1H), 6.90 (s, 1H), 4.40 (m, 2H), 3.60 (m, 2H), 3.10 (m, 2H), 3.05 (s, 3H), 2.30 (s, 3H).

Example 201

Preparation of (E)-8-chloro-5-(2-(2-chloro-4,5-difluorophenyl)prop-1-enyl)-2-methyl-2,3,4,5-tetrahydro-1H-pyrido[4,3-b]indole (Compound 241)

8-Chloro-2-methyl-2,3,4,4a,5,9b-hexahydro-1H-pyrido [4,3-b]indole (220 mg, 1 mmol) was dissolved in DMF. Copper (I) iodide (19 mg, 0.1 mmol), L-proline (23, 0.2 mmol) and potassium phosphate (424 mg, 2 mmol) were added and the reaction mixture was stirred for 10 min. at RT. 1-(1-Bromoprop-1-en-2-yl)-2-chloro-4,5-difluorobenzene (321 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. Yield: 60 mg. $^1$H NMR (CD$_3$OD, TFA salt) δ (ppm): 7.58 (m, 3H), 7.40 (d, 1H), 7.22 (d, 1H), 6.70 (s, 1H), 3.80 (m, 4H), 3.22 (m, 2H), 3.10 (s, 3H), 1.82 (s, 3H).

Example 202

Preparation of (Z)-5-(2-(2-chlorophenyl)prop-1-enyl)-2,8-dimethyl-2,3,4,5-tetrahydro-1H-pyrido[4, 3-b]indole (Compound 242)

2,8-Dimethyl-2,3,4,5-tetrahydro-1H-pyrido[4,3-b]indole (200 mg, 1 mmol) was dissolved in DMF. Copper (I) iodide (19 mg, 0.1 mmol), L-proline (23 mg, 0.2 mmol) and potassium phosphate (424 mg, 2 mmol) were added and the reaction mixture was stirred for 10 min. at RT. 1-(1-Bromoprop-1-en-2-yl)-2-chlorobenzene (277 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. Yield: 0.37 mg as the TFA salt. $^1$H NMR (CDCl$_3$, TFA salt) δ (ppm): 7.25 (m, 2H), 7.10 (t, 1H), 7.05 (s, 1H), 7.0 (m, 2H), 6.90 (d, 1H), 6.75 (s, 1H), 4.40 (d, 1H), 4.0 (d, 1H), 3.40 (m, 1H), 3.20 (m, 1H), 2.90 (m, 1H), 2.80 (s, 3H), 2.65 (m, 1H), 2.40 (s, 3H), 2.30 (s, 3H).

Example 203

Preparation of (E)-7,8-dichloro-2-methyl-5-(2-(pyridin-4-yl)prop-1-enyl)-2,3,4,5-tetrahydro-1H-pyrido[4,3-b]indole (Compound 243)

A solution of 1-(7,8-dichloro-2-methyl-3,4-dihydro-1H-pyrido[4,3-b]indol-5(2H)-yl)-2-(pyridin-4-yl)propan-2-ol (500 mg, 1.2 mmol) in thionylchloride (5 mL) and stirred at RT for 5 h. The reaction mixture was concentrated under reduced pressure. The residue was dissolved in N-methyl-2-pyrrolidone (5 mL) and the solution was stirred at RT for 5 min. Powdered KOH (482 mg, 8.5 mmol) was added and the reaction mixture was heated at 100° C. for 1 h. The progress of reaction was monitored by TLC and NMR. Upon completion, the reaction mixture was cooled at RT, diluted with water and extracted with EtOAc. The organic layer was washed with water, dried over anhydrous sodium sulfate, concentrated under reduced pressure and the residue purified by HPLC. $^1$H NMR (CD$_3$OD, formate salt) δ (ppm): 8.60 (d, 2H), 7.70 (d, 2H), 7.65 (s, 1H), 7.38 (s, 1H), 7.30 (s, 1H), 4.0 (s, 2H), 3.20 (t, 2H), 2.98 (t, 2H), 2.80 (s, 3H), 2.0 (s, 3H).

Example 204

Preparation of (Z)-7,8-dichloro-2-methyl-5-(2-(pyridin-4-yl)prop-1-enyl)-2,3,4,5-tetrahydro-1H-pyrido[4,3-b]indole (Compound 244)

7,8-Dichloro-5-(2-hydroxy-2-(pyridin-4-yl)propyl)-2-methyl-2,3,4,4a,5,9b-hexahydro-1H-pyrido[4,3-b]indole (500 mg, 1.2 mmol) in thionylchloride (5 mL) was stirred at RT for 5 h. The reaction mixture was concentrated under reduced pressure. The residue was dissolved in N-methyl-2-pyrrolidone (5 mL) and the solution was stirred for 5 min. at RT. Powdered KOH (482 mg, 8.5 mmol) was added and the reaction mixture was heated at 100° C. for 1 h. The progress of reaction was monitored by TLC and NMR. The reaction mixture was cooled at RT, diluted with water and extracted with EtOAc. The organic layer was washed with water, dried over anhydrous sodium sulfate, concentrated under reduced pressure and the residue purified by HPLC. $^1$H NMR (CD$_3$OD, formate salt) δ (ppm): 8.30 (d, 2H), 7.50 (s, 1H), 7.20 (s, 1H), 7.05 (d, 2H), 6.95 (s, 1H), 3.70 (m, 2H), 2.85 (m, 2H), 2.70 (m, 2H), 2.58 (s, 3H), 2.38 (s, 3H).

Example 205

Preparation of (E)-8,9-dichloro-2-methyl-5-(2-(pyridin-4-yl)prop-1-enyl)-2,3,4,5-tetrahydro-1H-pyrido[4,3-b]indole (Compound 245)

8,9-Dichloro-5-(2-hydroxy-2-(pyridin-4-yl)propyl)-2-methyl-2,3,4,4a,5,9b-hexahydro-1H-pyrido[4,3-b]indole (500 mg, 1.2 mmol) was dissolved in thionylchloride (5 mL) and stirred at RT for 5 h. The reaction mixture was concentrated under reduced pressure. The residue was dissolved in N-methyl-2-pyrrolidone (5 mL) and the solution was stirred for 5 min. at RT. Powdered KOH (482 mg, 8.5 mmol) was added and the reaction mixture was heated at 100° C. for 1 h. The progress of reaction was monitored by TLC and NMR. Upon completion, the reaction mixture was cooled at RT, diluted with water and extracted with EtOAc. The organic layer was washed with water, dried over anhydrous sodium sulfate, concentrated under reduced pressure and the residue purified by HPLC. $^1$H NMR (CD$_3$OD, formate salt) δ (ppm): 8.60 (d, 2H), 7.70 (d, 2H), 7.30 (m, 2H), 7.18 (d, 1H), 4.60 (m, 2H), 3.40 (m, 2H), 3.10 (m, 2H), 2.90 (s, 3H), 2.0 (s, 3H).

Example 206

Preparation of (E)-8-methoxy-2-methyl-5-(2-(pyridin-4-yl)prop-1-enyl)-2,3,4,5-tetrahydro-1H-pyrido[4,3-b]indole (Compound 246)

1-(8-Methoxy-2-methyl-2,3,4,4a-tetrahydro-1H-pyrido[4,3-b]indol-5(9bH)-yl)-2-(pyridin-4-yl)propan-2-ol (500 mg, 1.4 mmol) in thionylchloride (5 mL) and stirred at RT for 2 h. The reaction mixture was concentrated followed under reduced pressure. The residue was dissolved in N-methyl-2-pyrrolidone (4 mL) and the solution was stirred for 5 min. at RT. Powdered KOH (798 mg, 14.2 mmol) was added, the reaction mixture was stirred at RT for 5 min. and then at 100° C. for 1 h. The progress of reaction was monitored by TLC and NMR. Upon completion the reaction mixture was cooled at RT, diluted with water and extracted with EtOAc. The organic layer was washed with water, dried over anhydrous sodium sulfate, concentrated under reduced pressure and the residue purified by HPLC. $^1$H NMR (CD$_3$OD, TFA salt) δ (ppm): 8.58 (d, 2H), 7.70 (d, 2H), 7.30 (s, 1H), 7.10 (d, 1H), 6.95 (s, 1H), 6.80 (d, 1H), 3.95 (s, 2H), 3.80 (s, 3H), 3.10 (t, 2H), 2.90 (t, 2H), 2.70 (s, 3H), 2.0 (s, 3H).

Example 207

Preparation of (Z)-5-(2-(3,4-dichlorophenyl)prop-1-enyl)-2,8-dimethyl-2,3,4,5-tetrahydro-1H-pyrido[4,3-b]indole (Compound 247)

2,8-Dimethyl-2,3,4,5-tetrahydro-1H-pyrido[4,3-b]indole (200 mg, 1 mmol) was dissolved in DMF. Copper (I) iodide (19 mg, 0.1 mmol), L-proline (23 mg, 0.2 mmol) and potassium phosphate (424 mg, 2 mmol) were added and the reaction mixture was stirred for 10 min. at RT. (1-Bromoprop-1-en-2-yl)-3,4-dichlorobenzene (318 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. The product was further purified by HPLC. Yield: 10 mg as the TFA salt. $^1$H NMR (CD$_3$OD, TFA salt) δ (ppm): 7.30 (d, 1H), 7.22 (d, 2H), 7.10 (d, 1H), 7.0 (d, 1H), 6.92 (d, 1H), 6.85 (d, 1H), 4.40 (d, 1H), 4.30 (d, 1H), 3.70 (m, 1H), 3.40 (m, 1H), 3.0 (s, 3H), 2.80 (m, 2H), 2.40 (s, 3H), 2.30 (s, 3H).

Example 208

Preparation of (E)-2,3,4,5-tetrahydro-2,8-dimethyl-5-(2-(6-methylpyridin-3-yl)prop-1-enyl)-1H-pyrido[4,3-b]indole (Compound 85)

1-(1,2,3,4-Tetrahydro-2,8-dimethylpyrido[4,3-b]indol-5-yl)-2-(6-methylpyridin-3-yl)propan-2-ol (1 g, 2.86 mmol, 1 equiv.) was refluxed with 25% sulfuric acid (7 mL) for 2 h. The reaction mixture was cooled to 5° C. in ice-water bath. KOH (15% aqueous solution) was added dropwise to the reaction mixture until pH 9-10 was achieved. The reaction mixture was extracted with EtOAc (3×10 mL). The combined organic layer was washed with water (10 mL) followed by brine, dried over sodium sulfate and evaporated under vacuum. The crude product was purified by silica gel chromatography (100-200 mesh) using a gradient of MeOH-EtOAc (0-10%), followed by further purification by HPLC.
$^1$HNMR (CD$_3$OD, TFA salt) δ (ppm) 8.90 (s, 1H), 8.60 (d, 1H), 7.80 (d, 1H), 7.30 (d, 2H), 7.16 (d, 1H), 7.10 (d, 1H), 4.78 (m, 1H), 4.40 (m, 1H), 3.90 (m, 1H), 3.60 (m, 1H), 3.20 (m, 2H), 3.16 (s, 3H), 3.80 (s, 3H), 2.42 (s, 3H), 2.05 (s, 3H).

Example 209

Preparation of (E)-7,8-dichloro-5-(2-(4-fluorophenyl)prop-1-enyl)-2-methyl-2,3,4,5-tetrahydro-1H-pyrido[4,3-b]indole (Compound 248)

7,8-Dichloro-2-methyl-2,3,4,5-tetrahydro-1H-pyrido[4,3-b]indole (900 mg, 3.54 mmol) was dissolved in DMF (5 mL). Copper (I) iodide (66 mg, 0.354 mmol), L-proline (81 mg, 0.69 mmol) and potassium phosphate (1.5 g, 7.08 mmol) were added and the reaction mixture was stirred for 10 min. at RT. 1-(2-Bromovinyl)-4-fluorobenzene (900 mg, 4.23 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh) eluting with 0-10% MeOH-DCM. The product was further purified by HPLC.

Example 210

Preparation of (E)-2-methyl-5-(2-(pyridin-4-yl)prop-1-enyl)-8-(trifluoromethyl)-2,3,4,5-tetrahydro-1H-pyrido[4,3-b]indole (Compound 249)

2-Methyl-8-(trifluoromethyl)-2,3,4,5-tetrahydro-1H-pyrido[4,3-b]indole (239 mg, 0.94 mmol), and potassium phosphate (399 mg, 1.88 mmol) were mixed in DMF and the suspension was purged with nitrogen. The suspension was heated at 140° C. for 10 min. Copper (I) iodide (17.86 mg, 0.094 mmol) and L-proline (21.64 mg, 0.188 mmol) were added followed by a solution of 4-(1-bromoprop-1-en-2-yl)pyridine (399 mg, 1.88 mmol) in DMF. The contents were purged with nitrogen and heated overnight at 140° C. The contents were cooled to RT and poured into water. The precipitate obtained was filtered, dried and purified by silica gel chromatography (100-200 mesh) eluting with 0-10% MeOH-DCM as eluent. The compound was further purified by HPLC. $^1$H NMR (CD$_3$OD, TFA salt) δ (ppm): 8.82 (d, 2H), 8.30 (d, 2H), 7.95 (s, 1H), 7.70 (s, 1H), 7.58 (d, 1H), 7.45 (d, 1H), 4.50 (m, 1H), 3.95 (m, 1H), 3.62 (m, 1H), 3.30 (m, 3H), 3.18 (s, 3H), 2.10 (s, 3H).

Example 211

Preparation of (E)-2-methyl-5-(2-(6-methylpyridin-3-yl)prop-1-enyl)-7-(trifluoromethyl)-2,3,4,5-tetrahydro-1H-pyrido[4,3-b]indole (Compound 250)

2-Methyl-8-(trifluoromethyl)-2,3,4,5-tetrahydro-1H-pyrido[4,3-b]indole (203 mg, 0.8 mmol) was dissolved in DMF (5 mL). Copper (I) iodide (19 mg, 0.10 mmol), L-proline (23 mg, 0.20 mmol) and potassium phosphate (424 mg, 2 mmol) were added and the reaction mixture was stirred for 10 min. at RT. 5-(1-Bromoprop-1-en-2-yl)-2-methylpyridine (212 mg, 1 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-5% MeOH-DCM. The product was further purified by HPLC.
$^1$H NMR (CDCl$_3$, TFA salt) δ (ppm): 9.10 (s, 1H), 8.30 (d, 1H), 7.65 (d, 1H), 7.55 (d, 1H), 7.45 (d, 1H), 7.40 (s, 1H), 7.10 (s, 1H), 4.80 (m, 1H), 4.20 (m, 1H), 3.90 (m, 1H), 3.40 (m, 2H), 3.10 (s, 3H), 3.0 (m, 1H), 2.82 (s, 3H), 2.0 (s, 3H).

Example 212

Preparation of (E)-8-fluoro-2-methyl-5-(2-(6-methylpyridin-3-yl)prop-1-enyl)-2,3,4,5-tetrahydro-1H-pyrido[4,3-b]indole (Compound 251)

8-Fluoro-2-methyl-2,3,4,5-tetrahydro-1H-pyrido[4,3-b]indole (203 mg, 0.8 mmol) was dissolved in DMF (5 mL). Copper (I) iodide (19 mg, 0.10 mmol), L-proline (23 mg, 0.20 mmol) and potassium phosphate (424 mg, 2 mmol) were added and the reaction mixture was stirred for 10 min. at RT. 5-(1-Bromoprop-1-en-2-yl)-2-methylpyridine (212 mg, 1 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh). The product was further purified by HPLC.
$^1$H NMR (CDCl$_3$, TFA salt) δ (ppm): 9.0 (s, 1H), 8.10 (d, 1H), 7.50 (d, 1H), 7.0 (m, 4H), 4.70 (m, 1H), 4.10 (m, 1H), 3.90 (m, 1H), 3.30 (m, 2H), 3.05 (s, 3H), 2.90 (m, 1H), 2.80 (s, 3H), 2.0 (s, 3H).

Example 213

Preparation of (E)-6-chloro-2-methyl-5-(2-(6-methylpyridin-3-yl)prop-1-enyl)-2,3,4,5-tetrahydro-1H-pyrido[4,3-b]indole (Compound 252)

6-Chloro-2-methyl-2,3,4,5-tetrahydro-1H-pyrido[4,3-b]indole (203 mg, 0.8 mmol) was dissolved in DMF (5 mL). Copper (I) iodide (19 mg, 0.10 mmol), L-proline (23 mg, 0.20 mmol) and potassium phosphate (424 mg, 2 mmol) were added and the reaction mixture was stirred for 10 min. at RT. 5-(1-Bromoprop-1-en-2-yl)-2-methylpyridine (212 mg, 1 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh). The product was further purified by HPLC. $^1$H NMR (CDCl$_3$, TFA salt) δ (ppm): 9.10 (s, 1H), 8.20 (d, 1H), 7.60 (d, 1H), 7.30 (m, 2H), 7.20 (d, 1H), 7.10 (t, 1H), 4.75 (m, 1H), 4.18 (m, 1H), 3.90 (m, 1H), 3.30 (m, 2H), 3.05 (s, 3H), 2.90 (m, 1H), 2.80 (s, 3H), 1.90 (s, 3H).

Example 214

Preparation of (E)-7-chloro-2-methyl-5-(2-(6-methylpyridin-3-yl)prop-1-enyl)-2,3,4,5-tetrahydro-1H-pyrido[4,3-b]indole (Compound 253)

7-Chloro-2-methyl-2,3,4,5-tetrahydro-1H-pyrido[4,3-b]indole (176 mg, 0.8 mmol) was dissolved in DMF (5 mL). Copper (I) iodide (19 mg, 0.10 mmol), L-proline (23 mg, 0.20 mmol) and potassium phosphate (424 mg, 2.00 mmol) were added and the reaction mixture was stirred for 10 min. at RT. 5-(1-Bromoprop-1-en-2-yl)-2-methylpyridine (212 mg, 1 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh). The product was further purified by HPLC. $^1$H NMR (CDCl$_3$, TFA salt) δ (ppm): 9.10 (s, 1H), 8.30 (d, 1H), 7.65 (d, 1H), 7.38 (d, 1H), 7.18 (d, 1H), 7.10 (m, 2H), 4.80 (d, 1H), 4.18 (d, 1H), 3.90 (m, 1H), 3.30 (m, 2H), 3.10 (s, 3H), 2.98 (m, 1H), 2.82 (s, 3H), 2.05 (s, 3H).

Example 215

Preparation of (E)-2-methyl-5-(2-(6-methylpyridin-3-yl)prop-1-enyl)-2,3,4,5-tetrahydro-1H-pyrido[4,3-b]indole (Compound 254)

2-Methyl-2,3,4,5-tetrahydro-1H-pyrido[4,3-b]indole (186 mg, 0.8 mmol) was dissolved in DMF (5 mL). Copper (I) iodide (19 mg, 0.10 mmol), L-proline (23 mg, 0.20 mmol) and potassium phosphate (424 mg, 2 mmol) were added and the reaction mixture was stirred for 10 min. at RT. 5-(1-Bromoprop-1-en-2-yl)-2-methylpyridine (212 mg, 1 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh). The product was further purified by HPLC. $^1$H NMR (CDCl$_3$, TFA salt) δ (ppm): 9.10 (s, 1H), 8.30 (d, 1H), 7.70 (m, 1H), 7.42 (d, 1H), 7.25 (m, 2H), 7.10 (d, 2H), 4.80 (m, 1H), 4.20 (m, 1H), 3.90 (m, 1H), 3.40 (m, 2H), 3.10 (s, 3H), 3.0 (m, 1H), 2.82 (s, 3H), 2.05 (s, 3H).

Example 216

Preparation of (E)-7,8-difluoro-2-methyl-5-(2-(6-methylpyridin-3-yl)prop-1-enyl)-2,3,4,5-tetrahydro-1H-pyrido[4,3-b]indole (Compound 255)

7,8-Difluoro-2-methyl-2,3,4,5-tetrahydro-1H-pyrido[4,3-b]indole (177 mg, 0.8 mmol) was dissolved in DMF (5 mL). Copper (I) iodide (19 mg, 0.10 mmol), L-proline (23 mg, 0.20 mmol) and potassium phosphate (424 mg, 2 mmol) were added and the reaction mixture was stirred for 10 min. at RT. 5-(1-Bromoprop-1-en-2-yl)-2-methylpyridine (212 mg, 1 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh). The product was further purified by HPLC. $^1$H NMR (CDCl$_3$, TFA salt) δ (ppm): 9.10 (s, 1H), 8.22 (d, 1H), 7.60 (d, 1H), 7.15 (t, 1H), 7.02 (s, 1H), 6.95 (t, 1H), 4.70 (m, 1H), 4.10 (m, 1H), 3.90 (m, 1H), 3.30 (m, 2H), 3.05 (s, 3H), 2.90 (m, 1H), 2.80 (s, 3H), 2.0 (s, 3H).

Example 217

Preparation of (Z)-8-chloro-5-(2-(3,4-dichlorophenyl)prop-1-enyl)-2-methyl-2,3,4,5-tetrahydro-1H-pyrido[4,3-b]indole (Compound 256)

8-Chloro-2-methyl-2,3,4,5-tetrahydro-1H-pyrido[4,3-b]indole (200 mg, 1 mmol) was dissolved in DMF. Copper (I) iodide (19 mg, 0.1 mmol), L-proline (24 mg, 0.2 mmol) and potassium phosphate (424 mg, 2 mmol) were added and the reaction mixture was stirred for 10 min. at RT. 1-(1-Bromoprop-1-en-2-yl)-4-fluorobenzene (318 mg, 1.2 mmol) was added dropwise and the reaction mixture was purged with nitrogen. The reaction mixture was heated overnight at 90° C. (prolonged heating in some cases was required). DMF was evaporated under reduced pressure, the residue was diluted with water and the solid was filtered. The solid material was purified by silica gel chromatography (100-200 mesh) eluting with 0-3% MeOH-DCM. The product was further purified by HPLC. Yield: 13 mg as the TFA salt. $^1$H NMR (CD$_3$OD, TFA salt) δ (ppm): 7.45 (d, 1H), 7.30 (d, 1H), 7.20 (d, 2H), 7.10 (d, 1H), 6.90 (dd, 1H), 6.82 (s, 1H), 4.62 (m, 1H), 4.30 (m, 1H), 3.70 (m, 1H), 3.42 (m, 1H), 3.0 (s, 3H), 2.80 (m, 2H), 2.35 (s, 3H).

Example 218

E)-2,3,8-trimethyl-5-(2-(pyridin-4-yl)prop-1-enyl)-2,3,4,5-tetrahydro-1H-pyrido[4,3-b]indole (Compound 257

2,3,8-Trimethyl-2,3,4,5-tetrahydro-1H-pyrido[4,3-b]indole (107 mg, 0.5 mmol), and potassium phosphate (414 mg, 2 mmol) were mixed in DMF and the suspension was purged with nitrogen. The suspension was heated at 140° C. for 10 min. Copper (I) iodide (9.5 mg, 0.05 mmol) and L-proline (11.5 mg, 0.1 mmol) were added followed by a solution of 4-(1-Bromoprop-1-en-2-yl)pyridine (107.83 mg, 0.55 mmol) in DMF. The contents were purged with nitrogen and heated overnight at 140° C. The contents were cooled to RT and poured into water. The precipitate obtained was filtered, dried and purified by silica gel chromatography (100-200 mesh, neutralized with aqueous ammonia) eluting with 0-4% MeOH-DCM as eluent. The compound was further purified by HPLC. $^1$H NMR (CDCl$_3$, freebase) δ (ppm): 8.62 (d, 2H), 7.42 (d, 2H), 7.25 (d, 1H), 7.10 (s, 1H), 7.0 (s, 2H), 3.90 (d, 1H), 3.70 (d, 1H), 2.90 (m, 1H), 2.80 (m, 1H), 2.52 (m, 1H), 2.50 (s, 3H), 2.42 (s, 3H), 2.0 (s, 3H), 1.20 (d, 3H).

Example 219

Preparation of (E)-5-(2-(4-fluorophenyl)prop-1-enyl)-2,3,8-trimethyl-2,3,4,5-tetrahydro-1H-pyrido[4,3-b]indole (Compound 258)

2,3,8-Trimethyl-2,3,4,5-tetrahydro-1H-pyrido[4,3-b]indole (107 mg, 0.5 mmol) was dissolved in DMF. Copper (I) iodide (9.5 mg, 0.05 mmol), L-proline (11.5 mg, 0.1 mmol) and potassium phosphate (414 mg, 2 mmol) were added and the reaction mixture was stirred for 10 min. at RT. 1-(2-bromovinyl)-4-fluorobenzene (107.83 mg, 0.55 mmol) was added dropwise and the reaction mixture was purged with nitrogen. The reaction mixture was heated overnight at 100° C. (prolonged heating in some cases was required). DMF was evaporated under reduced pressure, the residue was diluted with water and the solid was filtered. The solid material was purified by silica gel chromatography (100-200 mesh) eluting with 0-7% MeOH-DCM. Yield: 92 mg. $^1$H NMR (CD$_3$OD, oxalate salt) δ (ppm): 7.70 (m, 2H), 7.30 (s, 1H), 7.10 (m, 4H), 6.95 (s, 1H), 4.70 (m, 1H), 4.60 (m, 1H), 3.90 (m, 1H), 3.20 (m, 1H), 2.95 (m, 4H), 2.42 (s, 3H), 1.90 (s, 3H), 1.50 (d, 3H).

Example 220

Preparation of (E)-2,3,8-trimethyl-5-(2-(6-methylpyridin-3-yl)prop-1-enyl)-2,3,4,5-tetrahydro-1H-pyrido[4,3-b]indole (Compound 259)

2,3,8-Trimethyl-2,3,4,5-tetrahydro-1H-pyrido[4,3-b]indole (107 mg, 0.5 mmol) was dissolved in DMF. Copper (I) iodide (9.5 mg, 0.05 mmol), L-proline (11.5 mg, 0.1 mmol) and potassium phosphate (414 mg, 2 mmol) were added and the reaction mixture was stirred for 10 min. at RT. 5-(2-bromovinyl)-2-methylpyridine (116 mg, 0.55 mmol) was added dropwise and the reaction mixture was purged with nitrogen. The reaction mixture was heated overnight at 100° C. (prolonged heating in some cases was required). DMF was evaporated under reduced pressure, the residue was diluted with water and the solid was filtered. The solid material was purified by silica gel chromatography (100-200 mesh) eluting with 0-7% MeOH-DCM. Yield: 125 mg. $^1$H NMR (CD$_3$OD, oxalate salt) δ (ppm): 8.78 (s, 1H), 8.22 (d, 1H), 7.90 (s, 1H), 7.58 (d, 1H), 7.30 (s, 1H), 7.18 (d, 1H), 7.10 (d, 1H), 4.60 (m, 2H), 4.0 (m, 1H), 3.30 (m, 1H), 3.05 (m, 3H), 2.95 (m, 1H), 2.65 (s, 3H), 2.42 (s, 3H), 2.0 (s, 3H), 1.50 (d, 3H).

Example 221

Preparation of (E)-6-fluoro-2-methyl-5-(2-(6-methylpyridin-3-yl)prop-1-enyl)-2,3,4,5-tetrahydro-1H-pyrido[4,3-b]indole (Compound 260)

6-Fluoro-2-methyl-2,3,4,5-tetrahydro-1H-pyrido[4,3-b]indole (203 mg, 0.8 mmol) was dissolved in DMF (5 mL). Copper (I) iodide (19 mg, 0.10 mmol), L-proline (23 mg, 0.20 mmol) and potassium phosphate (424 mg, 2 mmol) were added and the reaction mixture was stirred for 10 min. at RT. 5-(1-Bromoprop-1-en-2-yl)-2-methylpyridine (212 mg, 1 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh). The product was further purified by HPLC. $^1$H NMR (CDCl$_3$, TFA salt) δ (ppm): 9.10 (s, 1H), 8.30 (d, 1H), 7.62 (m, 1H), 7.22 (s, 1H), 7.18 (d, 1H), 7.10 (m, 1H), 6.95 (m, 1H), 5.80 (m, 1H), 4.10 (m, 1H), 3.90 (m, 1H), 3.30 (m, 2H), 3.05 (s, 3H), 2.95 (m, 1H), 2.80 (s, 3H), 2.0 (s, 3H).

Example 222

Preparation of (E)-7-fluoro-2-methyl-5-(2-(6-methylpyridin-3-yl)prop-1-enyl)-2,3,4,5-tetrahydro-1H-pyrido[4,3-b]indole (Compound 261)

7,8-Fluoro-2-methyl-2,3,4,5-tetrahydro-1H-pyrido[4,3-b]indole (177 mg, 0.8 mmol) was dissolved in DMF (5 mL). Copper (I) iodide (19 mg, 0.10 mmol), L-proline (23 mg, 0.20 mmol) and potassium phosphate (424 mg, 2.00 mmol) were added and the reaction mixture was stirred for 10 min. at RT. 5-(1-Bromoprop-1-en-2-yl)-2-methylpyridine (212 mg, 1.00 mmol) was added dropwise and the reaction mixture was purged with nitrogen. The reaction mixture was heated overnight at 80° C. (prolonged heating in some cases was required). DMF was evaporated under reduced pressure, the residue was diluted with water and the solid was filtered. The solid material was purified by silica gel chromatography (100-200 mesh). The product was further purified by HPLC. $^1$H NMR (CDCl$_3$, TFA salt) δ (ppm): 9.10 (s, 1H), 8.26 (d, 1H), 7.64 (d, 2H), 7.35 (m, 1H), 7.08 (s, 1H), 6.99 (t, 1H), 6.82 (dd, 1H), 4.78 (m, 1H), 4.10 (m, 1H), 3.82 (m, 1H), 3.50-3.30 (m, 2H), 3.06 (s, 3H), 2.90 (m, 1H), 2.82 (s, 3H), 2.05 (s, 3H).

Example 223

Preparation of (E)-8-chloro-5-(2-(4-fluorophenyl)prop-1-enyl)-2,3-dimethyl-2,3,4,5-tetrahydro-1H-pyrido[4,3-b]indole (Compound 262)

8-Chloro-2,3-dimethyl-2,3,4,5-tetrahydro-1H-pyrido[4,3-b]indole (117 mg, 0.5 mmol) was dissolved in DMF. Copper (I) iodide (9.5 mg, 0.05 mmol), L-proline (11.5 mg, 0.1 mmol) and potassium phosphate (212 mg, 1 mmol) were added and the reaction mixture was stirred for 10 min. at RT. 1-(1-Bromoprop-1-en-2-yl)-4-fluorobenzene (118 mg, 0.55 mmol) was added dropwise and the reaction mixture was purged with nitrogen. The reaction mixture was heated overnight at 90° C. (prolonged heating in some cases was required). DMF was evaporated under reduced pressure, the residue was diluted with water and the solid was filtered. The solid material was purified by silica gel chromatography (100-200 mesh) eluting with 0-7% MeOH-DCM. $^1$H NMR (DMSO-d6, oxalate salt) δ (ppm): 7.72 (m, 2H), 7.61 (s, 1H), 7.30 (m, 3H), 7.20 (d, 1H), 7.11 (s, 1H), 4.40 (m, 2H), 3.20 (m, 1H), 2.80 (m, 5H), 1.84 (s, 3H), 1.40 (d, 3H).

Example 224

Preparation of (E)-2-methyl-5-(2-(pyridin-4-yl)prop-1-enyl)-8-(trifluoromethoxy)-2,3,4,5-tetrahydro-1H-pyrido[4,3-b]indole (Compound 263)

2-Methyl-8-(trifluoromethoxy)-2,3,4,5-tetrahydro-1H-pyrido[4,3-b]indole (135 mg, 0.5 mmol) was dissolved in DMF. Copper (I) iodide (9.5 mg, 0.05 mmol), L-proline (11.5 mg, 0.1 mmol) and potassium phosphate (414 mg, 2 mmol) were added and the reaction mixture was stirred for 10 min. at RT. 4-(1-Bromoprop-1-en-2-yl)pyridine (116 mg, 0.55 mmol) was added dropwise and the reaction mixture was purged with nitrogen. The reaction mixture was heated overnight at 90° C. (prolonged heating in some cases was required). DMF was evaporated under reduced pressure, the residue was diluted with water and the solid was filtered. The solid material was purified by silica gel chromatography (100-200 mesh) eluting with 0-7% MeOH-DCM. Yield: 12 mg. $^1$H NMR (CD$_3$OD, TFA salt) δ (ppm): 8.82 (d, 2H), 8.30 (d, 2H), 7.78 (s, 1H), 7.50 (s, 1H), 7.38 (d, 1H), 7.22 (d, 1H), 4.70 (m, 1H), 4.40 (m, 1H), 3.90 (m, 1H), 3.60 (m, 1H), 3.20 (m, 2H), 3.10 (s, 3H), 2.10 (s, 3H).

Example 225

Preparation of (Z)-2,8-dimethyl-5-(3-methyl-2-(pyridin-4-yl)but-1-enyl)-2,3,4,5-tetrahydro-1H-pyrido[4,3-b]indole (Compound 264)

2,3,4,5-Tetrahydro-2,8-dimethyl-1H-pyrido[4,3-b]indole (0.08 g, 0.4 mmol), 4-(1-bromo-3-methylbut-1-en-2-yl)pyridine (0.1 g, 0.44 mmol), potassium phosphate (0.169 g, 0.797 mmol), L-proline (0.013 g, 0.113 mmol), and copper (I) iodide (0.015 g, 0.079 mmol) were mixed in DMF (5 mL) and purged with nitrogen. The contents were cooled to RT and poured into water. The precipitate obtained was filtered, dried and purified by HPLC. $^1$H NMR (CD$_3$OD, TFA salt) δ (ppm): 8.50 (d, 2H), 7.60 (d, 2H), 7.20 (s, 1H), 7.10 (d, 1H), 6.95 (d, 2H), 4.60 (m, 1H), 4.30 (m, 1H), 3.80 (m, 1H), 3.50 (m, 1H), 3.10 (m, 1H), 3.05 (m, 5H), 2.38 (s, 3H), 1.38 (d, 6H).

Example 226

Preparation of (Z)-8-chloro-2-methyl-5-(3-methyl-2-(pyridin-4-yl)but-1-enyl)-2,3,4,5-tetrahydro-1H-pyrido[4,3-b]indole (Compound 265)

8-Chloro-2,3,4,5-tetrahydro-2-methyl-1H-pyrido[4,3-b]indole (500 mg, 2.27 mmol) was dissolved in DMF (10 mL). Copper (I) iodide (86 mg, 0.452 mmol), L-proline (0.075 g, 0.652 mmol) and potassium phosphate (0.963 g, 4.54 mmol) were added and the reaction mixture was stirred for 10 min. at RT. 4-(1-Bromo-3-methylbut-1-en-2-yl)pyridine (0.65 g, 2.87 mmol) was added dropwise and the reaction mixture was purged with nitrogen. The reaction mixture was heated overnight at 100° C. (prolonged heating in some cases was required). DMF was evaporated under reduced pressure, the residue was diluted with water and the solid was filtered. The solid material was purified by silica gel chromatography (100-200 mesh). The product was further purified by HPLC. $^1$H NMR (CD$_3$OD, TFA salt) δ (ppm): 8.50 (d, 2H), 7.60 (d, 2H), 7.40 (s, 1H), 7.10 (d, 2H), 7.05 (s, 1H), 4.70 (m, 1H), 4.30 (m, 1H), 3.80 (m, 1H), 3.50 (m, 1H), 3.10 (m, 6H), 1.30 (d, 6H).

Example 227

Preparation of (E)-2-ethyl-5-(2-(pyridin-4-yl)prop-1-enyl)-2,3,4,5-tetrahydro-1H-pyrido[4,3-b]indole (Compound 266)

2-Ethyl-2,3,4,5-tetrahydro-1H-pyrido[4,3-b]indole (150 mg, 0.65 mmol) was dissolved in DMF. Copper (I) iodide (14 mg, 0.13 mmol), L-proline (12 mg, 0.065 mmol) and potassium phosphate (275 mg, 1.3 mmol) were added and the reaction mixture was stirred for 10 min. at RT. 4-(1-Bromoprop-1-en-2-yl)pyridine (195 mg, 0.9 mmol) was added and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh). The product was further purified by HPLC. $^1$H NMR (CD$_3$OD, TFA salt) δ (ppm): 8.70 (d, 2H), 8.0 (d, 2H), 7.60 (d, 2H), 7.30 (m, 2H), 7.20 (t, 1H), 4.40 (m, 1H), 3.90 (m, 1H), 3.60 (m, 1H), 3.50 (q, 2H), 3.36 (m, 1H), 3.20 (m, 2H), 2.10 (s, 3H), 1.50 (t, 3H).

Example 228

Preparation of (E)-8-isopropyl-2-methyl-5-(2-(pyridin-4-yl)prop-1-enyl)-2,3,4,5-tetrahydro-1H-pyrido[4,3-b]indole (Compound 267)

8-Isopropyl-2-methyl-2,3,4,5-tetrahydro-1H-pyrido[4,3-b]indole (150 mg, 0.65 mmol) was dissolved in DMF. Copper (I) iodide (14 mg, 0.074 mmol), L-proline (17 mg, 0.015 mmol) and potassium phosphate (340 mg, 1.48 mmol) were added and the reaction mixture was stirred for 10 min. at RT. 4-(1-Bromoprop-1-en-2-yl)pyridine (220 mg, 0.9 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh). The product was further purified by HPLC. $^1$H NMR (CD$_3$OD, TFA salt) δ (ppm): 8.80 (d, 2H), 8.20 (d, 2H), 7.70 (s, 1H), 7.40 (s, 1H), 7.20 (m, 2H), 4.40 (m, 1H), 3.90 (m, 1H), 3.70 (m, 1H), 3.22 (m, 3H), 3.15 (s, 3H), 3.0 (m, 1H), 2.10 (s, 3H), 1.30 (d, 6H).

Example 229

Preparation of (E)-5-(2-(4-fluorophenyl)prop-1-enyl)-2-methyl-8-(trifluoromethyl)-2,3,4,5-tetrahydro-1H-pyrido[4,3-b]indole (Compound 268)

2-Methyl-8-(trifluoromethyl)-2,3,4,5-tetrahydro-1H-pyrido[4,3-b]indole (127 mg, 0.5 mmol) was dissolved in DMF. Copper (I) iodide (9.5 mg, 0.05 mmol), L-proline (11.5 mg, 0.1 mmol) and potassium phosphate (212 mg, 1 mmol) were added and the reaction mixture was stirred for 10 min. at RT. 1-(1-Bromoprop-1-en-2-yl)-4-fluorobenzene (118 mg, 0.55 mmol) was added dropwise and the reaction mixture was purged with nitrogen. The reaction mixture was heated overnight at 90° C. (prolonged heating in some cases was required). DMF was evaporated under reduced pressure, the residue was diluted with water and the solid was filtered. The solid material was purified by silica gel chromatography (100-200 mesh) eluting with 0-3% MeOH-DCM. The free base was converted into oxalate salt by treatment of oxalic acid (1 equiv) in THF. Yield: 65 mg as the oxalate salt. $^1$H NMR (CD$_3$OD, oxalate salt) δ (ppm): 7.90 (s, 1H), 7.70 (t, 2H), 7.50 (d, 1H), 7.40 (d, 1H), 7.20 (t, 2H), 7.0 (s, 1H), 4.60 (m, 2H), 3.78 (m, 2H), 3.20 (m, 2H), 3.10 (s, 3H), 1.90 (s, 3H).

Example 230

Preparation of 8-chloro-5-((Z)-2-(2,4-difluorophenyl)prop-1-enyl)-2,3,4,5-tetrahydro-2-methyl-1H-pyrido[4,3-b]indole (Compound 107)

8-Chloro-2-methyl-2,3,4,5-tetrahydro-1H-pyrido[4,3-b]indole (220 mg, 1 mmol) was dissolved in DMF. Copper (I)

iodide (19 mg, 0.1 mmol), L-proline (23 mg, 0.2 mmol) and potassium phosphate (424 mg, 2 mmol) were added and the reaction mixture was stirred for 10 min. at RT. 1-(2-Bromo-1-methyl-vinyl)-2,4-difluoro-benzene (279 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-2% MeOH-DCM. The product was further purified by HPLC. Yield: 23 mg. $^1$H NMR (CD$_3$OD, freebase) δ (ppm): 7.27 (d, 1H), 7.00 (m, 2H), 6.93 (dd, 1H), 7.83 (d, 1H), 6.78 (m, 1H), 6.70 (m, 1H), 3.52 (s, 2H), 2.80 (t, 2H), 2.70 (t, 2H), 2.50 (s, 3H), 2.30 (s, 3H).

Example 231

Preparation of (E)-2-ethyl-8-methyl-5-(2-(pyridin-4-yl)prop-1-enyl)-2,3,4,5-tetrahydro-1H-pyrido[4,3-b]indole (Compound 269)

2-Ethyl-8-methyl-2,3,4,4a,5,9b-hexahydro-1H-pyrido[4,3-b]indole (150 mg, 0.69 mmol) potassium phosphate (292.5 mg, 1.382 mmol), Copper (I) iodide (13.11 mg, 0.069 mmol) and L-proline (15.8 mg, 0.138 mmol) were mixed in DMF and the purged with nitrogen. The contents were heated at 80° C. for 10 min. 4-(1-Bromoprop-1-en-2-yl)pyridine (208 mg, 1.04 mmol) was added, the reaction mixture was purged nitrogen and heated overnight at 140° C. The contents were cooled to RT and poured into water. The precipitate obtained was filtered, dried and purified by HPLC. $^1$H NMR (CD$_3$OD, freebase) δ (ppm): 8.58 (d, 2H), 7.70 (d, 2H), 7.35 (s, 1H), 7.30 (s, 1H), 7.05 (m, 2H), 3.95 (s, 2H), 3.10 (q, 2H), 2.95 (m, 4H), 2.42 (s, 3H), 2.00 (s, 3H), 1.30 (t, 3H).

Example 232

Preparation of (E)-8-ethyl-2-methyl-5-(2-(pyridin-4-yl)prop-1-enyl)-2,3,4,5-tetrahydro-1H-pyrido[4,3-b]indole (Compound 270)

8-Ethyl-2-methyl-2,3,4,4a,5,9b-hexahydro-1H-pyrido[4,3-b]indole (200 mg, 0.9345 mmol), potassium phosphate (396 mg, 1.8 mmol), copper (I) iodide (21 mg, 0.18 mmol), L-proline (17 mg, 0.09345 mmol) and 4-(1-bromoprop-1-en-2-yl)pyridine (277 mg, 1.40 mmol) were mixed in DMF and the reaction mixture was purged with nitrogen. The contents were cooled to RT and poured into water. The precipitate obtained was filtered, dried and purified by HPLC. $^1$H NMR (CD$_3$OD, TFA salt) δ (ppm): 8.58 (d, 2H), 7.70 (d, 2H), 7.36 (s, 1H), 7.22 (s, 1H), 7.05 (m, 2H), 3.75 (s, 2H), 2.95 (m, 2H), 2.85 (m, 2H), 2.70 (q, 2H), 2.38 (s, 3H), 2.00 (s, 3H), 1.25 (t, 3H).

Example 233

Preparation of (E)-8-tert-butyl-2-methyl-5-(2-(pyridin-4-yl)prop-1-enyl)-2,3,4,5-tetrahydro-1H-pyrido[4,3-b]indole (Compound 271)

8-tert-Butyl-2-methyl-2,3,4,5-tetrahydro-1H-pyrido[4,3-b]indole (123 mg, 0.5 mmol) was dissolved in DMF. Copper (I) iodide (9.5 mg, 0.05 mmol), L-proline (11.5 mg, 0.1 mmol) and potassium phosphate (212 mg, 1 mmol) were added and the reaction mixture was stirred for 10 min. at RT. 4-(1-Bromoprop-1-en-2-yl)pyridine (107.83 mg, 0.55 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh). The product was further purified by HPLC. Yield: 12 mg. $^1$H NMR (CD$_3$OD, freebase) δ (ppm): 8.60 (d, 2H), 7.70 (d, 2H), 7.42 (d, 1H), 7.36 (s, 1H), 7.30 (dd, 1H), 7.10 (d, 1H), 3.80 (m, 2H), 2.95 (m, 2H), 2.85 (m, 2H), 2.60 (s, 3H), 2.00 (s, 3H), 1.38 (s, 9H).

Example 234

Preparation of (E)-2-isopropyl-8-methyl-5-(2-(pyridin-4-yl)prop-1-enyl)-2,3,4,5-tetrahydro-1H-pyrido[4,3-b]indole (Compound 272)

2-Isopropyl-8-methyl-2,3,4,5-tetrahydro-1H-pyrido[4,3-b]indole (114 mg, 0.5 mmol), potassium phosphate (212 mg, 1 mmol), copper (I) iodide (9.5 mg, 0.05 mmol) and L-proline (11.5 mg, 0.1 mmol) were mixed in DMF and the contents were purged with nitrogen. 4-(1-Bromoprop-1-en-2-yl)pyridine (107.83 mg, 0.55 mmol) was added, the reaction mixture was purged with nitrogen and heated overnight at 140° C. The contents were purged with nitrogen and heated overnight at 140° C. The contents were cooled to RT and poured into water. The precipitate obtained was filtered, dried and purified by silica gel chromatography (100-200 mesh, neutralized with aqueous ammonia) eluting with 0-4% MeOH-DCM as eluent. The compound was further purified by HPLC. $^1$H NMR (DMSO-d6, oxalate salt) δ (ppm): 8.60 (d, 2H), 7.70 (d, 2H), 7.45 (s, 1H), 7.40 (s, 1H), 7.18 (d, 1H), 7.05 (d, 1H), 4.50 (m, 2H), 3.80 (m, 3H), 3.10 (m, 2H), 2.42 (s, 3H), 2.00 (s, 3H), 1.40 (d, 6H).

Example 235

Preparation of (E)-8-chloro-2,3-dimethyl-5-(2-(6-methylpyridin-3-yl)prop-1-enyl)-2,3,4,5-tetrahydro-1H-pyrido[4,3-b]indole (Compound 273)

8-Chloro-2,3-dimethyl-2,3,4,5-tetrahydro-1H-pyrido[4,3-b]indole (117 mg, 0.5 mmol) was dissolved in DMF. Copper (I) iodide (9.5 mg, 0.05 mmol), L-proline (11.5 mg, 0.1 mmol) and potassium phosphate (212 mg, 1 mmol) were added and the reaction mixture was stirred for 10 min. at RT. 5-(2-Bromo-1-methyl-vinyl)-2-methyl-pyridine (107.83 mg, 0.55 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-30% EtOAc-Hexane. The product was further purified by HPLC. $^1$H NMR (CDCl$_3$, TFA salt) δ (ppm): 9.0 (s, 1H), 8.10 (d, 1H), 7.50 (d, 1H), 7.40 (s, 1H), 7.22 (m, 1H), 7.08 (d, 1H), 7.0 (s, 1H), 4.70 (m, 1H), 4.18 (m, 1H), 4.05 (m, 1H), 3.30 (m, 1H), 2.90 (s, 3H), 2.80 (s, 3H), 2.70 (m, 1H), 2.0 (s, 3H), 1.50 (d, 3H).

Example 236

Preparation of (Z)-5-(2-(2,4-difluorophenyl)prop-1-enyl)-2,8-dimethyl-2,3,4,5-tetrahydro-1H-pyrido[4,3-b]indole (Compound 274)

2,8-Dimethyl-2,3,4,5-tetrahydro-1H-pyrido[4,3-b]indole (200 mg, 1 mmol) was dissolved in DMF. Copper (I) iodide (19 mg, 0.1 mmol) L-proline (23 mg, 0.2 mmol) and potassium phosphate (424 mg, 2 mmol) were added and the reaction mixture was stirred for 10 min. at RT. 1-(2-Bromo-1-methyl-vinyl)-2,4-difluoro-benzene (279 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-2% MeOH-DCM. The product was further purified by HPLC. Yield: 16 mg. $^1$H NMR (CDCl$_3$, freebase) δ (ppm): 7.10 (s, 1H), 7.0 (d, 1H), 6.90 (m, 2H), 6.70 (m, 2H), 6.58 (t, 1H), 3.60 (s, 2H), 2.65 (t, 2H), 2.50 (m, 5H), 2.40 (s, 3H), 2.22 (s, 3H).

Example 237

Preparation of (E)-8-chloro-2,3-dimethyl-5-(2-(pyridin-4-yl)prop-1-enyl)-2,3,4,5-tetrahydro-1H-pyrido[4,3-b]indole (Compound 275)

8-Chloro-2,3-dimethyl-2,3,4,5-tetrahydro-1H-pyrido[4,3-b]indole (117 mg, 0.5 mmol) and potassium phosphate (212 mg, 1 mmol) were mixed in DMF and the suspension was purged with nitrogen. The suspension was heated at 140° C. for 10 min. In a separate round bottomed flask, 4-(1-bromoprop-1-en-2-yl)pyridine (107.83 mg, 0.55 mmol), L-proline (11.5 mg, 0.1 mmol) and Copper (I) iodide (9.5 mg, 0.05 mmol) were mixed in DMF, the suspension was purged with nitrogen, and heated at 90° C. for 5 min. at which point it became a clear solution. The contents in the two reaction flasks were mixed and the reaction mixture was heated overnight at 90° C. The contents were cooled to RT and poured into water The precipitate obtained was filtered, dried and purified by silica gel chromatography (100-200 mesh, neutralized with aqueous ammonia) eluting with 0-10% MeOH-DCM as eluent. Compound was further purified by HPLC. $^1$H NMR (CD$_3$OD, freebase) δ (ppm): 8.60 (d, 2H), 7.70 (d, 2H), 7.45 (s, 1H), 7.30 (s, 1H), 7.10 (s, 2H), 4.05 (d, 1H), 3.80 (d, 1H), 3.10 (m, 1H), 2.95 (m, 1H), 2.65 (m, 1H), 2.60 (s, 3H), 2.0 (s, 3H), 1.30 (d, 3H).

Example 238

Preparation of (E)-5-(2-(2,4-difluorophenyl)prop-1-enyl)-2,8-dimethyl-2,3,4,5-tetrahydro-1H-pyrido[4,3-b]indole (Compound 276)

2,8-Dimethyl-2,3,4,5-tetrahydro-1H-pyrido[4,3-b]indole (200 mg, 1 mmol) was dissolved in DMF Copper (I) iodide (19 mg, 0.1 mmol) L-proline (23 mg, 0.2 mmol) and potassium phosphate (424 mg, 2 mmol) were added and the reaction mixture was stirred for 10 min. at RT. 1-(2-Bromo-1-methyl-vinyl)-2,4-difluoro-benzene (279 mg, 1.2 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-2% MeOH-DCM. The product was further purified by HPLC. Yield: 14 mg. $^1$H NMR (CDCl$_3$, freebase) δ (ppm): 7.40 (m, 1H), 7.22 (s, 1H), 7.10 (d, 1H), 7.0 (d, 1H), 6.90 (m, 2H), 6.70 (s, 1H), 3.70 (s, 2H), 2.85 (m, 4H), 2.60 (s, 3H), 2.45 (s, 3H), 1.95 (s, 3H).

Example 239

Preparation of (E)-8-chloro-5-(2-(2,4-difluorophenyl)prop-1-enyl)-2-methyl-2,3,4,5-tetrahydro-1H-pyrido[4,3-b]indole (Compound 277)

8-Chloro-2-methyl-2,3,4,5-tetrahydro-1H-pyrido[4,3-b]indole (220 mg, 1 mmol) was dissolved in DMF. Copper (I) iodide (19 mg, 0.1 mmol), L-proline (23 mg, 0.2 mmol) and potassium phosphate (424 mg, 2 mmol) were added and the reaction mixture was stirred for 10 min. at RT. 1-(2-Bromo-1-methyl-vinyl)-2,4-difluoro-benzene (279 mg, 1.2 mmol) was added dropwise and the reaction mixture was purged with nitrogen. The reaction mixture was heated at 85° C. (prolonged heating in some cases was required). DMF was evaporated under reduced pressure, the residue was diluted with water and the solid was filtered. The solid material was purified by silica gel chromatography (100-200 mesh) eluting with 0-2% MeOH-DCM. The product was further purified by HPLC. Yield: 12 mg. $^1$H NMR (CD$_3$OD, freebase) δ (ppm): 7.58 (m, 2H), 7.40 (s, 1H), 7.14 (s, 1H), 7.12 (d, 1H), 7.05 (m, 2H), 3.70 (s, 2H), 2.95 (m, 2H), 2.85 (m, 2H), 2.40 (s, 3H), 1.82 (s, 3H).

Example 240

Preparation of (E)-2,8-dimethyl-5-(2-(pyridin-2-yl)prop-1-enyl)-2,3,4,5-tetrahydro-1H-pyrido[4,3-b]indole (Compound 278)

2,8-Dimethyl-2,3,4,5-tetrahydro-1H-pyrido[4,3-b]indole (700 mg, 3.5 mmol) was dissolved in DMF. Copper (I) iodide, L-proline (0.116 g, 0.7 mmol) and potassium phosphate (1.484 g, 7 mmol) were added and the reaction mixture was stirred for 10 min. at RT. 2-(1-Bromoprop-1-en-2-yl)pyridine (1.03 g, 5.25 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh). $^1$H NMR (CDCl$_3$, HCl salt) δ (ppm): 8.62 (d, 1H), 7.78 (t, 1H), 7.60 (s, 1H), 7.50 (d, 1H), 7.28 (m, 1H), 7.18 (s, 1H), 7.10 (d, 1H), 7.05 (d, 1H), 4.40 (s, 2H), 3.50 (m, 2H), 3.20 (m, 2H), 2.95 (s, 3H), 2.42 (s, 3H), 2.05 (s, 3H).

Example 241

Preparation of (E)-2,8-dimethyl-5-(2-(pyrimidin-4-yl)prop-1-enyl)-2,3,4,5-tetrahydro-1H-pyrido[4,3-b]indole (Compound 279)

To a solution of 1-(2,8-dimethyl-3,4-dihydro-1H-pyrido[4,3-b]indol-5(2H)-yl)-2-(pyrimidin-4-yl)propan-2-ol (100 mg, 0.29 mmol) in DCM (2 mL) was added a drop of DMF and the solution was cooled to 0° C. Thionyl chloride (0.1 mL) diluted in 1 mL DCM was added dropwise at 0° C. and the reaction was stirred at 0° C. 30 min. and at RT for additional 2.5 h. The solvent was removed under reduced pressure and the residue was basified with ice cold 1N aqueous NaOH. The aqueous lager was extracted with EtOAc and the organic layer was washed with water and brine, dried over sodium sulfate and concentrated. The residue was purified by HPLC to obtain the product as the TFA salt. $^1$H NMR (CDCl$_3$, TFA salt) δ (ppm): 9.20 (s, 1H), 8.80 (d, 1H), 8.0 (s, 1H), 7.50 (d, 1H), 7.20 (s, 1H), 7.10 (m, 2H), 4.80 (d, 1H), 4.18 (d, 1H), 3.80 (m, 1H), 3.36 (m, 2H), 3.05 (s, 3H), 2.90 (m, 1H), 2.42 (s, 3H), 2.05 (s, 3H).

Example 242

Preparation of (E)-5-(3,3-dimethyl-2-(pyridin-4-yl)but-1-enyl)-2,8-dimethyl-2,3,4,5-tetrahydro-1H-pyrido[4,3-b]indole (Compound 280)

2,3,4,5-Tetrahydro-2,8-dimethyl-1H-pyrido[4,3-b]indole (30 mg, 0.15 mmol) was dissolved in DMF. Copper (I) iodide, L-proline (4 mg, 0.03 mmol) and potassium phosphate (63 mg, 0.29 mmol) were added and the reaction mixture was stirred for 10 min. at RT. 4-(1-bromo-3,3-dimethylbut-1-en-2-yl)pyridine (43 mg, 0.18 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh) eluting with 0-7% MeOH-DCM. The product was further purified by HPLC. $^1$H NMR (CD$_3$OD, freebase) δ (ppm): 8.21 (d, 2H), 7.15 (m, 3H), 7.05 (s, 1H), 6.94 (d, 1H), 6.80 (s, 1H), 3.90 (s, 2H), 3.18 (t, 2H), 2.90 (t, 2H), 2.70 (s, 3H), 2.36 (s, 3H), 1.30 (s, 9H).

Example 243

Preparation of (Z)-2,8-dimethyl-5-(2-(pyridin-4-yl)but-1-enyl)-2,3,4,5-tetrahydro-1H-pyrido[4,3-b]indole (Compound 281)

1-(1,2,3,4-Tetrahydro-2,8-dimethylpyrido[4,3-b]indol-5-yl)-2-(pyridin-4-yl)butan-2-ol (0.5 g, 1.43 mmol) was dissolved in dry DCM (15 mL) and a drop of DMF was added. The solution was cooled to 0° C. and thionyl chloride (0.5 g, 4.29 mmol) diluted with dry DCM (2 mL) was added dropwise. Stirring was continued for 1 h at 0° C. and then at RT for 2 h. The solution was basified with saturated aqueous sodium bicarbonate and extracted with EtOAc (3×50 mL). The organic layer was dried over anhydrous sodium sulfate and concentrated under reduced pressure. The residue was purified by HPLC. $^1$H NMR (CDCl$_3$, freebase) δ (ppm): 8.36 (d, 2H), 7.16 (s, 1H), 7.0 (d, 1H), 6.90 (d, 1H), 6.85 (d, 2H), 6.75 (s, 1H), 3.70 (s, 2H), 2.78 (t, 2H), 2.65 (q, 2H), 2.50 (s, 3H), 2.42 (m, 2H), 2.40 (s, 3H), 1.18 (t, 3H).

Example 244

Preparation of (Z)-8-chloro-2-methyl-5-(2-(pyridin-4-yl)but-1-enyl)-2,3,4,5-tetrahydro-1H-pyrido[4,3-b]indole (Compound 282)

1-(8-Chloro-1,2,3,4-tetrahydro-2-methylpyrido[4,3-b]indol-5-yl)-2-(pyridin-4-yl)butan-2-ol (0.2 g, 0.542 mmol) was dissolved in dry DCM (10 mL) and a drop of DMF was added. The solution was cooled to 0° C. and thionyl chloride (0.1 mL, 1.6 mmol) diluted with dry DCM (2 mL) was added dropwise. Stirring was continued for 1 h at 0° C. and then at RT for 2 h. The solution was basified with saturated aqueous sodium bicarbonate and extracted with EtOAc (3×50 mL). The organic layer was dried over anhydrous sodium sulfate and concentrated under reduced pressure. The residue was purified by HPLC. $^1$H NMR (CDCl$_3$, freebase) δ (ppm): 8.36 (d, 2H), 7.30 (s, 1H), 6.98 (m, 2H), 6.82 (d, 2H), 6.70 (s, 1H), 3.60 (s, 2H), 2.70 (m, 4H), 2.50 (m, 5H), 1.20 (t, 3H).

Example 245

Preparation of (E)-2,8-dimethyl-5-(2-(pyridin-4-yl)but-1-enyl)-2,3,4,5-tetrahydro-1H-pyrido[4,3-b]indole (Compound 283)

1-(1,2,3,4-Tetrahydro-2,8-dimethylpyrido[4,3-b]indol-5-yl)-2-(pyridin-4-yl)butan-2-ol (0.5 g, 1.43 mmol) was dissolved in dry DCM (15 mL) and a drop of DMF was added. The solution was cooled to 0° C. and thionyl chloride (0.5 g, 4.29 mmol) diluted with dry DCM (2 mL) was added dropwise. Stirring was continued for 1 h at 0° C. and then at RT for 2 h. The solution was basified with saturated aqueous sodium bicarbonate and extracted with EtOAc (3×50 mL). The organic layer was dried over anhydrous sodium sulfate and concentrated under reduced pressure. The residue was purified by HPLC. $^1$H NMR (CDCl$_3$, freebase) δ (ppm): 8.65 (d, 2H), 7.40 (d, 2H), 7.20 (s, 1H), 7.10 (d, 1H), 7.0 (d, 1H), 6.80 (s, 1H), 3.70 (s, 2H), 2.90 (m, 2H), 2.80 (m, 2H), 2.60 (s, 3H), 2.45 (m, 5H), 0.9 (t, 3H).

Example 246

Preparation of (E)-8-chloro-2-methyl-5-(2-(pyridin-4-yl)but-1-enyl)-2,3,4,5-tetrahydro-1H-pyrido[4,3-b]indole (Compound 284)

1-(8-Chloro-1,2,3,4-tetrahydro-2-methylpyrido[4,3-b]indol-5-yl)-2-(pyridin-4-yl)butan-2-ol (0.2 g, 0.542 mmol) was dissolved in dry DCM (10 mL) and a drop of DMF was added. The solution was cooled to 0° C. and thionyl chloride (0.1 mL, 1.6 mmol) diluted with dry DCM (2 mL) was added dropwise. Stirring was continued for 1 h at 0° C. and then at RT for 2 h. The solution was basified with saturated aqueous sodium bicarbonate and extracted with EtOAc (3×50 mL). The organic layer was dried over anhydrous sodium sulfate and concentrated under reduced pressure. The residue was purified by HPLC. $^1$H NMR (CDCl$_3$, freebase) δ (ppm): 8.65 (d, 2H), 7.40 (m, 3H), 7.10 (m, 2H), 6.80 (s, 1H), 3.65 (s, 2H), 2.80 (m, 4H), 2.60 (s, 3H), 2.45 (m, 2H), 0.9 (t, 3H).

Example 247

Preparation of (E)-1,2,3,8-tetramethyl-5-(2-(pyridin-4-yl)prop-1-enyl)-2,3,4,5-tetrahydro-1H-pyrido[4,3-b]indole (Compound 285)

2,3,4,5-Tetrahydro-1,2,3,8-tetramethyl-1H-pyrido[4,3-b]indole (550 mg, 2 mmol) was dissolved in DMF. Copper (I) iodide L-proline (46 mg, 0.4 mmol) and potassium phosphate (848 mg, 4 mmol) were added and the reaction mixture was stirred for 10 min. at RT. 4-(1-bromo-3,3-dimethylbut-1-en-2-yl)pyridine (294 mg, 3.0 mmol) was added dropwise and the reaction mixture was purged with nitrogen. The reaction mixture was heated overnight at 85° C. (prolonged heating in some cases was required). DMF was evaporated under reduced pressure, the residue was diluted with water and the solid was filtered. The solid material was purified by silica gel chromatography (100-200 mesh). The product was further purified by HPLC. The free base was converted into oxalate salt by treatment of oxalic acid (1 equiv) in THF. Yield: 8 mg as the oxalate salt. $^1$H NMR (CD$_3$OD, freebase) δ (ppm): 8.60 (d, 2H), 7.70 (d, 2H), 7.35 (s, 1H), 7.30 (s, 1H), 7.10 (m, 2H), 4.50 (m, 1H), 4.0 (m, 1H), 3.10 (m, 1H), 2.90 (s, 3H), 2.80 (m, 1H), 2.42 (s, 3H), 2.0 (s, 3H), 1.76 (d, 3H), 1.50 (d, 3H).

Example 248

Preparation of (E)-2,8-dimethyl-5-(2-(pyrazin-2-yl) prop-1-enyl)-2,3,4,5-tetrahydro-1H-pyrido[4,3-b] indole (Compound 287)

To a solution of 1-(1,2,3,4-tetrahydro-2,8-dimethylpyrido [4,3-b]indol-5-yl)-2-(pyrazin-2-yl)propan-2-ol (336 mg, 1.0 mmol) in DCM (8 mL) was added at 0° C. a solution of thionyl chloride (594 mg, 5 mmol) in DCM (8 mL). The reaction mixture was stirred at RT for 30 min., volatiles were evaporated under reduced pressure and the residue was dissolved in N-methyl-2-pyrrolidone (4 mL). KOH (392 mg, 7.0 mmol) was added and the reaction mixture was stirred at RT for 5 min. and at 100° C. for 30 min. The reaction mixture was cooled to RT, diluted with water and extracted with EtOAc. The organic layer was dried over anhydrous sodium sulfate, concentrated under reduced pressure and the residue purified by HPLC. $^1$H NMR (CD$_3$OD, TFA salt) δ (ppm): 9.0 (d, 1H), 8.70 (s, 1H), 8.60 (d, 1H), 7.70 (s, 1H), 7.38 (s, 1H), 7.15 (m, 2H), 4.78 (d, 1H), 4.40 (d, 1H), 3.90 (m, 1H), 3.60 (m, 1H), 3.25 (m, 2H), 3.20 (s, 3H), 2.50 (s, 3H), 2.10 (s, 3H).

Example 249

Preparation of (E)-3-(8-methyl-5-(2-(pyridin-4-yl) prop-1-enyl)-3,4-dihydro-1H-pyrido[4,3-b]indol-2 (5H)-yl)propan-1-ol (Compound 288)

3-(3,4-Dihydro-8-methyl-1H-pyrido[4,3-b]indol-2(5H)-yl)propan-1-ol (500 mg, 2.04 mmol) was dissolved in DMF (10 mL) and to this solution were added potassium phosphate (865 mg, 4.08 mmol), copper(I) iodide (38.76 mg, 0.204 mmol) and L-proline (46.92 mg, 0.408 mmol). The reaction mixture was stirred for 10 min. and 4-(1-bromoprop-1-en-2-yl)pyridine (600 mg, 3.06 mmol) in DMF (2 mL) was added dropwise. The reaction mixture was purged with nitrogen and heated overnight at 85° C. (prolonged heating was required some cases). DMF was evaporated; the residue was diluted with water and filtered. The solid was purified by silica gel chromatography (100-200 mesh, neutralized by aq. ammonia) eluting with 0-10% MeOH-DCM. The compound was further purified by HPLC. $^1$H NMR (CD$_3$OD, di-HCl salt) δ (ppm): 8.70 (m, 2H), 7.98 (m, 2H), 7.56 (s, 1H), 7.38 (s, 1H), 7.10 (m, 2H), 4.40 (m, 1H), 4.0 (m, 1H), 3.78 (t, 2H), 3.60 (m, 1H), 3.50 (t, 2H), 3.40-3.20 (m, 3H), 2.42 (s, 3H), 2.15 (m, 2H), 2.10 (s, 3H).

Example 250

Preparation of (E)-8-chloro-2-methyl-5-(2-(pyrimidin-4-yl)prop-1-enyl)-2,3,4,5-tetrahydro-1H-pyrido [4,3-b]indole (Compound 289)

1-(8-Chloro-2-methyl-1,2,3,4-tetrahydro-pyrido[4,3-b] indol-5-yl)-2-pyrimidin-4-yl-propan-2-ol (200 mg, 0.56 mmol) was dissolved in DCM (5 mL), and a drop of DMF was added. The solution was cooled to 0° C. and a solution of thionyl chloride (0.2 mL) in 1 mL DCM was added dropwise. The solution was stirred at RT for 30 min. and at RT for 2.5 h. Volatiles were evaporated under reduced pressure, the residue was basified with ice cold aqueous 1N NaOH (10 mL) and the product was extracted with EtOAc. The combined organic layer was washed with water and brine, dried over sodium sulfate and concentrated under reduced pressure. The residue was purified by HPLC to obtain 14 mg of product as the TFA salt. $^1$H NMR (CD$_3$OD, TFA salt) δ (ppm): 9.18 (s, 1H), 8.80 (d, 1H), 8.0 (s, 1H), 7.80 (d, 1H), 7.58 (s, 1H), 7.25 (m, 2H), 4.75 (m, 1H), 4.40 (m, 1H), 3.90 (m, 1H), 3.60 (m, 1H), 3.20 (m, 2H), 3.10 (s, 3H), 2.05 (s, 3H).

Example 251

Preparation of 4-(2-isopropyloxiran-2-yl)pyridine (Compound 167)

Potassium tert-butoxide (0.098 g, 0.80 mmol) and trimethylsulfonium iodide (0.164 g, 0.8 mmol) were mixed at RT and stirred at 0° C. To this was added 2-methyl-1-(pyridin-4-yl)propan-1-one (0.100 g, 0.671 mmol) slowly. The reaction mixture was stirred at 0° C. for 15 min. and then warmed to and stirred at 70° C. for 1 h. The reaction mixture diluted with water and extracted with EtOAc (3 10 mL), organic layer dried on sodium sulfate and concentrated under vacuum to obtain 4-(2-isopropyloxiran-2-yl)pyridine (0.1 g). $^1$H NMR (CDCl$_3$, freebase) δ (ppm): 8.6 (d, 2H) 7.26 (d, 2H), 3.05 (d, 1H), 2.29 (septet, 1H), 2.26 (d, 1H), 1.65 (d, 6H).

Example 252

Preparation of 4-(2-ethyloxiran-2-yl)pyridine (Compound 168)

A mixture of potassium tert-butoxide (0.098 g, 0.80 mmol) and trimethylsulfonium iodide (0.164 g, 0.8 mmol) was stirred at 0° C. To this was added 2-methyl-1-(pyridin-4-yl)propan-1-one (0.100 g, 0.671 mmol) slowly. The reaction mixture was stirred at 0° C. for 15 min. and then warmed to and stirred at 70° C. for 1 h. The reaction mixture was diluted with water and extracted with EtOAc (3×10 mL), organic layer dried on sodium sulfate and concentrated under vacuum to obtain 4-(2-isopropyloxiran-2-yl)pyridine (0.1 g). $^1$H NMR (CDCl$_3$, freebase) δ (ppm): 8.19 (d, 2H), 7.26 (d, 2H), 3.05 (d, 1H), 2.71 (d, 1H), 2.28 (m, 1H), 1.80 (m, 1H), 0.97 (t, 3H).

Example 253

Preparation of 4-(2-methyloxiran-2-yl)pyridine (Compound 169)

Trimethylsulfonium iodide (43.8 g, 210 mmol) was dissolved in 100 mL DMF and NaH (19.8 g, 495 mmol) was added. The reaction mixture was stirred for 5 min. and a solution of 4-acetylpyridine (20 g, 165 mmol) in 20 mL DMSO was added dropwise at RT. After the addition was complete, reaction mixture was stirred at RT for 2 h after which it was poured into ice water. The product was extracted with EtOAc, organic layer was washed with water, dried over sodium sulfate and concentrated under reduced pressure. Yield: 21 g.

Example 253A

A solution of potassium tert-butoxide (2.22 g, 19.83 mmol) in dry THF (20 ml) was stirred at 0° C. for 10 min (ice-ethanol bath). Trimethylsulfonium iodide (4.045 g, 19.83 mmoL) was added portionwise at 0° C. within 15 min. The reaction mixture was stirred at 0° C. for 30 min. 4-acetyl pyridine (2 g, 16.52 mmol) was added dropwise at 0° C. within 15 min. The reaction mixture stirred at 0° C. for 30 min and at RT for 3-4 h. Gradual conversion of reactant into product is seen during this time as monitored by NMR (TLC stained with KMnO₄ solution was also indicative of the reaction progress). The reaction mixture was diluted with DCM, filtered through Celite, and the filtrate concentrated under reduced pressure (water bath temp 35° C., pressure 20 mbar) to obtain product (2.1 g dark red oil that was pure by NMR). Ice water was added and the product was partitioned with DCM, the organic layer separated, dried over sodium sulfate and concentrated under reduced pressure. Yield 1.6 g light yellow oil. $^1$H NMR (CDCl₃, freebase) δ (ppm): 8.55 (d, 2H), 7.3 (d, 2H), 3.05 (d, 1H), 2.85 (d, 1H), 1.75 (s, 3H).

Example 254

Preparation of 4-(2-methyloxiran-2-yl)pyrimidine Compound (170)

Trimethylsulfonium iodide (3.34 g, 16.3 mmol) was dissolved in DMF (20 mL) and stirred at RT for 5 min. Sodium hydride (600 mg, 25 mmol) was added portionwise at the same temperature and stirred for 15 min. 4-Acetyl pyrimidine (1 g, 8.1 mmol) in 0.5 mL DMSO was added dropwise and the reaction mixture stirred for 1 h. After completion of reaction, the mixture was poured into ice-cold water and extracted with Ether (3×). The combined organic layer was washed with water several times followed by brine, and dried over sodium sulfate, then evaporated to provide 600 mg of 4-(2-Methyl-oxiranyl)-pyrimidine. $^1$H NMR (CDCl₃, freebase) δ (ppm): 9.15 (s, 1H), 8.7 (d, 1H), 7.35 (d, 1H), 2.95 (d, 1H), 2.88 (d, 1H), 1.8 (s, 3H).

Example 255

Preparation of (E)-8-methyl-5-(2-(pyridin-4-yl)prop-1-enyl)-2-(2,2,2-trifluoroethyl)-2,3,4,5-tetrahydro-1H-pyrido[4,3-b]indole (Compound 291)

1-(2-(2,2,2-Trifluoroethyl)-1,2,3,4-tetrahydro-8-methyl-pyrido[4,3-b]indol-5-yl)-2-(pyridin-4-yl)propan-2-ol (200 mg, 0.4 mmol) was dissolved in thionyl chloride (2 mL), and stirred for 2 h at RT. The reaction mixture was concentrated under reduced pressure; the residue was cooled in ice water and basified with saturated aqueous NaHCO₃. The product was extracted with EtOAc and organic layer was washed with water, dried over anhydrous sodium sulfate and concentrated under reduced pressure. The residue was purified by HPLC. Yield: 195 mg. $^1$H NMR (CD₃OD, TFA salt) δ (ppm): 8.70 (d, 2H), 8.10 (d, 2H), 7.70 (s, 1H), 7.22 (s, 1H), 7.05 (m, 2H), 3.95 (s, 2H), 3.40 (m, 2H), 3.10 (m, 2H), 2.82 (m, 2H), 2.42 (s, 3H), 2.12 (s, 3H).

Example 256

Preparation of (E)-2-cyclopropyl-8-methyl-5-(2-(pyridin-4-yl)prop-1-enyl)-2,3,4,5-tetrahydro-1H-pyrido[4,3-b]indole (Compound 292)

1-(2-Cyclopropyl-1,2,3,4-tetrahydro-8-methylpyrido[4,3-b]indol-5-yl)-2-(pyridin-4-yl)propan-2-ol (100 mg, 0.27 mmol) was dissolved in thionyl chloride (1 mL), and stirred for 1-2 h at RT. The reaction mixture was concentrated under reduced pressure; the residue was cooled in ice water and basified with saturated aqueous NaHCO₃. The product was extracted with EtOAc and organic layer was washed with water, dried over anhydrous sodium sulfate and concentrated under reduced pressure. The residue was purified by HPLC. Yield: 100 mg. $^1$H NMR (CD₃OD, TFA salt) δ (ppm): 8.80 (d, 2H), 8.30 (d, 2H), 7.78 (s, 1H), 7.38 (s, 1H), 7.18 (m, 2H), 4.70 (m, 2H), 3.90 (m, 2H), 3.22 (m, 2H), 3.15 (m, 1H), 2.45 (s, 3H), 2.16 (s, 3H), 1.20 (m, 2H), 1.10 (m, 2H).

Example 257

Preparation of (E)-2,8-dimethyl-5-(2-(pyrimidin-5-yl)prop-1-enyl)-2,3,4,5-tetrahydro-1H-pyrido[4,3-b]indole (Compound 293)

2,3,4,5-Tetrahydro-2,8-dimethyl-1H-pyrido[4,3-b]indole (100 mg, 0.5 mmol) was dissolved in DMF (3 mL), potassium phosphate (212 mg, 1 mmol), copper(I) iodide (9 mg, 0.05 mmol) and L-proline (11 mg, 0.1 mmol) was added. 5-(1-Bromoprop-1-en-2-yl)pyrimidine (98 mg, 0.5 mmol) was dissolved in DMF (2 mL) and added dropwise. Nitrogen was purged for 2 min. and the reaction mixture was heated at 85° C. overnight (prolonged heating was required in some cases). DMF was evaporated under reduced pressure and water was added to the residue obtained. Compound was extracted with EtOAc (3×25 mL), the organic layer was washed with water (3×25 mL), dried over anhydrous sodium sulfate and concentrated under reduced pressure. The residue was purified by HPLC. Yield: 7 mg as the TFA salt. $^1$H NMR (CD₃OD, TFA salt) δ (ppm): 9.18 (s, 1H), 9.08 (s, 2H), 7.35 (s, 1H), 7.24 (s, 1H), 7.18 (d, 1H), 7.10 (d, 1H), 4.78 (m, 1H), 4.40 (m, 1H), 3.85 (m, 1H), 3.60 (m, 1H), 3.20 (m, 2H), 3.10 (s, 3H), 2.42 (s, 3H), 2.05 (s, 3H).

Example 258

Preparation of (E)-2,8-dimethyl-5-(2-(thiophen-2-yl)prop-1-enyl)-2,3,4,5-tetrahydro-1H-pyrido[4,3-b]indole (Compound 294)

2,3,4,5-Tetrahydro-2,8-dimethyl-1H-pyrido[4,3-b]indole (50 mg, 0.25 mmol) was dissolved in DMF (3 mL), potassium phosphate (106 mg, 0.5 mmol), copper (I) iodide (4.75 mg, 0.025 mmol) and L-proline (5.75 mg, 0.05 mmol) were added. 2-(1-Bromoprop-1-en-2-yl)thiophene (55 mg, 0.275 mmol) was dissolved in DMF (2 mL) and added dropwise to the reaction mixture. The reaction mixture was purged with nitrogen for 2 min. and heated at 85° C. overnight. DMF was evaporated under reduced pressure and water was added to the residue. The product was extracted with EtOAc (3×25 mL), the organic layer was washed with water (3×25 mL), dried over anhydrous sodium sulfate and concentrated under reduced pressure. The residue was purified by HPLC. Yield: 0.4 mg as the TFA salt. $^1$H NMR (CDCl₃, TFA salt) δ (ppm): 7.30-7.20 (m, 3H), 7.10 (m, 3H), 7.0 (s, 1H), 4.78 (m, 1H), 4.15 (m, 1H), 3.82 (m, 1H), 3.30 (m, 2H), 3.05 (s, 3H), 2.90 (m, 1H), 2.42 (s, 3H), 1.98 (s, 3H).

Example 259

Preparation of 1-cyclohexyl-2-(2,8-dimethyl-3,4-dihydro-1H-pyrido[4,3-b]indol-5(2H)-yl)-1-(4-fluorophenyl)ethanol (Compound No. 171)

Activated magnesium turnings (480 mg, 20 g/atom) and 2-3 crystals of iodine were stirred under anhydrous conditions. The excess of iodine was removed by heating with a heat gun. The magnesium turnings were now yellow in color. To this was added diethyl ether (15 mL) at 0° C. and stirred for 15 min. (until the color of the magnesium becomes white). To this was added cyclohexyl bromide (2.5 mL, 20 mmol) dropwise with constant stirring. The reaction mixture was stirred until a dark grey-colored solution was obtained. Into a separate flask was placed 2-(2,8-dimethyl-3,4-dihydro-1H-pyrido[4,3-b]indol-5(2H)-yl)-1-(4-fluorophenyl)ethanone (168 mg, 5 mmol) in THF under anhydrous conditions. The solution of the prepared cyclohexylmagnesium bromide (5 mL) was added dropwise. After addition, the mixture was allowed to come to RT and stirred at RT for 2 h. The reaction was monitored by TLC and NMR. The reaction was quenched with ice water and the product extracted into EtOAc. The organic extracts were concentrated and the residue purified by silica gel column chromatography (#100-200 mesh) using 0-3% MeOH:DCM as eluent. The compound was further purified by HPLC. $^1$H NMR (CD$_3$OD, TFA salt) δ (ppm): 7.25 (m, 2H), 7.10 (d, 1H), 6.92 (m, 1H), 6.80 (m, 3H), 4.60 (m, 1H), 4.65 (m, 1H), 4.22 (m, 2H), 3.70 (m, 1H), 3.40 (m, 1H), 3.20 (m, 2H), 3.0 (s, 3H), 2.70 (m, 1H), 2.38 (s, 3H), 2.20 (m, 2H), 1.80 (m, 2H), 1.70 (m, 3H), 1.50-1.20 (m, 4H).

Example 260

Preparation of 2-(2,8-dimethyl-3,4-dihydro-1H-pyrido[4,3-b]indol-5(2H)-yl)-1-(4-fluorophenyl)ethanol (Compound No. 172)

Activated magnesium turnings (480 mg, 20 g/atom) and 2-3 crystals of iodine were stirred under anhydrous conditions. The excess of iodine was removed by heating with a heat gun. The magnesium turnings were now yellow in color. To this was added diethyl ether (15 mL) at 0° C. and stirred for 15 min. (until the color of the magnesium becomes white). To this was added cyclopentyl bromide (480 mg, 20 g/atom) dropwise with constant stirring. The reaction mixture was stirred until a dark grey-colored solution was obtained. Into a separate flask was placed the starting material (168 mg, 5 mmol) in THF under anhydrous conditions. The solution of the prepared cyclopentylmagnesium bromide (5 mL) was added dropwise. After addition, the mixture was allowed to come to RT and stirred at RT for 2 h. The reaction was monitored by TLC and NMR. The reaction was quenched with ice water and the product extracted into EtOAc. The organic extracts were concentrated and the residue purified by silica gel column chromatography (#100-200 mesh) using 0-3% MeOH:DCM as eluent. (Note: Desired compound not formed but reduction of keto group occurs). $^1$H NMR (DMSO-d6, oxalate salt) δ (ppm): 7.55 (m, 3H), 7.18 (m, 3H), 6.95 (d, 1H), 4.85 (s, 1H), 4.30 (m, 2H), 4.15 (m, 2H), 3.60 (m, 2H), 3.10 (m, 3H), 2.90 (s, 3H), 2.40 (s, 3H).

Example 261

Preparation of 1-(2,8-dimethyl-3,4-dihydro-1H-pyrido[4,3-b]indol-5(2H)-yl)-2-(3-fluoro-4-methoxyphenyl)propan-2-ol (Compound No. 173)

A flask was charged with sodium hydride 60% (461 mg, 1.15 mmol) in DMF and stirred at RT for 10 min. The carboline (0.76 g, 3.8 mmol) was added and the mixture stirred at RT for 1 h. 2-(3-Fluoro-4-methoxyphenyl)-2-methyloxirane (1 g, 5.4 mmol) was added and the mixture stirred at RT overnight. Ice water was added and the mixture extracted with EtOAc (3×). The combined organic layers were washed with water (4×) and concentrated, followed by purification of the product on silica gel (#100-200 mesh) using 0-5% MeOH:DCM as eluent. $^1$H NMR (DMSO-d6, oxalate salt) δ (ppm): 7.30 (m, 3H), 7.18 (s, 1H), 7.10 (d, 1H), 6.90 (d, 1H), 4.30 (m, 2H), 4.18 (d, 1H), 4.05 (d, 1H), 3.80 (s, 3H), 3.60 (m, 2H), 3.0 (m, 2H), 2.80 (s, 3H), 2.35 (s, 3H), 1.70 (m, 1H), 1.40 (s, 3H).

Example 262

Preparation of 1-(2,8-dimethyl-3,4-dihydro-1H-pyrido[4,3-b]indol-5(2H)-yl)-2-(4-methoxyphenyl)propan-2-ol (Compound No. 174)

A flask was charged with sodium hydride 60% (0.803 mg, 20.12 mmol) in DMF and stirred at RT for 10 min. The carboline (1.28 g, 6.4 mmol) was added and the mixture stirred at RT for 1 h. 2-(4-Methoxyphenyl)-2-methyloxirane (1.5 g, 9.14 mmol) was added and the mixture stirred at RT overnight. Ice water was added and the mixture extracted with EtOAc (3×). The combined organic layers were washed with water (4×) and concentrated, followed by purification of the product on silica gel (#100-200 mesh) using 0-5% MeOH:DCM as eluent. $^1$H NMR (DMSO-d6, oxalate salt) δ (ppm): 7.40 (d, 2H), 7.35 (m, 1H), 7.18 (d, 1H), 6.90 (m, 3H), 4.30 (m, 1H), 4.20 (d, 1H), 4.0 (m, 1H), 3.80 (s, 3H), 3.60 (m, 2H), 3.0 (m, 4H), 2.90 (s, 3H), 2.38 (s, 3H), 1.40 (d, 3H).

Example 263

Preparation of 1-(2,8-dimethyl-3,4-dihydro-1H-pyrido[4,3-b]indol-5(2H)-yl)-2-(4-fluorophenyl)butan-2-ol (Compound No. 175)

2-(2,8-Dimethyl-3,4-dihydro-1H-pyrido[4,3-b]indol-5(2H)-yl)-1-(4-fluorophenyl)ethanone (168 mg, 5 mmol) was dissolved in 10 mL anhydrous THF. Ethyl magnesium bromide (1.5 mL, 0.0015 mol) was then added dropwise at RT under nitrogen. The reaction mixture was stirred at RT for 2 h. The reaction was monitored by LCMS. On completion of the reaction, water (3 mL) was added to the reaction mixture and the product extracted with EtOAc (3×). The combined organic layers were washed with water, dried over sodium sulfate, and the solvent evaporated under reduced pressure to obtain the crude product, which was purified by HPLC. The pure compound was isolated as the TFA salt. $^1$H NMR (CD$_3$OD, TFA salt) δ (ppm): 7.38 (m, 2H), 7.18 (d, 1H), 7.10 (m, 1H), 7.0 (m, 2H), 6.85 (d, 1H), 4.60 (m, 1H), 4.30 (m, 2H), 3.75 (m, 1H), 3.42 (m, 1H), 3.10 (s, 3H), 2.90 (m, 2H), 2.42 (d, 1H), 2.38 (s, 3H), 2.20 (m, 1H), 1.80 (m, 2H), 0.8 (t, 3H).

Example 264

Preparation of 2-(8-chloro-2-methyl-3,4-dihydro-1H-pyrido[4,3-b]indol-5(2H)-yl)-1-cyclobutyl-1-(4-fluorophenyl)ethanol (Compound No. 177)

8-Chloro-2,3,4,5-tetrahydro-2-methyl-1H-pyrido[4,3-b]indole (1.5 g, 6 mmol) was dissolved in DMF (15 mL) and stirred for 5 min. Sodium hydride (720 mg, 10 mmol) was then added portionwise under nitrogen. This was followed by addition of 2-cyclobutyl-2-(4-fluorophenyl)oxirane (1.906 g, 18 mmol) at RT, and the reaction mixture was stirred for 18 h. After completion of reaction, the reaction mixture was poured into ice water and the product extracted with EtOAc. The organic layer was washed with water, dried over sodium sulfate and concentrated under reduced pressure to give the crude product which was purified by silica gel (#100-200 mesh) column chromatography using 1% MeOH in DCM as eluent. The pure compound was converted into the oxalate salt. $^1$H NMR (CDCl$_3$, oxalate salt) δ (ppm): 7.30 (d, 1H), 7.20 (m, 2H), 6.95 (m, 4H), 4.20 (m, 1H), 4.0 (m, 1H), 3.80 (m, 2H), 3.10 (m, 1H), 2.70 (m, 4H), 2.50 (s, 3H), 2.20 (m, 2H), 2.0 (d, 1H), 1.80 (t, 2H), 1.70 (m, 1H).

Example 265

Preparation of 1-(8-chloro-2-methyl-3,4-dihydro-1H-pyrido[4,3-b]indol-5(2H)-yl)-2-(4-fluorophenyl)hexan-2-ol (Compound No. 178)

8-Chloro-2,3,4,5-tetrahydro-2-methyl-1H-pyrido[4,3-b]indole (1.3 g, 5 mmol) was dissolved in DMF (10 mL) and stirred for 5 min. Sodium hydride (709 mg, 17.7 mmol) was then added portionwise under nitrogen. This was followed by addition of 2-butyl-2-(4-fluorophenyl)oxirane (3.4 g, 17.7 mmol) at RT and the reaction mixture was stirred for 18 h. After completion of reaction, the reaction mixture was poured into ice water and the product extracted with EtOAc. The organic layer was washed with water, dried over sodium sulfate and concentrated under reduced pressure to give the crude product which was purified by silica gel (#100-200 mesh) column chromatography using 1% MeOH in DCM as eluent. The pure compound was converted into the oxalate salt. $^1$H NMR (CDCl$_3$, oxalate salt) δ (ppm): 7.30 (m, 3H), 7.10 (d, 1H), 6.95 (m, 3H), 4.20 (m, 1H), 4.0 (m, 1H), 3.62 (m, 2H), 2.70 (m, 3H), 2.50 (s, 3H), 2.20 (m, 1H), 2.0 (m, 1H), 1.80 (m, 1H), 1.22 (m, 3H), 1.0 (m, 1H), 0.80 (t, 3H).

Example 266

Preparation of 2-(2,8-dimethyl-3,4-dihydro-1H-pyrido[4,3-b]indol-5(2H)-yl)-1-(pyridin-4-yl)ethanol (Compound No. 180)

Sodium hydride (2.4 g, 100 mmol) was washed with hexane and dried under vacuum. To this was added DMF (15 mL) and cooled to 0° C. Then to this was added 2,8-dimethyl-2,3,4,5-tetrahydro-1 h-pyrido[4,3-b]indole (4 g, 20 mmol) and the mixture stirred at 0° C. for 30 min. Then 4-oxirannyl-pyridine (2.90 g, 23.96 mmol) was dissolved in 5 mL DMF and added dropwise to the mixture, which was then left stirred at RT overnight. The reaction was monitored by TLC. The reaction mixture was poured into ice water and extracted with EtOAc (3×). The combined organic layer was washed with water, dried over anhydrous sodium sulfate and concentrated. The resultant solid material was washed with hexane and crystallized from EtOH and ether. $^1$H NMR (DMSO-d6, HCl salt) δ (ppm): 8.70 (d, 2H), 7.70 (d, 2H), 7.38 (m, 1H), 7.20 (s, 1H), 6.90 (d, 1H), 5.05 (m, 1H), 4.58 (m, 1H), 4.30 (m, 1H), 4.20 (m, 2H), 3.70 (m, 2H), 3.20 (m, 4H), 2.90 (s, 1H), 2.38 (s, 3H).

Example 267

Preparation of 1-(8-fluoro-2-methyl-3,4-dihydro-1H-pyrido[4,3-b]indol-5(2H)-yl)-2-(pyridin-4-yl)propan-2-ol (Compound No. 181)

A flask was charged with 6-fluoro-2-methyl-2,3,4,5-tetrahydro-1H-pyrido[4,3-b]indole (1.9 g, 4.5 mmol) in DMF (20 mL) and stirred for 5 min. To this was added NaH (60% in hexane) (1.16 g, 27.9 mmol) and stirred at RT for 10 min., followed by 4-(2-methyloxiran-2-yl)pyridine (2.5 g, 18.6 mmol) and stirred at RT for 16 h. The progress of reaction was monitored by TLC. The mixture was poured into ice water and filtered. The filtrate was washed with water and concentrated. The residue was recrystallized from ether to get pure product. $^1$H NMR (DMSO-d6, HCl salt) δ (ppm): 8.78 (d, 2H), 8.0 (d, 2H), 7.40 (s, 1H), 7.20 (d, 1H), 6.80 (m, 1H), 6.10 (m, 1H), 4.50 (m, 1H), 4.30 (m, 2H), 4.20 (m, 1H), 3.70 (m, 2H), 3.20 (m, 2H), 2.90 (s, 3H), 1.60 (s, 3H).

Example 268

Preparation of 1-(6-chloro-2-methyl-3,4-dihydro-1H-pyrido[4,3-b]indol-5(2H)-yl)-2-(pyridin-4-yl)propan-2-ol (Compound No. 182)

A flask was charged with 6-chloro-2-methyl-2,3,4,5-tetrahydro-1H-pyrido[4,3-b]indole (1.0 g, 4.5 mmol) in DMF (10 mL) and stirred for 5 min. To this was added NaH (60% in hexane) (220 mg, 6.8 mmol) and stirred at RT for 10 min., followed by 4-(2-methyloxiran-2-yl)pyridine (1.08 g, 9 mmol) and stirred at RT for 16 h. The progress of reaction was monitored by TLC. The mixture was poured into ice water and filtered. The filtrate was washed with water and concentrated. The residue was recrystallized from ether to get pure product. $^1$H NMR (DMSO-d6, HCl salt) δ (ppm): 8.70 (d, 2H), 7.90 (d, 2H), 7.40 (m, 1H), 7.0 (m, 2H), 6.0 (m, 1H), 4.80 (m, 1H), 4.60 (m, 2H), 4.25 (m, 2H), 3.80 (m, 2H), 2.90 (s, 3H), 1.60 (s, 3H).

Example 269

Preparation of 2-(8-chloro-2-methyl-3,4-dihydro-1H-pyrido[4,3-b]indol-5(2H)-yl)-1-(pyridin-4-yl)ethanol (Compound No. 183)

Sodium hydride (2.72 g, 113.33 mmol) was washed with hexane and dried under vacuum. To this was added DMF (15 mL) and the mixture cooled to 0° C. 8-Chloro-2-methyl-2,3,4,5-tetrahydro-1H-pyrido[4,3-b]indole (5 g, 22.72 mmol) was added and the mixture stirred at 0° C. for 30 min., followed by 4-oxirannyl-pyridine (3.3 g, 27.27 mmol) dissolved in 5 mL DMF added dropwise. The reaction mixture was stirred at RT overnight. The reaction was monitored by TLC. The reaction mixture was poured into ice water and the product extracted into EtOAc (3×). The combined organic layers were washed with water, dried over anhydrous sodium sulfate and concentrated. The resultant solid material was washed with hexane and crystallized from EtOH and ether. $^1$H NMR (CD$_3$OD, HCl salt) δ (ppm): 8.80 (d, 2H), 8.18 (d, 2H), 7.50 (s, 1H), 7.30 (m, 1H), 7.10 (d, 1H), 5.30 (m, 1H), 4.70 (m, 1H), 4.50 (m, 1H), 4.40 (m, 2H), 3.90 (m, 1H), 3.60 (m, 2H), 3.40 (m, 2H), 3.10 (s, 3H).

Example 270

Preparation of 1-(7-chloro-2-methyl-3,4-dihydro-1H-pyrido[4,3-b]indol-5(2H)-yl)-2-(pyridin-4-yl)propan-2-ol (Compound No. 184)

A flask was charged with 7-chloro-2-methyl-2,3,4,5-tetrahydro-1H-pyrido[4,3-b]indole (1.2 g, 5.0 mmol) in DMF (10 mL) and stirred for 5 min. NaH (60% in hexane) (654 mg, 16 mmol) was added and the mixture stirred at RT for 10 min. Then 4-(2-methyloxiran-2-yl)pyridine (1.35 g, 10 mmol) was added and the mixture stirred at RT for 16 h. The progress of reaction was monitored by TLC. The reaction mixture was poured into ice water and filtered. The filtrate was washed with water and concentrated. The residue was recrystallized from ether to get pure product. $^1$H NMR (DMSO-d6, HCl salt) δ (ppm): 8.70 (d, 2H), 7.95 (d, 2H), 7.50 (m, 1H), 7.40 (m, 1H), 7.0 (t, 1H), 6.10 (m, 1H), 4.60 (m, 1H), 4.42-4.20 (m, 3H), 3.30 (m, 3H), 2.90 (s, 3H), 1.60 (d, 3H).

Example 271

Preparation of 1-(6-fluoro-2-methyl-3,4-dihydro-1H-pyrido[4,3-b]indol-5(2H)-yl)-2-(pyridin-4-yl)propan-2-ol (Compound No. 185)

A flask was charged with 6-fluoro-2-methyl-2,3,4,5-tetrahydro-1H-pyrido[4,3-b]indole (1.2 g, 5.8 mmol) in DMF (10 mL) and stirred for 5 min. NaH (60% in hexane) (705 mg, 17.6 mmol) was added and the mixture stirred at RT for 10 min. Then 4-(2-methyloxiran-2-yl)pyridine (1.56 g, 11.6 mmol) was added and the mixture stirred at RT for 16 h. The progress of reaction was monitored by TLC. The reaction mixture was poured into ice water and filtered. The filtrate was washed with water and concentrated. The residue was recrystallized from ether to get pure product. $^1$H NMR (DMSO-d6, HCl salt) δ (ppm): 8.70 (d, 2H), 8.0 (d, 2H), 7.40 (m, 1H), 7.20 (d, 1H), 6.85 (m, 1H), 6.10 (m, 1H), 4.58 (d, 1H), 4.38 (m, 2H), 4.22 (m, 1H), 3.20 (m, 3H), 2.90 (s, 3H), 1.60 (d, 3H).

Example 272

Preparation of 1-(2-methyl-3,4-dihydro-1H-pyrido[4,3-b]indol-5(2H)-yl)-2-(pyridin-4-yl)propan-2-ol (Compound No. 186)

2-methyl-2,3,4,5-tetrahydro-1H-pyrido[4,3-b]indole (740 mg, 3.9 mmol) was dissolved in DMF and the mixture stirred for 5 min. NaH (60% in oil) (468 mg, 11.7 mmol) was added and the mixture stirred for 10 min., followed by 4-(oxiran-2-yl)pyridine (1.0 g, 7.9 mmol) and the mixture stirred at RT for 3 h. The progress of reaction was monitored by TLC. The reaction mixture was poured into ice water and filtered. The filtrate was washed with water and concentrated. The residue was recrystallized from ether to get pure product. $^1$H NMR (CD$_3$OD, HCl salt) δ (ppm): 8.70 (d, 2H), 8.20 (d, 2H), 7.40 (m, 1H), 7.10 (m, 1H), 7.0 (m, 2H), 4.70 (d, 1H), 4.45 (m, 2H), 4.38 (m, 1H), 3.90 (m, 1H), 3.45 (m, 2H), 3.40 (m, 1H), 3.10 (s, 3H), 1.70 (d, 3H).

Example 273

Preparation of 4-(1-(2,8-dimethyl-3,4-dihydro-1H-pyrido[4,3-b]indol-5(2H)-yl)-2-hydroxypropan-2-yl)phenol (Compound No. 187)

To a stirred solution of 1-(1,2,3,4-tetrahydro-2,8-dimethylpyrido[4,3-b]indol-5-yl)-2-(4-methoxyphenyl)propan-2-ol (0.145 g, 0.39 mmol) in DCM (10 mL) at −78° C. was added borontribromide (0.293 g in 5 mL DCM). The reaction mixture was stirred at −78° C. for 30 min. and then at 25° C. for 1 h. The solution was poured into ice water, saturated NaHCO$_3$ was added, and the mixture extracted with EtOAc. The organic layer was dried over anhydrous sodium sulfate, and the solvent was removed under reduced pressure. The crude product was purified by column chromatography (silica gel, 0-75% MeOH:DCM) to give the product as an off white solid, 20 mg. $^1$H NMR (CDCl$_3$, freebase) δ (ppm): 7.25 (d, 1H), 7.10 (m, 3H), 6.98 (d, 1H), 6.70 (d, 2H), 4.10 (m, 2H), 3.82 (m, 2H), 2.80 (m, 2H), 2.60 (s, 3H), 2.42 (s, 3H), 2.38 (m, 2H), 1.60 (s, 3H).

Example 274

Preparation of 1-(8-methoxy-2-methyl-3,4-dihydro-1H-pyrido[4,3-b]indol-5(2H)-yl)-2-(pyridin-4-yl)propan-2-ol (Compound No. 188)

A flask was charged with 8-methoxy-2-methyl-2,3,4,5-tetrahydro-1H-pyrido[4,3-b]indole (1.5 g, 6.9 mmol) in DMF (15 mL) and stirred for 5 min. To this was added NaH (60% in hexane) (828 mg, 20 mmol) and the mixture stirred at RT for 10 min. 4-(2-Methyloxiran-2-yl)pyridine (1.89 g, 13.8 mmol) was added and the mixture stirred at RT for 16 h. The progress of reaction was monitored by TLC. The reaction mixture was poured into ice water and filtered. The filtrate was washed with water and concentrated. The residue was recrystallized from ether to get pure product. $^1$H NMR (DMSO-d6, di-HCl salt) δ (ppm): 8.75 (m, 2H), 8.0 (dd, 2H), 7.30 (d, 1H), 6.90 (s, 1H), 6.60 (t, 1H), 6.10 (bs, 1H), 4.50 (m, 1H), 4.30 (m, 2H), 4.18 (m, 1H), 3.80 (s, 3H), 3.60 (m, 2H), 3.25 (m, 1H), 2.10 (m, 1H), 2.95 (s, 3H), 1.60 (s, 3H).

Example 275

Preparation of 1-(7,8-dichloro-2-methyl-3,4-dihydro-1H-pyrido[4,3-b]indol-5(2H)-yl)-2-(pyridin-4-yl)propan-2-ol (Compound No. 189)

A flask was charged with 7,8-dichloro-2-methyl-2,3,4,4a,5,9b-hexahydro-1H-pyrido[4,3-b]indole (1 g, 3.9 mmol) in DMF (10 mL) and stirred for 5 min. To this was added NaH (60% in hexane) (470 mg, 11.7 mmol) and the mixture stirred at RT for 10 min. 4-(2-Methyloxiran-2-yl)pyridine (795 mg, 5.8 mmol) was added and the mixture stirred at RT for 16 h. The progress of reaction was monitored by TLC. The reaction mixture was poured into ice water and filtered. The filtrate was washed with water and concentrated. The residue was recrystallized from ether to get pure product. $^1$H NMR (CD$_3$OD, formate salt) δ (ppm): 8.38 (d, 2H), 7.56 (s, 1H), 7.48 (d, 2H), 7.30 (s, 1H), 4.60 (m, 2H), 4.30 (m, 2H), 3.58 (m, 1H), 3.50 (m, 1H), 3.35 (m, 1H), 3.10 (m, 1H), 3.0 (s, 3H), 1.70 (s, 3H).

Example 276

Preparation of 1-(8,9-dichloro-2-methyl-3,4-dihydro-1H-pyrido[4,3-b]indol-5(2H)-yl)-2-(pyridin-4-yl)propan-2-ol (Compound No. 190)

A flask was charged with 7,8-dichloro-2-methyl-2,3,4,4a,5,9b-hexahydro-1H-pyrido[4,3-b]indole (1 g, 3.9 mmol) in DMF (10 mL) and stirred for 5 min. To this was added NaH (60% in hexane) (470 mg, 11.7 mmol) and the mixture stirred at RT for 10 min. 4-(2-Methyloxiran-2-yl)pyridine (795 mg, 5.8 mmol) was added and the mixture stirred at RT for 16 h. The progress of reaction was monitored by TLC. The reaction mixture was poured into ice water and filtered. The filtrate was washed with water and concentrated. The residue was recrystallized from ether to get pure product. $^1$H NMR (CD$_3$OD, formate salt) δ (ppm): 8.40 (m, 2H), 7.50 (d, 2H), 7.10 (m, 2H), 4.60 (m, 2H), 4.35 (m, 2H), 3.60 (m, 2H), 3.16 (m, 2H), 3.10 (s, 3H), 1.62 (s, 3H).

Example 277

Preparation of 1-(2,8-dimethyl-3,4-dihydro-1H-pyrido[4,3-b]indol-5(2H)-yl)-2-(4-methoxyphenyl)propan-2-ol (Compound No. 191)

A flask was charged with sodium hydride 60% (0.803 mg, 20.12 mmol) in DMF and stirred at RT for 10 min. To this was added the carboline (1.28 g, 6.4 mmol) and again stirred at RT for 1 h. 2-(4-Methoxyphenyl)-2-methyloxirane (1.5 g, 9.14 mmol) was added and the mixture stirred at RT overnight. Ice water was added and the mixture extracted with EtOAc (3×). The combined organic layers were washed with water (4×) and concentrated. The product was purified on silica gel (#100-200 mesh) using 0-5% MeOH:DCM as eluent. This compound was separated from its enantiomer Compound No. 192, by chiral HPLC. $^1$H NMR (DMSO-d6, oxalate salt) δ (ppm): 7.40 (d, 2H), 7.35 (d, 1H), 7.15 (s, 1H), 6.86 (m, 3H), 4.30 (m, 2H), 4.18 (d, 1H), 4.0 (d, 1H), 3.80 (s, 3H), 3.40 (m, 3H), 2.90 (m, 1H), 2.82 (s, 3H), 2.38 (s, 3H), 1.40 (s, 3H).

Example 278

Preparation of 1-(2,8-dimethyl-3,4-dihydro-1H-pyrido[4,3-b]indol-5(2H)-yl)-2-(4-methoxyphenyl)propan-2-ol (Compound No. 192)

A flask was charged with sodium hydride 60% (0.803 mg, 20.12 mmol) in DMF and stirred at RT for 10 min. To this was added the carboline (1.28 g, 6.4 mmol) and again stirred at RT for 1 h. 2-(4-Methoxyphenyl)-2-methyloxirane (1.5 g, 9.14 mmol) was added and the mixture stirred at RT overnight. Ice water was added and the mixture extracted with EtOAc (3×). The combined organic layers were washed with water (4×) and concentrated. The product was purified on silica gel (#100-200 mesh) using 0-5% MeOH:DCM as eluent. This compound was separated from its enantiomer Compound No. 191, by chiral HPLC. $^1$H NMR (DMSO-d6, oxalate salt) δ (ppm): 7.40 (d, 2H), 7.35 (d, 1H), 7.15 (s, 1H), 6.86 (m, 3H), 4.30 (m, 2H), 4.18 (d, 1H), 4.0 (d, 1H), 3.80 (s, 3H), 3.40 (m, 3H), 2.90 (m, 1H), 2.82 (s, 3H), 2.38 (s, 3H), 1.40 (s, 3H).

Example 279

Preparation of 1-(8-chloro-2-methyl-3,4-dihydro-1H-pyrido[4,3-b]indol-5(2H)-yl)-3-methyl-2-(pyridin-4-yl)butan-2-ol (Compound No. 193)

To a stirred solution of sodium hydride (0.261 g, 50-60%) in dry DMF (5 mL) at 0° C. was added 8-chloro-2,3,4,5-tetrahydro-2-methyl-1H-pyrido[4,3-b]indole (0.3 g). The reaction mixture was stirred at RT for 30 min. To the reaction mixture was added 4-(2-isopropyloxiran-2-yl)pyridine (0.288 g in 2 mL DMF) at RT. After 12 h stirring, the reaction mixture was diluted with ice-water and extracted with EtOAc (3×10 mL). The combined organic layers were washed with brine, dried over anhydrous sodium sulfate and evaporated. The crude product was triturated with diethyl ether to obtain pure product, 90 mg). $^1$H NMR (DMSO-d6, oxalate salt) δ (ppm): 8.30 (d, 2H), 7.30 (m, 3H), 7.10 (d, 1H), 6.82 (d, 1H), 4.50 (m, 2H), 4.22 (m, 2H), 3.42 (m, 1H), 3.30 (m, 2H), 2.80 (s, 3H), 2.62 (m, 1H), 1.78 (m, 1H), 1.15 (d, 3H), 0.6 (d, 3H).

Example 280

Preparation of 1-(2,8-dimethyl-3,4-dihydro-1H-pyrido[4,3-b]indol-5(2H)-yl)-3-methyl-2-(pyridin-4-yl)butan-2-ol (Compound No. 194)

To a stirred solution of sodium hydride (0.192 g, 50-60%) in dry DMF (5 mL) at 0° C. was added 2,3,4,5-tetrahydro-2,8-dimethyl-1H-pyrido[4,3-b]indole (0.3 g). The reaction mixture was stirred at RT for 30 min. To the reaction mixture was added 4-(2-isopropyloxiran-2-yl)pyridine (0.317 g in 2 mL DMF) at RT. After 12 h stirring, the reaction mixture was diluted with ice-water and extracted with EtOAc (3×10 mL). The combined organic layers were washed with brine, dried over anhydrous sodium sulfate and evaporated. The crude product was purified by column chromatography (silica gel 100-200 mesh, 5% MeOH:DCM) to obtain pure product (50 mg). $^1$H NMR (DMSO-d6, oxalate salt) δ (ppm): 8.30 (d, 2H), 7.30 (d, 2H), 7.15 (s, 1H), 7.10 (d, 1H), 6.82 (d, 1H), 4.40 (m, 2H), 4.22 (m, 2H), 3.4 (m, 2H), 3.20 (m, 1H), 2.80 (s, 3H), 2.62 (m, 1H), 2.5 (m, 1H), 2.25 (s, 3H), 1.15 (d, 3H), 0.6 (d, 3H).

Example 281

Preparation of 1-(8-chloro-2-methyl-3,4-dihydro-1H-pyrido[4,3-b]indol-5(2H)-yl)-2-(pyridin-4-yl)butan-2-ol (Compound No. 195)

A flask was charged with sodium hydride (0.581 g, 50-60%) in dry DMF (10 mL) at 0° C. and to it was added 8-chloro-2,3,4,5-tetrahydro-2-methyl-1H-pyrido[4,3-b]indole (0.8 g). The reaction mixture was stirred at RT for 30 min., and then to this was added 4-(2-ethyloxiran-2-yl)pyridine (0.758 g) dissolved in DMF (2 mL), stirred at RT for 12 h. The reaction mixture was diluted with ice-water and extracted with EtOAc (3×30 mL). The combined organic layers were washed with brine, dried over anhydrous sodium sulfate and evaporated. The crude product was triturated with diethyl ether to obtain the desired compound. $^1$H NMR (DMSO-d6, oxalate salt) δ (ppm): 8.45 (d, 2H), 7.40 (m, 4H), 7.0 (d, 1H), 4.38 (m, 1H), 4.22 (m, 1H), 3.60 (m, 2H), 3.35 (m, 2H), 3.10 (m, 2H), 2.90 (s, 3H), 2.10 (m, 2H), 0.6 (t, 3H).

Example 282

Preparation of 1-(2,8-dimethyl-3,4-dihydro-1H-pyrido[4,3-b]indol-5(2H)-yl)-2-(pyridin-4-yl)butan-2-ol (Compound No. 196)

A flask was charged with sodium hydride (0.640 g, 50-60%) in dry DMF (10 mL) at 0° C. and to this was added 2,8-dimethyl-2,3,4,4a,5,9b-hexahydro-1H-pyrido[4,3-b]indole (0.8 g). The mixture was stirred at RT for 30 min. and then 4-(2-ethyloxiran-2-yl)pyridine (0.834 g) dissolved in DMF (2 mL) was added, stirred at RT for 12 h. The reaction mixture was diluted with ice-water and extracted with EtOAc (3×30 mL). The combined organic layers were washed with brine, dried over anhydrous sodium sulfate and evaporated. The crude product was triturated with diethyl ether to obtain the desired compound. $^1$H NMR (DMSO-d6, oxalate salt) δ (ppm): 8.45 (d, 2H), 7.42 (d, 2H), 7.30 (d, 1H), 7.10 (s, 1H), 6.82 (d, 1H), 4.30 (d, 1H), 4.18 (d, 1H), 3.60 (s, 2H), 3.50 (m, 2H), 3.38 (m, 1H), 3.0 (m, 2H), 2.90 (s, 3H), 3.32 (s, 3H), 2.10 (m, 1H), 0.6 (t, 3H).

Example 283

Preparation of 1-(2,8-dimethyl-3,4-dihydro-1H-pyrido[4,3-b]indol-5(2H)-yl)-2-(pyrimidin-4-yl)propan-2-ol (Compound No. 197)

Sodium hydride (200 mg, 8.33 mmol) was washed with hexane and dried under vacuum. DMF (4 mL) was added, resulting in a suspension. The carboline (400 mg, 2 mmol) in 2 mL DMF was added dropwise and stirred for 30 min. at RT. 4-(2-Methyl-oxiranyl)-pyrimidine (490 mg, 3.60 mmol) in 2 mL DMF was added dropwise and the reaction mixture was stirred overnight at RT. After the completion of reaction, the reaction mixture was quenched with ice-cold water and extracted three times with EtOAc. The combined organic layers were washed with water several times followed by brine, and then dried over sodium sulfate. The solvent was evaporated and the residue washed with hexane and crystallized from ether-DCM and hexane to obtain 350 mg of desired product. $^1$H NMR (CD$_3$OD, oxalate salt) δ (ppm): 9.10 (s, 1H), 8.50 (d, 1H), 7.50 (d, 1H), 7.10 (s, 1H), 6.95 (d, 1H), 6.80 (d, 1H), 4.40 (m, 4H), 3.60 (m, 2H), 3.40 (m, 1H), 3.20 (m, 1H), 3.0 (s, 3H), 2.50 (s, 3H), 1.60 (s, 3H).

Example 284

Preparation of 1-(8-chloro-2-methyl-3,4-dihydro-1H-pyrido[4,3-b]indol-5(2H)-yl)-2-(pyrimidin-4-yl)propan-2-ol (Compound No. 198)

Sodium hydride (275 mg, 11.45 mmol) was washed with hexane and dried under vacuum. DMF (4 mL) was added, resulting in a suspension. 2,3,4,5-Tetrahydro-2-methyl-8-chloro-1H-pyrido[4,3-b]indole (500 mg, 2.27 mmol) dissolved in DMF (2 mL) was added dropwise and the reaction mixture stirred for 30 min. at RT. 4-(2-Methyl-oxiranyl)-pyrimidine (620 mg, 4.55 mmol) dissolved in DMF (2 mL) was added dropwise and the reaction mixture was stirred overnight at RT. The progress of reaction was monitored by TLC. The mixture was quenched with ice-cold water and the mixture extracted with EtOAc (3×30 mL). The combined organic layer was washed with water (4×20 mL) followed by brine (1×20 mL), dried over sodium sulfate and the solvent evaporated under vacuum. The residue was washed with hexane and crystallized from ether: DCM and hexane. $^1$H NMR (CD$_3$OD, oxalate salt) δ (ppm): 9.10 (s, 1H), 8.50 (d, 1H), 7.50 (d, 1H), 7.36 (s, 1H), 7.10 (d, 1H), 6.95 (d, 1H), 4.40 (m, 4H), 3.60 (m, 2H), 3.40 (m, 1H), 3.20 (m, 1H), 3.05 (s, 3H), 1.60 (s, 3H).

Example 285

Preparation of 1-(8-chloro-2-methyl-3,4-dihydro-1H-pyrido[4,3-b]indol-5(2H)-yl)-2-(pyrazin-2-yl)propan-2-ol (Compound No. 199)

The target compound was prepared according to General Method 3. $^1$H NMR (DMSO-d6, oxalate salt) δ (ppm): 8.65 (s, 1H), 8.55 (s, 1H), 8.50 (d, 1H), 7.42 (s, 1H), 7.05 (d, 1H), 6.95 (d, 1H), 4.40 (m, 4H), 3.20 (m, 2H), 3.0 (m, 2H), 2.90 (s, 3H), 1.58 (s, 3H).

Example 286

Preparation of 1-(2,8-dimethyl-3,4-dihydro-1H-pyrido[4,3-b]indol-5(2H)-yl)-2-(pyrazin-2-yl)propan-2-ol (Compound No. 200)

The target compound was prepared according to General Method 3. $^1$H NMR (DMSO-d6, oxalate salt) δ (ppm): 8.65 (s, 1H), 8.55 (s, 1H), 8.50 (d, 1H), 7.10 (s, 1H), 6.90 (d, 1H), 6.78 (d, 1H), 4.30 (m, 4H), 3.20 (m, 2H), 3.0 (m, 2H), 2.90 (s, 3H), 2.30 (s, 3H), 1.50 (s, 3H).

Example 287

Preparation of 1-(8-methyl-2-(2,2,2-trifluoroethyl)-3,4-dihydro-1H-pyrido[4,3-b]indol-5(2H)-yl)-2-(pyridin-4-yl)propan-2-ol (Compound No. 341)

The target compound was prepared according to General Method 3. $^1$H NMR (DMSO-d6, HCl salt) δ (ppm): 8.65 (d, 2H), 8.05 (d, 2H), 7.10 (m, 2H), 6.78 (d, 1H), 4.25 (m, 2H), 4.0 (s, 2H), 3.60 (m, 2H), 3.16 (m, 2H), 2.85 (m, 2H), 2.30 (s, 3H), 1.58 (s, 3H).

Example 288

Preparation of 1-(2-cyclopropyl-8-methyl-3,4-dihydro-1H-pyrido[4,3-b]indol-5(2H)-yl)-2-(pyridin-4-yl)propan-2-ol (Compound No. 342)

The target compound was prepared according to General Method 3. $^1$H NMR (CD$_3$OD, TFA salt) δ (ppm): 8.62 (d, 2H), 8.18 (d, 2H), 7.20 (s, 1H), 6.95 (d, 1H), 6.80 (d, 1H), 4.50 (m, 1H), 4.40 (s, 2H), 4.0 (m, 1H), 3.70 (m, 1H), 3.30 (m, 3H), 3.10 (m, 1H), 2.36 (s, 3H), 1.78 (s, 3H), 1.20 (m, 4H).

Example 289

Preparation of 1-(6-methoxy-2-methyl-3,4-dihydro-1H-pyrido[4,3-b]indol-5(2H)-yl)-2-(pyridin-4-yl)propan-2-ol (Compound No. 343)

The target compound was prepared according to General Method 3. $^1$H NMR (CD$_3$OD, TFA salt) δ (ppm): 8.60 (m, 2H), 7.95 (m, 2H), 6.95 (m, 2H), 6.50 (m, 1H), 4.65 (m, 2H), 4.30 (m, 2H), 3.90 (m, 2H), 3.80 (s, 3H), 3.60 (m, 2H), 3.10 (s, 3H), 1.70 (s, 3H).

Example 290

Preparation of 1-(7-isopropyl-2-methyl-3,4-dihydro-1H-pyrido[4,3-b]indol-5(2H)-yl)-2-(pyridin-4-yl)propan-2-ol (Compound No. 344)

The target compound was prepared according to General Method 3. $^1$H NMR (CD$_3$OD, TFA salt) δ (ppm): 8.60 (d, 2H), 8.05 (d, 2H), 7.25 (d, 1H), 6.90 (d, 1H), 6.78 (s, 1H), 4.65 (m, 1H), 4.42 (s, 2H), 4.30 (m, 1H), 3.90 (m, 1H), 3.60 (m, 2H), 3.30 (m, 1H), 3.10 (s, 3H), 2.85 (m, 1H), 1.80 (s, 3H), 1.18 (m, 6H).

Example 291

Preparation of 2-(pyridin-4-yl)-1-(2,3,8-trimethyl-3,4-dihydro-1H-pyrido[4,3-b]indol-5(2H)-yl)propan-2-ol (Compound No. 345)

The target compound was prepared according to General Method 3. $^1$H NMR (DMSO-d6, HCl salt) δ (ppm): 8.62 (d, 2H), 8.10 (d, 2H), 7.18 (s, 1H), 6.90 (m, 1H), 6.80 (m, 1H), 4.62 (m, 2H), 4.40 (m, 3H), 4.05 (m, 1H), 3.80 (m, 1H), 3.05 (s, 3H), 2.38 (s, 3H), 1.75 (d, 3H), 1.70-1.50 (m, 3H).

Example 292

Preparation of (E)-8-chloro-2-methyl-5-(2-(pyrimidin-5-yl)prop-1-enyl)-2,3,4,5-tetrahydro-1H-pyrido[4,3-b]indole (Compound No. 346)

1-(8-Chloro-1,2,3,4-tetrahydro-2-methylpyrido[4,3-b]indol-5-yl)-2-(pyrimidin-5-yl)propan-2-ol (1 g, 2.80 mmol, 1 eq.) was refluxed with 25% sulfuric acid (7 ml) for 2 h. The reaction mixture was cooled to 5 deg C. in ice-water bath. KOH (15% aqueous solution) was added dropwise to the reaction mixture till pH of 9-10 was achieved. The reaction mixture was extracted with EtOAc (3×10 mL). The combined organic layer was washed with water (10 ml) followed by brine, dried over sodium sulfate and evaporated under vacuum. The crude product was purified by silica gel chromatography (100-200 mesh) using a gradient of MeOH-EtOAc (0-10%) followed by preparative HPLC. $^1$H NMR (CD$_3$OD, TFA salt) δ (ppm): 9.20 (s, 1H), 9.10 (s, 2H), 7.58 (s, 1H), 7.30-7.20 (m, 3H), 4.78 (m, 1H), 4.40 (m, 1H), 3.90 (m, 1H), 3.60 (m, 1H), 3.20 (m, 2H), 3.10 (s, 3H), 2.0 (s, 3H).

Example 293

Preparation of (E)-5-(2-cyclohexylprop-1-enyl)-2,8-dimethyl-2,3,4,5-tetrahydro-1H-pyrido[4,3-b]indole (Compound No. 320)

2,3,4,5-tetrahydro-2,8-dimethyl-1H-pyrido[4,3-b]indole (100 mg, 0.5 mmol) was dissolved in DMF (3 mL) and potassium phosphate (212.4 mg, 1 mmol), copper(I) iodide (9.5 mg, 0.05 mmol) and L-proline (11.51 mg, 0.1 mmol) was added in to it. (1-bromoprop-1-en-2-yl)cyclohexane (121.8 mg, 0.6 mmol) was dissolved in DMF (2 mL) and added dropwise. Nitrogen was purged for 2 min. and the reaction mixture was heated at 85° C. overnight (prolonged heating was required in some cases). DMF was evaporated and water was added. The precipitate obtained was filtered and purified by silica gel chromatography (100-200 mesh) using 0-3% MeOH:DCM as eluent. The compound was further purified through reverse phase purification. Yield: 11 mg. $^1$H NMR (CD$_3$OD, TFA salt) δ (ppm): 7.24 (s, 1H), 7.06 (d, 1H), 7.0 (d, 1H), 6.25 (s, 1H), 4.70 (m, 1H), 4.35 (m, 1H), 3.82 (m, 1H), 3.48 (m, 1H), 3.10 (s, 3H), 3.04 (m, 2H), 2.42 (s, 3H), 2.10 (m, 1H), 1.90 (s, 3H), 1.65 (m, 2H), 1.60-1.40 (m, 5H), 1.20-1.0 (m, 3H).

Example 294

Preparation of (E)-2-(8-methyl-5-(2-(pyridin-4-yl)prop-1-enyl)-3,4-dihydro-1H-pyrido[4,3-b]indol-2(5H)-yl)ethanol (Compound No. 332)

2-(3,4-dihydro-8-methyl-1H-pyrido[4,3-b]indol-2(5H)-yl)ethanol (232 mg, 1 mmol) was dissolved in DMF (3 mL) and potassium phosphate (424 mg, 2 mmol), copper(I) iodide (19 mg, 0.1 mmol) and L-proline (23 mg, 0.2 mmol) was added in to it. 4-(1-bromoprop-1-en-2-yl)pyridine (294 mg, 1.5 mmol) was dissolved in DMF (2 mL) and added dropwise. Nitrogen was purged for 2 min. and the reaction mixture was heated at 85° C. overnight (prolonged heating was required in some cases). DMF was evaporated and water was added. The precipitate obtained was filtered and purified by silica gel chromatography (100-200 mesh) using 0-8% MeOH:DCM as eluent. The compound was further purified through reverse phase purification. Yield: 115 mg. $^1$H NMR (CD$_3$OD, oxalate salt) δ (ppm): 8.70 (d, 2H), 7.68 (d, 2H), 7.38 (m, 2H), 7.10 (m, 2H), 4.60 (m, 2H), 4.0 (m, 2H), 3.78 (m, 2H), 3.50 (m, 2H), 3.15 (m, 2H), 2.42 (s, 3H), 2.05 (s, 3H).

Example 295

Preparation of (E)-8-chloro-2-methyl-5-(2-(pyrazin-2-yl)prop-1-enyl)-2,3,4,5-tetrahydro-1H-pyrido[4,3-b]indole (Compound No. 333)

A solution of 1-(8-chloro-2-methyl-1,2,3,4-tetrahydro-pyrido[4,3-b]indol-5-yl)-2-pyrazin-2-yl-propan-2-ol (500 mg, 1.4 mmol) in DCM (8 mL) and DMF (2 drops) was stirred at 0-10° C. Thionyl chloride (0.5 mL, 7.0 mmol) was diluted in DCM (8 mL) and added and the reaction mixture was stirred at RT for 1 h. The solvent was removed under vacuum to obtain the crude foamy solid. The Solid was dissolved in NMP (6 mL) stirred for 5 min and powdered KOH (551 mg, 9.83 mmol) was and heated at 100° C. for 30 min. After completion of reaction, the reaction mixture was poured in water and extracted with EtOAc (100 mL×3). The organic layer washed with water, concentrated under vacuum to obtain the crude product and purified by prep HPLC. $^1$H NMR (CDCl$_3$, freebase) δ (ppm): 8.80 (s, 1H), 8.58 (d, 1H), 8.50 (d, 1H), 7.62 (s, 1H), 7.40 (s, 1H), 7.15 (d, 1H), 7.05 (d, 1H), 3.70 (s, 2H), 2.82 (m, 4H), 2.58 (s, 3H), 2.10 (s, 3H).

Example 296

Preparation of (E)-7-isopropyl-2-methyl-5-(2-(pyridin-4-yl)prop-1-enyl)-2,3,4,5-tetrahydro-1H-pyrido[4,3-b]indole (Compound No. 334)

1-(7-Isopropyl-2-methyl-1,2,3,4-tetrahydro-pyrido[4,3-b]indol-5-yl)-2-pyridin-4-yl-propan-2-ol (100 mg, 0.2 mmol) was dissolved in SOCl$_2$ (1.0 mL) and stirred the reaction at RT for 2 h. After completion of starting material by monitoring TLC reaction mixture was concentrated under reduced pressure and saturated bicarbonate was added, extracted with EtOAc, organic layer was washed with water, dried over sodium sulfate and concentrated, and purified by reverse phase Chromatography. Yield: 68 mg. $^1$H NMR (DMSO-d6, oxalate salt) δ (ppm): 8.62 (d, 2H), 7.70 (d, 2H), 7.48 (s, 1H), 7.42 (d, 1H), 7.05 (m, 2H), 4.40 (m, 2H), 3.58 (m, 2H), 3.05 (m, 3H), 2.95 (s, 3H), 1.95 (s, 3H), 1.25 (d, 6H).

Example 297

Preparation of (E)-8-chloro-2-methyl-5-(2-(thiophen-2-yl)prop-1-enyl)-2,3,4,5-tetrahydro-1H-pyrido[4,3-b]indole (Compound No. 338)

8-Chloro-2,3,4,5-tetrahydro-2-methyl-1H-pyrido[4,3-b]indole (110 mg, 0.5 mmol) was dissolved in DMF (3 mL) and potassium phosphate (212.4 mg, 1 mmol), copper(I) iodide (9.5 mg, 0.05 mmol) and L-proline (11.51 mg, 0.1 mmol) was added in to it. 2-(1-bromoprop-1-en-2-yl)thiophene (121.8 mg, 0.6 mmol) was dissolved in DMF (2 mL) and added dropwise. Nitrogen was purged for 2 min and the reaction mixture was heated at 85° C. overnight (prolonged heating was required in some cases). DMF was evaporated and water was added. The precipitate obtained was filtered and purified by silica gel chromatography (100-200 mesh) using 0-3% MeOH:DCM as eluent. The compound was further purified through reverse phase purification. Yield: 20 mg. $^1$H NMR (CD$_3$OD, oxalate salt) δ (ppm): 7.55 (s, 1H), 7.42 (d, 1H), 7.38 (d, 1H), 7.20 (s, 2H), 7.10 (m, 2H), 4.50 (m, 2H), 3.70 (m, 2H), 3.10 (m, 5H), 2.0 (s, 3H).

Example 298

Preparation of (E)-8-chloro-5-(2-cyclohexylprop-1-enyl)-2-methyl-2,3,4,5-tetrahydro-1H-pyrido[4,3-b]indole (Compound No. 367)

8-Chloro-2,3,4,5-tetrahydro-2-methyl-1H-pyrido[4,3-b]indole (110 mg, 0.5 mmol) was dissolved in DMF (3 mL) and potassium phosphate (212.4 mg, 1 mmol), copper(I) iodide (9.5 mg, 0.05 mmol) and L-proline (11.51 mg, 0.1 mmol) was added in to it. (1-bromoprop-1-en-2-yl)cyclohexane (121.8 mg, 0.6 mmol) was dissolved in DMF (2 mL) and added dropwise. Nitrogen was purged for 2 min and the reaction mixture was heated at 85° C. overnight (prolonged heating was required in some cases). DMF was evaporated and water was added. The precipitate obtained was filtered and purified by silica gel chromatography (100-200 mesh) using 0-3% MeOH:DCM as eluent. The compound was further purified through reverse phase purification. Yield: 35 mg. $^1$H NMR (CD$_3$OD, TFA salt) δ (ppm): 7.50 (s, 1H), 7.18 (m, 2H), 6.28 (s, 1H), 4.70 (m, 1H), 4.58 (m, 1H), 3.82 (m, 1H), 3.60 (m, 1H), 3.15 (s, 3H), 3.10 (m, 2H), 2.0 (m, 1H), 1.90 (s, 3H), 1.70 (m, 2H), 1.58 (m, 1H), 1.50 (m, 4H), 1.15 (m, 3H).

Example 299

Preparation of (Z)-5-(2-cyclohexylprop-1-enyl)-2,8-dimethyl-2,3,4,5-tetrahydro-1H-pyrido[4,3-b]indole (Compound No. 368)

2,3,4,5-Tetrahydro-2,8-dimethyl-1H-pyrido[4,3-b]indole (100 mg, 0.5 mmol) was dissolved in DMF (3 mL) and potassium phosphate (212.4 mg, 1 mmol), copper(I) iodide (9.5 mg, 0.05 mmol) and L-proline (11.51 mg, 0.1 mmol) was added in to it. (1-bromoprop-1-en-2-yl)cyclohexane (121.8 mg, 0.6 mmol) was dissolved in DMF (2 mL) and added dropwise. Nitrogen was purged for 2 min and the reaction mixture was heated at 85° C. overnight (prolonged heating was required in some cases). DMF was evaporated and water was added. The precipitate obtained was filtered and purified by silica gel chromatography (100-200 mesh) using 0-3% MeOH:DCM as eluent. The compound was further purified through reverse phase purification. Yield: 0.45 mg. $^1$H NMR (CD$_3$OD, TFA salt) δ (ppm): 7.25 (s, 1H), 7.0 (m, 2H), 6.42 (s, 1H), 4.70 (m, 1H), 4.35 (m, 1H), 3.85 (m, 1H), 3.58 (m, 1H), 3.12 (s, 3H), 3.05 (m, 2H), 2.42 (s, 3H), 2.30 (m, 1H), 1.90 (m, 5H), 1.78 (m, 1H), 1.50-1.30 (m, 7H).

Example 300

Preparation of (Z)-8-chloro-5-(2-cyclohexylprop-1-enyl)-2-methyl-2,3,4,5-tetrahydro-1H-pyrido[4,3-b]indole (Compound No. 369)

8-Chloro-2,3,4,5-tetrahydro-2-methyl-1H-pyrido[4,3-b]indole (110 mg, 0.5 mmol) was dissolved in DMF (3 mL) and potassium phosphate (212.4 mg, 1 mmol), copper(I) iodide (9.5 mg, 0.05 mmol) and L-proline (11.51 mg, 0.1 mmol) was added in to it. (1-bromoprop-1-en-2-yl)cyclohexane (121.8 mg, 0.6 mmol) was dissolved in DMF (2 mL) and added dropwise. Nitrogen was purged for 2 min and the reaction mixture was heated at 85° C. overnight (prolonged heating was required in some cases). DMF was evaporated and water was added. The precipitate obtained was filtered and purified by silica gel chromatography (100-200 mesh) using 0-3% MeOH:DCM as eluent. The compound was further purified through reverse phase purification. Yield: 6 mg. $^1$H NMR (CD$_3$OD, TFA salt) δ (ppm): 7.50 (s, 1H), 7.18 (d, 1H), 7.10 (d, 1H), 6.42 (s, 1H), 4.70 (m, 1H), 4.38 (m, 1H), 3.82 (m, 1H), 3.58 (m, 1H), 3.10 (s, 3H), 3.05 (m, 2H), 2.30 (m, 1H), 1.90 (m, 4H), 1.78 (m, 1H), 1.42-1.30 (m, 8H).

Example 301

Preparation of 8-chloro-2,3-dimethyl-5-(2-(pyridin-4-yl)allyl)-2,3,4,5-tetrahydro-1H-pyrido[4,3-b]indole (Compound No. 365)

1-(8-Chloro-2,3-dimethyl-1,2,3,4-tetrahydro-pyrido[4,3-b]indol-5-yl)-2-pyridin-4-yl-propan-2-ol (900 mg, 2.43 mmol) was dissolved in 5 mL DCM. To this, thionyl Chloride (2 mL in DCM) was added dropwise at 0° C. and stirred for 2.5 h at RT. After completion of starting material (TLC) excess thionyl chloride and solvent was evaporated under vacuum. The residue was neutralized with saturated solution of Sodium bicarbonate at 0° C. and extracted with EtOAc (3 times). The combined organic layer was washed with water, dried over anhydrous sodium sulfate, concentrated to obtain 720 mg of crude which was subjected to reverse phase chromatography to obtain 80 mg of product as the TFA salt. $^1$H NMR (CD$_3$OD, TFA salt) δ (ppm): 8.70 (d, 2H), 7.95 (d, 2H), 7.55 (s, 1H), 7.42 (d, 1H), 7.20 (d, 1H), 5.85 (s, 1H), 5.30 (s, 2H), 4.78 (s, 1H), 4.70 (m, 1H), 4.40 (m, 1H), 4.10 (m, 1H), 3.85 (m, 1H), 3.05 (s, 3H), 2.95 (m, 1H), 1.50 (m, 2H).

Example 302

Preparation of (E)-2-(1-(8-chloro-2-methyl-3,4-dihydro-1H-pyrido[4,3-b]indol-5(2H)-yl)prop-1-en-2-yl)thiazole (Compound No. 370)

8-Chloro-2,3,4,5-tetrahydro-2-methyl-1H-pyrido[4,3-b]indole (110 mg, 0.5 mmol) was dissolved in DMF (3 mL) and potassium phosphate (212.4 mg, 1 mmol), copper(I) iodide (9.5 mg, 0.05 mmol) and L-proline (11.51 mg, 0.1 mmol) was added in to it. Then 2-(1-bromoprop-1-en-2-yl)thiazole (122.4 mg, 0.6 mmol) was dissolved in DMF (2 mL) and added dropwise. Nitrogen was purged for 2 min and the reaction mixture was heated at 85° C. overnight (prolonged heating was required some cases). DMF was evaporated and water was added. The precipitate obtained was filtered and purified by silica gel chromatography (100-200 mesh) using 0-3% MeOH:DCM as eluent. The compound was further purified through reverse phase purification. Yield: 9 mg. $^1$H NMR (CD$_3$OD, oxalate salt) δ (ppm): 7.90 (d, 1H), 7.65 (d, 2H), 7.55 (s, 1H), 7.22 (s, 2H), 4.55 (m, 2H), 3.70 (m, 2H), 3.18 (m, 2H), 3.10 (s, 3H), 2.10 (s, 3H).

Example 303

Preparation of (E)-5-(2-cyclohexylprop-1-enyl)-2,8-dimethyl-2,3,4,5-tetrahydro-1H-pyrido[4,3-b]indole (Compound No. 375)

2,3,4,5-Tetrahydro-2,8-dimethyl-1H-pyrido[4,3-b]indole (100 mg, 0.5 mmol) was dissolved in DMF (3 mL). potassium phosphate (212.4 mg, 1 mmol), copper (I) iodide (9.5 mg, 0.05 mmol) and L-proline (11.51 mg, 0.1 mmol) were added. (1-Bromoprop-1-en-2-yl)cyclohexane (121.8 mg, 0.6 mmol) dissolved in DMF (2 mL) was added dropwise to it. Nitrogen was purged for 2 min and the reaction mixture was heated at 85° C. overnight (prolonged heating required in some cases). DMF was evaporated and water added to the reaction mixture. The precipitate obtained was filtered and purified by silica gel chromatography (100-200 mesh) using 0-3% MeOH: DCM as eluent. The compound was further purified through reverse phase HPLC. Yield: 11 mg. $^1$H NMR (CD$_3$OD, TFA salt) δ (ppm): 7.24 (s, 1H), 7.06 (d, 1H), 7.0 (d, 1H), 6.25 (s, 1H), 4.70 (m, 1H), 4.35 (m, 1H), 3.82 (m, 1H), 3.48 (m, 1H), 3.10 (s, 3H), 3.04 (m, 2H), 2.42 (s, 3H), 2.10 (m, 1H), 1.90 (s, 3H), 1.65 (m, 2H), 1.60-1.40 (m, 5H), 1.20-1.0 (m, 3H).

Example 304

Preparation of (E)-2-(8-methyl-5-(2-(pyridin-4-yl) prop-1-enyl)-3,4-dihydro-1H-pyrido[4,3-b]indol-2 (5H)-yl)ethanol (Compound No. 376)

2-(3,4-Dihydro-8-methyl-1H-pyrido[4,3-b]indol-2 (5H)-yl)ethanol (232 mg, 1 mmol) was dissolved in DMF (3 mL). potassium phosphate (424 mg, 2 mmol), copper (I) iodide (19 mg, 0.1 mmol) and L-proline (23 mg, 0.2 mmol) were added. 4-(1-bromoprop-1-en-2-yl)pyridine (294 mg, 1.5 mmol) dissolved in DMF (2 mL) was added dropwise to the reaction mixture. Nitrogen was purged for 2 min in the reaction mixture which was heated at 85° C. overnight (prolonged heating was required in some cases). DMF was evaporated and water added to the reaction mixture. The precipitate obtained was filtered and purified by silica gel chromatography (100-200 mesh) using 0-8% MeOH:DCM as eluent. The compound was further purified through reverse phase purification. Yield: 115 mg. $^1$H NMR (CD$_3$OD, oxalate salt) δ (ppm): 8.70 (d, 2H), 7.68 (d, 2H), 7.38 (m, 2H), 7.10 (m, 2H), 4.60 (m, 2H), 4.0 (m, 2H), 3.78 (m, 2H), 3.50 (m, 2H), 3.15 (m, 2H), 2.42 (s, 3H), 2.05 (s, 3H).

Example 305

Preparation of (E)-8-chloro-2-methyl-5-(2-(pyrazin-2-yl)prop-1-enyl)-2,3,4,5-tetrahydro-1H-pyrido[4,3-b]indole (Compound No. 377)

A solution of 1-(8-chloro-2-methyl 1,2,3,4 tetrahydropyrido (4,3-b) indol-5-yl)-2-pyrazin-2-yl-propan-2-ol (500 mg, 1.4 mmol) in DCM (8 mL) and DMF (2 drops) was stirred at 0-10° C. Thionyl chloride (0.5 mL, 7.0 mmol) diluted in DCM (8 mL) was added to the reaction mixture, which was stirred at RT for 1 h. The solvent was removed under vacuum to obtain the crude foamy solid. The solid was dissolved in NMP (6 mL) and the reaction mixture stirred for 5 min. Powdered KOH (551 mg, 9.83 mmol) was added to the reaction mixture and the mixture heated at 100° C. for 30 min. After completion of reaction, the reaction mixture was poured in water and extracted with EtOAc (100 mL×3). The organic layer was washed with water, concentrated under vacuum to obtain the crude product which was purified by reverse phase HPLC. $^1$H NMR (CDCl$_3$, free base) δ (ppm): 8.80 (s, 1H), 8.58 (d, 1H), 8.50 (d, 1H), 7.62 (s, 1H), 7.40 (s, 1H), 7.15 (d, 1H), 7.05 (d, 1H), 3.70 (s, 2H), 2.82 (m, 4H), 2.58 (s, 3H), 2.10 (s, 3H).

Example 306

Preparation of (E)-7-isopropyl-2-methyl-5-(2-(pyridin-4-yl)prop-1-enyl)-2,3,4,5-tetrahydro-1H-pyrido [4,3-b]indole (Compound No. 378)

1-(7-Isopropyl-2-methyl-1,2,3,4-tetrahydro-pyrido[4,3-b] indol-5-yl)-2-pyridin-4-yl-propan-2-ol (100 mg, 0.2 mmol) was dissolved in SOCl2 (1.0 mL) and the reaction was stirred at RT for 2 h. After completion of reaction (as monitored by TLC) reaction mixture was concentrated under vacuum and saturated bicarbonate solution was added. The desired compound was extracted with EtOAc, organic layer washed with water, dried over sodium sulfate and concentrated under vacuum. The crude compound was purified by reverse phase chromatography. Yield: 68 mg. $^1$H NMR (DMSO, oxalate salt) δ (ppm): 8.62 (d, 2H), 7.70 (d, 2H), 7.48 (s, 1H), 7.42 (d, 1H), 7.05 (m, 2H), 4.40 (m, 2H), 3.58 (m, 2H), 3.05 (m, 3H), 2.95 (s, 3H), 1.95 (s, 3H), 1.25 (d, 2H).

Example 307

Preparation of (E)-8-chloro-2-methyl-5-(2-(thiophen-2-yl)prop-1-enyl)-2,3,4,5-tetrahydro-1H-pyrido [4,3-b]indole (Compound No. 379)

8-Chloro-2,3,4,5-tetrahydro-2-methyl-1H-pyrido[4,3-b] indole (110 mg, 0.5 mmol) was dissolved in DMF (3 mL). Potassium phosphate (212.4 mg, 1 mmol), copper (I) iodide (9.5 mg, 0.05 mmol) and L-proline (11.51 mg, 0.1 mmol) were added. 2-(1-Bromoprop-1-en-2-yl)thiophene (121.8 mg, 0.6 mmol) was dissolved in DMF (2 mL) and added dropwise to the reaction mixture. Nitrogen was purged for 2 min and the reaction mixture was heated at 85° C. overnight (prolonged heating required in some cases). DMF was evaporated and water added to the reaction mixture. The precipitate obtained was filtered and purified by silica gel chromatography (100-200 mesh) using 0-3% MeOH:DCM as eluent. The compound was further purified through reverse phase purification. Yield: 20 mg. $^1$H NMR (CD$_3$OD, oxalate salt) δ (ppm): 7.55 (s, 1H), 7.42 (d, 1H), 7.38 (d, 1H), 7.20 (s, 2H), 7.10 (m, 2H), 4.50 (m, 2H), 3.70 (m, 2H), 3.10 (m, 5H), 2.0 (s, 3H).

Example 308

Preparation of (E)-8-chloro-5-(2-cyclohexylprop-1-enyl)-2-methyl-2,3,4,5-tetrahydro-1H-pyrido[4,3-b] indole (Compound No. 380)

8-Chloro-2,3,4,5-tetrahydro-2-methyl-1H-pyrido[4,3-b] indole (110 mg, 0.5 mmol) was dissolved in DMF (3 mL) and potassium phosphate (212.4 mg, 1 mmol), copper (I) iodide (9.5 mg, 0.05 mmol), L-proline (11.51 mg, 0.1 mmol) were added. (1-Bromoprop-1-en-2-yl)cyclohexane (121.8 mg, 0.6 mmol) was dissolved in DMF (2 mL) and added dropwise to it. Nitrogen was purged for 2 min and the reaction mixture was heated at 85° C. overnight (prolonged heating required in some cases). DMF was evaporated and water added. The precipitate obtained was filtered and purified by silica gel chromatography (100-200 mesh) using 0-3% MeOH:DCM as eluent. The compound was further purified through reverse phase purification. Yield: 35 mg. $^1$H NMR (CD$_3$OD, TFA salt) δ (ppm): 7.50 (s, 1H), 7.18 (m, 2H), 6.28 (s, 1H), 4.70 (m, 1H), 4.58 (m, 1H), 3.82 (m, 1H), 3.60 (m, 1H), 3.15 (s, 3H), 3.10 (m, 2H), 2.0 (m, 1H), 1.90 (s, 3H), 1.70 (m, 2H), 1.58 (m, 1H), 1.50 (m, 4H), 1.15 (m, 3H).

Example 309

Preparation of (Z)-5-(2-cyclohexylprop-1-enyl)-2,8-dimethyl-2,3,4,5-tetrahydro-1H-pyrido[4,3-b]indole (Compound No. 381)

2,3,4,5-Tetrahydro-2,8-dimethyl-1H-pyrido[4,3-b]indole (100 mg, 0.5 mmol) was dissolved in DMF (3 mL) and potassium phosphate (212.4 mg, 1 mmol), copper (I) iodide (9.5 mg, 0.05 mmol), L-proline (11.51 mg, 0.1 mmol) were added. (1-bromoprop-1-en-2-yl)cyclohexane (121.8 mg, 0.6 mmol) was dissolved in DMF (2 mL) and added dropwise. Nitrogen was purged for 2 min and the reaction mixture heated at 85° C. overnight (prolonged heating required in some cases). DMF was evaporated and water added. The precipitate obtained was filtered and the crude purified by silica gel chromatography (100-200 mesh) using 0-3% MeOH:DCM as eluent. The compound was further purified through reverse phase purification. Yield: 0.45 mg. $^1$H NMR (CD$_3$OD, TFA salt) δ (ppm): 7.25 (s, 1H), 7.0 (m, 2H), 6.42 (s, 1H), 4.70 (m, 1H), 4.35 (m, 1H), 3.85 (m, 1H), 3.58 (m, 1H), 3.12 (s, 3H), 3.05 (m, 2H), 2.42 (s, 3H), 2.30 (m, 1H), 1.90 (m, 5H), 1.78 (m, 1H), 1.50-1.30 (m, 7H).

Example 310

Preparation of (Z)-8-chloro-5-(2-cyclohexylprop-1-enyl)-2-methyl-2,3,4,5-tetrahydro-1H-pyrido[4,3-b]indole (Compound No. 382)

8-Chloro-2,3,4,5-tetrahydro-2-methyl-1H-pyrido[4,3-b]indole (110 mg, 0.5 mmol) was dissolved in DMF (3 mL). Potassium phosphate (212.4 mg, 1 mmol), copper (I) iodide (9.5 mg, 0.05 mmol) and L-proline (11.51 mg, 0.1 mmol) were added. (1-Bromoprop-1-en-2-yl)cyclohexane (121.8 mg, 0.6 mmol) was dissolved in DMF (2 mL) and added dropwise to the reaction mixture. Nitrogen was purged for 2 min and the reaction mixture heated at 85° C. overnight (prolonged heating required in some cases). DMF was evaporated and water added. The precipitate obtained was filtered and crude Compound was purified by silica gel chromatography (100-200 mesh) using 0-3% MeOH:DCM as eluent. The compound was further purified through reverse phase purification. Yield: 6 mg. $^1$H NMR (CD$_3$OD, TFA salt) δ (ppm): 7.50 (s, 1H), 7.18 (d, 1H), 7.10 (d, 1H), 6.42 (s, 1H), 4.70 (m, 1H), 4.38 (m, 1H), 3.82 (m, 1H), 3.58 (m, 1H), 3.10 (s, 3H), 3.05 (m, 2H), 2.30 (m, 1H), 1.90 (m, 4H), 1.78 (m, 1H), 1.42-1.30 (m, 8H).

Example 311

Preparation of (E)-2-(1-(8-chloro-2-methyl-3,4-dihydro-1H-pyrido[4,3-b]indol-5(2H)-yl)prop-1-en-2-yl)thiazole (Compound No. 383)

8-Chloro-2,3,4,5-tetrahydro-2-methyl-1H-pyrido[4,3-b]indole (110 mg, 0.5 mmol) was dissolved in DMF (3 mL), potassium phosphate (212.4 mg, 1 mmol), copper (I) iodide (9.5 mg, 0.05 mmol) and L-proline (11.51 mg, 0.1 mmol) were added. 2-(1-Bromoprop-1-en-2-yl)thiazole (122.4 mg, 0.6 mmol) was dissolved in DMF (2 mL) and the solution added dropwise to the reaction mixture. Nitrogen was purged for 2 min and the reaction mixture heated at 85° C. overnight (prolonged heating required in some cases). DMF was evaporated and water added. The precipitate obtained was filtered and the crude compound was purified by silica gel chromatography (100-200 mesh) using 0-3% MeOH:DCM as eluent. The compound was further purified through reverse phase purification. Yield: 9 mg. $^1$H NMR (CD$_3$OD, oxalate salt) δ (ppm): 7.90 (d, 1H), 7.65 (d, 2H), 7.55 (s, 1H), 7.22 (s, 2H), 4.55 (m, 2H), 3.70 (m, 2H), 3.18 (m, 2H), 3.10 (s, 3H), 2.10 (s, 3H).

Example 312

Preparation of (Z)-8-chloro-2-methyl-5-(2-(pyridin-4-yl)prop-1-enyl)-2,3,4,5-tetrahydro-1H-pyrido[4,3-b]indole (Compound No. 384)

4-(1-Bromoprop-1-en-2-yl)pyridine (346 mg, 1.75 mmol) was adsorbed in potassium phosphate (617 mg, 2.9 mmol) and DMF (5 mL) was added followed by copper (I) iodide (27 mg, 0.145 mmol) and L-proline (33 mg, 0.29 mmol). 8-Chloro-2,3,4,5-tetrahydro-2-methyl-1H-pyrido[4,3-b]indole (321 mg, 1.45 mmol) was added to the reaction mixture and nitrogen gas purged for 2 min. The reaction mixture was stirred at 100° C. for 12 h. The reaction mixture was cooled to RT and water (20 mL) was added. The compound was extracted with EtOAc (3×50 mL). The organic layer was washed with water (2×50 mL) and compound was purified through silica gel (100-200 mesh) using 0-5% MeOH:DCM as eluent and further purified through reverse phase HPLC. Yield: 46 mg. $^1$H NMR (DMSO, Di-HCl salt) δ (ppm): 8.60 (d, 2H), 7.55 (s, 1H), 7.50 (d, 2H), 7.30 (s, 1H), 7.12 (d, 1H), 7.02 (d, 1H), 4.50 (m, 1H), 4.20 (m, 1H), 3.60 (m, 1H), 3.38 (m, 1H), 2.85 (m, 2H), 2.80 (s, 3H), 2.36 (s, 3H).

Example 313

Preparation of (E)-8-chloro-2-methyl-5-(2-(5-methylpyrazin-2-yl)prop-1-enyl)-2,3,4,5-tetrahydro-1H-pyrido[4,3-b]indole (Compound No. 385)

8-Chloro 2-methyl-2,3,4,5-tetrahydro-1H-pyrido (4,3-b) indole (200 mg, 0.909 mmol), copper (I) iodide (17.2 mg, 0.09 mmol), L-proline (20.9 mg, 0.1818 mmol), Potassium phosphate tribasic (385 mg, 1.818 mmol) were charged in DMF (3 mL) and stirred for 5 min. 2-(2-bromo-1-methylvinyl))-5-methyl pyrazine (210 mg, 0.0.999 mmol) was added and nitrogen gas purged into the reaction mixture for a min. The resulting solution was stirred at RT for 5 min followed by heating at 90° C. for 14 h. After completion of the reaction, DMF was evaporated, water was added and the reaction mixture filtered. The crude product was purified by reverse phase HPLC to obtain 40 mg desired product. $^1$H NMR (CDCl$_3$, free base) δ (ppm): 8.70 (s, 1H), 8.50 (s, 1H), 7.58 (s, 1H), 7.40 (s, 1H), 7.18 (d, 1H), 7.10 (d, 1H), 3.90 (s, 2H), 3.10 (m, 2H), 3.0 (m, 2H), 2.75 (s, 3H), 2.60 (s, 3H), 2.05 (s, 3H).

Example 314

Preparation of (E)-2,8-dimethyl-5-(2-(5-methylpyrazin-2-yl)prop-1-enyl)-2,3,4,5-tetrahydro-1H-pyrido[4,3-b]indole (Compound No. 386)

2,8-Dimethyl-2,3,4,5-tetrahydro-1H-pyrido (4,3-b) indole (70 mg, 0.35 mmol), copper (I) iodide (6.6 mg, 0.035 mmol), L-proline (8.05 mg, 0.07 mmol), Potassium phosphate tribasic (148 mg, 0.7 mmol) were dissolved in DMF (3 mL) and stirred for 5 min. 2-(2-bromo-1-methyl-vinyl))-5-methyl pyrazine (81 mg, 0.385 mmol) was added and nitrogen gas purged into the reaction mixture for a min. The reaction mixture was stirred at RT for 5 min followed by heating at 90° C. for 14 h. After completion of the reaction, DMF was evaporated. Water was added to the reaction mixture and the mixture filtered to obtain the solid crude, which was purified by reverse phase HPLC to obtain 20 mg desired product. $^1$H NMR (CDCl$_3$, free base) δ (ppm): 8.70 (s, 1H), 8.50 (s, 1H), 7.60 (s, 1H), 7.24 (s, 1H), 7.05 (m, 2H), 3.80 (s, 2H), 2.90 (m, 4H), 2.64 (s, 3H), 2.62 (s, 3H), 2.42 (s, 3H), 2.14 (s, 3H).

Example 315

Preparation of (E)-2,8-dimethyl-5-(2-(thiophen-3-yl) prop-1-enyl)-2,3,4,5-tetrahydro-1H-pyrido[4,3-b] indole (Compound No. 387)

2,3,4,5-tetrahydro-2,8-dimethyl-1H-pyrido[4,3-b]indole (100 mg, 0.5 mmol) was dissolved in DMF (3 mL). potassium phosphate (212.4 mg, 1 mmol), Copper (I) iodide (9.5 mg, 0.05 mmol) and L-proline (11.51 mg, 0.1 mmol) were added. 3-(1-bromoprop-1-en-2-yl)thiophene (121.8 mg, 0.6 mmol) dissolved in DMF (2 mL) was added dropwise to the reaction mixture. Nitrogen was purged for 2 min and the reaction mixture heated at 85° C. overnight (prolonged heating required some cases). DMF was evaporated and water added to the reaction mixture. The precipitate obtained was filtered and purified through silica gel chromatography (100-200 mesh) using 0-3% MeOH:DCM as eluent. The compound was further purified through reverse phase purification. Yield: 80 mg. $^1$H NMR (CD$_3$OD, oxalate salt) δ (ppm): 7.60 (s, 1H), 7.50 (m, 2H), 7.30 (s, 1H), 7.18 (s, 1H), 7.10 (m, 2H), 4.55 (m, 2H), 3.70 (m, 2H), 3.10 (m, 5H), 2.42 (s, 3H), 1.95 (s, 3H).

Example 316

Preparation of (E)-8-chloro-2-methyl-5-(2-(thiophen-3-yl)prop-1-enyl)-2,3,4,5-tetrahydro-1H-pyrido [4,3-b]indole (Compound No. 388)

8-Chloro-2,3,4,5-tetrahydro-2-methyl-1H-pyrido[4,3-b] indole (110 mg, 0.5 mmol) was dissolved in DMF (3 mL). potassium phosphate (212.4 mg, 1 mmol), Copper (I) iodide (9.5 mg, 0.05 mmol) and L-proline (11.51 mg, 0.1 mmol) were added. 3-(1-bromoprop-1-en-2-yl)thiophene (121.8 mg, 0.6 mmol) dissolved in DMF (2 mL) was added dropwise to it. Nitrogen was purged for 2 min and the reaction mixture was heated at 85° C. overnight (prolonged heating required in some cases). DMF was evaporated and water added. The precipitate obtained was filtered and purified through silica gel chromatography (100-200 mesh) using 0-3% MeOH:DCM as eluent. The compound was further purified through reverse phase purification. Yield: 110 mg. $^1$H NMR (CD$_3$OD, oxalate salt) δ (ppm): 7.62 (s, 1H), 7.56 (m, 3H), 7.20 (s, 2H), 7.16 (s, 1H), 4.58 (s, 2H), 3.70 (m, 2H), 3.16 (m, 5H), 1.98 (s, 3H).

Example 317

Preparation of (S,E)-2,3,8-trimethyl-5-(2-(pyridin-4-yl)prop-1-enyl)-2,3,4,5-tetrahydro-1H-pyrido[4,3-b] indole (Compound No. 389)

This optically active compound was obtained by chiral HPLC separation of Compound No. 257. $^1$H NMR (D$_2$O, di-HCl salt) δ (ppm): 8.60 (d, 2H), 8.10 (d, 2H), 7.50 (s, 1H), 7.30 (s, 1H), 7.10 (m, 2H), 4.30 (m, 2H), 4.0 (m, 1H), 3.80 (m, 1H), 3.10 (m, 1H), 2.82 (s, 3H), 2.38 (s, 3H), 1.98 (s, 3H), 1.40 (dd, 3H).

Example 318

Preparation of (R,E)-2,3,8-trimethyl-5-(2-(pyridin-4-yl)prop-1-enyl)-2,3,4,5-tetrahydro-1H-pyrido[4,3-b]indole (Compound No. 390)

This optically active compound was obtained by chiral HPLC separation of Compound No. 257. $^1$H NMR (D$_2$O, di-HCl salt) δ (ppm): 8.60 (d, 2H), 8.10 (d, 2H), 7.50 (s, 1H), 7.30 (s, 1H), 7.10 (m, 2H), 4.30 (m, 2H), 3.95 (m, 1H), 3.75 (m, 1H), 3.10 (m, 1H), 2.82 (s, 3H), 2.30 (s, 3H), 1.98 (s, 3H), 1.40 (dd, 3H).

Example 319

Preparation of (S,E)-8-chloro-2,3-dimethyl-5-(2-(pyridin-4-yl)prop-1-enyl)-2,3,4,5-tetrahydro-1H-pyrido[4,3-b]indole (Compound No. 391)

This optically active compound was obtained by chiral HPLC separation of Compound No. 275. $^1$H NMR (D$_2$O, di-HCl salt) δ (ppm): 8.62 (d, 2H), 8.10 (d, 2H), 7.50 (s, 2H), 7.20 (m, 2H), 4.35 (m, 2H), 3.95 (m, 1H), 3.75 (m, 1H), 3.10 (m, 1H), 2.82 (s, 3H), 1.98 (s, 3H), 1.40 (dd, 3H).

Example 320

Preparation of (R,E)-8-chloro-2,3-dimethyl-5-(2-(pyridin-4-yl)prop-1-enyl)-2,3,4,5-tetrahydro-1H-pyrido[4,3-b]indole (Compound No. 392)

This optically active compound was obtained by chiral HPLC separation of Compound No. 275. $^1$H NMR (D$_2$O, di-HCl salt) δ (ppm): 8.62 (d, 2H), 8.10 (d, 2H), 7.50 (s, 2H), 7.20 (m, 2H), 4.35 (m, 2H), 3.95 (m, 1H), 3.75 (m, 1H), 3.10 (m, 1H), 2.82 (s, 3H), 1.98 (s, 3H), 1.40 (dd, 3H).

Example 321

Preparation of (E)-8-chloro-5-(2-(2,6-dimethylpyridin-4-yl)prop-1-enyl)-2-methyl-2,3,4,5-tetrahydro-1H-pyrido[4,3-b]indole (Compound No. 393)

8-Chloro-2,3,4,5-tetrahydro-2-methyl-1H-pyrido[4,3-b]indole (220 mg, 1 mmol) was dissolved in DMF and sodium hydride (120 mg, 3 mmol) was added. The reaction mixture was stirred for 10 min and 2,6-dimethyl-4-(2-methyloxiran-2-yl)pyridine (210.6 mg, 1.3 mmol) was added dropwise to the reaction mixture with constant stirring. The reaction mixture was stirred at RT overnight. The reaction mixture was poured on crushed ice and the precipitate obtained was filtered under vacuum; washed with water and hexane to obtain 1-(8-chloro-1,2,3,4-tetrahydro-2-methylpyrido[4,3-b]indol-5-yl)-2-(2,6-dimethylpyridin-4-yl)propan-2-ol (323 mg) which was dissolved in DCM (3 mL) and cooled to 0° C. Thionylchloride (3 mL) was added dropwise and the reaction mixture was allowed to cool to RT. The reaction mixture was then stirred at RT for 2 h. Thionylchloride was evaporated under vacuum by azeotropic distillation with DCM. 1N NaOH solution was added to basify (pH-12-13) the reaction mixture and the compound extracted with EtOAc (2×30 mL). The organic layer was concentrated under vacuum to get the crude desired product. The crude compound was further purified through reverse phase HPLC. Yield: 17 mg. $^1$H NMR (CD$_3$OD, Di-HCl salt) δ (ppm): 7.95 (s, 2H), 7.66 (s, 1H), 7.58 (s, 1H), 7.25 (m, 2H), 4.70 (m, 1H), 4.40 (m, 1H), 3.90 (m, 1H), 3.62 (m, 1H), 3.22 (m, 2H), 3.10 (s, 6H), 2.10 (s, 3H).

Example 322

Preparation of (E)-8-chloro-2-methyl-5-(2-(2-methylpyridin-4-yl)prop-1-enyl)-2,3,4,5-tetrahydro-1H-pyrido[4,3-b]indole (Compound No. 394)

1-(8-Chloro-1,2,3,4-tetrahydro-2-methylpyrido[4,3-b]indol-5-yl)-2-(2-methylpyridin-4-yl)propan-2-ol (150 mg, 0.4 mmol) in DCM (12 mL) and DMF (2 drops) was stirred at 0-10° C. Thionyl chloride (145 mg, 1.2 mmol) diluted in DCM (8 mL) was added dropwise and the RM stirred at RT for 2 h. The solvent was removed and the residue dried to obtain foamy solid. The solid was dissolved in NMP (2 mL), stirred for 5 min. Powdered KOH (141 mg, 2.52 mmol) was added to the reaction mixture, which was heated at 80° C. for 1 h. After completion of reaction, the reaction mixture was poured in water and the compound extracted with DCM (3×50 mL). The organic layer was washed with water, dried over sodium sulfate and concentrated under vacuum to obtain the crude product which was purified by reverse phase HPLC to obtain 20 mg of 8-chloro-2,3,4,5-tetrahydro-2-methyl-5-((E)-2-(2-methylpyridin-4-yl)prop-1-enyl)-1H-pyrido[4,3-b]indole as the free base. The free base was converted to HCl salt by treating with ethanolic HCl. $^1$H NMR (CD$_3$OD, Di-HCl salt) δ (ppm): 8.70 (d, 1H), 8.20 (s, 1H), 8.15 (d, 1H), 7.72 (s, 1H), 7.60 (s, 1H), 7.25 (m, 2H), 4.70 (m, 1H), 4.40 (m, 1H), 3.80 (m, 1H), 3.60 (m, 1H), 3.20 (m, 2H), 3.10 (s, 3H), 2.82 (s, 3H), 2.10 (s, 3H).

Example 323

Preparation of (E)-4-(8-chloro-5-(2-(pyridin-4-yl)prop-1-enyl)-3,4-dihydro-1H-pyrido[4,3-b]indol-2(5H)-yl)-1-(4-fluorophenyl)butan-1-ol (Compound No. 395)

4-(8-Chloro-3,4-dihydro-1H-pyrido[4,3-b]indol-2 (5H)-yl)-1-(4-fluorophenyl)butan-1-ol (200 mg, 0.538 mmol) was dissolved in DMF (5 mL). potassium phosphate (457 mg, 2.15 mmol), copper (I) iodide (10.22 mg, 0.054 mmol) and L-proline (12.4 mg, 0.108 mmol) were added. followed by addition of 4-(1-bromoprop-1-en-2-yl)pyridine (158.1 mg, 0.806 mmol). Nitrogen gas was purged for 2 min and the reaction mixture was heated at 85° C. overnight (prolonged heating required in some cases). DMF was evaporated, water (20 mL) added and the compound extracted with EtOAc (3×50 mL). The organic layer was washed with water (2×50 mL) and the desired compound purified through silica gel (100-200 mesh) using 0-10% MeOH:DCM as eluent. It was further purified through reverse phase HPLC. Yield: 5.4 mg (di HCL salt). $^1$H NMR (CD$_3$OD, Di-HCl salt) δ (ppm): 8.85 (d, 2H), 8.38 (d, 2H), 7.82 (s, 1H), 7.62 (s, 1H), 7.42 (t, 2H), 7.30 (s, 2H), 7.10 (t, 2H), 4.78 (m, 3H), 4.40 (m, 1H), 3.95 (m, 1H), 3.60 (m, 1H), 3.45 (t, 2H), 3.20 (m, 1H), 2.18 (s, 3H), 2.10-1.85 (m, 4H).

Example 324

Preparation of (E)-benzyl 8-chloro-5-(2-(pyridin-4-yl)prop-1-enyl)-3,4-dihydro-1H-pyrido[4,3-b]indole-2(5H)-carboxylate (Compound No. 396)

4-(1-Bromoprop-1-en-2-yl)pyridine (237 mg, 1.2 mmol) was dissolved in DMF and potassium phosphate (424 mg, 2 mmol) was added followed by the addition of copper (I)iodide (19 mg, 0.1 mmol) and L-proline (23 mg, 0.2 mmol). Benzyl 8-chloro-3,4-dihydro-1H-pyrido[4,3-b]indole-2 (5H)-carboxylate (340 mg, 1 mmol) was added and nitrogen gas purged for 2 min. The reaction mixture was heated at 80° C. overnight. The reaction mixture was cooled to RT and water (20 mL) was added. The compound was extracted with EtOAc (3×50 mL). The organic layer was washed with water (2×50 mL) and compound was purified through reverse phase HPLC. Yield: 13.4 mg. $^1$H NMR (CDCl$_3$, free base) δ (ppm): 8.64 (d, 2H), 7.25-7.15 (m, 8H), 7.18 (d, 1H), 7.05 (m, 2H), 5.20 (s, 2H), 4.70 (s, 2H), 3.90 (m, 2H), 2.78 (m, 2H), 1.98 (s, 3H).

Example 325

Preparation of (Z)-8-chloro-5-(2-(4-fluorophenyl)prop-1-enyl)-2-methyl-2,3,4,5-tetrahydro-1H-pyrido[4,3-b]indole (Compound No. 397)

1-(1-Bromoprop-1-en-2-yl)-4-fluorobenzene (511.2 mg, 2.4 mmol) was dissolved in DMF. Potassium phosphate (848 mg, 4 mmol) was added followed by the addition of copper (I)iodide (38 mg, 0.2 mmol) and L-proline (46 mg, 0.4 mmol). 8-chloro-2,3,4,5-tetrahydro-2-methyl-1H-pyrido[4, 3-b]indole (440 mg, 2 mmol) was added to the reaction mixture and nitrogen gas purged for 2 min. The reaction mixture was heated at 85° C. overnight. The reaction mixture was cooled to RT and ice water was added. Solid mass was filtered under vacuum and crude purified by silica gel chromatography using 0-3% MeOH:DCM as eluent. Two isomers were further purified through reverse phase HPLC and peak 1 was submitted as the final compound. Yield: 120 mg. $^1$H NMR (DMSO, HCl salt) δ (ppm): 7.50 (s, 1H), 7.10-6.95 (m, 6H), 6.82 (s, 1H), 4.50 (m, 1H), 4.20 (m, 1H), 3.60 (m, 2H), 2.85 (s, 3H), 2.80 (m, 2H), 2.25 (s, 3H).

Example 326

Preparation of (E)-8-chloro-2-(3-(2-(4-fluorophenyl)-1,3-dioxolan-2-yl)propyl)-5-(2-(pyridin-4-yl)prop-1-enyl)-2,3,4,5-tetrahydro-1H-pyrido[4,3-b]indole (Compound No. 398)

8-Chloro-2-(3-(2-(4-fluorophenyl)-1,3-dioxolan-2-yl)propyl)-2,3,4,5-tetrahydro-5-((E)-2-(pyridin-4-yl)prop-1-enyl)-1H-pyrido[4,3-b]indole (207 mg, 0.5 mmol) along with CuI (9.5 mg, 0.05 mmol), L-proline (11.5 mg, 0.1 mmol), potassium phosphate (212 mg, 1 mmol) and 4-(1-bromoprop-1-en-2-yl)pyridine (0.285 mg, 1.44 mmol) were charged in DMF (5 mL) and nitrogen gas was purged into the reaction mixture for 2 min. The reaction mixture was heated to 85° C. over night. Ice water (4-5 mL) was added and solid mass was filtered to obtain the crude product which was purified by column chromatography by Silica gel (100-200 mesh) using 0-3% MeOH:DCM as eluent. The purified product was further purified by reverse phase HPLC. Yield: 7 mg (oxalate salt). $^1$H NMR (CD$_3$OD, free base) δ (ppm): 8.58 (d, 2H), 7.70 (d, 2H), 7.50 (m, 2H), 7.42 (s, 1H), 7.30 (s, 1H), 7.12 (s, 2H), 7.05 (t, 2H), 4.60 (s, 2H), 4.05 (t, 2H), 3.78 (t, 2H), 3.70 (s, 2H), 2.90 (m, 2H), 2.82 (m, 2H), 2.64 (m, 2H), 2.0 (s, 3H), 1.90 (m, 2H).

Example 327

Preparation of (E)-5-(2-(2,6-dimethylpyridin-4-yl)prop-1-enyl)-2,8-dimethyl-2,3,4,5-tetrahydro-1H-pyrido[4,3-b]indole (Compound No. 399)

2,3,4,5-Tetrahydro-2,8-dimethyl-1H-pyrido[4,3-b]indole (200 mg, 1 mmol) was dissolved in DMF and sodium hydride (120 mg, 3 mmol) was added. The reaction mixture was stirred for 10 min and 2,6-dimethyl-4-(2-methyloxiran-2-yl)pyridine (210.6 mg, 1.3 mmol) was added dropwise to it with constant stirring. The reaction mixture was stirred at RT overnight. The reaction mixture was poured on crushed ice and the precipitate obtained was filtered under vacuum; washed with water and hexane to obtain 1-(1,2,3,4-tetrahydro-2,8-dimethylpyrido[4,3-b]indol-5-yl)-2-(2,6-dimethylpyridin-4-yl)propan-2-ol (260 mg), which was dissolved in DCM (3 mL) and cooled to 0° C. Thionylchloride (3 mL) was added dropwise to it and the reaction mixture cooled to RT. The reaction mixture was stirred at RT for 2 h. Thionylchloride was evaporated under vacuum by azeotropic distillation with DCM. 1N NaOH solution was added to basify (pH-12-13) the reaction mixture and extracted with EtOAc (40 mL×2). The organic layer was concentrated under vacuum to get the desired product. The crude compound was further purified through reverse phase HPLC. Yield: 13 mg (HCl salt). $^1$H NMR (CD$_3$OD, Di-HCl salt) δ (ppm): 8.0 (s, 2H), 7.70 (s, 1H), 7.30 (s, 1H), 7.10 (s, 2H), 4.76 (d, 1H), 4.40 (d, 1H), 3.90 (m, 1H), 3.60 (m, 1H), 3.28 (m, 1H), 3.20 (m, 1H), 3.16 (s, 3H), 2.80 (s, 6H), 2.42 (s, 3H), 2.10 (s, 3H).

Example 328

Preparation of (E)-2-(3-methoxypropyl)-8-methyl-5-(2-(pyridin-4-yl)prop-1-enyl)-2,3,4,5-tetrahydro-1H-pyrido[4,3-b]indole (Compound No. 400)

1-[2-(3-Methoxy-propyl)-8-methyl-1,2,3,4-tetrahydro-pyrido[4,3-b]indol-5-yl]-2-pyridin-4-yl-propan-2-ol (550 mg, 1.39 mmol) was dissolved in thionyl chloride (5 mL), stirred at RT for 1 h. Progress of the reaction was monitored by TLC/LCMS. After completion of the reaction, excess thionyl chloride was evaporated under vacuum. The solid mass obtained was neutralized with aqueous sodium bicarbonate and the desired compound extracted with EtOAc (100 mL×2). The organic layer was dried over anhydrous sodium sulfate, concentrated under vacuum to obtain crude product, which was purified by silica gel column chromatography (100-200 mesh) using MeOH:DCM (0-10%) as eluent followed by reverse phase HPLC to obtain 35 mg of 2-(3-Methoxy-propyl)-8-methyl-5-(2-pyridin-4-yl-propenyl)-2,3,4,5-tetrahydro-1H-pyrido[4,3-b]indole. $^1$H NMR (CDCl$_3$, free base) δ (ppm): 8.62 (d, 2H), 7.42 (d, 2H), 7.22 (s, 1H), 7.10 (s, 1H), 7.0 (s, 2H), 3.80 (s, 2H), 3.50 (t, 2H), 3.36 (s, 3H), 2.92 (m, 2H), 2.78 (m, 4H), 2.42 (s, 3H), 2.02 (s, 3H), 1.95 (m, 2H). $^1$H NMR (CD$_3$OD oxalate salt) δ (ppm): 8.82 (d, 2H), 8.30 (d, 2H), 7.80 (s, 1H), 7.38 (s, 1H), 7.16 (s, 2H), 4.40 (m, 1H), 3.98 (m, 1H), 3.60 (m, 4H), 3.50 (t, 2H), 3.40 (s, 3H), 3.25 (m, 2H), 2.42 (s, 3H), 2.20 (m, 2H), 2.18 (s, 3H).

Example 329

Preparation of (E)-8-methyl-5-(2-(pyridin-4-yl)prop-1-enyl)-2,3,4,5-tetrahydro-1H-pyrido[4,3-b]indole (Compound No. 401)

To a solution of (E)-2-allyl-8-methyl-5-(2-(pyridin-4-yl) prop-1-enyl)-2,3,4,5-tetrahydro-1H-pyrido[4,3-b]indole in dry degassed DCM (2.5 mL per mmol of amine) was added the catalyst (tetrakis(triphenylphosphine) palladium (0.01 molar equiv per allyl group to be removed) and N,N'-dimethylbarbituric acid (3 equiv per allyl group) under Argon. The usually homogenous mixture was stirred at RT for 3-4 h. DCM was removed under vacuum and replaced by ether. The ethereal mixture was extracted twice with small volumes of saturated aqueous K$_2$CO$_3$, dried over anhydrous sodium sulfate and evaporated under reduced pressure. $^1$H NMR (CD$_3$OD, TFA salt) δ (ppm): 8.78 (d, 2H), 8.22 (d, 2H), 7.70 (s, 1H), 7.34 (s, 1H0, 7.15 (s, 2H), 4.46 (s, 2H), 3.64 (t, 2H), 3.10 (t, 2H), 2.44 (s, 3H), 2.12 (s, 3H).

Example 330

Preparation of (E)-8-chloro-5-(2-(pyridin-4-yl)prop-1-enyl)-2,3,4,5-tetrahydro-1H-pyrido[4,3-b]indole (Compound No. 402)

To a solution of the (E)-2-allyl-8-chloro-5-(2-(pyridin-4-yl)prop-1-enyl)-2,3,4,5-tetrahydro-1H-pyrido[4,3-b]indole in dry degassed DCM (2.5 mL per mmol of amine) was added the catalyst (tetrakis(triphenylphosphine) palladium (0.01 molar equiv per allyl group to be removed)) and N,N'-dimethylbarbituric acid (3 equiv per allyl group) under argon. The usually homogenous mixture was stirred at RT for 3-4 h. DCM was removed under vacuum and replaced by ether. The ethereal mixture was extracted twice with small volumes of saturated aqueous K2CO3, dried over anhydrous sodium sulfate and evaporated under reduced pressure. $^1$H NMR (CD$_3$OD, Oxalate salt) δ (ppm): 8.62 (d, 2H), 7.78 (d, 2H), 7.58 (s, 1H), 7.38 (s, 1H), 7.24 (s, 2H), 4.50 (s, 2H), 3.65 (m, 2H), 3.10 (m, 2H), 2.02 (s, 3H).

Example 331

Preparation of (E)-2,8-dimethyl-5-(3-(pyridin-4-yl) but-2-en-2-yl)-2,3,4,5-tetrahydro-1H-pyrido[4,3-b] indole (Compound No. 403)

4-(3-Bromobut-2-en-2-yl)pyridine (127 mg, 0.59 mmol) was dissolved in DMF (5 mL) and potassium phosphate (212 mg, 1 mmol) was added followed by copper (I) iodide (9.5 mg, 0.05 mmol) and L-proline (11.5 mg, 0.1 mmol). 2,3,4,5-tetrahydro-2,8-dimethyl-1H-pyrido[4,3-b]indole (100 mg, 0.5 mmol) was added and nitrogen gas purged for 2 min. The reaction mixture was stirred at 85° C. overnight. Water was added and the reaction mixture filtered to obtain the solid mass under vacuum. The crude product was purified on silica gel (100-200 mesh) using 0-10% MeOH: DCM as eluent. The compound was further purified through reverse phase chromatography. Yield: 5 mg (TFA salt). $^1$H NMR (CD$_3$OD, free base) δ (ppm): 8.60 (d, 2H), 7.50 (d, 2H), 7.24 (s, 1H), 7.12 (d, 1H), 6.99 (d, 1H), 3.78 (s, 2H), 2.98 (m, 2H), 2.90 (m, 2H), 2.60 (s, 3H), 2.42 (s, 3H), 1.92 (s, 3H), 1.66 (s, 3H).

Example 332

Preparation of (E)-4-(8-chloro-5-(2-(pyridin-4-yl) prop-1-enyl)-3,4-dihydro-1H-pyrido[4,3-b]indol-2 (5H)-yl)-2-methylbutan-2-ol (Compound No. 404)

4-(8-Chloro-1,3,4,5-tetrahydro-pyrido[4,3-b]indol-2-yl-) 2-methyl butan-2-ol (100 mg, 0.341 mmol), 4-(2-bromo-1-methyl-)vinyl pyridine (81 mg, 0.409 mmol), L-proline (8 mg, 0.069 mmol), copper (I) iodide (7 mg, 0.036 mmol), potassium phosphate (144 mg, 0.677 mmol) in DMF (2.0 mL) were charged together and nitrogen gas was purged into it. The reaction mixture was heated at 95° C. overnight and the reaction monitored by TLC/LCMS. The reaction mixture was diluted with 20 mL water and extracted with DCM (20 mL×3). The organic layer was dried over sodium sulfate and concentrated under vacuum to obtain the crude product which was purified by reverse phase HPLC to obtain 40 mg 4-(8-chloro-3,4-dihydro-5-((E)-2-(pyridin-4-yl)prop-1-enyl)-1H-pyrido[4,3-b]indol-2 (5H)-yl)-2-methylbutan-2-ol as the free base. The free base compound was converted to HCl salt by treated with ethanolic HCl. $^1$H NMR (CD$_3$OD, HCl salt) δ (ppm): 8.84 (d, 2H), 8.38 (d, 2H), 7.80 (s, 1H), 7.62 (s, 1H), 7.24 (s, 2H), 4.80 (m, 2H), 4.42 (m, 1H), 3.98 (m, 1H), 3.56 (m, 2H), 3.24 (m, 2H), 2.16 (s, 3H), 2.05 (m, 2H), 1.35 (s, 6H).

Example 333

Preparation of (E)-2-allyl-8-methyl-5-(2-(pyridin-4-yl)prop-1-enyl)-2,3,4,5-tetrahydro-1H-pyrido[4,3-b] indole (Compound No. 405)

4-(2-Bromo-1-methyl-vinyl)-pyridine (2.5 g, 13 mmol) and potassium phosphate (4.2 g, 20 mmol) were stirred for 5 min. DMF (20 mL) was added and the solution stirred for 5 min followed by addition of L-proline (230 mg, 2.0 mmol) and cuprous iodide (190 mg, 1.0 mmol). N$_2$ gas was bubbled into the reaction mixture, and 2-Allyl-8-methyl-2,3,4,5-tetrahydro-1H-pyrido[4,3-b]indole (2.0 g, 10 mmol) was added. The reaction mixture was heated at 120° C. for 16 h. After completion of reaction (as monitored by TLC) the mixture was concentrated under vacuum and diluted with water. The compound was extracted with EtOAc (4×100 mL) and organic layer dried over sodium sulfate, concentrated under vacuum under vacuum. The crude product was purified by column chromatography [Eluent: 2% MeOH in DCM]. $^1$H NMR (CD$_3$OD, HCl salt) δ (ppm): 8.82 (d, 2H), 8.38 (d, 2H), 7.82 (s, 1H), 7.39 (s, 1H), 7.18 (s, 2H), 6.15 (m, 1H), 5.70 (m, 2H), 4.75 (m, 1H), 4.40 (m, 1H), 4.05 (d, 2H), 3.98 (m, 1H), 3.60 (m, 1H), 3.25 (m, 1H), 3.20 (m, 1H), 2.42 (s, 3H), 2.18 (s, 3H).

Example 334

Preparation of (E)-2-allyl-8-chloro-5-(2-(pyridin-4-yl)prop-1-enyl)-2,3,4,5-tetrahydro-1H-pyrido[4,3-b] indole (Compound No. 406)

In a 100 mL screw-cap bottle, potassium phosphate tribasic (1.75 g, 8.25 mmol) was taken. 4-(2-Bromo-1-methyl-vinyl)-pyridine (1.1 g, 5.55 mmol) was added under nitrogen at RT. DMF (15 mL) was added and nitrogen was purged into it for 1-2 min. L-proline, (140 mg, 1.21 mmol), copper Iodide (235 mg, 1.21 mmol), and 2-allyl-8-chloro-2,3,4,5-tetrahydro-1H-pyrido[4,3-b]indole (1 g, 4.06 mmol) were added one by one with nitrogen purging. The screw-cap bottle was closed tightly and the contents heated to 120° C. for 12 h. The reaction was monitored by TLC. The reaction mixture was cooled at RT. DMF was evaporated under vacuum, residue diluted with water (100 mL) and the compound extracted with EtOAc (3×50 mL). The combined organic layers were washed with water (200 mL×3), dried over anhydrous sodium sulfate and concentrated under vacuum to obtain the crude, which was subjected to chromatography (100-200 mesh silica gel and 3% MeOH in DCM as eluent) and recrystallized in ether:hexane (10:90 ratio) to obtain 380 mg of 2-Allyl-8-chloro-5-(2-pyridin-4-yl-propenyl)-2,3,4,5-tetrahydro-1H-pyrido[4,3-b]indole. $^1$H NMR (CD$_3$OD, HCl salt) δ (ppm): 8.84 (d, 2H), 8.38 (d, 2H), 7.82 (s, 1H), 7.60 (s, 1H), 7.24 (s, 2H), 6.10 (m, 1H), 5.70 (m, 2H), 4.75 (m, 2H), 4.40 (m, 1H), 4.05 (d, 2H), 4.0 (m, 1H), 3.60 (m, 1H), 3.25 (m, 1H), 2.18 (s, 3H).

Example 335

Preparation of 8-chloro-5-(2,2-diphenylvinyl)-2-methyl-2,3,4,5-tetrahydro-1H-pyrido[4,3-b]indole (Compound No. 407)

A solution of 2-(8-chloro-2-methyl-1,2,3,4-tetrahydro-pyrido[4,3-b]indol-5-yl)-1,1-diphenyl-ethanol (100 mg, 0.24 mmol) in DCM (5 mL) and DMF (2 drops) was stirred at 0-10° C. Thionyl chloride (1.5 mL, 20.67 mmol) was added and the reaction mixture was stirred at RT for 2 h. The solvent was removed under vacuum to obtain the crude yellow solid. 1N NaOH (10 mL) was added to the reaction mixture and the compound extracted with EtOAc (2×20 mL). The organic layer was dried over anhydrous sodium sulfate, concentrated under vacuum to obtain the crude product (100 mg) which was purified by column chromatography on silica gel (100-200 mesh) [Eluent: 0-2.5% MeOH and DCM] to yield 35 mg product which was converted to HCL salt. $^1$H NMR (CD$_3$OD, HCl salt) δ (ppm): 7.46-7.40 (m, 6H), 7.25-7.16 (m, 5H), 7.10 (d, 1H), 6.98 (d, 2H), 4.62 (d, 1H), 4.30 (d, 1H), 3.70 (m, 1H), 3.40 (m, 1H), 3.0 (s, 3H), 2.90 (m, 2H).

Example 336

Preparation of (Z)-2,8-dimethyl-5-(1-phenylprop-1-enyl)-2,3,4,5-tetrahydro-1H-pyrido[4,3-b]indole (Compound No. 408)

Iodo benzene (0.5 g, 2.4 mmol) and 2,8-dimethyl-5-(prop-1-enyl)-2,3,4,5-tetrahydro-1H-pyrido[4,3-b]indole (588 mg, 2.4 mmol) were charged in triethanolamine (4 mL). Palladium (II)acetate (5 mg, 0.024 mmol) was added and stirred at 100° C. for 14 h. The reaction was monitored by TLC and LCMS. After completion of the reaction, water was added. The desired compound was extracted with diethyl ether twice. The organic layer was dried over anhydrous sodium sulfate and evaporated under reduced pressure. The crude product was purified by column chromatography to afford 0.3 g of product. $^1$H NMR (CD$_3$OD, TFA salt) δ (ppm): 7.24 (s, 1H), 7.18 (m, 3H), 6.96-6.82 (m, 4H), 6.62 (m, 1H), 4.66 (m, 1H), 4.30 (m, 1H), 3.64 (m, 1H), 3.42 (m, 1H), 3.0 (s, 1H), 2.80 (m, 1H), 2.60 (m, 1H), 2.36 (s, 3H), 1.50 (d, 3H).

Example 337

Preparation of 5-(2,2-diphenylvinyl)-2,8-dimethyl-2,3,4,5-tetrahydro-1H-pyrido[4,3-b]indole (Compound No. 409)

A solution of 2-(2,8-Dimethyl-1,2,3,4-tetrahydro-pyrido [4,3-b]indol-5-yl)-1,1-diphenyl-ethanol (100 mg, 0.25 mmol) in DCM (5 mL) and DMF (2 drops) was stirred at 0-10° C. Thionyl chloride (1.55 mL, 21.46 mmol) was added and the reaction mixture was stirred at RT for 2.5 h. The solvent was removed under vacuum to obtain crude yellow solid. 1N NaOH (10 mL) was added to the reaction mixture and the desired compound extracted with EtOAc (20 mLX$^2$). The organic layer was dried over anhydrous sodium sulfate, concentrated under vacuum to obtain the crude product (90 mg) which was purified by column chromatography on silica gel (100-200 mesh) using eluent 0-3% MeOH and DCM to obtain 15 mg product which was converted to HCL salt. $^1$H NMR (CD$_3$OD, HCl salt) δ (ppm): 7.40 (m, 5H), 7.22-7.16 (m, 6H), 6.98 (m, 3H), 4.62 (d, 1H), 4.30 (m, 1H), 3.62 (m, 1H), 3.36 (m, 1H), 2.98 (s, 3H), 2.80 (m, 2H), 2.40 (s, 3H).

Example 338

Preparation of (E)-5-(2-(3,5-dichlorophenyl)prop-1-enyl)-2,8-dimethyl-2,3,4,5-tetrahydro-1H-pyrido[4,3-b]indole (Compound No. 410)

1-(2-Bromo-1-methyl-vinyl)-3,5-dichloro-benzene (315 mg, 1.2 mmol) was dissolved in DMF (2 mL) and potassium phosphate (414 mg, 2 mmol) was added followed by CuI (19 mg, 0.1 mmol), L-Proline (23 mg, 0.2 mmol) and 2,8-Dimethyl-2,3,4,5-tetrahydro-1H-pyrido[4,3-b]indole (0.2 g, 1 mmol). Nitrogen was purged in the reaction mixture for 5 min and the contents stirred at 85° C. overnight. The reaction mixture was poured into ice water (10 mL) to get the solid mass which was filtered off under vacuum. The residue obtained was purified through reverse phase HPLC to get desired product. $^1$H NMR (CD$_3$OD, oxalate salt) δ (ppm): 7.80 (s, 1H), 7.50 (s, 2H), 7.38 (s, 1H), 7.20 (s, 1H), 7.0 (m, 2H), 4.42 (m, 2H), 3.60 (m, 2H), 3.05 (m, 2H), 3.0 (s, 3H), 2.38 (s, 3H), 1.82 (s, 3H).

Example 339

Preparation of (E)-8-methyl-5-(2-(pyridin-4-yl)prop-1-enyl)-3,4-dihydro-1H-pyrido[4,3-b]indole-2(5H)-carbaldehyde (Compound No. 411)

4-(2-Bromo-1-methyl-vinyl)-pyridine (2.5 g, 13 mmol) and potassium phosphate (4.2 g, 20 mmol) were stirred for 5 min. DMF (20 mL) was added and the contents stirred for 5 min. L-proline (230 mg, 2.0 mmol) and cuprous iodide (190 mg, 1.0 mmol) were added to the reaction mixture and N2 bubbled into the reaction mixture. 2-Allyl-8-methyl-2,3,4,5-tetrahydro-1H-pyrido[4,3-b]indole (2.0 g, 10 mmol) was added and the contents heated at 120° C. for 16 h. After completion of reaction (as monitored by TLC) the reaction mixture was concentrated under vacuum and diluted with water. The desired compound was extracted with EtOAc (4×100 mL). The organic layer was dried over sodium sulfate and concentrated under vacuum to obtain the crude product, which was purified by column chromatography [Eluent: 2% MeOH in DCM]. $^1$H NMR (DMSO, free base) δ (ppm): 8.60 (d, 2H), 8.20 (s, 1H), 7.64 (d, 2H), 7.42 (s, 1H), 7.32 (s, 1H), 7.10 (d, 1H), 6.98 (s, 1H), 4.60 (d, 2H), 3.80 (m, 2H), 2.80 (m, 2H), 2.41 (s, 3H), 1.96 (s, 3H).

Example 340

Preparation of (E)-8-methyl-2-phenethyl-5-(2-(pyridin-4-yl)prop-1-enyl)-2,3,4,5-tetrahydro-1H-pyrido[4,3-b]indole (Compound No. 412)

8-Methyl-5-(2-pyridin-4-yl-propenyl)-2,3,4,5-tetrahydro-1H-pyrido[4,3-b]indole (100 mg, 0.33 mmol) was dissolved in acetonitrile (1 mL) and (2-Bromo-ethyl)-benzene (62 mg, 0.33 mmol) was added to the reaction mixture. The contents were heated to 80° C. for 2 h. The reaction mixture was cooled to RT after 2 h and diluted with saturated bicarbonate (20 mL). The desired compound was extracted with EtOAc (2×50 mL). The organic layer dried over sodium sulfate and concentrated under vacuum to obtain the crude product which was purified by reverse phase chromatography to obtain 8.7 mg of 8-Methyl-2-phenethyl-5-(2-pyridin-4-yl-propenyl)-2,3,4,5-tetrahydro-1H-pyrido[4,3-b]indole. $^1$H NMR (CDCl$_3$, TFA salt) δ (ppm): 8.82 (d, 2H), 7.90 (d, 2H), 7.42 (s, 1H), 7.38-7.22 (m, 6H) 7.16 (d, 1H), 7.02 (d, 1H), 4.90 (m, 1H), 4.20 (m, 1H), 3.98 (m, 1H), 3.60-3.40 (m, 4H), 3.24 (m, 2H), 2.95 (m, 1H), 2.44 (s, 3H), 2.12 (s, 3H).

Example 341

Preparation of (Z)-5-(2-methoxy-2-(pyridin-4-yl)vinyl)-2,8-dimethyl-2,3,4,5-tetrahydro-1H-pyrido[4,3-b]indole (Compound No. 413)

2-(2,8-Dimethyl-1,2,3,4-tetrahydro-pyrido[4,3-b]indol-5-yl)-1-pyridin-4-yl-ethanone (100 mg) was dissolved in DMF (5 mL). Sodium hydride was added at once under nitrogen atmosphere followed by addition of methyl iodide. The contents were stirred at RT overnight. The reaction was monitored by LCMS. The reaction mixture was poured into 25 mL ice cold water and extracted with EtOAc (20 mL×3). The combined organic layers were given water washing (30 mL×2), dried over sodium sulfate and concentrated under vacuum to obtain the crude product, which was purified by reverse phase column chromatography to get 2 mg product as the TFA salt. $^1$H NMR (CD$_3$OD, TFA salt) δ (ppm): 8.78 (d, 2H), 8.22 (d, 2H), 7.70 (s, 1H), 7.34 (m, 2H), 7.18 (d, 1H), 4.80 (m, 1H), 4.40 (m, 2H), 3.80 (m, 1H), 3.60 (m, 1H), 3.40 (s, 3H), 3.26 (m, 2H), 3.16 (s, 3H), 2.44 (s, 3H).

Example 342

Preparation of (E)-4-(8-chloro-5-(2-(4-fluorophenyl)prop-1-enyl)-3,4-dihydro-1H-pyrido[4,3-b]indol-2(5H)-yl)-2-methylbutan-2-ol (Compound No. 414)

4-(8-Chloro-1,3,4,5-tetrahydro-pyrido[4,3-b]indol-2-yl-)2-methyl butan-2-ol (292 mg, 1.0 mmol), 1-((1-bromoprop-1-en-2-yl)-4-fluorobenzene (322 mg, 1.5 mmol), L-proline (23 mg, 0.2 mmol), Cuprous (I) iodide (19 mg, 0.1 mmol), potassium phosphate (636 mg, 3.0 mmol) in DMF (5 mL) were charged in a reaction vessel and nitrogen gas purged into the reaction mixture. The reaction mixture was heated at 95° C. overnight. The reaction was monitored by TLC/LCMS. The reaction mixture was diluted with water (20 mL) and the desired compound extracted with DCM (20 mL×3). The organic layer was dried over sodium sulfate and concentrated under vacuum to obtain the crude compound which was purified by reverse phase HPLC to obtain 280 mg of desired product as the free base. The free base compound was converted to HCl salt by treatment with ethanolic HCl. $^1$H NMR (CD$_3$OD, HCl salt) δ (ppm): 7.68 (m, 2H), 7.58 (s, 1H), 7.20 (m, 4H), 6.98 (s, 1H), 4.80 (m, 1H), 4.40 (m, 1H), 3.98 (m, 1H), 3.61 (m, 1H), 3.55 (m, 2H), 3.20 (m, 2H), 2.06 (m, 2H), 1.96 (s, 3H), 1.35 (s, 6H).

Example 343

Preparation of (E)-8-chloro-2-methyl-5-styryl-2,3,4,5-tetrahydro-1H-pyrido[4,3-b]indole (Compound No. 415)

8-Chloro-2-methyl-2,3,4,5-tetrahydro-1H-pyrido[4,3-b]indole (20 mg, 0.09 mmol), (2-Bromo-vinyl)-benzene (22 mg, 0.12 mmol), potassium phosphate (50 mg, 0.24 mmol), L-Proline (2 mg, 0.017 mmol), CuI (2 mg, 0.01 mmol) were stirred together in dry DMF (1 mL) at RT and N2 gas was purged into it for 5 min. The reaction mixture was heated in microwave at 100° C. for 5 h and then diluted with water. The desired compound was extracted with EtOAc, organic layer dried on anhydrous sodium sulfate, concentrated under vacuum to obtain crude compound which was purified by RHPLC to obtained 8-Chloro-2-methyl-5-styryl-2,3,4,5-tetrahydro-1H-pyrido[4,3-b]indole as an off-white solid. Yield: 11 mg. $^1$H NMR (DMSO, TFA salt) δ (ppm): 7.90 (d, 1H), 7.80 (d, 1H), 7.65 (m, 3H), 7.42 (t, 2H), 7.30 (m, 2H), 6.98 (d, 1H), 4.60-4.30 (m, 2H), 4.0 (m, 1H), 3.70 (m, 1H), 3.25 (m, 2H), 3.02 (s, 3H).

Example 344

Preparation of (Z)-5-(2-(6-bromopyridin-3-yl)-2-fluorovinyl)-2,8-dimethyl-2,3,4,5-tetrahydro-1H-pyrido[4,3-b]indole (Compound No. 416)

A mixture of 5-Ethynyl-2,8-dimethyl-2,3,4,5-tetrahydro-1H-pyrido[4,3-b]indole (113 mg, 0.50 mmol), 2,5-dibromopyridine (100 mg, 0.42 mmol), dichlorobistriphenylphosphine palladium (II) (8 mg, 0.012 mmol) and TBAF.3H$_2$O (396 mg, 1.26 mmol) were charged in a reaction vessel and heated at 80° C. for 5 min in microwave. After completion of reaction (as monitored by TLC & LCMS) the reaction mixture was poured into water (10 mL) and the desired compound extracted with EtOAc (20 mL×2). The organic layer was dried over sodium sulfate, concentrated under vacuum and purified by reverse phase chromatography to obtain 20 mg of 5-[2-(6-Bromo-pyridin-3-yl)-1-fluoro-vinyl]-2,8-dimethyl-2,3,4,5-tetrahydro-1H-pyrido[4,3-b]indole. $^1$H NMR (CD$_3$OD, HCl salt) δ (ppm): 8.62 (s, 1H), 8.08 (d, 1H), 7.78 (d, 1H), 7.41 (d, 1H), 7.24 (s, 1H), 7.16 (d, 1H), 6.10 (d, 1H), 4.62 (d, 2H), 4.30 (d, 1H), 3.80 (m, 1H), 3.50 (m, 2H), 3.05 (s, 3H), 2.38 (s, 3H).

Example 345

Preparation of (Z)-8-chloro-2-methyl-5-(2-(3-methylpyridin-4-yl)prop-1-enyl)-2,3,4,5-tetrahydro-1H-pyrido[4,3-b]indole (Compound No. 417)

1-(8-Chloro-1,2,3,4-tetrahydro-2-methylpyrido[4,3-b]indol-5-yl)-2-(3-methylpyridin-4-yl)propan-2-ol (300 mg, 0.813 mmol) in SOCl$_2$ (4 mL) was stirred at RT for 1 h. Excess SOCl$_2$ was removed under vacuum to obtain 8-chloro-5-[2-chloro-2-(3-methyl-pyridin-4-yl)-propyl]-2-methyl-2,3,4,5-tetrahydro-1H-pyrido[4,3-b]indole (305 mg, 0.78 mmol) which was dissolved in NMP (3 mL). Powdered KOH (308.14 mg, 5.50 mmol) was added and the contents heated at 80° C. for 2 h. The progress of the reaction was monitored by TLC and LCMS. After completion of reaction, The reaction mixture was poured on ice cold water. The aqueous phase was extracted with EtOAc (500 mL). The organic layer was washed with water (100 mL), dried over anhydrous sodium sulfate and concentrated under vacuum to obtain the crude product, which was subjected to reverse phase HPLC to yield 5 mg of the desired product. $^1$H NMR (CD$_3$OD, HCl salt) δ (ppm): 8.84 (s, 1H), 8.78 (d, 1H), 8.18 (d, 1H), 7.60 (s, 1H), 7.38 (d, 1H), 7.30 (d, 1H), 6.98 (s, 1H), 4.78 (d, 1H), 4.40 (d, 1H), 3.90 (m, 1H), 3.62 (m, 1H), 3.22 (m, 2H), 3.16 (s, 3H), 2.70 (s, 3H), 2.0 (s, 3H).

Example 346

Preparation of (Z)-5-(1-methoxy-1-(pyridin-4-yl)prop-1-en-2-yl)-2,8-dimethyl-2,3,4,5-tetrahydro-1H-pyrido[4,3-b]indole (Compound No. 418)

LAH (87 mg, 52.63 mmol) was taken in dry THF (10 mL) under inert atmosphere stirred for 10 min, 8-methyl-5-(2-methyl-1-oxo-1-(pyridin-4-yl)propan-2-yl)-3,4-dihydro-1H-pyrido[4,3-b]indole-2(5H)-carbaldehyde (0.33 g, 0.914 mmol) was added portionwise and stirred at RT for 1 h. The reaction was monitored by TLC. LAH was quenched with sat. sodium sulfate (aqueous) at 0° C., filtered the reaction mass. The filtrate was extracted with EtOAc, dried over anhydrous sodium sulfate and evaporated to dryness to afford 0.24 g of the title compound as a yellow sticky solid. $^1$H NMR (CDCl$_3$, free base) δ (ppm): 8.36 (d, 2H), 7.20 (s, 1H), 7.10 (d, 1H), 7.0 (d, 1H), 6.78 (d, 2H), 3.78 (s, 2H), 3.60 (s, 3H), 2.82 (m, 1H), 2.74 (m, 1H), 2.60 (m, 1H), 2.50 (s, 3H), 2.42 (s, 3H), 2.30 (m, 1H), 2.19 (s, 3H).

Example 347

Preparation of (E)-5-(2-fluoro-1,2-bis(6-methylpyridin-3-yl)vinyl)-2,8-dimethyl-2,3,4,5-tetrahydro-1H-pyrido[4,3-b]indole (Compound No. 419)

A mixture of 5-Ethynyl-2,8-dimethyl-2,3,4,5-tetrahydro-1H-pyrido[4,3-b]indole (156 mg, 0.69 mmol), 5-bromo-2-methyl-pyridine (100 mg, 0.58 mmol), dichlorobistriphenylphosphine palladium (II) (12 mg, 0.017 mmol) and TBAF.3H$_2$O (548 mg, 1.74 mmol) were added to a reaction vessel and the contents heated at 80° C. for 5 min in microwave. After completion of starting material (as monitored by TLC & LCMS), the reaction mixture was poured into water (25 mL) and the desired compound extracted with EtOAc (3×50 mL). The organic layer was dried over sodium sulfate, concentrated under vacuum and purified by reverse phase chromatography to obtain 27 mg of 2,8-dimethyl-5-(6-methyl-pyridin-3-ylethynyl)-2,3,4,5-tetrahydro-1H-pyrido[4,3-b]indole and 20 mg of 5-[1-fluoro-2,2-bis-(6-methyl-pyridin-3-yl)-vinyl]-2,8-dimethyl-2,3,4,5-tetrahydro-1H-pyrido[4,3-b]indole. $^1$H NMR (CDCl$_3$, free base) δ (ppm): 8.58 (s, 1H), 7.98 (s, 1H), 7.58 (d, 1H), 7.20 (d, 1H), 7.10 (d, 2H), 7.0 (d, 1H), 6.96 (d, 1H), 6.82 (d, 1H), 3.62 (m, 2H), 2.90-2.70 (m, 4H), 2.60 (s, 3H), 2.50 (s, 3H), 2.40 (s, 6H).

Example 348

Preparation of (E)-5-(2-fluoro-1,2-bis(6-methoxypyridin-3-yl)vinyl)-2,8-dimethyl-2,3,4,5-tetrahydro-1H-pyrido[4,3-b]indole (Compound No. 420)

A mixture of 5-Ethynyl-2,8-dimethyl-2,3,4,5-tetrahydro-1H-pyrido[4,3-b]indole (538 mg, 2.4 mmol), 5-Bromo-2-methoxy-pyridine (376 mg, 2.0 mmol), dichlorobistriphenylphosphine palladium (II) (42 mg, 0.059 mmol) and TBAF.3H$_2$O (1.8 g, 5.71 mmol) were added to a reaction vessel and the contents heated at 80° C. for 5 min in microwave. After completion of reaction (as monitored by TLC & LCMS) reaction mixture was poured into water (40 mL) and the desired compound extracted with EtOAc (3×40 mL). The organic layer was washed with water (3×30 mL), dried over sodium sulfate, concentrated under vacuum and purified by reverse phase chromatography to obtain 52 mg of 5-[1-fluoro-2,2-bis-(6-methoxy-pyridin-3-yl)-vinyl]-2,8-dimethyl-2,3,4,5-tetrahydro-1H-pyrido[4,3-b]indole and 41 mg of 5-(6-methoxy-pyridin-3-ylethynyl)-2,8-dimethyl-2,3,4,5-tetrahydro-1H-pyrido[4,3-b]indole. $^1$H NMR (CDCl$_3$, free base) δ (ppm): 8.22 (s, 1H), 7.70 (s, 1H), 7.60 (d, 1H), 7.16 (d, 2H), 7.02 (d, 1H), 6.98 (d, 1H), 6.78 (d, 1H), 6.42 (d, 1H), 3.98 (s, 3H), 3.80 (s, 3H), 3.64 (d, 1H), 3.58 (d, 1H), 2.82 (m, 1H), 2.78 (m, 2H), 2.58 (m, 1H), 2.50 (s, 3H), 2.40 (s, 3H).

Example 349

Preparation of (E)-5-(3-(4-fluorophenyl)but-2-en-2-yl)-2,8-dimethyl-2,3,4,5-tetrahydro-1H-pyrido[4,3-b]indole (Compound No. 421)

1-(3-Bromobut-2-en-2-yl)-4-fluorobenzene (250 mg, 1.2 mmol) was dissolved in DMF (5 mL). potassium phosphate (424 mg, 2 mmol) was added followed by copper (I) iodide (19 mg, 0.1 mmol) and L-proline (23 mg, 0.2 mmol). 2,3,4,5-tetrahydro-2,8-dimethyl-1H-pyrido[4,3-b]indole (200 mg, 1 mmol) was added and nitrogen gas was purged into the reaction mixture for 2 min. The contents were stirred at 85° C. overnight. Water (5 mL) was added and the solid mass was filtered under vacuum to obtain crude compound which was purified on silica gel (100-200 mesh) using 0-3% MeOH:DCM as eluent. The compound was further purified through reverse phase chromatography. Yield: 6 mg. $^1$H NMR (CD$_3$OD, HCl salt) δ (ppm): 7.42 (m, 2H), 7.30 (s, 1H), 7.20 (m, 3H), 7.10 (d, 1H), 4.70 (d, 1H), 4.40 (d, 1H), 3.90 (m, 1H), 3.62 (m, 1H), 3.25 (m, 1H), 3.16 (s, 3H), 3.10 (m, 1H), 2.42 (s, 3H), 1.94 (d, 3H), 1.64 (d, 3H).

Example 350

Preparation of (E)-2-(2-fluoroethyl)-8-methyl-5-(2-(pyridin-4-yl)prop-1-enyl)-2,3,4,5-tetrahydro-1H-pyrido[4,3-b]indole (Compound No. 422)

8-Methyl-5-(2-pyridin-4-yl-propenyl)-2,3,4,5-tetrahydro-1H-pyrido[4,3-b]indole (60 mg, 0.19 mmol) was dissolved in acetonitrile (1 mL). Potassium carbonate (82 mg, 0.9 mmol) and 1-Fluoro-2-iodo-ethane (45 mg, 0.25 mmol) were added and stirred at RT for 1 h. The reaction mixture was heated at 80° C. for 1 h. After 1 h the reaction mixture was cooled to RT, diluted with water (10 mL) and extracted with EtOAc (3×20 mL). The organic layer was dried over sodium sulfate and concentrated under vacuum to obtained 33 mg of desired product. $^1$H NMR (CD$_3$OD, oxalate salt) δ (ppm): 8.62 (d, 2H), 7.80 (d, 2H), 7.42 (s, 1H), 7.36 (s, 1H), 7.10 (m, 2H), 5.05 (m, 1H), 4.92 (m, 1H), 4.65 (s, 2H), 3.82 (m, 3H), 3.78 (m, 1H), 3.20 (m, 2H), 2.42 (s, 3H), 2.05 (s, 3H).

Example 351

Preparation of (E)-4,4'-(1-(2,8-dimethyl-3,4-dihydro-1H-pyrido[4,3-b]indol-5(2H)-yl)-2-fluoroethene-1,2-diyl)bis(2-fluoro-N-methylbenzamide) (Compound No. 423)

A mixture of 5-ethynyl-2,8-dimethyl-2,3,4,5-tetrahydro-1H-pyrido[4,3-b]indole (268 mg, 1.2 mmol), 4-bromo-2-fluoro-N-methyl-benzamide (230 mg, 1.0 mmol), dichlorobistriphenyl phosphinepalladium (II) (21 mg, 0.03 mmol) and TBAF.3H$_2$O (945 mg, 3.0 mmol) were added to a reaction vessel and the contents heated at 80° C. for 5 min in microwave. After completion of reaction (as monitored by TLC & LCMS), the reaction mixture was poured into water (25 mL) and the compound extracted with EtOAc (3×60 mL). The combined organic layers were dried over sodium sulfate, concentrated under vacuum and purified by reverse phase chromatography to obtain 22 mg of 4-[2-(2,8-dimethyl-1,2,3,4-tetrahydro-pyrido[4,3-b]indol-5-yl)-2-fluoro-vinyl]-2-fluoro-N-methyl-benzamide and 63 mg of product. $^1$H NMR (CD$_3$OD, oxalate salt) δ (ppm): 8.30 (m, 1H), 8.80 (t, 1H), 7.50 (t, 1H), 7.38-7.24 (m, 3H), 7.10 (d, 1H), 6.80 (m, 2H), 4.50 (m, 2H), 3.60 (m, 2H), 3.25 (m, 2H), 3.04 (s, 3H), 2.96 (d, 3H), 2.82 (s, 3H), 2.40 (s, 3H).

Example 352

Preparation of (Z)-4-(2-(2,8-dimethyl-3,4-dihydro-1H-pyrido[4,3-b]indol-5(2H)-yl)-1-fluorovinyl)-2-fluoro-N-methylbenzamide (Compound No. 424)

A mixture of 5-ethynyl-2,8-dimethyl-2,3,4,5-tetrahydro-1H-pyrido[4,3-b]indole (268 mg, 1.2 mmol), 4-bromo-2-fluoro-N-methyl-benzamide (230 mg, 1.0 mmol), dichlorobistriphenyl phosphinepalladium (II) (21 mg, 0.03 mmol) and TBAF.3H$_2$O (945 mg, 3.0 mmol) were added to a reaction vessel and the contents heated at 80° C. for 5 min in microwave. After completion of reaction (as monitored by TLC & LCMS), the reaction mixture was poured into water (25 mL) and the compound extracted with EtOAc (3×60 mL). The combined organic layers were dried over sodium sulfate, concentrated under vacuum and purified by reverse phase chromatography to obtain 22 mg of 4-[2-(2,8-dimethyl-1,2,3,4-tetrahydro-pyrido[4,3-b]indol-5-yl)-2-fluoro-vinyl]-2-fluoro-N-methyl-benzamide and 63 mg of product. $^1$H NMR (CD$_3$OD, TFA salt) δ (ppm): 7.80 (t, 1H), 7.55-7.42 (m, 3H), 7.36 (s, 1H), 7.18 (d, 1H), 6.20 (d, 1H), 4.75 (m, 2H), 4.40 (m, 1H), 3.90 (m, 1H), 3.60 (m, 2H), 3.18 (s, 3H), 2.94 (s, 3H), 2.42 (s, 3H).

Example 353

Preparation of (E)-5-(2-fluoro-1,2-di(pyridin-4-yl)vinyl)-2,8-dimethyl-2,3,4,5-tetrahydro-1H-pyrido[4,3-b]indole (Compound No. 425)

A mixture of 5-ethynyl-2,8-dimethyl-2,3,4,5-tetrahydro-1H-pyrido[4,3-b]indole (138 mg, 0.6 mmol), 4-bromopyridinehydrochloride (100 mg, 0.51 mmol), dichlorobistriphenyl phosphine palladium (II) (10 mg, 0.015 mmol) and TBAF.3H$_2$O (481 mg, 1.5 mmol) were added to a reaction vessel and the contents heated at 80° C. (exothermicity observed; temperature 140° C.) for 5 min in microwave. After completion of the reaction (as monitored by TLC & LCMS) reaction mixture was poured into water (20 mL) and saturated bicarbonate solution was added. The desired compound was extracted with EtOAc (3×20 mL). The organic layer was washed with water (2×20 mL), dried over sodium sulfate and concentrated under vacuum to obtain crude product which was purified by reverse phase HPLC. $^1$H NMR (CDCl$_3$, TFA salt) δ (ppm): 8.60 (d, 2H), 8.22 (d, 2H), 7.35 (d, 2H), 7.06 (s, 1H), 6.90 (d, 2H), 6.70 (d, 2H), 4.30 (m, 2H), 3.60 (m, 1H), 3.46 (m, 2H), 3.10 (m, 1H), 2.90 (s, 3H), 2.30 (s, 3H).

Example 354

Preparation of (Z)-5-(2-fluoro-2-(pyridin-4-yl)vinyl)-2,8-dimethyl-2,3,4,5-tetrahydro-1H-pyrido[4,3-b]indole (Compound No. 426)

A mixture of 5-ethynyl-2,8-dimethyl-2,3,4,5-tetrahydro-1H-pyrido[4,3-b]indole (138 mg, 0.6 mmol), 4-bromopyridinehydrochloride (100 mg, 0.51 mmol), dichlorobistriphenylphosphine palladium (II) (10 mg, 0.015 mmol) and TBAF.3H$_2$O (481 mg, 1.5 mmol) was added and heated at 80° C. (exothermicity observed; temperature 140° C.) for 5 min in microwave. After completion of reaction (as monitored by TLC & LCMS) reaction mixture was poured into water (20 mL) and saturated bicarbonate solution was added. The desired compound was extracted with EtOAc (3×20 mL) and the organic layer washed with water (2×20 mL), dried over sodium sulfate and concentrated under vacuum to obtain crude product that was purified by reverse phase HPLC. $^1$H NMR (CD$_3$OD, TFA salt) δ (ppm): 8.78 (d, 2H), 8.18 (d, 2H), 7.62 (d, 1H), 7.40 (s, 1H), 7.28 (d, 1H), 6.42 (d, 1H), 4.75 (m, 1H), 4.40 (m, 1H), 3.90 (m, 1H), 3.60 (m, 1H), 3.40 (m, 2H), 3.18 (s, 3H), 2.44 (s, 3H).

Example 355

Preparation of (E)-1-(8-methyl-5-(2-(pyridin-4-yl) prop-1-enyl)-3,4-dihydro-1H-pyrido[4,3-b]indol-2 (5H)-yl)propan-2-one (Compound No. 427)

8-Methyl-5-(2-pyridin-4-yl-propenyl)-2,3,4,5-tetrahydro-1H-pyrido[4,3-b]indole (50 mg, 0.165 mmol) was dissolved in 1 mL acetonitrile. Potassium carbonate (70 mg, 0.50 mmol) and chloroacetone (30 mg, 0.33 mmol) were added to the reaction mixture under nitrogen and the contents heated to 70° C. for 2 h. The reaction was monitored by TLC and LCMS. Acetonitrile was evaporated under vacuum and the reaction mixture diluted with water (10 mL). The desired compound was extracted with EtOAc (3×20 mL). The combined organic layers were washed with water (2×20 mL), dried over anhydrous sodium sulfate and concentrated under vacuum to obtain crude compound which was purified by column chromatography (Eluent: 3% MeOH in DCM) to obtain 19 mg of 1-[8-methyl-5-(2-pyridin-4-yl-propenyl)-1,3,4,5-tetrahydro-pyrido[4,3-b]indol-2-yl]-propan-2-one. $^1$H NMR (CD$_3$OD, oxalate salt) δ (ppm): 8.60 (d, 2H), 7.78 (d, 2H), 7.40 (s, 1H), 7.30 (s, 1H), 7.15 (m, 2H), 4.59 (s, 2H), 4.50 (s, 2H), 3.70 (m, 2H), 3.20 (m, 2H), 3.44 (s, 3H), 3.30 (s, 3H), 2.06 (s, 3H).

Example 356

Preparation of (E)-2,8-dimethyl-5-(1-phenylprop-1-en-2-yl)-2,3,4,5-tetrahydro-1H-pyrido[4,3-b]indole (Compound No. 428)

A solution of 2-(2,8-dimethyl-1,2,3,4-tetrahydro-pyrido [4,3-b]indol-5-yl)-1-phenyl-propan-1-ol (100 mg, 0.29 mmol) in DCM (5 mL) and DMF (2 drops) was stirred at 0-10° C. Thionyl chloride (0.8 mL, 11.02 mmol) was added and the reaction mixture stirred at RT for 2 h. The solvent was removed under vacuum to obtain the crude as a dark brown solid, which was dissolved in NMP (2 mL) and stirred for 5 min. Powdered KOH (167 mg, 2.99 mmol) was added to the reaction mixture and the contents heated at 85° C. for 45 min. After completion of reaction, the reaction mixture was poured in water and the desired compound extracted with EtOAc (3×100 mL). The organic layer was dried over anhydrous sodium sulfate, concentrated under vacuum to obtain the crude product (40 mg) which was purified by reverse phase HPLC to yield (Z)-2,8-Dimethyl-5-(1-methyl-2-phenyl-vinyl)-2,3,4,5-tetrahydro-1H-pyrido[4,3-b]indole (10 mg) and (E)-2,8-Dimethyl-5-(1-methyl-2-phenyl-vinyl)-2,3,4,5-tetrahydro-1H-pyrido[4,3-b]indole (12 mg) which were converted to their respective HCl salts. $^1$H NMR (CDCl$_3$, free base) δ (ppm): 7.40 (m, 3H), 7.30-7.20 (m, 4H), 6.98 (d, 1H), 6.60 (s, 1H), 3.76 (s, 2H), 2.60 (s, 3H), 2.44 (s, 3H), 2.30 (s, 3H).

Example 357

Preparation of (Z)-2,8-dimethyl-5-(1-phenylprop-1-en-2-yl)-2,3,4,5-tetrahydro-1H-pyrido[4,3-b]indole (Compound No. 429)

A solution of 2-(2,8-dimethyl-1,2,3,4-tetrahydro-pyrido [4,3-b]indol-5-yl)-1-phenyl-propan-1-ol (100 mg, 0.29 mmol) in DCM (5 mL) and DMF (2 drops) was stirred at 0-10° C. Thionyl chloride (0.8 mL, 11.02 mmol) was added and the reaction mixture was stirred at RT for 2 h. The solvent was removed under vacuum to obtain the crude as a dark brown solid; which was dissolved in NMP (2 mL). The contents were stirred for 5 min, powdered KOH (167 mg, 2.99 mmol) was added and the reaction mixture heated at 85° C. for 45 min. After completion of reaction, the reaction mixture was poured in water and extracted with EtOAc (3×100 mL). The organic layer was dried over anhydrous sodium sulfate, concentrated under vacuum to obtain the crude product (40 mg) which was purified by reverse phase HPLC to yield (Z)-2,8-dimethyl-5-(1-methyl-2-phenyl-vinyl)-2,3,4,5-tetrahydro-1H-pyrido[4,3-b]indole (10 mg) and (E)-2,8-Dimethyl-5-(1-methyl-2-phenyl-vinyl)-2,3,4,5-tetrahydro-1H-pyrido[4,3-b]indole (12 mg) which were converted to their respective HCl salts. $^1$H NMR (CDCl$_3$, free base) δ (ppm): 7.22 (s, 1H), 7.16 (d, 1H), 7.08 (m, 3H), 6.98 (d, 1H), 6.70 (m, 2H), 6.60 (s, 1H), 3.82 (m, 2H), 2.78-2.62 (m, 3H), 2.50 (s, 3H), 2.42 (s, 3H), 2.38 (m, 1H), 2.20 (s, 3H).

Example 358

Preparation of (Z)-5-(2-fluoro-2-(6-methoxypyridin-3-yl)vinyl)-2,8-dimethyl-2,3,4,5-tetrahydro-1H-pyrido[4,3-b]indole (Compound No. 430)

5-Ethynyl-2,8-dimethyl-2,3,4,5-tetrahydro-1H-pyrido[4, 3-b]indole (285 mg, 0.00127 mol) and 5-bromo-2-methoxypyridine (200 mg, 0.001063 mol), dichlorobistriphenylphosphine palladium (II) (20 mg, 0.0000285 mol) and TBAF.3H$_2$O (1 g, 0.00317 mol) were charged in a microwave tube. The reaction mixture was heated at 80° C. for 5 min in microwave. It was then cooled to RT. The reaction was monitored by TLC and LCMS. The reaction mixture was diluted with water (100 mL) and the compound extracted with EtOAc (3×30 mL). The combined organic layers were washed with water, dried over sodium sulfate and concentrated under vacuum to obtain the crude product, which was purified on neutral alumina (Eluent: 0-20%, Hexane/EtOAc). 2 mg of pure product was obtained as a liquid. $^1$H NMR (CDCl$_3$, free base) δ (ppm): 8.22 (s, 1H), 7.92 (d, 1H), 7.36 (d, 1H), 7.20 (s, 1H), 7.04 (d, 1H), 6.80 (d, 1H), 5.70 (d, 1H), 3.68 (s, 2H), 3.92 (m, 2H), 3.88 (m, 2H), 2.60 (s, 3H), 2.42 (s, 3H).

Example 359

Preparation of (E)-5-(2-(4-fluorophenyl)prop-1-enyl)-N,2-dimethyl-2,3,4,5-tetrahydro-1H-pyrido[4,3-b]indol-8-amine (Compound No. 431)

Palladium (II)acetate (314 mg, 1.4 mmol) and 2-(di-t-butylphosphino)biphenyl (418 mg, 1.4 mmol) were charged in a reaction bottle which was evacuated and backfilled with nitrogen. Toluene (10 mL) was added dropwise under nitrogen and stirred at RT overnight. The reaction mass was passed through basic alumina using 0-30% ether: hexane and triturated with pentane to yield 300 mg of brownish solid. 8-Chloro-5-(2-(4-fluorophenyl)prop-1-enyl)-2,3,4,5-tetrahydro-2-methyl-1H-pyrido[4,3-b]indole (50 mg, 0.282 mmol), sodium tert-butoxide (81.2 mg, 0.846 mmol), and palladacycle[palladium (II)acetate+2-(di-t-butylphosphino) biphenyl) (10.7 mg, 0.0282 mmol)] was charged in a reaction bottle which was evacuated and back filled with nitrogen for 5 min. Dry toluene (1 mL) was added under nitrogen atmosphere. Finally, 2M methyl amine in THF (0.39 mL, 0.198 mmol) was added and the contents heated at 100° C. overnight. The reaction mixture was filtered and washed with EtOAc (2×25 mL). The filtrate was concentrated under vacuum and purified by reverse phase chromatography to yield 10 mg of free base. $^1$H NMR (DMSO, oxalate salt) δ (ppm): 7.62 (d, 2H), 7.20 (d, 2H), 6.96 (d, 2H), 6.58 (d, 1H), 6.50 (s, 1H), 4.24 (m, 2H), 3.40 (m, 2H0, 2.95 (m, 2H), 2.88 (s, 3H), 2.64 (s, 3H), 1.82 (s, 3H).

Example 360

Preparation of (E)-N-butyl-5-(2-(4-fluorophenyl) prop-1-enyl)-2-methyl-2,3,4,5-tetrahydro-1H-pyrido [4,3-b]indol-8-amine (Compound No. 432)

Palladium (II)acetate (314 mg, 1.4 mmol) and 2-(di-t-butylphosphino)biphenyl (418 mg, 1.4 mmol) were charged in a reaction bottle which was evacuated and backfilled with nitrogen. Toluene (10 mL) was added dropwise under nitrogen and stirred at RT overnight. The reaction mixture was passed through basic alumina using 0-30% ether: hexane and triturated with pentane to get brownish solid. Yield: 300 mg. 8-Chloro-5-(2-(4-fluorophenyl)prop-1-enyl)-2,3,4,5-tetrahydro-2-methyl-1H-pyrido[4,3-b]indole (50 mg, 0.282 mmol), Sodium tert-butoxide (81.2 mg, 0.846 mmol), and palladacycle[palladium (II)acetate+2-(di-t-butylphosphino) biphenyl) (10.7 mg, 0.0282 mmol)] were charged in a reaction bottle which was evacuated and back filled with nitrogen for 5 min. Dry toluene (1 mL) was added under nitrogen atmosphere. Finally, butylamine (14.43 mg, 0.197 mmol) was added and the contents heated at 100° C. overnight. The reaction mixture was filtered and the precipitate washed with EtOAc (2×25 mL). The filtrate was concentrated under vacuum and purified by reverse phase chromatography to yield 15 mg of free base. $^1$H NMR (CD$_3$OD, free base) δ (ppm): 7.60 (m, 2H), 7.12 (t, 2H), 6.96 (d, 1H), 6.90 (s, 1H), 6.72 (s, 1H), 6.68 (d, 1H), 3.76 (s, 2H), 3.10 (t, 2H), 2.95 (m, 2H), 2.84 (m, 2H), 2.60 (s, 3H), 1.96 (s, 3H), 1.82 (q, 2H), 1.45 (q, 2H), 0.95 (t, 3H).

Example 361

Preparation of (E)-N,2-dimethyl-5-(2-(pyridin-4-yl) prop-1-enyl)-2,3,4,5-tetrahydro-1H-pyrido[4,3-b] indol-8-amine (Compound No. 433)

8-Chloro-2-methyl-5-(2-pyridin-4-yl-propenyl)-2,3,4,5-tetrahydro-1H-pyrido[4,3-b]indole (0.050 g, 0.123 mmol), sodium tertbutoxide (0.140 g, 0.738 mmol), palladium acetate (0.010 g, 0.049 mmol) and 2-di-tertbutylphosphino-2'-4'-6'-triisopropylbiphenyl (0.031 g, 0.0735 mmol) were charged in a reaction bottle which was evacuated and back filled with nitrogen for 5 min. Dry toluene (2 mL) was added under nitrogen atmosphere. Finally, 2M methyl amine in THF (0.5 mL) was added and the contents heated at 100° C. overnight. The reaction mixture was filtered, precipitate washed with EtOAc (25 mL×2). The filtrate was concentrated under vacuum and purified by reverse phase chromatography to yield 15 mg of free base. $^1$H NMR (CD$_3$OD, oxalate salt) δ (ppm): 8.58 (d, 2H), 7.62 (d, 2H), 7.30 (s, 1H), 7.04 (d, 1H), 6.76 (d, 2H), 4.40 (s, 2H), 3.60 (m, 2H), 3.10 (m, 2H), 3.05 (s, 3H), 2.80 (s, 3H), 2.02 (s, 3H).

Example 363

Preparation of (E)-4-(1-(2,8-dimethyl-3,4-dihydro-1H-pyrido[4,3-b]indol-5(2H)-yl)prop-1-en-2-yl)-N-methylbenzamide (Compound No. 435)

Thionyl chloride (1.5 mL, 20.67 mmol) was added to a solution of 4-[2-(2,8-dimethyl-1,2,3,4-tetrahydro-pyrido[4,3-b]indol-5-yl)-1-hydroxy-1-methyl-ethyl]-N-methyl-benzamide (130 mg, 0.33 mmol) and the reaction mixture stirred at RT for 30 min. The solvent was removed under vacuum to obtain the crude as a foamy solid, which was dissolved in NMP (3 mL). The reaction mixture was stirred for 5 min. Powdered KOH (186 mg, 3.32 mmol) was added and the contents heated at 80° C. for 20 min. After completion of reaction, the reaction mixture was poured in water and the desired compound extracted with EtOAc (3×40 mL). The organic layer was washed with water, concentrated under vacuum to obtain the crude product (100 mg) which was purified by reverse phase HPLC to yield 6.0 mg of 4-[2-(2,8-dimethyl-1,2,3,4-tetrahydro-pyrido[4,3-b]indol-5-yl)-1methyl-vinyl]-N-methyl-benzamide as the free base. $^1$H NMR (CDCl$_3$, free base) δ (ppm): 7.78 (d, 2H), 7.58 (d, 2H), 7.22 (s, 1H), 7.05 (m, 2H), 6.96 (s, 1H), 6.20 (bs, 1H), 4.0 (s, 2H), 3.16 (m, 2H), 3.05 (d, 3H), 2.90 (m, 2H), 2.70 (s, 3H), 2.42 (s, 3H), 1.99 (s, 3H).

Example 364

Preparation of (E)-4-(1-(2,8-dimethyl-3,4-dihydro-1H-pyrido[4,3-b]indol-5(2H)-yl)prop-1-en-2-yl)-N, N-dimethylbenzamide (Compound No. 436)

4-(1-Bromoprop-1-en-2-yl)-N,N-dimethylbenzamide (264 mg, 1 mmol) was dissolved in DMF (2 mL). Potassium phosphate (424 mg, 2 mmol) was added followed by copper (I) iodide (19 mg, 0.1 mmol) and L-proline (23 mg, 0.2 mmol). 2,3,4,5-Tetrahydro-2,8-dimethyl-1H-pyrido[4,3-b] indole (200 mg, 1 mmol) was added under nitrogen for 2 min. The reaction mixture was stirred at 85° C. overnight. Ice water (5 mL) was added and the resulting solid mass was filtered to obtain the crude compound which was purified on silica gel chromatography (100-200 mesh) using 0-7% MeOH:DCM as eluent. Yield: 60 mg. $^1$H NMR (CD$_3$OD, HCl salt) δ (ppm): 7.76 (d, 2H), 7.50 (d, 2H), 7.30 (s, 1H), 7.10 (m, 3H), 4.75 (d, 1H), 4.40 (d, 1H), 3.84 (m, 1H), 3.60 (m, 1H), 3.18 (m, 2H), 3.10 (d, 6H), 3.05 (s, 3H), 2.42 (s, 3H), 2.0 (s, 3H).

Example 365

Preparation of (E)-2-methyl-8-(4-methylpiperazin-1-yl)-5-(2-(pyridin-4-yl)prop-1-enyl)-2,3,4,5-tetrahydro-1H-pyrido[4,3-b]indole (Compound No. 437)

Palladium (II) acetate (314 mg, 1.4 mmol) and 2-(di-t-butylphosphino)biphenyl (418 mg, 1.4 mmol) were charged in a reaction bottle which was evacuated and backfilled with nitrogen. Toluene (10 mL) was added dropwise under nitrogen and stirred at RT overnight. The reaction mixture was passed through basic alumina using 0-30% ether: hexane and triturated with pentane to get brownish solid. Yield: 300 mg. 8-chloro-2,3,4,5-tetrahydro-2-methyl-5-(2-(pyridin-4-yl)prop-1-enyl)-1H-pyrido[4,3-b]indole (100 mg, 0.29 mmol), Sodium tert-butoxide (134 mg, 1.45 mmol), palladacycle (palladium (II)acetate+2-(di-t-butylphosphino)biphenyl) (26 mg, 0.058 mmol) was charged in a reaction bottle which was evacuated and back filled with nitrogen for 5 min. and dry toluene (2 mL) was added under nitrogen atmosphere. 1-Methylpiperazine (37 mg, 0.37 mmol) was added and heated at 100° C. overnight. The reaction mixture was filtered and washed with EtOAc (2×25 mL). The filtrate was concentrated under vacuum and purified on reverse phase chromatography. Yield: 30 mg. $^1$H NMR (CDCl$_3$, free base) δ (ppm): 8.50 (d, 2H), 7.50 (d, 2H), 7.16 (s, 1H), 7.05 (d, 1H), 6.95 (m, 2H), 3.78 (s, 2H), 3.20 (m, 4H), 2.92 (m, 2H), 2.82 (m, 2H), 2.74 (m, 4H), 2.60 (s, 3H), 2.40 (s, 3H), 2.0 (s, 3H).

Example 366

Preparation of (Z)-4-(2-(2,8-dimethyl-3,4-dihydro-1H-pyrido[4,3-b]indol-5(2H)-yl)-1-fluorovinyl)thiazole (Compound No. 438)

4-Bromothiazole (100 mg, 0.609 mmol), 5-ethynyl-2,8-dimethyl-2,3,4,5-tetrahydro-1H-pyrido[4,3-b]indole 163 mg, 0.731 mmol), dichlorobistrifluorophosphine palladium (12 mg, 0.01 mmol) and tetrabutylammonium fluoride trihydrate (575 mg, 1.827 mmol) were charged in a microwave vial and heated to 85° C. for 5 min in microwave oven. On completion of reaction (as observed by LCMS), the reaction mixture was poured into 20 mL water and compound extracted with EtOAc (3×50 mL). The combined organic layers were washed with water (2×50 mL) and dried over anhydrous sodium sulfate and concentrated under vacuum. The crude product (190 mg) obtained was purified by reverse phase chromatography to afford 7 mg of 5-(2-Fluoro-2-thiazol-4-yl-vinyl)-2,8-dimethyl-2,3,4,5-tetrahydro-1H-pyrido[4,3-b]indole. $^1$H NMR (CDCl$_3$, free base) δ (ppm): 8.80 (s, 1H), 7.60 (s, 1H), 7.38 (d, 1H), 7.18 (s, 1H), 7.05 (d, 1H), 6.22 (d, 1H), 3.80 (m, 2H), 3.0 (m, 4H), 3.62 (s, 3H), 2.40 (s, 3H).

Example 367

Preparation of (E)-N-methyl-N-(2-methyl-5-(2-(pyridin-4-yl)prop-1-enyl)-2,3,4,5-tetrahydro-1H-pyrido[4,3-b]indol-8-yl)acetamide (Compound No. 439)

2,3,4,5-Tetrahydro-N, 2-dimethyl-5-(2-(pyridin-4-yl) prop-1-enyl)-1H-pyrido[4,3-b]indol-8-amine (23 mg) was charged in round bottom flask and acetic anhydride (0.7 mL) was added. The contents were stirred at RT for 30 min. The reaction mixture was basified with 1N NaOH and compound extracted with EtOAc (2×25 mL). The organic layer was concentrated under vacuum and recrystallized in DCM: Hexane (1:3) to yield 2.38 mg of desired compound. $^1$H NMR (CDCl$_3$, free base) δ (ppm): 8.62 (d, 2H), 7.42 (d, 2H), 7.25 (s, 1H), 7.10 (dd, 2H), 6.98 (d, 1H), 3.70 (s, 2H), 3.30 (s, 3H), 2.82 (m, 4H), 3.60 (s, 3H), 2.04 (s, 3H), 1.90 (s, 3H).

Example 368

Preparation of (E)-N-(2-methoxyethyl)-2-methyl-5-(2-(pyridin-4-yl)prop-1-enyl)-2,3,4,5-tetrahydro-1H-pyrido[4,3-b]indol-8-amine (Compound No. 440)

8-Chloro-2-methyl-5-(2-pyridin-4-yl-propenyl)-2,3,4,5-tetrahydro-1H-pyrido[4,3-b]indole (0.100 g, 0.245 mmol), sodium tertbutoxide (0.283 g, 2.948 mmol), palladium acetate (0.010 g, 0.049 mmol) and 2-di-tertbutylphosphino-2'-4'-6'-triisopropylbiphenyl (0.031 g, 0.0735 mmol) were charged in a reaction bottle which was evacuated and back filled with nitrogen for 5 min. Dry toluene (2 mL) was added under nitrogen atmosphere. Finally, 2-methoxy-ethylamine (0.029 mL, 0.343 mmol) was added and the contents heated at 100° C. overnight. The reaction mixture was filtered and precipitate washed with EtOAc (2×25 mL). The filtrate was concentrated under vacuum and purified by reverse phase chromatography to yield 15 mg of free base. $^1$H NMR (CDCl$_3$, free base) δ (ppm): 8.60 (d, 2H), 7.40 (d, 2H), 7.10 (s, 1H), 6.96 (d, 1H), 6.62 (d, 2H), 3.80 (m, 2H), 3.64 (t, 2H), 3.40 (s, 3H0, 3.30 (t, 2H), 2.95 (m, 2H), 2.82 (m, 2H), 2.62 (s, 3H), 2.0 (s, 3H).

Example 369

Preparation of (E)-5-(2-(6-methoxypyridin-3-yl) prop-1-enyl)-2,8-dimethyl-2,3,4,5-tetrahydro-1H-pyrido[4,3-b]indole (Compound No. 441)

5-(–1-Bromoprop-1-en-2-yl)-2-methoxypyridine (50 mg, 0.25 mmol) was dissolved in DMF (2 mL). Potassium phosphate (106 mg, 0.5 mmol) was added followed by copper (I) iodide (4 mg, 0.02 mmol) and L-proline (5 mg, 0.04 mmol). 2,3,4,5-Tetrahydro-2,8-dimethyl-1H-pyrido[4,3-b]indole (50 mg, 0.25 mmol) was added under nitrogen (Nitrogen purged for 2 min). The reaction mixture was stirred at 85° C. overnight. Water (15 mL) was added and compound extracted with EtOAc (3×30 mL). The organic layer was concentrated under vacuum and purified through reverse phase chromatography. Yield: 3.87 mg (TFA salt). $^1$H NMR (CD$_3$OD, TFA salt) δ (ppm): 8.30 (s, 1H), 7.90 (d, 1H), 7.20 (s, 1H), 7.02 (d, 1H), 6.99 (d, 1H), 4.62 (m, 1H), 4.30 (m, 1H), 3.86 (s, 3H), 3.78 (m, 1H), 3.50 (m, 1H), 3.05 (m, 2H), 3.02 (s, 3H), 2.38 (s, 3H), 1.82 (s, 3H).

Example 370

Preparation of (E)-5-(2-(4-fluorophenyl)prop-1-enyl)-N,N,2-trimethyl-2,3,4,5-tetrahydro-1H-pyrido[4,3-b]indol-8-amine (Compound No. 442)

8-Chloro-5-(2-(4-fluorophenyl)prop-1-enyl)-2,3,4,5-tetrahydro-2-methyl-1H-pyrido[4,3-b]indole (100 mg, 0.282 mmol), sodium tertbutoxide (324 mg, 2.948 mmol), palladium acetate (12 mg, 0.049 mmol) and 2-di-tertbutylphosphino-2'-4'-6'-triisopropylbiphenyl (31 mg, 0.0735 mmol) were charged in a reaction bottle which was evacuated and back filled with nitrogen for 5 min. Anhydrous toluene (2 mL) was added under nitrogen atmosphere. Finally, dimethylamine hydrochloride (45.13 mg, 0.564 mmol) was added to the reaction mixture and contents heated at 100° C. overnight. The reaction mixture was filtered, and washed with EtOAc (2×25 mL). The filtrate obtained was concentrated under vacuum and purified on reverse phase chromatography to yield 34 mg of desired compound as the TFA salt. $^1$H NMR (CD$_3$OD, TFA salt) δ (ppm): 7.78 (s, 1H), 7.58 (m, 2H), 7.38 (s, 2H), 7.10 (t, 2H), 6.90 (s, 1H), 4.70 (m, 1H), 4.40 (m, 1H), 3.80 (m, 1H), 3.58 (m, 1H), 3.28 (s, 6H), 3.10 (m, 2H), 3.05 (s, 3H), 1.80 (s, 3H).

Example 371

Preparation of (E) N (5 (2 (4 fluorophenyl)prop-1-enyl)-2-methyl-2,3,4,5-tetrahydro-1H-pyrido[4,3-b] indol-8-yl)-N-methylacetamide (Compound No. 443)

5-(2-(4-Fluorophenyl)prop-1-enyl)-2,3,4,5-tetrahydro-N,2-dimethyl-1H-pyrido[4,3-b]indol-8-amine (30 mg) was charged in a round bottom flask. Acetic anhydride (0.5 mL) was added and the contents stirred at RT for 30 min. The reaction mixture was then basified with 1N NaOH and extracted with EtOAc (2×25 mL). The organic layer was concentrated under vacuum and purified through reverse phase column chromatography to yield 19.38 mg of the desired compound. $^1$H NMR (CD$_3$OD, TFA salt) δ (ppm): 7.70 (m, 2H), 7.50 (s, 1H), 7.36 (d, 1H), 7.18 (m, 3H), 7.0 (s, 1H), 4.78 (d, 1H), 4.41 (d, 1H), 3.90 (m, 1H), 3.62 (m, 1H), 3.28 (s, 3H), 3.20 (m, 2H), 3.10 (s, 3H), 1.96 (s, 3H), 1.82 (s, 3H).

Example 372

Preparation of (E)-N-butyl-2-methyl-5-(2-(pyridin-4-yl)prop-1-enyl)-2,3,4,5-tetrahydro-1H-pyrido[4,3-b]indol-8-amine (Compound No. 444)

8-Chloro-2-methyl-5-(2-pyridin-4-yl-propenyl)-2,3,4,5-tetrahydro-1H-pyrido[4,3-b]indole (0.100 g, 0.245 mmol), sodium tertbutoxide (0.283 g, 2.948 mmol), palladium acetate (0.010 g, 0.049 mmol) and 2-di-tertbutylphosphino-2'-4'-6'-triisopropylbiphenyl (0.031 g, 0.0735 mmol) were charged in a reaction bottle which were evacuated and back filled with nitrogen for 5 min. Dry toluene (2 mL) was added under nitrogen atmosphere. Finally, N-butyl amine (0.034 mL, 0.343 mmol) was added to the reaction mixture and contents heated at 100° C. overnight. The reaction mixture was filtered and precipitate washed with EtOAc (2×25 mL). The filtrate was concentrated under vacuum and purified by reverse phase chromatography to yield 91 mg of desired compound as the TFA salt. $^1$H NMR (CD$_3$OD, TFA salt) δ (ppm): 8.82 (d, 2H), 8.24 (d, 2H), 7.74 (d, 2H), 7.50 (d, 1H), 7.38 (d, 1H), 4.50 (m, 2H), 3.90 (m, 1H), 3.70 (m, 1H), 3.42 (m, 2H), 3.26 (m, 2H), 3.18 (s, 3H), 2.10 (s, 3H), 1.76 (m, 2H), 1.46 (m, 2H), 1.0 (t, 3H).

Example 373

Preparation of (E)-2-methyl-8-(piperidin-1-yl)-5-(2-(pyridin-4-yl)prop-1-enyl)-2,3,4,5-tetrahydro-1H-pyrido[4,3-b]indole (Compound No. 445)

8-Chloro-2-methyl-5-(2-pyridin-4-yl-propenyl)-2,3,4,5-tetrahydro-1H-pyrido[4,3-b]indole (0.100 g, 0.245 mmol), sodium tertbutoxide (0.283 g, 2.948 mmol), palladium acetate (0.010 g, 0.049 mmol) and 2-di-tertbutylphosphino-2'-4'-6'-triisopropylbiphenyl (0.031 g, 0.0735 mmol) were charged in a reaction bottle which was evacuated and back filled with nitrogen for 5 min. Dry toluene (2 mL) was added under nitrogen atmosphere. Finally, piperidine (0.0339 mL, 0.343 mmol) was added and the contents heated at 100° C. overnight. The reaction mixture was filtered and precipitate washed with EtOAc (2×25 mL). The filtrate was concentrated under vacuum and purified on reverse phase chromatography to yield 25 mg of the desired compound as the TFA salt. $^1$H NMR (CD$_3$OD, TFA salt) δ (ppm): 8.82 (d, 2H), 8.30 (d, 2H), 7.95 (s, 1H), 7.76 (s, 1H), 7.59 (d, 1H), 7.50 (d, 1H), 4.80 (m, 1H), 4.50 (m, 1H), 3.92 (m, 1H), 3.76-3.60 (m, 5H), 3.25 (m, 2H), 3.18 (s, 3H), 2.10 (s, 3H), 2.08 (m, 4H), 1.82 (m, 2H).

Example 374

Preparation of (E)-2-methyl-5-(2-(pyridin-4-yl)prop-1-enyl)-8-(pyrrolidin-1-yl)-2,3,4,5-tetrahydro-1H-pyrido[4,3-b]indole (Compound No. 446)

8-Chloro-2-methyl-5-(2-pyridin-4-yl-propenyl)-2,3,4,5-tetrahydro-1H-pyrido[4,3-b]indole (0.100 g, 0.245 mmol), sodium tertbutoxide (0.283 g, 2.948 mmol), palladium acetate (0.010 g, 0.049 mmol) and 2-di-tertbutylphosphino-2'-4'-6'-triisopropylbiphenyl (0.031 g, 0.0735 mmol) were charged in a reaction bottle which was evacuated and back filled with nitrogen for 5 min. Dry toluene (2 mL) was added under nitrogen atmosphere. Finally, pyrrolidine (0.033 mL, 0.343 mmol) was added to the reaction mixture and the contents heated to 100° C. overnight. The reaction mixture was filtered and precipitate washed with EtOAc (2×25 mL). The filtrate was concentrated under vacuum and purified by reverse phase chromatography to yield 25 mg of desired compound as the TFA salt. $^1$H NMR (CD$_3$OD, TFA salt) δ (ppm): 8.78 (d, 2H), 8.18 (d, 2H), 7.68 (s, 1H), 7.50 (s, 1H), 7.39 (d, 1H), 7.24 (d, 1H), 4.78 (m, 1H), 4.45 (m, 1H), 3.90 (m, 1H), 3.74-3.60 (m, 5H), 3.24 (m, 2H), 3.18 (s, 3H), 2.24 (m, 4H), 2.10 (s, 3H).

Example 375

Preparation of (E)-N-cyclopropyl-2-methyl-5-(2-(pyridin-4-yl)prop-1-enyl)-2,3,4,5-tetrahydro-1H-pyrido[4,3-b]indol-8-amine (Compound No. 447)

8-Chloro-2-methyl-5-(2-pyridin-4-yl-propenyl)-2,3,4,5-tetrahydro-1H-pyrido[4,3-b]indole (0.100 g, 0.245 mmol), sodium tertbutoxide (0.283 g, 2.948 mmol), palladium acetate (0.010 g, 0.049 mmol) and 2-di-tertbutylphosphino-2'-4'-6'-triisopropylbiphenyl (0.031 g, 0.0735 mmol) were charged in a reaction bottle which was evacuated and back filled with nitrogen for 5 min. Dry toluene (2 mL) was added under nitrogen atmosphere. Finally, cyclopropylamine (24.3 mg, 0.343 mmol) was added to the reaction mixture and the contents heated to 100° C. overnight. The reaction mixture was filtered and precipitate washed with EtOAc (2×25 mL). The filtrate was concentrated under vacuum and purified by reverse phase chromatography to yield 2.74 mg of compound as the oxalate salt. $^1$H NMR (CD$_3$OD, oxalate salt) δ (ppm): 8.60 (d, 2H), 7.82 (d, 2H), 7.44 (s, 1H), 7.10 (d, 1H), 7.04 (s, 1H), 6.90 (d, 1H), 4.60 (m, 2H), 3.70 (m, 2H), 3.18 (m, 2H), 3.10 (s, 3H), 2.50 (m, 1H), 2.05 (s, 3H), 0.78 (m, 2H), 0.58 (m, 2H).

Example 376

Preparation of (E)-N-cyclobutyl-2-methyl-5-(2-(pyridin-4-yl)prop-1-enyl)-2,3,4,5-tetrahydro-1H-pyrido[4,3-b]indol-8-amine (Compound No. 448)

8-Chloro-2-methyl-5-(2-pyridin-4-yl-propenyl)-2,3,4,5-tetrahydro-1H-pyrido[4,3-b]indole (0.100 g, 0.245 mmol), sodium tertbutoxide (0.283 g, 2.948 mmol), palladium acetate (0.010 g, 0.049 mmol) and 2-di-tertbutylphosphino-2'-4'-6'-triisopropylbiphenyl (0.031 g, 0.0735 mmol) were charged in a reaction bottle which was evacuated and back filled with nitrogen for 5 min. Dry toluene (2 mL) was added under nitrogen atmosphere. Finally, cyclobutylamine (24.3 mg, 0.343 mmol) was added to the reaction mixture and the contents heated to 100° C. overnight. The reaction mixture was filtered and precipitate washed with EtOAc (2×25 mL). The filtrate was concentrated under vacuum and purified by reverse phase chromatography to yield 34 mg of desired compound as the TFA salt. $^1$H NMR (CD$_3$OD, TFA salt) δ (ppm): 8.80 (d, 2H), 8.10 (d, 2H), 7.62 (d, 2H), 7.44 (d, 1H), 7.30 (d, 1H), 4.50 (m, 2H), 4.18 (m, 1H), 3.85 (m, 1H), 3.70 (m, 1H), 3.26 (m, 2H), 3.18 (s, 3H), 2.38 (m, 4H), 2.10 (s, 3H), 2.02-1.85 (m, 2H).

Example 377

Preparation of (E)-2-(2-methyl-5-(2-(pyridin-4-yl)prop-1-enyl)-2,3,4,5-tetrahydro-1H-pyrido[4,3-b]indol-8-ylamino)ethanol (Compound No. 449)

(2-Methoxy-ethyl)-[2-methyl-5-(2-pyridin-4-yl-propenyl)-2,3,4,5-tetrahydro-1H-pyrido[4,3-b]indol-8-yl]-amine (350 mg, 0.9 mmol) was dissolved in DCM and the reaction mixture was cooled in dry ice (−78° C.). Boron tribromide (699 mg, 2.7 mmol), diluted with DCM (3 mL) was added to the solution dropwise at −78° C. After completion of this addition, the reaction mixture was allowed to come to RT gradually, and was stirred at RT for 1 h. After completion of reaction (reaction monitored by TLC & LCMS), the reaction mixture was concentrated under vacuum and the crude compound was basified with 1N NaOH solution. The compound was extracted with EtOAc (3×60 mL). The combined organic layers were dried over sodium sulfate and concentrated under vacuum under vacuum to obtain the crude compound which was recrystallized in diethyl ether (20 mL) to yield 170 mg of 2-[2-Methyl-5-(2-pyridin-4-yl-propenyl)-2,3,4,5-tetrahydro-1H-pyrido[4,3-b]indol-8-ylamino]-ethanol. $^1$H NMR (CD$_3$OD, HCl salt) δ (ppm): 8.90 (d, 2H), 8.40 (d, 2H), 7.84 (s, 1H), 7.78 (s, 1H), 7.52 (d, 1H), 7.42 (d, 1H), 4.84 (m, 1H), 4.50 (m, 1H), 3.90 (m, 1H), 3.80 (t, 2H), 3.68 (m, 1H), 3.58 (t, 2H), 3.40-3.30 (m, 2H), 3.18 (s, 3H), 2.17 (s, 3H).

Example 378

Preparation of (E)-N,N,2-trimethyl-5-(2-(pyridin-4-yl)prop-1-enyl)-2,3,4,5-tetrahydro-1H-pyrido[4,3-b]indol-8-amine (Compound No. 450)

8-Chloro-2-methyl-5-(2-pyridin-4-yl-propenyl)-2,3,4,5-tetrahydro-1H-pyrido[4,3-b]indole (0.100 g, 0.245 mmol), sodium tertbutoxide (0.283 g, 2.948 mmol), palladium acetate (0.010 g, 0.049 mmol) and 2-di-tertbutylphosphino-2'-4'-6'-triisopropylbiphenyl (0.031 g, 0.0735 mmol) were charged in a reaction bottle which was evacuated and back filled with nitrogen for 5 min. Dry toluene (2 mL) was added under nitrogen atmosphere. Finally, di-methylamine hydrochloride (0.040 g, 0.490 mmol) was added and the contents heated at 100° C. overnight. The reaction mixture was filtered and precipitate washed with EtOAc (2×25 mL). The filtrate was concentrated under vacuum and purified by reverse phase chromatography to yield 15 mg of free base. $^1$H NMR (CD$_3$OD, HCl salt) δ (ppm): 8.90 (d, 2H), 8.38 (d, 2H), 7.99 (s, 1H), 7.80 (s, 1H), 7.56 (m, 2H), 4.50 (m, 2H), 3.90 (m, 1H), 3.70 (m, 1H), 3.38 (s, 6H), 3.22 (m, 2H), 3.18 (s, 3H), 2.16 (s, 3H).

Example 379

Preparation of (Z)-5-(2-fluoro-2-(thiophen-2-yl)vinyl)-2,8-dimethyl-2,3,4,5-tetrahydro-1H-pyrido[4,3-b]indole (Compound No. 451)

5-Ethynyl-2,8-dimethyl-2,3,4,5-tetrahydro-1H-pyrido[4,3-b]indole (165 mg, 0.736 mmol), 2-bromo-thiophene (100 mg, 0.613 mmol), dichlorobis(triphenylphosphine) palladium (II) (13 mg, 0.018 mmol) and TBAF.3H$_2$O (580 mg, mmol) were added in a microwave tube. The reaction mixture was heated at 80° C. for 5 min. It was then cooled to RT. The reaction was monitored by TLC and LCMS. The reaction mixture was diluted with water (100 mL) and the compound extracted with EtOAc (3×30 mL). The combined organic layers were washed with water and dried over sodium sulfate and concentrated under vacuum to yield the crude product which was purified on neutral alumina (Eluent: 0-10%, Hexane/Ethyl acetate). The compound was subjected to reverse phase HPLC to obtain fluoro compound (7 mg) as a liquid. $^1$H NMR (CDCl$_3$, free base) δ (ppm): 7.38 (d, 2H), 7.18 (dd, 1H), 7.05 (m, 2H), 6.10 (d, 1H), 3.64 (s, 2H), 2.94 (m, 2H), 2.84 (m, 2H), 2.60 (s, 3H), 2.42 (s, 3H).

Example 380

Preparation of (E)-4-(1-(2,8-dimethyl-3,4-dihydro-1H-pyrido[4,3-b]indol-5(2H)-yl)prop-1-en-2-yl)-2,6-difluorophenol (Compound No. 452)

5-(1-Bromoprop-1-en-2-yl)-1,3-difluoro-2-methoxybenzene (223 mg, 1.2 mmol) was dissolved in DMF (5 mL) and potassium phosphate (424 mg, 2 mmol) was added followed by copper (I) iodide (19 mg, 0.1 mmol) and L-proline (23 mg, 0.2 mmol). 2,3,4,5-Tetrahydro-2,8-dimethyl-1H-pyrido[4,3-b]indole (200 mg, 1 mmol) was added and the mixture purged with nitrogen for 2 min. The reaction mixture was stirred at 85° C. overnight. Water was added and the solid mass was filtered under vacuum. The crude product was purified on silica gel (100-200 mesh) using 0-10% MeOH:DCM as eluent. Yield: 52 mg. $^1$H NMR (CD$_3$OD, HCl salt) δ (ppm): 7.30 (s, 1H), 7.24 (d, 2H), 7.10 (m, 2H), 7.0 (s, 1H), 4.70 (m, 1H), 4.40 (m, 1H), 3.82 (m, 1H), 3.60 (m, 1H), 3.18 (s, 3H), 3.14 (m, 2H), 2.42 (s, 3H), 1.90 (s, 3H).

Example 381

Preparation of (Z)-2,8-dimethyl-5-(2-phenyl-2-(pyridin-4-yl)vinyl)-2,3,4,5-tetrahydro-1H-pyrido[4,3-b]indole (Compound No. 453)

4-(2-Bromo-1-phenylvinyl)pyridine (310 mg, 1.1 mmol) was dissolved in DMF (5 mL) and potassium phosphate (424 mg, 2 mmol) was added followed by copper (I) iodide (19 mg, 0.1 mmol) and L-proline (23 mg, 0.2 mmol). 2,3,4,5-Tetrahydro-2,8-dimethyl-1H-pyrido[4,3-b]indole (200 mg, 1 mmol) was added and the mixture purged with nitrogen for 2 min. The reaction mixture was stirred at 85° C. overnight. Water was added and the solid mass was filtered under vacuum. The crude product was purified on silica gel (100-200 mesh) using 0-10% MeOH:DCM as eluent. The compound was further purified through reverse phase HPLC. Yield: 28 mg. $^1$H NMR (CD$_3$OD, free base) δ (ppm): 8.40 (d, 2H), 7.39 (m, 3H), 7.32 (d, 2H), 7.16 (s, 1H), 7.10 (s, 1H), 6.90 (m, 4H), 3.62 (s, 2H), 2.68 (m, 2H), 2.50 (m, 5H), 2.39 (s, 3H).

Example 382

Preparation of (E)-8-chloro-5-(2-(6-methoxypyridin-3-yl)prop-1-enyl)-2-methyl-2,3,4,5-tetrahydro-1H-pyrido[4,3-b]indole (Compound No. 454)

5-(1-Bromoprop-1-en-2-yl)-2-methoxypyridine (113 mg, 0.5 mmol) was dissolved in DMF (2 mL) and potassium phosphate (212 mg, 1 mmol) was added followed by copper (I) iodide (9 mg, 0.05 mmol) and L-proline (11.5 mg, 0.1 mmol). 8-chloro-2,3,4,5-tetrahydro-2-methyl-1H-pyrido[4,3-b]indole (110 mg, 0.5 mmol) was added and the mixture purged with nitrogen for 2 min. The reaction mixture was stirred at 85° C. overnight. Water was added and the solid mass was filtered under vacuum. The crude product was purified on silica gel (100-200 mesh) using 0-4% MeOH:DCM as eluent. The compound was further purified through reverse phase HPLC. Yield: 15 mg. $^1$H NMR (CD$_3$OD, oxalate salt) δ (ppm): 8.40 (s, 1H), 7.98 (d, 1H), 7.56 (s, 1H), 7.22 (s, 2H), 7.0 (s, 1H), 6.84 (d, 1H), 4.50 (s, 2H), 3.96 (s, 3H), 3.70 (m, 2H), 3.18 (m, 2H), 3.12 (s, 3H), 1.96 (s, 3H).

Example 383

Preparation of (E)-2,8-dimethyl-5-(2-phenyl-2-(pyridin-4-yl)vinyl)-2,3,4,5-tetrahydro-1H-pyrido[4,3-b]indole (Compound No. 455)

4-(2-Bromo-1-phenylvinyl)pyridine (310 mg, 1.1 mmol) was dissolved in DMF (5 mL) and potassium phosphate (424 mg, 2 mmol) was added followed by copper (I) iodide (19 mg, 0.1 mmol) and L-proline (23 mg, 0.2 mmol). 2,3,4,5-Tetrahydro-2,8-dimethyl-1H-pyrido[4,3-b]indole (200 mg, 1 mmol) was added and the mixture purged with nitrogen for 2 min. The reaction mixture was stirred at 85° C. overnight. Water was added and the solid mass was filtered under vacuum. The crude product was purified on silica gel (100-200 mesh) using 0-10% MeOH:DCM as eluent. The compound was further purified through reverse phase HPLC. Yield: 15 mg. $^1$H NMR (CDCl$_3$, free base) δ (ppm): 8.60 (d, 2H), 7.30-7.15 (m, 7H), 7.0 (m, 3H), 6.90 (d, 1H), 3.70 (s, 2H), 2.70 (m, 2H), 2.50 (s, 3H), 2.42 (s, 3H), 2.36 (m, 2H).

Example 384

Preparation of (E)-5-(2-(3,5-difluoro-4-methoxyphenyl)prop-1-enyl)-2,8-dimethyl-2,3,4,5-tetrahydro-1H-pyrido[4,3-b]indole (Compound No. 456)

5-(1-Bromoprop-1-en-2-yl)-1,3-difluoro-2-methoxybenzene (223 mg, 1.2 mmol) was dissolved in DMF (5 mL) and potassium phosphate (424 mg, 2 mmol) was added followed by copper (I) iodide (19 mg, 0.1 mmol) and L-proline (23 mg, 0.2 mmol). 2,3,4,5-Tetrahydro-2,8-dimethyl-1H-pyrido[4,3-b]indole (200 mg, 1 mmol) was added and the mixture purged with nitrogen for 2 min. The reaction mixture was stirred at 85° C. overnight. Water was added and the solid mass was filtered under vacuum. The crude product was purified on silica gel (100-200 mesh) using 0-10% MeOH:DCM as eluent. Yield: 63 mg. $^1$H NMR (CD$_3$OD, HCl salt) δ (ppm): 7.32 (s, 1H), 7.30 (s, 2H), 7.08 (m, 3H), 4.72 (m, 1H), 4.39 (m, 1H), 4.0 (s, 3H), 3.82 (m, 1H), 3.60 (m, 1H), 3.20-3.10 (m, 5H), 2.42 (s, 3H), 1.90 (s, 3H).

Example 385

Preparation of (E)-3-(1-(2,8-dimethyl-3,4-dihydro-1H-pyrido[4,3-b]indol-5(2H)-yl)prop-1-en-2-yl)-N,N-dimethylbenzamide (Compound No. 457)

Thionyl chloride (0.8 mL, 11.02 mmol) was added to a solution of 3-[2-(2,8-dimethyl-1,2,3,4-tetrahydropyrido[4,3-b]indol-5-yl)-1-hydroxy-1-methyl-ethyl]-N,N-dimethylbenzamide (500 mg, 1.23 mmol) and the reaction mixture was stirred at RT for 1 h. The solvent was removed under vacuum to obtain the crude product as a foamy solid which was dissolved in NMP (5 mL). The mixture was stirred for 5 min and powdered KOH (553 mg, 9.87 mmol) was added, and the mixture heated at 85° C. for 45 min. After completion of reaction, the mixture was poured into water and extracted with EtOAc (3×30 mL). The organic layer washed with water, dried over sodium sulfate and concentrated under vacuum to obtain the crude product (600 mg) which was purified by reverse phase HPLC to yield 3-[2-(2,8-dimethyl-1,2,3,4-tetrahydro-pyrido[4,3-b]indol-5-yl)-1-methyl-vinyl]-N,N-dimethyl-benzamide (30 mg) as free base. $^1$H NMR (CD$_3$OD, oxalate salt) δ (ppm): 7.76 (d, 1H), 7.70 (s, 1H), 7.52 (t, 1H), 7.44 (d, 1H), 7.30 (s, 1H), 7.18-7.06 (m, 3H), 4.58 (m, 2H), 3.70 (m, 2H), 3.18 (m, 2H), 3.12 (s, 6H), 3.05 (s, 3H), 2.42 (s, 3H), 1.98 (s, 3H).

Example 386

Preparation of (Z)-3-(1-(2,8-dimethyl-3,4-dihydro-1H-pyrido[4,3-b]indol-5(2H)-yl)prop-1-en-2-yl)-N,N-dimethylbenzamide (Compound No. 458)

4-(1-Bromoprop-1-en-2-yl)-N,N-dimethylbenzamide (264 mg, 1 mmol) was dissolved in DMF (5 mL) and potassium phosphate (424 mg, 2 mmol) was added followed by copper (I) iodide (19 mg, 0.1 mmol) and L-proline (23 mg, 0.2 mmol). 2,3,4,5-Tetrahydro-2,8-dimethyl-1H-pyrido[4,3-b]indole (200 mg, 1 mmol) was added and the mixture purged with nitrogen for 2 min. The reaction mixture was stirred at 85° C. overnight. Water was added and the solid mass was filtered under vacuum. The crude compound was purified on silica gel (100-200 mesh) using 0-7% MeOH:DCM as eluent. Yield: 60 mg. $^1$H NMR (CD$_3$OD, oxalate salt) δ (ppm): 7.30 (m, 2H), 7.20 (s, 2H), 7.10 (d, 1H), 6.95 (d, 1H), 6.86 (s, 1H), 6.80 (s, 1H), 4.58 (m, 1H), 4.30 (m, 1H), 3.60 (m, 1H), 3.10 (m, 1H), 3.0 (s, 3H), 2.92 (s, 3H), 2.80 (m, 2H), 2.50 (s, 3H), 2.39 (s, 3H), 2.36 (s, 3H).

Example 387

Preparation of (E)-2,8-dimethyl-5-(2-(4-(methylthio)phenyl)prop-1-enyl)-2,3,4,5-tetrahydro-1H-pyrido[4,3-b]indole (Compound No. 459)

(4-(1-Bromoprop-1-en-2-yl)phenyl)(methyl)sulfane (241 mg, 1 mmol) was dissolved in DMF (5 mL) and potassium phosphate (424 mg, 2 mmol) was added followed by copper (I) iodide (19 mg, 0.1 mmol) and L-proline (23 mg, 0.2 mmol). 2,3,4,5-Tetrahydro-2,8-dimethyl-1H-pyrido[4,3-b]indole (200 mg, 1 mmol) was added and the mixture purged with nitrogen for 2 min. The reaction mixture was stirred at 85° C. overnight. Water was added and the solid mass was filtered under vacuum. The crude compound was purified on silica gel (100-200 mesh) using 0-3% MeOH:DCM as eluent. Yield: 72 mg. $^1$H NMR (CD$_3$OD, oxalate salt) δ (ppm): 7.59 (d, 2H), 7.30 (m, 3H), 7.10 (m, 2H), 7.0 (s, 1H), 4.60 (m, 2H), 3.70 (m, 2H), 3.28 (m, 2H), 3.10 (s, 3H), 2.54 (s, 3H), 2.42 (s, 3H), 1.96 (s, 3H).

Example 388

Preparation of (E)-8-chloro-2-methyl-5-(2-phenyl-2-(pyridin-4-yl)vinyl)-2,3,4,5-tetrahydro-1H-pyrido[4,3-b]indole (Compound No. 460)

4-(2-Bromo-1-phenylvinyl)pyridine (310 mg, 1.1 mmol) was dissolved in DMF (5 mL) and potassium phosphate (424 mg, 2 mmol) was added followed by copper (I) iodide (19 mg, 0.1 mmol) and L-proline (23 mg, 0.2 mmol). 8-Chloro-2,3,4,5-tetrahydro-2-methyl-1H-pyrido[4,3-b]indole (220 mg, 1 mmol) was added and the mixture purged with nitrogen for 2 min. The reaction mixture was stirred at 85° C. overnight. Water was added and the solid mass was filtered under vacuum. The crude compound was purified on silica gel (100-200 mesh) using 0-10% MeOH:DCM as eluent. The compound was further purified through reverse phase HPLC. Yield: 20 mg (TFA salt). $^1$HNMR (CDCl$_3$, TFA salt) δ (ppm): 8.78 (d, 2H), 7.64 (d, 2H), 7.40-7.28 (m, 5H), 7.10 (m, 2H), 6.92 (d, 2H), 4.65 (m, 1H), 4.0 (m, 1H), 3.60 (m, 1H), 3.05 (m, 1H), 2.84 (s, 3H), 2.76 (m, 2H).

Example 389

Preparation of (Z)-8-chloro-2-methyl-5-(2-phenyl-2-(pyridin-4-yl)vinyl)-2,3,4,5-tetrahydro-1H-pyrido[4,3-b]indole (Compound No. 461)

4-(2-Bromo-1-phenylvinyl)pyridine (310 mg, 1.1 mmol) was dissolved in DMF (5 mL) and potassium phosphate (424 mg, 2 mmol) was added followed by copper (I) iodide (19 mg, 0.1 mmol) and L-proline (23 mg, 0.2 mmol). 8-Chloro-2,3,4,5-tetrahydro-2-methyl-1H-pyrido[4,3-b]indole (220 mg, 1 mmol) was added and the mixture purged with nitrogen for 2 min. The reaction mixture was stirred at 85° C. overnight. Water was added and the solid mass was filtered under vacuum. The crude compound was purified on silica gel (100-200 mesh) using 0-10% MeOH:DCM as eluent. The compound was further purified through reverse phase HPLC. Yield: 21 mg (TFA salt). $^1$HNMR (CDCl$_3$, TFA salt) δ (ppm): 8.58 (d, 2H), 7.50 (m, 2H), 7.36-7.18 (m, 7H), 7.08 (d, 1H), 6.90 (d, 1H), 4.65 (m, 1H), 4.05 (m, 1H), 3.80 (m, 1H), 3.30 (m, 1H), 3.0 (s, 3H), 2.80 (m, 1H).

Example 390

Preparation of (E)-2,8-dimethyl-5-(2-(4-(methylsulfonyl)phenyl)prop-1-enyl)-2,3,4,5-tetrahydro-1H-pyrido[4,3-b]indole (Compound No. 462)

1-(1-Bromoprop-1-en-2-yl)-4-(methylsulfonyl)benzene (241 mg, 0.9 mmol) was dissolved in DMF (2 mL) and potassium phosphate (424 mg, 2 mmol) was added followed by copper (I) iodide (19 mg, 0.1 mmol) and L-proline (23 mg, 0.2 mmol). 2,3,4,5-Tetrahydro-2,8-dimethyl-1H-pyrido[4,3-b]indole (200 mg, 1 mmol) was added and the mixture purged with nitrogen for 2 min. The reaction mixture was stirred at 85° C. overnight. Water was added and the solid mass was filtered under vacuum. The crude compound was purified on silica gel (100-200 mesh) using 0-3% MeOH:DCM as eluent. Yield: 140 mg. $^1$H NMR (CD$_3$OD, oxalate salt) δ (ppm): 8.02 (d, 2H), 7.90 (d, 2H), 7.32 (s, 1H), 7.19 (s, 1H), 7.10 (m, 2H), 4.56 (m, 2H), 3.70 (m, 2H), 3.18 (m, 5H), 3.10 (s, 3H), 2.42 (s, 1H), 2.04 (s, 3H).

Example 392

Preparation of 4-(8-chloro-5-(2-hydroxy-2-(pyridin-4-yl)propyl)-3,4-dihydro-1H-pyrido[4,3-b]indol-2(5H)-yl)-1-(4-fluorophenyl)butan-1-one (Compound No. 464)

To a solution of 4-(8-chloro-1,3,4,5-tetrahydro-pyrido (4,3-b) indole-2-yl)-1-(4-fluorphenyl)-butan-1-one (500 mg, 1.35 mmol) in 5 mL DMF, was added sodium hydride (60% dispersion in oil) (162 mg, 4.05 mmol) and the reaction mixture stirred for 5 min. 4-(2-Methyloxaranyl)pyridine (237 g, 1.75 mmol) was added dropwise and the reaction mixture was again stirred at RT for 16 h. The reaction mixture was poured into ice water and compound extracted with EtOAc. The organic layer was washed with water, dried over sodium sulfate and concentrated under vacuum to obtain the crude product, which was purified by column chromatography on silica gel (100-200 mesh) [Eluent: 4% MeOH and DCM) to afford 180 mg pure product. $^1$H NMR (CD$_3$OD, oxalate salt) δ (ppm): 8.40 (d, 2H), 8.10 (m, 2H), 7.56 (d, 2H), 7.42 (s, 1H), 7.25 (t, 2H), 7.18 (d, 1H), 6.98 (d, 1H), 4.58 (m, 2H), 4.30 (m, 2H), 3.70 (m, 3H), 3.40 (m, 2H), 3.30-3.10 (m, 3H), 2.30 (m, 2H), 1.64 (s, 3H).

Example 393

Preparation of 2-(2,8-dimethyl-3,4-dihydro-1H-pyrido[4,3-b]indol-5(2H)-yl)-1,1-diphenylethanol (Compound No. 465)

To a solution of 2,8-dimethyl-2,3,4,5-tetrahydro-1H-pyrido (4,3-b) indole (800 g, 4.0 mmol) in DMF (8 mL), sodium hydride [60% dispersion in oil] (480 mg, 12.0 mmol) was added and the reaction mixture stirred for 5 min. 2,2-Diphenyl oxirane (1.176 g, 6.0 mmol) was added dropwise at RT and reaction mixture was stirred at RT for 16 h. The reaction mixture was poured into ice water and the compound extracted with EtOAc (3×200 mL). The organic layer was washed with water, dried over sodium sulfate and concentrated under vacuum to obtain the crude product. The crude compound was crystallized in ether (50 mL) to obtain 950 mg of white solid product as the free base. 100 mg free base was converted to HCL salt. $^1$H NMR (DMSO, HCl salt) δ (ppm): 7.50 (d, 2H), 7.30 (m, 3H), 7.20 (m, 5H), 7.10 (s, 1H), 7.05 (d, 1H), 6.70 (d, 1H), 6.08 (bs, 1H), 4.80 (m, 2H), 4.50 (m, 1H), 4.18 (m, 1H), 3.18 (m, 2H), 2.82 (s, 3H), 2.80 (m, 2H), 2.30 (s, 3H).

Example 394

Preparation of 2-(8-chloro-2-methyl-3,4-dihydro-1H-pyrido[4,3-b]indol-5(2H)-yl)-1,1-diphenylethanol (Compound No. 466)

To a solution of 8-chloro 2-methyl-2,3,4,5-tetrahydro-1H-pyrido (4,3-b) indole (800 g, 3.6 mmol) in 8 mL DMF, was added sodium hydride [60% dispersion in oil] (436 mg, 10.9 mmol) and the reaction mixture was stirred for 5 min. 2,2-Diphenyl oxirane (1.06 g, 5.4 mmol) was added dropwise at RT and reaction mixture stirred at RT for 16 h. The reaction mixture was poured into ice water and the desired compound extracted with EtOAc (3×200 mL). The organic layer was washed with water, dried over sodium sulfate and concentrated under vacuum to obtain the crude product, which was crystallized in ether (50 mL) to obtain 950 mg of white solid product as the free base. 100 mg free base was converted to HCL salt. $^1$H NMR (DMSO, HCl salt) δ (ppm): 7.50 (m, 2H), 7.40 (s, 1H), 7.30 (m, 3H), 7.22 (m, 5H), 7.14 (d, 1H), 6.82 (d, 1H), 6.15 (bs, 1H), 4.82 (d, 2H), 4.55 (m, 1H), 4.38 (m, 1H), 4.20 (m, 1H), 3.56 (m, 1H), 3.20 (m, 2H), 2.86 (s, 3H).

Example 395

Preparation of 2-(2,8-dimethyl-3,4-dihydro-1H-pyrido[4,3-b]indol-5(2H)-yl)-2-methyl-1-phenylpropan-1-ol (Compound No. 467)

Phenyl magnesium bromide (1M solution in THF) (3.7 mL, 3.69 mmol) was added dropwise at −70° C. to a stirred solution of 2-(2,8-dimethyl-1,2,3,4-tetrahydro-pyrido[4,3-b]indol-5-yl)-2-methyl-propionaldehyde (200 mg, 0.73 mmol) in THF (30 mL). The contents were stirred at RT for 16 h, diluted with EtOAc (50 mL) and water (40 mL). The layers were separated and the aqueous layer was again extracted with EtOAc (2×50 mL). The combined organic extracts were dried over sodium sulfate and concentrated under vacuum to obtain crude compound (300 mg), which was purified by column chromatography on silica gel (100-200 mesh) [Eluent: 0-5% MeOH in DCM] to afford 2-(2,8-dimethyl-1,2,3,4-tetrahydro-pyrido[4,3-b]indol-5-yl)-2-methyl-1-phenyl-propan-1-ol (120 mg) which was repurified by prep. TLC to yield free base (25 mg) compound. The free base was converted into the HCl salt. $^1$H NMR (CD$_3$OD, HCl salt) δ (ppm): 7.80 (m, 1H), 7.25-7.0 (m, 6H), 6.80 (d, 1H), 5.58 (s, 1H), 4.40 (m, 2H), 4.25 (m, 2H), 3.50 (m, 2H), 2.95 (s, 3H), 2.42 (s, 3H), 2.0 (s, 3H), 1.64 (s, 3H).

Example 396

Preparation of 2-(2,8-dimethyl-3,4-dihydro-1H-pyrido[4,3-b]indol-5(2H)-yl)-1-phenylpropan-1-ol (Compound No. 468)

Phenyl magnesium bromide (1M solution in THF) (6.24 mL, 6.24 mmol) was added dropwise at −70° C. to a stirred solution of 2-(2,8-dimethyl-1,2,3,4-tetrahydro-pyrido[4,3-b]indol-5-yl)-propionaldehyde (400 mg, 1.56 mmol) in THF (40 mL). The contents were stirred at RT for 16 h, diluted with EtOAc (75 mL) and water (60 mL). The layers were separated and the aqueous layer was again extracted with EtOAc (2×75 mL). The combined organic extracts were dried over sodium sulfate and concentrated under vacuum to obtain the crude compound (500 mg) which was purified by reverse phase HPLC to afford 2-(2,8-dimethyl-1,2,3,4-tetrahydro-pyrido[4,3-b]indol-5-yl)1-phenyl-propan-1-ol as the TFA salt (65 mg). $^1$H NMR (CD$_3$OD, TFA salt) δ (ppm): 7.56 (m, 1H), 7.20-7.0 (m, 6H), 6.90 (m, 1H), 5.18 (d, 1H), 4.50 (m, 2H), 4.30-4.10 (m, 2H), 3.58 (m, 2H), 3.10 (m, 1H), 3.0 (s, 3H), 2.42 (s, 3H), 1.82 (d, 3H).

Example 397

Preparation of (S)-1-(6-chloro-2-methyl-3,4-dihydro-1H-pyrido[4,3-b]indol-5(2H)-yl)-2-(pyridin-4-yl)propan-2-ol (Compound No. 469)

This optically active compound was obtained by chiral HPLC separation of Compound No. 182. $^1$H NMR (CDCl$_3$, freebase) δ (ppm): 8.58 (d, 2H), 7.40 (d, 2H), 7.28 (s, 1H), 7.10 (d, 1H), 6.98 (dd, 1H), 5.10 (m, 1H), 4.20 (m, 1H), 3.80 (d, 1H), 3.58 (d, 1H), 3.20 (m, 1H), 2.90 (m, 1H), 2.75 (m, 2H), 2.58 (s, 3H), 1.42 (s, 3H).

Example 398

Preparation of (R)-1-(6-chloro-2-methyl-3,4-dihydro-1H-pyrido[4,3-b]indol-5(2H)-yl)-2-(pyridin-4-yl)propan-2-ol (Compound No. 470)

This optically active compound was obtained by chiral HPLC separation of Compound No. 182. $^1$H NMR (CDCl$_3$, freebase) δ (ppm): 8.58 (d, 2H), 7.40 (d, 2H), 7.28 (s, 1H), 7.10 (d, 1H), 6.98 (dd, 1H), 5.10 (m, 1H), 4.20 (m, 1H), 3.80 (d, 1H), 3.58 (d, 1H), 3.20 (m, 1H), 2.90 (m, 1H), 2.75 (m, 2H), 2.58 (s, 3H), 1.42 (s, 3H).

Example 399

Preparation of Certain Intermediates

Preparation of 1-(2,2-dibromovinyl)-4-fluorobenzene

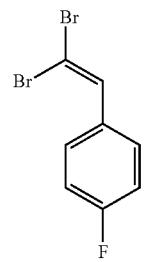 [SMILES: Fc1ccc(C=C(Br)Br)cc1]

4-Fluoro benzaldehyde (1.23 g, 0.00995 mol) was dissolved in DCM (120 mL). Carbon tetrabromide (6.6 g, 0.0199 mol) and triphenylphosphine (10.42 g, 0.0398 mol) were added. The mixture was stirred at RT for 3 h. Insoluble material was removed by filtration, and the filtrate was concentrated under reduced pressure. The residue was purified through column chromatography (100% pentane in silica 100-200 mesh, Diameter of column—5.0 cm, height of silica—approx. 5 inch) to provide the desired compound as a yellow colored oil (1.1 g, 44% yield).

Preparation of 5-(2,2-dibromovinyl)-2-methylpyridine

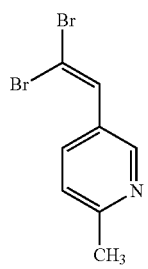

6-Methylnicotinaldehyde (1.0 g, 0.00826 mol) was dissolved in DCM (100 mL). Carbon tetrabromide (5.48 g, 0.0165 mol) and triphenylphosphine (8.66 g, 0.033 mol) was added to the solution followed by stirring at RT for 3 h. Insoluble material was removed by filtration, and the filtrate was concentrated under reduced pressure. The residue was purified through column chromatography (8% EtOAc: hexane in silica 100-200 mesh, diameter of column—5.0 cm, height of silica—approx. 5 inch) to provide the desired compound as a yellow colored oil (1.6 g, 70% yield).

Preparation of 4-(2,2-dibromovinyl)-2-fluoro-1-methoxybenzene

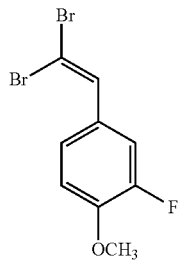 [SMILES: COc1ccc(C=C(Br)Br)cc1F]

3-Fluoro-4-methoxy benzaldehyde (0.5 g, 0.00324 mol) was dissolved in DCM (30 mL). Carbon tetrabromide (2.15 g, 0.0064 mol) and triphenylphosphine (3.4 g, 0.013 mol) were added to the solution followed by stirring at RT for 3 h. Insoluble material was removed by filtration, and the filtrate was concentrated under reduced pressure. The residue was purified through column chromatography (2% ethylacetate:hexane in silica 100-200 mesh) to provide the desired compound as a yellow colored oil (0.6 g, 60% yield).

Preparation of 5-(2,2-dibromovinyl)-2-propylpyridine

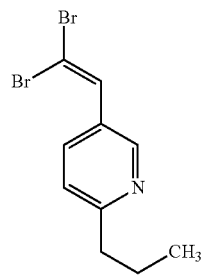

6-Propylnicotinaldehyde (0.2 g, 0.00134 mol) was dissolved in DCM (4 mL). Carbon tetrabromide (0.887 g, 0.00268 mol) and triphenylphosphine (1.4 g, 0.00536 mol) were added to the solution followed by stirring at RT overnight. After insoluble matter was removed by filtration, the filtrate was concentrated under reduced pressure. The residue was purified through column chromatography (3% ethylacetate:hexane in silica 100-200 mesh, diameter of column—5.0 cm, height of silica—approx. 5 inch) to provide the desired compound as a yellow colored oil (0.05 g).

Preparation of 1-(bromoethynyl)-4-fluorobenzene

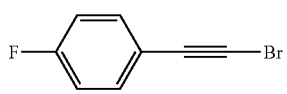

A mixture of 1-(2,2-dibromo-vinyl)-4-fluoro-benzene (0.6 g, 0.00214 mol), potassium tertbutoxide (0.48 g, 0.00428 mol) and toluene (6 mL) were heated at 80° C. for 4 h. After completion of reaction, the reaction mixture was cooled to RT, diluted with water (15 mL), and extracted with EtOAc (3×50 mL). The organic layer was dried over anhydrous sodium sulfate and concentrated under reduce pressure to obtain product as a yellow oil (0.3 g, 70%).

Preparation of 5-(bromoethynyl)-2-methylpyridine

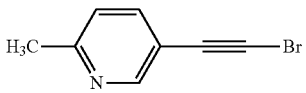

A mixture of 5-(2,2-dibromovinyl)-2-methylpyridine (0.10.9 g, 0.00393 mol), potassium tertbutoxide (0.88 g, 0.00787 mol) and toluene (13 mL) were heated at 80° C. for 4 h. After completion of reaction, the reaction mixture was cooled to RT, diluted with water (15 mL), and extracted with EtOAc (3×50 mL). The organic layer was dried over anhydrous sodium sulfate and concentrated under reduce pressure to obtain product as a yellow oil (0.25 g, 32.4%).

Preparation of 4-(bromoethynyl)-2-fluoro-1-methoxybenzene

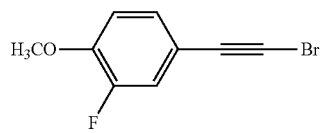 [SMILES: COc1ccc(C#CBr)cc1F]

A mixture of 1-(2,2-dibromo-vinyl)-3-fluoro-4-methoxybenzene (0.5 g, 0.00161 mol), potassium tertbutoxide (0.36 g, 0.00322 mol) and toluene (6 mL) were heated at 80° C. for 4 h. After completion, the reaction mixture was cooled to RT, diluted with water (15 mL), and extracted with EtOAc (3×50 mL). The organic layer was dried over anhydrous sodium sulfate and concentrated under reduce pressure to obtain product as a yellow oil (0.3 g, 81%).

Preparation of 1-(bromoethynyl)-4-chlorobenzene

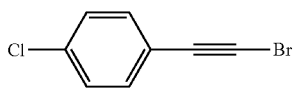

To a solution of 1-chloro-4-(2,2-dibromovinyl)benzene (9.60 g, 32.7 mmol) in toluene was added potassium tert-butoxide (7.35 g, 65.6 mmol) at RT. The reaction mixture was heated at 80° C. for 3 h. The reaction was monitored by LCMS and TLC. The reaction mixture was diluted with water and extracted with EtOAc. The organic was dried over sodium sulfate and concentrated under reduced pressure to give the desired product (5.5 g).

Preparation of 5-(bromoethynyl)-2-propylpyridine

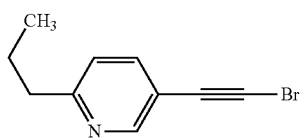

A mixture of 5-(2,2-dibromovinyl)-2-propylpyridine (0.8 g, 0.0026 mol), potassium tertbutoxide (1.2 g, 0.0105 mol) and toluene (14 mL) were heated at 80° C. for 4 h. After completion of reaction, the reaction mixture was cooled to RT, diluted with water (15 mL), and extracted with EtOAc (3×50 mL). The organic layer was dried over anhydrous sodium sulfate and concentrated under reduce pressure to obtain product as a yellow oil (0.55 g).

Preparation of 2,8-dimethyl-5-((triisopropylsilyl)ethynyl)-2,3,4,5-tetrahydro-1H-pyrido[4,3-b]indole

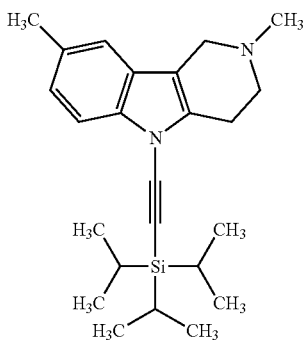

To a stirred solution of 2,8-dimethyl-2,3,4,5-tetrahydro-1H-pyrido[4,3-b]indole (10 g, 0.05 mol) and copper sulfate (1.24 g, 0.005 mol) in toluene (200 mL) was added potassium carbonate (13.8 g, 0.1 mol) and 1,10 phenanthroline (1.8 g, 0.01 mol). The reaction mixture was stirred for 5 min at RT. (Bromoethynyl)triisopropylsilane (14.4 g, 0.055 mol) was added to the reaction mixture at the same temperature. After completion of addition, the reaction mixture was stirred overnight at 80° C. The reaction was monitored by TLC. After completion of reaction, the mixture was cooled to RT, diluted with water (500 mL), and extracted with EtOAc (3×500 mL). The organic layer was dried over anhydrous sodium sulfate and solvent was removed under reduced pressure. The crude product was purified by column chromatography (1% MeOH:DCM in silica 100-200 mesh, diameter of column—5 cm, height of silica—approx. 5 inch) to provide the desired compound as a dark brown colored oil (9.5 g, 50% yield).

Preparation of 8-chloro-2-methyl-5-((triisopropylsilyl)ethynyl)-2,3,4,5-tetrahydro-1H-pyrido[4,3-b]indole

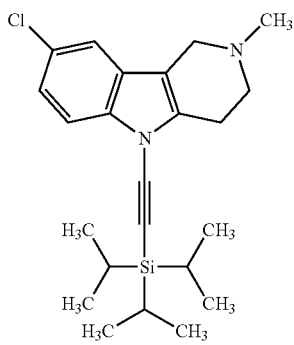 [SMILES: CC(C)[Si](C#Cn1c2c(c3cc(Cl)ccc31)CN(C)CC2)(C(C)C)C(C)C]

To a stirred solution of 8-chloro-2-methyl-2,3,4,5-tetrahydro-1H-pyrido[4,3-b]indole (10 g, 0.0454 mol) and copper sulfate (1.13 g, 0.00454 mol) in toluene (100 mL) was added potassium carbonate (12.5 g, 0.0909 mol) and 1,10 phenanthroline (1.6 g, 0.00909 mol). The reaction mixture was stirred for 5 min at RT. Bromoethynyl triisopropylsilane (13.0 g, 0.0499 mol) was added to the reaction mixture at the same temperature. After completion of addition, the reaction mixture was stirred overnight at 80° C., After completion of reaction (monitored by TLC), the mixture was cooled to RT, diluted with water (500 mL), and extracted with EtOAc (3×500 mL). The organic layer was dried over anhydrous sodium sulfate and solvent was removed under pressure. The product was purified by column chromatography (1% MeOH:DCM in silica 100-200 mesh, diameter of column—5 cm, height of silica—approx. 5 inch) to provide the desired compound as a dark brown colored oil (8.0 g, 44% yield).

Preparation of 5-ethynyl-2,8-dimethyl-2,3,4,5-tetrahydro-1H-pyrido[4,3-b]indole

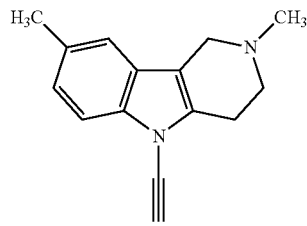

To a cooled solution of 2,8-dimethyl-5-((triisopropylsilyl)ethynyl)-2,3,4,5-tetrahydro-1H-pyrido[4,3-b]indole (10 g, 0.0236 mol) in THF (100 mL) was added tetrabutylammonium fluoride solution (1.0M in THF, 49 mL, 0.0526 mol) at 0° C. over 15 min. The reaction mixture was stirred for 1 h at 0° C., and the reaction monitored by TLC. After completion of reaction, the mixture was diluted with water (100 mL) and extracted with EtOAc (3×100 mL). The organic layer was dried over anhydrous sodium sulfate and concentrated under reduce pressure to obtain product as a brown colored oil (9.4 g).

Preparation of 8-chloro-5-ethynyl-2-methyl-2,3,4,5-tetrahydro-1H-pyrido[4,3-b]indole

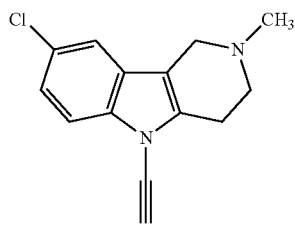 [SMILES: C#Cn1c2c(c3cc(Cl)ccc31)CN(C)CC2]

To a cooled solution of 8-chloro-2-methyl-5-((triisopropylsilyl)ethynyl)-2,3,4,5-tetrahydro-1H-pyrido[4,3-b]indole (8.0 g, 0.02 mol) in THF (100 mL) was added tetrabutylammonium fluoride solution (1.0M in THF, 40 mL, 0.04 mol) at 0° C. over 15 min. The reaction mixture was stirred for 1 h at 0° C., after completion of reaction (monitored by TLC), the mixture was diluted with water (100 mL) and extracted with EtOAc (3×100 mL). The organic layer was dried over anhydrous sodium sulfate and concentrated under reduce pressure to obtain product as a brown colored oil (7.0 g).

Example 400

Preparation of (E)-1-methyl-4-(1-(8-methyl-3,4-dihydro-1H-pyrido[4,3-b]indol-5(2H)-yl)prop-1-en-2-yl)pyridinium (Compound No. 471)

Zinc-copper couple (800 mg) was dissolved in THF and a crystal of iodine was added. The reaction mixture was stirred at 85° C. until the brown color disappeared. A mixture of 2,2,2-trichloroethyl 3,4-dihydro-8-methyl-5-(2-(pyridin-4-yl)prop-1-enyl)-1H-pyrido[4,3-b]indole-2(5H)-carboxylate (400 mg, 0.83 mmol) and methylene iodide (447 mg, 1.67 mmol) was added at the same temperature and the mixture was heated at 85° C. overnight. The reaction mixture was filtered under vacuum and the filtrate purified by reverse phase HPLC to obtain 2,2,2-trichloroethyl 3,4-dihydro-8-methyl-5-(2-(N-methyl-pyridin-4-yl)prop-1-enyl)-1H-pyrido[4,3-b]indole-2(5H)-carboxylate (130 mg TFA salt). To the purified compound (130 mg) was added acetic acid (2 mL) and zinc dust (35 mg). The reaction mixture was stirred at RT for 2 days. MeOH (10 mL) was added and the mixture filtered under vacuum. The filtrate residue was washed with additional MeOH (2×10 mL) and concentrated under reduced pressure. The product obtained was purified on reverse phase chromatography. Yield: 25 mg (TFA salt). $^1$H NMR (CD$_3$OD, TFA salt): δ (ppm): 8.8 (d, 2H), 8.3 (d, 2H), 7.8 (s, 1H), 7.4 (s, 1H), 7.1 (s, 2H), 4.5 (s, 2H), 4.4 (s, 3H), 3.6 (bs, 2H), 3.1 (bs, 2H), 2.4 (s, 3H), 2.2 (s, 3H).

Example 401

Preparation of (E)-3-(1-(2,8-dimethyl-3,4-dihydro-1H-pyrido[4,3-b]indol-5(2H)-yl)prop-1-en-2-yl)-N-methylbenzamide (Compound No. 472)

3-(1-Bromoprop-1-en-2-yl)-N-methylbenzamide (202 mg, 0.8 mmol) was dissolved in DMF (5 mL) and potassium phosphate (424 mg, 2 mmol) was added followed by copper (I) iodide (19 mg, 0.1 mmol) and L-proline (23 mg, 0.2 mmol). 2,3,4,5-Tetrahydro-2,8-dimethyl-1H-pyrido[4,3-b]indole (200 mg, 1 mmol) was added and the mixture purged with nitrogen for 2 min. The reaction mixture was stirred at 85° C. overnight. Water was added and the solid mass was filtered under vacuum. The crude product was purified on silica (100-200 mesh) using 0-7% MeOH: DCM as eluent. Yield: 101 mg. $^1$H NMR (CD$_3$OD, oxalate salt) δ (ppm): 8.1 (s, 1H), 7.8 (m, 2H), 7.6 (t, 1H), 7.3 (s, 1H), 7.15 (d, 1H), 7.1 (d, 1H), 7.05 (s, 1H), 4.6 (bs, 2H), 3.7 (bs, 2H), 3.1 (bs, 5H), 3.0 (s, 3H), 2.4 (s, 3H), 2.0 (s, 3H).

Example 402

Preparation of (E)-2,8-dimethyl-5-(2-(3-(methylsulfonyl)phenyl)prop-1-enyl)-2,3,4,5-tetrahydro-1H-pyrido[4,3-b]indole (Compound No. 473)

1-(1-Bromoprop-1-en-2-yl)-3-(methylsulfonyl)benzene (189 mg, 0.7 mmol) was dissolved in DMF (5 mL) and potassium phosphate (424 mg, 2 mmol) was added followed by copper (I) iodide (19 mg, 0.1 mmol) and L-proline (23 mg, 0.2 mmol). 2,3,4,5-Tetrahydro-2,8-dimethyl-1H-pyrido[4,3-b]indole (200 mg, 1 mmol) was added and the mixture purged with nitrogen for 2 min. The reaction mixture was stirred at 85° C. overnight. Water was added and the solid mass was filtered under vacuum. The crude product was purified on silica (100-200 mesh) using 0-6% MeOH: DCM as eluent. Yield: 158 mg. $^1$H NMR (CD$_3$OD, oxalate salt) δ (ppm): 8.19 (s, 1H), 8.0 (m, 2H), 7.72 (t, 1H), 7.32 (s, 1H), 7.16 (m, 2H), 7.10 (d, 1H), 4.58 (m, 2H), 3.70 (m, 2H), 3.19 (s, 3H), 3.16 (m, 2H), 3.10 (s, 3H), 2.44 (s, 3H), 2.04 (s, 3H).

Example 403

Preparation of (E)-2,8-dimethyl-5-(2-(3-(methylthio)phenyl)prop-1-enyl)-2,3,4,5-tetrahydro-1H-pyrido[4,3-b]indole (Compound No. 474)

(3-(1-Bromoprop-1-en-2-yl)phenyl)(methyl)sulfane (194 mg, 0.8 mmol) was dissolved in DMF (5 mL) and potassium phosphate (424 mg, 2 mmol) was added followed by copper (I) iodide (19 mg, 0.1 mmol) and L-proline (23 mg, 0.2 mmol). 2,3,4,5-Tetrahydro-2,8-dimethyl-1H-pyrido[4,3-b]indole (200 mg, 1 mmol) was added and the mixture purged with nitrogen for 2 min. The reaction mixture was stirred at 85° C. overnight. Water was added and the solid mass was filtered under vacuum. The crude product was purified on silica (100-200 mesh) using 0-4% MeOH: DCM as eluent. Yield: 160 mg. $^1$H NMR (CD$_3$OD, oxalate salt) δ (ppm): 7.50 (s, 1H), 7.38 (m, 2H), 7.30 (s, 2H), 7.10 (m, 2H), 6.99 (s, 1H), 4.50 (m, 2H), 3.70 (m, 2H), 3.10 (m, 4H), 2.56 (s, 3H), 2.42 (s, 3H), 1.95 (s, 3H).

Example 404

Preparation of 8-chloro-5-((4-fluorophenyl)ethynyl)-2-methyl-2,3,4,5-tetrahydro-1H-pyrido[4,3-b]indole (Compound No. 475)

To a stirred solution of 8-chloro-2-methyl-2,3,4,5-tetrahydro-1H-pyrido[4,3-b]indole (0.2 g, 0.00090 mol) and copper sulfate (0.026 g, 0.00009 mol) in toluene (5 mL) was added potassium carbonate (0.25 g, 0.0018 mol) and 1,10-phenanthroline (0.032 g, 0.000018 mol). The reaction mixture was stirred for 5 min at RT. A solution of 1-bromoethynyl-4-fluoro-benzene (0.199 g, 0.00099 mol) in toluene (2 mL) was added to the reaction mixture. After addition, the reaction mixture was stirred for 2 h at 80° C. After completion of reaction (monitored by TLC), solvent was removed under reduced pressure, and the product obtained was purified by column chromatography (2% MeOH:DCM as eluent on silica (100-200 mesh), diameter of column—5.0 cm, height of silica—approx. 5 inch) to provide the desired compound as a yellow colored oil (0.05 g, 16% yield). The free base was converted to its oxalate salt by treatment with oxalic acid (1 equiv) in THF. $^1$H NMR (DMSO, oxalate salt) δ (ppm): 7.65 (m, 4H), 7.30 (m, 3H), 4.20 (m, 2H), 3.40 (m, 2H), 3.10 (m, 2H), 2.80 (s, 3H).

Example 405

Preparation of 2,8-dimethyl-5-((6-methylpyridin-3-yl)ethynyl)-2,3,4,5-tetrahydro-1H-pyrido[4,3-b]indole (Compound No. 476)

To a stirred solution of 2,8-dimethyl-2,3,4,5-tetrahydro-1H-pyrido[4,3-b]indole (0.14 g, 0.00070 mol) and copper sulfate (0.017 g, 0.00007 mol) in toluene (4 mL) was added potassium carbonate (0.193 g, 0.0014 mol) and 1,10-phenanthroline (0.025 g, 0.000014 mol). The reaction mixture was stirred for 5 min at RT. A solution of 5-(bromoethynyl)-2-methylpyridine (0.150 g, 0.00077 mol) in toluene (2 mL) was added to the reaction mixture. After addition, the reaction mixture was stirred for 12 h at 80° C. After completion of reaction (monitored by TLC), solvent was removed under reduced pressure, and the crude product was purified by column chromatography (4% MeOH:DCM as eluent on silica (100-200 mesh), diameter of column—5.0 cm, height of silica—approx. 5 inch). The product was further purified by preparative TLC to give the desired compound as a yellow colored oil (0.010 g, 4.5% yield). 2,8-Dimethyl-5-((6-methylpyridin-3-yl)ethynyl)-2,3,4,5-tetrahydro-1H-pyrido[4,3-b]indole (0.01 g, 0.0000317 mol) was dissolved in THF (1.0 mL). A solution of oxalic acid dihydrate (0.004 g, 0.0000317 mol) in THF (1 mL) was added and stirred for 30 min at RT. The precipitate was filtered and dried to give the oxalate salt as a white solid (0.006 g, 46.8% yield). $^1$H NMR (DMSO, oxalate salt) δ (ppm): 8.70 (s, 1H), 7.90 (d, 1H), 7.60 (d, 1H), 7.38 (d, 2H), 7.18 (d, 1H), 4.20 (m, 2H), 3.40 (m, 2H), 3.10 (m, 2H), 2.80 (s, 3H), 2.50 (s, 3H), 2.40 (s, 3H).

Example 406

Preparation of 8-chloro-5-((3-fluoro-4-methoxyphenyl)ethynyl)-2-methyl-2,3,4,5-tetrahydro-1H-pyrido[4,3-b]indole (Compound No. 477)

8-Chloro-2-methyl-2,3,4,5-tetrahydro-1H-pyrido[4,3-b]indole (100 mg, 0.45 mmol) was dissolved in toluene (5 mL). Copper sulfate (23 mg, 0.090 mmol), 1,10-phenanthroline (33 mg, 0.18 mmol), potassium phosphate (192 mg, 0.90 mmol), and 4-(bromoethynyl)-2-fluoro-1-methoxybenzene (113 mg, 0.49 mmol) were added, and the mixture was flushed with nitrogen. The reaction mixture was heated at 80° C. overnight (16 h). Product was detected by LCMS. The reaction mixture was filtered through Celite, and washed with DCM. The combined organic layer was concentrated under reduced pressure to obtain product, which was purified by column chromatography using silica gel and 60-80% EtOAc in hexane as eluent, and repurified by preparative TLC to obtain product as a brown solid (20 mg). $^1$H NMR (DMSO, oxalate salt) δ (ppm): 7.70 (d, 2H), 7.58 (d, 1H), 7.42 (d, 1H), 7.38 (d, 1H), 7.25 (m, 1H), 4.20 (m, 2H), 3.85 (s, 3H), 3.40 (m, 2H), 3.10 (m, 2H), 2.80 (s, 3H).

Example 407

Preparation of 5-((4-fluorophenyl)ethynyl)-2,8-dimethyl-2,3,4,5-tetrahydro-1H-pyrido[4,3-b]indole (Compound No. 478)

2,8-Dimethyl-2,3,4,5-tetrahydro-1H-pyrido[4,3-b]indole (200 mg, 1.00 mmol) was dissolved in toluene (5 mL). The mixture was stirred for 10 min, and copper sulfate (24.9 mg, 0.01 mmol) and 1,10-phenanthroline (36 mg, 0.2 mmol) were added, and the mixture further stirred for 10 min. To this was added 1-(bromoethynyl)-4-fluorobenzene compound (220 mg, 1.1 mmol) dissolved in toluene and the mixture purged with nitrogen. The reaction mixture was heated at 80-85° C. overnight. The progress of reaction was monitored by TLC and LCMS. The toluene was evaporated under reduced pressure and the crude product purified by column chromatography using silica (100-200 mesh) and 0-50% Ethylacetate:hexane as eluent. $^1$H NMR (DMSO, oxalate salt) δ (ppm): 7.70 (m, 2H), 7.55 (d, 1H), 7.30 (m, 3H), 7.20 (d, 1H), 4.30 (m, 2H), 3.16 (m, 4H), 2.90 (s, 3H), 2.40 (s, 3H).

Example 408

Preparation of methyl 5-((4-fluorophenyl)ethynyl)-2-methyl-2,3,4,5-tetrahydro-1H-pyrido[4,3-b]indole-8-carboxylate (Compound No. 479)

Methyl 2,3,4,5-tetrahydro-2-methyl-1H-pyrido[4,3-b]indole-8-carboxylate (122 mg, 0.5 mmol) was dissolved in toluene (3 mL) and stirred for 10 min. Potassium carbonate (138 mg, 1.0 mmol), copper sulfate (124 mg, 0.05 mmol) and 1,10-phenanthraline (18 mg, 0.1 mmol) were added. The reaction mixture was stirred for 10 min. A solution of 1-(bromoethynyl)-4-fluorobenzene (110 mg, 0.11 mmol) in toluene (2 mL) was added to the reaction mixture, which was heated to 80-85° C. overnight. TLC monitoring showed 10% conversion of reactant to product. As such, more of 1-(bromoethynyl)-4-fluorobenzene (110 mg, 0.5 mmol) was added and heating was continued for 10-12 h. Toluene was removed under reduced pressure to obtain the product, which was purified by column chromatography using silica (100-200 mesh) and 0-5% DCM: MeOH as eluent. The pure compound was converted to its oxalate salt. $^1$H NMR (CD$_3$OD, oxalate salt) δ (ppm): 8.30 (d, 1H), 8.05 (m, 1H), 7.78 (d, 1H), 7.62 (m, 2H), 7.20 (m, 2H), 3.95 (s, 3H), 3.80 (m, 2H), 3.70 (m, 2H), 3.35 (m, 2H), 3.15 (s, 3H).

Example 409

Preparation of 8-chloro-5-((4-chlorophenyl)ethynyl)-2-methyl-2,3,4,5-tetrahydro-1H-pyrido[4,3-b]indole (Compound No. 480)

8-Chloro-2-methyl-2,3,4,5-tetrahydro-1H-pyrido[4,3-b]indole (220 mg, 1 mmol) was dissolved in toluene (8-10 mL). Copper sulfate (50 mg, 0.2 mmol), 1,10-phenanthroline (72 mg, 0.4 mmol), potassium phosphate (425 mg, 2 mmol) and 1-(bromoethynyl)-4-chlorobenzene (237 mg, 1.1 mmol) was added and the mixture flushed with nitrogen. The reaction mixture was heated at 80° C. overnight (16 h). Product was detected by LCMS. The reaction mixture was filtered through Celite, washed with DCM. The combined organic layer was concentrated under vacuum to obtain product, which was purified by column chromatography using silica and 60-80% EtOAc in hexane as eluent to obtain product (120 mg) as a brown semi solid. $^1$H NMR (CDCl$_3$, HCl salt) δ (ppm): 7.52-7.42 (m, 3H), 7.38-7.32 (m, 2H), 7.30 (s, 1H), 7.23-7.20 (d, 1H), 3.62 (s, 2H), 3.02-2.97 (m, 2H), 2.96-2.86 (m 2H), 2.60 (s, 3H).

Example 410

Preparation of 5-((4-chlorophenyl)ethynyl)-2,8-dimethyl-2,3,4,5-tetrahydro-1H-pyrido[4,3-b]indole (Compound No. 481)

2,8-Dimethyl-2,3,4,5-tetrahydro-1H-pyrido[4,3-b]indole (200 mg, 1 mmol) was dissolved in toluene (8-10 mL). Copper sulfate (50 mg, 0.2 mmol), 1,10-phenanthroline (72 mg, 0.4 mmol), potassium phosphate (425 mg, 2 mmol) and 1-(bromoethynyl)-4-chlorobenzene (237 mg, 1.1 mmol) was added and the mixture flushed with nitrogen. The reaction mixture was heated at 80° C. overnight (16 h). Product was detected by LCMS. The reaction mixture was filtered through Celite, washed with DCM. The combined organic layer was concentrated under vacuum to obtain product, which was purified by column chromatography (Silica gel-60-80% EtOAc in hexane) to obtain product (38 mg) as a yellow solid. $^1$H NMR (CDCl$_3$, TFA salt) δ (ppm): 7.52-7.40 (m, 3H), 7.36-7.30 (m, 2H), 7.20 (s, 1H), 7.12-7.09 (d, 1H), 3.77 (s, 2H), 3.06-2.94 (m, 4H), 2.62 (s, 3H), 2.42 (s, 3H).

Example 411

Preparation of 5-((4-fluorophenyl)ethynyl)-2-methyl-2,3,4,5-tetrahydro-1H-pyrido[4,3-b]indole-8-carboxylic acid (Compound No. 482)

Methyl 5-((4-fluorophenyl)ethynyl)-2-methyl-2,3,4,5-tetrahydro-1H-pyrido[4,3-b]indole-8-carboxylate (0.280 g) was dissolved in MeOH (10 mL) and added 10% aq. KOH solution (5 mL). The reaction mixture was heated at 50° C. for 48 h. Progress of the reaction was monitored by TLC and LCMS. The solvent was evaporated and the residue acidified with 1% aq. HCl solution. The solid was filtered and the residue was washed with water (2-3x). The product was washed with hexane. The product was obtained as a white solid. $^1$H NMR (CD$_3$OD, freebase) δ (ppm): 8.30 (d, 1H), 8.10 (m, 1H), 7.70 (m, 3H), 7.20 (m, 2H), 4.60 (m, 2H), 3.80 (m, 2H), 3.38 (m, 2H), 3.15 (s, 3H).

Example 412

Preparation of 5-((4-fluorophenyl)ethynyl)-N, 2-dimethyl-2,3,4,5-tetrahydro-1H-pyrido[4,3-b]indole-8-carboxamide (Compound No. 483)

5-(4-Fluoro-phenylethynyl)-2-methyl-2,3,4,5-tetrahydro-1H-pyrido[4,3-b]indole-8-carboxylic acid (20 mg, 0.0044 mmol) was dissolved in DMF and EDCI.HCl (42.17 mg, 0.22 mmol) was added. Methyl amine (2.0 M) in THF (0.0446 mL, 0.0089 mmol) was added. The reaction mixture was stirred at RT overnight. The progress of reaction was monitored by TLC and LCMS. The DMF was evaporated under vacuum and the product purified by HPLC. $^1$H NMR (CD$_3$OD, TFA salt) δ (ppm): 8.05 (s, 1H), 7.82 (d, 1H), 7.62 (m, 3H), 7.20 (t, 2H), 4.40 (m, 1H), 3.70 (m, 1H), 3.38 (m, 4H), 3.20 (s, 3H), 2.90 (s, 3H).

Example 413

Preparation of 8-chloro-2-methyl-5-((6-methylpyridin-3-yl)ethynyl)-2,3,4,5-tetrahydro-1H-pyrido[4,3-b]indole (Compound No. 484)

8-Chloro-2-methyl-2,3,4,5-tetrahydro-1H-pyrido[4,3-b]indole (56 mg, 0.255 mmol) was dissolved in toluene and copper sulfate (6.3 mg.0.0255 mmol) was added, followed by 1,10-phenanthroline (9.18 mg, 0.051 mmol) and potassium carbonate (70.38 mg, 0.51 mmol). 5-(Bromoethynyl)-2-methylpyridine (50 mg, 0.255 mmol) dissolved in toluene was added and the mixture purged with nitrogen in it. The reaction mixture was heated at 85° C. overnight. The reaction was monitored by TLC and LCMS. Toluene was concentrated under vacuum and the residue washed with water. The crude product was purified by column chromatography using 0-3% MeOH:DCM as eluent, to give the product as a yellow solid. $^1$H NMR (CDCl$_3$, freebase) δ (ppm): 8.65 (s, 1H), 7.70 (d, 1H), 7.48 (d, 1H), 7.38 (s, 1H), 7.25 (d, 1H), 7.16 (d, 1H), 3.60 (s, 2H), 2.96 (m, 2H), 2.80 (m, 2H), 2.60 (s, 3H), 2.56 (s, 3H).

Example 414

Preparation of 5-((3-fluoro-4-methoxyphenyl)ethynyl)-2,8-dimethyl-2,3,4,5-tetrahydro-1H-pyrido[4,3-b]indole (Compound No. 485)

2,8-Dimethyl-2,3,4,5-tetrahydro-1H-pyrido[4,3-b]indole (100 mg, 0.49 mmol) was dissolved in toluene (5 mL), and copper sulfate (24 mg, 0.099 mmol) was added, followed by 1,10-phenanthroline (35 mg, 0.19 mmol), potassium phosphate (0.211 mg, 0.99 mmol) and 4-(bromoethynyl)-2-fluoro-1-methoxybenzene (125 mg, 0.54 mmol), and the mixture flushed with nitrogen. The reaction mixture was heated at 80° C. overnight (16 h). Product was detected by LCMS. The reaction mixture was filtered through Celite, and washed with DCM. The combined organic layer was concentrated under vacuum to obtain product which was purified by column chromatography (60-80% EtOAc in hexane as eluent), and repurified by preparative TLC to obtain product as a brown solid (13 mg). $^1$H NMR (CDCl$_3$, freebase) δ (ppm): 7.42 (d, 1H), 7.25 (m, 2H), 7.18 (s, 1H), 7.10 (d, 1H), 6.92 (t, 1H), 3.95 (s, 3H), 3.62 (s, 2H), 2.95 (m, 2H), 2.85 (m, 2H), 2.60 (s, 3H), 2.40 (s, 3H).

Example 415

Preparation of 8-chloro-2-methyl-5-((6-(trifluoromethyl)pyridin-3-yl)ethynyl)-2,3,4,5-tetrahydro-1H-pyrido[4,3-b]indole (Compound No. 486)

A mixture of 5-bromo-2-(trifluoromethyl)pyridine (4.6 g, 0.02 mol), triphenylphosphine (0.053 g, 0.00020 mol), triethylamine (1.7 mL, 0.01227 mol) and 8-chloro-5-ethynyl-2-methyl-2,3,4,5-tetrahydro-1H-pyrido[4,3-b]indole (1 g, 0.00409 mol) was dissolved in acetonitrile (30 mL) and heated by microwave at 80° C. for 30 min. The reaction was monitored by TLC. After completion of reaction, the mixture was cooled to RT and diluted with water (100 mL). The mixture was extracted with EtOAc (3×100 mL), and the organic layer was dried over anhydrous sodium sulfate and concentrated under reduced pressure to obtain product. Product was purified by column chromatography using silica (100-200 mesh) and 3% MeOH:DCM as eluent, diameter of column—5 cm, height of silica—approx. 5 inch) then further purified by preparative TLC to give the desired compound as a yellow colored solid (0.06 g, 4% yield). The product (0.02 g, 0.000051 mol) was dissolved in THF (1.0 mL). A solution of oxalic acid dihydrate (0.007 g, 0.000055 mol) in THF (2 mL) was added and stirred for 30 min at RT. The precipitate was filtered and dried to give oxalate salt as an off-white solid (0.015 g, 60% yield). $^1$H NMR (CD$_3$OD, oxalate salt) δ (ppm): 8.90 (s, 1H), 8.25 (d, 1H), 7.85 (d, 1H), 7.70 (d, 1H), 7.60 (s, 1H), 7.40 (d, 1H), 4.50 (m, 2H), 3.80 (m, 2H), 3.40 (m, 1H), 3.18 (m, 1H), 3.10 (s, 3H).

Example 416

Preparation of 8-chloro-2-methyl-5-((6-propylpyridin-3-yl)ethynyl)-2,3,4,5-tetrahydro-1H-pyrido[4,3-b]indole (Compound No. 487)

To a stirred solution of 8-chloro-2-methyl-2,3,4,5-tetrahydro-1H-pyrido[4,3-b]indole (0.2 g, 0.00090 mol) and copper sulfate (0.023 g, 0.00009 mol) in toluene (15 mL) was added potassium carbonate (0.25 g, 0.0018 mol) and 1,10 phenanthroline (0.033 g, 0.000018 mol). The reaction mixture was stirred for 5 min at RT. A solution of 5-(bromoethynyl)-2-propylpyridine (0.221 g, 0.00099 mol) in toluene (5 mL) was added to the reaction mixture. The reaction mixture was stirred for 18 h at 80° C. The reaction was monitored by TLC. After completion of reaction, water (30 mL) was added, and the mixture extracted with EtOAc (3×30 mL). The organic layer was dried over anhydrous sodium sulfate, solvent was removed under reduced pressure, and the crude product purified by column chromatography using silica (100-200 mesh) and 3% MeOH:DCM as eluent, diameter of column—5.0 cm, height of silica—approx. 5 inch) to provide the desired compound as a yellow colored oil (0.06 g, 18% yield). 8-Chloro-2-methyl-5-((6-propylpyridin-3-yl)ethynyl)-2,3,4,5-tetrahydro-1H-pyrido[4,3-b]indole (0.056 g, 0.000153 mol) was dissolved in THF (1.0 mL). A solution of oxalic acid dihydrate (0.02 g, 0.000153 mol) in THF (2 mL) was added and stirred for 30 min at RT. The precipitate was filtered and dried to give the oxalate salt as an off-white solid (0.050 g, 80% yield). $^1$H NMR (CD$_3$OD, oxalate salt) δ (ppm): 8.65 (s, 1H), 7.95 (d, 1H), 7.62 (d, 1H), 7.60 (s, 1H), 7.38 (dd, 2H), 4.78 (m, 2H), 4.50 (s, 2H), 3.76 (m, 2H), 3.10 (s, 3H), 2.80 (m, 2H), 1.76 (m, 2H), 1.0 (t, 3H).

Example 417

Preparation of 4-((2,8-dimethyl-3,4-dihydro-1H-pyrido[4,3-b]indol-5(2H)-yl)ethynyl)-2-fluoro-N-methylbenzamide (Compound No. 488)

4-Bromo-2-fluoro-N-methyl-benzamide (100 mg, 0.5 mmol), 5-ethynyl-2,8-dimethyl-2,3,4,4a, 5,9b-hexahydro-1H-pyrido[4,3-b]indole (123 mg, 0.5 mmol), dichlorobis(triphenylphosphine) palladium(II) (17 mg, 0.25 mmol) and TBAF.3H$_2$O (475 mg, 1.5 mmol) were mixed and stirred at 80° C. for 30 min under nitrogen. The progress of reaction was monitored by TLC and LCMS. The mixture was cooled to RT, water was added, and extracted with EtOAc. The organic layer was washed with water (1×10 mL), dried over anhydrous sodium sulfate and concentrated under reduced pressure. The crude product obtained was purified by column chromatography using silica (100-200 mesh) and 0-2% MeOH:DCM as eluent. $^1$H NMR (CDCl$_3$, free base) δ (ppm): 8.10 (t, 1H), 7.42 (d, 1H), 7.36 (d, 1H), 7.22 (d, 1H), 7.18 (m, 2H), 6.70 (bs, 1H), 3.95 (m, 2H), 3.20 (m, 4H), 3.05 (d, 3H), 2.80 (s, 3H), 2.42 (s, 3H).

Example 418

Preparation of 3-((2,8-dimethyl-3,4-dihydro-1H-pyrido[4,3-b]indol-5(2H)-yl)ethynyl)-N,N-dimethylaniline (Compound No. 489)

(3-Bromo-phenyl)-dimethylamine (100 mg, 0.5 mmol), 5-ethynyl-2,8-dimethyl-2,3,4,4a, 5,9b-hexahydro-1H-pyrido[4,3-b]indole (123 mg, 0.5 mmol), dichlorobis(triphenylphosphine) palladium(II) (17 mg, 0.25 mmol) and TBAF.3H$_2$O (275 mg, 1.5 mmol) were mixed and stirred at 80° C. for 30 min under nitrogen. The progress of reaction was monitored by TLC and LCMS. The mixture was cooled to RT, water was added, and extracted with EtOAc. The organic layer was washed with water (1×10 mL), dried over anhydrous sodium sulfate and concentrated under vacuum. The crude product was purified by column chromatography using silica gel (100-200 mesh), neutralizing the silica gel with aq. Ammonia, and using 0-2% MeOH:DCM as eluent. $^1$H NMR (CDCl$_3$, TFA salt) δ (ppm): 7.50 (d, 1H), 7.30 (m, 1H), 7.18 (d, 2H), 7.05 (d, 2H), 6.90 (m, 1H), 4.78 (m, 1H), 4.10 (m, 1H), 3.90 (m, 1H), 3.40 (m, 2H), 3.20 (m, 1H), 3.0 (s, 9H), 2.42 (s, 3H).

Example 419

Preparation of 2,8-dimethyl-5-(phenylethynyl)-2,3,4,5-tetrahydro-1H-pyrido[4,3-b]indole (Compound No. 490)

A mixture of 5-ethynyl-2,8-dimethyl-2,3,4,5-tetrahydro-1H-pyrido[4,3-b]indole (171 mg, 0.76 mmol), bromo benzene (100 mg, 0.6 mmol), dichlorobistriphenylphosphine palladium(II) (12 mg, 0.018 mmol) and TBAF.3H$_2$O (567 mg, 1.8 mmol) were heated 80° C. for 5 min by microwave. After completion of reaction (monitored by TLC), the mixture was poured into water (10 mL) and extracted with EtOAc (2×20 mL). The organic layer was dried over sodium sulfate and concentrated under vacuum and the crude product purified by column chromatography using silica gel (100-200 mesh) and 1% MeOH in DCM as eluent, followed by reverse phase chromatography to obtain 8 mg of 2,8-dimethyl-5-phenylethynyl-2,3,4,5-tetrahydro-1H-pyrido[4,3-b]indole. $^1$H NMR (CDCl$_3$, freebase) δ (ppm): 7.55 (d, 2H), 7.50 (d, 1H), 7.40-7.31 (m, 3H), 7.20 (s, 1H), 7.10 (d, 1H), 3.70 (s, 2H), 3.0 (t, 2H), 2.90 (t, 2H), 2.60 (s, 3H), 2.45 (s, 3H).

Example 420

Preparation of 2,8-dimethyl-5-(thiophen-3-ylethynyl)-2,3,4,5-tetrahydro-1H-pyrido[4,3-b]indole (Compound No. 491)

A mixture of 5-ethynyl-2,8-dimethyl-2,3,4,5-tetrahydro-1H-pyrido[4,3-b]indole (165 mg, 0.736 mmol), 3-bromothiophene (100 mg, 0.613 mmol), TBAF.3H$_2$O (580 mg, 1.84 mmol), and dichlorobis(triphenylphosphine)palladium (II) (13 mg, 0.018 mmol) were heated by microwave at 80° C. for 5 min. The reaction was monitored by TLC and LCMS. The reaction mixture was diluted with water (30 mL) and extracted with EtOAc (3×50 mL). The combined organic layers were washed with water (2×50 mL), dried over anhydrous sodium sulfate, and concentrated under vacuum. The crude product obtained was purified by HPLC to yield 12.2 mg of 2,8-dimethyl-5-thiophen-3-ylethynyl-2,3,4,5-tetrahydro-1H-pyrido[4,3-b]indole. $^1$H NMR (CDCl$_3$, freebase) δ (ppm): 7.50 (s, 1H), 7.40 (d, 1H), 7.38 (d, 1H), 7.20 (m, 2H), 7.10 (d, 1H), 3.68 (s, 2H), 2.98 (t, 2H), 2.90 (t, 2H), 2.58 (s, 3H), 2.42 (s, 3H).

Example 421

Preparation of 5-(furan-3-ylethynyl)-2,8-dimethyl-2,3,4,5-tetrahydro-1H-pyrido[4,3-b]indole (Compound No. 492)

A mixture of 5-ethynyl-2,8-dimethyl-2,3,4,5-tetrahydro-1H-pyrido[4,3-b]indole (180 mg, 0.81 mmol), 3-bromofuran (100 mg, 0.68 mmol), dichlorobis(triphenylphosphine)palladium (II) (14 mg, 0.02 mmol) and TBAF.3H$_2$O (642 mg, 2.0 mmol) was heated at 80° C. for 5 min by microwave. After completion of reaction (monitored by TLC), the mixture was poured into water (10 mL) and extracted with EtOAc (3×10 mL). The organic layer was dried over sodium sulfate and concentrated under vacuum to obtain product, which was purified by reverse phase chromatography to obtain 10 mg of 5-furan-3-ylethynyl-2,8-dimethyl-2,3,4,5-tetrahydro-1H-pyrido[4,3-b]indole. $^1$H NMR (CDCl$_3$, free-base) δ (ppm): 7.70 (s, 1H), 7.50-7.4 (m, 2H), 7.20 (s, 1H), 7.10 (d, 1H), 6.55 (s, 1H), 3.68 (s, 2H), 3.0-2.90 (m, 4H), 2.60 (s, 3H), 2.40 (s, 3H).

Example 422

Preparation of 2,8-dimethyl-5-(thiophen-2-ylethynyl)-2,3,4,5-tetrahydro-1H-pyrido[4,3-b]indole (Compound No. 493)

5-Ethynyl-2,8-dimethyl-2,3,4,5-tetrahydro-1H-pyrido[4,3-b]indole (165 mg, 0.736 mmol) 2-bromothiophene (100 mg, 0.613 mmol), TBAF.3H$_2$O (580 mg, 1.84 mmol), and dichlorobis(triphenylphosphine)palladium (II) (13 mg, 0.018 mmol) were placed in microwave vial and heated by microwave at 80° C. for 5 min. The reaction was monitored by TLC and LCMS. The reaction mixture was diluted with water (30 mL) and extracted with EtOAc (3×50 mL). The combined organic layer was washed with water (2×50 mL), dried over anhydrous sodium sulfate, and concentrated under vacuum to obtain product, which was subjected to preparative HPLC to yield 20 mg of 2,8-dimethyl-5-thiophen-3-ylethynyl-2,3,4,5-tetrahydro-1H-pyrido[4,3-b]indole. $^1$H NMR (CDCl$_3$, freebase) δ (ppm): 7.40 (d, 1H), 7.30-7.25 (m, 2H), 7.19 (s, 1H), 7.10-7.0 (m, 2H), 3.65 (s, 2H), 2.95 (t, 2H), 2.90 (t, 2H), 2.59 (s, 3H), 2.45 (s, 3H).

Example 423

Preparation of 5-((6-methoxypyridin-3-yl)ethynyl)-2,8-dimethyl-2,3,4,5-tetrahydro-1H-pyrido[4,3-b]indole (Compound No. 494)

A mixture of 5-ethynyl-2,8-dimethyl-2,3,4,5-tetrahydro-1H-pyrido[4,3-b]indole (538 mg, 2.4 mmol), 5-bromo-2-methoxy-pyridine (376 mg, 2.0 mmol), dichlorobistriphenylphosphine palladium(II) (42 mg, 0.059 mmol) and TBAF.3H$_2$O (1.8 g, 5.71 mmol) was heated at 80° C. for 5 min by microwave (reaction temperature increased to 120° C.). After completion of reaction (monitored by TLC & LCMS), the mixture was poured into water (40 mL) and extracted with EtOAc (3×40 mL). The organic layer was washed with water (3×30 mL) and dried over sodium sulfate and concentrated under vacuum. The product was purified by reverse phase chromatography to obtain 52 mg of 5-[1-fluoro-2,2-bis-(6-methoxy-pyridin-3-yl)-vinyl]-2,8-dimethyl-2,3,4,5-tetrahydro-1H-pyrido[4,3-b]indole, and 41 mg of 5-(6-methoxy-pyridin-3-ylethynyl)-2,8-dimethyl-2,3,4,5-tetrahydro-1H-pyrido[4,3-b]indole. 5% of the vinyl fluoride was also isolated. $^1$H NMR (CDCl$_3$, free base) δ (ppm): 8.36 (s, 1H), 7.70 (d, 1H), 7.42 (d, 1H), 7.18 (s, 1H), 7.10 (d, 1H), 6.72 (d, 1H), 3.98 (s, 3H), 3.65 (s, 2H), 2.95 (m, 4H), 2.60 (s, 3H), 2.42 (s, 3H).

Example 424

Preparation of 2,8-dimethyl-5-(pyridin-4-ylethynyl)-2,3,4,5-tetrahydro-1H-pyrido[4,3-b]indole (Compound No. 495)

A mixture of 5-ethynyl-2,8-dimethyl-2,3,4,5-tetrahydro-1H-pyrido[4,3-b]indole (138 mg, 0.6 mmol), 4-bromopyridinehydrochloride (100 mg, 0.51 mmol), dichlorobistriphenylphosphine palladium (II) (10 mg, 0.015 mmol) and TBAF.3H$_2$O (481 mg, 1.5 mmol) was heated at 50° C. (observed exothermic temperature was 99° C.) for 5 min by microwave. After completion of reaction (monitored by TLC&LCMS), the mixture was poured into water (20 mL), saturated bicarbonate was added, and the mixture extracted with EtOAc (3×20 mL). The organic layer was washed with water (2×20 mL), dried over sodium sulfate and concentrated under vacuum to obtain 170 mg of 2,8-dimethyl-5-pyridin-4-ylethynyl-2,3,4,5-tetrahydro-1H-pyrido[4,3-b]indole. $^1$H NMR (CDCl$_3$, free base) δ (ppm): 8.58 (d, 2H), 7.42 (d, 1H), 7.34 (d, 2H), 7.20 (s, 1H), 7.10 (d, 1H), 3.62 (s, 2H), 3.98 (m, 2H0, 3.92 (m, 2H), 2.60 (s, 3H0, 2.42 (s, 3H).

Example 425

Preparation of 5-((6-cyclopropylpyridin-3-yl)ethynyl)-2,8-dimethyl-2,3,4,5-tetrahydro-1H-pyrido[4,3-b]indole (Compound No. 496)

A mixture of 5-ethynyl-2,8-dimethyl-2,3,4,5-tetrahydro-1H-pyrido[4,3-b]indole (102 mg, 0.45 mmol), 5-bromo-2-cyclopropyl-pyridine (75 mg, 0.38 mmol), dichlorobistriphenylphosphine palladium(II) (7 mg, 0.0114 mmol) and TBAF.3H$_2$O (359 mg, 1.14 mmol) was heated at 80° C. for 5 min by microwave. After completion of reaction (monitored by TLC), the mixture was poured into water (10 mL) and extracted with EtOAc (2×20 mL). The organic layer was dried over sodium sulfate, concentrated under vacuum to obtain crude product, which was purified by reverse phase chromatography to obtain 9 mg of 5-(6-cyclopropyl-pyridin-3-ylethynyl)-2,8-dimethyl-2,3,4,5-tetrahydro-1H-pyrido[4,3-b]indole. $^1$H NMR (CDCl$_3$, free base) δ (ppm): 8.58 (s, 1H), 7.62 (d, 1H), 7.40 (d, 1H), 7.18 (s, 1H), 7.08 (m, 2H), 3.65 (s, 2H), 2.90 (m, 4H), 2.60 (s, 3H), 2.42 (s, 3H), 2.05 (m, 1H), 1.05 (m, 4H).

Example 426

Preparation of 2,8-dimethyl-5-((1-methyl-1H-imidazol-5-yl)ethynyl)-2,3,4,5-tetrahydro-1H-pyrido[4,3-b]indole (Compound No. 497)

A mixture of 5-ethynyl-2,8-dimethyl-2,3,4,5-tetrahydro-1H-pyrido[4,3-b]indole (166 mg, 0.74 mmol), 5-bromo-1-methyl-1H-imidazole (100 mg, 0.62 mmol), dichlorobistriphenyl phosphinepalladium (II) (13 mg, 0.018 mmol) and TBAF.3H$_2$O (586 mg, 1.86 mmol) was heated at 80° C. (observed exothermic temperature was 120° C.) for 5 min by microwave. After completion of reaction (monitored by TLC&LCMS), the mixture was poured into water (20 mL) and saturated bicarbonate was added. The mixture was extracted with EtOAc (3×20 mL), the organic layer was washed with water (2×20 mL), dried over sodium sulfate and concentrated under vacuum to obtain 16 mg of 2,8-dimethyl-5-(3-methyl-3H-imidazol-4-ylethynyl)-2,3,4,5-tetrahydro-1H-pyrido[4,3-b]indole. $^1$H NMR (CDCl$_3$, free base) δ (ppm): 7.56 (s, 1H), 7.38 (d, 2H), 7.20 (s, 1H), 7.10 (d, 1H), 3.72 (s, 3H), 3.66 (s, 2H), 2.92 (m, 4H), 2.60 (s, 3H), 2.44 (s, 3H).

Example 427

Preparation of 4-((2,8-dimethyl-3,4-dihydro-1H-pyrido[4,3-b]indol-5(2H)-yl)ethynyl)thiazole (Compound No. 498)

A mixture of 5-ethynyl-2,8-dimethyl-2,3,4,5-tetrahydro-1H-pyrido[4,3-b]indole (163 mg, 0.731 mmol), 4-bromothiazole (100 mg, 0.60 mmol), dichlorobistriphenylphosphinepalladium(II) (12 mg, 0.01 mmol) and TBAF.3H$_2$O (575 mg, 1.82 mmol) was heated at 80° C. (observed exothermic temperature was 120° C.) for 5 min by microwave. After completion of reaction (monitored by TLC&LCMS), the mixture was poured into water (20 mL) and saturated bicarbonate was added. The mixture was extracted with EtOAc (3×20 mL), the organic layer was washed with water (3×50 mL), dried over sodium sulfate and concentrated under vacuum to obtain 10 mg of 2,8-dimethyl-5-thiazol-4-ylethynyl-2,3,4,5-tetrahydro-1H-pyrido[4,3-b]indole. $^1$H NMR (CDCl$_3$, free base) δ (ppm): 8.80 (s, 1H), 7.56 (s, 1H), 7.44 (d, 2H), 7.18 (s, 1H), 7.08 (d, 1H), 3.64 (s, 2H), 3.0 (m, 2H), 2.90 (m, 2H), 2.60 (s, 3H), 2.42 (s, 3H).

Example 428

Preparation of 2-(2,8-dimethyl-3,4-dihydro-1H-pyrido[4,3-b]indol-5(2H)-yl)-1-(4-fluorophenyl)-1-phenylethanol (Compound No. 176)

2-(2,8-Dimethyl-3,4-dihydro-1H-pyrido[4,3-b]indol-5 (2H)-yl)-1-(4-fluorophenyl)ethanone (168 mg, 0.5 mmol) was dissolved in 10 mL of anhydrous THF. Phenyl magnesium bromide (1.5 mL, 1.5 mmol) was added dropwise at RT under nitrogen atmosphere. The reaction mixture was stirred at RT for 1 h. Water (3 mL) was added to the reaction mixture and the product was extracted with EtOAc. The combined organic layers were washed with water and dried over sodium sulfate. The solvent was evaporated under reduced pressure to obtain the crude compound, which was purified by preparative HPLC. $^1$H NMR (CD$_3$OD, TFA salt) δ (ppm): 7.40-7.20 (m, 7H), 7.10 (d, 1H), 7.95 (m, 2H), 7.85 (m, 1H), 6.75 (m, 1H), 4.80 (m, 2H), 4.60 (m, 1H), 4.30 (m, 1H), 3.62 (m, 2H), 3.0 (s, 3H), 2.80-2.60 (m, 3H), 2.40 (s, 3H).

Example 429

Preparation of 8-chloro-2-methyl-5-(2-(pyridin-3-yl)cyclohex-1-enyl)-2,3,4,5-tetrahydro-1H-pyrido[4,3-b]indole (Compound No. 166)

2,8-Dimethyl-2,3,4,5-tetrahydro-1H-pyrido[4,3-b]indole (200 mg, 1.0 mmol) was dissolved in DMF (2 mL). Sodium hydride (50%) (60 mg, 2.5 mmol) was added in portions at 0° C. and the reaction mixture was stirred at RT for 15 min. A solution of 5-(1,2-dibromocyclohexyl)-2-methylpyridine (99 mg, 1.3 mmol) in DMF (2 mL) was added dropwise over 10 min and stirring was continued for additional 2 h at RT. The reaction mixture was quenched with ice water and extracted with EtOAc. The organic layer was washed with brine, dried over anhydrous sodium sulfate and evaporated under reduced pressure. The crude product was purified by preparative TLC to afford 13 mg of title compound. $^1$H NMR (CDCl$_3$, TFA salt) δ (ppm): 7.30 (s, 1H), 7.21 (d, 1H), 7.13-7.05 (m, 2H), 6.83-6.81 (m, 2H), 3.60-3.48 (m, 2H), 2.90-2.86 (m, 4H), 2.53 (s, 2H), 2.41-2.36 (m, 6H), 2.05-1.81 (m, 6H), 1.26-1.20 (m, 3H).

Example 430

Preparation of (E)-8-chloro-5-(3,3-dimethyl-2-(pyridin-4-yl)but-1-enyl)-2-methyl-2,3,4,5-tetrahydro-1H-pyrido[4,3-b]indole (Compound No. 286)

8-Chloro-2,3,4,5-tetrahydro-2-methyl-1H-pyrido[4,3-b]indole (220 mg, 1 mmol) was dissolved in DMF (3 mL). Potassium phosphate (424 mg, 2 mmol), copper (I) iodide (19 mg, 0.1 mmol) and L-proline (23 mg, 0.2 mmol) were added. A solution of 4-(1-bromo-3,3-dimethylbut-1-en-2-yl) pyridine (294 mg, 1.5 mmol) in DMF (2 mL) was added dropwise, the reaction mixture was purged with nitrogen, and heated at 85° C. overnight. The DMF was evaporated under reduced pressure and the reaction mixture was diluted with water. The resultant precipitate was filtered and purified by silica gel chromatography (100-200 mesh) using 0-8% MeOH:DCM as eluant. The compound was further purified by HPLC. Yield: 77.03 mg. $^1$H NMR (CD$_3$OD, TFA salt) δ (ppm): 8.30 (d, 2H), 7.30 (m, 4H), 7.18 (d, 1H), 6.90 (s, 1H) 4.50 (m, 1H), 4.20 (m, 1H), 3.80 (m, 1H), 3.50 (m, 1H), 3.15 (m, 2H), 3.05 (s, 3H), 1.35 (s, 9H).

Example 431

Preparation of 2,8-dimethyl-5-(pyrimidin-4-ylethynyl)-2,3,4,5-tetrahydro-1H-pyrido[4,3-b]indole (Compound No. 499)

5-Ethynyl-2,8-dimethyl-2,3,4,5-tetrahydro-1H-pyrido[4,3-b]indole (100 mg, 0.466 mmol) and 4-bromopyrimidine (126 mg, 0.797 mmol) were dissolved in triethylamine (1.5 mL), and the solution was purged with nitrogen. Dichlorobis (triphenylphosphine) palladium (12.5 mg, 0.017 mmol) and copper iodide (6.7 mg, 0.035 mmol) were added and the reaction mixture was purged again with nitrogen. The reaction mixture was heated by microwave at 40° C. for 90 min. The reaction mixture was quenched with 30 mL water and extracted with EtOAc (3×15 mL). The combined organic layers were dried over sodium sulfate and concentrated under reduced pressure to obtain crude product. The crude product was purified with column chromatography (silica gel: 100-200 mesh, eluent 0-10% MeOH in DCM) to obtain 25 mg product. $^1$H NMR (CDCl$_3$, freebase) δ (ppm): 9.17 (s, 1H), 8.76 (d, 1H), 7.57 (d, 1H), 7.40 (d, 1H), 7.18 (m, 2H), 3.64 (s, 2H), 3.06 (d, 2H), 2.98 (d, 2H), 2.61 (s, 3H), 2.43 (s, 3H).

Example 432

Preparation of 2,3,4,5-tetrahydro-2,8-dimethyl-5-(3-(pyridin-2-yl)prop-2-ynyl)-1H-pyrido[4,3-b]indole (Compound No. 500)

A mixture of 2,3,4,5-tetrahydro-2,8-dimethyl-5-(prop-2-ynyl)-1H-pyrido[4,3-b]indole[(p-tolylhydrazine hydrochloride (600 mg, 3.7 mmol), propargyl bromide (80 wt % solution in toluene, 0.34 mL, 3.7 mmol), triethyl amine (1.5 mL, 11.3 mmol) and N-methyl-4-piperidone hydrochloride (316 mg, 2.1 mmol) were taken in ethanol (15 mL) to obtain 80 mg of 2,3,4,5-tetrahydro-2,8-dimethyl-5-(prop-2-ynyl)-1H-pyrido[4,3-b]indole after purification on silica gel (230-400 mesh) chromatography eluting with MeOH-DCM gradient) (150 mg, 0.6 mmol)], 2-bromopyridine (0.06 mL, 0.6 mmol), dichlorobis(triphenylphosphine) palladium (8 mg, 0.012 mmol), CuI (1 mg, 0.006 mmol), and triethylamine (0.01 mL 0.071 mmol) in acetonitrile (5 mL) was heated at 80° C. for 1.5 h to obtain 108 mg of 2,3,4,5-tetrahydro-2, 8-dimethyl-5-(3-(pyridin-2-yl)prop-2-ynyl)-1H-pyrido[4,3-b]indole after purification by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL). $^1$H NMR (DMSO-d6, TFA salt) δ (ppm): 8.45-8.40 (d, 1H), 7.80-7.70 (t, 1H), 7.45-7.40 (m, 1H), 7.30-7.25 (t, 1H), 7.25 (s, 2H), 7.10-7.00

(d, 1H), 5.60 (s, 2H), 4.60-4.55 (d, 1H), 4.25-4.20 (d, 2H), 3.85-3.75 (d, 1H), 3.65-3.40 (m, 2H), 3.00 (s, 3H), 2.30 (s, 3H).

Example 433

Preparation of (E)-ethyl 4-(2,8-dimethyl-3,4-dihydro-1H-pyrido[4,3-b]indol-5(2H)-yl)-3-phenylbut-2-enoate (Compound No. 347)

2-(2,8-Dimethyl-3,4-dihydro-1H-pyrido[4,3-b]indol-5(2H)-yl)-1-phenylethanone (100 mg, 3 mmol) was dissolved in 3 mL of toluene. (Carbethoxymethylene)triphenylphosphorane (200 mg, 0.56 mmol) was added and the reaction mixture was heated at 100° C. overnight. Solvent was removed under reduced pressure and the residue was purified by silica gel chromatography (100-200) eluting with 2% MeOH-DCM. $^1$H NMR (CDCl$_3$, oxalate salt) δ (ppm): 7.70 (m, 1H), 7.50 (m, 2H), 7.38 (m, 3H), 7.20 (m, 1H), 7.10 (m, 1H), 5.30 (m, 1H), 4.80 (s, 2H), 3.90 (m, 2H), 2.90 (m, 2H), 2.80 (m, 2H), 2.60 (s, 3H), 2.42 (s, 3H), 2.0 (m, 2H), 1.0 (t, 3H).

Example 434

Preparation of (Z)-5-(8-chloro-2-methyl-3,4-dihydro-1H-pyrido[4,3-b]indol-5(2H)-yl)-4-(4-fluorophenyl)pent-3-en-1-ol (Compound No. 348)

2-(8-Chloro-2-methyl-3,4-dihydro-1H-pyrido[4,3-b]indol-5(2H)-yl)-1-cyclopropyl-1-(4-fluorocyclohexa-1,2,3,5-tetraenyl)ethanol (1 g, 25 mmol) was dissolved in 10 mL 25% sulfuric acid and and heated at 110° C. for 4 h. The reaction mixture was cooled to RT, diluted with water and the resultant solid was filtered, washed with water, and diethylether. The solid was purified by reverse phase HPLC, and separated from the regioisomeric Compound No. 349. $^1$H NMR (CD$_3$OD, HCl salt) δ (ppm): 7.50 (m, 1H), 7.38 (d, 1H), 7.15 (m, 3H), 7.0 (m, 1H), 6.80 (m, 2H), 5.80 (m, 1H), 5.22 (m, 2H), 4.60 (m, 1H), 4.25 (m, 1H), 3.80 (m, 2H), 3.45 (m, 2H), 3.15 (m, 2H), 3.0 (s, 3H), 2.65 (m, 2H).

Example 435

Preparation of (E)-5-(8-chloro-2-methyl-3,4-dihydro-1H-pyrido[4,3-b]indol-5(2H)-yl)-4-(4-fluorophenyl)pent-3-en-1-ol (Compound No. 349)

2-(8-Chloro-2-methyl-3,4-dihydro-1H-pyrido[4,3-b]indol-5(2H)-yl)-1-cyclopropyl-1-(4-fluorocyclohexa-1,2,3,5-tetraenyl)ethanol (1 g, 25 mmol) was dissolved in 10 mL 25% sulfuric acid and and heated at 110° C. for 4 h. The reaction mixture was cooled to RT, diluted with water and the resultant solid was filtered, washed with water, and diethylether. The solid was purified by reverse phase HPLC, and separated from the regioisomeric Compound No. 348. $^1$H NMR (CD$_3$OD, HCl salt) δ (ppm): 7.48 (d, 1H), 7.40 (m, 1H), 7.15 (m, 1H), 7.0 (m, 4H), 5.60 (m, 1H), 5.0 (m, 2H), 4.80 (m, 2H), 4.60 (m, 1H), 4.30 (m, 1H), 3.80 (m, 1H), 3.42 (m, 2H), 3.05 (s, 3H), 3.0 (m, 1H), 2.10 (m, 2H).

Example 436

Preparation of (E)-ethyl 4-(2,8-dimethyl-3,4-dihydro-1H-pyrido[4,3-b]indol-5(2H)-yl)-3-(4-fluorophenyl)but-2-enoate (Compound No. 350)

2-(2,8-Dimethyl-3,4-dihydro-1H-pyrido[4,3-b]indol-5(2H)-yl)-1-(4-fluorophenyl)ethanone (500 mg, 1.5 mmol) was dissolved in toluene. Phosphorane (1 g, 2.8 mmol) was added and the reaction mixture was heated at 100° C. overnight. Solvent was removed under reduced pressure and the residue was purified by silica gel chromatography (100-200) eluting with 0-100% EtOAc-hexane. The product was re-purified by reverse phase HPLC. $^1$H NMR (CD$_3$OD, TFA salt) δ (ppm): 7.30 (m, 2H), 7.20 (m, 2H), 7.08 (m, 3H), 5.2 (m, 1H), 5.05 (s, 2H), 4.70 (m, 2H), 4.38 (m, 1H), 3.90 (q, 2H), 3.80 (m, 1H), 3.55 (m, 1H), 3.10 (m, 1H), 3.05 (s, 3H), 2.40 (s, 3H), 1.0 (t, 3H).

Example 437

Preparation of (E)-8-chloro-5-(2-(4-fluorophenyl)hex-2-enyl)-2-methyl-2,3,4,5-tetrahydro-1H-pyrido[4,3-b]indole (Compound No. 351)

This product was isolated as a regioisomer from Example 160 (Compound No. 208). $^1$H NMR (DMSO-d6, oxalate salt) δ (ppm): 7.50 (m, 2H), 7.20 (m, 1H), 7.10 (m, 3H), 6.90 (m, 1H), 5.40 (m, 1H), 5.0 (s, 2H), 4.20 (m, 3H), 3.40 (m, 2H), 2.90 (m, 2H), 2.80 (t, 3H), 2.40 (m, 1H), 1.80 (m, 1H), 1.20 (m, 1H), 0.7 (t, 3H).

Example 438

Preparation of (E)-4-(2,8-dimethyl-3,4-dihydro-1H-pyrido[4,3-b]indol-5(2H)-yl)-3-(4-fluorophenyl)but-2-enoic acid (Compound No. 352)

Ethyl 4-(2,8-dimethyl-3,4-dihydro-1H-pyrido[4,3-b]indol-5(2H)-yl)-3-(4-fluorophenyl)but-2-enoate (100 mg, 0.246 mmol) was dissolved in NMP (1 mL). Powdered KOH (100 mg) was added and the reaction mixture was heated at 100° C. overnight. The reaction mixture was cooled to RT and acidified with conc. HCl (pH 5-6). The product was isolated by reverse phase chromatography. $^1$H NMR (CD$_3$OD, TFA salt) δ (ppm): 7.40 (d, 1H), 7.18 (m, 3H), 7.05 (m, 1H), 6.90 (m, 2H), 6.10 (s, 1H), 5.90 (m, 1H), 5.70 (m, 1H), 4.50 (m, 2H), 4.22 (m, 2H), 3.70 (m, 2H), 3.0 (s, 3H), 2.40 (s, 3H).

Example 439

Preparation of 6-fluoro-5-(2-(4-fluorophenyl)allyl)-2-methyl-2,3,4,5-tetrahydro-1H-pyrido[4,3-b]indole (Compound No. 353)

6-Fluoro-2-methyl-2,3,4,5-tetrahydro-1H-pyrido[4,3-b]indole (200 mg, 0.98 mmol) was dissolved in DMF (4 mL). Copper (I) iodide (18 mg, 0.098 mmol), L-proline (22 mg, 0.19 mmol) and K$_3$PO$_4$ (416 mg, 1.96 mmol) were added and the reaction mixture was stirred for 10 min at RT. 1-(1-Bromoprop-1-en-2-yl)-4-fluorobenzene (250 mg, 1.17 mmol) was added dropwise and the reaction mixture was purged with nitrogen. The reaction mixture was heated at 85° C. overnight (prolonged heating in some cases was required). DMF was evaporated under reduced pressure, the residue was diluted with water, and the solid was filtered. The solid material was purified by silica gel chromatography (100-200 mesh) eluting with 0-5% MeOH-DCM. $^1$H NMR (DMSO-d6, oxalate salt) δ (ppm): 7.60 (m, 2H), 7.30-7.20 (m, 3H), 7.0 (m, 1H), 6.95 (m, 1H), 5.38 (s, 1H), 5.22 (s, 2H), 4.30 (m, 2H), 4.08 (s, 1H), 3.8-3.3 (m, 2H), 3.0 (m, 2H), 2.90 (s, 3H).

Example 440

Preparation of 6-chloro-5-(2-(4-fluorophenyl)allyl)-2-methyl-2,3,4,5-tetrahydro-1H-pyrido[4,3-b]indole (Compound No. 354)

6-Chloro-2-methyl-2,3,4,5-tetrahydro-1H-pyrido[4,3-b]indole (200 mg, 0.909 mmol) was dissolved in DMF (4 mL). Copper (I) iodide (14 mg, 0.089 mmol), L-proline (20 mg, 0.173 mmol) and $K_3PO_4$ (380 mg, 1.79 mmol) were added and the reaction mixture was stirred for 10 min at RT. 1-(1-Bromoprop-1-en-2-yl)-4-fluorobenzene (250 mg, 1.17 mmol) was added dropwise and the reaction mixture was purged with nitrogen. The reaction mixture was heated at 85° C. overnight (prolonged heating in some cases was required). DMF was evaporated under reduced pressure, the residue was diluted with water, and the solid was filtered. The solid material was purified by silica gel chromatography (100-200 mesh) eluting with 0-5% MeOH-DCM. $^1$H NMR (CD$_3$OD, oxalate salt) δ (ppm): 7.60 (m, 2H), 7.45 (d, 1H), 7.20-7.05 (m, 4H), 5.50 (s, 2H), 5.30 (s, 1H), 4.55 (m, 2H), 4.05 (s, 1H), 3.70 (m, 2H), 3.18 (m, 2H), 3.10 (s, 3H).

Example 441

Preparation of 4-(3-(2,8-dimethyl-3,4-dihydro-1H-pyrido[4,3-b]indol-5(2H)-yl)prop-1-en-2-yl)phenol (Compound No. 355)

This product was isolated as a regioisomer from Example 194 (Compound No. 235). $^1$H NMR (CD$_3$OD, TFA salt) δ (ppm): 7.38 (d, 2H), 7.25 (d, 2H), 7.05 (d, 1H), 6.78 (d, 2H), 5.22 (s, 1H), 5.10 (s, 2H), 4.70 (m, 1H), 4.40 (m, 1H), 4.30 (s, 1H), 3.80 (m, 1H), 3.56 (m, 1H), 3.18 (m, 2H), 3.10 (s, 3H), 2.40 (s, 3H).

Example 442

Preparation of 8-methoxy-2-methyl-5-(2-(pyridin-4-yl)allyl)-2,3,4,5-tetrahydro-1H-pyrido[4,3-b]indole (Compound No. 356)

This product was isolated as a regioisomer from Example 199 (Compound No. 239) and Example 206 (Compound No. 246). $^1$H NMR (CD$_3$OD, TFA salt) δ (ppm): 8.50 (d, 2H), 7.58 (d, 2H), 7.22 (d, 1H), 6.92 (s, 1H), 6.80 (d, 1H), 5.60 (s, 1H), 5.18 (s, 2H), 4.62 (s, 1H), 4.0 (s, 2H), 3.80 (s, 3H), 3.20 (m, 2H), 2.95 (m, 2H), 2.78 (s, 3H).

Example 443

Preparation of 8-chloro-2-methyl-5-(3-methyl-2-(pyridin-4-yl)but-2-enyl)-2,3,4,5-tetrahydro-1H-pyrido[4,3-b]indole (Compound No. 357)

1-(8-Chloro-1,2,3,4-tetrahydro-2-methylpyrido[4,3-b]indol-5-yl)-3-methyl-2-(pyridin-4-yl)butan-2-ol (0.668 g, 1.77 mmol) was dissolved in thionyl chloride (0.32 mL, 2.5 eq) and the solution was stirred at RT for 12 h. Volatiles were removed under reduced pressure, the residue was basified with saturated aqueous sodium bicarbonate, and the product was extracted with EtOAc (3×50 mL). Combined organic layer was dried over anhydrous sodium sulfate and concentrated under reduced pressure. The residue was purified silica gel chromatography (100-200 mesh) eluting with 5% MeOH:DCM to obtain 0.120 g of product. $^1$H NMR (DMSO-d6, oxalate salt) δ (ppm): 8.22 (d, 2H), 7.40 (s, 1H), 7.25 (d, 1H), 7.05 (d, 1H), 7.85 (d, 2H), 5.18 (s, 2H), 4.22 (m, 2H), 3.45 (m, 2H), 2.95 (m, 2H), 2.82 (s, 3H), 2.10 (s, 3H), 1.50 (s, 3H).

Example 444

Preparation of 2,8-dimethyl-5-(3-methyl-2-(pyridin-4-yl)but-2-enyl)-2,3,4,5-tetrahydro-1H-pyrido[4,3-b]indole (Compound No. 358)

1-(1,2,3,4-Tetrahydro-2,8-dimethylpyrido[4,3-b]indol-5-yl)-3-methyl-2-(pyridin-4-yl)butan-2-ol (0.2 g, 0.55 mmol) was dissolved in dry DCM and a drop of DMF was added. The solution was cooled to 0° C. and thionyl chloride (0.194 g, 1.65 mmoL) dissolved in dry DCM (1 mL) was added. Stirring was continued for 1 h at 0° C. and for 2 h at RT. Volatiles were removed under reduced pressure, the residue was basified with saturated aqueous sodium bicarbonate, and the product was extracted with EtOAc (3×50 mL). The combined organic layers were dried over anhydrous sodium sulfate and concentrated under reduced pressure. The residue was purified by reverse phase HPLC. $^1$H NMR (CD$_3$OD, TFA salt) δ (ppm): 8.42 (d, 2H), 7.50 (d, 2H), 7.12 (s, 1H), 7.10 (d, 1H), 6.90 (d, 1H), 5.22 (d, 2H), 4.60 (d, 1H), 4.22 (d, 1H), 3.82 (m, 1H), 3.50 (m, 1H), 3.16 (m, 2H), 3.05 (s, 3H), 2.38 (s, 3H), 2.20 (s, 3H), 1.65 (s, 3H).

Example 445

Preparation of (Z)-2,8-dimethyl-5-(2-(pyridin-4-yl)but-2-enyl)-2,3,4,5-tetrahydro-1H-pyrido[4,3-b]indole (Compound No. 359)

This product was isolated as a regioisomer from Example 243 (Compound No. 281). $^1$H NMR (CD$_3$OD, freebase) δ (ppm): 8.20 (d, 2H), 7.30 (d, 1H), 7.18 (d, 2H), 7.10 (s, 1H), 6.98 (d, 1H), 6.10 (q, 1H), 5.20 (s, 2H), 4.02 (s, 2H), 3.30 (m, 2H), 3.05 (m, 2H), 2.80 (s, 3H), 2.40 (s, 3H), 2.05 (d, 3H).

Example 446

Preparation of (Z)-8-chloro-2-methyl-5-(2-(pyridin-4-yl)but-2-enyl)-2,3,4,5-tetrahydro-1H-pyrido[4,3-b]indole (Compound No. 360)

This product was isolated as a regioisomer from Example 246 (Compound No. 284). $^1$H NMR (CD$_3$OD, freebase) δ (ppm): 8.20 (d, 2H), 7.35 (d, 1H), 7.30 (s, 1H), 7.18 (d, 2H), 7.05 (d, 1H), 6.10 (q, 1H), 5.20 (s, 2H), 3.62 (s, 2H), 2.90 (m, 4H), 2.51 (s, 3H), 2.05 (d, 3H).

Example 447

Preparation of (E)-2,8-dimethyl-5-(2-(pyridin-4-yl)but-2-enyl)-2,3,4,5-tetrahydro-1H-pyrido[4,3-b]indole (Compound No. 361)

This product was isolated as a regioisomer from Example 245 (Compound No. 283). $^1$H NMR (CD$_3$OD, freebase) δ (ppm): 8.40 (d, 2H), 7.21 (d, 1H), 7.18 (s, 1H), 7.10 (d, 2H), 6.95 (d, 1H), 5.60 (q, 1H), 4.9 (s, 2H), 4.02 (s, 2H), 3.20 (m, 2H), 2.90 (m, 2H), 2.76 (s, 3H), 2.40 (s, 3H), 1.50 (d, 3H).

Example 448

Preparation of (E)-8-chloro-2-methyl-5-(2-(pyridin-4-yl)but-2-enyl)-2,3,4,5-tetrahydro-1H-pyrido[4,3-b]indole (Compound No. 362)

This product was isolated as a regioisomer from Example 246 (Compound No. 284). $^1$H NMR (CD$_3$OD, freebase) δ

(ppm): 8.40 (d, 2H), 7.35 (s, 1H), 7.28 (d, 1H), 7.10 (d, 2H), 7.0 (d, 1H), 5.60 (q, 1H), 4.92 (s, 2H), 3.62 (s, 2H), 2.82 (m, 2H), 2.76 (m, 2H), 2.50 (s, 3H), 1.50 (d, 3H).

Example 449

Preparation of 6-fluoro-2-methyl-5-(2-(pyridin-4-yl)allyl)-2,3,4,5-tetrahydro-1H-pyrido[4,3-b]indole (Compound No. 363)

This product was isolated as a regioisomer from Example 179 (Compound No. 223). $^1$H NMR (CD$_3$OD, oxalate salt) δ (ppm): 8.55 (d, 2H), 7.60 (d, 2H), 7.30 (d, 1H), 7.10 (m, 1H), 6.90 (m, 1H), 5.62 (s, 1H), 5.38 (s, 2H), 4.58 (m, 2H), 4.50 (s, 1H), 3.70 (m, 2H), 3.20 (m, 2H), 3.10 (s, 3H).

Example 450

Preparation of 2,8-dimethyl-5-(2-(pyrazin-2-yl)allyl)-2,3,4,5-tetrahydro-1H-pyrido[4,3-b]indole (Compound No. 364)

This product was isolated as a regioisomer from Example 248 (Compound No. 287). $^1$H NMR (CD$_3$OD, TFA salt) δ (ppm): 9.0 (d, 1H), 8.70 (s, 1H), 8.60 (d, 1H), 7.70 (s, 1H), 7.38 (s, 1H), 7.15 (m, 2H), 4.78 (d, 1H), 4.40 (d, 1H), 3.90 (m, 1H), 3.60 (m, 1H), 3.25 (m, 2H), 3.20 (s, 3H), 2.50 (s, 3H), 2.10 (s, 3H).

Example 451

Characterization Data for Representative Compounds

Characterization data for representative compounds prepared according to the examples are further detailed in Table 7.

Example B1

Determination of the Ability of Compounds of the Invention to Bind a Histamine Receptor Histamine H$_1$ To evaluate in radioligand binding assays the activity of compounds of the invention, human recombinant histamine H$_1$ receptor expressed in Chinese hamster ovary (CHO) cells (De Backer, M. D. et al., Biochem. Biophys. Res. Comm. 197(3):1601, 1993) in a modified Tris-HCl buffer (50 mM Tris-HCl, pH 7.4, 2 mM MgCl$_2$, 100 mM NaCl, 250 mM Sucrose) was used. Compounds of the invention were incubated with 1.2 nM [$^3$H]Pyrilamine for 180 min. at 25° C. Non-specific binding was estimated in the presence of 1 μM pyrilamine. Receptor proteins were filtered and washed, the filters were then counted to determine [$^3$H]Pyrilamine specifically bound. Compounds were screened at 1 μM or lower, using 1% DMSO as vehicle. Biochemical assay results are presented as the percent inhibition of specific binding in Table 8.

Histamine H$_2$

To evaluate in radioligand binding assays the activity of compounds of the invention, human recombinant histamine H$_2$ receptor expressed in Chinese hamster ovary (CHO) K1 cells (Ruat, M., Proc. Natl. Acad. Sci. USA. 87(5):1658, 1990) in a 50 mM Phosphate buffer, pH 7.4 was used. Compounds of the invention were incubated with 0.1 nM [$^{125}$I]Aminopotentidine for 120 min. at 25° C. Non-specific binding was estimated in the presence of 3 μM Tiotidine. Receptor proteins were filtered and washed, the filters were then counted to determine [$^{125}$I]Aminopotentidine specifically bound. Compounds were screened at 1 μM or lower, using 1% DMSO as vehicle. Biochemical assay results are presented as the percent inhibition of specific binding in Table 8.

TABLE 7

Representative Characterization Data

| Ex. No. | Salt | MW | NMR Solvent | NMR Data | MS observed | HPLC Method[1] | HPLC Rt (min.) |
|---|---|---|---|---|---|---|---|
| 1. | Oxalate | 462.86 | CD$_3$OD | 7.4 (m, 3H), 7.18 (d, 1H), 6.98 (m, 3H), 4.45 (bs, 2H), 4.3 (d, 1H), 4.19 (d, 1H), 3.6- (bs, 2H), 3.0 (s, 3H), 3.1-2.9 (m, 2H), 1.60 (s, 3H) | 373 | 1 | 3.66 |
| 2. | TFA | 468.85 | CD$_3$OD | 7.68 (t, 2H), 7.54 (s, 1H), 7.21 (s, 2H), 7.16 (t, 2H), 6.97 (s, 1H), 4.8 (bs, 1H), 4.39 (bs, 1H), 3.85 (bs, 1H), 3.60 (bs, 1H), 3.13 (bs, 5H), 1.92 (s, 3H) | 355 | 1 | 3.93 |
| 3. | TFA | 448.43 | DMSO | 10.0 (bs, 1H), 7.7 (m, 2H), 7.2 (m, 3H), 7.10 (d, 2H), 7.0 (d, 1H), 4.6 (d, 1H), 4.3 (d, 1H), 3.7 (bs, 1H), 3.49 (bs, 1H), 3.0 (bs, 2H), 3.0 (s, 3H), 2.4 (s, 3H), 1.8 (s, 3H). | NONE | 1 | 6.22 |

Method-1    Column: Zorbax SB C18 (50 × 4.6 mm) 1.8 micron
Mobile Phase: Gradient of ACN and 0.05% TFA
Flow rate: 1.0 mL/min.
Wavelength 230 nm Histamine $H_3$ To evaluate in radioligand binding assays the activity of compounds of the invention, human recombinant histamine $H_3$ receptor expressed in Chinese hamster ovary (CHO-K1) cells (Yanai K et al. Jpn J Pharmacol. 65(2): 107, 1994; Zhu Y et al. Mol Pharmacol. 59(3): 434, 2001) in a modified Tris-HCl buffer (50 mM Tris-HCl, pH 7.4, 5 mM $MgCl_2$, 0.04% BSA) is used. Compounds of invention are incubated with 3 nM [$^3$H]R(−)-α-Methylhistamine for 90 min. at 25° C. Non-specific binding is estimated in the presence of 1 μM R(−)-α-Methylhistamine. Receptor proteins are filtered and washed, the filters are then counted to determine [$^3$H]R(−)-α-Methylhistamine specifically bound. Compounds are screened at 1 μM or lower, using 1% DMSO as vehicle. Compounds of the invention are tested in this biochemical assay and percent inhibition of specific binding is determined.

Example B2

Determination of the Ability of Compounds of the Invention to Bind a Imidazoline $I_2$ Receptor Central Imidazoline $I_2$ To evaluate in radioligand binding assays the activity of compounds of the invention, rat central imidazoline $I_2$ receptor obtained from Wistar Rat cerebral cortex (Brown, C. M. et al., Br. J. Pharmacol. 99:803, 1990) in a modified Tris-HCl buffer (50 mM Tris-HCl buffer, pH 7.4, 0.5 mM EDTA) was used. Compounds of the invention were incubated with 2 nM [$^3$H]Idazoxan for 30 min. at 25° C. Non-specific binding was estimated in the presence of 1 μM Idazoxan. Receptor proteins were filtered and washed, the filters were then counted to determine [$^3$H]Idazoxan specifically bound. Compounds were screened at 1 μM or lower, using 1% DMSO as vehicle. Compounds of the invention were tested in this biochemical assay and percent inhibition of specific binding was determined. Certain compounds showed inhibition of specific binding by at least about 80%.

TABLE 8

| | | Binding data | | |
|---|---|---|---|---|
| Example No. | Compound No. | Imidazoline $I_2$ Central (1 μM) | Histamine Binding (1 μM) $H_1$ | $H_2$ |
| 2 | 3 | 58 | 30 | 6 |
| 43 | 43 | 76/79 | 81/85 | 58/84 |
| 49 | 44 | 46 | 54 | 26 |
| 44 | 45 | — | 65/73 | 94 |
| 45 | 47 | — | 33 | 48 |
| 51 | 48 | — | 93 | 47 |
| 47 | 51 | 79 | 100 | 59 |
| 53 | 52 | — | 46 | 51 |
| 48 | 53 | 78 | 47 | 58 |
| 54 | 54 | — | 68 | 5 |
| 56 | 55 | — | 91 | 88 |
| 55 | 56 | — | 90 | 26 |
| 57 | 57 | — | 41 | 82 |
| 58 | 59 | — | 63 | 58 |
| 60 | 60 | — | 52 | 40 |
| 61 | 61 | — | 52 | 41 |
| 62 | 62 | — | 38 | 43 |
| 63 | 63 | — | 46 | 53 |
| 80 | 78 | — | 52/69 | 89 |
| 82 | 82 | — | 35/64 | 99 |
| 83 | 83 | 85 | 60/79/84 | 99 |
| 84 | 85 | — | 9/13 | — |
| 89 | 86 | — | 72 | 54 |
| 85 | 87 | — | 65/81 | 100 |
| 90 | 88 | — | 16/19/37/28 | 30 |
| 86 | 89 | — | 43 | 91 |
| 91 | 90 | — | 48/59 | 60 |
| 88 | 91 | — | 11 | 52 |
| 92 | 92 | — | 44 | 99 |
| 93 | 93 | — | 39 | 100 |
| 94 | 95 | — | 85 | 41 |
| 99 | 98 | — | 53 | 99 |
| 100 | 100 | — | 65/67 | 100 |
| 105 | 102 | — | 60 | 98 |
| 102 | 103 | — | 81 | 101 |
| 107 | 106 | — | 84 | 99 |
| 104 | 107 | — | 88 | — |
| 113 | 110 | — | 77/83 | 102 |
| 110 | 111 | — | 73/74 | 91 |
| 125 | 125 | — | 96 | 48 |
| 126 | 126 | — | 103 | 85 |
| 127 | 127 | — | 100 | 22 |
| 83 | 128 | — | 98 | 100 |
| 85 | 132 | — | 96 | 96 |
| 89 | 133 | — | 101 | 60 |
| 86 | 136 | — | 99 | 85 |
| 93 | 140 | — | 98 | 99 |
| 429 | 166 | — | 14 | 56 |
| 259 | 171 | — | 13/22 | 85 |
| 260 | 172 | — | 95 | 65 |
| 261 | 173 | — | 91 | 78 |
| 262 | 174 | — | 34/43 | 80 |
| 263 | 175 | — | 71 | 91 |
| 428 | 176 | — | 21 | 74 |
| 264 | 177 | — | 83 | 101 |
| 265 | 178 | — | 30 | 89 |
| 266 | 180 | — | 84 | 24 |
| 267 | 181 | — | 0 | 25 |
| 268 | 182 | — | 26 | 53 |
| 269 | 183 | — | 91 | 47 |
| 270 | 184 | — | 23 | 57 |
| 271 | 185 | — | 8 | 29 |
| 272 | 186 | — | 1 | 22 |
| 273 | 187 | — | 36 | 57 |
| 274 | 188 | — | 8 | 13 |
| 275 | 189 | — | 77 | 85 |
| 276 | 190 | — | −11 | 9 |
| 277 | 191 | — | 23 | — |
| 278 | 192 | — | 61 | — |
| 279 | 193 | — | −7 | — |
| 280 | 194 | — | 9 | — |
| 281 | 195 | — | 20 | — |
| 282 | 196 | — | 19 | — |
| 283 | 197 | — | 61 | — |
| 284 | 198 | — | 64 | — |
| 285 | 199 | — | 61 | — |
| 286 | 200 | — | 45 | — |
| 152 | 202 | — | 100 | 97 |
| 155 | 203 | — | 64/72 | 99 |
| 156 | 204 | — | 55 | 101 |
| 157 | 205 | — | 31/39 | 95 |
| 158 | 206 | — | 76 | 102 |
| 159 | 207 | — | 15 | 46 |
| 160 | 208 | — | 64 | 102 |
| 161 | 209 | — | 9 | 20 |
| 163 | 210 | — | 53 | 96 |
| 165 | 211 | — | 53/54 | 100 |
| 166 | 212 | — | 70 | 84 |
| 167 | 213 | — | 69 | 99 |
| 168 | 214 | — | 23 | 100 |
| 169 | 215 | — | 89 | 98 |
| 170 | 216 | — | 47/49 | 61 |
| 171 | 217 | — | 12/38 | 50 |
| 172 | 218 | — | 78/79 | 98 |
| 173 | 219 | — | 60/66 | 82 |
| 174 | 220 | — | 91 | 99 |

TABLE 8-continued

Binding data

| Example No. | Compound No. | Imidazoline I₂ Central (1 μM) | Histamine Binding (1 μM) H₁ | Histamine Binding (1 μM) H₂ |
|---|---|---|---|---|
| 175 | 221 | — | 90 | 98 |
| 176 | 222 | — | 25 | 91 |
| 179 | 223 | — | 6/11 | 44 |
| 180 | 224 | — | 24/26 | 58 |
| 181 | 225 | — | 81 | 98 |
| 182 | 226 | — | 71 | 100 |
| 185 | 227 | — | 52 | 101 |
| 186 | 228 | — | 66 | 102 |
| 187 | 229 | — | 54 | 96 |
| 189 | 230 | — | 35 | 96 |
| 190 | 231 | — | 58 | 97 |
| 191 | 232 | — | 71 | 95 |
| 192 | 233 | — | 85 | 99 |
| 193 | 234 | — | 69 | 94 |
| 194 | 235 | — | 73 | 96 |
| 195 | 236 | — | 20 | 99 |
| 196 | 237 | — | 88 | 95 |
| 197 | 238 | — | 58 | 93 |
| 199 | 239 | — | 14 | 28 |
| 200 | 240 | — | 95 | 99 |
| 201 | 241 | — | 89 | 98 |
| 202 | 242 | — | 88 | 97 |
| 203 | 243 | — | 95 | 90 |
| 204 | 244 | — | 87 | 88 |
| 205 | 245 | — | 60 | 71 |
| 206 | 246 | — | 7 | 29 |
| 207 | 247 | — | 75 | 99 |
| 209 | 248 | — | 90 | — |
| 210 | 249 | — | 48 | — |
| 211 | 250 | — | 12 | — |
| 212 | 251 | — | 15 | — |
| 213 | 252 | — | 22 | — |
| 214 | 253 | — | 20 | — |
| 215 | 254 | — | 7 | — |
| 216 | 255 | — | 11 | — |
| 217 | 256 | — | 92 | — |
| 218 | 257 | — | 18 | — |
| 219 | 258 | — | 59 | — |
| 220 | 259 | — | 10 | — |
| 221 | 260 | — | −19 | — |
| 222 | 261 | — | 11 | — |
| 223 | 262 | — | 66 | — |
| 224 | 263 | — | 8 | — |
| 225 | 264 | — | 24 | — |
| 226 | 265 | — | 22 | — |
| 227 | 266 | — | −1 | — |
| 228 | 267 | — | 6 | — |
| 229 | 268 | — | 53 | — |
| 231 | 269 | — | −2 | — |
| 232 | 270 | — | 19 | — |
| 233 | 271 | — | −16 | — |
| 234 | 272 | — | 48 | — |
| 235 | 273 | — | 41 | — |
| 236 | 274 | — | 72 | — |
| 237 | 275 | — | 39 | — |
| 238 | 276 | — | 63 | — |
| 239 | 277 | — | 95 | — |
| 240 | 278 | — | 24 | — |
| 241 | 279 | — | 21 | — |
| 242 | 280 | — | 12 | — |
| 243 | 281 | — | 42 | — |
| 244 | 282 | — | 31 | — |
| 245 | 283 | — | 23 | — |
| 246 | 284 | — | 40 | — |
| 247 | 285 | — | 21 | — |
| 430 | 286 | — | 19 | — |
| 248 | 287 | — | 33 | — |
| 249 | 288 | — | 25 | — |
| 250 | 289 | — | 34 | — |
| 255 | 291 | — | −4 | — |
| 256 | 292 | — | 11 | — |
| 257 | 293 | — | 9 | — |
| 258 | 294 | — | 83 | — |
| 293 | 320 | — | 65 | — |
| 294 | 332 | — | 23 | — |
| 295 | 333 | — | 29 | — |
| 296 | 334 | — | 18 | — |
| 297 | 338 | — | 83 | — |
| 287 | 341 | — | 11 | — |
| 288 | 342 | — | 48 | — |
| 289 | 343 | — | 22 | — |
| 290 | 344 | — | 7 | — |
| 291 | 345 | — | 56 | — |
| 292 | 346 | — | 17 | — |
| 433 | 347 | — | 42/56 | 87 |
| 434 | 348 | — | 32/38 | 73 |
| 435 | 349 | — | 53/65 | 84 |
| 436 | 350 | — | 27/37 | 93 |
| 437 | 351 | — | 78/80 | 100 |
| 438 | 352 | — | 4 | 15 |
| 439 | 353 | — | 100 | 93 |
| 440 | 354 | — | 86 | 97 |
| 441 | 355 | — | 116 | 93 |
| 442 | 356 | — | 70 | 17 |
| 443 | 357 | — | 61 | — |
| 444 | 358 | — | 47 | — |
| 445 | 359 | — | 38 | — |
| 446 | 360 | — | 47 | — |
| 447 | 361 | — | 96 | — |
| 448 | 362 | — | 98 | — |
| 449 | 363 | — | 62 | — |
| 450 | 364 | — | 95 | — |
| 301 | 365 | — | 92 | — |
| 298 | 367 | — | 64 | — |
| 299 | 368 | — | 82 | — |
| 300 | 369 | — | 29 | — |
| 302 | 370 | — | 72 | — |
| 303 | 375 | — | 65 | — |
| 304 | 376 | — | 23 | — |
| 305 | 377 | — | 29 | — |
| 306 | 378 | — | 18 | — |
| 307 | 379 | — | 83 | — |
| 308 | 380 | — | 64 | — |
| 309 | 381 | — | 82 | — |
| 310 | 382 | — | 29 | — |
| 311 | 383 | — | 72 | — |
| 312 | 384 | — | 66 | — |
| 313 | 385 | — | 68 | — |
| 314 | 386 | — | 8 | — |
| 315 | 387 | — | 84 | — |
| 316 | 388 | — | 100 | — |
| 317 | 389 | — | 39 | — |
| 318 | 390 | — | 49 | — |
| 319 | 391 | — | 84 | — |
| 320 | 392 | — | 84 | — |
| 321 | 393 | — | 69 | — |
| 322 | 394 | — | 75 | — |
| 323 | 395 | — | 102 | — |
| 324 | 396 | — | 15 | — |
| 325 | 397 | — | 89 | — |
| 326 | 398 | — | 95 | — |
| 327 | 399 | — | 13 | — |
| 328 | 400 | — | 22 | — |
| 329 | 401 | — | 8 | — |
| 330 | 402 | — | 15 | — |
| 331 | 403 | — | 37 | — |
| 332 | 404 | — | 37 | — |
| 333 | 405 | — | 67 | — |
| 334 | 406 | — | 74 | — |
| 335 | 407 | — | 10 | — |
| 336 | 408 | — | 98 | — |
| 337 | 409 | — | 18 | — |
| 338 | 410 | — | 36 | — |
| 339 | 411 | — | 0 | — |
| 340 | 412 | — | 27 | — |
| 341 | 413 | — | 16 | — |

TABLE 8-continued

Binding data

| Example No. | Compound No. | Imidazoline I₂ Central (1 µM) | Histamine Binding (1 µM) H₁ | H₂ |
|---|---|---|---|---|
| 342 | 414 | — | 61 | — |
| 343 | 415 | — | 97 | — |
| 344 | 416 | — | 91 | — |
| 345 | 417 | — | 48 | — |
| 346 | 418 | — | 33 | — |
| 347 | 419 | — | 52 | — |
| 348 | 420 | — | 13 | — |
| 349 | 421 | — | 93 | — |
| 350 | 422 | — | 8 | — |
| 351 | 423 | — | 31 | — |
| 352 | 424 | — | 43 | — |
| 353 | 425 | — | 4 | — |
| 354 | 426 | — | 50 | — |
| 355 | 427 | — | 1 | — |
| 356 | 428 | — | 97 | — |
| 357 | 429 | — | 101 | — |
| 358 | 430 | — | 72 | — |
| 359 | 431 | — | 33 | — |
| 360 | 432 | — | 46 | — |
| 361 | 433 | — | 13 | — |
| 363 | 435 | — | 11 | — |
| 364 | 436 | — | 12 | — |
| 365 | 437 | — | 44 | — |
| 366 | 438 | — | 92 | — |
| 367 | 439 | — | 9 | — |
| 368 | 440 | — | 4 | — |
| 369 | 441 | — | 91 | — |
| 370 | 442 | — | 29 | — |
| 371 | 443 | — | −5 | — |
| 372 | 444 | — | −13 | — |
| 373 | 445 | — | 1 | — |
| 374 | 446 | — | −4 | — |
| 375 | 447 | — | −1 | — |
| 376 | 448 | — | −10 | — |
| 377 | 449 | — | −7 | — |
| 378 | 450 | — | 43 | — |
| 379 | 451 | — | 99 | — |
| 380 | 452 | — | 18 | — |
| 381 | 453 | — | 26 | — |
| 382 | 454 | — | 21 | — |
| 383 | 455 | — | 13 | — |
| 384 | 456 | — | 17 | — |
| 385 | 457 | — | 37 | — |
| 386 | 458 | — | 56 | — |
| 387 | 459 | — | 53 | — |
| 388 | 460 | — | 17 | — |
| 389 | 461 | — | 31 | — |
| 390 | 462 | — | 32 | — |
| 392 | 464 | — | 66 | — |
| 393 | 465 | — | −14 | — |
| 394 | 466 | — | 10 | — |
| 395 | 467 | — | 54 | — |
| 396 | 468 | — | 82 | — |
| 397 | 469 | — | 14 | — |
| 398 | 470 | — | 17 | — |
| 400 | 471 | — | 2 | — |
| 401 | 472 | — | 21 | — |
| 402 | 473 | — | 35 | — |
| 403 | 474 | — | 98 | — |
| 404 | 475 | — | 34 | 91 |
| 405 | 476 | — | 27 | 88 |
| 406 | 477 | — | 17 | 97 |
| 407 | 478 | — | 28 | 94 |
| 408 | 479 | — | 11 | 51 |
| 409 | 480 | — | 40 | 93 |
| 410 | 481 | — | 12 | 97 |
| 411 | 482 | — | 13 | −3 |
| 412 | 483 | — | −1 | 10 |
| 413 | 484 | — | 6 | 77 |
| 414 | 485 | — | −6 | 97 |
| 415 | 486 | — | 22 | — |
| 416 | 487 | — | 75 | — |
| 417 | 488 | — | 9 | — |
| 418 | 489 | — | 13 | — |
| 419 | 490 | — | 18 | — |
| 420 | 491 | — | 52 | — |
| 421 | 492 | — | 68 | — |
| 422 | 493 | — | 69 | — |
| 423 | 494 | — | 2 | — |
| 424 | 495 | — | 52 | — |
| 425 | 496 | — | 15 | — |
| 426 | 497 | — | 17 | — |
| 427 | 498 | — | 65 | — |
| 430 | 499 | — | 26 | — |
| 432 | 500 | 54 | 70 | 30 |

Example B3

Determination of the Ability of Compounds of the Invention to Bind an Adrenergic Receptor Adrenergic $\alpha_{1A}$ To evaluate in radioligand binding assays the activity of compounds of the invention, rat adrenergic $\alpha_{1A}$ receptor obtained from Wistar Rat submaxillary glands (Michel, A. D. et al., Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prozosin for 60 min. at 25° C. Non-specific binding was estimated in the presence of 10 µM phentolamine. Receptor proteins were filtered and washed, the filters were then counted to determine [$^3$H] Prozosin specifically bound. Compounds of the invention were screened at 1 µM or lower, using 1% DMSO as vehicle. Compounds of the invention were tested in this biochemical assay and percent inhibition of specific binding was determined. Certain compounds showed inhibition of specific binding by at least about 80%.

Adrenergic $\alpha_{1B}$

To evaluate in radioligand binding assays the activity of compounds of the invention, rat adrenergic $\alpha_{1B}$ receptor obtained from Wistar Rat liver (Garcia-S'ainz, J. A. et al., Biochem. Biophys. Res. Commun. 186:760, 1992; Michel A. D. et al., Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prozosin for 60 min. at 25° C. Non-specific binding was estimated in the presence of 10 µM phentolamine. Receptor proteins were filtered and washed, the filters were then counted to determine [$^3$H] Prozosin specifically bound. Compounds were screened at 1 µM or lower, using 1% DMSO as vehicle. Compounds of the invention were tested in this biochemical assay and percent inhibition of specific binding was determined. Certain compounds showed inhibition of specific binding by at least about 80%.

Adrenergic $\alpha_{1D}$

To evaluate in radioligand binding assays the activity of compounds of the invention, human recombinant adrenergic $\alpha_{1D}$ receptor expressed in human embryonic kidney (HEK-293) cells (Kenny, B. A. et al. Br. J. Pharmacol. 115(6):981, 1995) in a 50 mM Tris-HCl buffer, pH 7.4, was used. Compounds of invention were incubated with 0.6 nM [$^3$H]

Prozosin for 60 min. at 25° C. Non-specific binding was estimated in the presence of 10 µM phentolamine. Receptor proteins were filtered and washed, the filters were then counted to determine [$^3$H]Prozosin specifically bound. Compounds were screened at 1 µM or lower, using 1% DMSO as vehicle. Biochemical assay results are presented as the percent inhibition of specific binding in Table 9.

Adrenergic $\alpha_{2A}$

To evaluate in radioligand binding assays the activity of compounds of the invention, human recombinant adrenergic $\alpha_{2A}$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM MgCl$_2$, 2 mM EDTA) was used. Compounds of invention were incubated with 1 nM [$^3$H]MK-912 for 60 min. at 25° C. MK912 is (2S-trans)-1,3,4,5',6,6',7,12b-octahydro-1',3'-dimethyl-spiro[2H-benzofuro[2,3-a]quinolizine-2,4'(1'H)-pyrimidin]-2'(3'H)-one hydrochloride Non-specific binding was estimated in the presence of 10 µM WB-4101 (2-(2,6-Dimethoxyphenoxyethyl)aminomethyl-1,4-benzodioxane hydrochloride). Receptor proteins were filtered and washed, the filters were then counted to determine [$^3$H]MK-912 specifically bound. Compounds were screened at 1 µM or lower, using 1% DMSO as vehicle. Biochemical assay results are presented as the percent inhibition of specific binding in Table 9.

Adrenergic $\alpha_{2B}$

To evaluate in radioligand binding assays the activity of compounds of the invention, human recombinant adrenergic $\alpha_{2B}$ receptor expressed in Chinese hamster ovary (CHO-K1) cells (Uhlen S et al. Eur J Pharmacol. 343(1):93, 1998) in a modified Tris-HCl buffer (50 mM Tris-HCl, pH 7.4, 12.5 mM MgCl$_2$, 1 mM EDTA, 0.2% BSA) was used. Compounds of the invention were incubated with 2.5 nM [$^3$H] Rauwolscine for 60 min. at 25° C. Non-specific binding was estimated in the presence of 10 µM Prozosin. Receptor proteins were filtered and washed, the filters were then counted to determine [$^3$H]Rauwolscine specifically bound. Compounds were screened at 1 µM or lower, using 1% DMSO as vehicle. Biochemical assay results are presented as the percent inhibition of specific binding in Table 9.

Adrenergic $\alpha_{2C}$

To evaluate in radioligand binding assays the activity of compounds of the invention, human recombinant adrenergic $\alpha_{2C}$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM MgCl$_2$, 2 mM EDTA) was used. Compounds of the invention were incubated with 1 nM [$^3$H]MK-912 for 60 min. at 25° C. Non-specific binding was estimated in the presence of 10 µM WB-4101. Receptor proteins were filtered and washed, the filters were then counted to determine [$^3$H]MK-912 specifically bound. Compounds were screened at 1 µM or lower, using 1% DMSO as vehicle. Compounds of the invention were tested in this biochemical assay and percent inhibition of specific binding was determined. Certain compounds showed inhibition of specific binding by at least about 80%.

Example B4

Determination of the Ability of Compounds of the Invention to Bind a Dopamine Receptor Dopamine $D_{2L}$ To evaluate in radioligand binding assays the activity of compounds of the invention, human recombinant dopamine $D_{2L}$ receptor expressed in Chinese hamster ovary (CHO) cells (Grandy, D. K. et al. Proc. Natl. Acad. Sci. USA. 86:9762, 1989; Hayes, G. et al., Mol. Endocrinol. 6:920, 1992) in a modified Tris-HCl buffer (50 mM Tris-HCl, pH 7.4, 1.4 mM Ascorbic Acid, 0.001% BSA, 150 mM NaCl) was used. Compounds of the invention were incubated with 0.16 nM [$^3$H]Spiperone for 120 min. at 25° C. Non-specific binding was estimated in the presence of 10 µM Haloperidol. Receptor proteins were filtered and washed, the filters were then counted to determine [$^3$H]Spiperone specifically bound. Compounds were screened at 1 µM or lower, using 1% DMSO as vehicle. Biochemical assay results are presented as the percent inhibition of specific binding in Table 9.

TABLE 9

Inhibition of ligand binding to aminergic G protein-coupled receptors by compounds of the invention:

| Example No. | Compound No. | Adrenergic (1 µM) | | | | | | Dopamine (1 µM) |
| --- | --- | --- | --- | --- | --- | --- | --- | --- |
| | | $\alpha_{1A}$ | $\alpha_{1B}$ | $\alpha_{1D}$ | $\alpha_{2A}$ | $\alpha_{2B}$ | $\alpha_{2C}$ | $D_{2L}$ |
| 2 | 3 | — | — | 42 | 58 | 91 | — | 14 |
| 43 | 43 | 90/96 | 97/96 | 87/89 | 98/100 | 108/102 | 100/94 | 65 |
| 49 | 44 | 39 | 38 | 35 | 65 | 94 | 35 | — |
| 44 | 45 | — | — | 61 | 89 | 109 | — | 34/35 |
| 45 | 47 | — | — | 82 | 81 | 106 | — | 7 |
| 51 | 48 | — | — | 45 | 83 | 100 | — | 8 |
| 47 | 51 | 86 | 95 | 89 | 91 | 118 | 92 | — |
| 53 | 52 | — | — | 39 | 84 | 104 | — | 12 |
| 48 | 53 | 74 | 66 | 55 | 93 | 114 | 82 | — |
| 54 | 54 | — | — | 15 | 39 | 103 | — | −4 |
| 56 | 55 | — | — | 64 | 85 | 108 | — | 34 |
| 55 | 56 | — | — | 43 | 65 | 112 | — | 4 |
| 57 | 57 | — | — | 84 | 70 | 108 | — | 22 |
| 58 | 59 | — | — | 81 | 83 | 95 | — | 17 |
| 60 | 60 | — | — | 33 | 81 | 96 | — | 6 |
| 61 | 61 | — | — | 87 | 76 | 107 | — | 19 |
| 62 | 62 | — | — | 82 | 57 | 103 | — | 7 |
| 63 | 63 | — | — | 84 | 74 | 101 | — | 17 |
| 80 | 78 | — | — | 49 | 91 | 87 | — | 27/33 |
| 82 | 82 | — | — | 62 | 96 | 99 | — | 39/45 |
| 83 | 83 | 90 | 96 | 96 | 98 | 121 | 99 | 98 |

TABLE 9-continued

Inhibition of ligand binding to aminergic G protein-coupled receptors by compounds of the invention:

| Example No. | Compound No. | Adrenergic (1 μM) | | | | | | Dopamine (1 μM) |
| --- | --- | --- | --- | --- | --- | --- | --- | --- |
| | | $\alpha_{1A}$ | $\alpha_{1B}$ | $\alpha_{1D}$ | $\alpha_{2A}$ | $\alpha_{2B}$ | $\alpha_{2C}$ | $D_{2L}$ |
| 84 | 85 | — | — | — | — | — | — | 43/57 |
| 89 | 86 | — | — | — | — | — | — | 40 |
| 85 | 87 | — | — | 99 | 95 | 121 | — | 97 |
| 90 | 88 | — | — | 78 | 65 | 107 | — | 41/66/93 |
| 86 | 89 | — | — | 87 | 97 | 108 | — | 68 |
| 91 | 90 | — | — | 93 | 95 | 104 | — | 93/98 |
| 88 | 91 | — | — | — | — | — | — | 27 |
| 92 | 92 | — | — | 99 | 89 | 103 | — | 83/97 |
| 93 | 93 | — | — | 96 | 94 | 108 | — | 85/97 |
| 94 | 95 | — | — | 89 | 95 | 103 | — | 17 |
| 99 | 98 | — | — | — | — | — | — | 78 |
| 100 | 100 | — | — | 87 | 101 | 97 | — | 67/68 |
| 105 | 102 | — | — | — | — | — | — | 99 |
| 102 | 103 | — | — | — | — | — | — | 49 |
| 107 | 106 | — | — | 92 | 93 | 114 | — | 90 |
| 104 | 107 | — | — | — | — | — | — | 72 |
| 113 | 110 | — | — | 86 | 99 | 92 | — | 96/98 |
| 110 | 111 | — | — | 47 | 101 | 90 | — | 27/29 |
| 125 | 125 | — | — | 51 | 76 | 110 | — | 20 |
| 126 | 126 | — | — | 50 | 87 | 116 | — | 84 |
| 127 | 127 | — | — | 46 | 60 | 68 | — | 10 |
| 83 | 128 | — | — | 91 | 99 | 120 | — | 97 |
| 85 | 132 | — | — | 93 | 97 | 118 | — | 91 |
| 89 | 133 | — | — | 55 | 89 | 103 | — | 29 |
| 86 | 136 | — | — | 70 | 95 | 90 | — | 54 |
| 93 | 140 | — | — | 84 | 86 | 106 | — | 57 |
| 429 | 166 | — | — | 28 | 44 | 63 | — | −2 |
| 259 | 171 | — | — | 49 | 83 | 86 | — | 12/13 |
| 260 | 172 | — | — | 88 | 98 | 104 | — | 36 |
| 261 | 173 | — | — | 58 | 94 | 98 | — | 32 |
| 262 | 174 | — | — | 57 | 93 | 88 | — | 34/34 |
| 263 | 175 | — | — | 75 | 94 | 96 | — | 24 |
| 428 | 176 | — | — | 42 | 94 | 95 | — | 6 |
| 264 | 177 | — | — | 70 | 96 | 94 | — | 33 |
| 265 | 178 | — | — | 46 | 88 | 79 | — | 30 |
| 266 | 180 | — | — | 60 | 84 | 105 | — | 10 |
| 267 | 181 | — | — | — | — | — | — | 8 |
| 268 | 182 | — | — | — | — | — | — | 8 |
| 269 | 183 | — | — | — | — | — | — | 15 |
| 270 | 184 | — | — | — | — | — | — | 1 |
| 271 | 185 | — | — | — | — | — | — | −1 |
| 272 | 186 | — | — | — | — | — | — | 3 |
| 273 | 187 | — | — | — | — | — | — | 35 |
| 274 | 188 | — | — | — | — | — | — | −5 |
| 275 | 189 | — | — | — | — | — | — | 2 |
| 276 | 190 | — | — | — | — | — | — | −15 |
| 277 | 191 | — | — | — | — | — | — | 15 |
| 278 | 192 | — | — | — | — | — | — | 34 |
| 279 | 193 | — | — | — | — | — | — | 14 |
| 280 | 194 | — | — | — | — | — | — | 12 |
| 281 | 195 | — | — | — | — | — | — | 17 |
| 282 | 196 | — | — | — | — | — | — | 9 |
| 283 | 197 | — | — | — | — | — | — | 14 |
| 284 | 198 | — | — | — | — | — | — | 5 |
| 285 | 199 | — | — | — | — | — | — | 16 |
| 286 | 200 | — | — | — | — | — | — | 6 |
| 152 | 202 | — | — | 98 | 98 | 98 | — | 83 |
| 155 | 203 | — | — | 89 | 100 | 108 | — | 72/78 |
| 156 | 204 | — | — | 67 | 99 | 86 | — | 87 |
| 157 | 205 | — | — | 90 | 99 | 101 | — | 98/99 |
| 158 | 206 | — | — | 102 | 96 | 89 | — | 76 |
| 159 | 207 | — | — | 100 | 86 | 80 | — | 12 |
| 160 | 208 | — | — | 89 | 99 | 103 | — | 78 |
| 161 | 209 | — | — | 21 | 30 | 59 | — | 7 |
| 163 | 210 | — | — | 17 | 79 | 102 | — | 52 |
| 165 | 211 | — | — | 96 | 97 | 114 | — | 39/49 |
| 166 | 212 | — | — | 78 | 88 | 105 | — | 32 |
| 167 | 213 | — | — | 76 | 88 | 103 | — | 76 |
| 168 | 214 | — | — | — | — | — | — | 83 |
| 169 | 215 | — | — | — | — | — | — | 36 |
| 170 | 216 | — | — | — | — | — | — | 97/98 |
| 171 | 217 | — | — | — | — | — | — | 86/88 |

TABLE 9-continued

Inhibition of ligand binding to aminergic G protein-coupled receptors by compounds of the invention:

| Example No. | Compound No. | Adrenergic (1 μM) | | | | | | Dopamine (1 μM) |
| --- | --- | --- | --- | --- | --- | --- | --- | --- |
| | | $\alpha_{1A}$ | $\alpha_{1B}$ | $\alpha_{1D}$ | $\alpha_{2A}$ | $\alpha_{2B}$ | $\alpha_{2C}$ | $D_{2L}$ |
| 172 | 218 | — | — | — | — | — | — | 40/43 |
| 173 | 219 | — | — | — | — | — | — | 96/97 |
| 174 | 220 | — | — | — | — | — | — | 32 |
| 175 | 221 | — | — | — | — | — | — | 34 |
| 176 | 222 | — | — | — | — | — | — | 82 |
| 179 | 223 | — | — | — | — | — | — | 96/97 |
| 180 | 224 | — | — | — | — | — | — | 65/80 |
| 181 | 225 | — | — | — | — | — | — | 43 |
| 182 | 226 | — | — | — | — | — | — | 46 |
| 185 | 227 | — | — | — | — | — | — | 97 |
| 186 | 228 | — | — | — | — | — | — | 98 |
| 187 | 229 | — | — | — | — | — | — | 100 |
| 189 | 230 | — | — | — | — | — | — | 44 |
| 190 | 231 | — | — | — | — | — | — | 40 |
| 191 | 232 | — | — | — | — | — | — | 91 |
| 192 | 233 | — | — | — | — | — | — | 48 |
| 193 | 234 | — | — | — | — | — | — | 73 |
| 194 | 235 | — | — | — | — | — | — | 80 |
| 195 | 236 | — | — | — | — | — | — | 76 |
| 196 | 237 | — | — | — | — | — | — | 45 |
| 197 | 238 | — | — | — | — | — | — | 81 |
| 199 | 239 | — | — | — | — | — | — | 39 |
| 200 | 240 | — | — | — | — | — | — | 34 |
| 201 | 241 | — | — | — | — | — | — | 47 |
| 202 | 242 | — | — | — | — | — | — | 55 |
| 203 | 243 | — | — | — | — | — | — | 96 |
| 204 | 244 | — | — | — | — | — | — | 86 |
| 205 | 245 | — | — | — | — | — | — | 92 |
| 206 | 246 | — | — | — | — | — | — | 57 |
| 207 | 247 | — | — | — | — | — | — | 28 |
| 209 | 248 | — | — | — | — | — | — | 95 |
| 210 | 249 | — | — | — | — | — | — | 93 |
| 211 | 250 | — | — | — | — | — | — | 18 |
| 212 | 251 | — | — | — | — | — | — | 25 |
| 213 | 252 | — | — | — | — | — | — | 13 |
| 214 | 253 | — | — | — | — | — | — | 22 |
| 215 | 254 | — | — | — | — | — | — | 11 |
| 216 | 255 | — | — | — | — | — | — | 29 |
| 217 | 256 | — | — | — | — | — | — | 34 |
| 218 | 257 | — | — | — | — | — | — | 72 |
| 219 | 258 | — | — | — | — | — | — | 81 |
| 220 | 259 | — | — | — | — | — | — | −12 |
| 221 | 260 | — | — | — | — | — | — | 9 |
| 222 | 261 | — | — | — | — | — | — | 28 |
| 223 | 262 | — | — | — | — | — | — | 97 |
| 224 | 263 | — | — | — | — | — | — | 89 |
| 225 | 264 | — | — | — | — | — | — | 49 |
| 226 | 265 | — | — | — | — | — | — | 73 |
| 227 | 266 | — | — | — | — | — | — | 94 |
| 228 | 267 | — | — | — | — | — | — | 85 |
| 229 | 268 | — | — | — | — | — | — | 98 |
| 231 | 269 | — | — | — | — | — | — | 91 |
| 232 | 270 | — | — | — | — | — | — | 88 |
| 233 | 271 | — | — | — | — | — | — | 63 |
| 234 | 272 | — | — | — | — | — | — | 85 |
| 235 | 273 | — | — | — | — | — | — | 12 |
| 236 | 274 | — | — | — | — | — | — | 56 |
| 237 | 275 | — | — | — | — | — | — | 92 |
| 238 | 276 | — | — | — | — | — | — | 82 |
| 239 | 277 | — | — | — | — | — | — | 98 |
| 240 | 278 | — | — | — | — | — | — | 51 |
| 241 | 279 | — | — | — | — | — | — | 69 |
| 242 | 280 | — | — | — | — | — | — | 52 |
| 243 | 281 | — | — | — | — | — | — | 51 |
| 244 | 282 | — | — | — | — | — | — | 57 |
| 245 | 283 | — | — | — | — | — | — | 66 |
| 246 | 284 | — | — | — | — | — | — | 84 |
| 247 | 285 | — | — | — | — | — | — | 53 |
| 248 | 287 | — | — | — | — | — | — | 72 |
| 430 | 286 | — | — | — | — | — | — | 23 |
| 249 | 288 | — | — | — | — | — | — | 92 |
| 250 | 289 | — | — | — | — | — | — | 90 |

TABLE 9-continued

Inhibition of ligand binding to aminergic G protein-coupled receptors by compounds of the invention:

| Example No. | Compound No. | Adrenergic (1 µM) | | | | | | Dopamine (1 µM) |
|---|---|---|---|---|---|---|---|---|
| | | $\alpha_{1A}$ | $\alpha_{1B}$ | $\alpha_{1D}$ | $\alpha_{2A}$ | $\alpha_{2B}$ | $\alpha_{2C}$ | $D_{2L}$ |
| 255 | 291 | — | — | — | — | — | — | 0 |
| 256 | 292 | — | — | — | — | — | — | 71 |
| 257 | 293 | — | — | — | — | — | — | 31 |
| 258 | 294 | — | — | — | — | — | — | 83 |
| 293 | 320 | — | — | — | — | — | — | 61 |
| 294 | 332 | — | — | — | — | — | — | 79 |
| 295 | 333 | — | — | — | — | — | — | 51 |
| 296 | 334 | — | — | — | — | — | — | 90 |
| 297 | 338 | — | — | — | — | — | — | 97 |
| 287 | 341 | — | — | — | — | — | — | 2 |
| 288 | 342 | — | — | — | — | — | — | 11 |
| 289 | 343 | — | — | — | — | — | — | 9 |
| 290 | 344 | — | — | — | — | — | — | 10 |
| 291 | 345 | — | — | — | — | — | — | 15 |
| 292 | 346 | — | — | — | — | — | — | 26 |
| 433 | 347 | — | — | 90 | 96 | 111 | — | 27/30 |
| 434 | 348 | — | — | 35 | 92 | 105 | — | 18/29 |
| 435 | 349 | — | — | 60 | 97 | 102 | — | 34/46 |
| 436 | 350 | — | — | 85 | 95 | 107 | — | 12/21 |
| 437 | 351 | — | — | 45 | 84 | 99 | — | 70/80 |
| 438 | 352 | — | — | 11 | 34 | 47 | — | 0 |
| 439 | 353 | — | — | — | — | — | — | 92 |
| 440 | 354 | — | — | — | — | — | — | 98 |
| 441 | 355 | — | — | — | — | — | — | 81 |
| 442 | 356 | — | — | — | — | — | — | 37 |
| 443 | 357 | — | — | — | — | — | — | 14 |
| 444 | 358 | — | — | — | — | — | — | 14 |
| 445 | 359 | — | — | — | — | — | — | 27 |
| 446 | 360 | — | — | — | — | — | — | 36 |
| 447 | 361 | — | — | — | — | — | — | 51 |
| 448 | 362 | — | — | — | — | — | — | 79 |
| 449 | 363 | — | — | — | — | — | — | 53 |
| 450 | 364 | — | — | — | — | — | — | 27 |
| 301 | 365 | — | — | — | — | — | — | 49 |
| 298 | 367 | — | — | — | — | — | — | 48 |
| 299 | 368 | — | — | — | — | — | — | 74 |
| 300 | 369 | — | — | — | — | — | — | 64 |
| 302 | 370 | — | — | — | — | — | — | 63 |
| 312 | 384 | — | — | — | — | — | — | 91 |
| 313 | 385 | — | — | — | — | — | — | 51 |
| 314 | 386 | — | — | — | — | — | — | 25 |
| 315 | 387 | — | — | — | — | — | — | 99 |
| 316 | 388 | — | — | — | — | — | — | 99 |
| 317 | 389 | — | — | — | — | — | — | 49 |
| 318 | 390 | — | — | — | — | — | — | 97 |
| 319 | 391 | — | — | — | — | — | — | 72 |
| 320 | 392 | — | — | — | — | — | — | 99 |
| 321 | 393 | — | — | — | — | — | — | 99 |
| 322 | 394 | — | — | — | — | — | — | 99 |
| 323 | 395 | — | — | — | — | — | — | 99 |
| 324 | 396 | — | — | — | — | — | — | 7 |
| 325 | 397 | — | — | — | — | — | — | 80 |
| 326 | 398 | — | — | — | — | — | — | 97 |
| 327 | 399 | — | — | — | — | — | — | 73 |
| 328 | 400 | — | — | — | — | — | — | 94 |
| 329 | 401 | — | — | — | — | — | — | 57 |
| 330 | 402 | — | — | — | — | — | — | 87 |
| 331 | 403 | — | — | — | — | — | — | 66 |
| 332 | 404 | — | — | — | — | — | — | 92/97 |
| 333 | 405 | — | — | — | — | — | — | 88 |
| 334 | 406 | — | — | — | — | — | — | 96 |
| 335 | 407 | — | — | — | — | — | — | 74 |
| 336 | 408 | — | — | — | — | — | — | 44 |
| 337 | 409 | — | — | — | — | — | — | 54 |
| 338 | 410 | — | — | — | — | — | — | 47 |
| 339 | 411 | — | — | — | — | — | — | 55 |
| 340 | 412 | — | — | — | — | — | — | 94 |
| 341 | 413 | — | — | — | — | — | — | 60 |
| 342 | 414 | — | — | — | — | — | — | 100 |
| 343 | 415 | — | — | — | — | — | — | 95 |
| 344 | 416 | — | — | — | — | — | — | 20 |
| 345 | 417 | — | — | — | — | — | — | 87 |

TABLE 9-continued

Inhibition of ligand binding to aminergic G protein-coupled receptors by compounds of the invention:

| Example No. | Compound No. | Adrenergic (1 μM) | | | | | | Dopamine (1 μM) |
|---|---|---|---|---|---|---|---|---|
| | | $\alpha_{1A}$ | $\alpha_{1B}$ | $\alpha_{1D}$ | $\alpha_{2A}$ | $\alpha_{2B}$ | $\alpha_{2C}$ | $D_{2L}$ |
| 346 | 418 | — | — | — | — | — | — | 14 |
| 347 | 419 | — | — | — | — | — | — | 20 |
| 348 | 420 | — | — | — | — | — | — | 29 |
| 349 | 421 | — | — | — | — | — | — | 79 |
| 350 | 422 | — | — | — | — | — | — | 68 |
| 351 | 423 | — | — | — | — | — | — | −10 |
| 352 | 424 | — | — | — | — | — | — | 20 |
| 353 | 425 | — | — | — | — | — | — | 6 |
| 354 | 426 | — | — | — | — | — | — | 32 |
| 355 | 427 | — | — | — | — | — | — | 17 |
| 356 | 428 | — | — | — | — | — | — | 57 |
| 357 | 429 | — | — | — | — | — | — | 30 |
| 358 | 430 | — | — | — | — | — | — | 25 |
| 359 | 431 | — | — | — | — | — | — | 80 |
| 360 | 432 | — | — | — | — | — | — | 79 |
| 361 | 433 | — | — | — | — | — | — | 61 |
| 363 | 435 | — | — | — | — | — | — | 71 |
| 364 | 436 | — | — | — | — | — | — | 69 |
| 365 | 437 | — | — | — | — | — | — | 15 |
| 366 | 438 | — | — | — | — | — | — | 17 |
| 367 | 439 | — | — | — | — | — | — | 16 |
| 368 | 440 | — | — | — | — | — | — | 16 |
| 369 | 441 | — | — | — | — | — | — | 64 |
| 370 | 442 | — | — | — | — | — | — | 77 |
| 371 | 443 | — | — | — | — | — | — | 92 |
| 372 | 444 | — | — | — | — | — | — | 36 |
| 373 | 445 | — | — | — | — | — | — | 20 |
| 374 | 446 | — | — | — | — | — | — | 42 |
| 375 | 447 | — | — | — | — | — | — | 59 |
| 376 | 448 | — | — | — | — | — | — | 79 |
| 377 | 449 | — | — | — | — | — | — | 59 |
| 378 | 450 | — | — | — | — | — | — | 35 |
| 379 | 451 | — | — | — | — | — | — | 70 |
| 380 | 452 | — | — | — | — | — | — | 71 |
| 381 | 453 | — | — | — | — | — | — | 51 |
| 382 | 454 | — | — | — | — | — | — | 80 |
| 383 | 455 | — | — | — | — | — | — | 56 |
| 384 | 456 | — | — | — | — | — | — | 80 |
| 385 | 457 | — | — | — | — | — | — | 53 |
| 386 | 458 | — | — | — | — | — | — | 15 |
| 387 | 459 | — | — | — | — | — | — | 71 |
| 388 | 460 | — | — | — | — | — | — | 67 |
| 389 | 461 | — | — | — | — | — | — | 78 |
| 390 | 462 | — | — | — | — | — | — | 76 |
| 392 | 464 | — | — | — | — | — | — | 93 |
| 393 | 465 | — | — | — | — | — | — | 21 |
| 394 | 466 | — | — | — | — | — | — | 54 |
| 395 | 467 | — | — | — | — | — | — | 7 |
| 396 | 468 | — | — | — | — | — | — | 12 |
| 397 | 469 | — | — | — | — | — | — | 12 |
| 398 | 470 | — | — | — | — | — | — | 1 |
| 400 | 471 | — | — | — | — | — | — | 2 |
| 401 | 472 | — | — | — | — | — | — | 53 |
| 402 | 473 | — | — | — | — | — | — | 59 |
| 403 | 474 | — | — | — | — | — | — | 53 |
| 404 | 475 | — | — | 91 | 93 | 106 | — | 95 |
| 405 | 476 | — | — | 95 | 96 | 87 | — | 19 |
| 406 | 477 | — | — | 79 | 97 | 107 | — | 25 |
| 407 | 478 | — | — | 92 | 96 | 106 | — | 89 |
| 408 | 479 | — | — | 55 | 83 | 37 | — | 72 |
| 409 | 480 | — | — | 68 | 94 | 100 | — | 18 |
| 410 | 481 | — | — | 77 | 99 | 98 | — | 24 |
| 411 | 482 | — | — | 21 | 8 | 6 | — | −2 |
| 412 | 483 | — | — | 59 | 77 | 14 | — | 37 |
| 413 | 484 | — | — | — | — | — | — | −4 |
| 414 | 485 | — | — | — | — | — | — | 14 |
| 415 | 486 | — | — | — | — | — | — | 14 |
| 416 | 487 | — | — | — | — | — | — | 17 |
| 417 | 488 | — | — | — | — | — | — | 19 |
| 418 | 489 | — | — | — | — | — | — | 9 |
| 419 | 490 | — | — | — | — | — | — | 74 |
| 420 | 491 | — | — | — | — | — | — | 82 |

TABLE 9-continued

Inhibition of ligand binding to aminergic G protein-coupled receptors by compounds of the invention:

| Example No. | Compound No. | Adrenergic (1 μM) | | | | | | Dopamine (1 μM) |
| --- | --- | --- | --- | --- | --- | --- | --- | --- |
| | | $\alpha_{1A}$ | $\alpha_{1B}$ | $\alpha_{1D}$ | $\alpha_{2A}$ | $\alpha_{2B}$ | $\alpha_{2C}$ | $D_{2L}$ |
| 421 | 492 | — | — | — | — | — | — | 60 |
| 422 | 493 | — | — | — | — | — | — | 56 |
| 423 | 494 | — | — | — | — | — | — | 13 |
| 424 | 495 | — | — | — | — | — | — | 58 |
| 425 | 496 | — | — | — | — | — | — | 25 |
| 426 | 497 | — | — | — | — | — | — | 14 |
| 427 | 498 | — | — | — | — | — | — | 9 |
| 430 | 499 | — | — | — | — | — | — | 18 |
| 432 | 500 | 27 | 27 | 11 | 72 | 23 | 43 | — |

Example B5

Determination of the Ability of Compounds of the Invention to Bind a Serotonin Receptor Serotonin (5-Hydroxytryptamine) 5-$HT_{1A}$ To evaluate in radioligand binding assays the activity of compounds of the invention, human recombinant serotonin (5-Hydroxytryptamine) 5-$HT_{1A}$ receptor expressed in Chinese hamster ovary (CHO-K1) cells (Martin G R and Humphrey P P A. Neuropharmacol. 33:261, 1994; May J A, et al. J Pharmacol Exp Ther. 306(1): 301, 2003) in a modified Tris-HCl buffer (50 mM Tris-HCl, pH 7.4, 0.1% Ascorbic Acid, 0.5 mM EDTA, 10 mM $MgSO_4$) is used. Compounds of invention are incubated with 1.5 nM [$^3$H]8-OH-DPAT for 60 min. at 25° C. Non-specific binding is estimated in the presence of 10 μM Metergoline. Receptor proteins are filtered and washed, the filters are then counted to determine [$^3$H]8-OH-DPAT specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-$HT_{1B}$

To evaluate in radioligand binding assays the activity of compounds of the invention, serotonin (5-Hydroxytryptamine) 5-$HT_{1B}$ receptor from Wistar Rat cerebral cortex (Hoyer et al. Eur J Pharmaco. 118: 1, 1985; Pazos et al. Eur J Pharmacol. 106: 531, 1985) in a modified Tris-HCl buffer (50 mM Tris-HCl, pH 7.4, 154 mM NaCl, 10 μM Pargyline, 30 μM Isoprenaline) is used. Compounds of invention are incubated with 10 pM [$^{125}$I]Cyanopindolol for 90 min. at 37° C. Non-specific binding is estimated in the presence of 10 μM Serotonin (5-HT). Receptor proteins are filtered and washed, the filters are counted to determine [$^{125}$I]Cyanopindolol specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-$HT_{2A}$

To evaluate in radioligand binding assays the activity of compounds of the invention, human recombinant serotonin (5-Hydroxytryptamine) 5-$HT_{2A}$ receptor expressed in Chinese hamster ovary (CHO-K1) cells (Bonhaus, D. W. et al. Br. J. Pharmacol. 115:622, 1995; Saucier, C. and Albert, P. R., J. Neurochem. 68:1998, 1997) in a 50 mM Tris-HCl buffer, pH 7.4, was used. Compounds of the invention were incubated with 0.5 nM [$^3$H]Ketanserin for 60 min. at 25° C. Non-specific binding was estimated in the presence of 1 μM Mianserin. Receptor proteins were filtered and washed, the filters were then counted to determine [$^3$H]Ketanserin specifically bound. Compounds were screened at 1 μM or lower, using 1% DMSO as vehicle. Biochemical assay results are presented as the percent inhibition of specific binding in Table 10.

Serotonin (5-Hydroxytryptamine) 5-$HT_{2B}$

To evaluate in radioligand binding assays the activity of compounds of the invention, human recombinant serotonin (5-Hydroxytryptamine) 5-$HT_{2B}$ receptor expressed in Chinese hamster ovary (CHO-K1) cells (Bonhaus, D. W. et al., Br. J. Pharmacol. 115:622, 1995) in a modified Tris-HCl buffer (50 mM Tris-HCl, pH 7.4, 4 mM $CaCl_2$, 0.1% Ascorbic Acid) was used. Compounds of invention were incubated with 1.2 nM [$^3$H]Lysergic acid diethylamide (LSD) for 60 min. at 37° C. Non-specific binding was estimated in the presence of 10 μM Serotonin (5-HT). Receptor proteins were filtered and washed, the filters were then counted to determine [$^3$H]LSD specifically bound. Compounds were screened at 1 μM or lower, using 1% DMSO as vehicle. Compounds of the invention were tested in this biochemical assay and percent inhibition of specific binding was determined. Biochemical assay results are presented as the percent inhibition of specific binding in Table 10.

Serotonin (5-Hydroxytryptamine) 5-$HT_{2C}$

To evaluate in radioligand binding assays the activity of compounds of the invention, human recombinant serotonin (5-Hydroxytryptamine) 5-$HT_{2C}$ receptor expressed in Chinese hamster ovary (CHO-K1) cells (Wolf, W. A. and Schutz, J. S., J. Neurochem. 69:1449, 1997) in a modified Tris-HCl buffer (50 mM Tris-HCl, pH 7.4, 0.1% Ascorbic Acid, 10 μM Pargyline) was used. Compounds of the invention were incubated with 1 nM [$^3$H]Mesulergine for 60 min. at 25° C. Non-specific binding was estimated in the presence of 1 μM Mianserin. Receptor proteins were filtered and washed, the filters were then counted to determine [$^3$H]Mesulergine specifically bound. Compounds were screened at 1 μM or lower, using 1% DMSO as vehicle. Biochemical assay results are presented as the percent inhibition of specific binding in Table 10.

Serotonin (5-Hydroxytryptamine) 5-$HT_3$

To evaluate in radioligand binding assays the activity of compounds of the invention, human recombinant serotonin (5-Hydroxytryptamine) 5-$HT_3$ receptor expressed in human embryonic kidney (HEK-293) cells (Miller K et al. Synapase. 11:58, 1992; Boess F G et al. Neuropharmacology. 36:637, 1997) in a modified Tris-HCl buffer (50 mM Tris-HCl, pH 7.4, 1 mM EDTA, 5 mM $MgCl_2$) is used. Compounds of invention are incubated with 0.69 nM [³]GR-65630 for 60 min. at 25° C. Non-specific binding is estimated in the presence of 10 µM MDL-72222. Receptor proteins are filtered and washed, the filters are then counted to determine [³]GR-65630 specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_4$

To evaluate in radioligand binding assays the activity of compounds of the invention, serotonin (5-Hydroxytryptamine) 5-HT$_4$ receptor from Duncan Hartley derived Guinea pig striatum (Grossman C J et al. Br J Pharmacol. 109:618, 1993) in a 50 mM Tris-HCl, pH 7.4, is used. Compounds of invention are incubated with 0.7 nM [³]GR-113808 for 30 min. at 25° C. Non-specific binding is estimated in the presence of 30 µM Serotonin (5-HT). Receptor proteins are filtered and washed, the filters are counted to determine [³]GR-113808 specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_{5A}$

To evaluate in radioligand binding assays the activity of compounds of the invention, human recombinant serotonin (5-Hydroxytryptamine) 5-HT$_{5A}$ receptor expressed in Chinese hamster ovary (CHO-K1) cells (Rees, S. et al., FEBS Lett. 355:242, 1994) in a modified Tris-HCl buffer (50 mM Tris-HCl, pH 7.4, 10 mM MgCl$_2$, 0.5 mM EDTA) is used. Compounds of the invention are incubated with 1.7 nM [³H]Lysergic acid diethylamide (LSD) for 60 min. at 37° C. Non-specific binding is estimated in the presence of 100 µM Serotonin (5-HT). Receptor proteins are filtered and washed, the filters are counted to determine [³H]LSD specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-HT$_6$

To evaluate in radioligand binding assays the activity of compounds of the invention, human recombinant serotonin (5-Hydroxytryptamine) 5-HT6 receptor expressed in human HeLa cells (Monsma, F. J. Jr. et al., Mol. Pharmacol. 43:320, 1993) in a modified Tris-HCl buffer (50 mM Tris-HCl, pH 7.4, 150 mM NaCl, 2 mM Ascorbic Acid, 0.001% BSA) was used. Compounds of the invention were incubated with 1.5 nM [3H]Lysergic acid diethylamide (LSD) for 120 min. at 37° C. Non-specific binding was estimated in the presence of 5 µM Serotonin (5-HT). Receptor proteins were filtered and washed, the filters were then counted to determine [3H]LSD specifically bound. Compounds were screened at 1 µM or lower, using 1% DMSO as vehicle. Biochemical assay results are presented as the percent inhibition of specific binding in Table 10.

Serotonin (5-Hydroxytryptamine) 5-HT$_7$

To evaluate in radioligand binding assays the activity of compounds of the invention, human recombinant serotonin (5-Hydroxytryptamine) 5-HT$_7$ receptor expressed in Chinese hamster ovary (CHO) cells (Roth, B. L. et al., J. Pharmacol. Exp. Ther. 268:1403, 1994; Shen, Y. et al., J. Biol. Chem. 268:18200, 1993) in a modified Tris-HCl buffer (50 mM Tris-HCl, pH 7.4, 10 mM MgCl$_2$, 0.5 mM EDTA) was used. Compounds of invention were incubated with 5.5 nM [³H]Lysergic acid diethylamide (LSD) for 2 h at 25° C. Non-specific binding was estimated in the presence of 10 µM Serotonin (5-HT). Receptor proteins were filtered and washed, the filters were then counted to determine [³H]LSD specifically bound. Compounds were screened at 1 µM or lower, using 1% DMSO as vehicle. Biochemical assay results are presented as the percent inhibition of specific binding in Table 10.

TABLE 10

Inhibition of ligand binding to aminergic G protein-coupled receptors by compounds of the invention:

| Example No. | Comp No. | 5-HT$_{2A}$ | 5-HT$_{2B}$ | 5-HT$_{2C}$ | 5-HT$_{5A}$ | 5-HT$_6$ | 5-HT$_7$ |
|---|---|---|---|---|---|---|---|
| | | | | Serotonin (1 µM) | | | |
| 2 | 3 | — | — | 96 | — | 58 | — |
| 43 | 43 | 100 | 70/77 | 96/100 | 61/73 | 95/99 | 98 |
| 49 | 44 | 80 | 11 | 36 | 0 | 9 | 42 |
| 44 | 45 | 99 | — | 95 | — | 94 | 92 |
| 45 | 47 | 84 | — | 81 | — | 39 | — |
| 51 | 48 | 73 | — | 67 | — | 59 | — |
| 47 | 51 | 102 | 32 | 84 | 27 | 83 | 91 |
| 53 | 52 | 83 | — | 87 | — | 37 | — |
| 48 | 53 | 100 | 23 | 82 | 26 | 49 | 87 |
| 54 | 54 | 42 | — | 22 | — | 31 | — |
| 56 | 55 | 100 | — | 93 | — | 90 | — |
| 55 | 56 | 68 | — | 38 | — | 62 | — |
| 57 | 57 | 95 | — | 86 | — | 68 | — |
| 58 | 59 | 96 | — | 99 | — | 54 | — |
| 60 | 60 | 78 | — | 86 | — | 50 | — |
| 61 | 61 | 77 | — | 90 | — | 65 | — |
| 62 | 62 | 88 | — | 89 | — | 43 | — |
| 63 | 63 | 95 | — | 95 | — | 73 | — |
| 80 | 78 | 97 | — | 103 | — | 101 | 97 |
| 82 | 82 | 100 | — | 105 | — | 103 | 93 |
| 83 | 83 | 99 | 88 | 98 | 97 | 102 | 93 |
| 84 | 85 | — | — | — | — | 68 | — |
| 89 | 86 | 95 | — | 94 | — | 77 | 93 |
| 85 | 87 | 99 | — | 100 | — | 101 | 100 |
| 90 | 88 | 98/101 | — | 99/100 | — | 102/103 | 93 |
| 86 | 89 | 101 | — | 98 | — | 67 | — |
| 91 | 90 | 100 | — | 97 | — | 103 | — |

TABLE 10-continued

Inhibition of ligand binding to aminergic G protein-coupled receptors by compounds of the invention:

| Example No. | Comp No. | 5-HT$_{2A}$ | 5-HT$_{2B}$ | 5-HT$_{2C}$ | 5-HT$_{5A}$ | 5-HT$_6$ | 5-HT$_7$ |
|---|---|---|---|---|---|---|---|
| 88 | 91 | 98 | — | 100 | — | 76 | 95 |
| 92 | 92 | 100 | — | 91 | — | 97 | — |
| 93 | 93 | 100 | — | 99 | — | 93 | — |
| 94 | 95 | 91 | — | 91 | — | 71 | — |
| 99 | 98 | 95 | — | 100 | — | 100 | 94 |
| 100 | 100 | 101 | — | 97 | — | 95 | 99 |
| 105 | 102 | 100 | — | 95 | — | 105 | 93 |
| 102 | 103 | 101 | — | 98 | — | 89 | 90 |
| 107 | 106 | 98 | — | 98 | — | 104 | 98 |
| 113 | 110 | 98 | — | 101 | — | 104 | 92 |
| 110 | 111 | 99 | — | 100 | — | 94 | 102 |
| 125 | 125 | 97 | — | 77 | — | 62 | — |
| 126 | 126 | 102 | — | 84 | — | 95 | — |
| 127 | 127 | 84 | — | 72 | — | 41 | — |
| 83 | 128 | 100 | — | 100 | — | 101 | 98 |
| 85 | 132 | 100 | — | 96 | — | 100 | 103 |
| 89 | 133 | 96 | — | 96 | — | 80 | — |
| 86 | 136 | 100 | — | 93 | — | 73 | — |
| 93 | 140 | 98 | — | 98 | — | 75 | — |
| 429 | 166 | 46 | — | 46 | — | 6 | — |
| 259 | 171 | 97 | — | 98 | — | 93 | 42 |
| 260 | 172 | 91 | — | 97 | — | 93 | 100 |
| 261 | 173 | 99 | — | 98 | — | 85 | 103 |
| 262 | 174 | 97/100 | — | 95/98 | — | 82/87 | 95/98 |
| 263 | 175 | 102 | — | 95 | — | 100 | 79 |
| 428 | 176 | 97 | — | 99 | — | 82 | 65 |
| 264 | 177 | 97 | — | 95 | — | 100 | 42 |
| 265 | 178 | 98 | — | 95 | — | 95 | 48 |
| 266 | 180 | 86 | — | 74 | — | 72 | 77 |
| 267 | 181 | 77 | — | 80 | — | 32 | 30 |
| 268 | 182 | 91 | — | 93 | — | 47 | 54 |
| 269 | 183 | 82 | — | 78 | — | 72 | 74 |
| 270 | 184 | 82 | — | 65 | — | 31 | 48 |
| 271 | 185 | 82 | — | 83 | — | 26 | 41 |
| 272 | 186 | 74 | — | 72 | — | 12 | 37 |
| 273 | 187 | 102 | — | 99 | — | 98 | 94 |
| 274 | 188 | 50 | — | 66 | — | 9 | 45 |
| 275 | 189 | 96 | — | 91 | — | 87 | 82 |
| 276 | 190 | 71 | — | 52 | — | 31 | 47 |
| 152 | 202 | 101 | — | 101 | — | 105 | 91 |
| 155 | 203 | 100 | — | 98 | — | 103 | 95 |
| 156 | 204 | 101 | — | 102 | — | 102 | 93 |
| 157 | 205 | 97 | — | 100 | — | 103 | 102 |
| 158 | 206 | 98 | — | 98 | — | 102 | 93 |
| 159 | 207 | 97 | — | 97 | — | 58 | 92 |
| 160 | 208 | 102 | — | 102 | — | 103 | 100 |
| 161 | 209 | 93 | — | 95 | — | 41 | 36 |
| 163 | 210 | 98 | — | 99 | — | 76 | 65 |
| 165 | 211 | 99 | — | 107 | — | 98 | 101 |
| 166 | 212 | 91 | — | 104 | — | 97 | 98 |
| 167 | 213 | 98 | — | 102 | — | 100 | 100 |
| 168 | 214 | 93 | — | 95 | — | 94 | 97 |
| 169 | 215 | 97 | — | 96 | — | 97 | 90 |
| 170 | 216 | 99 | — | 94 | — | 104 | 79 |
| 171 | 217 | 98 | — | 87/92 | — | 102 | 73/91 |
| 172 | 218 | 99 | — | 96 | — | 99 | 93 |
| 173 | 219 | 101 | — | 98 | — | 102 | 94 |
| 174 | 220 | 99 | — | 98 | — | 99 | 104 |
| 175 | 221 | 97 | — | 99 | — | 95 | 93 |
| 176 | 222 | 100 | — | 99 | — | 102 | 69 |
| 179 | 223 | 95 | — | 93 | — | 103 | 91 |
| 180 | 224 | 99 | — | 97 | — | 102 | 91 |
| 181 | 225 | 99 | — | 100 | — | 103 | 94 |
| 182 | 226 | 98 | — | 100 | — | 101 | 100 |
| 185 | 227 | 103 | — | 103 | — | 107 | 90 |
| 186 | 228 | 101 | — | 97 | — | 106 | 97 |
| 187 | 229 | 100 | — | 100 | — | 107 | 89 |
| 189 | 230 | 98 | — | 100 | — | 97 | 93 |
| 190 | 231 | 101 | — | 98 | — | 97 | 94 |
| 191 | 232 | 99 | — | 98 | — | 103 | 84 |
| 192 | 233 | 97 | — | 101 | — | 102 | 95 |
| 193 | 234 | 100 | — | 102 | — | 101 | 99 |
| 194 | 235 | 98 | — | 101 | — | 99 | 96 |
| 195 | 236 | 99 | — | 102 | — | 98 | 93 |
| 196 | 237 | 101 | — | 98 | — | 101 | 100 |

TABLE 10-continued

Inhibition of ligand binding to aminergic G protein-coupled receptors by compounds of the invention:

| Example No. | Comp No. | 5-HT$_{2A}$ | 5-HT$_{2B}$ | 5-HT$_{2C}$ | 5-HT$_{5A}$ | 5-HT$_6$ | 5-HT$_7$ |
|---|---|---|---|---|---|---|---|
| 197 | 238 | 101 | — | 99 | — | 99 | 98 |
| 199 | 239 | 93 | — | 93 | — | 104 | 98 |
| 200 | 240 | 99 | — | 99 | — | 104 | 99 |
| 201 | 241 | 93 | — | 100 | — | 101 | 96 |
| 202 | 242 | 98 | — | 99 | — | 107 | 100 |
| 203 | 243 | 100 | — | 99 | — | 107 | 97 |
| 204 | 244 | 103 | — | 99 | — | 106 | 99 |
| 205 | 245 | 102 | — | 96 | — | 103 | 74 |
| 206 | 246 | 97 | — | 94 | — | 104 | 88 |
| 207 | 247 | 101 | — | 100 | — | 103 | 101 |
| 433 | 347 | 100 | — | 104 | — | 101 | 101 |
| 434 | 348 | 99/100 | — | 91/95 | — | 94/98 | 93/93 |
| 435 | 349 | 97/100 | — | 96/98 | — | 102/103 | 93/100 |
| 436 | 350 | 100 | — | 87 | — | 103 | 71 |
| 437 | 351 | 100 | — | 101 | — | 103 | 90 |
| 438 | 352 | 84 | — | 93 | — | 32 | 52 |
| 439 | 353 | 98 | — | 97 | — | 100 | 87 |
| 440 | 354 | 100 | — | 101 | — | 103 | 75 |
| 441 | 355 | 92 | — | 99 | — | 101 | 92 |
| 442 | 356 | 81 | — | 83 | — | 90 | 60 |
| 332 | 404 | — | — | 90 | — | — | 95 |
| 397 | 469 | 87 | — | — | — | — | — |
| 398 | 470 | 89 | — | — | — | — | — |
| 404 | 475 | 99 | — | 96 | — | 99 | — |
| 405 | 476 | 100 | — | 95 | — | 64/86 | 90/92 |
| 406 | 477 | 95 | — | 99 | — | 89 | 65 |
| 407 | 478 | 99 | — | 110 | — | 97 | 96 |
| 408 | 479 | 78 | — | 69 | — | 91 | 17 |
| 409 | 480 | 98 | — | 102 | — | 67 | 84 |
| 410 | 481 | 101 | — | 104 | — | 87 | 84 |
| 411 | 482 | −8 | — | −12 | — | 4 | 22 |
| 412 | 483 | 34 | — | 35 | — | 53 | 16 |
| 413 | 484 | 98 | — | 95 | — | 34 | 83 |
| 414 | 485 | 96 | — | 102 | — | 89 | 77 |
| 432 | 500 | 40 | 34 | 77 | 23 | 18 | 48 |
| | | | Serotonin (0.1 μM) | | | | |
| 43 | 43 | — | −2 | 81 | 19 | 62 | — |
| 44 | 45 | 86 | — | 88 | — | 48 | — |
| 47 | 51 | — | 12 | 43 | — | 29 | — |
| 80 | 78 | 76 | — | 69 | — | 78 | — |
| 82 | 82 | 92 | — | 94 | — | 90 | 86/95 |
| 83 | 83 | 98 | — | 100 | — | 96 | 82/96 |
| 84 | 85 | 88/98 | — | 92 | — | 22/19 | — |
| 85 | 87 | 100 | — | 101 | — | 97 | — |
| 90 | 88 | 87/95 | — | 74/96 | — | 82/102 | 75/97 |
| 91 | 90 | 97 | — | 85 | — | 102 | 82 |
| 100 | 100 | 97 | — | 104 | — | 62 | — |
| 104 | 107 | 96 | — | 95 | — | 97 | 95 |
| 113 | 110 | 102 | — | 99 | — | 102 | — |
| 110 | 111 | 86 | — | 95 | — | 71 | — |
| 83 | 128 | 99 | — | — | — | 94 | — |
| 259 | 171 | 60 | — | 51 | — | 35 | — |
| 262 | 174 | 96 | — | 96 | — | 40 | 68 |
| 277 | 191 | 98 | — | 94 | — | 45 | 69 |
| 278 | 192 | 91 | — | 81 | — | 38 | 78 |
| 279 | 193 | 69 | — | 44 | — | 3 | 40 |
| 280 | 194 | 71 | — | 47 | — | 7 | 16 |
| 281 | 195 | 62 | — | 43 | — | 32 | 18 |
| 282 | 196 | 36 | — | 8 | — | 10 | 12 |
| 283 | 197 | 17 | — | 16 | — | 4 | 10 |
| 284 | 198 | 23 | — | −1 | — | 11 | 4 |
| 285 | 199 | 40 | — | 33 | — | 25 | 30 |
| 286 | 200 | 30 | — | 17 | — | 20 | 31 |
| 155 | 203 | 98 | — | 101 | — | 97 | — |
| 157 | 205 | 104 | — | 96 | — | 99 | — |
| 165 | 211 | 97 | — | 98 | — | 60 | — |
| 170 | 216 | 98 | — | 83 | — | 100 | 66 |
| 171 | 217 | 96 | — | 62 | — | 97 | 58 |
| 172 | 218 | 94 | — | 92 | — | 85 | — |
| 173 | 219 | 100 | — | 94 | — | 96 | — |
| 179 | 223 | 97 | — | 81 | — | 104 | 67 |
| 180 | 224 | 92 | — | 95 | — | 96 | 88 |
| 209 | 248 | 108 | — | 92 | — | 101 | 57 |
| 210 | 249 | 90 | — | 60 | — | 98 | 70 |

TABLE 10-continued

Inhibition of ligand binding to aminergic G protein-coupled receptors by compounds of the invention:

| Example No. | Comp No. | 5-HT$_{2A}$ | 5-HT$_{2B}$ | 5-HT$_{2C}$ | 5-HT$_{5A}$ | 5-HT$_6$ | 5-HT$_7$ |
|---|---|---|---|---|---|---|---|
| 211 | 250 | 36 | — | 31 | — | 13 | 33 |
| 212 | 251 | 85 | — | 77 | — | 8 | 74 |
| 213 | 252 | 67 | — | 50 | — | 9 | 23 |
| 214 | 253 | 85 | — | 49 | — | 9 | 54 |
| 215 | 254 | 65 | — | 52 | — | 15 | 63 |
| 216 | 255 | 81 | — | 69 | — | 4 | 54 |
| 217 | 256 | 100 | — | 90 | — | 96 | 85 |
| 218 | 257 | 94 | — | 94 | — | 71 | 75 |
| 219 | 258 | 98 | — | 98 | — | 81 | 84 |
| 220 | 259 | 96 | — | 92 | — | 21 | 81 |
| 221 | 260 | 34 | — | 29 | — | −7 | 5 |
| 222 | 261 | 74 | — | 31 | — | 4 | 47 |
| 223 | 262 | 99 | — | 100 | — | 99 | 94 |
| 224 | 263 | 64 | — | 18 | — | 99 | 15 |
| 225 | 264 | 99 | — | 94 | — | 89 | 51 |
| 226 | 265 | 96 | — | 89 | — | 97 | 52 |
| 227 | 266 | 67 | — | 12 | — | 81 | 18 |
| 228 | 267 | 66 | — | 54 | — | 87 | 85 |
| 229 | 268 | 98 | — | 86 | — | 97 | 87 |
| 231 | 269 | 87 | — | 55 | — | 102 | 51 |
| 232 | 270 | 92 | — | 84 | — | 97 | 79 |
| 233 | 271 | 41 | — | 19 | — | 90 | 10 |
| 234 | 272 | 62 | — | 40 | — | 98 | −1 |
| 235 | 273 | 94 | — | 100 | — | 46 | 85 |
| 236 | 274 | 98 | — | 99 | — | 97 | 94 |
| 237 | 275 | 93 | — | 98 | — | 101 | 72 |
| 238 | 276 | 99 | — | 96 | — | 81 | 86 |
| 239 | 277 | 100 | — | 98 | — | 98 | 103 |
| 240 | 278 | 88 | — | 91 | — | 69 | 79 |
| 241 | 279 | 75 | — | 70 | — | 90 | 53 |
| 242 | 280 | 83 | — | 86 | — | 56 | 20 |
| 243 | 281 | 103 | — | 96 | — | 78 | 93 |
| 244 | 282 | 100 | — | 94 | — | 102 | 91 |
| 245 | 283 | 101 | — | 90 | — | 88 | 71 |
| 246 | 284 | 103 | — | 93 | — | 101 | 75 |
| 247 | 285 | 52 | — | 45 | — | 67 | 44 |
| 430 | 286 | 79 | — | 74 | — | 56 | 10 |
| 248 | 287 | 50 | — | 74 | — | 25 | 48 |
| 249 | 288 | 82 | — | 72 | — | 99 | 56 |
| 250 | 289 | 85 | — | 64 | — | 100 | 41 |
| 255 | 291 | 1 | — | 1 | — | 7 | 0 |
| 256 | 292 | 45 | — | 12 | — | 60 | 27 |
| 257 | 293 | 30 | — | 32 | — | 6 | 50 |
| 258 | 294 | 102 | — | 98 | — | 97 | 84 |
| 293 | 320 | 94 | — | 107 | — | 92 | 91 |
| 294 | 332 | 80 | — | 53 | — | 92 | 48 |
| 295 | 333 | 55 | — | 73 | — | 32 | 39 |
| 296 | 334 | 103 | — | 109 | — | 76 | 14 |
| 297 | 338 | 104 | — | 112 | — | 103 | 94 |
| 287 | 341 | 11 | — | 3 | — | 2 | 2 |
| 288 | 342 | 14 | — | 4 | — | 1 | 6 |
| 289 | 343 | 8 | — | 5 | — | −7 | −1 |
| 290 | 344 | −6 | — | −6 | — | −1 | 31 |
| 291 | 345 | 43 | — | 56 | — | −1 | 40 |
| 292 | 346 | 26 | — | 26 | — | 5 | 57 |
| 433 | 347 | 90 | — | 99 | — | 70 | — |
| 434 | 348 | 96 | — | 88 | — | 62 | 62 |
| 435 | 349 | 100 | — | 99 | — | 92 | 72 |
| 436 | 350 | 94 | — | 101 | — | 84 | — |
| 437 | 351 | 98 | — | 100 | — | 100 | — |
| 443 | 357 | 45 | — | 53 | — | 18 | 11 |
| 444 | 358 | 49 | — | 67 | — | 0 | 6 |
| 445 | 359 | 56 | — | 74 | — | 22 | 12 |
| 446 | 360 | 64 | — | 52 | — | 13 | 22 |
| 447 | 361 | 89 | — | 81 | — | 80 | 78 |
| 448 | 362 | 88 | — | 92 | — | 100 | 92 |
| 449 | 363 | 79 | — | 47 | — | 49 | 26 |
| 450 | 364 | 38 | — | 45 | — | 24 | 44 |
| 301 | 365 | 99 | — | 102 | — | 50 | 72 |
| 298 | 367 | 91 | — | 106 | — | 75 | 85 |
| 299 | 368 | 92 | — | 96 | — | 76 | 71 |
| 300 | 369 | 72 | — | 105 | — | 52 | 63 |
| 302 | 370 | 79 | — | 99 | — | 79 | 78 |
| 312 | 384 | 96 | — | 92 | — | 107 | 98 |
| 313 | 385 | 67 | — | 69 | — | 19 | 69 |

TABLE 10-continued

Inhibition of ligand binding to aminergic G protein-coupled receptors by compounds of the invention:

| Example No. | Comp No. | 5-HT$_{2A}$ | 5-HT$_{2B}$ | 5-HT$_{2C}$ | 5-HT$_{5A}$ | 5-HT$_6$ | 5-HT$_7$ |
|---|---|---|---|---|---|---|---|
| 314 | 386 | 62 | — | 64 | — | 13 | 58 |
| 315 | 387 | 98 | — | 98 | — | 105 | 89 |
| 316 | 388 | 99 | — | 98 | — | 106 | 83 |
| 317 | 389 | 78 | — | 78 | — | 25 | 79 |
| 318 | 390 | 92 | — | 93 | — | 76 | 70 |
| 319 | 391 | 84 | — | 86 | — | 35 | 87 |
| 320 | 392 | 94 | — | 94 | — | 98 | 80 |
| 321 | 393 | 95 | — | 69 | — | 13 | 75 |
| 322 | 394 | 94 | — | 79 | — | 36 | 81 |
| 323 | 395 | 95 | — | 32 | — | 105 | 60 |
| 324 | 396 | −12 | — | 3 | — | 10 | −15 |
| 325 | 397 | 102 | — | 95 | — | 100 | 95 |
| 326 | 398 | 97 | — | 31 | — | 97 | 52 |
| 327 | 399 | 100 | — | 57 | — | 16 | 70 |
| 328 | 400 | 89 | — | 19 | — | 96 | 61 |
| 329 | 401 | 66 | — | 47 | — | 89 | 69 |
| 330 | 402 | 79 | — | 44 | — | 101 | 69 |
| 331 | 403 | 25 | — | 16 | — | 59 | 2 |
| 332 | 404 | 85/99 | — | 50/65 | — | 101/105 | 55/67 |
| 333 | 405 | 91 | — | 78 | — | 99 | 74 |
| 334 | 406 | 93 | — | 75 | — | 103 | 73 |
| 335 | 407 | 96 | — | 92 | — | 57 | 47 |
| 336 | 408 | 7272 | — | 6969 | — | 49 | 93 |
| 337 | 409 | 97 | — | 97 | — | 64 | 69 |
| 338 | 410 | 92 | — | 92 | — | 54 | 72 |
| 339 | 411 | 61 | — | 17 | — | 63 | 28 |
| 340 | 412 | 92 | — | 50 | — | 101 | 82 |
| 341 | 413 | 94 | — | 87 | — | 37 | 73 |
| 342 | 414 | 80 | — | 30 | — | 103 | 75 |
| 343 | 415 | 97 | — | 99 | — | 105 | 98 |
| 344 | 416 | 101 | — | 99 | — | 16 | 71 |
| 345 | 417 | 94 | — | 95 | — | 57 | 64 |
| 346 | 418 | 33 | — | 29 | — | 20 | 15 |
| 347 | 419 | 73 | — | 45 | — | 15 | 70 |
| 348 | 420 | 90 | — | 76 | — | 17 | 39 |
| 349 | 421 | 74 | — | 81 | — | 61 | 17 |
| 350 | 422 | 67 | — | 40 | — | 93 | 56 |
| 351 | 423 | 52 | — | 31 | — | 2 | 20 |
| 352 | 424 | 84 | — | 93 | — | 16 | 54 |
| 353 | 425 | 59 | — | 43 | — | 15 | 38 |
| 354 | 426 | 87 | — | 60 | — | 59 | 74 |
| 355 | 427 | 18 | — | 4 | — | 64 | 12 |
| 356 | 428 | 94 | — | 81 | — | 82 | 79 |
| 357 | 429 | 41 | — | 48 | — | 50 | 91 |
| 358 | 430 | 96 | — | 80 | — | 3 | 59 |
| 359 | 431 | 78 | — | 82 | — | 75 | 60 |
| 360 | 432 | 84 | — | 68 | — | 77 | 33 |
| 361 | 433 | 21 | — | 8 | — | 55 | 23 |
| 363 | 435 | 93 | — | 94 | — | 3 | 76 |
| 364 | 436 | 70 | — | 66 | — | 12 | 81 |
| 365 | 437 | 8 | — | 6 | — | 10 | −14 |
| 366 | 438 | 72 | — | 64 | — | 16 | 20 |
| 367 | 439 | −5 | — | 2 | — | 14 | 11 |
| 368 | 440 | −3 | — | 3 | — | 23 | −3 |
| 369 | 441 | 97 | — | 87 | — | 28 | 98 |
| 370 | 442 | 50 | — | 33 | — | 82 | 34 |
| 371 | 443 | 10 | — | 14 | — | 59 | 13 |
| 372 | 444 | 17 | — | 19 | — | 72 | 3 |
| 373 | 445 | 8 | — | 6 | — | 56 | −3 |
| 374 | 446 | 5 | — | −2 | — | 60 | 14 |
| 375 | 447 | 14 | — | 1 | — | 41 | 15 |
| 376 | 448 | 8 | — | 14 | — | 57 | 14 |
| 377 | 449 | 44 | — | 11 | — | 73 | 21 |
| 378 | 450 | 19 | — | −6 | — | 62 | 14 |
| 379 | 451 | 88 | — | 89 | — | 47 | 78 |
| 380 | 452 | 98 | — | 100 | — | 79 | 84 |
| 381 | 453 | 90 | — | 98 | — | 67 | 64 |
| 382 | 454 | 95 | — | 98 | — | 35 | 89 |
| 383 | 455 | 94 | — | 97 | — | 65 | 42 |
| 384 | 456 | 96 | — | 93 | — | 84 | 97 |
| 385 | 457 | 33 | — | 24 | — | 12 | 43 |
| 386 | 458 | 39 | — | 8 | — | 16 | 68 |
| 387 | 459 | 98 | — | 101 | — | 69 | 91 |
| 388 | 460 | 86 | — | 89 | — | 38 | 24 |
| 389 | 461 | 91 | — | 96 | — | 68 | 41 |

TABLE 10-continued

Inhibition of ligand binding to aminergic G protein-coupled receptors by compounds of the invention:

| Example No. | Comp No. | 5-HT$_{2A}$ | 5-HT$_{2B}$ | 5-HT$_{2C}$ | 5-HT$_{5A}$ | 5-HT$_6$ | 5-HT$_7$ |
|---|---|---|---|---|---|---|---|
| 390 | 462 | 99 | — | 99 | — | 23 | 88 |
| 392 | 464 | 89 | — | 36 | — | 49 | 38 |
| 393 | 465 | 97 | — | 83 | — | 38 | 29 |
| 394 | 466 | 93 | — | 86 | — | 33 | 34 |
| 395 | 467 | 55 | — | 20 | — | 15 | 19 |
| 396 | 468 | 28 | — | 3 | — | 6 | 11 |
| 397 | 469 | 44 | — | 57 | — | 4 | 31 |
| 398 | 470 | 49 | — | 1 | — | 16 | 18 |
| 400 | 471 | −2 | — | 3 | — | 5 | 1 |
| 401 | 472 | 82 | — | 75 | — | 53 | 68 |
| 402 | 473 | 96 | — | 55 | — | 38 | 45 |
| 403 | 474 | 103 | — | 98 | — | 81 | 98 |
| 404 | 475 | 98 | — | 100 | — | 54 | — |
| 405 | 476 | 97 | — | — | — | 27 | 67 |
| 407 | 478 | 99 | — | 104 | — | 56 | — |
| 415 | 486 | 98 | — | 103 | — | 33 | 10 |
| 416 | 487 | 100 | — | 101 | — | 21 | 28 |
| 417 | 488 | 94 | — | 97 | — | 44 | 7 |
| 418 | 489 | 96 | — | 85 | — | 37 | 40 |
| 419 | 490 | 99 | — | 95 | — | 66 | 55 |
| 420 | 491 | 99 | — | 103 | — | 94 | 92 |
| 421 | 492 | 98 | — | 100 | — | 89 | 77 |
| 422 | 493 | 97 | — | 96 | — | 49 | 69 |
| 423 | 494 | 99 | — | 97 | — | 26 | 36 |
| 424 | 495 | 91 | — | 77 | — | 65 | 45 |
| 425 | 496 | 103 | — | 100 | — | 25 | 13 |
| 426 | 497 | 34 | — | 10 | — | −9 | 25 |
| 427 | 498 | 79 | — | 69 | — | 22 | 41 |
| 430 | 499 | 79 | — | 66 | — | 30 | 0 |

Example B6

Determination of Serotonin (5-Hydroxytryptamine) 5-HT$_{2A}$ or 5-HT$_7$ Agonist/Antagonist Activity of Compounds of the Invention To determine for agonist or antagonist activity of compounds of the invention in functional assays, human recombinant serotonin 5-HT$_{2A}$ receptor expressed in human embryonic kidney (HEK-293) cells (Jerman J C, Brough S J, Gager T, Wood M, Coldwell M C, Smart D and Middlemiss D N, Eur J Pharmacol, 414: 23-30, 2001) or human recombinant serotonin 5-HT$_7$ receptor expressed in CHO cells (Adham, et al. J. Pharmacol. Exp. Ther. 287:508-514, 1998) was used. Cells were suspended in DMEM buffer, and distributed in microplates. For the 5-HT$_{2A}$ assay, a cytoplasmic calcium fluorescent indicator which varies proportionally to the free cytosolic Ca$^{2+}$ ion concentration was mixed with probenicid in HBSS buffer complemented with 20 mM Hepes (pH 7.4), added into each well and equilibrated with the cells for 30 min. at 37° C. followed by 30 min. at 22° C. For the 5-HT$_7$ assay, the reaction product was cAMP, detected by HTRF.

To measure 5-HT$_{2A}$ agonist effects, compounds of the invention, reference agonist or HBSS buffer (basal control) was added to the cells and changes in fluorescence intensity were measured using a microplate reader. For stimulated control measurements, 5-HT at 100 nM was added in separate assay wells. The results are expressed as a percent of the control response to 100 nM 5-HT. The standard reference agonist was 5-HT, which was tested in each experiment at several concentrations to generate a concentration-response curve from which its EC$_{50}$ value was calculated.

To measure antagonist effects, the addition of the compounds of the invention, reference antagonist or HBSS buffer was followed by the addition of 3 nM 5-HT (5-HT$_{2A}$), 100 nM 5-HT (5-HT$_7$) or HBSS buffer (basal control) prior the fluorescence measurements. The results are expressed as a percent inhibition of the control response to 3 nM 5-HT. The standard reference antagonist was ketanserin (5-HT$_{2A}$) or mesulergine (5-HT$_7$), which was tested in each experiment at several concentrations to generate a concentration-response curve from which its IC$_{50}$ value was calculated. Compounds were screened at 3 μM or lower, using DMSO as vehicle. Assay results are presented in Table 11.

TABLE 11

5-HT$_{2A}$ agonist/antagonist activity of compounds of the invention

| | 5-HT$_{2A}$ | |
|---|---|---|
| Compound No. | Agonist EC$_{50}$ (μM) | Antagonist IC$_{50}$ (μM) |
| 83 | 3.1 | 0.97, >1.0 |

| | 5-HT$_7$ Antagonist IC$_{50}$ (μM) |
|---|---|
| 83 | 0.46, 0.77 |

Example B7

Determination of Serotonin (5-Hydroxytryptamine) 5-HT$_6$ Agonist/Antagonist Activity of Compounds of the Invention To determine for agonist or antagonist activity of compounds of the invention in functional assays, human recombinant 5-HT$_6$ receptor is transfected in CHO cells (Kohen, R., Metcalf, M. A., Khan, N., Druck, T., Huebner, K., Lachowicz, J. E., Meltzer, H. Y., Sibley, D. R., Roth, B. L. And Hamblin, M. W. Cloning, characterisation and chromosomal localization of a human 5-HT$_6$ serotonin receptor, J. Neurochem., 66: 47, 1996) and the activity of compounds of the invention is determined by measuring their effects on cAMP production using the Homogeneous Time Resolved Fluorescence (HTRF) detection method. Cells are suspended in HBSS buffer complemented with HEPES 20 mM (pH 7.4) and 500 μM IBMX, and then distributed in microplates and incubated for 45 min. at 37° C. in the absence (control) or presence of compounds of the invention or the reference agonist or antagonist.

For agonist determinations, stimulated control measurement, separate assay wells contain 10 μM 5-HT. Following incubation, the cells are lysed and the fluorescence acceptor (D2-labeled cAMP) and fluorescence donor (anti-cAMP antibody labeled with europium cryptate) are added. After 60 min. at room temperature, the fluorescence transfer is measured at lex=337 nm and lem=620 and 665 nm using a microplate reader. The cAMP concentration is determined by dividing the signal measured at 665 nm by that measured at 620 nm (ratio).

The results are expressed as a percent of the control response to 10 μM 5-HT. The standard reference agonist is 5-HT, which is tested in each experiment at several concentrations to generate a concentration-response curve from which its $EC_{50}$ value is calculated.

For antagonist determinations, the reference agonist 5-HT is added at a final concentration of 100 nM. For basal control measurements, separate assay wells do not contain 5-HT. Following 45 min. incubation at 37° C., the cells are lysed and the fluorescence acceptor (D$_2$-labeled cAMP) and fluorescence donor (anti-cAMP antibody labeled with europium cryptate) are added.

After 60 min. at room temperature, the fluorescence transfer is measured as mentioned above. The results are expressed as a percent inhibition of the control response to 100 nM 5-HT. The standard reference antagonist is methiothepin.

Example B8

Determination of Dopamine D$_{2L}$ Antagonist Activity of Compounds

To determine for agonist or antagonist activity of compounds of the invention in functional assays, human recombinant dopamine D$_{2L}$ receptor stably expressed in Chinese hamster ovary (CHO) cells (Senogles S E et al. J Biol Chem. 265(8): 4507, 1990) was used. Compounds of invention were pre-incubated with the membranes (0.1 mg/mL) and 10 mM GDP in modified HEPES buffer (20 mM HEPES, pH 7.4, 100 mM NaCl, 10 mM MgCl$_2$, 1 mM DTT, 1 mM EDTA) for 20 min. and Scintillation Proximity Assay (SPA) beads were added for another 60 min. at 30° C. The reaction was initiated by 0.3 nM [$^{35}$S]GTPγS for an additional 15 min. incubation period. Increase of [$^{35}$S]GTPγS binding by 50% or more (350%) relative to the 1 mM dopamine response by compounds of the invention indicates possible dopamine D$_{2L}$ receptor agonist's activity. Inhibition of a 10 μM dopamine-induced increase of [$^{35}$S]GTPγS binding response by 50% or more (350%) by compounds of the invention indicated receptor antagonist activity. Compounds were screened at 3 μM or lower, using 0.4% DMSO as vehicle. Assay results are presented as the percent response of specific binding in Table 12.

TABLE 12

Dopamine D$_{2L}$ antagonist activity of compounds of the invention
D$_{2L}$ GTPgS

| Compound 83 conc. (nM) | % Inhibition |
|---|---|
| 1 | 16 |
| 3 | 28 |
| 10 | 49 |
| 30 | 55 |
| 100 | 77 |

Example B9

Determination of Dopamine D$_{2S}$ antagonist activity of compounds of the invention To determine for agonist or antagonist activity of compounds of the invention in functional assays, human recombinant dopamine D$_{2S}$ receptor stably expressed in Chinese hamster ovary (CHO) cells (Gilliland S L and Alper R H. Naunyn-Schmiedeberg's Archives of Pharmacology. 361: 498, 2000) was used. Compounds of invention were pre-incubated with the membranes (0.05 mg/mL) and 3 μM GDP in modified HEPES buffer (20 mM HEPES, pH 7.4, 100 mM NaCl, 10 mM MgCl$_2$, 1 mM DTT, 1 mM EDTA) for 20 min. and Scintillation Proximity Assay (SPA) beads were then added for another 60 min. at 30° C. The reaction was initiated by 0.3 nM [$^{35}$S]GTPγS for an additional 30 min. incubation period. Increase of [$^{35}$S]GTPγS binding by 50 percent or more (350%) relative to the 100 μM dopamine response by compounds of the invention indicates possible dopamine D$_{2S}$ receptor agonist's activity. Inhibition of a 3 μM dopamine-induced increase of [$^{35}$S]GTPγS binding response by 50 percent or more (350%) by compounds of the invention indicated receptor antagonist activity. Compounds were screened at 3 μM or lower, using 0.4% DMSO as vehicle. Assay results are presented as the percent response of specific binding in Table 13.

TABLE 13

Dopamine D$_{2S}$ antagonist activity of compounds of the invention
D$_{2S}$ GTPgS

| Compound 83 conc. (nM) | % Inhibition |
|---|---|
| 1 | 15 |
| 3 | 45 |
| 10 | 56 |
| 30 | 74 |
| 100 | 91 |

Example B10

Determination for Agonist or Antagonist Activity of Compounds of the Invention in a Histamine H$_1$ Functional Assay To determine for agonist or antagonist activity of compounds of the invention in functional assays, human recombinant Histamine H$_1$ receptor expressed in human embryonic kidney (HEK-293) cells (Miller, T. R., Witte, D. G., Ireland, L. M., Kang, C. H., Roch, J. M., Masters, J. N., Esbenshade, T. A And Hancock, A. A. J. Biomol. Screen., 4: 249-258, 1999) is used. Cells are suspended in DMEM buffer, and then distributed in microplates. A cytoplasmic calcium fluorescent indicator—which varies proportionally to the free cytosolic $Ca^{2+}$ ion concentration—is mixed with probenicid in HBSS buffer complemented with 20 mM Hepes (pH 7.4) and is then added into each well and equilibrated with the cells for 30 min. at 37° C. and then for another 30 min. at 22° C. To measure agonist effects, compounds of the invention, reference agonist or HBSS buffer (basal control) are added to the cells and changes in fluorescence intensity are measured using a microplate reader. For stimulated control measurements, histamine at 10 µM is added in separate assay wells.

The results are expressed as a percent of the control response to 10 µM histamine. The standard reference agonist is histamine, which is tested in each experiment at several concentrations to generate a concentration-response curve from which its $EC_{50}$ value is calculated.

To measure antagonist effects, the addition of the compounds of the invention, reference antagonist or HBSS buffer is followed by the addition of 300 nM histamine or HBSS buffer (basal control) prior the fluorescence measurements. The results are expressed as percent inhibition of the control response to 300 nM histamine. The standard reference antagonist is ketanserin, which is tested in each experiment at several concentrations to generate a concentration-response curve from which its $IC_{50}$ value is calculated. Compounds are screened at 3 µM or lower, using DMSO as vehicle.

Example B11

Determination of Binding Activity of Compounds of the Invention at the 5-$HT_{1B}$ Receptor with a Radioligand Binding Competition Assay To determine the binding activity at the human recombinant serotonin 5-$HT_{1B}$ receptor of compounds of the invention, CHO-K1 cell line expressing the human 5-$HT_{1B}$ recombinant receptor was amplified to prepare membranes used for the radioligand binding assay throughout the study. Radioligand binding competition on 5-$HT_{1B}$ was performed by adding successively in the wells of a 96 well plate (Master Block, Greiner, 786201). 50 µL of test compounds or reference ligand (5-HT, Sigma, H-9523) at increasing concentrations (diluted in binding buffer: 50 mM Tris pH 7.4, 12.5 mM $MgCl_2$, 0.1% Ascorbic Acid, 1 mM EDTA, pH 7.4), 25 µL [$^3$H]5-CT (Amersham, TRK1038, diluted in assay buffer for a final concentration of 0.6 nM) and 25 µL 5-HT1B membrane extracts (7 µs/well). Non specific binding was determined by co-incubation with 200-fold excess of 5-HT. The plate was incubated 60 min at 25° C. in a water bath and then filtered over GF/B filters (Perkin Elmer, 6005177, presoaked in 0.5% PEI for 2 h at room temperature) with a Filtration unit (Perkin Elmer). The filters were washed 3× with 0.5 mL of ice-cold washing buffer (50 mM Tris pH 7.4). 50 µL Microscint 20 (Packard) was added and the plate was incubated 15 min on an orbital shaker and then counted with a TopCount™ for 1 min/well.

On each day of experimentation and prior to the testing of compounds, the reference compound was tested at several concentrations in duplicate (n=2) to obtain a dose-response curve and an estimated $IC_{50}$ value. The reference value thus obtained for the test was compared to a historical value obtained from the same receptor and used to validate the experimental session. A session was considered as valid only if the reference value was found to be within a 0.5 logs interval from the historical value. For this 5-$HT_{1B}$ assay, the reference compound 5-HT had an $IC_{50}$ of 2.63 nM (historical $IC_{50}$ of 4.7 nM). For replicate determinations, the maximum variability tolerated in the test was of +/−20% around the average of the replicates.

Compounds were tested for binding activity in the radioligand binding competition assay on human 5-$HT_{1B}$ receptor, at one concentration 5 µM, in duplicate. Dose-response data from test compounds were analyzed with XLfit (IDBS) software using nonlinear regression applied to a sigmoidal dose-response model.

Assay results are presented as the percent binding average in Table 14.

TABLE 14

5-$HT_{1B}$ radioligand binding activity of compounds of the invention 5-$HT_{1B}$ (5 µM)

| Compound No. | % Binding relative to bound radioligand |
|---|---|
| 91 | 9 |
| 174 | 16 |
| 182 | 3 |
| 217 | 10 |
| 223 | 4 |
| 224 | 10 |
| 259 | 25 |
| 274 | 6 |
| 359 | 68 |

Compound No. 91 was retested in the 5-$HT_{1B}$ radioligand binding competition assay at concentrations of 0.08, 0.31, 1.2, 4.9, 19.5, 78.1, 312.5, 1250, 20000 and 50000 nM, in duplicate. Dose-response data was analyzed with XLfit (IDBS) software using non-linear regression applied to a sigmoidal dose-response model. The assay results are presented as the percent binding average and $IC_{50}$ in Table 15.

TABLE 15

5-$HT_{1B}$ radioligand competition binding assay

| Compound No. 91 Conc. (nM) | % Binding relative to bound radioligand | $IC_{50}$ |
|---|---|---|
| 0.08 | 120 | 365 nM |
| 0.31 | 138 | |
| 1.2 | 132 | |
| 5 | 129 | |
| 20 | 113 | |
| 78 | 103 | |
| 313 | 66 | |
| 1250 | 31 | |
| 20000 | 1 | |
| 50000 | −5 | |

Example B12

Functional Activity on Recombinant Dopamine D2L and Serotonin 5-HT2A Receptors Using Aequorin, cAMP and GTPγS Functional Assays To study the functional activity of compounds of the invention on the human recombinant dopamine $D_{2L}$ with Aequorin, GTPγS and cAMP functional assays and on the human recombinant serotonin 5-$HT_{2A}$ receptor with Aequorin, CHO-K1 cell lines expressing $D_{2L}$ or 5-$HT_{2A}$ recombinant receptor, mitochondrial apoaequorin and Gα16 were used for the Aequorin assay. CHO-K1 cell line expressing the recombinant $D_{2L}$ receptor was used for the cAMP assay and was amplified to prepare membranes used for the GTPγS assay.

Aequorin Assay Procedure: Aequorin dopamine $D_{2L}$ (FAST-0101A) or serotonin 5-$HT_{2A}$ (FAST-0505A) cells, grown 18 h prior to the test in media without antibiotics, were detached by gentle flushing with PBS-EDTA (5 mM EDTA), recovered by centrifugation and resuspended in "assay buffer" (DMEM/HAM's F12 with HEPES, without phenol red+0.1% BSA protease free). Cells were incubated at room temperature for at least 4 h with Coelenterazine h (Molecular Probes). Dose response curves with reference compounds were performed before testing the compounds of the invention. $D_{2L}$ reference agonist and antagonist were quinpirol (Tocris, 1061) and haloperidol (Tocris, 0931), respectively. 5-$HT_{2A}$ reference agonist and antagonist were α-methyt-5-HT (Sigma, M-110) and ketanserin (Tocris, 908), respectively. For agonist testing, 50 μL of cell suspension were injected on 50 μL of test compound or reference agonist plated in a 96-well plate. The resulting emission of light was recorded using the Hamamatsu Functional Drug Screening System 6000 (FDSS 6000). Following an incubation of 15 min after the first injection, 100 μL of reference agonist at a concentration corresponding to its $EC_{80}$ was injected on the 100 μL of the mixture of cell suspension and test compound, for antagonist testing. The resulting emission of light was recorded using the same luminometer as for agonist testing. To standardize the emission of recorded light (determination of the "100% signal") across plates and across different experiments, some of the wells contained 100 μM digitonin or a saturating concentration of ATP (20 μM). Plates also contained the reference agonist at a concentration equivalent to the $EC_{100}$ and $EC_{80}$ obtained during the test validation. Compounds were tested for agonist & antagonist activity at the human dopamine $D_{2L}$ receptor (FAST-0101A) and serotonin 5-$HT_{2A}$ receptor (FAST-0505A) at the following nanomolar concentrations, in duplicate: Agonist (nM): 10, 30, 100, 300, 1000, 3000, 10000, 30000; Antagonist (nM): 5, 15, 50, 150, 500, 1500, 5000, 15000.

Results of agonist/antagonist activity at the $D_{2L}$ receptor are presented in Table 16.

TABLE 16

Agonist/antagonist activity at the $D_{2L}$ receptor.

| Agonist Concentration | % Activation | |
|---|---|---|
| (nM) | Compound No. 83 | Compound No. 90 |
| 10 | 2.43 | 0.95 |
| 30 | 0.68 | 0.25 |
| 100 | 1.26 | −0.23 |
| 300 | 0.92 | −0.24 |
| 1000 | −0.12 | −0.48 |
| 3000 | 0.00 | −1.20 |
| 10000 | 6.32 | −0.78 |
| 30000 | 84.25 | −0.92 |

| Antagonist Concentration | % Inhibition | |
|---|---|---|
| (nM) | Compound No. 83 | Compound No. 90 |
| 5 | 93.51 | 95.45 |
| 15 | 96.42 | 97.28 |
| 50 | 96.75 | 93.46 |

TABLE 16-continued

Agonist/antagonist activity at the $D_{2L}$ receptor.

| 150 | 96.83 | 96.83 |
|---|---|---|
| 500 | 96.84 | 97.86 |
| 1500 | 95.95 | 97.19 |
| 5000 | 95.95 | 97.41 |
| 15000 | 92.35 | 96.07 |

Results of agonist/antagonist activity at the 5-$HT_{2A}$ receptor are presented in Table 17.

TABLE 17

Agonist/antagonist activity at the 5-$HT_{2A}$ receptor.

| Agonist Concentration | % Activation | |
|---|---|---|
| (nM) | Compound No. 83 | Compound No. 90 |
| 10 | 0.70 | 0.62 |
| 30 | 0.55 | 0.26 |
| 100 | 0.85 | 0.27 |
| 300 | 0.58 | 0.18 |
| 1000 | 0.62 | 0.11 |
| 3000 | 0.31 | 0.04 |
| 10000 | 0.34 | 0.02 |
| 30000 | 1.24 | 0.49 |

| Antagonist | % Inhibition | |
|---|---|---|
| (nM) | Compound No. 83 | Compound No. 90 |
| 5 | 85.40 | 73.03 |
| 15 | 96.57 | 95.03 |
| 50 | 98.47 | 98.52 |
| 150 | 98.70 | 98.32 |
| 500 | 98.82 | 98.44 |
| 1500 | 98.89 | 98.43 |
| 5000 | 97.83 | 98.52 |
| 15000 | 97.05 | 97.61 | cAMP Assay Procedure: $D_{2L}$ CHO-K1 cells (FAST-0101C), grown to mid-log phase in culture media without antibiotics, were detached with PBS-EDTA (5 mM EDTA), centrifuged and resuspended in assay buffer (KRH, 1 mM IBMX) at a concentration of $2.1 \times 10^5$ cells/mL. The test was performed in 96 well plates. For agonist testing, 12 μL of cells (2,500 cells/well) were mixed with 6 μL of increasing concentrations of test compound or reference agonist and 6 μL of Forskolin 10 μM final concentration (Calbiochem, cat n° 344270). For antagonist testing, 12 μL of cells (2,500 cells/well) were mixed with 6 μL of test compound or reference antagonist at increasing concentrations. After incubation of 10 min at room temperature, 6 μL of a mix of Forskolin 10 μM final concentration and the reference agonist at a final concentration corresponding to the $EC_{80}$ were added. The plates were then incubated for 30 min at room temperature. During the incubation, the anti-cAMP cryptate antibody (K) and the cAMP-D2 (D2) were prepared according to the manufacturer specifications (HTRF kit from Cis-Bio International (cat no 62AM2PEB). 12 μL of cAMP-$D_2$ solution followed by 12 μL of K solution were added to each well. The plate was then covered by a top-seal and incubated for at least 1 h at room temperature. The plate was then read on the Rubystar and data were analyzed by non-linear regression using a single site model. Compounds were tested for antagonist activity at the human dopamine $D_{2L}$ receptor (FAST-0101C) at the following nanomolar concentrations, in duplicate: Antagonist (nM): 5, 15, 50, 150, 500, 1500, 5000, 15000.

Results of antagonist activity at the $D_{2L}$ receptor are presented in Table 18.

TABLE 18

Antagonist activity at the $D_{2L}$ receptor.

| Antagonist Concentration (nM) | % Inhibition Compound No. 83 | % Inhibition Compound No. 90 |
|---|---|---|
| 5 | 75.50 | 84.10 |
| 15 | 97.82 | 91.69 |
| 50 | 98.15 | 94.68 |
| 150 | 103.93 | 93.97 |
| 500 | 106.41 | 93.68 |
| 1500 | 106.91 | 100.03 |
| 5000 | 106.46 | 100.06 |
| 15000 | 110.66 | 102.18 |

GTPγS Assay Procedure: Assay buffer [20 mM HEPES pH 7.4; 100 mM NaCl, 10 µg/mL saponin, 30 mM $MgCl_2$]; Membranes [Recombinant CHO-K1-$D_{2L}$ membrane extracts thawed on ice and diluted in assay buffer to give 1 mg/mL (10 µg/10 µL) and kept on ice]; GDP [diluted in assay buffer to give 3 µM final concentration]; Beads [PVT-WGA (Amersham, RPNQ0001), diluted in assay buffer at 25 mg/mL (0.25 mg/10 µL)]; GTPγ$^{35}$S [(PerkinElmer NEG030X), diluted in assay buffer to give 0.1 nM final concentration]; Ligand [Quinpirol (Tocris, 1061) as reference agonist and haloperidol (Tocris, 0931) as reference antagonist, diluted in assay buffer]. Membranes were mixed with GDP (volume:volume) and incubated for at least 15 min on ice. In parallel, GTPγ[$^{35}$S] was mixed with the beads (volume:volume) just before starting the reaction. For agonist testing, the following reagents are successively added in the wells of an Optiplate (Perkin Elmer): 50 µL of test or reference ligand, 20 µL of the membranes:GDP mix, 10 µL of assay buffer and 20 µL of the GTPγ[$^{35}$S]:beads mix. For antagonist testing, the following reagents were successively added in the wells of an Optiplate (Perkin Elmer): 50 µL of test or reference ligand, 20 µL of the membranes:GDP mix, and then after an incubation of 15 min at room temperature, 10 µL of reference agonist at historical $EC_{80}$ concentration and 20 µL of the GTPγ[$^{35}$S]:beads mix. The plates were covered with a top seal, mixed on an orbital shaker for 2 min, and then incubated for 1 h at room temperature. Then the plates were centrifuged for 10 min at 2000 rpm, incubated at room temperature 1 h and counted for 1 min/well with a Perkin Elmer TopCount reader. Compounds were tested for antagonist activity at the human dopamine $D_{2L}$ receptor (FAST-0101G) at the following nanomolar concentrations, in duplicate: Antagonist (nM): 5, 15, 50, 150, 500, 1500, 5000, 15000.

Results of antagonist activity at the $D_{2L}$ receptor are presented in Table 19.

TABLE 19

Antagonist activity at the $D_{2L}$ receptor.

| Antagonist Concentration (nM) | % Inhibition Compound No. 83 | % Inhibition Compound No. 90 |
|---|---|---|
| 5 | 51.76 | 58.98 |
| 15 | 89.96 | 101.12 |
| 50 | 103.73 | 106.43 |
| 150 | 109.48 | 109.15 |
| 500 | 117.78 | 109.33 |
| 1500 | 113.47 | 116.02 |
| 5000 | 110.56 | 112.00 |
| 15000 | 104.55 | 116.26 |

Example B13

Increase of Neurite Outgrowth of Neurons that were Cultured with Compounds of the Invention Example B13-A Neurite Outgrowth in Cortical Neurons Compounds are tested to determine their ability to stimulate neurite outgrowth of cortical neurons. Standard methods are used to isolate cortical neurons. For the isolation of primary rat cortical neurons, the fetal brain from a pregnant rat at 17 days of gestation is prepared in Leibovitz's medium (L15; Gibco). The cortex is dissected out, and the meninges are removed. Trypsin (Gibco) is used to dissociate cortical C with DNAse I. The cells are triturated for 30 min. with a pipette in Dulbecco's Modified Eagle Media ("DMEM"; Gibco) with 10% Fetal Bovine Serum ("FBS") (Gibco) and centrifuged at 350×g for 10 min. at RT. The cells are suspended in Neurobasal medium supplemented with 2% B27 (Gibco) and 0.5 mM L-glutamine (Gibco). The cells are maintained at 30,000 cells per well of poly-L-lysine coated plates at 37° C. in 5% $CO_2$-95% air atmosphere. After adhesion, a vehicle control or compounds of the invention are added at different concentrations to the medium. BDNF (50 ng/mL) is used as a positive control for neurite growth. After treatment, cultures are washed in phosphate-buffered saline ("PBS"; Gibco) and fixed in glutaraldehyde 2.5% in PBS. Cells are fixed after 3 days growth. Several pictures (~80) of cells with neurites are taken per condition with a camera. The length measurements are made by analysis of the pictures using software from Image-Pro Plus (France). The results are expressed as mean (s.e.m.). Statistical analysis of the data is performed using one way analysis of variance (ANOVA).

Neurite Outgrowth in Rat Mixed Cortical Cultures

Cortical mixed cultures are prepared from E18 Wistar rat embryos. The cortices are dissected out and the tissue was cut to small pieces. The cells are separated by 15-min. incubation with DNase and papain. The cells are collected by centrifugation (1500 rpm, 5 min.). The tissue is triturated with a pipette and the cells are plated using the micro-islet protocol (20 000 cells in 25 µl medium) on poly-L-lysine coated 48 wells, in MEM supplemented with 2 mM glutamine, 0, 1 µg/mL gentamicin, 10% heat-inactivated fetal bovine serum (FBS-HI) and 10% heat-inactivated horse serum (HS-HI). After the cells had attached to the well, 250 µl medium is added to the wells. Four hours after plating the medium is changed to fresh medium (MEM with supplements and 5% HS-HI) containing test compound at 0.5, 5 and 50 nM concentrations. As positive controls BDNF (50, 100 and/or 150 ng/mL), and/or NGF (50 ng/mL and/or 100 ng/mL) are used. After 2 days in vitro, the cell's conditioned media are collected from plates before fixing the cells. The media samples are centrifuged 13 000 rpm 3 min. to get rid of cell debris. The samples are stored at −20° C. for later analysis. Cells are formaldehyde-fixed and processed for immunocytochemistry. BDNF levels in the conditioned media are determined with a BDNF ELISA using the manufacturers (Promega, BDNF Emax® ImmunoAssay System, catalog number: G7610) instructions.

The cultures are fixed with 4% formaldehyde in 0.01 M PBS for 30 min. and washed once with PBS. The fixed cells are first permeabilized and non-specific binding was blocked by a 30-min. incubation with blocking buffer containing 1% bovine serum albumin and 0.3% Triton X-100 in PBS. Rabbit anti-MAP-2 (dilution 1:1000, AB5622, Chemicon, in blocking buffer) is used as a primary antibody. The cells are incubated with the primary antibody for 48 h at +4° C., washed with PBS and incubated with secondary antibody goat anti-rabbit IgG conjugated to Alexa Fluor568 (1:200, A11036, Molecular Probes) for 2 h at RT. The immunopositive cells are visualized by a fluorescence microscope equipped with appropriate filter set, and documented by a high resolution image capturing. The number of cells per field (4 field per well) are counted, and the neurite outgrowth was quantified using Image Pro Plus software. The number of wells per compound concentration used was 6 (n=6). All data are presented as mean±standard deviation (SD) or standard error of mean (SEM), and differences are considered to be statistically significant at the p<0.05 level. Statistical analysis is performed using StatsDirect statistical software. Differences between group means are analyzed by using 1-way-ANOVA followed by Dunnet's test (comparison to the vehicle treated group).

Example B13-B

Neurite Outgrowth in Rat Mixed Cortical Cultures

Compounds of the invention were evaluated on their effect on neurite outgrowth in rat mixed neuronal cultures. The cultures were prepared on E18 Wistar rat embryos, and compounds of the invention as well as positive controls (BDNF and NGF) were introduced to the cultures 4 h after plating. Formalin-fixed cells were processed for immunocytochemistry using MAP-2 antibody with fluorescent secondary antibody. The neurite outgrowth was quantified using image analysis software, and the number of cells, the amount and length of neurites in untreated and treated cultures were analyzed.

The mixed cortical cultures were prepared from E18 Wistar rat embryos (National Animal Center, Kuopio, Finland). The cortices were dissected out and the tissue was cut to small pieces. The cells were separated by 15-min incubation with DNase and papain. The cells were collected by centrifugation (1500 rpm, 5 min). The tissue was triturated and the cells were plated on poly-L-lysine-coated 48-well plates in MEM supplemented with 2 g/L glucose, 2 mM glutamine, 10 μg/mL gentamicin, 10% HS-HI, and 10% heat-inactivated fetal bovine serum (FBS-HI), and maintained at +37° C., 5% $CO_2$/95% air. Four hours after plating, test Compound No. 83 (0.5, 5, 50 nM) and positive controls (BDNF at 50 ng/mL; NGF at 75 ng/mL) were pipetted on wells in MEM+supplements+5% HS-HI. Cells were incubated 48 h at +37° C., 5% $CO_2$/95% air. The cells were fixed with 4% formaldehyde and washed twice with PBS. Cells were incubated with primary MAP-2 antibody (Chemicon, 1:1000) overnight at +4° C. After wash, the cells were incubated with AlexaFluor568 goat anti-rabbit secondary antibody (Molecular Probes, 1:200) for 2 h at RT. After wash, the digital images were taken using Olympus IX71 microscope equipped with appropriate filter set. The cell number and amount and length of processes were analyzed using ImagePro Plus-software.

The number of wells per compound concentration used was 6 (n=6). The following concentration of Compound No. 83 was studied (0.5, 5, 50 nM). Statistical analysis was performed using StatsDirect statistical software. The values were analyzed using one-way ANOVA followed by Dunnet's test (comparison to the vehicle-treated group). Results were presented as mean+standard deviation (SD) and differences were considered to be statistically significant at the P<0.05 level. Results are shown in FIG. 14.

Mean Process+Branch Number: The number of process branches originating from main processes was analyzed and studied as mean process+branch number. Compound No. 83 at 50 nM significantly increased the number of branched processes, so did BDNF and NGF.

Example B14

Use of an In Vivo Model to Evaluate the Ability of Compounds to Enhance Cognition, Learning and Memory in Scopolamine Treated Rats Example B14-A The two-trial object recognition paradigm developed by Ennaceur and Delacour in the rat was used as a model of episodic short term memory. Ennaceur, A., and Delacour, J. (1988), *Behav. Brain Res.* 31:47-59. The paradigm is based on spontaneous exploratory activity of rodents and does not involve rule learning or reinforcement. The novel object recognition paradigm is sensitive to the effects of ageing and cholinergic dysfunction. See, e.g., Scali, C., et al., (1994), *Neurosci. Letts.* 170:117-120; and Bartolini, L., et al., (1996), *Biochem. Behav.* 53:277-283.

Male Sprague-Dawley rats between six and seven weeks old, weighing between 220-300 grams are obtained from Centre d'Elevage (Rue Janvier, B. P. 55, Le Genest-Saint-Isle 53940, France). The animals are housed in groups of 2 to 4 in polypropylene cages (with a floor area of 1032 $cm^2$) under standard conditions: at RT (22±2° C.), under a 12 h light/12 h dark cycle, with food and water provided ad libitum. Animals are permitted to acclimate to environmental conditions for at least 5 days before the experiment begins, and are numbered on their tails with indelible marker.

The experimental arena is a square wooden box (60 cm×60 cm×40 cm) painted dark blue, with 15 cm×15 cm black squares under a clear plexiglass floor. The arena and objects placed inside the arena are cleaned with water between each trial to eliminate any odor trails left by rats. The arena is placed in a dark room illuminated only by halogen lamps directed towards the ceiling in order to produce a uniformly dim light in the box of approximately 60 lux. The day before testing, animals are allowed to freely explore the experimental arena for three min. in the presence of two objects (habituation). Animals to be tested are placed in the experimental room at least 30 min. before testing.

Novel object recognition test is comprised of two trials separated by an interval of 120 min. or 24 hours. When agents that disrupt memory such as the cholinergic antagonist scopolamine are used an inter-trial interval of 120 min. is preferred. Alternatively a 24 hours inter-trial interval is used when studying effect of natural forgetting on novel object recognition task. During the first, or acquisition, trial ($T_1$), rats are placed in the arena, where two identical objects have been previously placed. The time required for each animal to complete 15 seconds of object exploration is determined, with a cut-off time of four min. Exploration is considered to be directing the nose at a distance less than 2 centimeters ("cm") from the object and/or touching the object. During the second, or testing, trial ($T_2$), one of the objects presented in the first trial is replaced with an unknown or novel object, while the second, familiar object is left in place. Rats are placed back in the arena for three min., and exploration of both objects is determined. Locomotor activity of rats (number of times rats cross grid lines visible under the clear plexiglass floor) is scored for during $T_1$ and $T_2$. At the conclusion of the experiments, the rats are sacrificed by an overdose of pentobarbital given intraperitoneally.

The following parameters are measured as part of the novel object recognition task: (1) time required to achieve 15 seconds of object exploration during $T_1$; (2) locomotor activity during $T_1$ (number of crossed lines); (3) time spent in active exploration of the familiar object during $T_2$ ($T_{Familiar}$); (4) time spent in active exploration of the novel object during $T_2$ ($T_{Novel}$); and (5) locomotor activity during $T_2$ (number of crossed lines). The difference between time spent in active exploration of the novel object during $T_2$ and time spent in active exploration of the familiar object during $T_2$ (A $T_{Novel}$–$T_{Familiar}$) is evaluated. The % of animals in each group with $T_{Novel}$–$T_{Familiar}$ greater than or equal to 5 seconds is also derived; described as % of good learners.

Animals not meeting a minimal level of object exploration are excluded from the study as having naturally low levels of spontaneous exploration. Thus, only rats exploring the objects for at least five seconds ($T_{Novel}$+$T_{Familiar}$>5 seconds) are included in the study.

Animals are randomly assigned to groups of 14. Compounds of the invention and controls are administered to animals the groups as follows: Solutions of compounds are prepared freshly each day at a concentration of 0.25 mg/mL using purified water or saline as vehicle. Donepezil, used as a positive control, and scopolamine are administered simultaneously in a single solution of saline (5 mL/kg) prepared freshly each day. Scopolamine is purchased from Sigma Chemical Co. (Catalog No. S-1875; St. Quentin Fallavier, France) is dissolved in saline to a concentration of 0.06 mg/mL.

Donepezil or its vehicle and scopolamine are administered intraperitoneally forty min. before the acquisition trial ($T_1$). Compounds or their vehicle are administered by gavage twenty-five min. before the acquisition trial ($T_1$), i.e., five min. after administration of scopolamine. The volume of administration is 5 mL/kg body weight for compounds administered intraperitoneally, and 10 mL/kg for compounds administered orally.

Recognition scores and % of good learners for compounds of the invention are determined.

Example B14-B

The two-trial object recognition paradigm developed by Ennaceur and Delacour in the rat was used as a model of episodic short term memory. Ennaceur, A., and Delacour, J. (1988), *Behav. Brain Res.* 31:47-59. The paradigm is based on spontaneous exploratory activity of rodents and does not involve rule learning or reinforcement. The novel object recognition paradigm is sensitive to the effects of ageing and cholinergic dysfunction. See, e.g., Scali, C., et al., (1994), *Neurosci. Letts.* 170:117-120; and Bartolini, L., et al., (1996), *Biochem. Behav.* 53:277-283.

The experiments were carried out using 174-186 male Sprague Dawley rats (Centre d'Elevage R. Janvier, B. P. 55, 53940 Le Genest-Saint-Isle, F.). 143-146 rats met inclusion criteria described in the experimental procedure. In addition, 24 satellite animals were used for pharmacokinetic analysis. The rats (main study and pharmacokinetic study) weighed between 233 and 283 g (6-7 weeks old) at the beginning of the experiments. The animals were housed in groups of 2-4 in polypropylene cages (floor area=1032 $cm^2$) under standard conditions: room temperature (22±2° C.), hygrometry (55±10%), light/dark cycle (12 h/12 h), air replacement: 15-20 volumes/hour, water and food (SAFE A04) ad libitum. Rats were allowed to acclimate to environmental conditions for at least 5 days prior to experimentation. Rats were numbered by marking their tail with indelible markers.

Solutions of Compound No. 88 or 90 (concentrations of 0.003, 0.01, 0.03, 0.1, 0.3 and 1 mg/mL) were prepared in 5% PEG200 in water for injection as vehicle. Each solution was prepared fresh each day of dosing. Doses of Compound No. 88 or 90 are expressed as dihydrochloride salt. No corrective factor is required. Donepezil hydrochloride was dissolved in water for injection. The dose of donepezil is expressed as hydrochloride salt. PEG200 was dissolved in water for injection. The volume of administration was 10 mL/kg body weight for the oral route of administration and 5 mL/kg body weight for intraperitoneal route of administration. Each solution was prepared fresh each day of dosing.

The experimental arena is a square wooden box (60×60×40 cm) painted dark blue, with 15×15 cm black painted squares under a clear plexiglass floor. The arena and the objects were cleaned using water between each trial in order to avoid odour trails left by rats. The arena was placed in a dark room illuminated only by halogen lamps oriented towards the ceiling and giving an uniform dim light in the box (around 60 lux). Animals to be tested were placed in the experimental room at least 30 min before testing. The day before the test, rats were allowed to freely explore the box for 3 min in presence of 2 objects (habituation).

Rats were submitted to two trials spaced by an intertrial interval of 24 h. During the first trial (acquisition trial, $T_1$), rats were placed in the arena containing 2 identical objects and time required by each animal to complete 15 sec. of object exploration was determined with a cut-off time of 4 min. Exploration was considered to be directing the nose at a distance less than 2 cm from the object and/or touching the object. For the second trial (testing trial, $T_2$), one of the objects presented in the first trial was replaced by an unknown object (novel object), rats were placed back in the arena for 3 min and exploration of each object was determined. For both $T_1$ and $T_2$, locomotor activity of rats was scored. A criterion of minimal level of object exploration was used in the study to exclude animals with naturally low levels of spontaneous exploration: only animals having a minimal level of object exploration of 5 sec. during the testing trial (Novel+Familiar≥5 sec.) were included in the study.

Using group numbers of 18, rats were randomized to constitute the following groups: 1) Vehicle (5% PEG200 in water) p.o.; 2) Compound No. 88 or 90 (0.03 mg/kg) p.o.; 3. Compound No. 88 or 90 (0.1 mg/kg) p.o.; 4) Compound No. 88 or 90 (0.3 mg/kg), p.o.; 5) Compound No. 88 or 90 (1 mg/kg) p.o.; 6) Compound No. 88 or 90 (3 mg/kg) p.o.; 7) Compound No. 88 or 90 (10 mg/kg) p.o.; 8) Donepezil 1 mg/kg i.p. Vehicle, Compound No. 88 or 90 or donepezil was administered 30 min before $T_1$. The oral route of administration was used to evaluate the promnesiant effects of Compound No. 88 or 90 since it is the intended clinical route of administration.

The following parameters were measured: 1) Time required to achieve 15 sec. of object exploration on $T_1$ (sec.); 2) Locomotor activity on $T_1$ (number of crossed lines); 3) Time spent in active exploration of the familiar object on $T_2$ (sec.)=TF; 4) Time spent in active exploration of the novel object on $T_2$ (sec.)=TN; 5) Locomotor activity on $T_2$ (number of crossed lines).

All parameters were analysed using SAS software (version 8.2). Statistical tests were performed with an alpha level of 0.05. The following parameters were calculated: 1) Delta ($\Delta$=TN−TF) was calculated and represents the difference between the time spent in the active exploration of the novel object during $T_2$ (TN) and the time spent in active exploration of the familiar object during $T_2$ (TF); 2) Recognition index (RI) was calculated according to the following formula [TN−TF)/(TN−FTF)×100] and represents the difference between the time exploring the novel object and the time exploring the familiar object during $T_2$ expressed as a percentage of the total time exploring both objects during $T_2$. Tables presenting individual data as well as descriptive statistics (n, mean, SD, SEM, Min, median and max) by group and graphs of each group were performed. In addition, a graph presenting percentage of "good learners" during $T_2$ was performed. The animals were considered as "good learners" when they displayed as TN-TF value≥5 sec.

For each experiment, time required to achieve 15 sec. of object exploration on $T_1$, locomotor activity on $T_1$, locomotor activity on $T_2$ and RI were analysed as follows: 1) Comparison of vehicle versus donepezil using a two-sided Student's t test for independent samples; 2) Comparison of vehicle versus Compound No. 88 or 90 doses was performed using a one-way ANOVA (group). When group effect was found to be significant, a Dunnett's test was used to test each dose versus Vehicle.

For each experiment, the difference between time spent in active exploration of the novel object on $T_2$ (TN) and time spent in active exploration of the familiar object on $T_2$ (TF) ($\Delta$=TN−TF) was evaluated and analysed with: 1) Comparison of vehicle versus donepezil using a two-sided Student's t test for independent samples; 2) Comparison of vehicle versus Compound No. 88 or 90 doses using a one-way ANOVA (group). When group effect was found significant, a Dunnett's test was used to test each dose versus vehicle; 3) Intra-group analysis: study of A within each group using a two-sided Student's t test for paired samples.

Acquisition of the task (duration of $T_1$) was assessed by the time required by the animals to achieve 15 sec. of active object exploration. Memory performance was assessed by the evaluation of the time spent in active exploration of the novel (TN) and the familiar (TF) objects during $T_2$ ($\Delta$=TN−TF) and the evaluation of the recognition index (RI) calculated according the following formula [TN−TF)/(TN+TF)×100]. In addition, the percentage of animals displaying a N−F value≥5 sec. in each experimental group was assessed during $T_2$, these animals being considered as "good learners". Locomotor activity of animals was assessed by the mean number of lines crossed during $T_1$ and $T_2$. The acquisition trial ($T_1$) was performed until rats completed 15 sec. of active object exploration with a cut-off time of 4 min. Rats exceeding the cut-off time of 4 min. during $T_1$ were excluded from the study. In addition, a criterion of minimal level of object exploration was used in this study to exclude animals with low levels of exploration during $T_2$: only animals having a minimal level of object exploration of 5 sec. (TN+TF≥5 sec.) were included in the study.

Figure 3A:
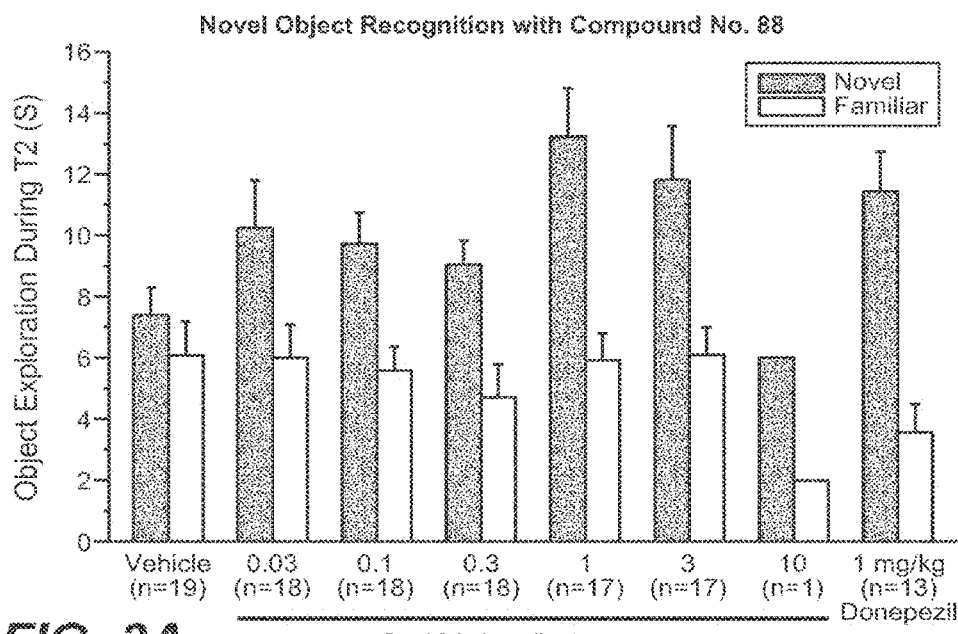
FIGS. 3A and 3B are graphs of time (in seconds) of object exploration during T2 for single administration of vehicle (p.o.), Compound 88 (0.03, 0.1, 0.3, 1, 3 and 10 mg/kg, p.o) or donepezil (1 mg/kg, i.p.) in a situation of natural forgetting in the rat object recognition model. All treatments were administered 30 minutes before T1. Time spent by rats exploring the novel and familiar objects during T2 is expressed as mean±SEM. In the figure, n is the number of rats per group; # is p<0.05; ## is p<0.01 and ### is p<0.001 versus novel object and is p<0.01 and * is p<0.001 versus vehicle group.
Figure 3B:
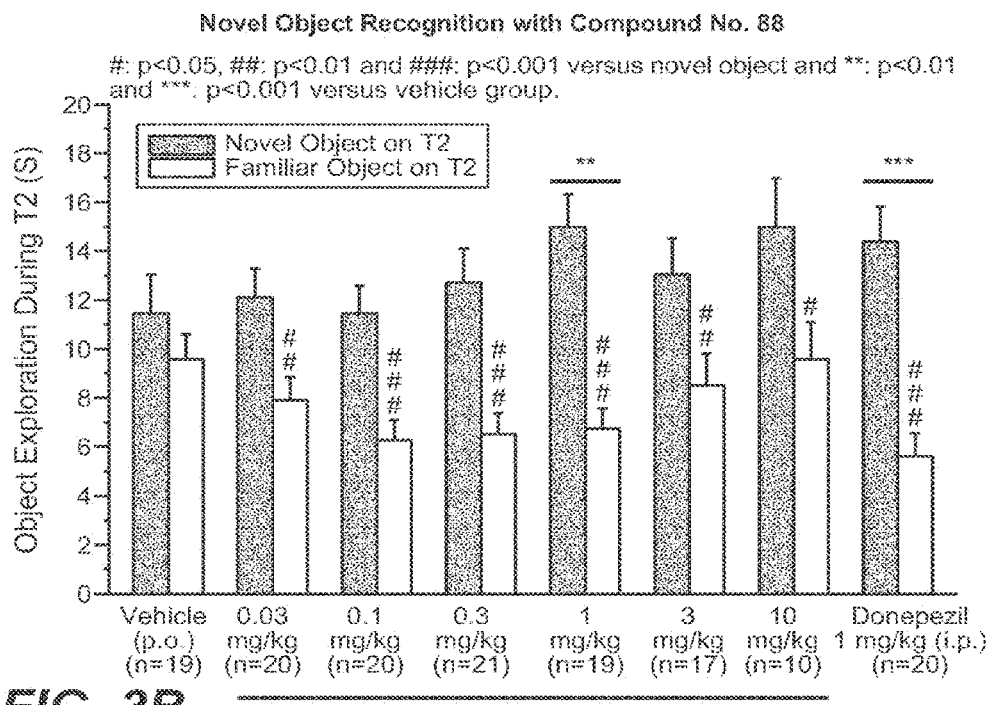
Figure 4A:
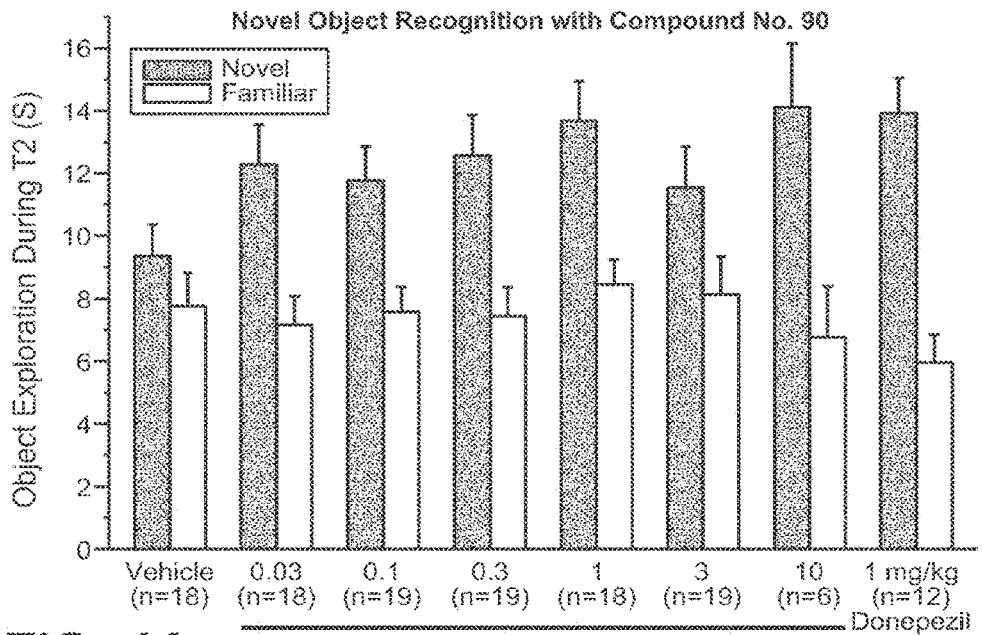
FIGS. 4A and 4B are graphs of time (in seconds) of object exploration during T2 for single administration of vehicle (p.o.), Compound 90, or donepezil (1 mg/kg, i.p.) in a situation of natural forgetting in the rat object recognition model.
Figure 4B:
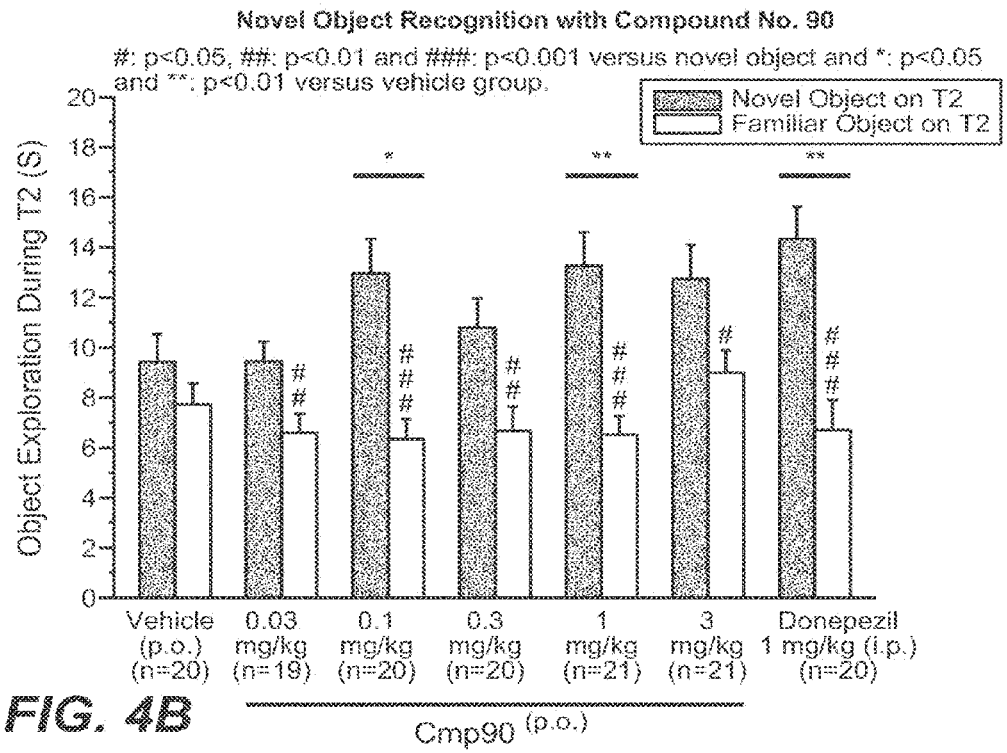

The results of the effect of Compound No. 88 on Object exploration on T2 are shown in FIGS. 3A and 3B. The results of the effect of Compound No. 90 on Object exploration on T2 are shown in FIGS. 4A and 4B.

The results demonstrated that, following a single oral administration, Compound No. 88 at 0.03, 0.1, 0.3, 1, 3 and 10 mg/kg, and Compound No. 90 at 0.03, 0.1, 0.3, 1 and 3 mg/kg, displayed a cognitive enhancing activity in the rat model of two-trial object recognition memory task in situation of natural forgetting. More specifically, a single oral administration of Compound No. 88 at 0.03, 0.1, 0.3, 1, 3 and 10 mg/kg, and Compound No. 90 at 0.03, 0.1, 0.3, 1 and 3 mg/kg, performed 30 min. before $T_1$, was able to delay the onset of natural forgetting. Donepezil (1 mg/kg, i.p.), used as a positive reference compound in the study, displayed a clear procognitive activity in these experimental conditions.

During the acquisition trial ($T_1$), animals submitted to the object recognition task had to explore both copies of the same object for a total of 15 sec. Thus, duration of $T_1$ depended on each individual. Significant modifications in duration of $T_1$ following treatment by a pharmacological agent could indicate effects of this agent on motivational and/or attentional components of the task. No statistically significant effects on duration of $T_1$ were observed for Compound No. 88 at 0.03, 0.1, 0.3, 1, 3 and 10 mg/kg, and Compound No. 90 at 0.03, 0.1, 0.3, 1 and 3 mg/kg. So, in the present experimental conditions, Compound No. 88 at 0.03, 0.1, 0.3, 1, 3 and 10 mg/kg, and Compound No. 90 at 0.03, 0.1, 0.3, 1 and 3 mg/kg did not alter motivational and/or attentional components of rat behaviour.

Evaluation of memory performance in this task corresponded to analysis of time spent with both categories of objects (novel and familiar) during $T_2$, recognition memory being assessed by the ability of the animals to discriminate between both objects. More precisely, memory performance was evaluated by the comparison between time spent exploring the novel object (TN) and time spent exploring the familiar one (TF) during the testing trial ($\Delta$=TN−TF).

In experimental conditions of the study, evaluation of the natural forgetting situation corresponded to the analysis of object exploration during the testing trial using an ITI long enough for the rats to forget the value (novel versus familiar) of the objects. In the present experimental conditions (ITI=24 h), vehicle-treated rats displayed a low memory performance, exploring almost identically the novel and the familiar one, thus validating the experimental conditions of natural forgetting. When rats were administered with donepezil, these rats could discriminate between both objects, thus demonstrating a clear cognitive enhancing activity.

The effects of a single oral administration of Compound No. 88 or 90 (0.03, 0.1, 0.3, 1, 3 or 10 mg/kg) performed 30 min before $T_1$, on recognition memory were evaluated in a situation of natural forgetting. No conclusions concerning the procognitive activity of Compound No. 88 or 90 at 10 mg/kg could be drawn from the experiment due to the low number of included animals in this group (n=2) with most of the rats treated with Compound No. 88 or 90 which could not reach the inclusion criterion of the first trial and displaying a reduced locomotor activity. Results showed that memory performance of rats treated with Compound No. 88 at 0.03, 0.1, 0.3, 1, 3 and 10 mg/kg, and Compound No. 90 at 0.03, 0.1, 0.3, 1 and 3 mg/kg was improved, as shown by the TN-TF and RI values, this effect reached the threshold of statistical significance when compared to vehicle for the doses of 0.1 (Compound No. 90), 0.3 (Compound No. 88)

and 1 mg/kg (global comparison using a one-way ANOVA followed by a Dunnett's test). In addition, the number of rats displaying a good memory performance, i.e. "good learners" animals (A≥5 sec.) confirmed the cognitive enhancing activity of Compound No. 88 at 0.03, 0.1, 0.3, 1, 3 and 10 mg/kg, and Compound No. 90 at 0.03, 0.1, 0.3, 1 and 3 mg/kg and donepezil. Maximal cognitive enhancing activity was observed after oral administration of Compound No. 88 at 0.03, 0.1, 0.3, 1, 3 and 10 mg/kg, and Compound No. 90 at 0.1, 0.3 and 1 mg/kg.

Treatment with Compound No. 88 at 0.03, 0.1, 0.3, 1, 3 and 10 mg/kg, or Compound No. 90 up to the dose of 3 mg/kg or donepezil (1 mg/kg) performed 30 min before $T_1$ had no statistically significant effects on locomotor activity assessed during $T_1$ and $T_2$. However, higher dose of Compound No. 90 (10 mg/kg) reduced locomotor activity.

It is concluded that, following a single oral administration, Compound No. 90 from 0.03 to 3 mg/kg displayed a clear cognitive enhancing activity in the two-trial object recognition task by delaying the onset of natural forgetting with a maximal efficacy obtained between 0.1 and 1 mg/kg. Compound No. 90 has been further shown to have activity when tested in the presence of scopolamine, at 0.3 mg/kg.

Example B15

Use of an In Vivo Model to Determine the Ability of Compounds to Treat, Prevent and/or Delay the Onset and/or the Development of Schizophrenia (Hyperactivity in PCP Treated Animals)

In vivo models of schizophrenia can be used to determine the ability of the compounds described herein to treat and/or prevent and/or delay the onset and/or the development of schizophrenia.

One exemplary model for testing the activity of one or more compounds described herein to treat and/or prevent and/or delay the onset and/or development of schizophrenia employs phencyclidine (PCP), which is administered to the animal (e.g., non-primate (rat) or primate (monkey)), resulting in dysfunctions similar to those seen in schizophrenic humans. See Jentsch et al., 1997, Science 277:953-955 and Piercey et al., 1988, Life Sci. 43(4):375-385). Standard experimental protocols may be employed in this or in other animal models. One protocol involves PCP-induced hyperactivity.

Male C57B1/6J mice from Jackson Laboratories (Bar Harbor, Me.) were used. Mice were received at 6-weeks of age. Upon receipt, mice were assigned unique identification numbers (tail marked) and were group housed with 4 mice/cage in OPTIMICE ventilated cages. All animals remained housed in groups of four during the remainder of the study. All mice were acclimated to the colony room for at least two weeks prior to testing and were subsequently tested at an average age of 8 weeks of age. During the period of acclimation, mice were examined on a regular basis, handled, and weighed to assure adequate health and suitability. Animals were maintained on a 12 h/12 h light/dark cycle. The room temperature was maintained between 20 and 23° C. with a relative humidity maintained between 30% and 70%. Food and water were provided ad libitum for the duration of the study. In each test, animals were randomly assigned across treatment groups.

The following compounds were used for this study: 1) Compound Nos 83, 88, 90 (0.03, 0.1, 0.3, 1, 3, 10 & 30 mg/kg) was dissolved in 5% PEG-200 in sterile water and administered p.o. 30 min prior to PCP injection; 2) Clozapine (1.0 mg/kg) was dissolved in 10% DMSO and administered i.p. 30 min prior to phencyclidine (PCP) injection; 3) PCP (5.0 mg/kg) was dissolved in sterile water and administered i.p. immediately before the 60 min. test. All compounds were administered at a dose volume of 10 mL/kg.

The open filed (OF) test assesses locomotor behavior, i.e. to measure mouse locomotor activity at baseline and in response to pharmacological agents. The open field chambers are Plexiglas square chambers (27.3×27.3×20.3 cm; Med Associates Inc., St Albans, Vt.) surrounded by infrared photobeams (16×16×16) to measure horizontal and vertical activity. The analysis was configured to divide the open field into a center and periphery zone such that the infrared photobeams allow measurement of activity in the center and periphery of the field. Distance traveled was measured from horizontal beam breaks as the mouse moved whereas rearing activity was measured from vertical beam breaks. Mice (10 to 12 animals per treatment group) were brought to the activity experimental room for at least 1 h acclimation to the experimental room conditions prior to testing. Eight animals were tested in each run. Mice were administered vehicle (e.g., 10% DMSO or 5% PEG200 and 1% Tween 80), Compound No. 90, clozapine (positive control, 1 mg/kg ip) and placed in the OF chambers for 30 min. following which they were injected with either water or PCP and placed back in the OF chambers for a 60-min. session. At the end of each OF test session the OF chambers were thoroughly cleaned.

Data were analyzed by analysis of variance (ANOVA) followed by post-hoc comparisons with Fisher Tests when appropriate. Baseline activity was measured during the first 30 min. of the test prior to PCP injection. PCP-induced activity was measured during the 60 min. following PCP injection. Statistical outliers that fell above or below 2 standard deviations from the mean were removed from the final analyses. An effect was considered significant if $p<0.05$.

Figure 1:
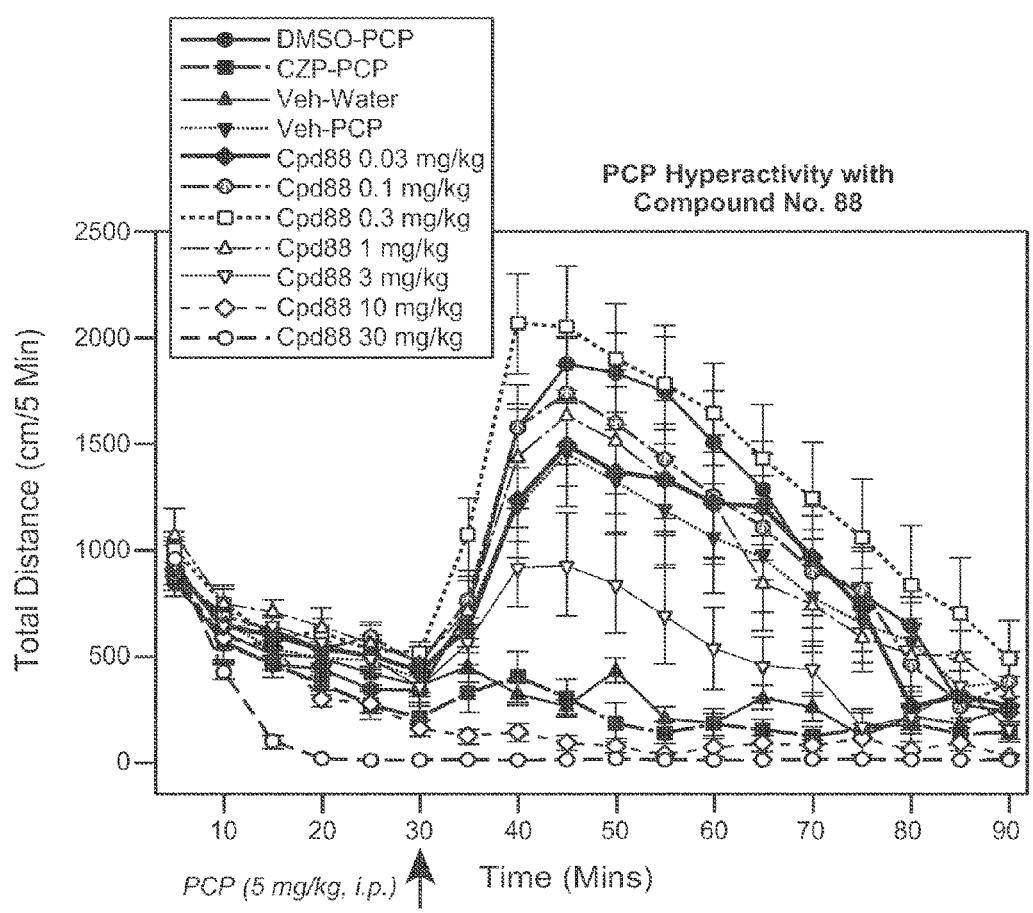
FIG. 1 is a graph of Total Distance Traveled (cm/5 min) verses Time (min) pre- and post-injection, showing the results of Compound 88 (0.03, 0.1, 0.3, 1, 3, 10 and 30 mg/kg) and clozapine in a PCP Hyperactivity Mouse Model of Schizophrenia. Total distance traveled in the OF during the 90 minute test period are shown, with data presented as mean±SEM
Figure 2:
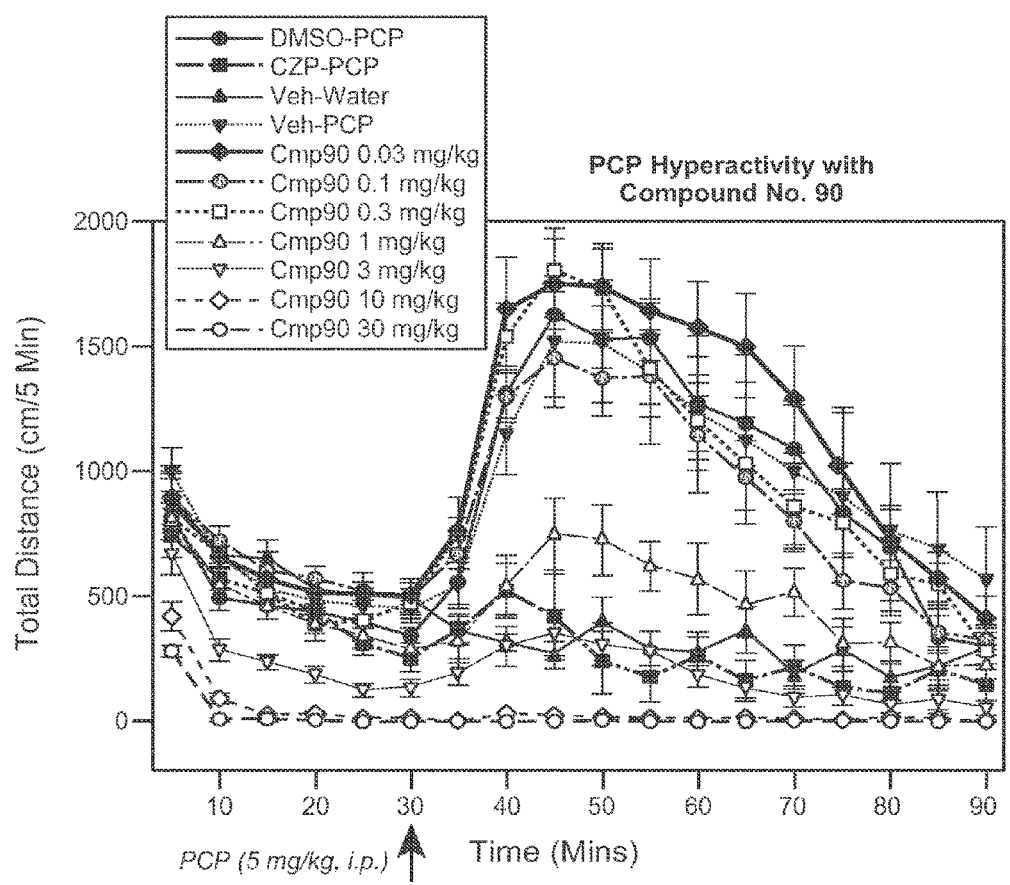
FIG. 2 is a graph of Total Distance Traveled (cm/5 min) verses Time (min) pre- and post-injection, showing the results of Compound 90 (0.03, 0.1, 0.3, 1, 3, 10 and 30 mg/kg) and clozapine in a PCP Hyperactivity Mouse Model of Schizophrenia. Total distance traveled in the OF during the 90 minute test period are shown, with data presented as mean±SEM

Results: Total Distance Traveled (center+periphery): The time course for the effects of clozapine and Compound No. 88, 90 or 83 on total distance traveled in the OF over the 90 min. test are presented in FIGS. 1, 2 and 10A/B, respectively. ANOVA found a significant treatment effect in each case.

Total Rearing (center+periphery): The effects of clozapine and Compound No. 83 on total rearing over the 90 min. test is presented in FIGS. 11A/B/C/D. ANOVA found a significant treatment effect.

Example B16

Use of an In Vivo Model to Determine the Ability of Compounds to Treat, Prevent and/or Delay the Onset and/or the Development of Schizophrenia (Hyperactivity in Amphetamine Treated Animals)

Male mice (various strains e.g., C57B1/6J) from appropriate supplier (for example Jackson Laboratories, Bar Harbor, Me.) were used. Mice typically were received at 6-weeks of age. Mice were acclimated to the colony room for at least two weeks prior to testing. During the period of acclimation, mice were examined on a regular basis, handled, and weighed to assure adequate health and suitability and maintained on a 12 h/12 h light/dark cycle. The room temperature was maintained between 20 and 23° C. with a relative humidity maintained between 30% and 70%. Food and water were provided ad libitum for the duration of the study. In each test, animals were randomly assigned between treatment groups.

The open field test (OF) was used to assess motor activity. The open field chambers were plexiglas square chambers (e.g., 27.3×27.3×20.3 cm; Med Associates Inc., St Albans, Vt.) surrounded by infrared photobeam sources (16×16×16). The enclosure was configured to split the open field into a center and periphery zone and the photocell beams were set to measure activity in the center and in the periphery of the OF chambers. Horizontal activity (distance traveled) and vertical activity (rearing) were measured from consecutive beam breaks.

On the day of testing, animals were brought to the experimental room for at least 1 h acclimation prior to start of treatment. Animals were administered with vehicle, haloperidol (positive control, 0.1 mg/kg ip) or compound of the invention and placed in the OF. The time of administration of test compound to each animal was recorded. Baseline activity was recorded for 30 min. following which mice received amphetamine (4 mg/kg) or water and were placed back in the OF chambers for a 60-min. session. At the end of each open field test session the OF chambers were thoroughly cleaned.

Typically ten to twelve mice were tested in each group. Test compound doses typically ranged from 0.01 mg/kg to 60 mg/kg.

Data were analyzed by analysis of variance (ANOVA) followed by post-hoc comparisons with Fisher Tests when appropriate. Baseline activity was measured during the first 30 min. of the test prior to amphetamine injection. Amphetamine-induced activity was measured during the 60 min. following amphetamine injection. Statistical outliers that fell above or below 2 standard deviations from the mean were removed from the final analyses. An effect was considered significant if p<0.05. Total distance traveled and total rearing following amphetamine administration were compared between groups treated with compound and groups treated with vehicle and positive control haloperidol.

Results: Total Distance Traveled (center+periphery): The time course for the effects of amphetamine and Compound No. 83 on total distance traveled in the OF over the 90 min. test is presented in FIG. 12. ANOVA found a significant treatment effect.

Total Rearing (center+periphery): The effects of amphetamine and Compound No. 83 on total rearing over the 90 min. test is presented in FIGS. 13A/B. ANOVA found a significant treatment effect.

Example B17

Use of the In Vivo Conditioned Avoidance Response (CAR) Model to Determine the Ability of Compounds to Treat, Prevent and/or Delay the Onset and/or the Development of Schizophrenia Example B17-A All currently approved antipsychotic agents (typical and atypical) are known to have the ability to selectively suppress conditioned avoidance response (CAR) behavior in the rat. This evidence makes CAR one of the primary tests to assess antipsychotic activity of novel compounds.

The effects of Compound Nos. 83, 88 and 90, at concentrations including 0.1, 0.3, 1, 3, 10 and 20 mg/kg, p.o., in the conditioned avoidance response model were assessed in the male Wistar rat. Risperidone (0.3 mg/kg, s.c.) was used in the present study as a positive reference compound.

For each testing session, animals were first placed for a 4-min. habituation period in a shuttlebox with an electrified grid floor. Then, rats were submitted to 30 trials spaced by intertribal intervals varying at random between 20 and 30 sec. Each trial consisted of a 10-sec. light stimulus (conditioned stimulus, CS) followed by a 10-sec. electric foot shock (unconditioned stimulus, US) in presence of the light presented in the compartment where the rat is located. If the animal moved to the other compartment during the initial 10-sec. of the trial, the light was terminated (no shock was delivered) and the response was recorded as an avoidance response. If the rat changed compartment during the foot shock, the light and the shock were terminated and the response was recorded as an unconditioned response. If the rat did not change compartment during the 10-sec. light period (CS) and during the 10-sec. shock+light period (US+CS), an escape failure was recorded. If a response was made during an intertrial interval, the response was recorded as an intertrial crossing. Training was performed 5 days per week with one session of 30 trials per day, until rats reached the performance criterion of 80% of avoidance response on at least two consecutive daily sessions. Once the performance criterion was reached, each animal was sequentially administered with vehicle (15% HPBCD, p.o.), Compound No. 83, 88 or 90 (0.1, 0.3, 1, 3, 10 and 20 mg/kg, p.o.) and risperidone (0.3 mg/kg, s.c.). A minimal wash-out period of 48 hours was allowed between 2 treatments. During the wash-out period, animals were trained until they recovered an avoidance performance of at least 80%.

Statistical analysis was performed using a Friedman two-way ANOVA by ranks followed by the Wilcoxon matched-pairs signed-ranks test to test each dose of the test compound administered versus vehicle control treated rats.

Results summarizing the effect of Compound Nos. 83, 88 and 90 at varying concentrations on Avoidance Responses, are presented together in FIG. 9 as a percentage avoidance versus pretest. Individual Avoidance Response results based on Number of Events for Compound Nos. 83, 88 and 90 are presented in FIGS. 16, 17 and 18, respectively.

When compared to vehicle, risperidone (0.3 mg/kg, s.c.) significantly decreased the number of avoidance responses (−61% versus pretreatment), slightly but significantly increased the number of escape failures in 7/12 animals (4±1 escape failures versus 0±0 escape failures before treatment) and significantly decreased the number of intertrial crossings (−69% versus pretreatment), thus validating this experiment. When compared to vehicle, Compound Nos 83, 88 and 90 each significantly and dose-dependently decreased the number of avoidance responses versus pretreatment.

Example B18

An Animal Model of the Negative Symptoms of Schizophrenia: Subchronic PCP-Induced Social Interaction Deficits Phencyclidine (PCP) administered to humans as well to experimental animals induces full-spectrum of schizophrenia symptoms, including negative symptoms and cognitive deficits. A major symptom of schizophrenia is considered to be social isolation/withdrawal as part of the cluster of negative symptoms. Subchronic treatment with PCP in rats leads to the development of clear signs of social withdrawal as measured by deficits in the interaction time with a cage intruder rat.

Male Sprague Dawley rats (~150 g on arrival) from Harlan (Indiana) were used in this study. Upon receipt, rats were group housed in OPTI rats ventilated cages. Rats were housed in groups of 2-3/cage for the remainder of the study.

During the period of acclimation, rats were examined on a regular basis, handled, and weighed to assure adequate health and suitability. Rats were maintained on a 12/12 light/dark cycle with the light on at 7:00 a.m. The room temperature was maintained between 20 and 23° C. with a relative humidity maintained between 30% and 70%. Chow and water were provided ad libitum for the duration of the study. Animals were randomly assigned across treatment groups and balanced by age. Animals were not disturbed between test days.

The following compounds were used. 1) Compound No. 88 or 90 (0.3, 1 and 3 mg/kg; p.o.) was dissolved in 3% Tween and PBS and administered 30 min prior to test; 2) PCP (2 mg/kg; s.c.) was dissolved in saline and administered twice daily for 5 days prior to test day; 3) Clozapine (2.5 mg/kg; i.p.) was dissolved in 5% PEG:5% Tween 80 in saline and administered 30 min. prior to test. All compounds were administered at a dose volume of 1 mL/kg.

For five days prior to test, rats were injected twice daily with either PCP (2 mg/kg; s.c) or saline (s.c). On day 6 and following a 30 min pretreatment with vehicle, clozapine or Compound No. 90, a pair of rats, unfamiliar to each other, receiving the same treatment were placed in a white plexiglas open field arena (24"×17"×8") and allowed to interact with each other for 6 min. Social interactions ('SI') included: sniffing the other rat; grooming the other rat; climbing over or under or around the other rat; following the other rat; or exploring the ano-genital area of the other rat. Passive contact and aggressive contact were not considered a measure of social interaction. The time the rats spent interacting with each other during the 6 min test was recorded by a trained observer. The social interaction chambers were thoroughly cleaned between the different rats.

Data were analyzed by analysis of variance (ANOVA) followed by post-hoc analysis (e.g., Fischer, Dunnett) when appropriate. An effect was considered significant if $p<0.05$.

The effects of Compound No. 88 on interaction time are shown in FIG. 5. One way ANOVA found a significant treatment effect. Chronic treatment with PCP significantly decreased social interaction time in rats. This effect was attenuated by pretreatment of the atypical antipsychotic clozapine as well as Compound No. 88 (0.3, 1 and 3 mg/kg).

Mild sedation in the home cage was seen at 3 mg/kg dose of Compound No. 90 during the 30 min pretreatment time. The effects of Compound No. 90 on interaction time are shown in FIG. 6. One way ANOVA found a significant treatment effect. Chronic treatment with PCP significantly decreased social interaction in rats. This effect was fully reversed by pretreatment with the atypical antipsychotic clozapine as well as Compound No. 90 (1 mg/kg). At 0.3 and 3 mg/kg, Compound No. 90, significantly attenuated the deficits in social interaction time induced by chronic administration of PCP. This effect however did not reach that of control levels suggesting partial reversal at these doses.

Example B19

An Animal Model of Extrapyramidal Syndrome (EPS): Measurement of Catalepsy in the Mouse Bar Test Antipsychotic drugs are known to induce extrapyramidal syndrome (EPS) in animals and in humans. An animal model considered to be predictive of EPS is the mouse bar test, which measures cataleptic responses to pharmacological agents.

Male C57B116J mice from Jackson Laboratories (Bar Harbor, Me.) were used. Mice were received at 6-weeks of age. Upon receipt, mice were assigned unique identification numbers (tail marked) and were group housed with 4 mice/cage in OptiMICE ventilated cages. All animals remained housed in groups of four during the remainder of the study. All mice were acclimated to the colony room for at least two weeks prior to testing and were subsequently tested at an average age of 8 weeks. During the period of acclimation, mice were examined on a regular basis, handled, and weighed to assure adequate health and suitability. Animals were maintained on a 12 h/12 h light/dark cycle. The room temperature was maintained between 20 and 23° C. with a relative humidity maintained between 30% and 70%. Chow and water were provided ad libitum for the duration of the study. In each test, animals were randomly assigned across treatment groups.

The following compounds were used for this study. 1) Compound No. 83, 88 or 90 (0.03, 0.1, 0.3, 1, 3, 10, 30) was dissolved in 3% Tween in PBS and administered orally at a dose volume of 10 mL/kg; 2) Haloperidol (2 mg/kg) was dissolved in 10% DMSO and administered i.p. at a dose volume of 10 mL/kg.

The front paws of a mouse were placed on a horizontal metal bar raised 2" above a Plexiglas platform and time was recorded for up to 30 seconds per trial. The test ended when the animal's front paws returned to the platform or after 30 seconds. The test was repeated three times and the average of the three trials was reported as the intensity index of catalepsy. Antipsychotic agents such as haloperidol cause rigidity as a side effect. Animals treated with haloperidol will hold on to the bar without moving for several minutes. Mice were brought to the activity experimental room for at least 1 h acclimation to the experimental room conditions prior to testing. Following injection of either vehicle, Compound No. 83, 88 or 90, or haloperidol, catalepsy was assessed at 3 time points: 30 min, 1 h, and 3 h. At the end of each trial, the apparatus was thoroughly cleaned with 70% ethanol.

Data were analyzed by analysis of variance (ANOVA) followed by post-hoc comparisons with Fisher Tests when appropriate. An effect was considered significant if $p<0.05$.

The effects of Compound No. 83 on catalepsy are shown in FIG. 15. ANOVA found a significant treatment effect. Haloperidol (2 mg/kg) increased catalepsy in mice. Compound No. 83 (30 mg/kg) caused sedation. Mice displayed straub tail and remained in a flattened position for the duration of the study. Mice also showed brief episodes of tremors immediately following movement of their cages. When placed on the bar, mice would either fall asleep or were unable to hold on. Compound No. 83 (10 mg/kg) also caused sedation, but at lower levels. Straub tail was also displayed, but decreased by the 3 h time point.

The effects of Compound No. 88 on catalepsy are shown in FIG. 7. ANOVA found a significant treatment effect. Haloperidol (2 mg/kg) increased catalepsy in mice. Compound No. 88 (30 mg/kg) caused sedation. Mice remained in a flattened position for the duration of the study. When placed on the bar, mice would either fall asleep or were unable to hold on. No other effects of Compound No. 88 were observed.

The effects of Compound No. 90 on catalepsy are shown in FIG. 8. ANOVA found a significant treatment effect. Haloperidol (2 mg/kg) increased catalepsy in mice. Compound No. 90 (30 mg/kg) caused high levels of sedation. Mice displayed straub tail and remained in a flattened position for the duration of the study. Mice also showed brief episodes of tremors immediately following movement of their cages. When placed on the bar, mice would either fall asleep or were unable to hold on. Compound No. 90 (10 mg/kg) also caused sedation, but at lower levels, resulting in an increase in the latency to hold the bar. Straub tail was also displayed, but decreased by the 3 h time point.

Example B20

Use of the 5-Choice Serial Reaction Task to Determine the Ability of Compounds to Enhance Attention/Vigilance and Reduce Impulsivity Attention and impulsivity are characteristic of several disease states. The continuous performance test (CPT), used in humans, is capable of detecting attention deficits in a number of disorders, including attention deficit hyperactivity disorder, schizophrenia and mild cognitive impairment. The pre-clinical analogue of the CPT is the 5-choice serial reaction time task (5CSRTT). In this operant-based test, rats are required to be attentive and withhold responding while they monitor 5 apertures for the appearance of a brief stimulus light in one of the apertures. The brief illumination of the stimulus light in the 5CSRTT is analogous to the appearance of the "correct" letters in the CPT in humans. Upon observing the stimulus light, the rat must nose-poke in the corresponding aperture to receive a food reward. The 5CSRTT allows the measurement of similar behavioral responses as the CPT, including accuracy, speed of responding, impulsive and compulsive responding. In this study, drug tests were performed under altered test parameters which resulted in increased premature responding. This premature responding was hypothesized to indicate impulsivity, i.e., a failure to withhold an inappropriate response, and has been shown to be sensitive to atomoxetine.

Thirteen male Long-Evans rats (275-300 g) were obtained from Harlan Laboratories, Indianapolis, Ind. At the time of testing for the current study, the rats were approximately 16-18 months old. Upon arrival, the rats were assigned unique identification numbers (tail marked). Rats were single-housed in OptiRAT cages and acclimated for 7 days prior to commencing a food-restriction regimen: rats were held at 85% of age-matched free-feeding control body-weights, receiving approximately 10-20 g of rat chow daily. Water was provided ad libitum, except during testing. Animals were maintained in a 12 h/12 h light/dark cycle (lights on at 0700 EST) with room temperature maintained at 22±2° C. and the relative humidity maintained at approximately 50%. All animals were examined, handled and weighed prior to initiation of the study to assure adequate health and suitability and to minimize non-specific stress associated with testing. The 5CSRTT sessions were performed during the animal's light cycle phase. All experiments and procedures were approved by the Institutional Animal Care and Use Committee of PsychoGenics, Inc.

The apparatus consisted of 10 aluminum and Plexiglas chambers with grid floors (width 31.5 cm, depth 25.0 cm, height 33.0 cm), housed in sound-attenuating cabinets. Each cabinet was fitted with a low-level noise extractor fan which also helped to mask external noise. The left wall of each chamber was concavely curved with 5 apertures evenly spaced, located approximately 2.5 cm from the floor. Each aperture contained a standard 3 W LED to serve as stimulus lights. The opposite wall contained a food magazine, located approximately 3.0 cm from the floor. Each chamber was illuminated with a 3 W house-light located in the center of the ceiling panel. After each test session the apparatus was cleaned with 70% ethanol.

The following compounds were used for this study. 1) Compound No. 90 was dissolved in saline, and administered p.o. at 0.1, 0.3 and 1.0 mg/kg, 30 min prior to testing at 1 mL/kg body weight; 2) The reference compound atomoxetine (1.0 mg/kg) was dissolved in saline and administered i.p. 30 min prior to testing at 1 mL/kg body weight.

Training:

Animals were trained to monitor the five apertures for stimulus light illumination. Each session was initiated by the illumination of the house light, and the delivery of a food reward into the magazine. The first trial began when the rat opened the magazine to obtain the food pellet. After the inter-trial interval (ITI) one of the stimulus lights was illuminated for 500 msec. The rat must nose-poke in the illuminated aperture either during or within 5 sec. of stimulus light illumination. Such a response was defined as a correct response, and was rewarded with delivery of a food pellet. Collection of the pellet initiated the next trial. A nose-poke response in a non-illuminated aperture (incorrect response) or a nose-poke after the 5 sec. limited hold (missed trial) resulted in termination of the trial with extinction of the house-light and imposition of a time-out period.

Testing:

After acquisition of the 5CSRTT with a high level of accuracy (at least 75% correct, at least 50 trials completed per session), drug testing began. Animals were treated with test compound (various doses, appropriate vehicle), vehicle and positive control (atomoxetine 1 mg/kg ip). During drug test sessions, the ITI was varied between 10, 7, 5 or 4 sec. in duration, presented in groups of 4 trials (each of which contained 1 trial at each ITI duration in a randomized order). The session ended when 60 min. had elapsed. All rats received all drug treatments, according to a randomized-order within-subjects design. Drug tests were performed on Wednesdays and Fridays of each week, only when rats have performed at least 75% correct trials for a minimum of 50 trials in the previous test session.

Measures obtained during the test sessions were: (1) percent correct, defined as the number of correct trials ×100, divided by the total number of correct and incorrect trials, (2) missed trials, defined as responding beyond the 5 sec. limited hold or failing to respond, (3) correct latency, defined as the time taken to make a correct response after the illumination of the stimulus, (4) magazine latency, defined as the time taken to enter the magazine to collect the food pellet after making a correct response, (5) premature responding, defined as the total number of nose-poke responses made during the ITI, and (6) perseverative responding, defined as the total number of additional responses emitted after the initial nose-poke.

The results indicated that Compound No. 90 reduces impulsivity-like and perserverative-like behavior in rats in this test with a median effective dose of between 0.3 and 1.0 mg/kg p.o.

Example B21

An Animal Model to Test the Anxiolytic Effects of Compounds Using the Elevated Plus Maze (EPM) Test This study aimed to test the anxiolytic properties of Compound No. 90 using the elevated plus maze (EPM) test in C57B1/6J mice.

Male C57B1/6J mice from Jackson Laboratories (Bar Harbor, Me.) were used for the open field study. Mice were received at 6-weeks of age. Upon receipt, mice were assigned unique identification numbers (tail marked) and were group housed with 4 mice/cage in OPTI mouse ventilated cages. All animals remained housed in groups of four during the remainder of the study. All mice were acclimated to the colony room for approximately 2 week prior to testing and were subsequently tested at an average age of 8 weeks of age. During the period of acclimation, mice and rats were examined on a regular basis, handled, and weighed to assure adequate health and suitability. Animals were maintained on a 12 h/12 h light/dark cycle. The room temperature was maintained between 20 and 23° C. with a relative humidity maintained between 30% and 70%. Chow and water were provided ad libitum for the duration of the study. In each test, animals were randomly assigned across treatment groups. All animals were euthanized after the completion of the study.

The following compounds were used for this study: 1) Compound No. 90 (0.03, 0.1, and 1 mg/kg) was dissolved in 5% PEG200/H$_2$O and administered orally at a dose volume of 10 mL/kg 30 min prior to test; 2) Diazepam (2.5 mg/kg) was dissolved in 45% hydroxypropyl-β-cyclodextrin and administered orally at a dose volume of 10 mL/kg 30 min prior to test.

The elevated plus maze test assessed anxiety. The maze (Hamilton Kinder) consists of two closed arms (14.5 h×5 w×35 cm length) and two open arms (6 w×35 1 cm) forming a cross, with a square center platform (6×6 cm). All visible surfaces are made of black acrylic. Each arm of the maze was placed on a support column 56 cm above the floor. Antistatic black vinyl curtains (7' tall) surround the EPM to make a 5'×5" enclosure. Animals were brought to acclimate to the experimental room at least 1 h before the test. Mice were placed in the center of the elevated plus maze facing the closed arm for a 5-min run. All animals were tested once. The time spent, distance traveled and entries in each arm were automatically recorded by the computer. The EPM was thoroughly cleaned after each mouse.

Data were analyzed using analysis of variance (ANOVA) followed by Fisher's LSD post hoc analysis when appropriate. An effect was considered significant if p<0.05.

Compound No. 90 did not exert any anxiolytic-like effect in the EPM test at any dose tested, compared to vehicle.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A method of treating a disorder selected from the group consisting of schizophrenia and Parkinson's disease in an individual comprising administering to an individual in need thereof an effective amount of a compound of the formula (J-1):

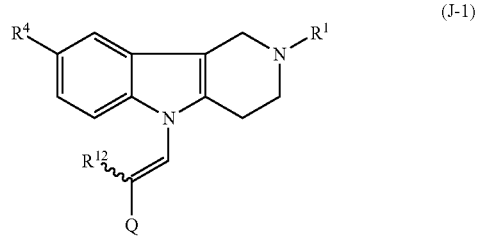

wherein:

$R^1$ is substituted or unsubstituted $C_1$-$C_8$ alkyl or perhaloalkyl;

$R^4$ is halo, trifluoromethyl, $C_1$-$C_8$ unsubstituted alkyl or substituted amino;

$R^{12}$ is halo, substituted or unsubstituted $C_1$-$C_8$ alkyl, substituted or unsubstituted $C_2$-$C_8$ alkenyl, substituted or unsubstituted aryl, substituted or unsubstituted heteroaryl, $C_1$-$C_8$ perhaloalkyl, $C_1$-$C_8$ alkoxy; the ⌇ bond indicates the presence of either an E or Z double bond configuration; and Q is substituted or unsubstituted aryl, or substituted or unsubstituted heteroaryl;

or a pharmaceutically acceptable salt thereof.

2. The method of claim 1, wherein $R^1$ is methyl, 2-fluoroethyl, 2,2,2-trifluoroethyl, or 3-hydroxy-3-methyl-but-1-yl; $R^4$ is CF$_3$, CH$_3$, F or Cl; $R^{12}$ is F, CH$_3$, ethyl, butyl, cyclopropyl, cyclobutyl, cyclopentyl, cyclohexyl, tert-butyl, CF$_3$, phenyl, pyridin-4-yl, —CH$_2$CO$_2$H, —CH$_2$CONHCH$_3$, or methoxy; and Q is 4-fluorophenyl, 4-methoxyphenyl, 3-fluoro-4-methoxyphenyl, pyridin-3-yl, pyridin-4-yl, 6-methylpyridin-3-yl, 6-trifluoromethylpyridin-3-yl, or pyrimidin-4-yl.

3. The method of claim 1, wherein the compound is selected from the group consisting of:

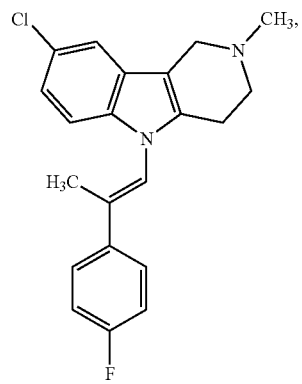

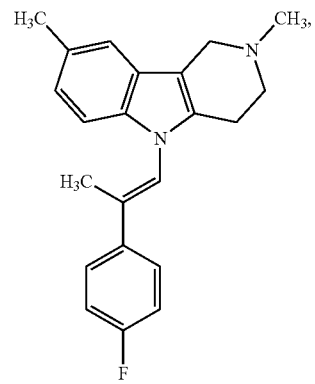

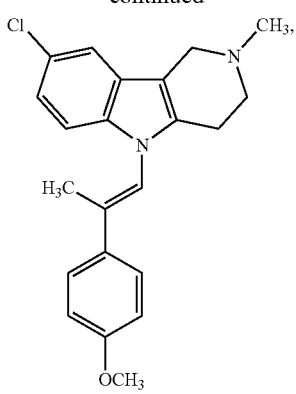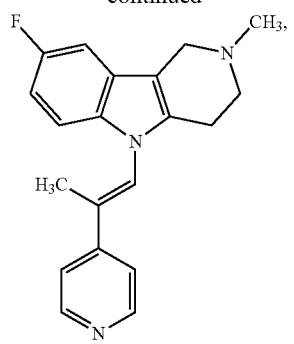

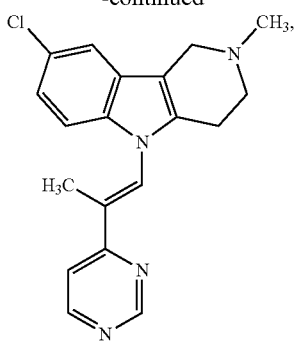
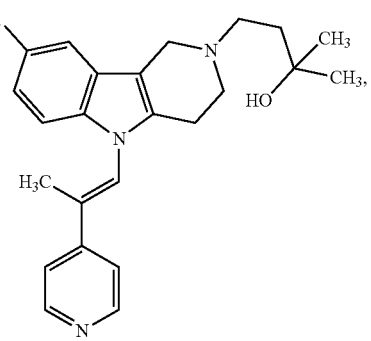
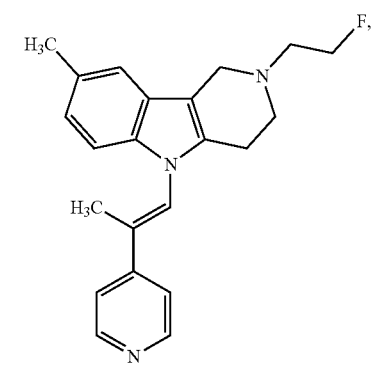
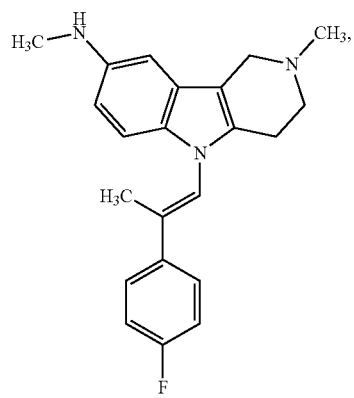
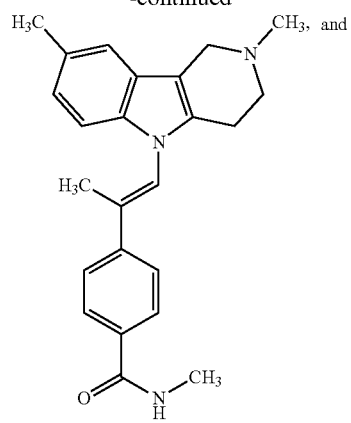
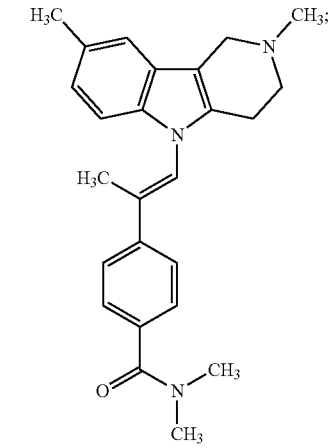

or a pharmaceutically acceptable salt thereof.

4. The method of claim 1, wherein $R^1$ is substituted or unsubstituted $C_1$-$C_8$ alkyl.

5. The method of claim 3, wherein and Q is substituted or unsubstituted heteroaryl.

6. The method of claim 1, wherein the disorder is schizophrenia.

7. The method of claim 1, wherein the disorder is Parkinson's disease.

8. The method of claim 1, wherein the compound is of the formula (J-1a):

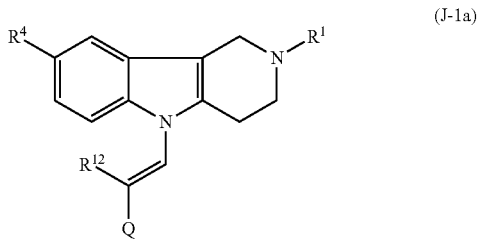

or a pharmaceutically acceptable salt thereof.

9. The method of claim 1, wherein the compound is of the formula (J-1b):

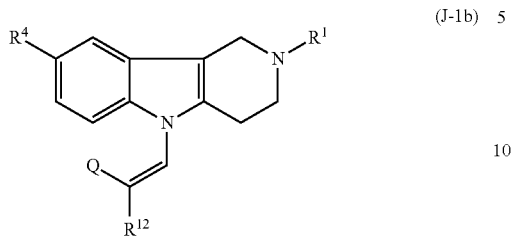

(J-1b)

or a pharmaceutically acceptable salt thereof.

10. The method of claim 8, wherein $R^1$ is unsubstituted $C_1$-$C_8$ alkyl.

11. The method of claim 10, wherein $R^1$ is methyl.

12. The method of claim 8, wherein $R^4$ is methyl or chloro.

13. The method of claim 12, wherein $R^4$ is methyl.

14. The method of claim 8, wherein $R^{12}$ is unsubstituted $C_1$-$C_8$ alkyl.

15. The method of claim 14, wherein $R^{12}$ is methyl.

16. The method of claim 8, wherein Q is substituted or unsubstituted pyridyl.

17. The method of claim 16, wherein Q is 3-pyridyl.

18. The method of claim 16, wherein Q is 4-pyridyl.

19. The method of claim 16, wherein Q is 6-methyl-3-pyridyl.

* * * * *